United States Patent
Siddiqui et al.

(10) Patent No.: US 10,537,558 B2
(45) Date of Patent: Jan. 21, 2020

(54) SUBSTITUTED PYRAZOLE AND PYRROLE COMPOUNDS AND METHODS FOR USING THEM FOR INHIBITION OF INITIATION OF TRANSLATION AND TREATMENT OF DISEASES AND DISORDERS RELATING THERETO

(71) Applicant: Bantam Pharmaceutical, LLC, New York, NY (US)

(72) Inventors: M. Arshad Siddiqui, Newton, MA (US); Stephane Ciblat, Montreal (CA); Martin Dery, Montreal (CA); Lea Constantineau-Forget, Montreal (CA); Chantal Grand-Maitre, Montreal (CA); Xiangyu Guo, Montreal (CA); Sanjay Srivastava, Pierrefonds (CA); Gerald W. Shipps, Boston, MA (US); Alan B. Cooper, Kenilworth, NJ (US); Nicolas Bruneau-Latour, Montreal (CA); Vu Linh Ly, Montreal (CA)

(73) Assignee: Bantam Pharmaceutical, LLC, New York, NY (US)

( * ) Notice: Subject to any disclaimer, the term of this patent is extended or adjusted under 35 U.S.C. 154(b) by 0 days.

(21) Appl. No.: 15/578,585

(22) PCT Filed: Jun. 1, 2016

(86) PCT No.: PCT/US2016/035288
§ 371 (c)(1),
(2) Date: Nov. 30, 2017

(87) PCT Pub. No.: WO2016/196644
PCT Pub. Date: Dec. 8, 2016

(65) Prior Publication Data
US 2018/0311218 A1    Nov. 1, 2018

Related U.S. Application Data

(60) Provisional application No. 62/169,376, filed on Jun. 1, 2015.

(51) Int. Cl.
*A61K 31/427* (2006.01)
*C07D 417/04* (2006.01)
(Continued)

(52) U.S. Cl.
CPC ............ *A61K 31/427* (2013.01); *A61P 25/28* (2018.01); *A61P 35/00* (2018.01)

(58) Field of Classification Search
CPC .................... C07D 417/04; A61K 31/427
See application file for complete search history.

(56) References Cited

U.S. PATENT DOCUMENTS

| 6,468,979 B1 | 10/2002 | Pellacini et al. |
| 6,649,636 B1 * | 11/2003 | Ando ............... C07D 405/14 514/341 |
| 2003/0220356 A1 | 11/2003 | Ibrahim et al. |

FOREIGN PATENT DOCUMENTS

| EP | 2 264 017 | 12/2010 |
| WO | 2004/094395 | 11/2004 |

(Continued)

OTHER PUBLICATIONS

Rida et al., "Synthesis of novel benzofuran and related benzimidazole derivatives for evaluation of in vitro anti-HIV-1, anticancer and antimicrobial activities," Archives of Pharmacal Research., vol. 29, No. 10, Oct. 1, 2006, pp. 326-833.

(Continued)

*Primary Examiner* — Karen Cheng
(74) *Attorney, Agent, or Firm* — McDonnell Boehnen Hulbert & Berghoff LLP

(57) ABSTRACT

Disclosed are pyrazole compounds, as well as pharmaceutical compositions and methods of use thereof. One embodiment is a compound having the structure (I) and pharmaceutically acceptable salts and/V-oxides thereof, wherein $X^1$, $X^2$, $Z^1$, $Z^2$, the ring system denoted by "a", $R^1$, $A^{1A}$, $L^{1B}$, $A^{1B}$, $L^{1A}$, $L^2$, Q, $L^3$, $R^3$, $A^{4A}$, $L^{4B}$, $A^{4B}$, $L^{4A}$, $R^4$, $L^5$, and $R^5$ are as described herein. In certain embodiments, compounds disclosed herein disrupt the eIF4E/eiF4G interaction, and can be used to treat hyperproliferative disorder, a neurological disease or disorder, or autism.

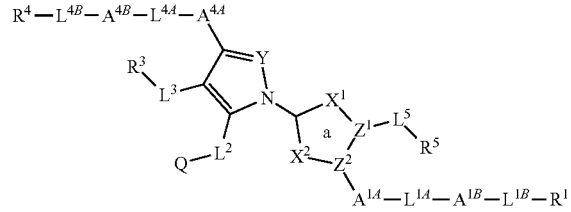

(I)

28 Claims, No Drawings

(51) Int. Cl.
*A61P 25/28* (2006.01)
*A61P 35/00* (2006.01)

(56) References Cited

FOREIGN PATENT DOCUMENTS

| | | |
|---|---|---|
| WO | 2007/138110 | 12/2007 |
| WO | 2009/027393 | 3/2009 |
| WO | 2014/066304 | 5/2014 |

OTHER PUBLICATIONS

International Search Report dated Jul. 22, 2016 for International Application No. PCT/US2016/035288 filed Jun. 1, 2016, 8 pages.

* cited by examiner

SUBSTITUTED PYRAZOLE AND PYRROLE COMPOUNDS AND METHODS FOR USING THEM FOR INHIBITION OF INITIATION OF TRANSLATION AND TREATMENT OF DISEASES AND DISORDERS RELATING THERETO

BACKGROUND OF THE DISCLOSURE

Field

This disclosure relates to the field of compounds, pharmaceutical compositions comprising them, and methods of using the compounds and compositions. This disclosure relates more particularly to compounds and pharmaceutical compositions thereof, and methods of inhibiting the initiation of translation of mRNA to protein with the compounds.

Technical Background

Translation is the mRNA-directed synthesis of proteins. It is generally described as occurring in three steps: initiation, elongation and termination. Initiation of translation involves the association of mRNA, methionyl tRNA and small and large ribosomal subunits, with protein chain elongation commencing with the AUG initiation codon of the mRNA. A ternary complex is formed among eukaryotic initiation factor 2 (eIF2), GTP and methionyl-tRNA. This ternary complex binds the 40S ribosomal subunit to form the 43S pre-initiation complex. mRNA is added to the complex along with other initiation factors such as the so-called eukaryotic initiation factors such as eukaryotic initiation factor 4F (eiF4F), resulting in the recognition of the 7-methylguanidine residue (termed the "cap") of the mRNA to form the 48S pre-initiation complex. Cap recognition facilitates the 43S complex entry at the 5' end of the capped mRNA; the complex migrates along the mRNA towards its 3' end until it reaches the first AUG codon, at which point a 60S ribosomal subunit joins the complex to form the 80S ribosome, and the first peptide bond is formed.

The structure of the mRNA itself influences translation efficiency. In particular, the length and secondary structure of the 5' untranslated region can have an important effect on efficiency. A moderately short, relatively unstructured 5' untranslated region with a low G and C base content has been linked to high translational efficiency. Many vertebrate mRNAs, in contrast, are relatively long and have a high proportion of G and C bases, which tend to form highly structured secondary structures. Such mRNAs are translated only relatively inefficiently and their translation can be highly dependent on the activity of translation initiation factors such as eIF3 and eIF4F. A disproportionately high number of proto-oncogenes, such as those coding for the G1 cyclins, transcription and growth factors, cytokines and other critical regulatory proteins, have complex, highly structured 5' untranslated region, and as such are translated relatively inefficiently in the absence of translation initiation factors. mRNAs that encode globulins, albumins and histones generally have high copy number and also short and/or unstructured 5'-untranslated regions, and as such the resulting protein levels do not depend strongly on the amount of eIF4F. This distinction between regulatory and housekeeping proteins suggests that the expression of regulatory genes is controlled significantly at the level of translation. Accordingly, for such genes, the low efficiency of translation is part of a control mechanism that modulates the yield of proteins such as cyclins, c-myc, VEGF, TNF, among others, that could be harmful if overproduced.

SUMMARY OF THE DISCLOSURE

Reproducing cells require increased levels of 7-methyl GTP Cap-dependent translation initiation of protein to support cellular proliferation. Inhibition of Cap-dependent translation initiation can prevent or slow down cellular proliferation, especially in situations characterized by aberrant proliferation. Described herein are certain compounds, pharmaceutical compositions comprising them, and methods that can specifically inhibit Cap-dependent translation initiation. As a result, the compounds and pharmaceutical compositions of the disclosure can be useful in methods of inhibition of the initiation of mRNA translation, e.g., especially in cases of aberrant mRNA translational regulation.

Disclosed herein are compounds having structural formula (I):

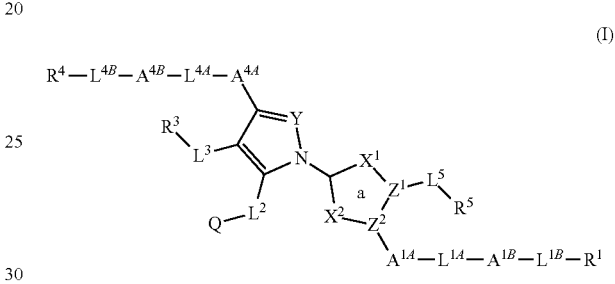

(I)

optionally in the form of a pharmaceutically acceptable salt or N-oxide, or a solvate or hydrate, wherein:

$A^{1A}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$—, —NR$^6$S(O)$_{1-2}$—, —OC(O)O—, —OC(O)NR$^6$—, —NR$^6$C(O)O—, —NR$^6$C(O)NR$^6$—, —SC(O)O—, —OC(O)S—, —SC(O)S—, —SC(O)NR$^6$—, —NR$^6$C(O)S—, —OC(S)O—, —OC(S)NR$^6$—, —NR$^6$C(S)O—, —NR$^6$C(S)NR$^6$—, —SC(S)O—, —OC(S)S—, —SC(S)S—, —SC(S)NR$^6$—, —NR$^6$C(S)S, —NR$^6$C(NR$^6$)NR$^6$— and —NR$^6$S(O)$_{1-2}$NR$^6$—;

$L^{1A}$ is selected from the group consisting of a bond, optionally substituted $C_1$-$C_4$ alkylene, optionally substituted $C_1$-$C_4$ alkenylene and optionally substituted $C_1$-$C_4$ alkynylene;

$A^{1B}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$—, —NR$^6$S(O)$_{1-2}$—, —OC(O)O—, —OC(O)NR$^6$—, —NR$^6$C(O)O—, —NR$^6$C(O)NR$^6$—, —SC(O)O—, —OC(O)S—, —SC(O)S—, —SC(O)NR$^6$—, —NR$^6$C(O)S—, —OC(S)O—, —OC(S)NR$^6$—, —NR$^6$C(S)O—, —NR$^6$C(S)NR$^6$—, —SC(S)O—, —OC(S)S—, —SC(S)S—, —SC(S)NR$^6$—, —NR$^6$C(S)S, —NR$^6$C(NR$^6$)NR$^6$— and —NR$^6$S(O)$_{1-2}$NR$^6$—;

$L^{1B}$ is selected from the group consisting of a bond, optionally substituted $C_1$-$C_4$ alkylene, optionally substituted $C_1$-$C_4$ alkenylene and optionally substituted $C_1$-$C_4$ alkynylene;

$R^1$ is selected from the group consisting of hydrogen,
optionally substituted $C_1$-$C_8$ alkyl, optionally-substituted $C_1$-$C_8$ alkenyl and optionally substituted $C_1$-$C_8$ alkynyl,
cycloalkyl and heterocycloalkyl, each optionally substituted with 1-5 $R^{1E}$, and
aryl and heteroaryl, each optionally substituted with 1-5 $R^{1E}$,
in which
each $R^{1E}$ is independently selected from oxo, optionally-substituted $C_1$-$C_4$ alkyl, $C_1$-$C_4$ fluoroalkyl, halogen, —CN, $SF_5$, —$N_3$, —C(O)$R^{1F}$, —$SR^{1F}$, —S(O)$_{1-2}R^{1F}$, —$OR^{1F}$, —$NR^{1G}R^{1F}$, —C(O)$R^{1F}$, —C(O)$NR^{1G}R^{1F}$, —$NR^{1G}$C(O)$R^{1F}$, —C(S)$NR^{1G}R^{1F}$, —$NR^{1G}$C(S)$R^{1F}$, —C(O)$OR^{1F}$, —OC(O)$R^{1F}$, —C(O)$SR^{1F}$, —SC(O)$R^{1F}$, —C(S)$OR^{1F}$, —OC(S)$R^{1F}$, —C(S)$SR^{1F}$, —SC(S)$R^{1F}$, —S(O)$_{1-2}OR^{1F}$, —OS(O)$_{1-2}R^{1F}$, —S(O)$_{1-2}NR^{1G}R^{1F}$, —$NR^{1G}$S(O)$_{1-2}R^{1F}$, —OC(O)$OR^{1F}$, —OC(O)$NR^{1G}R^{1F}$, —$NR^{1G}$C(O)$OR^{1F}$, —$NR^{1G}$C(O)$NR^{1G}R^{1F}$, —SC(O)$OR^{1F}$, —OC(O)$SR^{1F}$, —SC(O)$SR^{1F}$, —SC(O)$NR^{1G}R^{1F}$, —$NR^{1G}$C(O)$SR^{1F}$, —OC(S)$OR^{1F}$, —OC(S)$NR^{1G}R^{1F}$, —$NR^{1G}$C(S)$OR^{1F}$, —$NR^{1G}$C(S)$NR^{1G}R^{1F}$, —SC(S)$OR^{1F}$, —OC(S)$SR^{1F}$, —SC(S)$SR^{1F}$, —SC(S)$NR^{1G}R^{1F}$, —$NR^{1G}$C(S)$SR^{1F}$, —$NR^{1G}$C($NR^{1G}$)$NR^{1G}R^{1F}$ and —$NR^{1G}$S(O)$_{1-2}NR^{1G}R^{1F}$;

each $R^{1F}$ is independently selected from H, $C_1$-$C_3$ alkyl, $C_1$-$C_3$ fluoroalkyl, $C_1$-$C_3$ hydroxyalkyl, ($C_1$-$C_3$ alkoxy)$C_1$-$C_3$ alkyl, ($C_1$-$C_3$ alkoxy($C_1$-$C_3$ alkoxy))$C_1$-$C_3$ alkyl, ($C_1$-$C_3$ alkoxy($C_1$-$C_3$ alkoxy($C_1$-$C_3$ alkoxy)))$C_1$-$C_3$ alkyl, and each $R^{1G}$ is independently selected from H, $C_1$-$C_3$ alkyl, $C_1$-$C_3$ fluoroalkyl, $C_1$-$C_3$ hydroxyalkyl, ($C_1$-$C_3$ alkoxy)$C_1$-$C_3$ alkyl, —S(O)$_{1-2}$($C_1$-$C_3$ alkyl), —C(O)($C_1$-$C_3$ alkyl) and —C(O)O($C_1$-$C_3$ alkyl);

$L^2$ is selected from the group consisting of a bond, optionally substituted $C_1$-$C_4$ alkylene, optionally substituted $C_1$-$C_4$ alkenylene or optionally substituted $C_1$-$C_4$ alkynylene;

Q is selected from the group consisting of H, —$CH_2OH$, —C(O)OH, —C(O)$OR^{2A}$, —C(O)$NR^{2B}R^{2A}$, —C(O)$NR^{2B}$S(O)$_2R^{2A}$, —C(O)$NR^{2B}$S(O)$_2NR^{2B}R^{2A}$, —C(O)$R^{2A}$, —S(O)$_2OH$, —P(O)(OH)$_2$, —C(OH)(CF$_3$)$_2$, —S(O)$_2R^{2A}$, —N($R^{2B}$)S(O)$_2R^{2A}$, —S(O)$_2NR^{2B}R^{2A}$, —C(O)NHOH, —C(O)NH—O($C_1$-$C_3$ alkyl), —CO(NH)CN,

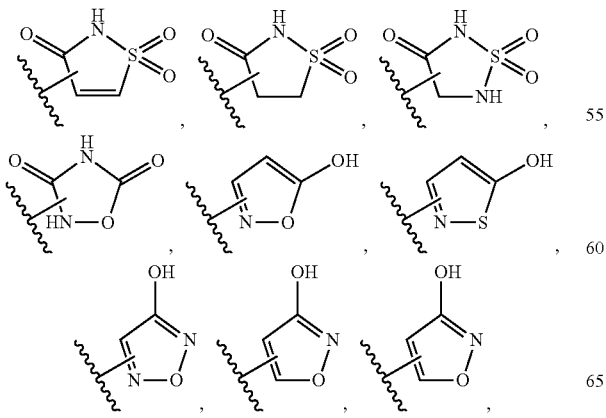

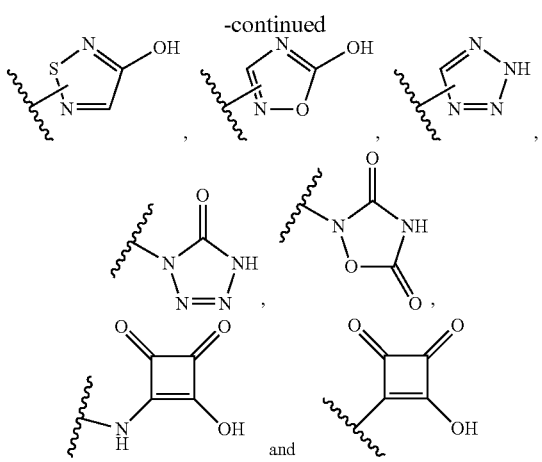

and in which
each $R^{2A}$ is independently selected from hydrogen, $C_1$-$C_3$ alkyl, $C_1$-$C_3$ fluoroalkyl, $C_1$-$C_3$ hydroxyalkyl $C_1$-$C_3$ aminoalkyl, $C_1$-$C_3$ thioalkyl, ($C_1$-$C_3$ alkoxy) $C_1$-$C_3$ alkyl, —($CH_2CH_2O$)$_{2-5}$-(optionally substituted $C_1$-$C_3$ alkyl)- and heteroaryl optionally substituted with 1-2 groups selected from substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —C(O)$C_1$-$C_3$ alkyl, and each $R^{2B}$ is independently selected from hydrogen, $C_1$-$C_3$ alkyl, $C_1$-$C_3$ fluoroalkyl, $C_1$-$C_3$ hydroxyalkyl, $C_1$-$C_3$ aminoalkyl, $C_1$-$C_3$ thioalkyl, ($C_1$-$C_3$ alkoxy) $C_1$-$C_3$ alkyl, —S(O)$_{1-2}$($C_1$-$C_3$ alkyl), —C(O)($C_1$-$C_3$ alkyl) and —C(O)O($C_1$-$C_3$ alkyl), or $R^{2A}$ and $R^{2B}$ come together with a nitrogen to which they are both directly bound to form a heterocycloalkyl optionally substituted with 1-3 substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —C(O)$C_1$-$C_3$ alkyl;

$L^3$ is selected from a -$L^{3A}$-$A^{3A}$- and -$A^{3B}L^{3B}$-, wherein $L^{3A}$ and $L^{3B}$ are independently selected from the group consisting of a bond, optionally substituted $C_1$-$C_4$ alkylene, optionally substituted $C_1$-$C_4$ alkenylene and optionally substituted $C_1$-$C_4$ alkynylene, and $A^{3A}$ and $A^{3B}$ are independently selected from a bond, —C(O)—, —S—, —S(O)$_{1-2}$—, —O—, —$NR^6$—, —C(O)$NR^6$—, —$NR^6$C(O)—, —C(S)$NR^6$—, —$NR^6$C(S)—, —C(O)O—, —OC(O)—, —S(O)$_{1-2}$O—, —OS(O)$_{1-2}$—, —S(O)$_{1-2}NR^6$— and —$NR^6$S(O)$_{1-2}$—;

$R^3$ is selected from the group consisting of
optionally substituted $C_1$-$C_8$ alkyl, optionally-substituted $C_1$-$C_8$ alkenyl and optionally substituted $C_1$-$C_8$ alkynyl,
cycloalkyl and heterocycloalkyl, each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$, and
aryl and heteroaryl each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$, in which each $L^{3C}$ is a bond, methylene, ethylene, —C(O)—, —S—, —S(O)$_{1-2}$—, —O— or —NR$^{3G}$—;

each $R^{3D}$ is independently selected from optionally-substituted C$_1$-C$_4$ alkyl, C$_1$-C$_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$, —OC(O)OR$^{3F}$, —OC(O)NR$^{3G}$R$^{3F}$, —NR$^{3G}$C(O)OR$^{3F}$, —NR$^{3G}$C(O)NR$^{3G}$R$^{3F}$, —SC(O)OR$^{3F}$, —OC(O)SR$^{3F}$, —SC(O)SR$^{3F}$, —SC(O)NR$^{3G}$R$^{3F}$, —NR$^{3G}$C(O)SR$^{3F}$, —OC(S)OR$^{3F}$, —OC(S)NR$^{3G}$R$^{3F}$, —NR$^{3G}$C(S)OR$^{3F}$, —NR$^{3G}$C(S)NR$^{3G}$R$^{3F}$, —SC(S)OR$^{3F}$, —OC(S)SR$^{3F}$, —SC(S)SR$^{3F}$, —SC(S)NR$^{3G}$R$^{3F}$, —NR$^{3G}$C(S)SR$^{3F}$, —NR$^{3G}$C(NR$^{3G}$)NR$^{3G}$R$^{3F}$ and —NR$^{3G}$S(O)$_{1-2}$NR$^{3G}$R$^{3F}$;

each $R^{3E}$ is independently selected from oxo, optionally-substituted C$_1$-C$_4$ alkyl, C$_1$-C$_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$, —OC(O)OR$^{3F}$, —OC(O)NR$^{3G}$R$^{3F}$, —NR$^{3G}$C(O)OR$^{3F}$, —NR$^{3G}$C(O)NR$^{3G}$R$^{3F}$, —SC(O)OR$^{3F}$, —OC(O)SR$^{3F}$, —SC(O)SR$^{3F}$, —SC(O)NR$^{3G}$R$^{3F}$, —NR$^{3G}$C(O)SR$^{3F}$, —OC(S)OR$^{3F}$, —OC(S)NR$^{3G}$R$^{3F}$, —NR$^{3G}$C(S)OR$^{3F}$, —NR$^{3G}$C(S)NR$^{3G}$R$^{3F}$, —SC(S)OR$^{3F}$, —OC(S)SR$^{3F}$, —SC(S)SR$^{3F}$, —SC(S)NR$^{3G}$R$^{3F}$, —NR$^{3G}$C(S)SR$^{3F}$, —NR$^{3G}$C(NR$^{3G}$)NR$^{3G}$R$^{3F}$ and —NR$^{3G}$S(O)$_{1-2}$NR$^{3G}$R$^{3F}$;

each $R^{3F}$ is independently selected from H, C$_1$-C$_3$ alkyl, C$_1$-C$_3$ fluoroalkyl and C$_1$-C$_3$ hydroxyalkyl and each $R^{3G}$ is independently selected from H, C$_1$-C$_3$ alkyl, C$_1$-C$_3$ fluoroalkyl, C$_1$-C$_3$ hydroxyalkyl, —S(O)$_{1-2}$(C$_1$-C$_3$ alkyl), —C(O)(C$_1$-C$_3$ alkyl) and —C(O)O(C$_1$-C$_3$ alkyl);

$A^{4A}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$—, —NR$^6$S(O)$_{1-2}$—, —OC(O)O—, —OC(O)NR$^6$—, —NR$^6$C(O)O—, —NR$^6$C(O)NR$^6$—, —SC(O)O—, —CO(O)S—, —SC(O)S—, —SC(O)NR$^6$—, —NR$^6$C(O)S—, —OC(S)O—, —OC(S)NR$^6$—, —NR$^6$C(S)O—, —NR$^6$C(S)NR$^6$—, —SC(S)O—, —SC(S)S—, —SC(S)NR$^6$—, —NR$^6$C(S)S, —NR$^6$C(NR$^6$)NR$^6$— and —NR$^6$S(O)$_{1-2}$NR$^6$—;

$L^{4A}$ is selected from the group consisting of a bond, optionally substituted C$_1$-C$_4$ alkylene, optionally substituted C$_1$-C$_4$ alkenylene and optionally substituted C$_1$-C$_4$ alkynylene;

$A^{4B}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —CO(S)—, —C(S)S—, —SC(S)—, —S(O)$_{1-2}$O—, —OS(O)$_{1-2}$—, —S(O)$_{1-2}$NR$^6$—, —NR$^6$S(O)$_{1-2}$—, —OC(O)O—, —OC(O)NR$^6$—, —NR$^6$C(O)O—, —NR$^6$C(O)NR$^6$—, —SC(O)O—, —CO(O)S—, —SC(O)S—, —SC(O)NR$^6$—, —NR$^6$C(O)S—, —OC(S)O—, —OC(S)NR$^6$—, —NR$^6$C(S)O—, —NR$^6$C(S)NR$^6$—, —SC(S)O—, —SC(S)S—, —SC(S)NR$^6$—, —NR$^6$C(S)S, —NR$^6$C(NR$^6$)NR$^6$— and —NR$^6$S(O)$_{1-2}$NR$^6$—;

$L^{4B}$ is selected from the group consisting of a bond, optionally substituted C$_1$-C$_4$ alkylene, optionally substituted C$_1$-C$_4$ alkenylene and optionally substituted C$_1$-C$_4$ alkynylene;

$R^4$ is selected from the group consisting of hydrogen, optionally substituted C$_1$-C$_8$ alkyl, optionally-substituted C$_1$-C$_8$ alkenyl and optionally substituted C$_1$-C$_8$ alkynyl, cycloalkyl and heterocycloalkyl, each optionally substituted with 1-5 $R^{4E}$, and aryl and heteroaryl, each optionally substituted with 1-5 $R^{4E}$, in which each $R^{4E}$ is independently selected from oxo, optionally-substituted C$_1$-C$_4$ alkyl, C$_1$-C$_4$ fluoroalkyl, halogen, —CN, —SF$_5$, —N$_3$, —C(O)R$^{4F}$, —SR$^{4F}$, —S(O)$_{1-2}$R$^{4F}$, —OR$^{4F}$, —NR$^{4G}$R$^{4F}$, —C(O)R$^{4F}$, —C(O)NR$^{4G}$R$^{4F}$, —NR$^{4G}$C(O)R$^{4F}$, —C(S)NR$^{4G}$R$^{4F}$, —NR$^{1G}$C(S)R$^{4F}$, —C(O)OR$^{4F}$, —OC(O)R$^{4F}$, —C(O)SR$^{4F}$, —SC(O)R$^{4F}$, —C(S)OR$^{4F}$, —OC(S)R$^{4F}$, —C(S)SR$^{4F}$, —SC(S)R$^{4F}$, —S(O)$_{1-2}$OR$^{4F}$, —OS(O)$_{1-2}$R$^{4F}$, —S(O)$_{1-2}$NR$^{4G}$R$^{4F}$, —NR$^{4G}$S(O)$_{1-2}$R$^{4F}$, —CO(O)OR$^{4F}$, —OC(O)NR$^{4G}$R$^{4F}$, —NR$^{4G}$C(O)OR$^{4F}$, —NR$^{4G}$C(O)NR$^{4G}$R$^{4F}$, —SC(O)OR$^{4F}$, —OC(O)SR$^{4F}$, —SC(O)SR$^{4F}$, —SC(O)NR$^{4G}$R$^{4F}$, —NR$^{4G}$C(O)SR$^{4F}$, —OC(S)OR$^{4F}$, —OC(S)NR$^{4G}$R$^{4F}$, —NR$^{4G}$C(S)OR$^{4F}$, —NR$^{4G}$C(S)NR$^{4G}$R$^{4F}$, —SC(S)OR$^{4F}$, —OC(S)SR$^{4F}$, —SC(S)SR$^{4F}$, —SC(S)NR$^{4G}$R$^{4F}$, —NR$^{4G}$C(S)SR$^{4F}$, —NR$^{4G}$C(NR$^{4G}$)NR$^{4G}$R$^{4F}$ and —NR$^{4G}$S(O)$_{1-2}$NR$^{4G}$R$^{4F}$;

each $R^{4F}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each $R^{4G}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

$L^5$ is selected from a -$L^{5A}$-$A^{5A}$- and -$A^{5B}$$L^{5B}$-, wherein $L^{5A}$ and $L^{5B}$ are independently selected from the group consisting of a bond, optionally substituted C$_1$-C$_3$ alkyl, optionally substituted C$_1$-C$_3$ alkenyl and optionally substituted C$_1$-C$_3$ alkynyl, and $A^{5A}$ and $A^{5B}$ are independently selected from a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —S(O)$_{1-2}$O—, —OS(O)$_{1-2}$—, —S(O)$_{1-2}$NR$^6$— and —NR$^6$S(O)$_{1-2}$—;

R$^5$ is selected from the group consisting of
- optionally substituted C$_1$-C$_8$ alkyl, optionally-substituted C$_1$-C$_8$ alkenyl and optionally substituted C$_1$-C$_8$ alkynyl,
- cycloalkyl and heterocycloalkyl, each (i) optionally substituted with a single substituent selected from -L$^{5C}$-(aryl optionally substituted with 1-5 R$^{5D}$), -L$^{5C}$-(heteroaryl optionally substituted with 1-5 R$^{5D}$), -L$^{5C}$-(cycloalkyl optionally substituted with 1-5 R$^{5E}$), -L$^{5C}$-(heterocycloalkyl optionally substituted with 1-5 R$^{5E}$) and (ii) optionally substituted with 1-5 R$^{5E}$, and
- aryl and heteroaryl each (i) optionally substituted with a single substituent selected from -L$^{5C}$-(aryl optionally substituted with 1-5 R$^{5D}$), -L$^{5C}$-(heteroaryl optionally substituted with 1-5 R$^{5D}$), -L$^{5C}$-(cycloalkyl optionally substituted with 1-5 R$^{5E}$), -L$^{5C}$-(heterocycloalkyl optionally substituted with 1-5 R$^{5E}$) and (ii) optionally substituted with 1-5 R$^{5E}$, in which
- each L$^{5C}$ is a bond, methylene, ethylene, —C(O)—, —S—, —S(O)$_{1-2}$—, —O— or —NR$^{5G}$—;
- each R$^{5D}$ is independently selected from optionally-substituted C$_1$-C$_4$ alkyl, C$_1$-C$_4$ fluoroalkyl, halogen, —CN, —SF$_5$, —N$_3$, —C(O)R$^{5F}$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{5G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$, —NR$^{5G}$S(O)$_{1-2}$R$^{5F}$, —OC(O)OR$^{5F}$, —OC(O)NR$^{5G}$R$^{5F}$, —NR$^{5G}$C(O)OR$^{5F}$, —NR$^{5G}$C(O)NR$^{5G}$R$^{5F}$, —SC(O)OR$^{5F}$, —OC(O)SR$^{5F}$, —SC(O)SR$^{5F}$, —SC(O)NR$^{5G}$R$^{5F}$, —NR$^{5G}$C(O)SR$^{5F}$, —OC(S)OR$^{5F}$, —OC(S)NR$^{5G}$R$^{5F}$, —NR$^{5G}$C(S)OR$^{5F}$, —NR$^{5G}$C(S)NR$^{5G}$R$^{5F}$, —SC(S)OR$^{5F}$, —OC(S)SR$^{5F}$, —SC(S)SR$^{5F}$, —SC(S)NR$^{5G}$R$^{5F}$, —NR$^{5G}$C(S)SR$^{5F}$, —NR$^{5G}$C(NR$^{5G}$)NR$^{5G}$R$^{5F}$ and —NR$^{5G}$S(O)$_{1-2}$NR$^{5G}$R$^{5F}$;
- each R$^{5E}$ is independently selected from oxo, optionally-substituted C$_1$-C$_4$ alkyl, C$_1$-C$_4$ fluoroalkyl, halogen, —CN, —SF$_5$, —N$_3$, —C(O)R$^{5F}$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{1G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$, —NR$^{5G}$S(O)$_{1-2}$R$^{5F}$, —OC(O)OR$^{5F}$, —OC(O)NR$^{5G}$R$^{5F}$, —NR$^{5G}$C(O)OR$^{5F}$, —NR$^{5G}$C(O)NR$^{5G}$R$^{5F}$, —SC(O)OR$^{5F}$, —OC(O)SR$^{5F}$, —SC(O)SR$^{5F}$, —SC(O)NR$^{5G}$R$^{5F}$, —NR$^{5G}$C(O)SR$^{5F}$, —OC(S)OR$^{5F}$, —NR$^{5G}$C(S)OR$^{5F}$, —NR$^{5G}$C(S)NR$^{5G}$R$^{5F}$, —SC(S)OR$^{5F}$, —OC(S)SR$^{5F}$, —SC(S)SR$^{5F}$, —SC(S)NR$^{5G}$R$^{5F}$, —NR$^{5G}$C(S)SR$^{5F}$, —NR$^{5G}$C(NR$^{5G}$)NR$^{5G}$R$^{5F}$ and —NR$^{5G}$S(O)$_{1-2}$NR$^{5G}$R$^{5F}$;
- each R$^{5F}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and
- each R$^{5G}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

X$^1$ is selected from the group consisting of CR$^{XA}$, C(R$^{XA}$)$_2$, S, O, N and NR$^{XB}$ and X$^2$ is selected from the group consisting of CR$^{XA}$, C(R$^{XA}$)$_2$, S, O, N and NR$^{XB}$ in which
- each R$^{XA}$ is independently selected from the group consisting of hydrogen, optionally substituted C$_1$-C$_4$ alkyl, optionally substituted C$_1$-C$_4$ alkenyl, optionally substituted C$_1$-C$_4$ alkynyl, halo, —CN, oxo, halogen, —CN, —SF$_5$, —N$_3$, —C(O)R$^{XC}$, —SR$^{XC}$, —S(O)$_{1-2}$R$^{XC}$, —OR$^{XC}$, —NR$^{XC}$R$^{XC}$, in which each R$^{XC}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^{XD}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —C(O)(C$_1$-C$_3$ alkyl) and —C(O)O(C$_1$-C$_3$ alkyl);
- each R$^{XB}$ is independently selected from the group consisting of hydrogen, optionally substituted C$_1$-C$_4$ alkyl, optionally substituted C$_1$-C$_4$ alkenyl, optionally substituted C$_1$-C$_4$ alkynyl, optionally substituted C$_1$-C$_4$ alkyl-C(O)—, optionally substituted C$_1$-C$_4$ alkyl-O—C(O)—, optionally substituted C$_1$-C$_4$ alkyl-S(O)$_{1-2}$—;

Y is CR$^Y$ or N, in which
R$^Y$ is selected from the group consisting of hydrogen, optionally substituted C$_1$-C$_4$ alkyl, optionally substituted C$_1$-C$_4$ alkenyl, optionally substituted C$_1$-C$_4$ alkynyl, halo, —CN, oxo, halogen, —CN, —SF$_5$, —N$_3$, —C(O)R$^{YC}$, —SR$^{YC}$, —S(O)$_{1-2}$R$^{YC}$, —OR$^{YC}$, —NR$^{YD}$R$^{YC}$, in which each R$^{YC}$ is independently selected from H, 1-C$_3$ alkyl, 1-C$_3$ fluoroalkyl, 1-C$_3$ hydroxyalkyl and (C$_1$-C$_3$ alkoxy)C$_1$-C$_3$ alkyl and each R$^{YD}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —C(O)(C$_1$-C$_3$ alkyl) and —C(O)O(C$_1$-C$_3$ alkyl);

Z$^1$ is selected from C, CR$^Z$ and N and Z$^2$ is selected from C, CR$^Z$ and N, in which
R$^Z$ is selected from the group consisting of hydrogen, optionally substituted C$_1$-C$_4$ alkyl, optionally substituted C$_1$-C$_4$ alkenyl, optionally substituted C$_1$-C$_4$ alkynyl, halo, —CN, oxo, halogen, —CN, —SF$_5$, —N$_3$, —C(O)R$^{ZC}$, —SR$^{ZC}$, —S(O)$_{1-2}$R$^{ZC}$, —OR$^{ZC}$, —NR$^{ZD}$R$^{ZC}$, in which each R$^{ZC}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^{ZD}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —C(O)(C$_1$-C$_3$ alkyl) and —C(O)O(C$_1$-C$_3$ alkyl); and the ring system denoted by "a" is saturated, partially unsaturated or aromatic, wherein
each R$^6$ is selected from the group consisting of hydrogen, optionally substituted C$_1$-C$_4$ alkyl, optionally substituted C$_1$-C$_4$ alkenyl, optionally substituted C$_1$-C$_4$ alkynyl, optionally substituted C$_1$-C$_4$ alkyl-C(O)—, optionally substituted C$_1$-C$_4$ alkyl-O—C(O)—, optionally substituted C$_1$-C$_4$ alkyl-S(O)$_{1-2}$—;

each alkyl, alkylene, alkenyl, alkenylene, alkynyl and alkynylene is straight-chain or branched;

each optionally substituted alkyl, alkenyl, alkynyl, alkylene, alkenylene and alkynylene is unsubstituted or substituted with 1-5 substituents independently selected from oxo, halogen, —CN, —SF$_5$, —N$_3$, —C(O)R$^8$, —SR$^8$, —S(O)$_{1-2}$R$^8$, —OR$^8$, —NR$^9$R$^8$, —C(O)NR$^9$R$^8$, —NR$^9$C(O)R$^8$, —C(S)NR$^9$R$^8$, —NR$^9$C(S)R$^8$, —C(O)OR$^8$, —OC(O)R$^8$, —C(O)SR$^8$, —SC(O)R$^8$, —C(S)OR$^8$, —OC(S)R$^8$, —C(S)SR$^8$, —SC(S)R$^8$, —S(O)$_{1-2}$OR$^8$, —OS(O)$_{1-2}$R$^8$, —S(O)$_{1-2}$NR$^9$R$^8$, —NR$^9$S(O)$_{1-2}$R$^8$, —OC(O)OR$^8$, —OC(O)NR$^9$R$^8$, —NR$^9$C(O)OR$^8$, —NR$^9$C(O)NR$^9$R$^8$, —SC(O)OR$^8$, —OC(O)SR$^8$, SC(O)SR$^8$, —SC(O)NR$^9$R$^8$, —NR$^9$C(O)SR$^8$, —OC(S)OR$^8$, —OC(S)NR$^9$R$^8$, —NR$^9$C(S)OR$^8$, —NR$^9$C(S)NR$^9$R$^8$, —SC(S)OR$^8$, —OC(S)SR$^8$, —SC(S)SR$^8$, —SC(S)NR$^9$R$^8$, —NR$^9$C(S)SR$^8$, —NR$^9$C(NR$^9$)NR$^9$R$^8$ and —NR$^9$S(O)$_{1-2}$NR$^9$R$^8$, in which each R$^8$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^9$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

each cycloalkyl has 3-10 ring carbons and is unsaturated or partially unsaturated, and optionally includes one or two fused cycloalkyl rings, each fused ring having 3-8 ring members;

each heterocycloalkyl has 3-10 ring members and 1-3 heteroatoms independently selected from nitrogen, oxygen and sulfur and is unsaturated or partially unsaturated, and optionally includes one or two fused cycloalkyl rings, each having 3-8 ring members;

each aryl is a phenyl or a naphthyl, and optionally includes one or two fused cycloalkyl or heterocycloalkyl rings, each fused cycloalkyl or heterocycloalkyl ring having 4-8 ring members;

each heteroaryl is a 5-6 membered monocyclic heteroaryl ring having 1-4 heteroatoms independently selected from nitrogen, oxygen and sulfur or a 8-10 membered bicyclic heteroaryl having 1-5 heteroatoms independently selected from nitrogen, oxygen or sulfur, and optionally includes one or two fused cycloalkyl or heterocycloalkyl rings, each fused cycloalkyl or heterocycloalkyl ring having 4-8 ring members.

Also disclosed herein are pharmaceutical compositions. Examples of such compositions include those having at least one pharmaceutically acceptable carrier, diluent, and/or excipient together with a compound as described herein, or a pharmaceutically acceptable salt or N-oxide thereof, or a solvate (e.g., a hydrate) thereof.

The present disclosure also provides methods for inhibiting the initiation of mRNA translation using the presently disclosed compounds, salts, N-oxides and pharmaceutical compositions.

All publications referenced herein are hereby incorporated herein by reference in their entirety to the extent they are not inconsistent with the specific disclosure provided herein.

DETAILED DESCRIPTION

In one aspect, the disclosure provides compounds that can inhibit the initiation of translation of mRNA to protein.

In certain embodiments, the disclosure provides compounds as described above with respect to structural formula (I). In certain such embodiments, each and every optionally substituted alkyl, alkylene, alkenyl, alkenylene, alkynyl and alkynylene is unsubstituted or fluorinated. For example, in certain such embodiments, each and every optionally substituted alkyl, alkylene, alkenyl, alkenylene, alkynyl and alkynylene is unsubstituted.

The disclosure also provides a variety of subgenera of compounds in which structural formula (I), $X^1$, $X^2$, $Z^1$, $Z^2$, the ring system denoted by "a", $R^1$, $A^{1A}$, $L^{1B}$, $A^{1B}$, $L^{1A}$, $L^2$, Q, $L^3$, $R^3$, $A^{4A}$, $L^{4B}$, $A^{4B}$, $L^{4A}$, $R^4$, $L^5$, and $R^5$ are optionally independently selected from the groups (Ia) et seq., (1a) et seq., (2a) et seq., (3a) et seq., (4a) et seq., (5a) et seq., (6a) et seq., (7a) et seq., (8a) et seq., (9a) et seq., (10a) et seq., (11a) et seq., (12a) et seq., (13a) et seq., (14a) et seq., (15a) et seq., (16a) et seq., (17a) et seq., (18a) et seq., (19a) et seq., (20a) et seq., and (21a) et seq. defined hereinbelow (e.g., wherein the compound is of structural formula (I) as defined in any combination of the embodiments below):

In certain embodiments, structural formula (I) is one of formulae (Ia)-(Ic):

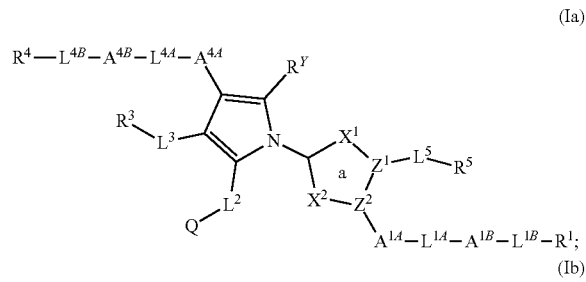

(Ia)

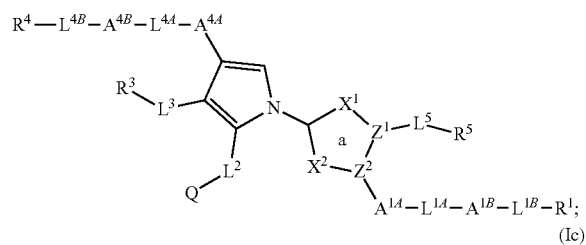

(Ib)

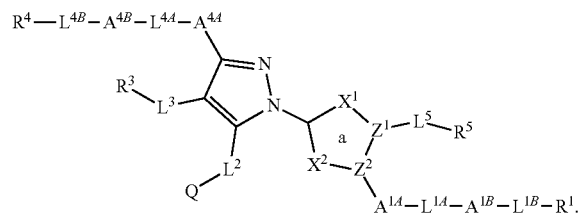

(Ic)

In certain embodiments, $X^1$ is selected from one of the following groups (1a)-(1i)

(1a) $X^1$ is selected from the group consisting of CR$^{XA}$, S, O, N and NR$^{XB}$;

(1b) $X^1$ is selected from the group consisting of S, O, N and NR$^{XB}$;

(1c) $X^1$ is O;

(1d) $X^1$ is S;

(1e) $X^1$ is N or NR$^{XB}$;

(1f) $X^1$ is N or NR$^{XB}$, wherein NR$^{XB}$ is hydrogen or optionally substituted C$_1$-C$_4$ alkyl;

(1g) $X^1$ is N;

(1h) $X^1$ is CR$^{XA}$;

(1i) $X^1$ is CR$^{XA}$, wherein R$^{XA}$ is hydrogen or optionally substituted C$_1$-C$_4$ alkyl;

In certain embodiments, each optionally substituted alkyl, alkenyl and alkynyl of $X^1$ (including those of R$^{XA}$ and R$^{XB}$) is unsubstituted or fluorinated. For example, in certain such embodiments each optionally substituted alkyl, alkenyl and alkynyl of $X^1$ (including those of $R^{XA}$ and $R^{XB}$) is unsubstituted. In certain embodiments each $RX^A$ and $RX^B$ is hydrogen.

In certain embodiments, $X^2$ is selected from one of the following groups (2a)-(2i)

(2a) $X^2$ is selected from the group consisting of $CR^{XA}$, S, O, N and $NR^{XB}$;

(2b) $X^2$ is selected from the group consisting of S, O, N and $NR^{XB}$;

(2c) $X^2$ is O;

(2d) $X^2$ is S;

(2e) $X^2$ is selected from N and $NR^{XB}$;

(2f) $X^2$ is selected from N and $NR^{XB}$, wherein $NR^{XB}$ is hydrogen or optionally substituted $C_1$-$C_4$ alkyl;

(2g) $X^2$ is N;

(2h) $X^2$ is $CR^{XA}$;

(2i) $X^2$ is $CR^{XA}$, wherein $R^{XA}$ is hydrogen or optionally substituted $C_1$-$C_4$ alkyl.

In certain such embodiments, each optionally substituted alkyl, alkenyl and alkynyl of $X^2$ (including those of $R^{XA}$ and $R^{XB}$) is unsubstituted or fluorinated. For example, in certain such embodiments each optionally substituted alkyl, alkenyl and alkynyl of $X^2$ (including those of $R^{XA}$ and $R^{XB}$) is unsubstituted. In certain embodiments each $RX^A$ and $RX^B$ is hydrogen.

In certain embodiments, $Z^1$ is selected from one of the following groups (3a)-(3c)

(3a) $Z^1$ is selected from C and N;

(3b) $Z^1$ is C;

(3c) $Z^1$ is N.

In certain embodiments, $Z^2$ is selected from one of the following groups (4a)-(4c)

(4a) $Z^2$ is selected from C and N;

(4b) $Z^2$ is C;

(4c) $Z^2$ is N.

In certain embodiments, the ring system denoted by "a" is one of the following groups (5a)-(5i):

(5a) the ring system denoted by "a" is heteroaromatic (i.e., at least one of $X^1$, $X^2$, $Z^1$ and $Z^2$ is not C or $CR^{XA}$);

(5b) the ring system denoted by "a" is saturated or partially unsaturated heterocyclic (e.g., in which each $R^Z$ is hydrogen);

(5c) the ring system denoted by "a" is thiazole;

(5d) the ring system denoted by "a" is thiazole and the compound is of formula (Id):

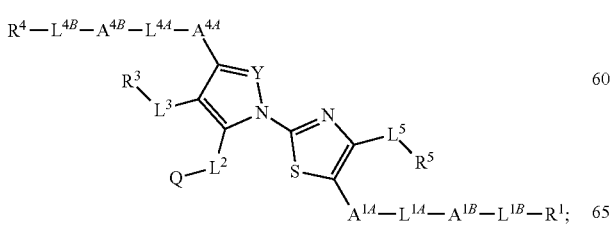

(Id)

(5e) the ring system denoted by "a" is thiazole, and the compound is of formula (Ie):

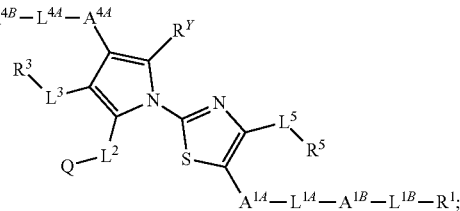

(Ie)

(5f) the ring system denoted by "a" is thiazole, and the compound is of formula (If):

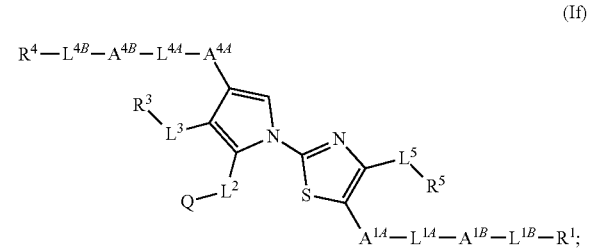

(If)

(5g) the ring system denoted by "a" is thiazole, and the compound is of formula (Ig):

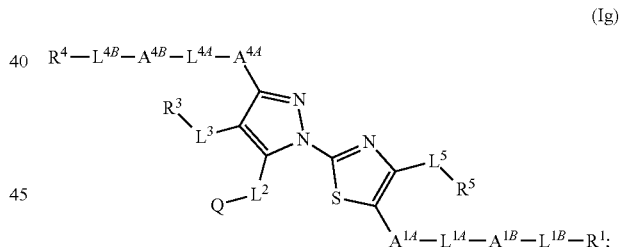

(Ig)

(5h) the ring system denoted by "a" is oxazole, imidazole, pyrazole, or triazole, e.g., having one of the following the structural formula:

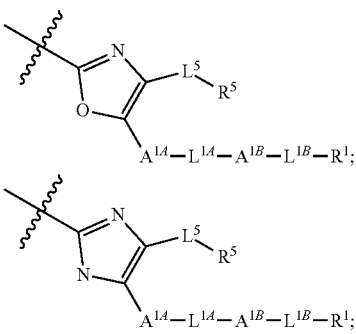

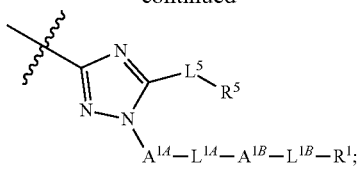

or (5i) the compound is of any of formulae (Ia)-(Ic), in which the ring system denoted by "a" is thiazole and the thiazole moiety has the structural formula:

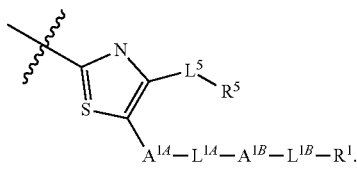

In certain embodiments according to embodiments (5a) and (5b), each $R^{XA}$ and $R^{XB}$ is hydrogen.

In certain embodiments, $R^1$ is selected from one of the following groups (6a)-(6q)

(6a) $R^1$ is selected from the group consisting of hydrogen, optionally substituted $C_1$-$C_8$ alkyl, optionally substituted $C_1$-$C_8$ alkenyl, optionally substituted $C_1$-$C_8$ alkynyl, cycloalkyl and heterocycloalkyl, wherein cycloalkyl and heterocycloalkyl are optionally substituted with 1-5 $R^{1E}$;

(6b) $R^1$ is selected from the group consisting of hydrogen, optionally substituted $C_1$-$C_8$ alkyl, optionally substituted $C_1$-$C_8$ alkenyl and optionally substituted $C_1$-$C_8$ alkynyl;

(6c) $R^1$ is selected from the group consisting of hydrogen, unsubstituted $C_1$-$C_8$ alkyl, unsubstituted $C_1$-$C_8$ alkenyl and unsubstituted $C_1$-$C_8$ alkynyl (for example, methyl, ethyl, propyl, butenyl, or butyl);

(6d) $R^1$ is cycloalkyl or heterocycloalkyl (e.g., cyclobutyl, cyclopentyl, cyclohexyl or cycloheptyl), each optionally substituted with 1-5 $R^{1E}$, for example, 1-5 alkyl groups;

(6e) $R^1$ is cycloalkyl optionally substituted with 1-5 $R^{1E}$;

(6f) $R^1$ is hydrogen, optionally substituted $C_1$-$C_8$ alkyl, or cycloalkyl optionally substituted with 1-5 $R^{1E}$;

(6g) $R^1$ is hydrogen or optionally substituted $C_1$-$C_6$ alkyl (e.g., ethyl, propyl, or butyl).

In certain such embodiments, each optionally substituted alkyl, alkenyl and alkynyl of $R^1$ (including those of $R^{1E}$) is unsubstituted or fluorinated. For example, in certain such embodiments each optionally substituted alkyl, alkenyl and alkynyl of $R^1$ (including those of $R^{1E}$) is unsubstituted.

In certain embodiments, $A^{1A}$ is selected from one of the following groups (7a)-(7d)

(7a) $A^{1A}$ is selected from the group consisting of a bond, —C(O)—, —S—, —S(O)$_{1-2}$—, —O—, —C(O)NR$^6$—, —NR$^6$C(O)—, —OC(O)— and —C(O)O—;

(7b) $A^{1A}$ is a bond;

(7c) $A^{1A}$ is selected from the group consisting of —C(O)—, —S—, —S(O)$_{1-2}$—, —O—, and —NR$^6$—;

(7d) $A^{1A}$ is O.

In certain such embodiments, each optionally substituted alkyl, alkenyl and alkynyl of $A^{1A}$ (including those of $R^6$) is unsubstituted or fluorinated. For example, in certain such embodiments each optionally substituted alkyl, alkenyl and alkynyl of $A^{1A}$ (including those of $R^6$) is unsubstituted.

In certain embodiments, $L^{1B}$ is selected from one of the following groups (8a)-(8c)

(8a) $L^{1B}$ is selected from a bond and optionally substituted $C_1$-$C_4$ alkylene;

(8b) $L^{1B}$ is a bond;

(8c) $L^{1B}$ is optionally substituted $C_1$-$C_4$ alkylene.

In certain such embodiments, each optionally substituted alkylene of $L^{1B}$ is unsubstituted or fluorinated. For example, in certain such embodiments each optionally substituted alkylene of $L^{1B}$ is unsubstituted.

In certain embodiments, $A^{1B}$ is selected from one of the following groups (9a)-(9f)

(9a) $A^{1B}$ is selected from the group consisting of —C(O)—, —S—, —S(O)$_{1-2}$—, —O—, —C(O)NR$^6$—, —NR$^6$C(O)—, —OC(O)— and —C(O)O—;

(9b) $A^{1B}$ is selected from the group consisting of —C(O)—, —S—, —S(O)$_{1-2}$—, —O—, and —C(O)O—;

(9c) $A^{1B}$ is —S—;

(9d) $A^{1B}$ is selected from —O(O)—, —S(O)—, —S(O)$_2$—, —OC(O)— and —C(O)O—;

(9e) $A^{1B}$ is —O—;

(9f) $A^{1B}$ is a bond.

In certain such embodiments, each optionally substituted alkyl, alkenyl and alkynyl of $A^{1B}$ (including those of $R^6$) is unsubstituted or fluorinated. For example, in certain such embodiments each optionally substituted alkyl, alkenyl and alkynyl of $A^{1B}$ (including those of $R^6$) is unsubstituted.

In certain embodiments, $L^{1A}$ is selected from one of the following groups (10a)-(10c)

(10a) $L^{1A}$ is selected from a bond and optionally substituted $C_1$-$C_4$ alkylene;

(10b) $L^{1A}$ is a bond;

(10c) $L^{1A}$ is optionally substituted $C_1$-$C_4$ alkylene.

In certain such embodiments, each optionally substituted alkylene of $L^{1A}$ is unsubstituted or fluorinated. For example, in certain such embodiments each optionally substituted alkylene of $L^{1A}$ is unsubstituted.

In certain embodiments, $A^{1A}$-$L^{1A}$-$A^{1B}$-$L^{1B}$ (together, $L^1$) is selected from one of the following groups (10d)-(10j)

(10d) $A^{1A}$-$L^{1A}$-$A^{1B}$-$L^{1B}$ is selected from a bond, optionally substituted $C_1$-$C_4$ alkylene, —C(O)—, —S—, —S(O)$_{1-2}$—, —O—, and —NR$^6$—;

(10e) $A^{1A}$-$L^{1A}$-$A^{1B}$-$L^{1B}$ is selected from a bond, —CH$_2$—, —CH(CH$_3$)—, —CH$_2$CH$_2$—, —C(O)—, —S—, —S(O)$_{1-2}$—, —O—, and —NR$^6$—;

(10f) $A^{1A}$-$L^{1A}$-$A^{1B}$-$L^{1B}$ is a bond.

(10g) $A^{1A}$-$L^{1A}$-$A^{1B}$-$L^{1B}$ is selected from —S—, —O—, —S(O)$_{1-2}$— and —NR$^6$—;

(10h) $A^{1A}$-$L^{1A}$-$A^{1B}$-$L^{1B}$ is selected from a bond, —S—, —S(O)— and —S(O)$_2$—;

(10i) $A^{1A}$-$L^{1A}$-$A^{1B}$-$L^{1B}$ is —O—;

(10j) $A^{1A}$-$L^{1A}$-$A^{1B}$-$L^{1B}$ is optionally substituted $C_1$-$C_4$ alkylene.

In certain such embodiments, each optionally substituted alkyl, alkylene, alkenyl, alkenylene, alkynyl and alkynylene of $A^{1A}$-$L^{1A}$-$A^{1B}$-$L^{1B}$ (including those of $R^6$) is unsubstituted or fluorinated. For example, in certain such embodiments each optionally substituted alkyl, alkylene, alkenyl, alkenylene, alkynyl and alkynylene of $A^{1A}$-$L^{1A}$-$A^{1B}$-$L^{1B}$ (including those of $R^6$) is unsubstituted.

In certain embodiments, $L^2$ is selected from one of the following groups (11a)-(11d)

(11a) $L^2$ is selected from a bond and optionally substituted $C_1$-$C_4$ alkylene;
(11b) $L^2$ is selected from a unsubstituted $C_1$-$C_4$ alkylene;
(11c) $L^2$ is —$CH_2$—, —$CH(CH_3)$— or —$CH_2CH_2$—;
(11d) $L^2$ is a bond.

In certain such embodiments, each optionally substituted alkylene of $L^2$ is unsubstituted or fluorinated. For example, in certain such embodiments each optionally substituted alkylene of $L^2$ is unsubstituted.

In certain embodiments, Q is selected from one of the following groups (12a)-(12j)

(12a) Q is selected from the group consisting of —$CH_2OH$, —$C(O)OH$, —$C(O)OR^{2A}$, —$C(O)NR^{2B}R^{2A}$, —$C(O)NR^{2B}S(O)_2R^{2A}$, —$C(O)NR^{2B}S(O)_2NR^{2B}R^{2A}$, —$C(O)R^{2A}$, —$S(O)_2OH$, —$P(O)(OH)_2$, —$C(OH)(CF_3)_2$, —$S(O)_2R^{2A}$, —$N(R^{2B})S(O)_2R^{2A}$, —$S(O)_2NR^{2B}R^{2A}$, —$C(O)NH$—$O(C_1$-$C_3$ alkyl), —$C(O)NHOH$, —$CO(NH)CN$,

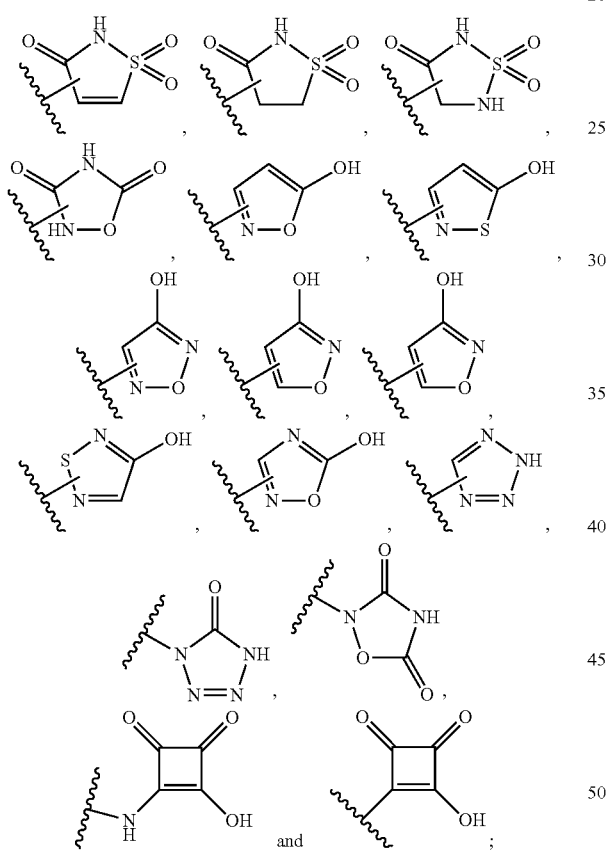

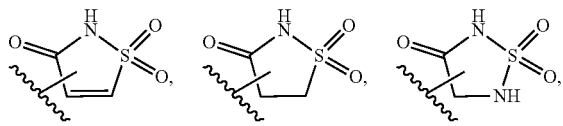

(12b) Q is selected from the group consisting of —$C(O)OH$, —$C(O)OR^{2A}$, —$C(O)NR^{2B}R^{2A}$, —$C(O)NR^{2B}S(O)_2R^{2A}$, —$C(O)NR^{2B}S(O)_2NR^{2B}R^{2A}$, —$C(O)R^{2A}$, —$S(O)_2OH$, —$P(O)(OH)_2$, —$C(OH)(CF_3)_2$, —$S(O)_2R^{2A}$, —$S(O)_2NR^{2B}R^{2A}$, —$C(O)NHOH$, —$CO(NH)CN$,

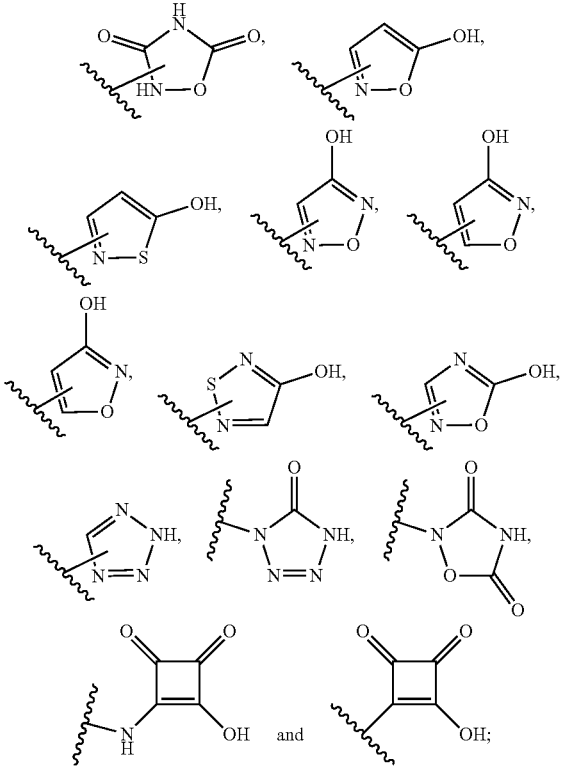

(12c) Q is selected from the group consisting of —$CH_2OH$, —$C(O)OH$, —$C(O)OR^{2A}$, —$C(O)NR^{2B}R^{2A}$, —$C(O)R^{2A}$, —$S(O)_2OH$, —$P(O)(OH)_2$, —$S(O)_2R^{2A}$, —$S(O)_2NR^{2B}R^{2A}$, and —$C(O)NHOH$;

(12d) Q is selected from —$C(O)OH$, —$C(O)OR^{2A}$, and —$C(O)NR^{2B}R^{2A}$ (e.g., —$C(O)OH$);

(12e) Q is selected from —$C(O)OH$ and —$C(O)O(C_1$-$C_3$ alkyl);

(12f) Q is —$C(O)OH$;

(12g) Q is —$C(O)O(C_1$-$C_3$ alkyl);

(12h) Q is —$C(O)NR^{2B}R^{2A}$, in which $R^{2A}$ is $C_1$-$C_3$ alkyl, $C_1$-$C_3$ hydroxyalkyl, $C_1$-$C_3$ aminoalkyl or $C_1$-$C_3$ thioalkyl and $R^{2B}$ is H or $C_1$-$C_3$ alkyl;

(12i) Q is —$C(O)NR^{2B}R^{2A}$, in which $R^{2A}$ and $R^{2B}$ come together with a nitrogen to which they are both directly bound to form a heterocycloalkyl optionally substituted with 1-3 substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —$C(O)$ $C_1$-$C_3$ alkyl;

(12j) Q is —$C(O)NR^{2B}R^{2A}$, in which $R^{2A}$ is —$S(O)_{1-2}$ ($C_1$-$C_3$ alkyl), —$S(O)_{1-2}$($C_1$-$C_3$ fluoroalkyl), or heteroaryl optionally substituted with 1-2 groups selected from substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —$C(O)$ $C_1$-$C_3$ alkyl and $R^{2B}$ is H or $C_1$-$C_3$ alkyl.

In certain embodiments, $L^3$ is selected from one of the following groups (13a)-(13i)

(13a) $L^3$ is selected from a bond (i.e., $L^3$ is -$L^{3A}$-$A^{3A}$- wherein both $A^{3A}$ and $L^{3A}$ are a bond, or $L^3$ is -$A^{3B}$-$L^{3B}$- wherein both $A^{3B}$ and $L^{3B}$ are a bond) and optionally substituted $C_1$-$C_4$ alkylene (e.g., $L^3$ is -$L^{3A}$-$A^{3A}$- wherein $A^{3A}$ is a bond and $L^{3A}$ is and optionally substituted $C_1$-$C_4$ alkylene);

(13b) $L^3$ is a bond (e.g., both $A^{3A}$ and $L^{3A}$ are a bond);
(13c) $L^3$ is optionally substituted $C_1$-$C_4$ alkylene (e.g., $A^{3A}$ is a bond and $L^{3A}$ is and optionally substituted $C_1$-$C_4$ alkylene);
(13d) $L^3$ is optionally substituted $C_1$-$C_4$ alkylene, optionally substituted $C_1$-$C_4$ alkenylene or optionally substituted $C_1$-$C_4$ alkynylene;
(13e) $L^3$ is unsubstituted $C_1$-$C_4$ alkylene;
(13f) $L^3$ is $C_1$-$C_3$ alkylene, optionally substituted with a hydroxyl;
(13g) $L^3$ is —C(O)—, —S—, —S(O)$_{1\text{-}2}$—, —O— or —NR$^6$—;
(13h) $L^3$ is —CH(CH$_3$)(OH)— or —CH(OH)—;
(13i) $L^3$ is selected from a bond, —CH$_2$—, —CH(CH$_3$)—, and —CH$_2$CH$_2$—.

In certain such embodiments, each optionally substituted alkyl, alkylene, alkenyl, alkenylene, alkynyl and alkynylene of $L^3$ (including those of $R^6$) is unsubstituted or fluorinated. For example, in certain such embodiments each optionally substituted alkyl, alkylene, alkenyl, alkenylene, alkynyl and alkynylene of $L^3$ (including those of $R^6$) is unsubstituted.

In certain embodiments, $R^3$ is selected from one of the following groups (14a)-(14k)

(14a) $R^3$ is aryl or heteroaryl each (i) optionally substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$;
(14b) $R^3$ is aryl (e.g., a phenyl, a benzodioxole, or a dihydro-1H-isoquinoline) optionally substituted with 1-5 R$^{3E}$;
(14c) $R^3$ is aryl (e.g., a phenyl, a benzodioxole, or a dihydro-1H-isoquinoline) (i) substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$;
(14d) $R^3$ is aryl (e.g., a phenyl, a benzodioxole, or a dihydro-1H-isoquinoline) (i) substituted with a single substituent selected from -L$^{3C}$-(phenyl optionally substituted with 1-5 R$^{3D}$), -L$^{3C}$-(monocyclic heteroaryl optionally substituted with 1-5 R$^{3D}$), -L$^{3C}$-(monocyclic cycloalkyl optionally substituted with 1-5 R$^{3E}$), -L$^{3C}$-(monocyclic heterocycloalkyl optionally substituted with 1-5 R$^{3E}$) and (ii) optionally substituted with 1-5 R$^{3E}$;
(14e) $R^3$ is as defined in (14a)-(14d), wherein the aryl is not substituted with any R$^{3E}$;
(14f) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) optionally substituted with 1-5 R$^{3E}$;
(14g) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$;
(14h) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -L$^{3C}$-(phenyl optionally substituted with 1-5 R$^{3D}$), -L$^{3C}$-(monocyclic heteroaryl optionally substituted with 1-5 R$^{3D}$), -L$^{3C}$-(monocyclic cycloalkyl optionally substituted with 1-5 R$^{3E}$), -L$^{3C}$-(monocyclic heterocycloalkyl optionally substituted with 1-5 R$^{3E}$) and (ii) optionally substituted with 1-5 R$^{3E}$;
(14i) $R^3$ is as defined in (14f)-(14h), wherein the heteroaryl is not substituted with any R$^{3E}$;
(14j) $R^3$ is selected from the group consisting of: phenyl, benzodioxolyl, dihydro-1H-isoquinolinyl, imidazolyl, oxazolyl, isoxazolyl, isothiazolyl, thiazolyl, pyridinyl, and pyrazinyl, pyridonyl, thiadiazolyl, pyrazolopyrimidinyl, pyrazolopyridinyl, benzofuranyl, indolyl, imidazopyridinyl, pyrazolyl, triazolopyridinyl, benzimidazolyl, a benzimidazolyl, a thienyl, a benzothienyl, a furanyl and pyrimidinyl, each (i) optionally substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$;
(14k) $R^3$ is selected from the group consisting of phenyl and monocyclic heteroaryl (e.g., pyridyl, pyrazolyl), optionally substituted with 1-5 R$^{3E}$.

In certain such embodiments, each optionally substituted alkyl, alkenyl and alkynyl of $R^3$ (including those of R$^{3D}$ and R$^{3E}$) is unsubstituted or fluorinated. For example, in certain such embodiments each optionally substituted alkyl, alkenyl and alkynyl of $R^3$ (including those of R$^{3D}$ and R$^{3E}$) is unsubstituted.

In certain embodiments, $R^4$ is selected from one of the following groups (15a)-(15k)

(15a) $R^4$ is selected from the group consisting of hydrogen, optionally substituted $C_1$-$C_8$ alkyl, optionally-substituted $C_1$-$C_8$ alkenyl and optionally substituted $C_1$-$C_8$ alkynyl;
(15b) $R^4$ is selected from the group consisting of hydrogen, unsubstituted $C_1$-$C_8$ alkyl, unsubstituted $C_1$-$C_8$ alkenyl and unsubstituted $C_1$-$C_8$ alkynyl;
(15c) $R^4$ is selected from the group consisting of hydrogen, optionally substituted $C_1$-$C_6$ alkyl, optionally-substituted $C_1$-$C_6$ alkenyl and optionally substituted $C_1$-$C_6$ alkynyl;
(15d) $R^4$ is selected from the group consisting of hydrogen, unsubstituted $C_1$-$C_6$ alkyl, unsubstituted $C_1$-$C_6$ alkenyl and unsubstituted $C_1$-$C_6$ alkynyl.
(15e) $R^4$ is hydrogen or optionally substituted $C_1$-$C_6$ alkyl;
(15f) $R^4$ is hydrogen or unsubstituted $C_1$-$C_6$ alkyl;
(15g) $R^4$ is hydrogen or optionally substituted $C_1$-$C_3$ alkyl;
(15h) $R^4$ is hydrogen or unsubstituted $C_1$-$C_3$ alkyl;
(15i) $R^4$ is optionally substituted $C_1$-$C_3$ alkyl;
(15j) $R^4$ is unsubstituted $C_1$-$C_3$ alkyl;
(15k) $R^4$ is methyl.

In certain embodiments, $A^{4A}$ is selected from one of the following groups (16a)-(16d)
- (16a) $A^{4A}$ is selected from the group consisting of a bond, —C(O)—, —S—, —S(O)$_{1-2}$—, —O—, —NR$^6$—, —C(O)NR$^6$—, —NR$^6$C(O)—, —OC(O)— and —C(O)O—;
- (16b) $A^{4A}$ is a bond;
- (16c) $A^{4A}$ is selected from the group consisting of —C(O)—, —S—, —S(O)$_{1-2}$—, —O— and —NR$^6$—;
- (16d) $A^{4A}$ is —O—.

In certain such embodiments, each optionally substituted alkyl, alkenyl and alkynyl of $A^{4A}$ (including those of R$^6$) is unsubstituted or fluorinated. For example, in certain such embodiments each optionally substituted alkyl, alkenyl and alkynyl of $A^{4A}$ (including those of R$^6$) is unsubstituted.

In certain embodiments, $L^{4B}$ is selected from one of the following groups (17a)-(17c)
- (17a) $L^{4B}$ is selected from a bond and optionally substituted $C_1$-$C_4$ alkylene;
- (17b) $L^{4B}$ is a bond
- (17c) $L^{4B}$ is optionally substituted $C_1$-$C_4$ alkylene.

In certain such embodiments, each optionally substituted alkylene of $L^{4B}$ is unsubstituted or fluorinated. For example, in certain such embodiments each optionally substituted alkylene of $L^{4B}$ is unsubstituted.

In certain embodiments, $A^{4B}$ is selected from one of the following groups (18a)-(18g)
- (18a) $A^{4B}$ is selected from the group consisting of a bond, —C(O)—, —S—, —S(O)$_{1-2}$—, —O—, —NR$^6$—, —C(O)NR$^6$—, —NR$^6$C(O)—, —OC(O)— and —C(O)O—;
- (18b) $A^{4B}$ is selected from the group consisting of —C(O)—, —S—, —S(O)$_{1-2}$—, —O—, —NR$^6$—, —C(O)NR$^6$—, —NR$^6$C(O)—, —OC(O)— and —C(O)O—;
- (18c) $A^{4B}$ is selected from the group consisting of —C(O)—, —S—, —S(O)$_{1-2}$—, —O—, and —C(O)O—;
- (18d) $A^{4B}$ is selected from —NR$^6$—, —C(O)NR$^6$— and —NR$^6$C(O)—;
- (18e) $A^{4B}$ is selected from —C(O)—, —OC(O)—, and —C(O)O—;
- (18f) $A^{4B}$ is a bond;
- (18g) $A^{4B}$ is —O—.

In certain such embodiments, each optionally substituted alkyl, alkenyl and alkynyl of $A^{4B}$ (including those of R$^6$) is unsubstituted or fluorinated. For example, in certain such embodiments each optionally substituted alkyl, alkenyl and alkynyl of $A^{4B}$ (including those of R$^6$) is unsubstituted.

In certain embodiments, $L^{4A}$ is selected from one of the following groups (19a)-(19c)
- (19a) $L^{4A}$ is selected from a bond and optionally substituted $C_1$-$C_4$ alkylene;
- (19b) $L^{4A}$ is a bond;
- (19c) $L^{4A}$ is optionally substituted $C_1$-$C_4$ alkylene.

In certain such embodiments, each optionally substituted alkylene of $L^{4A}$ is unsubstituted or fluorinated. For example, in certain such embodiments each optionally substituted alkylene of $L^{4A}$ is unsubstituted.

In certain embodiments, $L^{4B}$-$A^{4B}$-$L^{4A}$-$A^{4A}$ (together, L$^4$) is selected from one of the following groups (19d)-(19j)
- (19d) $L^{4B}$-$A^{4B}$-$L^{4A}$-$A^{4A}$ is selected from a bond, optionally substituted $C_1$-$C_4$ alkylene, —C(O)—, —S—, —S(O)$_{1-2}$—, —O—, and —NR$^6$—;
- (19e) $L^{4B}$-$A^{4B}$-$L^{4A}$-$A^{4A}$ is selected from a bond, —CH$_2$—, —CH(CH$_3$)—, —CH$_2$CH$_2$—, —C(O)—, —S—, —S(O)$_{1-2}$—, —O—, and —NR$^6$— (e.g., a bond);
- (19f) $L^{4B}$-$A^{4B}$-$L^{4A}$-$A^{4A}$ is a bond.
- (19g) $L^{4B}$-$A^{4B}$-$L^{4A}$-$A^{4A}$ is selected from —S(O)$_{1-2}$— and —NR$^6$—;
- (19h) $L^{4B}$-$A^{4B}$-$L^{4A}$-$A^{4A}$ is —S—;
- (19i) $L^{4B}$-$A^{4B}$-$L^{4A}$-$A^{4A}$ is —O—;
- (19j) $L^{4B}$-$A^{4B}$-$L^{4A}$-$A^{4A}$ is optionally substituted $C_1$-$C_4$ alkylene.

In certain such embodiments, each optionally substituted alkyl, alkylene, alkenyl, alkenylene, alkynyl and alkynylene of $L^{4B}$-$A^{4B}$-$L^{4A}$-$A^{4A}$ (including those of R$^6$) is unsubstituted or fluorinated. For example, in certain such embodiments each optionally substituted alkyl, alkylene, alkenyl, alkenylene, alkynyl and alkynylene of $L^{4B}$-$A^{4B}$-$L^{4A}$-$A^{4A}$ (including those of R$^6$) is unsubstituted.

In certain embodiments, L$^5$ is selected from one of the following groups (20a)-(20f)
- (20a) L$^5$ is selected from a bond (i.e., L$^5$ is -L$^{5A}$-A$^{5A}$- wherein both A$^{5A}$ and L$^{5A}$ are a bond, or L$^5$ is -A$^{5B}$-L$^{5B}$- wherein both A$^{5B}$ and L$^{5B}$ are a bond) and optionally substituted $C_1$-$C_4$ alkylene (e.g., L$^5$ is -L$^{5A}$-A$^{5A}$- wherein A$^{5A}$ is a bond and L$^{5A}$ is and optionally substituted $C_1$-$C_4$ alkylene);
- (20b) L$^5$ is a bond (e.g., both A$^{5A}$ and L$^{5A}$ are a bond);
- (20c) L$^5$ is selected from the group consisting of —C(O)—, —S—, —S(O)$_{1-2}$—, —O— and —NR$^6$—;
- (20d) L$^5$ is selected from the group consisting of a bond, —CH$_2$—, —CH(CH$_3$)—, —CH$_2$CH$_2$—, —CH=CH—, —C≡C—, —C(O)—, —S—, —S(O)$_{1-2}$—, —O—, and —C(O)O— (e.g., a bond);
- (20e) L$^5$ is selected from —S— and —O—;
- (20f) L$^5$ is selected from —C(O)—, —S(O)$_{1-2}$— and —C(O)O—.

In certain such embodiments, each optionally substituted alkyl, alkylene, alkenyl, alkenylene, alkynyl and alkynylene of L$^5$ (including those of R$^6$) is unsubstituted or fluorinated. For example, in certain such embodiments each optionally substituted alkyl, alkylene, alkenyl, alkenylene, alkynyl and alkynylene of L$^5$ (including those of R$^6$) is unsubstituted.

In certain embodiments, R$^5$ is selected from one of the following groups (21a)-(21i)
- (21a) R$^5$ is aryl (e.g., phenyl) (i) optionally substituted with a single substituent selected from -L$^{5C}$-(aryl optionally substituted with 1-5 R$^{5D}$), -L$^{5C}$-(heteroaryl optionally substituted with 1-5 R$^{5D}$), -L$^{5C}$-(cycloalkyl optionally substituted with 1-5 R$^{5E}$), -L$^{5C}$-(heterocycloalkyl optionally substituted with 1-5 R$^{5E}$) and (ii) optionally substituted with 1-5 R$^{5E}$;
- (21b) R$^5$ is aryl (e.g., phenyl) optionally substituted with 1-5 R$^{5E}$;
- (21c) R$^5$ is phenyl, optionally substituted with 1-5 R$^{5E}$, wherein each R$^{5E}$ is independently selected from optionally-substituted $C_1$-$C_4$ alkyl, $C_1$-$C_4$ fluoroalkyl, halogen, —OR$^{5F}$, and —NR$^{5G}$R$^{5F}$;
- (21d) R$^5$ is heteroaryl (e.g., an isoxazolyl, a pyridyl, an imidazopyridyl, a pyrazolyl, a benzoxazole, an indolyl, a pyrimidinyl) (i) optionally substituted with a single substituent selected from -L$^{5C}$-(aryl optionally substituted with 1-5 R$^{5D}$), -L$^{5C}$-(heteroaryl optionally substituted with 1-5 R$^{5D}$), -L$^{5C}$-(cycloalkyl optionally substituted with 1-5 R$^{5E}$), -L$^{5C}$-(heterocycloalkyl optionally substituted with 1-5 R$^{5E}$) and (ii) optionally substituted with 1-5 R$^{5E}$;

(21e) $R^5$ is heteroaryl (e.g., an isoxazolyl, a pyridyl, an imidazopyridyl, a pyrazolyl, a benzoxazole, an indolyl, a pyrimidinyl) optionally substituted with 1-5 $R^{5E}$;

(21f) $R^5$ is selected from the group consisting of phenyl, isoxazolyl, pyridyl, imidazopyridyl, pyrazolyl, benzoxazolyl, indolyl, and pyrimidinyl each (i) optionally substituted with a single substituent selected from -$L^{5C}$-(aryl optionally substituted with 1-5 $R^{5D}$), -$L^{5C}$-(heteroaryl optionally substituted with 1-5 $R^{5D}$), -$L^{5C}$-(cycloalkyl optionally substituted with 1-5 $R^{5E}$), -$L^{5C}$-(heterocycloalkyl optionally substituted with 1-5 $R^{5E}$) and (ii) optionally substituted with 1-5 $R^{5E}$;

(21g) $R^5$ is selected from the group consisting of phenyl, isoxazolyl, pyridyl, imidazopyridyl, pyrazolyl, benzoxazolyl, indolyl, and pyrimidinyl each optionally substituted with 1-5 $R^{5E}$.

In certain such embodiments, each optionally substituted alkyl, alkenyl and alkynyl of $R^5$ (including those of $R^{5D}$ and $R^{5E}$) is unsubstituted or fluorinated. For example, in certain such embodiments each optionally substituted alkyl, alkenyl and alkynyl of $R^5$ (including those of $R^{5D}$ and $R^{5E}$) is unsubstituted.

Various particular embodiments nos. 1-140 of this aspect of the disclosure include compounds of any one of the formulae (I) and (Ia)-(Ig), each as defined in each of the following rows (or a pharmaceutically acceptable salt or N-oxide thereof, or a solvate or hydrate thereof), wherein each entry is a group number as defined above (e.g., (11d) refers to $L^2$ being a bond), and a dash "-" indicates that the variable is as defined as described above with respect to formula (I) or defined according to any one of the applicable variable definitions (e.g., formulae (Ia)-(Ig), (5a)-(5i), (6a)-(6g), (11a)-(11d), etc. [e.g., when $R^1$ is a dash, it can be either as defined as described above with respect to formula (I) or any one of applicable definitions (6a)-(6h)]:

|  | (I) | "a" | $L^{1\dagger}$ | $R^1$ | $L^2$ | Q | $L^3$ | $R^3$ | $L^{4\dagger\dagger}$ | $R^4$ | $L^5$ | $R^5$ |
|---|---|---|---|---|---|---|---|---|---|---|---|---|
| 1 | (I) | (5a) | (10e) | (6a) | (11d) | (12b) | (13i) | (14b) | (19e) | (15j) | (20b) | (21c) |
| 2 | (I) | (5a) | (10e) | (6a) | (11d) | (12b) | (13i) | (14b) | (19e) | (15j) | (20b) | (21d) |
| 3 | (I) | (5a) | (10e) | (6a) | (11d) | (12b) | (13i) | (14j) | (19e) | (15j) | (20b) | (21c) |
| 4 | (I) | (5a) | (10e) | (6a) | (11d) | (12b) | (13i) | (14j) | (19e) | (15j) | (20b) | (21d) |
| 5 | (I) | (5a) | (10e) | (6a) | (11d) | (12d) | (13i) | (14b) | (19e) | (15j) | (20b) | (21c) |
| 6 | (I) | (5a) | (10e) | (6a) | (11d) | (12d) | (13i) | (14b) | (19e) | (15j) | (20b) | (21d) |
| 7 | (I) | (5a) | (10e) | (6a) | (11d) | (12d) | (13i) | (14j) | (19e) | (15j) | (20b) | (21c) |
| 8 | (I) | (5a) | (10e) | (6a) | (11d) | (12d) | (13i) | (14j) | (19e) | (15j) | (20b) | (21d) |
| 9 | (I) | (5a) | (10e) | (6g) | (11d) | (12b) | (13i) | (14b) | (19e) | (15j) | (20b) | (21c) |
| 10 | (I) | (5a) | (10e) | (6g) | (11d) | (12b) | (13i) | (14b) | (19e) | (15j) | (20b) | (21d) |
| 11 | (I) | (5a) | (10e) | (6g) | (11d) | (12b) | (13i) | (14j) | (19e) | (15j) | (20b) | (21c) |
| 12 | (I) | (5a) | (10e) | (6g) | (11d) | (12b) | (13i) | (14j) | (19e) | (15j) | (20b) | (21d) |
| 13 | (I) | (5a) | (10e) | (6g) | (11d) | (12d) | (13i) | (14b) | (19e) | (15j) | (20b) | (21c) |
| 14 | (I) | (5a) | (10e) | (6g) | (11d) | (12d) | (13i) | (14b) | (19e) | (15j) | (20b) | (21d) |
| 15 | (I) | (5a) | (10e) | (6g) | (11d) | (12d) | (13i) | (14j) | (19e) | (15j) | (20b) | (21c) |
| 16 | (I) | (5a) | (10e) | (6g) | (11d) | (12d) | (13i) | (14j) | (19e) | (15j) | (20b) | (21d) |
| 17 | (I) | (5a) | (10h) | (6a) | (11d) | (12b) | (13i) | (14b) | (19e) | (15j) | (20b) | (21c) |
| 18 | (I) | (5a) | (10h) | (6a) | (11d) | (12b) | (13i) | (14b) | (19e) | (15j) | (20b) | (21d) |
| 19 | (I) | (5a) | (10h) | (6a) | (11d) | (12b) | (13i) | (14j) | (19e) | (15j) | (20b) | (21c) |
| 20 | (I) | (5a) | (10h) | (6a) | (11d) | (12b) | (13i) | (14j) | (19e) | (15j) | (20b) | (21d) |
| 21 | (I) | (5a) | (10h) | (6a) | (11d) | (12d) | (13i) | (14b) | (19e) | (15j) | (20b) | (21c) |
| 22 | (I) | (5a) | (10h) | (6a) | (11d) | (12d) | (13i) | (14b) | (19e) | (15j) | (20b) | (21d) |
| 23 | (I) | (5a) | (10h) | (6a) | (11d) | (12d) | (13i) | (14j) | (19e) | (15j) | (20b) | (21c) |
| 24 | (I) | (5a) | (10h) | (6a) | (11d) | (12d) | (13i) | (14j) | (19e) | (15j) | (20b) | (21d) |
| 25 | (I) | (5a) | (10h) | (6g) | (11d) | (12b) | (13i) | (14b) | (19e) | (15j) | (20b) | (21c) |
| 26 | (I) | (5a) | (10h) | (6g) | (11d) | (12b) | (13i) | (14b) | (19e) | (15j) | (20b) | (21d) |
| 27 | (I) | (5a) | (10h) | (6g) | (11d) | (12b) | (13i) | (14j) | (19e) | (15j) | (20b) | (21c) |
| 28 | (I) | (5a) | (10h) | (6g) | (11d) | (12b) | (13i) | (14j) | (19e) | (15j) | (20b) | (21d) |
| 29 | (I) | (5a) | (10h) | (6g) | (11d) | (12d) | (13i) | (14b) | (19e) | (15j) | (20b) | (21c) |
| 30 | (I) | (5a) | (10h) | (6g) | (11d) | (12d) | (13i) | (14b) | (19e) | (15j) | (20b) | (21d) |
| 31 | (I) | (5a) | (10h) | (6g) | (11d) | (12d) | (13i) | (14j) | (19e) | (15j) | (20b) | (21c) |
| 32 | (I) | (5a) | (10h) | (6g) | (11d) | (12d) | (13i) | (14j) | (19e) | (15j) | (20b) | (21d) |
| 33 | (I) | (5i) | (10e) | (6a) | (11d) | (12b) | (13i) | (14b) | (19e) | (15j) | (20b) | (21c) |
| 34 | (I) | (5i) | (10e) | (6a) | (11d) | (12b) | (13i) | (14b) | (19e) | (15j) | (20b) | (21d) |
| 35 | (I) | (5i) | (10e) | (6a) | (11d) | (12b) | (13i) | (14j) | (19e) | (15j) | (20b) | (21c) |
| 36 | (I) | (5i) | (10e) | (6a) | (11d) | (12b) | (13i) | (14j) | (19e) | (15j) | (20b) | (21d) |
| 37 | (I) | (5i) | (10e) | (6a) | (11d) | (12d) | (13i) | (14b) | (19e) | (15j) | (20b) | (21c) |
| 38 | (I) | (5i) | (10e) | (6a) | (11d) | (12d) | (13i) | (14b) | (19e) | (15j) | (20b) | (21d) |
| 39 | (I) | (5i) | (10e) | (6a) | (11d) | (12d) | (13i) | (14j) | (19e) | (15j) | (20b) | (21c) |
| 40 | (I) | (5i) | (10e) | (6a) | (11d) | (12d) | (13i) | (14j) | (19e) | (15j) | (20b) | (21d) |
| 41 | (I) | (5i) | (10e) | (6g) | (11d) | (12b) | (13i) | (14b) | (19e) | (15j) | (20b) | (21c) |
| 42 | (I) | (5i) | (10e) | (6g) | (11d) | (12b) | (13i) | (14b) | (19e) | (15j) | (20b) | (21d) |
| 43 | (I) | (5i) | (10e) | (6g) | (11d) | (12b) | (13i) | (14j) | (19e) | (15j) | (20b) | (21c) |
| 44 | (I) | (5i) | (10e) | (6g) | (11d) | (12b) | (13i) | (14j) | (19e) | (15j) | (20b) | (21d) |
| 45 | (I) | (5i) | (10e) | (6g) | (11d) | (12d) | (13i) | (14b) | (19e) | (15j) | (20b) | (21c) |
| 46 | (I) | (5i) | (10e) | (6g) | (11d) | (12d) | (13i) | (14b) | (19e) | (15j) | (20b) | (21d) |
| 47 | (I) | (5i) | (10e) | (6g) | (11d) | (12d) | (13i) | (14j) | (19e) | (15j) | (20b) | (21c) |
| 48 | (I) | (5i) | (10e) | (6g) | (11d) | (12d) | (13i) | (14j) | (19e) | (15j) | (20b) | (21d) |
| 49 | (I) | (5i) | (10h) | (6a) | (11d) | (12b) | (13i) | (14b) | (19e) | (15j) | (20b) | (21c) |
| 50 | (I) | (5i) | (10h) | (6a) | (11d) | (12b) | (13i) | (14b) | (19e) | (15j) | (20b) | (21d) |
| 51 | (I) | (5i) | (10h) | (6a) | (11d) | (12b) | (13i) | (14j) | (19e) | (15j) | (20b) | (21c) |
| 52 | (I) | (5i) | (10h) | (6a) | (11d) | (12b) | (13i) | (14j) | (19e) | (15j) | (20b) | (21d) |
| 53 | (I) | (5i) | (10h) | (6a) | (11d) | (12d) | (13i) | (14b) | (19e) | (15j) | (20b) | (21c) |
| 54 | (I) | (5i) | (10h) | (6a) | (11d) | (12d) | (13i) | (14b) | (19e) | (15j) | (20b) | (21d) |
| 55 | (I) | (5i) | (10h) | (6a) | (11d) | (12d) | (13i) | (14j) | (19e) | (15j) | (20b) | (21c) |
| 56 | (I) | (5i) | (10h) | (6a) | (11d) | (12d) | (13i) | (14j) | (19e) | (15j) | (20b) | (21d) |

-continued

|     | (I)  | "a"  | L¹†   | R¹   | L²    | Q     | L³    | R³    | L⁴††  | R⁴    | L⁵    | R⁵    |
| --- | ---- | ---- | ----- | ---- | ----- | ----- | ----- | ----- | ----- | ----- | ----- | ----- |
| 57  | (I)  | (5i) | (10h) | (6g) | (11d) | (12b) | (13i) | (14b) | (19e) | (15j) | (20b) | (21c) |
| 58  | (I)  | (5i) | (10h) | (6g) | (11d) | (12b) | (13i) | (14b) | (19e) | (15j) | (20b) | (21d) |
| 59  | (I)  | (5i) | (10h) | (6g) | (11d) | (12b) | (13i) | (14j) | (19e) | (15j) | (20b) | (21c) |
| 60  | (I)  | (5i) | (10h) | (6g) | (11d) | (12b) | (13i) | (14j) | (19e) | (15j) | (20b) | (21d) |
| 61  | (I)  | (5i) | (10h) | (6g) | (11d) | (12d) | (13i) | (14b) | (19e) | (15j) | (20b) | (21c) |
| 62  | (I)  | (5i) | (10h) | (6g) | (11d) | (12d) | (13i) | (14b) | (19e) | (15j) | (20b) | (21d) |
| 63  | (I)  | (5i) | (10h) | (6g) | (11d) | (12d) | (13i) | (14j) | (19e) | (15j) | (20b) | (21c) |
| 64  | (I)  | (5i) | (10h) | (6g) | (11d) | (12d) | (13i) | (14j) | (19e) | (15j) | (20b) | (21d) |
| 65  | (Ic) | (5a) | (10e) | (6a) | (11d) | (12b) | (13i) | (14b) | (19e) | (15j) | (20b) | (21c) |
| 66  | (Ic) | (5a) | (10e) | (6a) | (11d) | (12b) | (13i) | (14b) | (19e) | (15j) | (20b) | (21d) |
| 67  | (Ic) | (5a) | (10e) | (6a) | (11d) | (12b) | (13i) | (14j) | (19e) | (15j) | (20b) | (21c) |
| 68  | (Ic) | (5a) | (10e) | (6a) | (11d) | (12b) | (13i) | (14j) | (19e) | (15j) | (20b) | (21d) |
| 69  | (Ic) | (5a) | (10e) | (6a) | (11d) | (12d) | (13i) | (14b) | (19e) | (15j) | (20b) | (21c) |
| 70  | (Ic) | (5a) | (10e) | (6a) | (11d) | (12d) | (13i) | (14b) | (19e) | (15j) | (20b) | (21d) |
| 71  | (Ic) | (5a) | (10e) | (6a) | (11d) | (12d) | (13i) | (14j) | (19e) | (15j) | (20b) | (21c) |
| 72  | (Ic) | (5a) | (10e) | (6a) | (11d) | (12d) | (13i) | (14j) | (19e) | (15j) | (20b) | (21d) |
| 73  | (Ic) | (5a) | (10e) | (6g) | (11d) | (12b) | (13i) | (14b) | (19e) | (15j) | (20b) | (21c) |
| 74  | (Ic) | (5a) | (10e) | (6g) | (11d) | (12b) | (13i) | (14b) | (19e) | (15j) | (20b) | (21d) |
| 75  | (Ic) | (5a) | (10e) | (6g) | (11d) | (12b) | (13i) | (14j) | (19e) | (15j) | (20b) | (21c) |
| 76  | (Ic) | (5a) | (10e) | (6g) | (11d) | (12b) | (13i) | (14j) | (19e) | (15j) | (20b) | (21d) |
| 77  | (Ic) | (5a) | (10e) | (6g) | (11d) | (12d) | (13i) | (14b) | (19e) | (15j) | (20b) | (21c) |
| 78  | (Ic) | (5a) | (10e) | (6g) | (11d) | (12d) | (13i) | (14b) | (19e) | (15j) | (20b) | (21d) |
| 79  | (Ic) | (5a) | (10e) | (6g) | (11d) | (12d) | (13i) | (14j) | (19e) | (15j) | (20b) | (21c) |
| 80  | (Ic) | (5a) | (10e) | (6g) | (11d) | (12d) | (13i) | (14j) | (19e) | (15j) | (20b) | (21d) |
| 81  | (Ic) | (5a) | (10h) | (6a) | (11d) | (12b) | (13i) | (14b) | (19e) | (15j) | (20b) | (21c) |
| 82  | (Ic) | (5a) | (10h) | (6a) | (11d) | (12b) | (13i) | (14b) | (19e) | (15j) | (20b) | (21d) |
| 83  | (Ic) | (5a) | (10h) | (6a) | (11d) | (12b) | (13i) | (14j) | (19e) | (15j) | (20b) | (21c) |
| 84  | (Ic) | (5a) | (10h) | (6a) | (11d) | (12b) | (13i) | (14j) | (19e) | (15j) | (20b) | (21d) |
| 85  | (Ic) | (5a) | (10h) | (6a) | (11d) | (12d) | (13i) | (14b) | (19e) | (15j) | (20b) | (21c) |
| 86  | (Ic) | (5a) | (10h) | (6a) | (11d) | (12d) | (13i) | (14b) | (19e) | (15j) | (20b) | (21d) |
| 87  | (Ic) | (5a) | (10h) | (6a) | (11d) | (12d) | (13i) | (14j) | (19e) | (15j) | (20b) | (21c) |
| 88  | (Ic) | (5a) | (10h) | (6a) | (11d) | (12d) | (13i) | (14j) | (19e) | (15j) | (20b) | (21d) |
| 89  | (Ic) | (5a) | (10h) | (6g) | (11d) | (12b) | (13i) | (14b) | (19e) | (15j) | (20b) | (21c) |
| 90  | (Ic) | (5a) | (10h) | (6g) | (11d) | (12b) | (13i) | (14b) | (19e) | (15j) | (20b) | (21d) |
| 91  | (Ic) | (5a) | (10h) | (6g) | (11d) | (12b) | (13i) | (14j) | (19e) | (15j) | (20b) | (21c) |
| 92  | (Ic) | (5a) | (10h) | (6g) | (11d) | (12b) | (13i) | (14j) | (19e) | (15j) | (20b) | (21d) |
| 93  | (Ic) | (5a) | (10h) | (6g) | (11d) | (12d) | (13i) | (14b) | (19e) | (15j) | (20b) | (21c) |
| 94  | (Ic) | (5a) | (10h) | (6g) | (11d) | (12d) | (13i) | (14b) | (19e) | (15j) | (20b) | (21d) |
| 95  | (Ic) | (5a) | (10h) | (6g) | (11d) | (12d) | (13i) | (14j) | (19e) | (15j) | (20b) | (21c) |
| 96  | (Ic) | (5a) | (10h) | (6g) | (11d) | (12d) | (13i) | (14j) | (19e) | (15j) | (20b) | (21d) |
| 97  | (Ic) | (5i) | (10e) | (6a) | (11d) | (12b) | (13i) | (14b) | (19e) | (15j) | (20b) | (21c) |
| 98  | (Ic) | (5i) | (10e) | (6a) | (11d) | (12b) | (13i) | (14b) | (19e) | (15j) | (20b) | (21d) |
| 99  | (Ic) | (5i) | (10e) | (6a) | (11d) | (12b) | (13i) | (14j) | (19e) | (15j) | (20b) | (21c) |
| 100 | (Ic) | (5i) | (10e) | (6a) | (11d) | (12b) | (13i) | (14j) | (19e) | (15j) | (20b) | (21d) |
| 101 | (Ic) | (5i) | (10e) | (6a) | (11d) | (12d) | (13i) | (14b) | (19e) | (15j) | (20b) | (21c) |
| 102 | (Ic) | (5i) | (10e) | (6a) | (11d) | (12d) | (13i) | (14b) | (19e) | (15j) | (20b) | (21d) |
| 103 | (Ic) | (5i) | (10e) | (6a) | (11d) | (12d) | (13i) | (14j) | (19e) | (15j) | (20b) | (21c) |
| 104 | (Ic) | (5i) | (10e) | (6a) | (11d) | (12d) | (13i) | (14j) | (19e) | (15j) | (20b) | (21d) |
| 105 | (Ic) | (5i) | (10e) | (6g) | (11d) | (12b) | (13i) | (14b) | (19e) | (15j) | (20b) | (21c) |
| 106 | (Ic) | (5i) | (10e) | (6g) | (11d) | (12b) | (13i) | (14b) | (19e) | (15j) | (20b) | (21d) |
| 107 | (Ic) | (5i) | (10e) | (6g) | (11d) | (12b) | (13i) | (14j) | (19e) | (15j) | (20b) | (21c) |
| 108 | (Ic) | (5i) | (10e) | (6g) | (11d) | (12b) | (13i) | (14j) | (19e) | (15j) | (20b) | (21d) |
| 109 | (Ic) | (5i) | (10e) | (6g) | (11d) | (12d) | (13i) | (14b) | (19e) | (15j) | (20b) | (21c) |
| 110 | (Ic) | (5i) | (10e) | (6g) | (11d) | (12d) | (13i) | (14b) | (19e) | (15j) | (20b) | (21d) |
| 111 | (Ic) | (5i) | (10e) | (6g) | (11d) | (12d) | (13i) | (14j) | (19e) | (15j) | (20b) | (21c) |
| 112 | (Ic) | (5i) | (10e) | (6g) | (11d) | (12d) | (13i) | (14j) | (19e) | (15j) | (20b) | (21d) |
| 113 | (Ic) | (5i) | (10h) | (6a) | (11d) | (12b) | (13i) | (14b) | (19e) | (15j) | (20b) | (21c) |
| 114 | (Ic) | (5i) | (10h) | (6a) | (11d) | (12b) | (13i) | (14b) | (19e) | (15j) | (20b) | (21d) |
| 115 | (Ic) | (5i) | (10h) | (6a) | (11d) | (12b) | (13i) | (14j) | (19e) | (15j) | (20b) | (21c) |
| 116 | (Ic) | (5i) | (10h) | (6a) | (11d) | (12b) | (13i) | (14j) | (19e) | (15j) | (20b) | (21d) |
| 117 | (Ic) | (5i) | (10h) | (6a) | (11d) | (12d) | (13i) | (14b) | (19e) | (15j) | (20b) | (21c) |
| 118 | (Ic) | (5i) | (10h) | (6a) | (11d) | (12d) | (13i) | (14b) | (19e) | (15j) | (20b) | (21d) |
| 119 | (Ic) | (5i) | (10h) | (6a) | (11d) | (12d) | (13i) | (14j) | (19e) | (15j) | (20b) | (21c) |
| 120 | (Ic) | (5i) | (10h) | (6a) | (11d) | (12d) | (13i) | (14j) | (19e) | (15j) | (20b) | (21d) |
| 121 | (Ic) | (5i) | (10h) | (6g) | (11d) | (12b) | (13i) | (14b) | (19e) | (15j) | (20b) | (21c) |
| 122 | (Ic) | (5i) | (10h) | (6g) | (11d) | (12b) | (13i) | (14b) | (19e) | (15j) | (20b) | (21d) |
| 123 | (Ic) | (5i) | (10h) | (6g) | (11d) | (12b) | (13i) | (14j) | (19e) | (15j) | (20b) | (21c) |
| 124 | (Ic) | (5i) | (10h) | (6g) | (11d) | (12b) | (13i) | (14j) | (19e) | (15j) | (20b) | (21d) |
| 125 | (Ic) | (5i) | (10h) | (6g) | (11d) | (12d) | (13i) | (14b) | (19e) | (15j) | (20b) | (21c) |
| 126 | (Ic) | (5i) | (10h) | (6g) | (11d) | (12d) | (13i) | (14b) | (19e) | (15j) | (20b) | (21d) |
| 127 | (Ic) | (5i) | (10h) | (6g) | (11d) | (12d) | (13i) | (14j) | (19e) | (15j) | (20b) | (21c) |
| 128 | (Ic) | (5i) | (10h) | (6g) | (11d) | (12d) | (13i) | (14j) | (19e) | (15j) | (20b) | (21d) |
| 129 | (I)  | (5a) | (10d) | (6a) | (11a) | (12b) | (13a) | (14a) | (19d) | (15a) | (20a) | (21a) |
| 130 | (I)  | (5i) | (10d) | (6a) | (11a) | (12b) | (13a) | (14a) | (19d) | (15a) | (20a) | (21a) |
| 131 | (Ic) | (5a) | (10d) | (6a) | (11a) | (12b) | (13a) | (14a) | (19d) | (15a) | (20a) | (21a) |
| 132 | (Ic) | (5i) | (10d) | (6a) | (11a) | (12b) | (13a) | (14a) | (19d) | (15a) | (20a) | (21a) |

-continued

| | (I) | "a" | L¹† | R¹ | L² | Q | L³ | R³ | L⁴†† | R⁴ | L⁵ | R⁵ |
|---|---|---|---|---|---|---|---|---|---|---|---|---|
| 133 | (I) | (5a) | (10e) | (6f) | (11d) | (12d) | (13i) | (14b), (14f) | (19f) | (15f) | (20d) | (21b), (21e) |
| 134 | (I) | (5i) | (10e) | (6f) | (11d) | (12d) | (13i) | (14b), (14f) | (19f) | (15f) | (20d) | (21b), (21e) |
| 135 | (Ic) | (5a) | (10e) | (6f) | (11d) | (12d) | (13i) | (14b), (14f) | (19f) | (15f) | (20d) | (21b), (21e) |
| 136 | (Ic) | (5i) | (10e) | (6f) | (11d) | (12d) | (13i) | (14b), (14f) | (19f) | (15f) | (20d) | (21b), (21e) |
| 137 | (I) | (5a) | (10h) | (6g) | (11d) | (12f) | (13b) | (14k) | (19f) | (15i) | (20b) | (21b) |
| 138 | (I) | (5i) | (10h) | (6g) | (11d) | (12f) | (13b) | (14k) | (19f) | (15i) | (20b) | (21b) |
| 139 | (Ic) | (5a) | (10h) | (6g) | (11d) | (12f) | (13b) | (14k) | (19f) | (15i) | (20b) | (21b) |
| 140 | (Ic) | (5i) | (10h) | (6g) | (11d) | (12f) | (13b) | (14k) | (19f) | (15i) | (20b) | (21b) |

†$L^1$ is $A^{1A}$-$L^{1A}$-$A^{1B}$-$L^{1B}$
††$L^4$ is $L^{4B}$-$A^{4B}$-$L^{4A}$-$A^{4A}$

In certain embodiments, the disclosure provides compounds of formula (Ih),

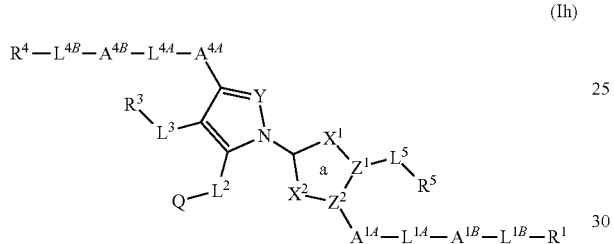

(Ih)

in which formula (Ih) the ring system denoted by "a" is defined as being heteroaromatic, optionally in the form of a pharmaceutically acceptable salt or N-oxide, or a solvate or hydrate, wherein $A^{1A}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

$L^{1A}$ is selected from the group consisting of a bond, unsubstituted $C_1$-$C_4$ alkylene, unsubstituted $C_1$-$C_4$ alkenylene and unsubstituted $C_1$-$C_4$ alkynylene;

$A^{1B}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

$L^{1B}$ is selected from the group consisting of a bond, unsubstituted $C_1$-$C_4$ alkylene, unsubstituted $C_1$-$C_4$ alkenylene and unsubstituted $C_1$-$C_4$ alkynylene;

$R^1$ is selected from the group consisting of hydrogen, optionally substituted $C_1$-$C_8$ alkyl, optionally-substituted $C_1$-$C_8$ alkenyl and optionally substituted $C_1$-$C_8$ alkynyl,
cycloalkyl and heterocycloalkyl, each optionally substituted with 1-5 $R^{1E}$, and
aryl and heteroaryl, each optionally substituted with 1-5 $R^{1E}$,
in which
each $R^{1E}$ is independently selected from oxo, optionally-substituted $C_1$-$C_4$ alkyl, $C_1$-$C_4$ fluoroalkyl, halogen, —CN, SF$_5$, —N$_3$, —C(O)R$^{1F}$, —SR$^{1F}$, —S(O)$_{1-2}$R$^{1F}$, —OR$^{1F}$, —NR$^{1G}$R$^{1F}$, —C(O)R$^{1F}$, —C(O)NR$^{1G}$R$^{1F}$, —NR$^{1G}$C(O)R$^{1F}$, —C(S)NR$^{1G}$R$^{1F}$, —NR$^{1G}$C(S)R$^{1F}$, —C(O)OR$^{1F}$, —OC(O)R$^{1F}$, —C(O)SR$^{1F}$, —SC(O)R$^{1F}$, —C(S)OR$^{1F}$, —OC(S)R$^{1F}$, —C(S)SR$^{1F}$, —SC(S)R$^{1F}$, —S(O)$_{1-2}$OR$^{1F}$, —OS(O)$_{1-2}$R$^{1F}$, —S(O)$_{1-2}$NR$^{1G}$R$^{1F}$, —NR$^{1G}$S(O)$_{1-2}$R$^{1F}$;

each $R^{1F}$ is independently selected from H, $C_1$-$C_3$ alkyl, $C_1$-$C_3$ fluoroalkyl, $C_1$-$C_3$ hydroxyalkyl and ($C_1$-$C_3$ alkoxy)$C_1$-$C_3$ alkyl, ($C_1$-$C_3$ alkoxy($C_1$-$C_3$ alkoxy))$C_1$-$C_3$ alkyl, ($C_1$-$C_3$ alkoxy($C_1$-$C_3$ alkoxy($C_1$-$C_3$ alkoxy)))$C_1$-$C_3$ alkyl, and each $R^{1G}$ is independently selected from H, $C_1$-$C_3$ alkyl, $C_1$-$C_3$ fluoroalkyl, $C_1$-$C_3$ hydroxyalkyl, ($C_1$-$C_3$ alkoxy)$C_1$-$C_3$ alkyl, —S(O)$_{1-2}$($C_1$-$C_3$ alkyl), —C(O)($C_1$-$C_3$ alkyl) and —C(O)O($C_1$-$C_3$ alkyl);

$L^2$ is selected from the group consisting of a bond, —CH$_2$—, —CH(CH$_3$)— or —CH$_2$CH$_2$—;

Q is selected from the group consisting of H, —CH$_2$OH, —C(O)OH, —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —C(O)R$^{2A}$, —S(O)$_2$OH, —P(O)(OH)$_2$, —C(OH)(CF$_3$)$_2$, S(O)$_2$R$^{2A}$, —N(R$^{2B}$)S(O)$_2$R$^{2A}$, —S(O)$_2$NR$^{2B}$R$^{2A}$, —C(O)NHOH, —C(O)NH—O($C_1$-$C_3$ alkyl), —CO(NH)CN,

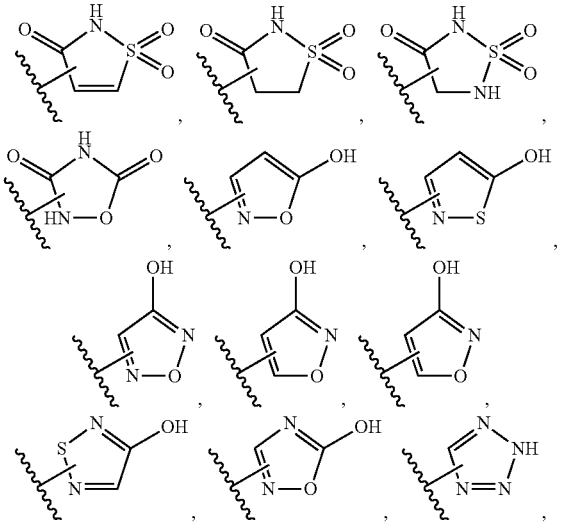

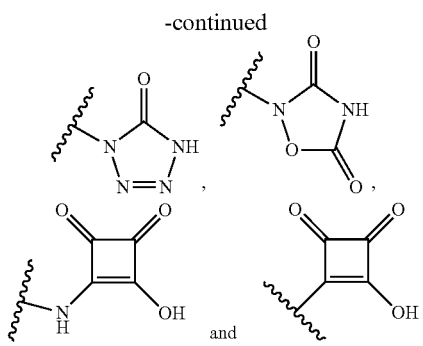

in which
each $R^{2A}$ is independently selected from H, $C_1$-$C_3$ alkyl, $C_1$-$C_3$ fluoroalkyl, $C_1$-$C_3$ hydroxyalkyl $C_1$-$C_3$ aminoalkyl, $C_1$-$C_3$ thioalkyl, ($C_1$-$C_3$ alkoxy)$C_1$-$C_3$ alkyl, —(CH$_2$CH$_2$O)$_{2-5}$-(optionally substituted $C_1$-$C_3$ alkyl)- and heteroaryl optionally substituted with 1-2 groups selected from substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —C(O)$C_1$-$C_3$ alkyl, and each $R^{2B}$ is independently selected from H, $C_1$-$C_3$ alkyl, $C_1$-$C_3$ fluoroalkyl, $C_1$-$C_3$ hydroxyalkyl, $C_1$-$C_3$ aminoalkyl, $C_1$-$C_3$ thioalkyl, ($C_1$-$C_3$ alkoxy)$C_1$-$C_3$ alkyl, —S(O)$_{1-2}$($C_1$-$C_3$ alkyl), —C(O)($C_1$-$C_3$ alkyl) and —C(O)O($C_1$-$C_3$ alkyl), or $R^{2A}$ and $R^{2B}$ come together with a nitrogen to which they are both directly bound to form a heterocycloalkyl optionally substituted with 1-3 substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —C(O)$C_1$-$C_3$ alkyl;

$L^3$ is a bond, —C(O)—, —S—, —S(O)$_{1-2}$—, —O—, —NR$^6$—, —CH$_2$—, —CH(CH$_3$)(OH)—, —CH(OH)—, —CH$_2$CH$_2$—, —C(O)NR$^6$—, —NR$^6$C(O)—, —C(S)NR$^6$—, —NR$^6$C(S)—, —C(O)O—, —OC(O)—, —S(O)$_{1-2}$O—, —OS(O)$_{1-2}$—, —S(O)$_{1-2}$NR$^6$— or —NR$^6$S(O)$_{1-2}$—;

$R^3$ is selected from the group consisting of
cycloalkyl and heterocycloalkyl, each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$, and aryl and heteroaryl each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$, in which
each $L^{3C}$ is a bond, methylene, ethylene, —C(O)—, —S—, —S(O)$_{1-2}$—, —O— or —NR$^{3G}$—;

each $R^{3D}$ is independently selected from optionally-substituted $C_1$-$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$, —OC(O)OR$^{3F}$, —OC(O)NR$^{3G}$R$^{3F}$, —NR$^{3G}$C(O)OR$^{3F}$, —NR$^{3G}$C(O)NR$^{3G}$R$^{3F}$, —SC(O)OR$^{3F}$, —OC(O)SR$^{3F}$, —SC(O)SR$^{3F}$, —SC(O)NR$^{3G}$R$^{3F}$, —NR$^{3G}$C(O)SR$^{3F}$, —OC(S)OR$^{3F}$, —OC(S)NR$^{3G}$R$^{3F}$, —NR$^{3G}$C(S)OR$^{3F}$, —NR$^{3G}$C(S)NR$^{3G}$R$^{3F}$, —SC(S)OR$^{3F}$, —OC(S)SR$^{3F}$, —SC(S)SR$^{3F}$, —SC(S)NR$^{3G}$R$^{3F}$, —NR$^{3G}$C(S)SR$^{3F}$, —NR$^{3G}$C(NR$^{3G}$)NR$^{3G}$R$^{3F}$ and —NR$^{3G}$S(O)$_{1-2}$NR$^{3G}$R$^{3F}$;

each $R^{3E}$ is independently selected from oxo, optionally-substituted $C_1$-$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$, —OC(O)OR$^{3F}$, —OC(O)NR$^{3G}$R$^{3F}$, —NR$^{3G}$C(O)OR$^{3F}$, —NR$^{3G}$C(O)NR$^{3G}$R$^{3F}$, —SC(O)OR$^{3F}$, —OC(O)SR$^{3F}$, —SC(O)SR$^{3F}$, —SC(O)NR$^{3G}$R$^{3F}$, —NR$^{3G}$C(O)SR$^{3F}$, —OC(S)OR$^{3F}$, —OC(S)NR$^{3G}$R$^{3F}$, —NR$^{3G}$C(S)OR$^{3F}$, —NR$^{3G}$C(S)NR$^{3G}$R$^{3F}$, —SC(S)OR$^{3F}$, —OC(S)SR$^{3F}$, —SC(S)SR$^{3F}$, —SC(S)NR$^{3G}$R$^{3F}$, —NR$^{3G}$C(S)SR$^{3F}$, —NR$^{3G}$C(NR$^{3G}$)NR$^{3G}$R$^{3F}$ and —NR$^{3G}$S(O)$_{1-2}$NR$^{3G}$R$^{3F}$;

each $R^{3F}$ is independently selected from H, $C_1$-$C_3$ alkyl, $C_1$-$C_3$ fluoroalkyl and $C_1$-$C_3$ hydroxyalkyl and each $R^{3G}$ is independently selected from H, $C_1$-$C_3$ alkyl, $C_1$-$C_3$ fluoroalkyl, $C_1$-$C_3$ hydroxyalkyl, —S(O)$_{1-2}$($C_1$-$C_3$ alkyl), —C(O)($C_1$-$C_3$ alkyl) and —C(O)O($C_1$-$C_3$ alkyl);

$A^{4A}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

$L^{4A}$ is selected from the group consisting of a bond, unsubstituted $C_1$-$C_4$ alkylene, unsubstituted $C_1$-$C_4$ alkenylene and unsubstituted $C_1$-$C_4$ alkynylene;

$A^{4B}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —CO(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

$L^{4B}$ is selected from the group consisting of a bond, unsubstituted $C_1$-$C_4$ alkylene, unsubstituted $C_1$-$C_4$ alkenylene and unsubstituted $C_1$-$C_4$ alkynylene;

$R^4$ is selected from the group consisting of
hydrogen,
optionally substituted $C_1$-$C_8$ alkyl, optionally-substituted $C_1$-$C_8$ alkenyl and
optionally substituted $C_1$-$C_8$ alkynyl,
cycloalkyl and heterocycloalkyl, each optionally substituted with 1-5 $R^{4E}$, and
in which
each $R^{4E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^{4F}$, —SR$^{4F}$, —S(O)$_{1-2}$R$^{4F}$, —OR$^{4F}$, —NR$^{4G}$R$^{4F}$, —C(O)R$^{4F}$, —C(O)NR$^{4G}$R$^{4F}$, —NR$^{4G}$C(O)R$^{4F}$, —C(S)NR$^{4G}$R$^{4F}$, —NR$^{1G}$C(S)R$^{4F}$, —C(O)OR$^{4F}$, —OC(O)R$^{4F}$, —C(O)SR$^{4F}$, —SC(O)R$^{4F}$, —C(S)OR$^{4F}$, —OC(S)R$^{4F}$, —C(S)SR$^{4F}$, —SC(S)R$^{4F}$, —S(O)$_{1-2}$OR$^{4F}$, —OS(O)$_{1-2}$R$^{4F}$, —S(O)$_{1-2}$NR$^{4G}$R$^{4F}$, —NR$^{4G}$S(O)$_{1-2}$R$^{4F}$, —CO(O)OR$^{4F}$, —OC(O)NR$^{4G}$R$^{4F}$, —NR$^{4G}$C(O)OR$^{4F}$, —NR$^{4G}$C(O)NR$^{4G}$R$^{4F}$, —SC(O)OR$^{4F}$, —OC(O)SR$^{4F}$, —SC(O)SR$^{4F}$, —SC(O)NR$^{4G}$R$^{4F}$, —NR$^{4G}$C(O)SR$^{4F}$, —OC(S)OR$^{4F}$, —OC(S)NR$^{4G}$R$^{4F}$, —NR$^{4G}$C(S)OR$^{4F}$, —NR$^{4G}$C(S)NR$^{4G}$R$^{4F}$, —SC(S)OR$^{4F}$, —OC(S)SR$^{4F}$, —SC(S)SR$^{4F}$, —SC(S)NR$^{4G}$R$^{4F}$, —NR$^{4G}$C(S)SR$^{4F}$, —NR$^{4G}$C(NR$^{4G}$)NR$^{4G}$R$^{4F}$ and —NR$^{4G}$S(O)$_{1-2}$NR$^{4G}$R$^{4F}$;

each R$^{4F}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^{4G}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

L$^5$ is —C(O)—, —S—, —S(O)$_{1-2}$—, —O—, —NR$^6$—, —CH$_2$—, —CH(CH$_3$)(OH)—, —CH(OH)—, —CH$_2$CH$_2$—, —C(O)NR$^6$—, —NR$^6$C(O)—, —C(S)NR$^6$—, —NR$^6$C(S)—, —C(O)O—, —OC(O)—, —S(O)$_{1-2}$O—, —OS(O)$_{1-2}$—, —S(O)$_{1-2}$NR$^6$— or —NR$^6$S(O)$_{1-2}$—;

R$^5$ is selected from the group consisting of cycloalkyl and heterocycloalkyl, each optionally substituted with 1-5 R$^{5E}$, and aryl and heteroaryl each optionally substituted with 1-5 R$^{5E}$, in which each R$^{5E}$ is independently selected from oxo, optionally-substituted C$_1$-C$_4$ alkyl, C$_1$-C$_4$ fluoroalkyl, halogen, —CN, —SF$_5$, —N$_3$, —C(O)R$^{5F}$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{1G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$, —NR$^{5G}$S(O)$_{1-2}$R$^{5F}$, —OC(O)OR$^{5F}$, —OC(O)NR$^{5G}$R$^{5F}$, —NR$^{5G}$C(O)OR$^{5F}$, —NR$^{5G}$C(O)NR$^{5G}$R$^{5F}$, —SC(O)OR$^{5F}$, —OC(O)SR$^{5F}$, —SC(O)SR$^{5F}$, —SC(O)NR$^{5G}$R$^{5F}$, —NR$^{5G}$C(O)SR$^{5F}$, —OC(S)OR$^{5F}$, —OC(S)NR$^{5G}$R$^{5F}$, —NR$^{5G}$C(S)OR$^{5F}$, —NR$^{5G}$C(S)NR$^{5G}$R$^{5F}$, —SC(S)OR$^{5F}$, —OC(S)SR$^{5F}$, —SC(S)SR$^{5F}$, —SC(S)NR$^{5G}$R$^{5F}$, —NR$^{5G}$C(S)SR$^{5F}$, —NR$^{5G}$C(NR$^{5G}$)NR$^{5G}$R$^{5F}$ and —NR$^{5G}$S(O)$_{1-2}$NR$^{5G}$R$^{5F}$;

each R$^{5F}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^{5G}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

X$^1$ is selected from the group consisting of CR$^{XA}$, S, O, NRX$^B$ and N and X$^2$ is selected from the group consisting of CR$^{XA}$, S, O, NRX$^B$ and N in which each R$^{XA}$ is independently selected from the group consisting of hydrogen, C$_1$-C$_4$ alkyl, C$_1$-C$_4$ fluoroalkyl, C$_1$-C$_3$ hydroxyalkyl, (C$_1$-C$_3$ alkoxy)C$_1$-C$_3$ alkyl, halo, —CN, oxo, —SF$_5$, —N$_3$, —C(O)R$^{XC}$, —SR$^{XC}$, —S(O)$_{1-2}$R$^{XC}$, —OR$^{XC}$, —NR$^{XD}$R$^{XC}$, in which each R$^{XC}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^{XD}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —C(O)(C$_1$-C$_3$ alkyl) and —C(O)O(C$_1$-C$_3$ alkyl);

each R$^{XB}$ is independently selected from the group consisting of H, C$_1$-C$_3$ alkyl, C$_1$-C$_3$ fluoroalkyl, C$_1$-C$_3$ hydroxyalkyl, (C$_1$-C$_3$ alkoxy)C$_1$-C$_3$ alkyl, —C(O)(C$_1$-C$_3$ alkyl) and —C(O)O(C$_1$-C$_3$ alkyl and C$_1$-C$_4$ alkyl-S(O)$_{1-2}$—;

Z$^1$ and Z$^2$ are independently selected from C and N; and

Y is CR$^Y$ or N, in which R$^Y$ is selected from the group consisting of hydrogen, C$_1$-C$_3$ alkyl, C$_1$-C$_3$ fluoroalkyl, C$_1$-C$_3$ hydroxyalkyl, C$_1$-C$_3$ aminoalkyl, C$_1$-C$_3$ thioalkyl, (C$_1$-C$_3$ alkoxy)C$_1$-C$_3$ alkyl, —S(O)$_{1-2}$(C$_1$-C$_3$ alkyl), halogen, —CN, —SF$_5$, —N$_3$, —C(O)R$^{YC}$, —SR$^{YC}$, —S(O)$_{1-2}$R$^{YC}$, —OR$^{YC}$ and —NR$^{YD}$R$^{YC}$, in which each R$^{YC}$ is independently selected from H, C$_1$-C$_3$ alkyl and C$_1$-C$_3$ fluoroalkyl, and each R$^{YD}$ is independently selected from H, C$_1$-C$_3$ alkyl and C$_1$-C$_3$ fluoroalkyl;

wherein each R$^6$ is selected from the group consisting of hydrogen, C$_1$-C$_3$ alkyl, C$_1$-C$_3$ fluoroalkyl, C$_1$-C$_3$ hydroxyalkyl, C$_1$-C$_3$ aminoalkyl, C$_1$-C$_3$ thioalkyl, (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

each alkyl, alkylene, alkenyl, alkenylene, alkynyl and alkynylene is straight-chain or branched;

each optionally substituted alkyl, alkenyl, alkynyl, alkylene, alkenylene and alkynylene is unsubstituted or substituted with 1-5 substituents independently selected from oxo, halogen, —CN, —SF$_5$, —N$_3$, —C(O)R$^8$, —SR$^8$, —S(O)$_{1-2}$R$^8$, —OR$^8$, —NR$^9$R$^8$, —C(O)NR$^9$R$^8$, —NR$^9$C(O)R$^8$, —C(S)NR$^9$R$^8$, —NR$^9$C(S)R$^8$, —C(O)OR$^8$, —OC(O)R$^8$, —C(O)SR$^8$, —SC(O)R$^8$, —O(S)OR$^8$, —OC(S)R$^8$, —C(S)SR$^8$, —SC(S)R$^8$, —S(O)$_{1-2}$OR$^8$, —OS(O)$_{1-2}$R$^8$, —S(O)$_{1-2}$NR$^9$R$^8$, —NR$^9$S(O)$_{1-2}$R$^8$, —OC(O)OR$^8$, —OC(O)NR$^9$R$^8$, —NR$^9$C(O)OR$^8$, —NR$^9$C(O)NR$^9$R$^8$, —SC(O)OR$^8$, —OC(O)SR$^8$, SC(O)SR$^8$, —SC(O)NR$^9$R$^8$, —NR$^9$C(O)SR$^8$, —OC(S)OR$^8$, —OC(S)NR$^9$R$^8$, —NR$^9$C(S)OR$^8$, —NR$^9$C(S)NR$^9$R$^8$, —SC(S)OR$^8$, —OC(S)SR$^8$, —SC(S)SR$^8$, —SC(S)NR$^9$R$^8$, —NR$^9$C(S)SR$^8$, —NR$^9$C(NR$^9$)NR$^9$R$^8$ and —NR$^9$S(O)$_{1-2}$NR$^9$R$^8$, in which each R$^8$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^9$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

each cycloalkyl has 3-10 ring carbons and is unsaturated or partially unsaturated, and optionally includes one or two fused cycloalkyl rings, each fused ring having 3-8 ring members;

each heterocycloalkyl has 3-10 ring members and 1-3 heteroatoms independently selected from nitrogen, oxygen and sulfur and is unsaturated or partially unsaturated, and optionally includes one or two fused cycloalkyl rings, each having 3-8 ring members;

each aryl is a phenyl or a naphthyl, and optionally includes one or two fused cycloalkyl or heterocycloalkyl rings, each fused cycloalkyl or heterocycloalkyl ring having 4-8 ring members;

each heteroaryl is a 5-6 membered monocyclic heteroaryl ring having 1-4 heteroatoms independently selected from nitrogen, oxygen and sulfur or a 8-10 membered bicyclic heteroaryl having 1-5 heteroatoms independently selected from nitrogen, oxygen or sulfur, and optionally includes one or two fused cycloalkyl or heterocycloalkyl rings, each fused cycloalkyl or heterocycloalkyl ring having 4-8 ring members.

In certain such embodiments, each and every optionally substituted alkyl, alkylene, alkenyl, alkenylene, alkynyl and alkynylene is unsubstituted or fluorinated. For example, in certain such embodiments, each and every optionally substituted alkyl, alkylene, alkenyl, alkenylene, alkynyl and alkynylene is unsubstituted.

The disclosure also provides a variety of subgenera of compounds of any of formulae (I) or (Ia)-(Ih) in which $R^1$, $A^{1A}$, $L^{1B}$, $A^{1B}$, $L^{1A}$, $L^2$, Q, $L^3$, $R^3$, $A^{4A}$, $L^{4B}$, $A^{4B}$, $L^{4A}$, $R^4$, $L^5$, and $R^5$ are optionally independently selected from the groups (6h) et seq., (7e) et seq., (8d) et seq., (9g) et seq., (10k) et seq., (11e) et seq., (12k) et seq., (13j) et seq., (14l) et seq., (15l) et seq., (16e) et seq., (17d) et seq., (18h) et seq., (19k) et seq., (20g) et seq., and (21h) et seq. defined hereinbelow (e.g., wherein the compound is of structural formula (I) or (Ia)-(Ih) as defined in any combination of the embodiments below):

In certain embodiments, the compound is of one of the following structural formulae:
(Id);
(Ie);
(If);
(Ig);
(Ih);
(Ii), in which (Ii) is formula (I) with the ring system denoted by "a" being oxazole, imidazole, pyrazole or triazole (e.g., in one of the following configurations:

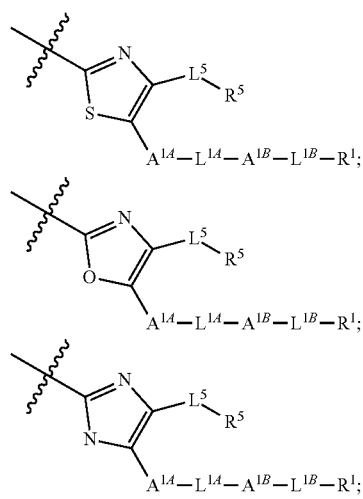

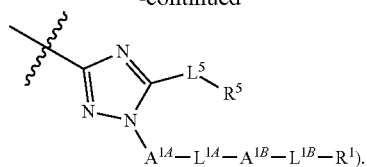

(Ij), in which (Ij) is formula (Ic) with the ring system denoted by "a" being oxazole, imidazole, pyrazole, or triazole (e.g., in one of the following configurations:

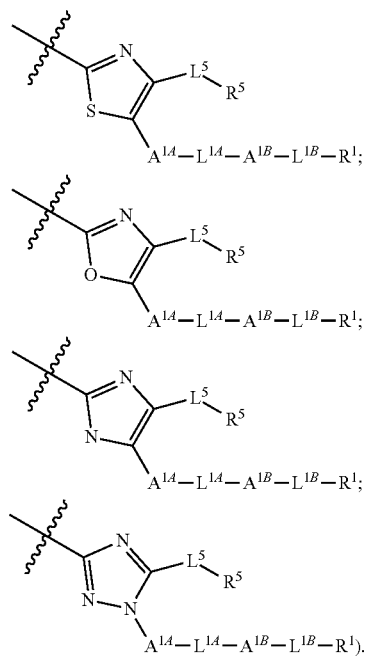

In certain embodiments, when the compound is of one of formulae (Id), (Ie), (Ih) and (Ii) as described above, $R^Y$ is H, —C(O)—$C_1$-$C_3$ alkyl, —C(O)—$C_1$-$C_3$ fluoroalkyl, —$C_1$-$C_3$ alkyl, —$C_1$-$C_3$ fluoroalkyl, —CN or halogen. In certain embodiments according to formulae (Id)-(Ij), each $RX^A$ and $RX^B$ is hydrogen.

In certain embodiments, $R^1$ is selected from one of the following groups (6h)-(6p)

(6h) $R^1$ is selected from the group consisting of hydrogen, optionally substituted $C_1$-$C_8$ alkyl, optionally substituted $C_1$-$C_8$ alkenyl, optionally substituted $C_1$-$C_8$ alkynyl, cycloalkyl and heterocycloalkyl, wherein cycloalkyl and heterocycloalkyl are optionally substituted with 1-5 $R^{1E}$;

(6i) $R^1$ is selected from the group consisting of hydrogen, optionally substituted $C_1$-$C_8$ alkyl, optionally substituted $C_1$-$C_8$ alkenyl and optionally substituted $C_1$-$C_8$ alkynyl;

(6j) $R^1$ is selected from optionally substituted $C_1$-$C_8$ alkyl, optionally-substituted $C_1$-$C_8$ alkenyl, and optionally substituted $C_1$-$C_8$ alkynyl;

(6k) $R^1$ is selected from the group consisting of hydrogen, unsubstituted $C_1$-$C_8$ alkyl, unsubstituted $C_1$-$C_8$ alkenyl and unsubstituted $C_1$-$C_8$ alkynyl (for example, methyl, ethyl, propyl or butyl);

(6l) $R^1$ is selected from the group consisting of unsubstituted $C_1$-$C_8$ alkyl, unsubstituted $C_1$-$C_8$ alkenyl and unsubstituted $C_1$-$C_8$ alkynyl (for example, methyl, ethyl, propyl, butenyl or butyl);

(6m) $R^1$ is cycloalkyl or heterocycloalkyl (e.g., cyclobutyl, cyclopentyl, cyclohexyl or cycloheptyl), each optionally substituted with 1-5 $R^{1E}$, for example, 1-5 alkyl groups;

(6n) $R^1$ is cycloalkyl optionally substituted with 1-5 $R^{1E}$;

(6o) $R^1$ is hydrogen, optionally substituted $C_1$-$C_8$ alkyl, or cycloalkyl optionally substituted with 1-5 $R^{1E}$;

(6p) $R^1$ is hydrogen or optionally substituted $C_1$-$C_6$ alkyl (e.g., ethyl, propyl, or butyl).

In certain such embodiments, each optionally substituted alkyl, alkenyl and alkynyl of $R^1$ (including those of $R^{1E}$) is unsubstituted or fluorinated. For example, in certain such embodiments each optionally substituted alkyl, alkenyl and alkynyl of $R^1$ (including those of $R^{1E}$) is unsubstituted.

In certain embodiments, $A^{1A}$ is selected from one of the following groups (7e)-(7h)

(7e) $A^{1A}$ is selected from the group consisting of a bond, —C(O)—, —S—, —S(O)$_{1-2}$—, —O—, —NR$^6$—, —C(O)NR$^6$—, —NR$^6$C(O)—, and —C(O)O—;

(7f) $A^{1A}$ is a bond;

(7g) $A^{1A}$ is selected from the group consisting of —C(O)—, —S—, —S(O)$_{1-2}$—, —O—, and —NR$^6$—;

(7h) $A^{1A}$ is O.

In certain embodiments, $L^{1B}$ is selected from one of the following groups (8d)-(8f)

(8d) $L^{1B}$ is selected from a bond and optionally substituted $C_1$-$C_4$ alkylene;

(8e) $L^{1B}$ is a bond;

(8f) $L^{1B}$ is unsubstituted $C_1$-$C_4$ alkylene.

In certain such embodiments, each optionally substituted alkylene of $L^{1B}$ is unsubstituted or fluorinated. For example, in certain such embodiments each optionally substituted alkylene of $L^{1B}$ is unsubstituted.

In certain embodiments, $A^{1B}$ is selected from one of the following groups (9g)-(9l)

(9g) $A^{1B}$ is selected from the group consisting of —C(O)—, —S—, —S(O)$_{1-2}$—, —O—, —NR$^6$—, —C(O)NR$^6$—, —NR$^6$C(O)—, —OC(O)— and —C(O)O—;

(9h) $A^{1B}$ is selected from the group consisting of —C(O)—, —S—, —S(O)$_{1-2}$—, —O—, and —C(O)O—;

(9i) $A^{1B}$ is —S—;

(9j) $A^{1B}$ is selected from —C(O)—, —S(O)—, —S(O)$_2$—, —OC(O)— and —C(O)O—;

(9k) $A^{1B}$ is —O—;

(9l) $A^{1B}$ is a bond.

In certain embodiments, $L^{1A}$ is selected from one of the following groups (10k)-(10m)

(10k) $L^{1A}$ is selected from a bond and optionally substituted $C_1$-$C_4$ alkylene;

(10l) $L^{1A}$ is a bond;

(10m) $L^{1A}$ is optionally substituted $C_1$-$C_4$ alkylene.

In certain such embodiments, each optionally substituted alkylene of $L^{1A}$ is unsubstituted or fluorinated. For example, in certain such embodiments each optionally substituted alkylene of $L^{1A}$ is unsubstituted.

In certain embodiments, $A^{1A}$-$L^{1A}$-$A^{1B}$-$L^{1B}$ (i.e., -$L^1$-) is selected from one of the following groups (10n)-(10v)

(10n) $A^{1A}$-$L^{1A}$-$A^{1B}$-$L^{1B}$, wherein $A^{1A}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—; $L^{1A}$ is selected from the group consisting of a bond, unsubstituted $C_1$-$C_4$ alkylene, unsubstituted $C_1$-$C_4$ alkenylene and unsubstituted $C_1$-$C_4$ alkynylene; $A^{1B}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—; and $L^{1B}$ is a bond;

(10o) $A^{1A}$-$L^{1A}$-$A^{1B}$-$L^{1B}$, wherein $A^{1A}$, $L^{1A}$ and $L^{1B}$ are a bond, and $A^{1B}$ as defined in formula (I) or in (10n);

(10p) $A^{1A}$-$L^{1A}$-$A^{1B}$-$L^{1B}$ is selected from a bond, optionally substituted $C_1$-$C_4$ alkylene, —C(O)—, —S—, —S(O)$_{1-2}$—, —O—, and —NR$^6$—;

(10q) $A^{1A}$-$L^{1A}$-$A^{1B}$-$L^{1B}$ is selected from a bond, —CH$_2$—, —CH(CH$_3$)—, —CH$_2$CH$_2$—, —C(O)—, —S—, —S(O)$_{1-2}$—, —O—, and —NR$^6$—;

(10r) $A^{1A}$-$L^{1A}$-$A^{1B}$-$L^{1B}$ is —O— or —S—.

(10s) $A^{1A}$-$L^{1A}$-$A^{1B}$-$L^{1B}$ is unsubstituted $C_1$-$C_4$ alkylene;

(10t) $A^{1A}$-$L^{1A}$-$A^{1B}$-$L^{1B}$ is selected from —C(O)—, —S(O)— and —S(O)$_2$—;

(10u) $A^{1A}$-$L^{1A}$-$A^{1B}$-$L^{1B}$ is selected from —CH$_2$—, —CH(CH$_3$)— and —CH$_2$CH$_2$—;

(10v) $A^{1A}$-$L^{1A}$-$A^{1B}$-$L^{1B}$ is a bond.

In certain such embodiments, each optionally substituted alkyl, alkylene, alkenyl, alkenylene, alkynyl and alkynylene of $A^{1A}$-$L^{1A}$-$A^{1B}$-$L^{1B}$ (including those of $R^6$) is unsubstituted or fluorinated. For example, in certain such embodiments each optionally substituted alkyl, alkylene, alkenyl, alkenylene, alkynyl and alkynylene of $A^{1A}$-$L^{1A}$-$A^{1B}$-$L^{1B}$ (including those of $R^6$) is unsubstituted.

In certain embodiments, $L^2$ is selected from one of the following groups (11e)-(11h)

(11e) $L^2$ is selected from a bond and optionally substituted $C_1$-$C_4$ alkylene;

(11f) $L^2$ is selected from a unsubstituted $C_1$-$C_4$ alkylene;

(11g) $L^2$ is a bond, —CH$_2$—, —CH(CH$_3$)— or —CH$_2$CH$_2$—;

(11h) $L^2$ is a bond.

In certain such embodiments, each optionally substituted alkylene of $L^2$ is unsubstituted or fluorinated. For example, in certain such embodiments each optionally substituted alkylene of $L^2$ is unsubstituted.

In certain embodiments, Q is selected from one of the following groups (12k)-(12t)

(12k) Q is selected from the group consisting of —CH$_2$OH, —C(O)OH, —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —C(O)R$^{2A}$, —S(O)$_2$OH, —P(O)(OH)$_2$, —C(OH)(CF$_3$)$_2$, —S(O)$_2$R$^{2A}$, —N(R$^{2B}$)S(O)$_2$R$^{2A}$, —S(O)$_2$NR$^{2B}$R$^{2A}$, —C(O)NH—O(C$_1$-C$_3$ alkyl), —C(O)NHOH, —CO(NH)CN,

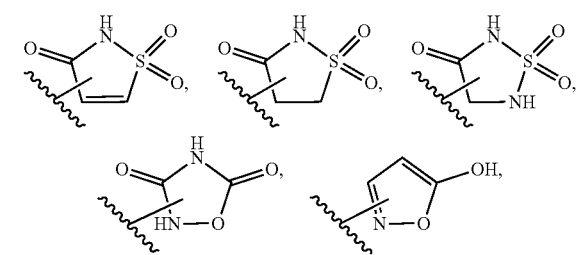

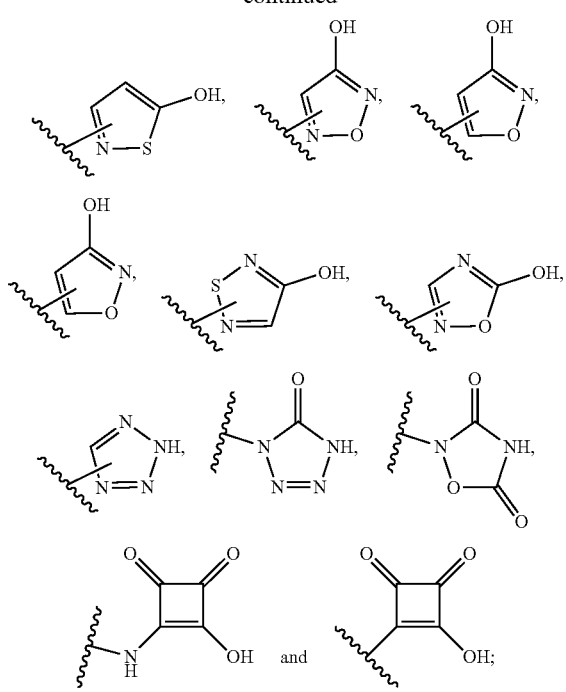
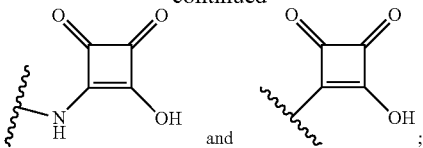

(12l) Q is selected from the group consisting of —C(O)OH, —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —C(O)R$^{2A}$, —S(O)$_2$OH, —P(O)(OH)$_2$, —C(OH)(CF$_3$)$_2$, —S(O)$_2$R$^{2A}$, —S(O)$_2$NR$^{2B}$R$^{2A}$, —C(O)NHOH, —CO(NH)CN,

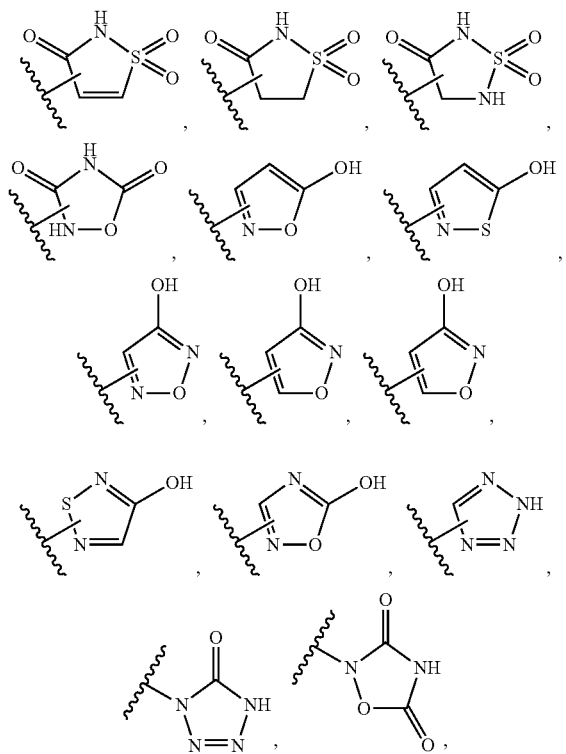

(12m) Q is selected from the group consisting of —CH$_2$OH, —C(O)OH, —C(O)OR$^{2A}$, —C(O)NR$^{2B}$R$^{2A}$, —C(O)R$^{2A}$, —S(O)$_2$OH, —P(O)(OH)$_2$, —S(O)$_2$R$^{2A}$, —S(O)$_2$NR$^{2B}$R$^{2A}$, and —C(O)NHOH;

(12n) Q is selected from —C(O)OH, —C(O)OR$^{2A}$, and —C(O)NR$^{2B}$R$^{2A}$;

(12o) Q is selected from —C(O)OH and —C(O)O(C$_1$-C$_3$ alkyl);

(12p) Q is —C(O)OH;

(12q) Q is —C(O)O(C$_1$-C$_3$ alkyl);

(12r) Q is —C(O)NR$^{2B}$R$^{2A}$, in which R$^{2A}$ is C$_1$-C$_3$ alkyl, C$_1$-C$_3$ hydroxyalkyl, C$_1$-C$_3$ aminoalkyl or C$_1$-C$_3$ thioalkyl and R$^{2B}$ is H or C$_1$-C$_3$ alkyl;

(12s) Q is —C(O)NR$^{2B}$R$^{2A}$, in which R$^{2A}$ and R$^{2B}$ come together with a nitrogen to which they are both directly bound to form a heterocycloalkyl optionally substituted with 1-3 substituents selected from C$_1$-C$_3$ alkyl, C$_1$-C$_3$ fluoroalkyl, hydroxyl, amino, thio, C$_1$-C$_3$ hydroxyalkyl, C$_1$-C$_3$ aminoalkyl, C$_1$-C$_3$ thioalkyl and —C(O)C$_1$-C$_3$ alkyl;

(12t) Q is —C(O)NR$^{2B}$R$^{2A}$, in which R$^{2A}$ is —S(O)$_{1-2}$(C$_1$-C$_3$ alkyl), —S(O)$_{1-2}$(C$_1$-C$_3$ fluoroalkyl), -or heteroaryl optionally substituted with 1-2 groups selected from substituents selected from C$_1$-C$_3$ alkyl, C$_1$-C$_3$ fluoroalkyl, hydroxyl, amino, thio, C$_1$-C$_3$ hydroxyalkyl, C$_1$-C$_3$ aminoalkyl, C$_1$-C$_3$ thioalkyl and —C(O)C$_1$-C$_3$ alkyl and R$^{2B}$ is H or C$_1$-C$_3$ alkyl.

In certain embodiments, L$^3$ is selected from one of the following groups (13j)-(13r)

(13j) L$^3$ is selected from a bond (i.e., L$^3$ is -L$^{3A}$-A$^{3A}$- wherein both A$^{3A}$ and L$^{3A}$ are a bond, or L$^3$ is -A$^{3B}$-L$^{3B}$- wherein both A$^{3B}$ and L$^{3B}$ are a bond) and optionally substituted C$_1$-C$_4$ alkylene (e.g., L$^3$ is -L$^{3A}$-A$^{3A}$- wherein A$^{3A}$ is a bond and L$^{3A}$ is and optionally substituted C$_1$-C$_4$ alkylene);

(13k) L$^3$ is a bond;

(13l) L$^3$ is optionally substituted C$_1$-C$_4$ alkylene (e.g., A$^{3A}$ is a bond and L$^{3A}$ is and optionally substituted C$_1$-C$_4$ alkylene);

(13m) L$^3$ is -L$^{3A}$-A$^{3A}$-, wherein A$^{3A}$ is a bond and L$^{3A}$ is optionally substituted C$_1$-C$_4$ alkylene, optionally substituted C$_1$-C$_4$ alkenylene or optionally substituted C$_1$-C$_4$ alkynylene;

(13n) L$^3$ is unsubstituted C$_1$-C$_4$ alkylene;

(13o) L$^3$ is C$_1$-C$_3$ alkylene, optionally substituted with a hydroxyl;

(13p) L$^3$ is —C(O)—, —S—, —S(O)$_{1-2}$—, —O—, —NR$^6$—;

(13q) L$^3$ is —CH$_2$—, —CH(CH$_3$)—, —CH$_2$CH$_2$—, —CH(CH$_3$)(OH)— or —CH(OH)—;

(13r) L$^3$ is selected from —CH$_2$—, —CH(CH$_3$)—, and —CH$_2$CH$_2$—.

In certain such embodiments, each optionally substituted alkyl, alkylene, alkenyl, alkenylene, alkynyl and alkynylene of L$^3$ (including those of R$^6$) is unsubstituted or fluorinated. For example, in certain such embodiments each optionally substituted alkyl, alkylene, alkenyl, alkenylene, alkynyl and alkynylene of L$^3$ (including those of R$^6$) is unsubstituted.

In certain embodiments, $R^3$ is selected from one of the following groups (14l)-(14v)
- (14l) $R^3$ is aryl or heteroaryl each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$;
- (14m) $R^3$ is aryl (e.g., a phenyl, a benzodioxole, or a dihydro-1H-isoquinoline) optionally substituted with 1-5 $R^{3E}$;
- (14n) $R^3$ is aryl (e.g., a phenyl, a benzodioxole, or a dihydro-1H-isoquinoline) (i) substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$;
- (14o) $R^3$ is aryl (e.g., a phenyl, a benzodioxole, or a dihydro-1H-isoquinoline) (i) substituted with a single substituent selected from -$L^{3C}$-(phenyl optionally substituted with 1-5 $R^{3D}$), -$L^{3C}$-(monocyclic heteroaryl optionally substituted with 1-5 $R^{3D}$), -$L^{3C}$-(monocyclic cycloalkyl optionally substituted with 1-5 $R^{3E}$), -$L^{3C}$-(monocyclic heterocycloalkyl optionally substituted with 1-5 $R^{3E}$) and (ii) optionally substituted with 1-5 $R^{3E}$;
- (14p) $R^3$ is as defined in (14k)-(14n), wherein the aryl is not substituted with any $R^{3E}$;
- (14q) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) optionally substituted with 1-5 $R^{3E}$;
- (14r) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$;
- (14s) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -$L^{3C}$-(phenyl optionally substituted with 1-5 $R^{3D}$), -$L^{3C}$-(monocyclic heteroaryl optionally substituted with 1-5 $R^{3D}$), -$L^{3C}$-(monocyclic cycloalkyl optionally substituted with 1-5 $R^{3E}$), -$L^{3C}$-(monocyclic heterocycloalkyl optionally substituted with 1-5 $R^{3E}$) and (ii) optionally substituted with 1-5 $R^{3E}$;
- (14t) $R^3$ is as defined in (14p)-(14r), wherein the heteroaryl is not substituted with any $R^{3E}$;
- (14u) $R^3$ is selected from the group consisting of: phenyl, benzodioxolyl, dihydro-1H-isoquinolinyl, imidazolyl, oxazolyl, isoxazolyl, isothiazolyl, thiazolyl, pyridinyl, and pyrazinyl, pyridonyl, thiadiazolyl, pyrazolopyrimidinyl, pyrazolopyridinyl, benzofuranyl, indolyl, imidazopyridinyl, pyrazolyl, triazolopyridinyl, benzimidazolyl, a benzimidazolyl, a thienyl, a benzothienyl, a furanyl and pyrimidinyl, each (i) optionally substituted with a single substituent selected from -$L^{3C}$-(aryl optionally substituted with 1-5 $R^{3D}$), -$L^{3C}$-(heteroaryl optionally substituted with 1-5 $R^{3D}$), -$L^{3C}$-(cycloalkyl optionally substituted with 1-5 $R^{3E}$), -$L^{3C}$-(heterocycloalkyl optionally substituted with 1-5 $R^{3E}$) and (ii) optionally substituted with 1-5 $R^{3E}$;
- (14v) $R^3$ is selected from the group consisting of phenyl and monocyclic heteroaryl (e.g., pyridyl, pyrazolyl), optionally substituted with 1-5 $R^{3E}$.

In certain such embodiments, each optionally substituted alkyl, alkenyl and alkynyl of $R^3$ (including those of $R^{3D}$ and $R^{3E}$) is unsubstituted or fluorinated. For example, in certain such embodiments each optionally substituted alkyl, alkenyl and alkynyl of $R^3$ (including those of $R^{3D}$ and $R^{3E}$) is unsubstituted.

In certain embodiments, $R^4$ is selected from one of the following groups (15l)-(15v)
- (15l) $R^4$ is selected from hydrogen, optionally substituted $C_1$-$C_8$ alkyl, optionally-substituted $C_1$-$C_8$ alkenyl and optionally substituted $C_1$-$C_8$ alkynyl;
- (15m) $R^4$ is selected from hydrogen, unsubstituted $C_1$-$C_8$ alkyl, unsubstituted $C_1$-$C_8$ alkenyl and unsubstituted $C_1$-$C_8$ alkynyl;
- (15n) $R^4$ is selected from hydrogen, optionally substituted $C_1$-$C_6$ alkyl, optionally-substituted $C_1$-$C_6$ alkenyl and optionally substituted $C_1$-$C_6$ alkynyl;
- (15o) $R^4$ is optionally substituted $C_1$-$C_8$ alkyl, optionally-substituted $C_1$-$C_8$ alkenyl or optionally substituted $C_1$-$C_8$ alkynyl;
- (15p) $R^4$ is selected from hydrogen, unsubstituted $C_1$-$C_6$ alkyl, optionally-substituted $C_1$-$C_8$ alkenyl, and optionally-substituted $C_1$-$C_8$ alkynyl.
- (15q) $R^4$ is selected from hydrogen, unsubstituted $C_1$-$C_6$ alkyl, unsubstituted $C_1$-$C_6$ alkenyl and unsubstituted $C_1$-$C_6$ alkynyl (for example, methyl, ethyl, propyl, butyl or pentyl);
- (15r) $R^4$ is hydrogen or optionally substituted $C_1$-$C_6$ alkyl;
- (15s) $R^4$ is hydrogen or unsubstituted $C_1$-$C_6$ alkyl;
- (15t) $R^4$ is hydrogen or optionally substituted $C_1$-$C_3$ alkyl;
- (15u) $R^4$ is hydrogen or unsubstituted $C_1$-$C_3$ alkyl;
- (15v) $R^4$ is optionally substituted $C_1$-$C_3$ alkyl;
- (15w) $R^4$ is unsubstituted $C_1$-$C_3$ alkyl;
- (15x) $R^4$ is methyl;
- (15y) $R^4$ is hydrogen.

In certain embodiments, $A^{4A}$ is selected from one of the following groups (16e)-(16h)
- (16e) $A^{4A}$ is selected from the group consisting of a bond, —C(O)—, —S—, —S(O)$_{1-2}$—, —O—, —NR$^6$—, —C(O)NR$^6$—, —NR$^6$C(O)—, and —C(O)O—;
- (16f) $A^{4A}$ is a bond;
- (16g) $A^{4A}$ is selected from the group consisting of —C(O)—, —S—, —S(O)$_{1-2}$—, —O— and —NR$^6$—;
- (16h) $A^{4A}$ is —O—.

In certain embodiments, $L^{4B}$ is selected from one of the following groups (17d)-(17f)
- (17d) $L^{4B}$ is selected from a bond and optionally substituted $C_1$-$C_4$ alkylene;
- (17e) $L^{4B}$ is a bond;
- (17f) $L^{4B}$ is optionally substituted $C_1$-$C_4$ alkylene.

In certain such embodiments, each optionally substituted alkylene of $L^{4B}$ is unsubstituted or fluorinated. For example, in certain such embodiments each optionally substituted alkylene of $L^{4B}$ is unsubstituted.

In certain embodiments, $A^{4B}$ is selected from one of the following groups (18h)-(18n)
- (18h) $A^{4A}$ is selected from the group consisting of a bond, —C(O)—, —S—, —S(O)$_{1-2}$—, —O—, —NR$^6$—, —C(O)NR$^6$—, —NR$^6$C(O)—, —OC(O)— and —C(O)O—;
- (18i) $A^{4A}$ is selected from the group consisting of —C(O)—, —S—, —S(O)$_{1-2}$—, —O—, —NR$^6$—, —C(O)NR$^6$—, —NR$^6$C(O)—, —OC(O)— and —C(O)O—;
- (18j) $A^{4A}$ is selected from the group consisting of —C(O)—, —S—, —S(O)$_{1-2}$—, —O—, and —C(O)O—;
- (18k) $A^{4A}$ is selected from —NR$^6$—, —C(O)NR$^6$— and —NR$^6$C(O)—;
- (18l) $A^{4A}$ is selected from —C(O)—, —OC(O)—, and —C(O)O—;
- (18m) $A^{4A}$ is a bond;
- (18n) $A^{4A}$ is —O—.

In certain embodiments, $L^{4A}$ is selected from one of the following groups (19k)-(19m)
- (19k) $L^{4A}$ is selected from a bond and optionally substituted $C_1$-$C_4$ alkylene;
- (19l) $L^{4A}$ is a bond;
- (19m) $L^{4A}$ is optionally substituted $C_1$-$C_4$ alkylene.

In certain such embodiments, each optionally substituted alkylene of $L^{4A}$ is unsubstituted or fluorinated. For example, in certain such embodiments each optionally substituted alkylene of $L^{4A}$ is unsubstituted.

In certain embodiments, $L^{4B}$-$A^{4B}$-$L^{4A}$-$A^{4A}$ is selected from one of the followings groups (19n)-(19v)
- (19n) $L^{4B}$-$A^{4B}$-$L^{4A}$-$A^{4A}$, wherein $A^{4A}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—; $L^{4A}$ is selected from the group consisting of a bond, unsubstituted $C_1$-$C_4$ alkylene, unsubstituted $C_1$-$C_4$ alkenylene and unsubstituted $C_1$-$C_4$ alkynylene; $A^{4B}$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—; and $L^{4B}$ is a bond;
- (19o) $L^{4B}$-$A^{4B}$-$L^{4A}$-$A^{4A}$, wherein, wherein $A^{4A}$, $L^{4A}$ and $L^{4B}$ are a bond, and wherein $A^{4B}$ are as defined in formula (I) or in (19n);
- (19p) $L^{4B}$-$A^{4B}$-$L^{4A}$-$A^{4A}$ is selected from a bond, optionally substituted $C_1$-$C_4$ alkylene, —C(O)—, —S—, —S(O)$_{1-2}$—, —O—, and —NR$^6$—;
- (19q) $L^{4B}$-$A^{4B}$-$L^{4A}$-$A^{4A}$ is selected from a bond, —CH$_2$—, —CH(CH$_3$)—, —CH$_2$CH$_2$—, —C(O)—, —S—, —S(O)$_{1-2}$—, —O—, and —NR$^6$— (e.g., a bond);
- (19r) $L^{4B}$-$A^{4B}$-$L^{4A}$-$A^{4A}$ is —O— or —S—;
- (19s) $L^{4B}$-$A^{4B}$-$L^{4A}$-$A^{4A}$ is unsubstituted $C_1$-$C_4$ alkylene;
- (19t) $L^{4B}$-$A^{4B}$-$L^{4A}$-$A^{4A}$ is selected from —C(O)—, —S(O)— and —S(O)$_2$—;
- (19u) $L^{4B}$-$A^{4B}$-$L^{4A}$-$A^{4A}$ is selected from —CH$_2$—, —CH(CH$_3$)—, and —CH$_2$CH$_2$—;
- (19v) $L^{4B}$-$A^{4B}$-$L^{4A}$-$A^{4A}$ is a bond.

In certain such embodiments, each optionally substituted alkyl, alkylene, alkenyl, alkenylene, alkynyl and alkynylene of $L^{4B}$-$A^{4B}$-$L^{4A}$-$A^{4A}$ (including those of $R^6$) is unsubstituted or fluorinated. For example, in certain such embodiments each optionally substituted alkyl, alkylene, alkenyl, alkenylene, alkynyl and alkynylene of $L^{4B}$-$A^{4B}$-$L^{4A}$-$A^{4A}$ (including those of $R^6$) is unsubstituted.

In certain embodiments, $L^5$ is selected from one of the following groups (20q)-(20l)
- (20g) $L^5$ is selected from a bond (i.e., $L^5$ is -$L^{5A}$-$A^{5A}$- wherein both $A^{5A}$ and $L^{5A}$ are a bond, or $L^5$ is -$A^{5B}$-$L^{5B}$- wherein both $A^{5B}$ and $L^{5B}$ are a bond) and optionally substituted $C_1$-$C_4$ alkylene (e.g., $L^5$ is -$L^{5A}$-$A^{5A}$- wherein $A^{5A}$ is a bond and $L^{5A}$ is and optionally substituted $C_1$-$C_4$ alkylene);
- (20h) $L^5$ is a bond (e.g., both $A^{5A}$ and $L^{5A}$ are a bond);
- (20i) $L^5$ is selected from the group consisting of —C(O)—, —S—, —S(O)$_{1-2}$—, —O— and —NR$^6$—;
- (20j) $L^5$ is selected from the group consisting of a bond, —CH$_2$—, —CH(CH$_3$)—, —CH$_2$CH$_2$—, —CH=CH—, —C≡C—, —C(O)—, —S—, —S(O)$_{1-2}$—, —O—, and —C(O)O— (e.g., a bond);
- (20k) $L^5$ is selected from —S— and —O—;
- (20l) $L^5$ is selected from —C(O)—, —S(O)$_{1-2}$—, and —C(O)O—.

In certain such embodiments, each optionally substituted alkyl, alkylene, alkenyl, alkenylene, alkynyl and alkynylene of $L^5$ (including those of $R^6$) is unsubstituted or fluorinated. For example, in certain such embodiments each optionally substituted alkyl, alkylene, alkenyl, alkenylene, alkynyl and alkynylene of $L^5$ (including those of $R^6$) is unsubstituted.

In certain embodiments, $R^5$ is selected from one of the following groups (21h)-(21n)
- (21h) $R^5$ is aryl (e.g., phenyl) (i) optionally substituted with a single substituent selected from -$L^{5C}$-(aryl optionally substituted with 1-5 $R^{5D}$), -$L^{5C}$-(heteroaryl optionally substituted with 1-5 $R^{5D}$), -$L^{5C}$-(cycloalkyl optionally substituted with 1-5 $R^{5E}$), -$L^{5C}$-(heterocycloalkyl optionally substituted with 1-5 $R^{5E}$) and (ii) optionally substituted with 1-5 $R^{5E}$;
- (21i) $R^5$ is aryl (e.g., phenyl) optionally substituted with 1-5 $R^{5E}$;
- (21j) $R^5$ is phenyl, optionally substituted with 1-5 $R^{5E}$, wherein each $R^{5E}$ is independently selected from optionally-substituted $C_1$-$C_4$ alkyl, $C_1$-$C_4$ fluoroalkyl, halogen, —OR$^{5F}$, and —NR$^{5G}$R$^{5F}$;
- (21k) $R^5$ is heteroaryl (e.g., an isoxazolyl, a pyridyl, an imidazopyridyl, a pyrazolyl, a benzoxazole, an indolyl, a pyrimidinyl) (i) optionally substituted with a single substituent selected from -$L^{5C}$-(aryl optionally substituted with 1-5 $R^{5D}$), -$L^{5C}$-(heteroaryl optionally substituted with 1-5 $R^{5D}$), -$L^{5C}$-(cycloalkyl optionally substituted with 1-5 $R^{5E}$), -$L^{5C}$-(heterocycloalkyl optionally substituted with 1-5 $R^{5E}$) and (ii) optionally substituted with 1-5 $R^{5E}$;
- (21l) $R^5$ is heteroaryl (e.g., an isoxazolyl, a pyridyl, an imidazopyridyl, a pyrazolyl) optionally substituted with 1-5 $R^{5E}$;
- (21m) $R^5$ is selected from the group consisting of phenyl, isoxazolyl, pyridyl, imidazopyridyl, and pyrazolyl, each (i) optionally substituted with a single substituent selected from -$L^{5C}$-(aryl optionally substituted with 1-5 $R^{5D}$), -$L^{5C}$-(heteroaryl optionally substituted with 1-5 $R^{5D}$), -$L^{5C}$-(cycloalkyl optionally substituted with 1-5 $R^{5E}$), -$L^{5C}$-(heterocycloalkyl optionally substituted with 1-5 $R^{5E}$) and (ii) optionally substituted with 1-5 $R^{5E}$;

(21n) $R^5$ is selected from the group consisting of phenyl, isoxazolyl, pyridyl, imidazopyridyl, and pyrazolyl, each optionally substituted with 1-5 $R^{5E}$.

In certain such embodiments, each optionally substituted alkyl, alkenyl and alkynyl of $R^5$ (including those of $R^{5D}$ and $R^{5E}$) is unsubstituted or fluorinated. For example, in certain such embodiments each optionally substituted alkyl, alkenyl and alkynyl of $R^5$ (including those of $R^{5D}$ and $R^{5E}$) is unsubstituted.

Various particular embodiments nos. 141-268 of the compounds of the disclosure include compounds of formula (I), each as defined in each of the following rows (or a pharmaceutically acceptable salt or N-oxide thereof, or a solvate or hydrate thereof), wherein each entry is a group number as defined above:

| | I | $L^{1\dagger}$ | $R^1$ | $L^2$ | Q | $L^3$ | $R^3$ | $L^{4\dagger\dagger}$ | $R^4$ | $L^5$ | $R^5$ |
|---|---|---|---|---|---|---|---|---|---|---|---|
| 141 | (Ig) | (10r) | (6o) | (11h) | (12n) | (13k) | (14l) | (19v) | (15l) | (20h) | (21h), (21k) |
| 142 | (Ig) | (10r) | (6o) | (11h) | (12n) | (13k) | (14l) | (19v) | (15l) | (20h) | (21j) |
| 143 | (Ig) | (10r) | (6o) | (11h) | (12n) | (13k) | (14l) | (19v) | (15s) | (20h) | (21h), (21k) |
| 144 | (Ig) | (10r) | (6o) | (11h) | (12n) | (13k) | (14l) | (19v) | (15s) | (20h) | (21j) |
| 145 | (Ig) | (10r) | (6o) | (11h) | (12n) | (13k) | (14v) | (19v) | (15l) | (20h) | (21h), (21k) |
| 146 | (Ig) | (10r) | (6o) | (11h) | (12n) | (13k) | (14v) | (19v) | (15l) | (20h) | (21j) |
| 147 | (Ig) | (10r) | (6o) | (11h) | (12n) | (13k) | (14v) | (19v) | (15s) | (20h) | (21h), (21k) |
| 148 | (Ig) | (10r) | (6o) | (11h) | (12n) | (13k) | (14v) | (19v) | (15s) | (20h) | (21j) |
| 149 | (Ig) | (10r) | (6o) | (11h) | (12p) | (13k) | (14l) | (19v) | (15l) | (20h) | (21h), (21k) |
| 150 | (Ig) | (10r) | (6o) | (11h) | (12p) | (13k) | (14l) | (19v) | (15l) | (20h) | (21j) |
| 151 | (Ig) | (10r) | (6o) | (11h) | (12p) | (13k) | (14l) | (19v) | (15s) | (20h) | (21h), (21k) |
| 152 | (Ig) | (10r) | (6o) | (11h) | (12p) | (13k) | (14l) | (19v) | (15s) | (20h) | (21j) |
| 153 | (Ig) | (10r) | (6o) | (11h) | (12p) | (13k) | (14v) | (19v) | (15l) | (20h) | (21h), (21k) |
| 154 | (Ig) | (10r) | (6o) | (11h) | (12p) | (13k) | (14v) | (19v) | (15l) | (20h) | (21j) |
| 155 | (Ig) | (10r) | (6o) | (11h) | (12p) | (13k) | (14v) | (19v) | (15s) | (20h) | (21h), (21k) |
| 156 | (Ig) | (10r) | (6o) | (11h) | (12p) | (13k) | (14v) | (19v) | (15s) | (20h) | (21j) |
| 157 | (Ig) | (10r) | (6l) | (11h) | (12n) | (13k) | (14l) | (19v) | (15l) | (20h) | (21h), (21k) |
| 158 | (Ig) | (10r) | (6l) | (11h) | (12n) | (13k) | (14l) | (19v) | (15l) | (20h) | (21j) |
| 159 | (Ig) | (10r) | (6l) | (11h) | (12n) | (13k) | (14l) | (19v) | (15s) | (20h) | (21h), (21k) |
| 160 | (Ig) | (10r) | (6l) | (11h) | (12n) | (13k) | (14l) | (19v) | (15s) | (20h) | (21j) |
| 161 | (Ig) | (10r) | (6l) | (11h) | (12n) | (13k) | (14v) | (19v) | (15l) | (20h) | (21h), (21k) |
| 162 | (Ig) | (10r) | (6l) | (11h) | (12n) | (13k) | (14v) | (19v) | (15l) | (20h) | (21j) |
| 163 | (Ig) | (10r) | (6l) | (11h) | (12n) | (13k) | (14v) | (19v) | (15s) | (20h) | (21h), (21k) |
| 164 | (Ig) | (10r) | (6l) | (11h) | (12n) | (13k) | (14v) | (19v) | (15s) | (20h) | (21j) |
| 165 | (Ig) | (10r) | (6l) | (11h) | (12p) | (13k) | (14l) | (19v) | (15l) | (20h) | (21h), (21k) |
| 166 | (Ig) | (10r) | (6l) | (11h) | (12p) | (13k) | (14l) | (19v) | (15l) | (20h) | (21j) |
| 167 | (Ig) | (10r) | (6l) | (11h) | (12p) | (13k) | (14l) | (19v) | (15s) | (20h) | (21h), (21k) |
| 168 | (Ig) | (10r) | (6l) | (11h) | (12p) | (13k) | (14l) | (19v) | (15s) | (20h) | (21j) |
| 169 | (Ig) | (10r) | (6l) | (11h) | (12p) | (13k) | (14v) | (19v) | (15l) | (20h) | (21h), (21k) |
| 170 | (Ig) | (10r) | (6l) | (11h) | (12p) | (13k) | (14v) | (19v) | (15l) | (20h) | (21j) |
| 171 | (Ig) | (10r) | (6l) | (11h) | (12p) | (13k) | (14v) | (19v) | (15s) | (20h) | (21h), (21k) |
| 172 | (Ig) | (10r) | (6l) | (11h) | (12p) | (13k) | (14v) | (19v) | (15s) | (20h) | (21j) |
| 173 | (Ig) | (10q) | (6o) | (11h) | (12n) | (13k) | (14l) | (19v) | (15l) | (20h) | (21h), (21k) |
| 174 | (Ig) | (10q) | (6o) | (11h) | (12n) | (13k) | (14l) | (19v) | (15l) | (20h) | (21j) |
| 175 | (Ig) | (10q) | (6o) | (11h) | (12n) | (13k) | (14l) | (19v) | (15s) | (20h) | (21h), (21k) |
| 176 | (Ig) | (10q) | (6o) | (11h) | (12n) | (13k) | (14l) | (19v) | (15s) | (20h) | (21j) |
| 177 | (Ig) | (10q) | (6o) | (11h) | (12n) | (13k) | (14v) | (19v) | (15l) | (20h) | (21h), (21k) |
| 178 | (Ig) | (10q) | (6o) | (11h) | (12n) | (13k) | (14v) | (19v) | (15l) | (20h) | (21j) |
| 179 | (Ig) | (10q) | (6o) | (11h) | (12n) | (13k) | (14v) | (19v) | (15s) | (20h) | (21h), (21k) |
| 180 | (Ig) | (10q) | (6o) | (11h) | (12n) | (13k) | (14v) | (19v) | (15s) | (20h) | (21j) |
| 181 | (Ig) | (10q) | (6o) | (11h) | (12p) | (13k) | (14l) | (19v) | (15l) | (20h) | (21h), (21k) |
| 182 | (Ig) | (10q) | (6o) | (11h) | (12p) | (13k) | (14l) | (19v) | (15l) | (20h) | (21j) |
| 183 | (Ig) | (10q) | (6o) | (11h) | (12p) | (13k) | (14l) | (19v) | (15s) | (20h) | (21h), (21k) |
| 184 | (Ig) | (10q) | (6o) | (11h) | (12p) | (13k) | (14l) | (19v) | (15s) | (20h) | (21j) |
| 185 | (Ig) | (10q) | (6o) | (11h) | (12p) | (13k) | (14v) | (19v) | (15l) | (20h) | (21h), (21k) |
| 186 | (Ig) | (10q) | (6o) | (11h) | (12p) | (13k) | (14v) | (19v) | (15l) | (20h) | (21j) |
| 187 | (Ig) | (10q) | (6o) | (11h) | (12p) | (13k) | (14v) | (19v) | (15s) | (20h) | (21h), (21k) |
| 188 | (Ig) | (10q) | (6o) | (11h) | (12p) | (13k) | (14v) | (19v) | (15s) | (20h) | (21j) |
| 189 | (Ig) | (10q) | (6l) | (11h) | (12n) | (13k) | (14l) | (19v) | (15l) | (20h) | (21h), (21k) |
| 190 | (Ig) | (10q) | (6l) | (11h) | (12n) | (13k) | (14l) | (19v) | (15l) | (20h) | (21j) |
| 191 | (Ig) | (10q) | (6l) | (11h) | (12n) | (13k) | (14l) | (19v) | (15s) | (20h) | (21h), (21k) |
| 192 | (Ig) | (10q) | (6l) | (11h) | (12n) | (13k) | (14l) | (19v) | (15s) | (20h) | (21j) |
| 193 | (Ig) | (10q) | (6l) | (11h) | (12n) | (13k) | (14v) | (19v) | (15l) | (20h) | (21h), (21k) |
| 194 | (Ig) | (10q) | (6l) | (11h) | (12n) | (13k) | (14v) | (19v) | (15l) | (20h) | (21j) |
| 195 | (Ig) | (10q) | (6l) | (11h) | (12n) | (13k) | (14v) | (19v) | (15s) | (20h) | (21h), (21k) |
| 196 | (Ig) | (10q) | (6l) | (11h) | (12n) | (13k) | (14v) | (19v) | (15s) | (20h) | (21j) |
| 197 | (Ig) | (10q) | (6l) | (11h) | (12p) | (13k) | (14l) | (19v) | (15l) | (20h) | (21h), (21k) |
| 198 | (Ig) | (10q) | (6l) | (11h) | (12p) | (13k) | (14l) | (19v) | (15l) | (20h) | (21j) |
| 199 | (Ig) | (10q) | (6l) | (11h) | (12p) | (13k) | (14l) | (19v) | (15s) | (20h) | (21h), (21k) |
| 200 | (Ig) | (10q) | (6l) | (11h) | (12p) | (13k) | (14l) | (19v) | (15s) | (20h) | (21j) |
| 201 | (Ig) | (10q) | (6l) | (11h) | (12p) | (13k) | (14v) | (19v) | (15l) | (20h) | (21h), (21k) |
| 202 | (Ig) | (10q) | (6l) | (11h) | (12p) | (13k) | (14v) | (19v) | (15l) | (20h) | (21j) |
| 203 | (Ig) | (10q) | (6l) | (11h) | (12p) | (13k) | (14v) | (19v) | (15s) | (20h) | (21h), (21k) |
| 204 | (Ig) | (10q) | (6l) | (11h) | (12p) | (13k) | (14v) | (19v) | (15s) | (20h) | (21j) |
| 205 | (Ih) | (10r) | (6o) | (11h) | (12n) | (13k) | (14l) | (19v) | (15l) | (20h) | (21h), (21k) |
| 206 | (Ih) | (10r) | (6o) | (11h) | (12n) | (13k) | (14l) | (19v) | (15l) | (20h) | (21j) |
| 207 | (Ih) | (10r) | (6o) | (11h) | (12n) | (13k) | (14l) | (19v) | (15s) | (20h) | (21h), (21k) |

| | I | L¹† | R¹ | L² | Q | L³ | R³ | L⁴†† | R⁴ | L⁵ | R⁵ |
|---|---|---|---|---|---|---|---|---|---|---|---|
| 208 | (Ih) | (10r) | (6o) | (11h) | (12n) | (13k) | (14l) | (19v) | (15s) | (20h) | (21j) |
| 209 | (Ih) | (10r) | (6o) | (11h) | (12n) | (13k) | (14v) | (19v) | (15l) | (20h) | (21h), (21k) |
| 210 | (Ih) | (10r) | (6o) | (11h) | (12n) | (13k) | (14v) | (19v) | (15l) | (20h) | (21j) |
| 211 | (Ih) | (10r) | (6o) | (11h) | (12n) | (13k) | (14v) | (19v) | (15s) | (20h) | (21h), (21k) |
| 212 | (Ih) | (10r) | (6o) | (11h) | (12n) | (13k) | (14v) | (19v) | (15s) | (20h) | (21j) |
| 213 | (Ih) | (10r) | (6o) | (11h) | (12p) | (13k) | (14l) | (19v) | (15l) | (20h) | (21h), (21k) |
| 214 | (Ih) | (10r) | (6o) | (11h) | (12p) | (13k) | (14l) | (19v) | (15l) | (20h) | (21j) |
| 215 | (Ih) | (10r) | (6o) | (11h) | (12p) | (13k) | (14l) | (19v) | (15s) | (20h) | (21h), (21k) |
| 216 | (Ih) | (10r) | (6o) | (11h) | (12p) | (13k) | (14l) | (19v) | (15s) | (20h) | (21j) |
| 217 | (Ih) | (10r) | (6o) | (11h) | (12p) | (13k) | (14v) | (19v) | (15l) | (20h) | (21h), (21k) |
| 218 | (Ih) | (10r) | (6o) | (11h) | (12p) | (13k) | (14v) | (19v) | (15l) | (20h) | (21j) |
| 219 | (Ih) | (10r) | (6o) | (11h) | (12p) | (13k) | (14v) | (19v) | (15s) | (20h) | (21h), (21k) |
| 220 | (Ih) | (10r) | (6o) | (11h) | (12p) | (13k) | (14v) | (19v) | (15s) | (20h) | (21j) |
| 221 | (Ih) | (10r) | (6l) | (11h) | (12n) | (13k) | (14l) | (19v) | (15l) | (20h) | (21h), (21k) |
| 222 | (Ih) | (10r) | (6l) | (11h) | (12n) | (13k) | (14l) | (19v) | (15l) | (20h) | (21j) |
| 223 | (Ih) | (10r) | (6l) | (11h) | (12n) | (13k) | (14l) | (19v) | (15s) | (20h) | (21h), (21k) |
| 224 | (Ih) | (10r) | (6l) | (11h) | (12n) | (13k) | (14l) | (19v) | (15s) | (20h) | (21j) |
| 225 | (Ih) | (10r) | (6l) | (11h) | (12n) | (13k) | (14v) | (19v) | (15l) | (20h) | (21h), (21k) |
| 226 | (Ih) | (10r) | (6l) | (11h) | (12n) | (13k) | (14v) | (19v) | (15l) | (20h) | (21j) |
| 227 | (Ih) | (10r) | (6l) | (11h) | (12n) | (13k) | (14v) | (19v) | (15s) | (20h) | (21h), (21k) |
| 228 | (Ih) | (10r) | (6l) | (11h) | (12n) | (13k) | (14v) | (19v) | (15s) | (20h) | (21j) |
| 229 | (Ih) | (10r) | (6l) | (11h) | (12p) | (13k) | (14l) | (19v) | (15l) | (20h) | (21h), (21k) |
| 230 | (Ih) | (10r) | (6l) | (11h) | (12p) | (13k) | (14l) | (19v) | (15l) | (20h) | (21j) |
| 231 | (Ih) | (10r) | (6l) | (11h) | (12p) | (13k) | (14l) | (19v) | (15s) | (20h) | (21h), (21k) |
| 232 | (Ih) | (10r) | (6l) | (11h) | (12p) | (13k) | (14l) | (19v) | (15s) | (20h) | (21j) |
| 233 | (Ih) | (10r) | (6l) | (11h) | (12p) | (13k) | (14v) | (19v) | (15l) | (20h) | (21h), (21k) |
| 234 | (Ih) | (10r) | (6l) | (11h) | (12p) | (13k) | (14v) | (19v) | (15l) | (20h) | (21j) |
| 235 | (Ih) | (10r) | (6l) | (11h) | (12p) | (13k) | (14v) | (19v) | (15s) | (20h) | (21h), (21k) |
| 236 | (Ih) | (10r) | (6l) | (11h) | (12p) | (13k) | (14v) | (19v) | (15s) | (20h) | (21j) |
| 237 | (Ih) | (10q) | (6o) | (11h) | (12n) | (13k) | (14l) | (19v) | (15l) | (20h) | (21h), (21k) |
| 238 | (Ih) | (10q) | (6o) | (11h) | (12n) | (13k) | (14l) | (19v) | (15l) | (20h) | (21j) |
| 239 | (Ih) | (10q) | (6o) | (11h) | (12n) | (13k) | (14l) | (19v) | (15s) | (20h) | (21h), (21k) |
| 240 | (Ih) | (10q) | (6o) | (11h) | (12n) | (13k) | (14l) | (19v) | (15s) | (20h) | (21j) |
| 241 | (Ih) | (10q) | (6o) | (11h) | (12n) | (13k) | (14v) | (19v) | (15l) | (20h) | (21h), (21k) |
| 242 | (Ih) | (10q) | (6o) | (11h) | (12n) | (13k) | (14v) | (19v) | (15l) | (20h) | (21j) |
| 243 | (Ih) | (10q) | (6o) | (11h) | (12n) | (13k) | (14v) | (19v) | (15s) | (20h) | (21h), (21k) |
| 244 | (Ih) | (10q) | (6o) | (11h) | (12n) | (13k) | (14v) | (19v) | (15s) | (20h) | (21j) |
| 245 | (Ih) | (10q) | (6o) | (11h) | (12p) | (13k) | (14l) | (19v) | (15l) | (20h) | (21h), (21k) |
| 246 | (Ih) | (10q) | (6o) | (11h) | (12p) | (13k) | (14l) | (19v) | (15l) | (20h) | (21j) |
| 247 | (Ih) | (10q) | (6o) | (11h) | (12p) | (13k) | (14l) | (19v) | (15s) | (20h) | (21h), (21k) |
| 248 | (Ih) | (10q) | (6o) | (11h) | (12p) | (13k) | (14l) | (19v) | (15s) | (20h) | (21j) |
| 249 | (Ih) | (10q) | (6o) | (11h) | (12p) | (13k) | (14v) | (19v) | (15l) | (20h) | (21h), (21k) |
| 250 | (Ih) | (10q) | (6o) | (11h) | (12p) | (13k) | (14v) | (19v) | (15l) | (20h) | (21j) |
| 251 | (Ih) | (10q) | (6o) | (11h) | (12p) | (13k) | (14v) | (19v) | (15s) | (20h) | (21h), (21k) |
| 252 | (Ih) | (10q) | (6o) | (11h) | (12p) | (13k) | (14v) | (19v) | (15s) | (20h) | (21j) |
| 253 | (Ih) | (10q) | (6l) | (11h) | (12n) | (13k) | (14l) | (19v) | (15l) | (20h) | (21h), (21k) |
| 254 | (Ih) | (10q) | (6l) | (11h) | (12n) | (13k) | (14l) | (19v) | (15l) | (20h) | (21j) |
| 255 | (Ih) | (10q) | (6l) | (11h) | (12n) | (13k) | (14l) | (19v) | (15s) | (20h) | (21h), (21k) |
| 256 | (Ih) | (10q) | (6l) | (11h) | (12n) | (13k) | (14l) | (19v) | (15s) | (20h) | (21j) |
| 257 | (Ih) | (10q) | (6l) | (11h) | (12n) | (13k) | (14v) | (19v) | (15l) | (20h) | (21h), (21k) |
| 258 | (Ih) | (10q) | (6l) | (11h) | (12n) | (13k) | (14v) | (19v) | (15l) | (20h) | (21j) |
| 259 | (Ih) | (10q) | (6l) | (11h) | (12n) | (13k) | (14v) | (19v) | (15s) | (20h) | (21h), (21k) |
| 260 | (Ih) | (10q) | (6l) | (11h) | (12n) | (13k) | (14v) | (19v) | (15s) | (20h) | (21j) |
| 261 | (Ih) | (10q) | (6l) | (11h) | (12p) | (13k) | (14l) | (19v) | (15l) | (20h) | (21h), (21k) |
| 262 | (Ih) | (10q) | (6l) | (11h) | (12p) | (13k) | (14l) | (19v) | (15l) | (20h) | (21j) |
| 263 | (Ih) | (10q) | (6l) | (11h) | (12p) | (13k) | (14l) | (19v) | (15s) | (20h) | (21h), (21k) |
| 264 | (Ih) | (10q) | (6l) | (11h) | (12p) | (13k) | (14l) | (19v) | (15s) | (20h) | (21j) |
| 265 | (Ih) | (10q) | (6l) | (11h) | (12p) | (13k) | (14v) | (19v) | (15l) | (20h) | (21h), (21k) |
| 266 | (Ih) | (10q) | (6l) | (11h) | (12p) | (13k) | (14v) | (19v) | (15l) | (20h) | (21j) |
| 267 | (Ih) | (10q) | (6l) | (11h) | (12p) | (13k) | (14v) | (19v) | (15s) | (20h) | (21h), (21k) |
| 268 | (Ih) | (10q) | (6l) | (11h) | (12p) | (13k) | (14v) | (19v) | (15s) | (20h) | (21j) |

†L¹ is $A^{1A}$-$L^{1A}$-$A^{1B}$-$L^{1B}$
††L⁴ is $L^{4B}$-$A^{4B}$-$L^{4A}$-$A^{4A}$

In certain embodiments, the disclosure provides compounds of any of formula (Ik), (Im), (In) or (Io) below:

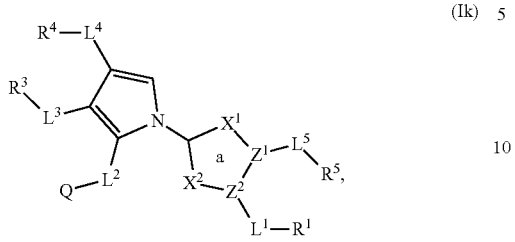
(Ik)

in which formula (Ik) the ring system denoted by "a" is heteroaromatic,

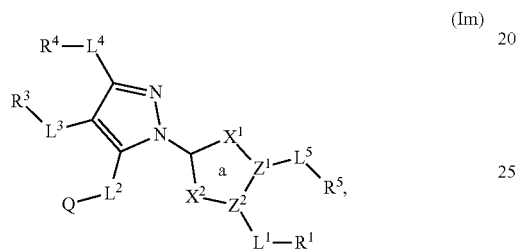
(Im)

in which formula (Im) the ring system denoted by "a" is heteroaromatic,

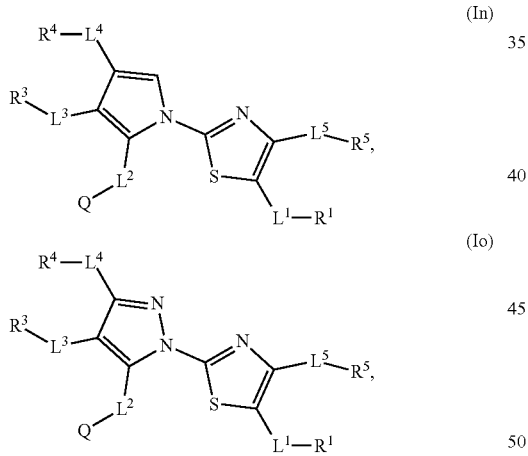
(In)

(Io)

optionally in the form of a pharmaceutically acceptable salt or N-oxide, or a solvate or hydrate, wherein $L^1$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

$R^1$ is selected from the group consisting of
hydrogen,
$C_1$-$C_8$ alkyl, $C_1$-$C_8$ alkenyl and $C_1$-$C_8$ alkynyl, each unsubstituted or fluorinated, cycloalkyl and heterocycloalkyl, each optionally substituted with 1-2 $R^{1E}$, and aryl and heteroaryl, each optionally substituted with 1-5 $R^{1E}$, in which
  each $R^{1E}$ is independently selected from oxo, optionally-substituted $C_1$-$C_4$ alkyl, $C_1$-$C_4$ fluoroalkyl, halogen, —CN, SF$_5$, —N$_3$, —C(O)R$^{1F}$, —SR$^{1F}$, —S(O)$_{1-2}$R$^{1F}$, —OR$^{1F}$, —NR$^{1G}$R$^{1F}$ and —C(O)R$^{1F}$;
  each $R^{1F}$ is independently selected from H, $C_1$-$C_3$ alkyl and $C_1$-$C_3$ fluoroalkyl and
  each $R^{1G}$ is independently selected from H and $C_1$-$C_3$ alkyl, or
or $A^{1A}$, $L^{1A}$, $A^{1B}$, $A^{1B}$, and $R^1$ are absent;

$L^2$ is selected from the group consisting of a bond, —CH$_2$—, —CH(CH$_3$)— or —CH$_2$CH$_2$—;

Q is selected from the group consisting of H, —CH$_2$OH, —C(O)OH, —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —C(O)R$^{2A}$, —S(O)$_2$OH, —P(O)(OH)$_2$, —C(OH)(CF$_3$)$_2$, S(O)$_2$ R$^{2A}$, —N(R$^{2B}$)S(O)$_2$R$^{2A}$, —S(O)$_2$NR$^{2B}$R$^{2A}$, —C(O)NHOH, —C(O)NH—O($C_1$-$C_3$ alkyl), and —CO(NH)CN, in which
  each $R^{2A}$ is independently selected from H and $C_1$-$C_3$ alkyl, and
  each $R^{2B}$ is independently selected from H and $C_1$-$C_3$ alkyl;

$L^3$ is a bond, —C(O)—, —S—, —S(O)$_{1-2}$—, —O—, —NR$^6$—, —CH$_2$—, —CH(CH$_3$)(OH)— or —CH(OH)—;

$R^3$ is aryl or heteroaryl each (i) optionally substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$,
in which
  each $L^{3C}$ is a bond, methylene, ethylene, —C(O)—, —S—, —S(O)$_{1-2}$—, —O— or —NR$^{3G}$—;
  each $R^{3D}$ is independently selected from optionally-substituted $C_1$-$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$ and —NR$^{3G}$S(O)$_{1-2}$R$^{3F}$;
  each $R^{3E}$ is independently selected from oxo, optionally-substituted $C_1$-$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$;
  each $R^{3F}$ is independently selected from H, $C_1$-$C_3$ alkyl and $C_1$-$C_3$ fluoroalkyl and
  each $R^{3G}$ is independently selected from H and $C_1$-$C_3$ alkyl, $C_1$-$C_3$ fluoroalkyl;

$L^4$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$— and —NR$^6$S(O)$_{1-2}$—;

R$^4$ is selected from the group consisting of hydrogen, optionally substituted C$_1$-C$_8$ alkyl, optionally-substituted C$_1$-C$_8$ alkenyl and optionally substituted C$_1$-C$_8$ alkynyl, L$^5$ is a bond, —C(O)—, —S—, —S(O)$_{1-2}$—, —O—, —NR$^6$—, —CH$_2$CH$_2$—, —CH═CH—, —C≡C—, —CH$_2$—, —CH(CH$_3$)(OH)— or —CH(OH)—;

R$^5$ is aryl, heteroaryl, cycloalkyl or heterocycloalkyl, each optionally substituted with 1-5 R$^{5E}$,
  in which
    each R$^{5E}$ is independently selected from oxo, optionally-substituted C$_1$-C$_4$ alkyl, C$_1$-C$_4$ fluoroalkyl, halogen, —CN, —SF$_5$, —N$_3$, —C(O)R$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{6G}$R$^{5F}$, —NR$^{1G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^F$, —S(O)$_{1-2}$OR$^{5F}$, —OS(O)$_{1-2}$R$^{5F}$, —S(O)$_{1-2}$NR$^{5G}$R$^{5F}$ and —NR$^{5G}$S(O)$_{1-2}$R$^{5F}$;
    each R$^{5F}$ is independently selected from H, C$_1$-C$_3$ alkyl and C$_1$-C$_3$ fluoroalkyl and
    each R$^{5G}$ is independently selected from H and C$_1$-C$_3$ alkyl;

Y is CR$^Y$ or N, in which R$^Y$ is selected from the group consisting of hydrogen, C$_1$-C$_3$ alkyl and C$_1$-C$_3$ fluoroalkyl;

X$^1$ is selected from the group consisting of CR$^{XA}$, S, O, NRX$^B$ and N and X$^2$ is selected from the group consisting of CR$^{XA}$, S, O, NRX$^B$ and N in which
  each R$^{XA}$ is independently selected from the group consisting of hydrogen, C$_1$-C$_4$ alkyl and C$_1$-C$_4$ fluoroalkyl; and
  each R$^{XB}$ is independently selected from the group consisting of hydrogen, C$_1$-C$_4$ alkyl and C$_1$-C$_4$ fluoroalkyl, C$_1$-C$_4$ alkyl-C(O)—, C$_1$-C$_4$ alkyl-S(O)$_{1-2}$—;

Z$^1$ and Z$^2$ are independently selected from C and N;
wherein
when Z$^1$ is N and is bound in the ring system denoted by "a" by a double bond, A$^{1A}$, L$^{1A}$, A$^{1B}$, A$^{1B}$, and R$^1$ are absent;

each R$^6$ is selected from the group consisting of hydrogen, C$_1$-C$_3$ alkyl and —C(O)(C$_1$-C$_3$ alkyl);

each optionally substituted alkyl, alkenyl and alkynyl is unsubstituted, fluorinated or substituted with one or two hydroxyl groups;

each cycloalkyl has 3-10 ring carbons and is unsaturated or partially unsaturated, and optionally includes one or two fused cycloalkyl rings, each fused ring having 3-8 ring members;

each heterocycloalkyl has 3-10 ring members and 1-3 heteroatoms independently selected from nitrogen, oxygen and sulfur and is unsaturated or partially unsaturated, and optionally includes one or two fused cycloalkyl rings, each having 3-8 ring members;

each aryl is a phenyl or a naphthyl, and optionally includes one or two fused cycloalkyl or heterocycloalkyl rings, each fused cycloalkyl or heterocycloalkyl ring having 4-8 ring members;

each heteroaryl is a 5-6 membered monocyclic heteroaryl ring having 1-4 heteroatoms independently selected from nitrogen, oxygen and sulfur or a 8-10 membered bicyclic heteroaryl having 1-5 heteroatoms independently selected from nitrogen, oxygen or sulfur, and optionally includes one or two fused cycloalkyl or heterocycloalkyl rings, each fused cycloalkyl or heterocycloalkyl ring having 4-8 ring members.

In certain such embodiments, each and every optionally substituted alkyl, alkylene, alkenyl, alkenylene, alkynyl and alkynylene is unsubstituted or fluorinated. For example, in certain such embodiments, each and every optionally substituted alkyl, alkylene, alkenyl, alkenylene, alkynyl and alkynylene is unsubstituted.

The disclosure also provides a variety of subgenera of compounds of any of formulae (1k)-(1o) in which R$^1$, L$^1$, L$^2$, Q, L$^3$, R$^3$, L$^4$, R$^4$, L$^5$, and R$^5$ are optionally independently selected from the groups (6q) et seq., (10w) et seq., (11i) et seq., (12u) et seq., (13s) et seq., (14w) et seq., (15z) et seq., (19w) et seq., (20m) et seq., and (21o) et seq. defined hereinbelow (e.g., wherein the compound is as defined in any combination of the embodiments below):

In certain embodiments, the compound is one of the following structural formulae:
  (Ik);
  (Im);
  (In);
  (Io).

In certain embodiments, R$^1$ is selected from one of the following groups (6q)-(6u)
  (6q) R$^1$ is selected from the group consisting of hydrogen, optionally substituted C$_1$-C$_8$ alkyl and cycloalkyl optionally substituted with 1-5 R$^{1E}$;
  (6r) R$^1$ is hydrogen;
  (6s) R$^1$ is optionally substituted C$_1$-C$_8$ alkyl;
  (6t) R$^1$ is unsubstituted C$_1$-C$_8$ alkyl or fluorinated C$_1$-C$_8$ alkyl;
  (6u) R$^1$ is unsubstituted cycloalkyl;

In certain such embodiments, each optionally substituted alkyl of R$^1$ (including those of R$^{1E}$) is unsubstituted or fluorinated. For example, in certain such embodiments each optionally substituted alkyl, alkenyl and alkynyl of R$^1$ (including those of R$^{1E}$) is unsubstituted.

In certain embodiments, is selected from one of the following groups (10w)-(10y)
  (10w) L$^1$ is a bond, —S—, —S(O)— or —S(O)$_2$—;
  (10x) L$^1$ is selected from a bond, —CH$_2$—, —CH(CH$_3$)—, —CH$_2$CH$_2$—, —C(O)—, —S—, —S(O)$_{1-2}$—, —O—, and —NR$^6$—;
  (10y) L$^1$ is —O— or —S—;

In certain embodiments, L$^2$ is selected from one of the following groups (11i)-(11k)
  (11i) L$^2$ is —CH$_2$—, —CH(CH$_3$)— or —CH$_2$CH$_2$—;
  (11j) L$^2$ is a bond;
  (11k) L$^2$ is a bond or —CH$_2$—.

In certain embodiments, Q is selected from one of the following groups (12u)-(12x)
  (12u) Q is selected from the group consisting of —CH$_2$OH, —C(O)OH, —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —C(O)R$^{2A}$, —S(O)$_2$OH, —P(O)(OH)$_2$, —C(OH)(CF$_3$)$_2$, S(O)$_2$R$^{2A}$, —N(R$^{2B}$)S(O)$_2$R$^{2A}$, —S(O)$_2$NR$^{2B}$R$^{2A}$, —C(O)NH—O(C$_1$-C$_3$ alkyl), —C(O)NHOH and —CO(NH)CN;
  (12v) Q is selected from the group consisting of —CH$_2$OH, —C(O)OH, —C(O)OR$^{2A}$, —C(O)NR$^{2B}$R$^{2A}$, —C(O)NR$^{2B}$S(O)$_2$R$^{2A}$, —C(O)NR$^{2B}$S(O)$_2$NR$^{2B}$R$^{2A}$, —C(O)R$^{2A}$, —S(O)$_2$OH, —P(O)(OH)$_2$.
  (12w) Q is —CH$_2$OH, —C(O)OH or —C(O)OR$^{2A}$;
  (12x) Q is —COOH.

In certain embodiments, L$^3$ is selected from one of the following groups (13s)-(13u)

(13s) $L^3$ is a bond, —C(O)—, —S—, —S(O)$_{1-2}$—, —O—, —NR$^6$—, —CH$_2$—, —CH(CH$_3$)(OH)— or —CH(OH)—;

(13t) $L^3$ is a bond;

(13u) $L^3$ is a bond, —CH$_2$—, —CH(CH$_3$)(OH)— or —CH(OH)—.

In certain embodiments, $R^3$ is selected from one of the following groups (14w)-(14gg)

(14w) $R^3$ is aryl or heteroaryl each (i) optionally substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$;

(14x) $R^3$ is aryl (e.g., a phenyl, a benzodioxole, or a dihydro-1H-isoquinoline) optionally substituted with 1-5 R$^{3E}$;

(14y) $R^3$ is aryl (e.g., a phenyl, a benzodioxole, or a dihydro-1H-isoquinoline) (i) substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$;

(14z) $R^3$ is aryl (e.g., a phenyl, a benzodioxole, or a dihydro-1H-isoquinoline) (i) substituted with a single substituent selected from -L$^{3C}$-(phenyl optionally substituted with 1-5 R$^{3D}$), -L$^{3C}$-(monocyclic heteroaryl optionally substituted with 1-5 R$^{3D}$), -L$^{3C}$-(monocyclic cycloalkyl optionally substituted with 1-5 R$^{3E}$), -L$^{3C}$-(monocyclic heterocycloalkyl optionally substituted with 1-5 R$^{3E}$) and (ii) optionally substituted with 1-5 R$^{3E}$;

(14aa) $R^3$ is as defined in (14u)-(14x), wherein the aryl is not substituted with any R$^{3E}$;

(14bb) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) optionally substituted with 1-5 R$^{3E}$;

(14cc) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$;

(14dd) $R^3$ is heteroaryl (e.g., an isothiazole, a pyridone, a thiadiazole, a pyrazine, a pyrazolopyrimidine, a pyrazolopyridine, an imidazole, a benzofuran, an indole, an imidazopyridine, a pyridine, a pyrazole, an isoxazole, a triazolopyridine, a benzimidazole, a thiophene, a benzothiophene, a furan or a pyrimidine) (i) substituted with a single substituent selected from -L$^{3C}$-(phenyl optionally substituted with 1-5 R$^{3D}$), -L$^{3C}$-(monocyclic heteroaryl optionally substituted with 1-5 R$^{3D}$), -L$^{3C}$-(monocyclic cycloalkyl optionally substituted with 1-5 R$^{3E}$), -L$^{3C}$-(monocyclic heterocycloalkyl optionally substituted with 1-5 R$^{3E}$) and (ii) optionally substituted with 1-5 R$^{3E}$;

(14ee) $R^3$ is as defined in (14z)-(14bb), wherein the heteroaryl is not substituted with any R$^{3E}$;

(14ff) $R^3$ is selected from the group consisting of: phenyl, benzodioxolyl, dihydro-1H-isoquinolinyl, imidazolyl, oxazolyl, isoxazolyl, isothiazolyl, thiazolyl, pyridinyl, and pyrazinyl, pyridonyl, thiadiazolyl, pyrazolopyrimidinyl, pyrazolopyridinyl, benzofuranyl, indolyl, imidazopyridinyl, pyrazolyl, triazolopyridinyl, benzimidazolyl, a benzimidazolyl, a thienyl, a benzothienyl, a furanyl and pyrimidinyl, each (i) optionally substituted with a single substituent selected from -L$^{3C}$-(aryl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$.

(14gg) $R^3$ is selected from the group consisting of phenyl and monocyclic heteroaryl (e.g., pyridyl, pyrazolyl), optionally substituted with 1-5 R$^{3E}$.

In certain such embodiments, each optionally substituted alkyl, alkenyl and alkynyl of $R^3$ (including those of R$^{3D}$ and R$^{3E}$) is unsubstituted or fluorinated. For example, in certain such embodiments each optionally substituted alkyl, alkenyl and alkynyl of $R^3$ (including those of R$^{3D}$ and R$^{3E}$) is unsubstituted.

In certain embodiments, $R^4$ is selected from one of the following groups (15z)-(15cc)

(15z) $R^4$ is hydrogen;

(15aa) $R^4$ is optionally substituted C$_1$-C$_8$ alkyl, optionally-substituted C$_1$-C$_8$ alkenyl or optionally substituted C$_1$-C$_8$ alkynyl;

(15bb) $R^4$ is hydrogen or unsubstituted C$_1$-C$_6$ alkyl;

(15cc) $R^4$ is unsubstituted C$_1$-C$_3$ alkyl.

In certain such embodiments, each optionally substituted alkyl, alkenyl and alkynyl of $R^4$ is unsubstituted or fluorinated. For example, in certain such embodiments each optionally substituted alkyl, alkenyl and alkynyl of $R^4$ is unsubstituted.

In certain embodiments, $L^4$ is selected from one of the following groups (19w)-(19x)

(19w) $L^4$ is selected from a bond, —C(O)—, —S—, —S(O)$_{1-2}$—, —O—, and —NR$^6$— (e.g., a bond);

(19x) $L^4$ is a bond.

In certain embodiments, $L^5$ is selected from one of the following groups (20m)-(20n)

(20m) $L^5$ is a bond, —C(O)—, —S—, —S(O)$_{1-2}$—, —O—, —NR$^6$—, —CH$_2$CH$_2$—, —CH$_2$—, —CH(CH$_3$)(OH)— or —CH(OH)—;

(20n) $L^5$ is a bond.

In certain embodiments, $R^5$ is selected from one of the following groups (21o)-(21q)

(21o) $R^5$ is aryl (e.g., phenyl) or heteroaryl (e.g., an isoxazolyl, a pyridyl, an imidazopyridyl, a pyrazolyl), each optionally substituted with 1-5 R$^{5E}$;

(21p) $R^5$ is phenyl optionally substituted with 1-5 R$^{5E}$;

(21q) $R^5$ is selected from the group consisting of phenyl, isoxazolyl, pyridyl, imidazopyridyl, and pyrazolyl, each optionally substituted with 1-5 R$^{5E}$;

In certain such embodiments, each optionally substituted alkyl, alkenyl and alkynyl of $R^5$ (including those of R$^{5D}$ and R$^{5E}$) is unsubstituted or fluorinated. For example, in certain such embodiments each optionally substituted alkyl, alkenyl and alkynyl of $R^5$ (including those of R$^{5D}$ and R$^{5E}$) is unsubstituted.

Various particular embodiments nos. 269-1292 of the compounds of the disclosure include compounds of formula (I), each as defined in each of the following rows (or a pharmaceutically acceptable salt or N-oxide thereof, or a solvate or hydrate thereof), wherein each entry is a group number as defined above:

| | I | L$^{1\dagger}$ | R$^1$ | L$^2$ | Q | L$^3$ | R$^3$ | L$^{4\dagger\dagger}$ | R$^4$ | L$^5$ | R$^5$ |
|---|---|---|---|---|---|---|---|---|---|---|---|
| 269 | (Ik), (Im) | (6q) | (10w) | (11k) | (12u) | (13t) | (14w) | (15z), (15aa) | (19x) | (20m) | (21o) |
| 270 | (Ik), (Im) | (6q) | (10w) | (11k) | (12u) | (13t) | (14w) | (15z), (15aa) | (19x) | (20m) | (21q) |
| 271 | (Ik), (Im) | (6q) | (10w) | (11k) | (12u) | (13t) | (14w) | (15z), (15aa) | (19x) | (20n) | (21o) |
| 272 | (Ik), (Im) | (6q) | (10w) | (11k) | (12u) | (13t) | (14w) | (15z), (15aa) | (19x) | (20n) | (21q) |
| 273 | (Ik), (Im) | (6q) | (10w) | (11k) | (12u) | (13t) | (14w) | (15cc) | (19x) | (20m) | (21o) |
| 274 | (Ik), (Im) | (6q) | (10w) | (11k) | (12u) | (13t) | (14w) | (15cc) | (19x) | (20m) | (21q) |
| 275 | (Ik), (Im) | (6q) | (10w) | (11k) | (12u) | (13t) | (14w) | (15cc) | (19x) | (20n) | (21o) |
| 276 | (Ik), (Im) | (6q) | (10w) | (11k) | (12u) | (13t) | (14w) | (15cc) | (19x) | (20n) | (21q) |
| 277 | (Ik), (Im) | (6q) | (10w) | (11k) | (12u) | (13t) | (14gg) | (15z), (15aa) | (19x) | (20m) | (21o) |
| 278 | (Ik), (Im) | (6q) | (10w) | (11k) | (12u) | (13t) | (14gg) | (15z), (15aa) | (19x) | (20m) | (21q) |
| 279 | (Ik), (Im) | (6q) | (10w) | (11k) | (12u) | (13t) | (14gg) | (15z), (15aa) | (19x) | (20n) | (21o) |
| 280 | (Ik), (Im) | (6q) | (10w) | (11k) | (12u) | (13t) | (14gg) | (15z), (15aa) | (19x) | (20n) | (21q) |
| 281 | (Ik), (Im) | (6q) | (10w) | (11k) | (12u) | (13t) | (14gg) | (15cc) | (19x) | (20m) | (21o) |
| 282 | (Ik), (Im) | (6q) | (10w) | (11k) | (12u) | (13t) | (14gg) | (15cc) | (19x) | (20m) | (21q) |
| 283 | (Ik), (Im) | (6q) | (10w) | (11k) | (12u) | (13t) | (14gg) | (15cc) | (19x) | (20n) | (21o) |
| 284 | (Ik), (Im) | (6q) | (10w) | (11k) | (12u) | (13t) | (14gg) | (15cc) | (19x) | (20n) | (21q) |
| 285 | (Ik), (Im) | (6q) | (10w) | (11k) | (12u) | (13s) | (14w) | (15z), (15aa) | (19x) | (20m) | (21o) |
| 286 | (Ik), (Im) | (6q) | (10w) | (11k) | (12u) | (13s) | (14w) | (15z), (15aa) | (19x) | (20m) | (21q) |
| 287 | (Ik), (Im) | (6q) | (10w) | (11k) | (12u) | (13s) | (14w) | (15z), (15aa) | (19x) | (20n) | (21o) |
| 288 | (Ik), (Im) | (6q) | (10w) | (11k) | (12u) | (13s) | (14w) | (15z), (15aa) | (19x) | (20n) | (21q) |
| 289 | (Ik), (Im) | (6q) | (10w) | (11k) | (12u) | (13s) | (14w) | (15cc) | (19x) | (20m) | (21o) |
| 290 | (Ik), (Im) | (6q) | (10w) | (11k) | (12u) | (13s) | (14w) | (15cc) | (19x) | (20m) | (21q) |
| 291 | (Ik), (Im) | (6q) | (10w) | (11k) | (12u) | (13s) | (14w) | (15cc) | (19x) | (20n) | (21o) |
| 292 | (Ik), (Im) | (6q) | (10w) | (11k) | (12u) | (13s) | (14w) | (15cc) | (19x) | (20n) | (21q) |
| 293 | (Ik), (Im) | (6q) | (10w) | (11k) | (12u) | (13s) | (14gg) | (15z), (15aa) | (19x) | (20m) | (21o) |
| 294 | (Ik), (Im) | (6q) | (10w) | (11k) | (12u) | (13s) | (14gg) | (15z), (15aa) | (19x) | (20m) | (21q) |
| 295 | (Ik), (Im) | (6q) | (10w) | (11k) | (12u) | (13s) | (14gg) | (15z), (15aa) | (19x) | (20n) | (21o) |
| 296 | (Ik), (Im) | (6q) | (10w) | (11k) | (12u) | (13s) | (14gg) | (15z), (15aa) | (19x) | (20n) | (21q) |
| 297 | (Ik), (Im) | (6q) | (10w) | (11k) | (12u) | (13s) | (14gg) | (15cc) | (19x) | (20m) | (21o) |
| 298 | (Ik), (Im) | (6q) | (10w) | (11k) | (12u) | (13s) | (14gg) | (15cc) | (19x) | (20m) | (21q) |
| 299 | (Ik), (Im) | (6q) | (10w) | (11k) | (12u) | (13s) | (14gg) | (15cc) | (19x) | (20n) | (21o) |
| 300 | (Ik), (Im) | (6q) | (10w) | (11k) | (12u) | (13s) | (14gg) | (15cc) | (19x) | (20n) | (21q) |
| 301 | (Ik), (Im) | (6q) | (10w) | (11k) | (12x) | (13t) | (14w) | (15z), (15aa) | (19x) | (20m) | (21o) |
| 302 | (Ik), (Im) | (6q) | (10w) | (11k) | (12x) | (13t) | (14w) | (15z), (15aa) | (19x) | (20m) | (21q) |
| 303 | (Ik), (Im) | (6q) | (10w) | (11k) | (12x) | (13t) | (14w) | (15z), (15aa) | (19x) | (20n) | (21o) |
| 304 | (Ik), (Im) | (6q) | (10w) | (11k) | (12x) | (13t) | (14w) | (15z), (15aa) | (19x) | (20n) | (21q) |
| 305 | (Ik), (Im) | (6q) | (10w) | (11k) | (12x) | (13t) | (14w) | (15cc) | (19x) | (20m) | (21o) |
| 306 | (Ik), (Im) | (6q) | (10w) | (11k) | (12x) | (13t) | (14w) | (15cc) | (19x) | (20m) | (21q) |
| 307 | (Ik), (Im) | (6q) | (10w) | (11k) | (12x) | (13t) | (14w) | (15cc) | (19x) | (20n) | (21o) |
| 308 | (Ik), (Im) | (6q) | (10w) | (11k) | (12x) | (13t) | (14w) | (15cc) | (19x) | (20n) | (21q) |
| 309 | (Ik), (Im) | (6q) | (10w) | (11k) | (12x) | (13t) | (14gg) | (15z), (15aa) | (19x) | (20m) | (21o) |
| 310 | (Ik), (Im) | (6q) | (10w) | (11k) | (12x) | (13t) | (14gg) | (15z), (15aa) | (19x) | (20m) | (21q) |
| 311 | (Ik), (Im) | (6q) | (10w) | (11k) | (12x) | (13t) | (14gg) | (15z), (15aa) | (19x) | (20n) | (21o) |
| 312 | (Ik), (Im) | (6q) | (10w) | (11k) | (12x) | (13t) | (14gg) | (15z), (15aa) | (19x) | (20n) | (21q) |
| 313 | (Ik), (Im) | (6q) | (10w) | (11k) | (12x) | (13t) | (14gg) | (15cc) | (19x) | (20m) | (21o) |
| 314 | (Ik), (Im) | (6q) | (10w) | (11k) | (12x) | (13t) | (14gg) | (15cc) | (19x) | (20m) | (21q) |
| 315 | (Ik), (Im) | (6q) | (10w) | (11k) | (12x) | (13t) | (14gg) | (15cc) | (19x) | (20n) | (21o) |
| 316 | (Ik), (Im) | (6q) | (10w) | (11k) | (12x) | (13t) | (14gg) | (15cc) | (19x) | (20n) | (21q) |
| 317 | (Ik), (Im) | (6q) | (10w) | (11k) | (12x) | (13s) | (14w) | (15z), (15aa) | (19x) | (20m) | (21o) |
| 318 | (Ik), (Im) | (6q) | (10w) | (11k) | (12x) | (13s) | (14w) | (15z), (15aa) | (19x) | (20m) | (21q) |
| 319 | (Ik), (Im) | (6q) | (10w) | (11k) | (12x) | (13s) | (14w) | (15z), (15aa) | (19x) | (20n) | (21o) |
| 320 | (Ik), (Im) | (6q) | (10w) | (11k) | (12x) | (13s) | (14w) | (15z), (15aa) | (19x) | (20n) | (21q) |
| 321 | (Ik), (Im) | (6q) | (10w) | (11k) | (12x) | (13s) | (14w) | (15cc) | (19x) | (20m) | (21o) |
| 322 | (Ik), (Im) | (6q) | (10w) | (11k) | (12x) | (13s) | (14w) | (15cc) | (19x) | (20m) | (21q) |
| 323 | (Ik), (Im) | (6q) | (10w) | (11k) | (12x) | (13s) | (14w) | (15cc) | (19x) | (20n) | (21o) |
| 324 | (Ik), (Im) | (6q) | (10w) | (11k) | (12x) | (13s) | (14w) | (15cc) | (19x) | (20n) | (21q) |
| 325 | (Ik), (Im) | (6q) | (10w) | (11k) | (12x) | (13s) | (14gg) | (15z), (15aa) | (19x) | (20m) | (21o) |
| 326 | (Ik), (Im) | (6q) | (10w) | (11k) | (12x) | (13s) | (14gg) | (15z), (15aa) | (19x) | (20m) | (21q) |
| 327 | (Ik), (Im) | (6q) | (10w) | (11k) | (12x) | (13s) | (14gg) | (15z), (15aa) | (19x) | (20n) | (21o) |
| 328 | (Ik), (Im) | (6q) | (10w) | (11k) | (12x) | (13s) | (14gg) | (15z), (15aa) | (19x) | (20n) | (21q) |
| 329 | (Ik), (Im) | (6q) | (10w) | (11k) | (12x) | (13s) | (14gg) | (15cc) | (19x) | (20m) | (21o) |
| 330 | (Ik), (Im) | (6q) | (10w) | (11k) | (12x) | (13s) | (14gg) | (15cc) | (19x) | (20m) | (21q) |
| 331 | (Ik), (Im) | (6q) | (10w) | (11k) | (12x) | (13s) | (14gg) | (15cc) | (19x) | (20n) | (21o) |
| 332 | (Ik), (Im) | (6q) | (10w) | (11k) | (12x) | (13s) | (14gg) | (15cc) | (19x) | (20n) | (21q) |
| 333 | (Ik), (Im) | (6q) | (10w) | (11j) | (12u) | (13t) | (14w) | (15z), (15aa) | (19x) | (20m) | (21o) |
| 334 | (Ik), (Im) | (6q) | (10w) | (11j) | (12u) | (13t) | (14w) | (15z), (15aa) | (19x) | (20m) | (21q) |
| 335 | (Ik), (Im) | (6q) | (10w) | (11j) | (12u) | (13t) | (14w) | (15z), (15aa) | (19x) | (20n) | (21o) |
| 336 | (Ik), (Im) | (6q) | (10w) | (11j) | (12u) | (13t) | (14w) | (15z), (15aa) | (19x) | (20n) | (21q) |
| 337 | (Ik), (Im) | (6q) | (10w) | (11j) | (12u) | (13t) | (14w) | (15cc) | (19x) | (20m) | (21o) |
| 338 | (Ik), (Im) | (6q) | (10w) | (11j) | (12u) | (13t) | (14w) | (15cc) | (19x) | (20m) | (21q) |
| 339 | (Ik), (Im) | (6q) | (10w) | (11j) | (12u) | (13t) | (14w) | (15cc) | (19x) | (20n) | (21o) |
| 340 | (Ik), (Im) | (6q) | (10w) | (11j) | (12u) | (13t) | (14w) | (15cc) | (19x) | (20n) | (21q) |
| 341 | (Ik), (Im) | (6q) | (10w) | (11j) | (12u) | (13t) | (14gg) | (15z), (15aa) | (19x) | (20m) | (21o) |
| 342 | (Ik), (Im) | (6q) | (10w) | (11j) | (12u) | (13t) | (14gg) | (15z), (15aa) | (19x) | (20m) | (21q) |

-continued

| | I | L¹† | R¹ | L² | Q | L³ | R³ | L⁴†† | R⁴ | L⁵ | R⁵ |
|---|---|---|---|---|---|---|---|---|---|---|---|
| 343 | (Ik), (Im) | (6q) | (10w) | (11j) | (12u) | (13t) | (14gg) | (15z), (15aa) | (19x) | (20n) | (21o) |
| 344 | (Ik), (Im) | (6q) | (10w) | (11j) | (12u) | (13t) | (14gg) | (15z), (15aa) | (19x) | (20n) | (21q) |
| 345 | (Ik), (Im) | (6q) | (10w) | (11j) | (12u) | (13t) | (14gg) | (15cc) | (19x) | (20m) | (21o) |
| 346 | (Ik), (Im) | (6q) | (10w) | (11j) | (12u) | (13t) | (14gg) | (15cc) | (19x) | (20m) | (21q) |
| 347 | (Ik), (Im) | (6q) | (10w) | (11j) | (12u) | (13t) | (14gg) | (15cc) | (19x) | (20n) | (21o) |
| 348 | (Ik), (Im) | (6q) | (10w) | (11j) | (12u) | (13t) | (14gg) | (15cc) | (19x) | (20n) | (21q) |
| 349 | (Ik), (Im) | (6q) | (10w) | (11j) | (12u) | (13s) | (14w) | (15z), (15aa) | (19x) | (20m) | (21o) |
| 350 | (Ik), (Im) | (6q) | (10w) | (11j) | (12u) | (13s) | (14w) | (15z), (15aa) | (19x) | (20m) | (21q) |
| 351 | (Ik), (Im) | (6q) | (10w) | (11j) | (12u) | (13s) | (14w) | (15z), (15aa) | (19x) | (20n) | (21o) |
| 352 | (Ik), (Im) | (6q) | (10w) | (11j) | (12u) | (13s) | (14w) | (15z), (15aa) | (19x) | (20n) | (21q) |
| 353 | (Ik), (Im) | (6q) | (10w) | (11j) | (12u) | (13s) | (14w) | (15cc) | (19x) | (20m) | (21o) |
| 354 | (Ik), (Im) | (6q) | (10w) | (11j) | (12u) | (13s) | (14w) | (15cc) | (19x) | (20m) | (21q) |
| 355 | (Ik), (Im) | (6q) | (10w) | (11j) | (12u) | (13s) | (14w) | (15cc) | (19x) | (20n) | (21o) |
| 356 | (Ik), (Im) | (6q) | (10w) | (11j) | (12u) | (13s) | (14w) | (15cc) | (19x) | (20n) | (21q) |
| 357 | (Ik), (Im) | (6q) | (10w) | (11j) | (12u) | (13s) | (14gg) | (15z), (15aa) | (19x) | (20m) | (21o) |
| 358 | (Ik), (Im) | (6q) | (10w) | (11j) | (12u) | (13s) | (14gg) | (15z), (15aa) | (19x) | (20m) | (21q) |
| 359 | (Ik), (Im) | (6q) | (10w) | (11j) | (12u) | (13s) | (14gg) | (15z), (15aa) | (19x) | (20n) | (21o) |
| 360 | (Ik), (Im) | (6q) | (10w) | (11j) | (12u) | (13s) | (14gg) | (15z), (15aa) | (19x) | (20n) | (21q) |
| 361 | (Ik), (Im) | (6q) | (10w) | (11j) | (12u) | (13s) | (14gg) | (15cc) | (19x) | (20m) | (21o) |
| 362 | (Ik), (Im) | (6q) | (10w) | (11j) | (12u) | (13s) | (14gg) | (15cc) | (19x) | (20m) | (21q) |
| 363 | (Ik), (Im) | (6q) | (10w) | (11j) | (12u) | (13s) | (14gg) | (15cc) | (19x) | (20n) | (21o) |
| 364 | (Ik), (Im) | (6q) | (10w) | (11j) | (12u) | (13s) | (14gg) | (15cc) | (19x) | (20n) | (21q) |
| 365 | (Ik), (Im) | (6q) | (10w) | (11j) | (12x) | (13t) | (14w) | (15z), (15aa) | (19x) | (20m) | (21o) |
| 366 | (Ik), (Im) | (6q) | (10w) | (11j) | (12x) | (13t) | (14w) | (15z), (15aa) | (19x) | (20m) | (21q) |
| 367 | (Ik), (Im) | (6q) | (10w) | (11j) | (12x) | (13t) | (14w) | (15z), (15aa) | (19x) | (20n) | (21o) |
| 368 | (Ik), (Im) | (6q) | (10w) | (11j) | (12x) | (13t) | (14w) | (15z), (15aa) | (19x) | (20n) | (21q) |
| 369 | (Ik), (Im) | (6q) | (10w) | (11j) | (12x) | (13t) | (14w) | (15cc) | (19x) | (20m) | (21o) |
| 370 | (Ik), (Im) | (6q) | (10w) | (11j) | (12x) | (13t) | (14w) | (15cc) | (19x) | (20m) | (21q) |
| 371 | (Ik), (Im) | (6q) | (10w) | (11j) | (12x) | (13t) | (14w) | (15cc) | (19x) | (20n) | (21o) |
| 372 | (Ik), (Im) | (6q) | (10w) | (11j) | (12x) | (13t) | (14w) | (15cc) | (19x) | (20n) | (21q) |
| 373 | (Ik), (Im) | (6q) | (10w) | (11j) | (12x) | (13t) | (14gg) | (15z), (15aa) | (19x) | (20m) | (21o) |
| 374 | (Ik), (Im) | (6q) | (10w) | (11j) | (12x) | (13t) | (14gg) | (15z), (15aa) | (19x) | (20m) | (21q) |
| 375 | (Ik), (Im) | (6q) | (10w) | (11j) | (12x) | (13t) | (14gg) | (15z), (15aa) | (19x) | (20n) | (21o) |
| 376 | (Ik), (Im) | (6q) | (10w) | (11j) | (12x) | (13t) | (14gg) | (15z), (15aa) | (19x) | (20n) | (21q) |
| 377 | (Ik), (Im) | (6q) | (10w) | (11j) | (12x) | (13t) | (14gg) | (15cc) | (19x) | (20m) | (21o) |
| 378 | (Ik), (Im) | (6q) | (10w) | (11j) | (12x) | (13t) | (14gg) | (15cc) | (19x) | (20m) | (21q) |
| 379 | (Ik), (Im) | (6q) | (10w) | (11j) | (12x) | (13t) | (14gg) | (15cc) | (19x) | (20n) | (21o) |
| 380 | (Ik), (Im) | (6q) | (10w) | (11j) | (12x) | (13t) | (14gg) | (15cc) | (19x) | (20n) | (21q) |
| 381 | (Ik), (Im) | (6q) | (10w) | (11j) | (12x) | (13s) | (14w) | (15z), (15aa) | (19x) | (20m) | (21o) |
| 382 | (Ik), (Im) | (6q) | (10w) | (11j) | (12x) | (13s) | (14w) | (15z), (15aa) | (19x) | (20m) | (21q) |
| 383 | (Ik), (Im) | (6q) | (10w) | (11j) | (12x) | (13s) | (14w) | (15z), (15aa) | (19x) | (20n) | (21o) |
| 384 | (Ik), (Im) | (6q) | (10w) | (11j) | (12x) | (13s) | (14w) | (15z), (15aa) | (19x) | (20n) | (21q) |
| 385 | (Ik), (Im) | (6q) | (10w) | (11j) | (12x) | (13s) | (14w) | (15cc) | (19x) | (20m) | (21o) |
| 386 | (Ik), (Im) | (6q) | (10w) | (11j) | (12x) | (13s) | (14w) | (15cc) | (19x) | (20m) | (21q) |
| 387 | (Ik), (Im) | (6q) | (10w) | (11j) | (12x) | (13s) | (14w) | (15cc) | (19x) | (20n) | (21o) |
| 388 | (Ik), (Im) | (6q) | (10w) | (11j) | (12x) | (13s) | (14w) | (15cc) | (19x) | (20n) | (21q) |
| 389 | (Ik), (Im) | (6q) | (10w) | (11j) | (12x) | (13s) | (14gg) | (15z), (15aa) | (19x) | (20m) | (21o) |
| 390 | (Ik), (Im) | (6q) | (10w) | (11j) | (12x) | (13s) | (14gg) | (15z), (15aa) | (19x) | (20m) | (21q) |
| 391 | (Ik), (Im) | (6q) | (10w) | (11j) | (12x) | (13s) | (14gg) | (15z), (15aa) | (19x) | (20n) | (21o) |
| 392 | (Ik), (Im) | (6q) | (10w) | (11j) | (12x) | (13s) | (14gg) | (15z), (15aa) | (19x) | (20n) | (21q) |
| 393 | (Ik), (Im) | (6q) | (10w) | (11j) | (12x) | (13s) | (14gg) | (15cc) | (19x) | (20m) | (21o) |
| 394 | (Ik), (Im) | (6q) | (10w) | (11j) | (12x) | (13s) | (14gg) | (15cc) | (19x) | (20m) | (21q) |
| 395 | (Ik), (Im) | (6q) | (10w) | (11j) | (12x) | (13s) | (14gg) | (15cc) | (19x) | (20n) | (21o) |
| 396 | (Ik), (Im) | (6q) | (10w) | (11j) | (12x) | (13s) | (14gg) | (15cc) | (19x) | (20n) | (21q) |
| 397 | (Ik), (Im) | (6q) | (10x) | (11k) | (12u) | (13t) | (14w) | (15z), (15aa) | (19x) | (20m) | (21o) |
| 398 | (Ik), (Im) | (6q) | (10x) | (11k) | (12u) | (13t) | (14w) | (15z), (15aa) | (19x) | (20m) | (21q) |
| 399 | (Ik), (Im) | (6q) | (10x) | (11k) | (12u) | (13t) | (14w) | (15z), (15aa) | (19x) | (20n) | (21o) |
| 400 | (Ik), (Im) | (6q) | (10x) | (11k) | (12u) | (13t) | (14w) | (15z), (15aa) | (19x) | (20n) | (21q) |
| 401 | (Ik), (Im) | (6q) | (10x) | (11k) | (12u) | (13t) | (14w) | (15cc) | (19x) | (20m) | (21o) |
| 402 | (Ik), (Im) | (6q) | (10x) | (11k) | (12u) | (13t) | (14w) | (15cc) | (19x) | (20m) | (21q) |
| 403 | (Ik), (Im) | (6q) | (10x) | (11k) | (12u) | (13t) | (14w) | (15cc) | (19x) | (20n) | (21o) |
| 404 | (Ik), (Im) | (6q) | (10x) | (11k) | (12u) | (13t) | (14w) | (15cc) | (19x) | (20n) | (21q) |
| 405 | (Ik), (Im) | (6q) | (10x) | (11k) | (12u) | (13t) | (14gg) | (15z), (15aa) | (19x) | (20m) | (21o) |
| 406 | (Ik), (Im) | (6q) | (10x) | (11k) | (12u) | (13t) | (14gg) | (15z), (15aa) | (19x) | (20m) | (21q) |
| 407 | (Ik), (Im) | (6q) | (10x) | (11k) | (12u) | (13t) | (14gg) | (15z), (15aa) | (19x) | (20n) | (21o) |
| 408 | (Ik), (Im) | (6q) | (10x) | (11k) | (12u) | (13t) | (14gg) | (15z), (15aa) | (19x) | (20n) | (21q) |
| 409 | (Ik), (Im) | (6q) | (10x) | (11k) | (12u) | (13t) | (14gg) | (15cc) | (19x) | (20m) | (21o) |
| 410 | (Ik), (Im) | (6q) | (10x) | (11k) | (12u) | (13t) | (14gg) | (15cc) | (19x) | (20m) | (21q) |
| 411 | (Ik), (Im) | (6q) | (10x) | (11k) | (12u) | (13t) | (14gg) | (15cc) | (19x) | (20n) | (21o) |
| 412 | (Ik), (Im) | (6q) | (10x) | (11k) | (12u) | (13t) | (14gg) | (15cc) | (19x) | (20n) | (21q) |
| 413 | (Ik), (Im) | (6q) | (10x) | (11k) | (12u) | (13s) | (14w) | (15z), (15aa) | (19x) | (20m) | (21o) |
| 414 | (Ik), (Im) | (6q) | (10x) | (11k) | (12u) | (13s) | (14w) | (15z), (15aa) | (19x) | (20m) | (21q) |
| 415 | (Ik), (Im) | (6q) | (10x) | (11k) | (12u) | (13s) | (14w) | (15z), (15aa) | (19x) | (20n) | (21o) |
| 416 | (Ik), (Im) | (6q) | (10x) | (11k) | (12u) | (13s) | (14w) | (15z), (15aa) | (19x) | (20n) | (21q) |
| 417 | (Ik), (Im) | (6q) | (10x) | (11k) | (12u) | (13s) | (14w) | (15cc) | (19x) | (20m) | (21o) |
| 418 | (Ik), (Im) | (6q) | (10x) | (11k) | (12u) | (13s) | (14w) | (15cc) | (19x) | (20m) | (21q) |
| 419 | (Ik), (Im) | (6q) | (10x) | (11k) | (12u) | (13s) | (14w) | (15cc) | (19x) | (20n) | (21o) |

| | I | L¹† | R¹ | L² | Q | L³ | R³ | L⁴†† | R⁴ | L⁵ | R⁵ |
|---|---|---|---|---|---|---|---|---|---|---|---|
| 420 | (Ik), (Im) | (6q) | (10x) | (11k) | (12u) | (13s) | (14w) | (15cc) | (19x) | (20n) | (21q) |
| 421 | (Ik), (Im) | (6q) | (10x) | (11k) | (12u) | (13s) | (14gg) | (15z), (15aa) | (19x) | (20m) | (21o) |
| 422 | (Ik), (Im) | (6q) | (10x) | (11k) | (12u) | (13s) | (14gg) | (15z), (15aa) | (19x) | (20m) | (21q) |
| 423 | (Ik), (Im) | (6q) | (10x) | (11k) | (12u) | (13s) | (14gg) | (15z), (15aa) | (19x) | (20n) | (21o) |
| 424 | (Ik), (Im) | (6q) | (10x) | (11k) | (12u) | (13s) | (14gg) | (15z), (15aa) | (19x) | (20n) | (21q) |
| 425 | (Ik), (Im) | (6q) | (10x) | (11k) | (12u) | (13s) | (14gg) | (15cc) | (19x) | (20m) | (21o) |
| 426 | (Ik), (Im) | (6q) | (10x) | (11k) | (12u) | (13s) | (14gg) | (15cc) | (19x) | (20m) | (21q) |
| 427 | (Ik), (Im) | (6q) | (10x) | (11k) | (12u) | (13s) | (14gg) | (15cc) | (19x) | (20n) | (21o) |
| 428 | (Ik), (Im) | (6q) | (10x) | (11k) | (12u) | (13s) | (14gg) | (15cc) | (19x) | (20n) | (21q) |
| 429 | (Ik), (Im) | (6q) | (10x) | (11k) | (12x) | (13t) | (14w) | (15z), (15aa) | (19x) | (20m) | (21o) |
| 430 | (Ik), (Im) | (6q) | (10x) | (11k) | (12x) | (13t) | (14w) | (15z), (15aa) | (19x) | (20m) | (21q) |
| 431 | (Ik), (Im) | (6q) | (10x) | (11k) | (12x) | (13t) | (14w) | (15z), (15aa) | (19x) | (20n) | (21o) |
| 432 | (Ik), (Im) | (6q) | (10x) | (11k) | (12x) | (13t) | (14w) | (15z), (15aa) | (19x) | (20n) | (21q) |
| 433 | (Ik), (Im) | (6q) | (10x) | (11k) | (12x) | (13t) | (14w) | (15cc) | (19x) | (20m) | (21o) |
| 434 | (Ik), (Im) | (6q) | (10x) | (11k) | (12x) | (13t) | (14w) | (15cc) | (19x) | (20m) | (21q) |
| 435 | (Ik), (Im) | (6q) | (10x) | (11k) | (12x) | (13t) | (14w) | (15cc) | (19x) | (20n) | (21o) |
| 436 | (Ik), (Im) | (6q) | (10x) | (11k) | (12x) | (13t) | (14w) | (15cc) | (19x) | (20n) | (21q) |
| 437 | (Ik), (Im) | (6q) | (10x) | (11k) | (12x) | (13t) | (14gg) | (15z), (15aa) | (19x) | (20m) | (21o) |
| 438 | (Ik), (Im) | (6q) | (10x) | (11k) | (12x) | (13t) | (14gg) | (15z), (15aa) | (19x) | (20m) | (21q) |
| 439 | (Ik), (Im) | (6q) | (10x) | (11k) | (12x) | (13t) | (14gg) | (15z), (15aa) | (19x) | (20n) | (21o) |
| 440 | (Ik), (Im) | (6q) | (10x) | (11k) | (12x) | (13t) | (14gg) | (15z), (15aa) | (19x) | (20n) | (21q) |
| 441 | (Ik), (Im) | (6q) | (10x) | (11k) | (12x) | (13t) | (14gg) | (15cc) | (19x) | (20m) | (21o) |
| 442 | (Ik), (Im) | (6q) | (10x) | (11k) | (12x) | (13t) | (14gg) | (15cc) | (19x) | (20m) | (21q) |
| 443 | (Ik), (Im) | (6q) | (10x) | (11k) | (12x) | (13t) | (14gg) | (15cc) | (19x) | (20n) | (21o) |
| 444 | (Ik), (Im) | (6q) | (10x) | (11k) | (12x) | (13t) | (14gg) | (15cc) | (19x) | (20n) | (21q) |
| 445 | (Ik), (Im) | (6q) | (10x) | (11k) | (12x) | (13s) | (14w) | (15z), (15aa) | (19x) | (20m) | (21o) |
| 446 | (Ik), (Im) | (6q) | (10x) | (11k) | (12x) | (13s) | (14w) | (15z), (15aa) | (19x) | (20m) | (21q) |
| 447 | (Ik), (Im) | (6q) | (10x) | (11k) | (12x) | (13s) | (14w) | (15z), (15aa) | (19x) | (20n) | (21o) |
| 448 | (Ik), (Im) | (6q) | (10x) | (11k) | (12x) | (13s) | (14w) | (15z), (15aa) | (19x) | (20n) | (21q) |
| 449 | (Ik), (Im) | (6q) | (10x) | (11k) | (12x) | (13s) | (14w) | (15cc) | (19x) | (20m) | (21o) |
| 450 | (Ik), (Im) | (6q) | (10x) | (11k) | (12x) | (13s) | (14w) | (15cc) | (19x) | (20m) | (21q) |
| 451 | (Ik), (Im) | (6q) | (10x) | (11k) | (12x) | (13s) | (14w) | (15cc) | (19x) | (20n) | (21o) |
| 452 | (Ik), (Im) | (6q) | (10x) | (11k) | (12x) | (13s) | (14w) | (15cc) | (19x) | (20n) | (21q) |
| 453 | (Ik), (Im) | (6q) | (10x) | (11k) | (12x) | (13s) | (14gg) | (15z), (15aa) | (19x) | (20m) | (21o) |
| 454 | (Ik), (Im) | (6q) | (10x) | (11k) | (12x) | (13s) | (14gg) | (15z), (15aa) | (19x) | (20m) | (21q) |
| 455 | (Ik), (Im) | (6q) | (10x) | (11k) | (12x) | (13s) | (14gg) | (15z), (15aa) | (19x) | (20n) | (21o) |
| 456 | (Ik), (Im) | (6q) | (10x) | (11k) | (12x) | (13s) | (14gg) | (15z), (15aa) | (19x) | (20n) | (21q) |
| 457 | (Ik), (Im) | (6q) | (10x) | (11k) | (12x) | (13s) | (14gg) | (15cc) | (19x) | (20m) | (21o) |
| 458 | (Ik), (Im) | (6q) | (10x) | (11k) | (12x) | (13s) | (14gg) | (15cc) | (19x) | (20m) | (21q) |
| 459 | (Ik), (Im) | (6q) | (10x) | (11k) | (12x) | (13s) | (14gg) | (15cc) | (19x) | (20n) | (21o) |
| 460 | (Ik), (Im) | (6q) | (10x) | (11k) | (12x) | (13s) | (14gg) | (15cc) | (19x) | (20n) | (21q) |
| 461 | (Ik), (Im) | (6q) | (10x) | (11j) | (12u) | (13t) | (14w) | (15z), (15aa) | (19x) | (20m) | (21o) |
| 462 | (Ik), (Im) | (6q) | (10x) | (11j) | (12u) | (13t) | (14w) | (15z), (15aa) | (19x) | (20m) | (21q) |
| 463 | (Ik), (Im) | (6q) | (10x) | (11j) | (12u) | (13t) | (14w) | (15z), (15aa) | (19x) | (20n) | (21o) |
| 464 | (Ik), (Im) | (6q) | (10x) | (11j) | (12u) | (13t) | (14w) | (15z), (15aa) | (19x) | (20n) | (21q) |
| 465 | (Ik), (Im) | (6q) | (10x) | (11j) | (12u) | (13t) | (14w) | (15cc) | (19x) | (20m) | (21o) |
| 466 | (Ik), (Im) | (6q) | (10x) | (11j) | (12u) | (13t) | (14w) | (15cc) | (19x) | (20m) | (21q) |
| 467 | (Ik), (Im) | (6q) | (10x) | (11j) | (12u) | (13t) | (14w) | (15cc) | (19x) | (20n) | (21o) |
| 468 | (Ik), (Im) | (6q) | (10x) | (11j) | (12u) | (13t) | (14w) | (15cc) | (19x) | (20n) | (21q) |
| 469 | (Ik), (Im) | (6q) | (10x) | (11j) | (12u) | (13t) | (14gg) | (15z), (15aa) | (19x) | (20m) | (21o) |
| 470 | (Ik), (Im) | (6q) | (10x) | (11j) | (12u) | (13t) | (14gg) | (15z), (15aa) | (19x) | (20m) | (21q) |
| 471 | (Ik), (Im) | (6q) | (10x) | (11j) | (12u) | (13t) | (14gg) | (15z), (15aa) | (19x) | (20n) | (21o) |
| 472 | (Ik), (Im) | (6q) | (10x) | (11j) | (12u) | (13t) | (14gg) | (15z), (15aa) | (19x) | (20n) | (21q) |
| 473 | (Ik), (Im) | (6q) | (10x) | (11j) | (12u) | (13t) | (14gg) | (15cc) | (19x) | (20m) | (21o) |
| 474 | (Ik), (Im) | (6q) | (10x) | (11j) | (12u) | (13t) | (14gg) | (15cc) | (19x) | (20m) | (21q) |
| 475 | (Ik), (Im) | (6q) | (10x) | (11j) | (12u) | (13t) | (14gg) | (15cc) | (19x) | (20n) | (21o) |
| 476 | (Ik), (Im) | (6q) | (10x) | (11j) | (12u) | (13t) | (14gg) | (15cc) | (19x) | (20n) | (21q) |
| 477 | (Ik), (Im) | (6q) | (10x) | (11j) | (12u) | (13s) | (14w) | (15z), (15aa) | (19x) | (20m) | (21o) |
| 478 | (Ik), (Im) | (6q) | (10x) | (11j) | (12u) | (13s) | (14w) | (15z), (15aa) | (19x) | (20m) | (21q) |
| 479 | (Ik), (Im) | (6q) | (10x) | (11j) | (12u) | (13s) | (14w) | (15z), (15aa) | (19x) | (20n) | (21o) |
| 480 | (Ik), (Im) | (6q) | (10x) | (11j) | (12u) | (13s) | (14w) | (15z), (15aa) | (19x) | (20n) | (21q) |
| 481 | (Ik), (Im) | (6q) | (10x) | (11j) | (12u) | (13s) | (14w) | (15cc) | (19x) | (20m) | (21o) |
| 482 | (Ik), (Im) | (6q) | (10x) | (11j) | (12u) | (13s) | (14w) | (15cc) | (19x) | (20m) | (21q) |
| 483 | (Ik), (Im) | (6q) | (10x) | (11j) | (12u) | (13s) | (14w) | (15cc) | (19x) | (20n) | (21o) |
| 484 | (Ik), (Im) | (6q) | (10x) | (11j) | (12u) | (13s) | (14w) | (15cc) | (19x) | (20n) | (21q) |
| 485 | (Ik), (Im) | (6q) | (10x) | (11j) | (12u) | (13s) | (14gg) | (15z), (15aa) | (19x) | (20m) | (21o) |
| 486 | (Ik), (Im) | (6q) | (10x) | (11j) | (12u) | (13s) | (14gg) | (15z), (15aa) | (19x) | (20m) | (21q) |
| 487 | (Ik), (Im) | (6q) | (10x) | (11j) | (12u) | (13s) | (14gg) | (15z), (15aa) | (19x) | (20n) | (21o) |
| 488 | (Ik), (Im) | (6q) | (10x) | (11j) | (12u) | (13s) | (14gg) | (15z), (15aa) | (19x) | (20n) | (21q) |
| 489 | (Ik), (Im) | (6q) | (10x) | (11j) | (12u) | (13s) | (14gg) | (15cc) | (19x) | (20m) | (21o) |
| 490 | (Ik), (Im) | (6q) | (10x) | (11j) | (12u) | (13s) | (14gg) | (15cc) | (19x) | (20m) | (21q) |
| 491 | (Ik), (Im) | (6q) | (10x) | (11j) | (12u) | (13s) | (14gg) | (15cc) | (19x) | (20n) | (21o) |
| 492 | (Ik), (Im) | (6q) | (10x) | (11j) | (12u) | (13s) | (14gg) | (15cc) | (19x) | (20n) | (21q) |
| 493 | (Ik), (Im) | (6q) | (10x) | (11j) | (12x) | (13t) | (14w) | (15z), (15aa) | (19x) | (20m) | (21o) |
| 494 | (Ik), (Im) | (6q) | (10x) | (11j) | (12x) | (13t) | (14w) | (15z), (15aa) | (19x) | (20m) | (21q) |
| 495 | (Ik), (Im) | (6q) | (10x) | (11j) | (12x) | (13t) | (14w) | (15z), (15aa) | (19x) | (20n) | (21o) |
| 496 | (Ik), (Im) | (6q) | (10x) | (11j) | (12x) | (13t) | (14w) | (15z), (15aa) | (19x) | (20n) | (21q) |

-continued

|  | I | L¹† | R¹ | L² | Q | L³ | R³ | L⁴†† | R⁴ | L⁵ | R⁵ |
|---|---|---|---|---|---|---|---|---|---|---|---|
| 497 | (Ik), (Im) | (6q) | (10x) | (11j) | (12x) | (13t) | (14w) | (15cc) | (19x) | (20m) | (21o) |
| 498 | (Ik), (Im) | (6q) | (10x) | (11j) | (12x) | (13t) | (14w) | (15cc) | (19x) | (20m) | (21q) |
| 499 | (Ik), (Im) | (6q) | (10x) | (11j) | (12x) | (13t) | (14w) | (15cc) | (19x) | (20n) | (21o) |
| 500 | (Ik), (Im) | (6q) | (10x) | (11j) | (12x) | (13t) | (14w) | (15cc) | (19x) | (20n) | (21q) |
| 501 | (Ik), (Im) | (6q) | (10x) | (11j) | (12x) | (13t) | (14gg) | (15z), (15aa) | (19x) | (20m) | (21o) |
| 502 | (Ik), (Im) | (6q) | (10x) | (11j) | (12x) | (13t) | (14gg) | (15z), (15aa) | (19x) | (20m) | (21q) |
| 503 | (Ik), (Im) | (6q) | (10x) | (11j) | (12x) | (13t) | (14gg) | (15z), (15aa) | (19x) | (20n) | (21o) |
| 504 | (Ik), (Im) | (6q) | (10x) | (11j) | (12x) | (13t) | (14gg) | (15z), (15aa) | (19x) | (20n) | (21q) |
| 505 | (Ik), (Im) | (6q) | (10x) | (11j) | (12x) | (13t) | (14gg) | (15cc) | (19x) | (20m) | (21o) |
| 506 | (Ik), (Im) | (6q) | (10x) | (11j) | (12x) | (13t) | (14gg) | (15cc) | (19x) | (20m) | (21q) |
| 507 | (Ik), (Im) | (6q) | (10x) | (11j) | (12x) | (13t) | (14gg) | (15cc) | (19x) | (20n) | (21o) |
| 508 | (Ik), (Im) | (6q) | (10x) | (11j) | (12x) | (13t) | (14gg) | (15cc) | (19x) | (20n) | (21q) |
| 509 | (Ik), (Im) | (6q) | (10x) | (11j) | (12x) | (13s) | (14w) | (15z), (15aa) | (19x) | (20m) | (21o) |
| 510 | (Ik), (Im) | (6q) | (10x) | (11j) | (12x) | (13s) | (14w) | (15z), (15aa) | (19x) | (20m) | (21q) |
| 511 | (Ik), (Im) | (6q) | (10x) | (11j) | (12x) | (13s) | (14w) | (15z), (15aa) | (19x) | (20n) | (21o) |
| 512 | (Ik), (Im) | (6q) | (10x) | (11j) | (12x) | (13s) | (14w) | (15z), (15aa) | (19x) | (20n) | (21q) |
| 513 | (Ik), (Im) | (6q) | (10x) | (11j) | (12x) | (13s) | (14w) | (15cc) | (19x) | (20m) | (21o) |
| 514 | (Ik), (Im) | (6q) | (10x) | (11j) | (12x) | (13s) | (14w) | (15cc) | (19x) | (20m) | (21q) |
| 515 | (Ik), (Im) | (6q) | (10x) | (11j) | (12x) | (13s) | (14w) | (15cc) | (19x) | (20n) | (21o) |
| 516 | (Ik), (Im) | (6q) | (10x) | (11j) | (12x) | (13s) | (14w) | (15cc) | (19x) | (20n) | (21q) |
| 517 | (Ik), (Im) | (6q) | (10x) | (11j) | (12x) | (13s) | (14gg) | (15z), (15aa) | (19x) | (20m) | (21o) |
| 518 | (Ik), (Im) | (6q) | (10x) | (11j) | (12x) | (13s) | (14gg) | (15z), (15aa) | (19x) | (20m) | (21q) |
| 519 | (Ik), (Im) | (6q) | (10x) | (11j) | (12x) | (13s) | (14gg) | (15z), (15aa) | (19x) | (20n) | (21o) |
| 520 | (Ik), (Im) | (6q) | (10x) | (11j) | (12x) | (13s) | (14gg) | (15z), (15aa) | (19x) | (20n) | (21q) |
| 521 | (Ik), (Im) | (6q) | (10x) | (11j) | (12x) | (13s) | (14gg) | (15cc) | (19x) | (20m) | (21o) |
| 522 | (Ik), (Im) | (6q) | (10x) | (11j) | (12x) | (13s) | (14gg) | (15cc) | (19x) | (20m) | (21q) |
| 523 | (Ik), (Im) | (6q) | (10x) | (11j) | (12x) | (13s) | (14gg) | (15cc) | (19x) | (20n) | (21o) |
| 524 | (Ik), (Im) | (6q) | (10x) | (11j) | (12x) | (13s) | (14gg) | (15cc) | (19x) | (20n) | (21q) |
| 525 | (Ik), (Im) | (6t) | (10w) | (11k) | (12u) | (13t) | (14w) | (15z), (15aa) | (19x) | (20m) | (21o) |
| 526 | (Ik), (Im) | (6t) | (10w) | (11k) | (12u) | (13t) | (14w) | (15z), (15aa) | (19x) | (20m) | (21q) |
| 527 | (Ik), (Im) | (6t) | (10w) | (11k) | (12u) | (13t) | (14w) | (15z), (15aa) | (19x) | (20n) | (21o) |
| 528 | (Ik), (Im) | (6t) | (10w) | (11k) | (12u) | (13t) | (14w) | (15z), (15aa) | (19x) | (20n) | (21q) |
| 529 | (Ik), (Im) | (6t) | (10w) | (11k) | (12u) | (13t) | (14w) | (15cc) | (19x) | (20m) | (21o) |
| 530 | (Ik), (Im) | (6t) | (10w) | (11k) | (12u) | (13t) | (14w) | (15cc) | (19x) | (20m) | (21q) |
| 531 | (Ik), (Im) | (6t) | (10w) | (11k) | (12u) | (13t) | (14w) | (15cc) | (19x) | (20n) | (21o) |
| 532 | (Ik), (Im) | (6t) | (10w) | (11k) | (12u) | (13t) | (14w) | (15cc) | (19x) | (20n) | (21q) |
| 533 | (Ik), (Im) | (6t) | (10w) | (11k) | (12u) | (13t) | (14gg) | (15z), (15aa) | (19x) | (20m) | (21o) |
| 534 | (Ik), (Im) | (6t) | (10w) | (11k) | (12u) | (13t) | (14gg) | (15z), (15aa) | (19x) | (20m) | (21q) |
| 535 | (Ik), (Im) | (6t) | (10w) | (11k) | (12u) | (13t) | (14gg) | (15z), (15aa) | (19x) | (20n) | (21o) |
| 536 | (Ik), (Im) | (6t) | (10w) | (11k) | (12u) | (13t) | (14gg) | (15z), (15aa) | (19x) | (20n) | (21q) |
| 537 | (Ik), (Im) | (6t) | (10w) | (11k) | (12u) | (13t) | (14gg) | (15cc) | (19x) | (20m) | (21o) |
| 538 | (Ik), (Im) | (6t) | (10w) | (11k) | (12u) | (13t) | (14gg) | (15cc) | (19x) | (20m) | (21q) |
| 539 | (Ik), (Im) | (6t) | (10w) | (11k) | (12u) | (13t) | (14gg) | (15cc) | (19x) | (20n) | (21o) |
| 540 | (Ik), (Im) | (6t) | (10w) | (11k) | (12u) | (13t) | (14gg) | (15cc) | (19x) | (20n) | (21q) |
| 541 | (Ik), (Im) | (6t) | (10w) | (11k) | (12u) | (13s) | (14w) | (15z), (15aa) | (19x) | (20m) | (21o) |
| 542 | (Ik), (Im) | (6t) | (10w) | (11k) | (12u) | (13s) | (14w) | (15z), (15aa) | (19x) | (20m) | (21q) |
| 543 | (Ik), (Im) | (6t) | (10w) | (11k) | (12u) | (13s) | (14w) | (15z), (15aa) | (19x) | (20n) | (21o) |
| 544 | (Ik), (Im) | (6t) | (10w) | (11k) | (12u) | (13s) | (14w) | (15z), (15aa) | (19x) | (20n) | (21q) |
| 545 | (Ik), (Im) | (6t) | (10w) | (11k) | (12u) | (13s) | (14w) | (15cc) | (19x) | (20m) | (21o) |
| 546 | (Ik), (Im) | (6t) | (10w) | (11k) | (12u) | (13s) | (14w) | (15cc) | (19x) | (20m) | (21q) |
| 547 | (Ik), (Im) | (6t) | (10w) | (11k) | (12u) | (13s) | (14w) | (15cc) | (19x) | (20n) | (21o) |
| 548 | (Ik), (Im) | (6t) | (10w) | (11k) | (12u) | (13s) | (14w) | (15cc) | (19x) | (20n) | (21q) |
| 549 | (Ik), (Im) | (6t) | (10w) | (11k) | (12u) | (13s) | (14gg) | (15z), (15aa) | (19x) | (20m) | (21o) |
| 550 | (Ik), (Im) | (6t) | (10w) | (11k) | (12u) | (13s) | (14gg) | (15z), (15aa) | (19x) | (20m) | (21q) |
| 551 | (Ik), (Im) | (6t) | (10w) | (11k) | (12u) | (13s) | (14gg) | (15z), (15aa) | (19x) | (20n) | (21o) |
| 552 | (Ik), (Im) | (6t) | (10w) | (11k) | (12u) | (13s) | (14gg) | (15z), (15aa) | (19x) | (20n) | (21q) |
| 553 | (Ik), (Im) | (6t) | (10w) | (11k) | (12u) | (13s) | (14gg) | (15cc) | (19x) | (20m) | (21o) |
| 554 | (Ik), (Im) | (6t) | (10w) | (11k) | (12u) | (13s) | (14gg) | (15cc) | (19x) | (20m) | (21q) |
| 555 | (Ik), (Im) | (6t) | (10w) | (11k) | (12u) | (13s) | (14gg) | (15cc) | (19x) | (20n) | (21o) |
| 556 | (Ik), (Im) | (6t) | (10w) | (11k) | (12u) | (13s) | (14gg) | (15cc) | (19x) | (20n) | (21q) |
| 557 | (Ik), (Im) | (6t) | (10w) | (11k) | (12x) | (13t) | (14w) | (15z), (15aa) | (19x) | (20m) | (21o) |
| 558 | (Ik), (Im) | (6t) | (10w) | (11k) | (12x) | (13t) | (14w) | (15z), (15aa) | (19x) | (20m) | (21q) |
| 559 | (Ik), (Im) | (6t) | (10w) | (11k) | (12x) | (13t) | (14w) | (15z), (15aa) | (19x) | (20n) | (21o) |
| 560 | (Ik), (Im) | (6t) | (10w) | (11k) | (12x) | (13t) | (14w) | (15z), (15aa) | (19x) | (20n) | (21q) |
| 561 | (Ik), (Im) | (6t) | (10w) | (11k) | (12x) | (13t) | (14w) | (15cc) | (19x) | (20m) | (21o) |
| 562 | (Ik), (Im) | (6t) | (10w) | (11k) | (12x) | (13t) | (14w) | (15cc) | (19x) | (20m) | (21q) |
| 563 | (Ik), (Im) | (6t) | (10w) | (11k) | (12x) | (13t) | (14w) | (15cc) | (19x) | (20n) | (21o) |
| 564 | (Ik), (Im) | (6t) | (10w) | (11k) | (12x) | (13t) | (14w) | (15cc) | (19x) | (20n) | (21q) |
| 565 | (Ik), (Im) | (6t) | (10w) | (11k) | (12x) | (13t) | (14gg) | (15z), (15aa) | (19x) | (20m) | (21o) |
| 566 | (Ik), (Im) | (6t) | (10w) | (11k) | (12x) | (13t) | (14gg) | (15z), (15aa) | (19x) | (20m) | (21q) |
| 567 | (Ik), (Im) | (6t) | (10w) | (11k) | (12x) | (13t) | (14gg) | (15z), (15aa) | (19x) | (20n) | (21o) |
| 568 | (Ik), (Im) | (6t) | (10w) | (11k) | (12x) | (13t) | (14gg) | (15z), (15aa) | (19x) | (20n) | (21q) |
| 569 | (Ik), (Im) | (6t) | (10w) | (11k) | (12x) | (13t) | (14gg) | (15cc) | (19x) | (20m) | (21o) |
| 570 | (Ik), (Im) | (6t) | (10w) | (11k) | (12x) | (13t) | (14gg) | (15cc) | (19x) | (20m) | (21q) |
| 571 | (Ik), (Im) | (6t) | (10w) | (11k) | (12x) | (13t) | (14gg) | (15cc) | (19x) | (20n) | (21o) |
| 572 | (Ik), (Im) | (6t) | (10w) | (11k) | (12x) | (13t) | (14gg) | (15cc) | (19x) | (20n) | (21q) |
| 573 | (Ik), (Im) | (6t) | (10w) | (11k) | (12x) | (13s) | (14w) | (15z), (15aa) | (19x) | (20m) | (21o) |

| | I | L¹† | R¹ | L² | Q | L³ | R³ | L⁴†† | R⁴ | L⁵ | R⁵ |
|---|---|---|---|---|---|---|---|---|---|---|---|
| 574 | (Ik), (Im) | (6t) | (10w) | (11k) | (12x) | (13s) | (14w) | (15z), (15aa) | (19x) | (20m) | (21q) |
| 575 | (Ik), (Im) | (6t) | (10w) | (11k) | (12x) | (13s) | (14w) | (15z), (15aa) | (19x) | (20n) | (21o) |
| 576 | (Ik), (Im) | (6t) | (10w) | (11k) | (12x) | (13s) | (14w) | (15z), (15aa) | (19x) | (20n) | (21q) |
| 577 | (Ik), (Im) | (6t) | (10w) | (11k) | (12x) | (13s) | (14w) | (15cc) | (19x) | (20m) | (21o) |
| 578 | (Ik), (Im) | (6t) | (10w) | (11k) | (12x) | (13s) | (14w) | (15cc) | (19x) | (20m) | (21q) |
| 579 | (Ik), (Im) | (6t) | (10w) | (11k) | (12x) | (13s) | (14w) | (15cc) | (19x) | (20n) | (21o) |
| 580 | (Ik), (Im) | (6t) | (10w) | (11k) | (12x) | (13s) | (14w) | (15cc) | (19x) | (20n) | (21q) |
| 581 | (Ik), (Im) | (6t) | (10w) | (11k) | (12x) | (13s) | (14gg) | (15z), (15aa) | (19x) | (20m) | (21o) |
| 582 | (Ik), (Im) | (6t) | (10w) | (11k) | (12x) | (13s) | (14gg) | (15z), (15aa) | (19x) | (20m) | (21q) |
| 583 | (Ik), (Im) | (6t) | (10w) | (11k) | (12x) | (13s) | (14gg) | (15z), (15aa) | (19x) | (20n) | (21o) |
| 584 | (Ik), (Im) | (6t) | (10w) | (11k) | (12x) | (13s) | (14gg) | (15z), (15aa) | (19x) | (20n) | (21q) |
| 585 | (Ik), (Im) | (6t) | (10w) | (11k) | (12x) | (13s) | (14gg) | (15cc) | (19x) | (20m) | (21o) |
| 586 | (Ik), (Im) | (6t) | (10w) | (11k) | (12x) | (13s) | (14gg) | (15cc) | (19x) | (20m) | (21q) |
| 587 | (Ik), (Im) | (6t) | (10w) | (11k) | (12x) | (13s) | (14gg) | (15cc) | (19x) | (20n) | (21o) |
| 588 | (Ik), (Im) | (6t) | (10w) | (11k) | (12x) | (13s) | (14gg) | (15cc) | (19x) | (20n) | (21q) |
| 589 | (Ik), (Im) | (6t) | (10w) | (11j) | (12u) | (13t) | (14w) | (15z), (15aa) | (19x) | (20m) | (21o) |
| 590 | (Ik), (Im) | (6t) | (10w) | (11j) | (12u) | (13t) | (14w) | (15z), (15aa) | (19x) | (20m) | (21q) |
| 591 | (Ik), (Im) | (6t) | (10w) | (11j) | (12u) | (13t) | (14w) | (15z), (15aa) | (19x) | (20n) | (21o) |
| 592 | (Ik), (Im) | (6t) | (10w) | (11j) | (12u) | (13t) | (14w) | (15z), (15aa) | (19x) | (20n) | (21q) |
| 593 | (Ik), (Im) | (6t) | (10w) | (11j) | (12u) | (13t) | (14w) | (15cc) | (19x) | (20m) | (21o) |
| 594 | (Ik), (Im) | (6t) | (10w) | (11j) | (12u) | (13t) | (14w) | (15cc) | (19x) | (20m) | (21q) |
| 595 | (Ik), (Im) | (6t) | (10w) | (11j) | (12u) | (13t) | (14w) | (15cc) | (19x) | (20n) | (21o) |
| 596 | (Ik), (Im) | (6t) | (10w) | (11j) | (12u) | (13t) | (14w) | (15cc) | (19x) | (20n) | (21q) |
| 597 | (Ik), (Im) | (6t) | (10w) | (11j) | (12u) | (13t) | (14gg) | (15z), (15aa) | (19x) | (20m) | (21o) |
| 598 | (Ik), (Im) | (6t) | (10w) | (11j) | (12u) | (13t) | (14gg) | (15z), (15aa) | (19x) | (20m) | (21q) |
| 599 | (Ik), (Im) | (6t) | (10w) | (11j) | (12u) | (13t) | (14gg) | (15z), (15aa) | (19x) | (20n) | (21o) |
| 600 | (Ik), (Im) | (6t) | (10w) | (11j) | (12u) | (13t) | (14gg) | (15z), (15aa) | (19x) | (20n) | (21q) |
| 601 | (Ik), (Im) | (6t) | (10w) | (11j) | (12u) | (13t) | (14gg) | (15cc) | (19x) | (20m) | (21o) |
| 602 | (Ik), (Im) | (6t) | (10w) | (11j) | (12u) | (13t) | (14gg) | (15cc) | (19x) | (20m) | (21q) |
| 603 | (Ik), (Im) | (6t) | (10w) | (11j) | (12u) | (13t) | (14gg) | (15cc) | (19x) | (20n) | (21o) |
| 604 | (Ik), (Im) | (6t) | (10w) | (11j) | (12u) | (13t) | (14gg) | (15cc) | (19x) | (20n) | (21q) |
| 605 | (Ik), (Im) | (6t) | (10w) | (11j) | (12u) | (13s) | (14w) | (15z), (15aa) | (19x) | (20m) | (21o) |
| 606 | (Ik), (Im) | (6t) | (10w) | (11j) | (12u) | (13s) | (14w) | (15z), (15aa) | (19x) | (20m) | (21q) |
| 607 | (Ik), (Im) | (6t) | (10w) | (11j) | (12u) | (13s) | (14w) | (15z), (15aa) | (19x) | (20n) | (21o) |
| 608 | (Ik), (Im) | (6t) | (10w) | (11j) | (12u) | (13s) | (14w) | (15z), (15aa) | (19x) | (20n) | (21q) |
| 609 | (Ik), (Im) | (6t) | (10w) | (11j) | (12u) | (13s) | (14w) | (15cc) | (19x) | (20m) | (21o) |
| 610 | (Ik), (Im) | (6t) | (10w) | (11j) | (12u) | (13s) | (14w) | (15cc) | (19x) | (20m) | (21q) |
| 611 | (Ik), (Im) | (6t) | (10w) | (11j) | (12u) | (13s) | (14w) | (15cc) | (19x) | (20n) | (21o) |
| 612 | (Ik), (Im) | (6t) | (10w) | (11j) | (12u) | (13s) | (14w) | (15cc) | (19x) | (20n) | (21q) |
| 613 | (Ik), (Im) | (6t) | (10w) | (11j) | (12u) | (13s) | (14gg) | (15z), (15aa) | (19x) | (20m) | (21o) |
| 614 | (Ik), (Im) | (6t) | (10w) | (11j) | (12u) | (13s) | (14gg) | (15z), (15aa) | (19x) | (20m) | (21q) |
| 615 | (Ik), (Im) | (6t) | (10w) | (11j) | (12u) | (13s) | (14gg) | (15z), (15aa) | (19x) | (20n) | (21o) |
| 616 | (Ik), (Im) | (6t) | (10w) | (11j) | (12u) | (13s) | (14gg) | (15z), (15aa) | (19x) | (20n) | (21q) |
| 617 | (Ik), (Im) | (6t) | (10w) | (11j) | (12u) | (13s) | (14gg) | (15cc) | (19x) | (20m) | (21o) |
| 618 | (Ik), (Im) | (6t) | (10w) | (11j) | (12u) | (13s) | (14gg) | (15cc) | (19x) | (20m) | (21q) |
| 619 | (Ik), (Im) | (6t) | (10w) | (11j) | (12u) | (13s) | (14gg) | (15cc) | (19x) | (20n) | (21o) |
| 620 | (Ik), (Im) | (6t) | (10w) | (11j) | (12u) | (13s) | (14gg) | (15cc) | (19x) | (20n) | (21q) |
| 621 | (Ik), (Im) | (6t) | (10w) | (11j) | (12x) | (13t) | (14w) | (15z), (15aa) | (19x) | (20m) | (21o) |
| 622 | (Ik), (Im) | (6t) | (10w) | (11j) | (12x) | (13t) | (14w) | (15z), (15aa) | (19x) | (20m) | (21q) |
| 623 | (Ik), (Im) | (6t) | (10w) | (11j) | (12x) | (13t) | (14w) | (15z), (15aa) | (19x) | (20n) | (21o) |
| 624 | (Ik), (Im) | (6t) | (10w) | (11j) | (12x) | (13t) | (14w) | (15z), (15aa) | (19x) | (20n) | (21q) |
| 625 | (Ik), (Im) | (6t) | (10w) | (11j) | (12x) | (13t) | (14w) | (15cc) | (19x) | (20m) | (21o) |
| 626 | (Ik), (Im) | (6t) | (10w) | (11j) | (12x) | (13t) | (14w) | (15cc) | (19x) | (20m) | (21q) |
| 627 | (Ik), (Im) | (6t) | (10w) | (11j) | (12x) | (13t) | (14w) | (15cc) | (19x) | (20n) | (21o) |
| 628 | (Ik), (Im) | (6t) | (10w) | (11j) | (12x) | (13t) | (14w) | (15cc) | (19x) | (20n) | (21q) |
| 629 | (Ik), (Im) | (6t) | (10w) | (11j) | (12x) | (13t) | (14gg) | (15z), (15aa) | (19x) | (20m) | (21o) |
| 630 | (Ik), (Im) | (6t) | (10w) | (11j) | (12x) | (13t) | (14gg) | (15z), (15aa) | (19x) | (20m) | (21q) |
| 631 | (Ik), (Im) | (6t) | (10w) | (11j) | (12x) | (13t) | (14gg) | (15z), (15aa) | (19x) | (20n) | (21o) |
| 632 | (Ik), (Im) | (6t) | (10w) | (11j) | (12x) | (13t) | (14gg) | (15z), (15aa) | (19x) | (20n) | (21q) |
| 633 | (Ik), (Im) | (6t) | (10w) | (11j) | (12x) | (13t) | (14gg) | (15cc) | (19x) | (20m) | (21o) |
| 634 | (Ik), (Im) | (6t) | (10w) | (11j) | (12x) | (13t) | (14gg) | (15cc) | (19x) | (20m) | (21q) |
| 635 | (Ik), (Im) | (6t) | (10w) | (11j) | (12x) | (13t) | (14gg) | (15cc) | (19x) | (20n) | (21o) |
| 636 | (Ik), (Im) | (6t) | (10w) | (11j) | (12x) | (13t) | (14gg) | (15cc) | (19x) | (20n) | (21q) |
| 637 | (Ik), (Im) | (6t) | (10w) | (11j) | (12x) | (13s) | (14w) | (15z), (15aa) | (19x) | (20m) | (21o) |
| 638 | (Ik), (Im) | (6t) | (10w) | (11j) | (12x) | (13s) | (14w) | (15z), (15aa) | (19x) | (20m) | (21q) |
| 639 | (Ik), (Im) | (6t) | (10w) | (11j) | (12x) | (13s) | (14w) | (15z), (15aa) | (19x) | (20n) | (21o) |
| 640 | (Ik), (Im) | (6t) | (10w) | (11j) | (12x) | (13s) | (14w) | (15z), (15aa) | (19x) | (20n) | (21q) |
| 641 | (Ik), (Im) | (6t) | (10w) | (11j) | (12x) | (13s) | (14w) | (15cc) | (19x) | (20m) | (21o) |
| 642 | (Ik), (Im) | (6t) | (10w) | (11j) | (12x) | (13s) | (14w) | (15cc) | (19x) | (20m) | (21q) |
| 643 | (Ik), (Im) | (6t) | (10w) | (11j) | (12x) | (13s) | (14w) | (15cc) | (19x) | (20n) | (21o) |
| 644 | (Ik), (Im) | (6t) | (10w) | (11j) | (12x) | (13s) | (14w) | (15cc) | (19x) | (20n) | (21q) |
| 645 | (Ik), (Im) | (6t) | (10w) | (11j) | (12x) | (13s) | (14gg) | (15z), (15aa) | (19x) | (20m) | (21o) |
| 646 | (Ik), (Im) | (6t) | (10w) | (11j) | (12x) | (13s) | (14gg) | (15z), (15aa) | (19x) | (20m) | (21q) |
| 647 | (Ik), (Im) | (6t) | (10w) | (11j) | (12x) | (13s) | (14gg) | (15z), (15aa) | (19x) | (20n) | (21o) |
| 648 | (Ik), (Im) | (6t) | (10w) | (11j) | (12x) | (13s) | (14gg) | (15z), (15aa) | (19x) | (20n) | (21q) |
| 649 | (Ik), (Im) | (6t) | (10w) | (11j) | (12x) | (13s) | (14gg) | (15cc) | (19x) | (20m) | (21o) |
| 650 | (Ik), (Im) | (6t) | (10w) | (11j) | (12x) | (13s) | (14gg) | (15cc) | (19x) | (20m) | (21q) |

-continued

|  | I | L¹† | R¹ | L² | Q | L³ | R³ | L⁴†† | R⁴ | L⁵ | R⁵ |
|---|---|---|---|---|---|---|---|---|---|---|---|
| 651 | (Ik), (Im) | (6t) | (10w) | (11j) | (12x) | (13s) | (14gg) | (15cc) | (19x) | (20n) | (21o) |
| 652 | (Ik), (Im) | (6t) | (10w) | (11j) | (12x) | (13s) | (14gg) | (15cc) | (19x) | (20n) | (21q) |
| 653 | (Ik), (Im) | (6t) | (10x) | (11k) | (12u) | (13t) | (14w) | (15z), (15aa) | (19x) | (20m) | (21o) |
| 654 | (Ik), (Im) | (6t) | (10x) | (11k) | (12u) | (13t) | (14w) | (15z), (15aa) | (19x) | (20n) | (21o) |
| 655 | (Ik), (Im) | (6t) | (10x) | (11k) | (12u) | (13t) | (14w) | (15z), (15aa) | (19x) | (20n) | (21q) |
| 656 | (Ik), (Im) | (6t) | (10x) | (11k) | (12u) | (13t) | (14w) | (15z), (15aa) | (19x) | (20n) | (21q) |
| 657 | (Ik), (Im) | (6t) | (10x) | (11k) | (12u) | (13t) | (14w) | (15cc) | (19x) | (20n) | (21o) |
| 658 | (Ik), (Im) | (6t) | (10x) | (11k) | (12u) | (13t) | (14w) | (15cc) | (19x) | (20m) | (21q) |
| 659 | (Ik), (Im) | (6t) | (10x) | (11k) | (12u) | (13t) | (14w) | (15cc) | (19x) | (20n) | (21o) |
| 660 | (Ik), (Im) | (6t) | (10x) | (11k) | (12u) | (13t) | (14w) | (15cc) | (19x) | (20n) | (21q) |
| 661 | (Ik), (Im) | (6t) | (10x) | (11k) | (12u) | (13t) | (14gg) | (15z), (15aa) | (19x) | (20m) | (21o) |
| 662 | (Ik), (Im) | (6t) | (10x) | (11k) | (12u) | (13t) | (14gg) | (15z), (15aa) | (19x) | (20m) | (21q) |
| 663 | (Ik), (Im) | (6t) | (10x) | (11k) | (12u) | (13t) | (14gg) | (15z), (15aa) | (19x) | (20n) | (21o) |
| 664 | (Ik), (Im) | (6t) | (10x) | (11k) | (12u) | (13t) | (14gg) | (15z), (15aa) | (19x) | (20n) | (21q) |
| 665 | (Ik), (Im) | (6t) | (10x) | (11k) | (12u) | (13t) | (14gg) | (15cc) | (19x) | (20m) | (21o) |
| 666 | (Ik), (Im) | (6t) | (10x) | (11k) | (12u) | (13t) | (14gg) | (15cc) | (19x) | (20m) | (21q) |
| 667 | (Ik), (Im) | (6t) | (10x) | (11k) | (12u) | (13t) | (14gg) | (15cc) | (19x) | (20n) | (21o) |
| 668 | (Ik), (Im) | (6t) | (10x) | (11k) | (12u) | (13t) | (14gg) | (15cc) | (19x) | (20n) | (21q) |
| 669 | (Ik), (Im) | (6t) | (10x) | (11k) | (12u) | (13s) | (14w) | (15z), (15aa) | (19x) | (20m) | (21o) |
| 670 | (Ik), (Im) | (6t) | (10x) | (11k) | (12u) | (13s) | (14w) | (15z), (15aa) | (19x) | (20m) | (21q) |
| 671 | (Ik), (Im) | (6t) | (10x) | (11k) | (12u) | (13s) | (14w) | (15z), (15aa) | (19x) | (20n) | (21o) |
| 672 | (Ik), (Im) | (6t) | (10x) | (11k) | (12u) | (13s) | (14w) | (15z), (15aa) | (19x) | (20n) | (21q) |
| 673 | (Ik), (Im) | (6t) | (10x) | (11k) | (12u) | (13s) | (14w) | (15cc) | (19x) | (20m) | (21o) |
| 674 | (Ik), (Im) | (6t) | (10x) | (11k) | (12u) | (13s) | (14w) | (15cc) | (19x) | (20m) | (21q) |
| 675 | (Ik), (Im) | (6t) | (10x) | (11k) | (12u) | (13s) | (14w) | (15cc) | (19x) | (20n) | (21o) |
| 676 | (Ik), (Im) | (6t) | (10x) | (11k) | (12u) | (13s) | (14w) | (15cc) | (19x) | (20n) | (21q) |
| 677 | (Ik), (Im) | (6t) | (10x) | (11k) | (12u) | (13s) | (14gg) | (15z), (15aa) | (19x) | (20m) | (21o) |
| 678 | (Ik), (Im) | (6t) | (10x) | (11k) | (12u) | (13s) | (14gg) | (15z), (15aa) | (19x) | (20m) | (21q) |
| 679 | (Ik), (Im) | (6t) | (10x) | (11k) | (12u) | (13s) | (14gg) | (15z), (15aa) | (19x) | (20n) | (21o) |
| 680 | (Ik), (Im) | (6t) | (10x) | (11k) | (12u) | (13s) | (14gg) | (15z), (15aa) | (19x) | (20n) | (21q) |
| 681 | (Ik), (Im) | (6t) | (10x) | (11k) | (12u) | (13s) | (14gg) | (15cc) | (19x) | (20m) | (21o) |
| 682 | (Ik), (Im) | (6t) | (10x) | (11k) | (12u) | (13s) | (14gg) | (15cc) | (19x) | (20m) | (21q) |
| 683 | (Ik), (Im) | (6t) | (10x) | (11k) | (12u) | (13s) | (14gg) | (15cc) | (19x) | (20n) | (21o) |
| 684 | (Ik), (Im) | (6t) | (10x) | (11k) | (12u) | (13s) | (14gg) | (15cc) | (19x) | (20n) | (21q) |
| 685 | (Ik), (Im) | (6t) | (10x) | (11k) | (12x) | (13t) | (14w) | (15z), (15aa) | (19x) | (20m) | (21o) |
| 686 | (Ik), (Im) | (6t) | (10x) | (11k) | (12x) | (13t) | (14w) | (15z), (15aa) | (19x) | (20m) | (21q) |
| 687 | (Ik), (Im) | (6t) | (10x) | (11k) | (12x) | (13t) | (14w) | (15z), (15aa) | (19x) | (20n) | (21q) |
| 688 | (Ik), (Im) | (6t) | (10x) | (11k) | (12x) | (13t) | (14w) | (15z), (15aa) | (19x) | (20n) | (21q) |
| 689 | (Ik), (Im) | (6t) | (10x) | (11k) | (12x) | (13t) | (14w) | (15cc) | (19x) | (20m) | (21o) |
| 690 | (Ik), (Im) | (6t) | (10x) | (11k) | (12x) | (13t) | (14w) | (15cc) | (19x) | (20m) | (21q) |
| 691 | (Ik), (Im) | (6t) | (10x) | (11k) | (12x) | (13t) | (14w) | (15cc) | (19x) | (20n) | (21o) |
| 692 | (Ik), (Im) | (6t) | (10x) | (11k) | (12x) | (13t) | (14w) | (15cc) | (19x) | (20n) | (21q) |
| 693 | (Ik), (Im) | (6t) | (10x) | (11k) | (12x) | (13t) | (14gg) | (15z), (15aa) | (19x) | (20m) | (21o) |
| 694 | (Ik), (Im) | (6t) | (10x) | (11k) | (12x) | (13t) | (14gg) | (15z), (15aa) | (19x) | (20m) | (21q) |
| 695 | (Ik), (Im) | (6t) | (10x) | (11k) | (12x) | (13t) | (14gg) | (15z), (15aa) | (19x) | (20n) | (21o) |
| 696 | (Ik), (Im) | (6t) | (10x) | (11k) | (12x) | (13t) | (14gg) | (15z), (15aa) | (19x) | (20n) | (21q) |
| 697 | (Ik), (Im) | (6t) | (10x) | (11k) | (12x) | (13t) | (14gg) | (15cc) | (19x) | (20m) | (21o) |
| 698 | (Ik), (Im) | (6t) | (10x) | (11k) | (12x) | (13t) | (14gg) | (15cc) | (19x) | (20m) | (21q) |
| 699 | (Ik), (Im) | (6t) | (10x) | (11k) | (12x) | (13t) | (14gg) | (15cc) | (19x) | (20n) | (21o) |
| 700 | (Ik), (Im) | (6t) | (10x) | (11k) | (12x) | (13t) | (14gg) | (15cc) | (19x) | (20n) | (21q) |
| 701 | (Ik), (Im) | (6t) | (10x) | (11k) | (12x) | (13s) | (14w) | (15z), (15aa) | (19x) | (20m) | (21o) |
| 702 | (Ik), (Im) | (6t) | (10x) | (11k) | (12x) | (13s) | (14w) | (15z), (15aa) | (19x) | (20m) | (21q) |
| 703 | (Ik), (Im) | (6t) | (10x) | (11k) | (12x) | (13s) | (14w) | (15z), (15aa) | (19x) | (20n) | (21o) |
| 704 | (Ik), (Im) | (6t) | (10x) | (11k) | (12x) | (13s) | (14w) | (15z), (15aa) | (19x) | (20n) | (21q) |
| 705 | (Ik), (Im) | (6t) | (10x) | (11k) | (12x) | (13s) | (14w) | (15cc) | (19x) | (20m) | (21o) |
| 706 | (Ik), (Im) | (6t) | (10x) | (11k) | (12x) | (13s) | (14w) | (15cc) | (19x) | (20m) | (21q) |
| 707 | (Ik), (Im) | (6t) | (10x) | (11k) | (12x) | (13s) | (14w) | (15cc) | (19x) | (20n) | (21o) |
| 708 | (Ik), (Im) | (6t) | (10x) | (11k) | (12x) | (13s) | (14w) | (15cc) | (19x) | (20n) | (21q) |
| 709 | (Ik), (Im) | (6t) | (10x) | (11k) | (12x) | (13s) | (14gg) | (15z), (15aa) | (19x) | (20m) | (21o) |
| 710 | (Ik), (Im) | (6t) | (10x) | (11k) | (12x) | (13s) | (14gg) | (15z), (15aa) | (19x) | (20m) | (21q) |
| 711 | (Ik), (Im) | (6t) | (10x) | (11k) | (12x) | (13s) | (14gg) | (15z), (15aa) | (19x) | (20n) | (21o) |
| 712 | (Ik), (Im) | (6t) | (10x) | (11k) | (12x) | (13s) | (14gg) | (15z), (15aa) | (19x) | (20n) | (21q) |
| 713 | (Ik), (Im) | (6t) | (10x) | (11k) | (12x) | (13s) | (14gg) | (15cc) | (19x) | (20m) | (21o) |
| 714 | (Ik), (Im) | (6t) | (10x) | (11k) | (12x) | (13s) | (14gg) | (15cc) | (19x) | (20m) | (21q) |
| 715 | (Ik), (Im) | (6t) | (10x) | (11k) | (12x) | (13s) | (14gg) | (15cc) | (19x) | (20n) | (21o) |
| 716 | (Ik), (Im) | (6t) | (10x) | (11k) | (12x) | (13s) | (14gg) | (15cc) | (19x) | (20n) | (21q) |
| 717 | (Ik), (Im) | (6t) | (10x) | (11j) | (12u) | (13t) | (14w) | (15z), (15aa) | (19x) | (20m) | (21o) |
| 718 | (Ik), (Im) | (6t) | (10x) | (11j) | (12u) | (13t) | (14w) | (15z), (15aa) | (19x) | (20m) | (21q) |
| 719 | (Ik), (Im) | (6t) | (10x) | (11j) | (12u) | (13t) | (14w) | (15z), (15aa) | (19x) | (20n) | (21o) |
| 720 | (Ik), (Im) | (6t) | (10x) | (11j) | (12u) | (13t) | (14w) | (15z), (15aa) | (19x) | (20n) | (21q) |
| 721 | (Ik), (Im) | (6t) | (10x) | (11j) | (12u) | (13t) | (14w) | (15cc) | (19x) | (20m) | (21o) |
| 722 | (Ik), (Im) | (6t) | (10x) | (11j) | (12u) | (13t) | (14w) | (15cc) | (19x) | (20m) | (21q) |
| 723 | (Ik), (Im) | (6t) | (10x) | (11j) | (12u) | (13t) | (14w) | (15cc) | (19x) | (20n) | (21o) |
| 724 | (Ik), (Im) | (6t) | (10x) | (11j) | (12u) | (13t) | (14w) | (15cc) | (19x) | (20n) | (21q) |
| 725 | (Ik), (Im) | (6t) | (10x) | (11j) | (12u) | (13t) | (14gg) | (15z), (15aa) | (19x) | (20m) | (21o) |
| 726 | (Ik), (Im) | (6t) | (10x) | (11j) | (12u) | (13t) | (14gg) | (15z), (15aa) | (19x) | (20m) | (21q) |
| 727 | (Ik), (Im) | (6t) | (10x) | (11j) | (12u) | (13t) | (14gg) | (15z), (15aa) | (19x) | (20n) | (21o) |

-continued

| | I | L¹† | R¹ | L² | Q | L³ | R³ | L⁴†† | R⁴ | L⁵ | R⁵ |
|---|---|---|---|---|---|---|---|---|---|---|---|
| 728 | (Ik), (Im) | (6t) | (10x) | (11j) | (12u) | (13t) | (14gg) | (15z), (15aa) | (19x) | (20n) | (21q) |
| 729 | (Ik), (Im) | (6t) | (10x) | (11j) | (12u) | (13t) | (14gg) | (15cc) | (19x) | (20m) | (21o) |
| 730 | (Ik), (Im) | (6t) | (10x) | (11j) | (12u) | (13t) | (14gg) | (15cc) | (19x) | (20n) | (21q) |
| 731 | (Ik), (Im) | (6t) | (10x) | (11j) | (12u) | (13t) | (14gg) | (15cc) | (19x) | (20n) | (21o) |
| 732 | (Ik), (Im) | (6t) | (10x) | (11j) | (12u) | (13t) | (14gg) | (15cc) | (19x) | (20n) | (21q) |
| 733 | (Ik), (Im) | (6t) | (10x) | (11j) | (12u) | (13s) | (14w) | (15z), (15aa) | (19x) | (20m) | (21o) |
| 734 | (Ik), (Im) | (6t) | (10x) | (11j) | (12u) | (13s) | (14w) | (15z), (15aa) | (19x) | (20n) | (21q) |
| 735 | (Ik), (Im) | (6t) | (10x) | (11j) | (12u) | (13s) | (14w) | (15z), (15aa) | (19x) | (20n) | (21o) |
| 736 | (Ik), (Im) | (6t) | (10x) | (11j) | (12u) | (13s) | (14w) | (15z), (15aa) | (19x) | (20n) | (21q) |
| 737 | (Ik), (Im) | (6t) | (10x) | (11j) | (12u) | (13s) | (14w) | (15cc) | (19x) | (20m) | (21o) |
| 738 | (Ik), (Im) | (6t) | (10x) | (11j) | (12u) | (13s) | (14w) | (15cc) | (19x) | (20n) | (21q) |
| 739 | (Ik), (Im) | (6t) | (10x) | (11j) | (12u) | (13s) | (14w) | (15cc) | (19x) | (20n) | (21o) |
| 740 | (Ik), (Im) | (6t) | (10x) | (11j) | (12u) | (13s) | (14w) | (15cc) | (19x) | (20n) | (21q) |
| 741 | (Ik), (Im) | (6t) | (10x) | (11j) | (12u) | (13s) | (14gg) | (15z), (15aa) | (19x) | (20m) | (21o) |
| 742 | (Ik), (Im) | (6t) | (10x) | (11j) | (12u) | (13s) | (14gg) | (15z), (15aa) | (19x) | (20n) | (21q) |
| 743 | (Ik), (Im) | (6t) | (10x) | (11j) | (12u) | (13s) | (14gg) | (15z), (15aa) | (19x) | (20n) | (21o) |
| 744 | (Ik), (Im) | (6t) | (10x) | (11j) | (12u) | (13s) | (14gg) | (15z), (15aa) | (19x) | (20n) | (21q) |
| 745 | (Ik), (Im) | (6t) | (10x) | (11j) | (12u) | (13s) | (14gg) | (15cc) | (19x) | (20m) | (21o) |
| 746 | (Ik), (Im) | (6t) | (10x) | (11j) | (12u) | (13s) | (14gg) | (15cc) | (19x) | (20n) | (21q) |
| 747 | (Ik), (Im) | (6t) | (10x) | (11j) | (12u) | (13s) | (14gg) | (15cc) | (19x) | (20n) | (21o) |
| 748 | (Ik), (Im) | (6t) | (10x) | (11j) | (12u) | (13s) | (14gg) | (15cc) | (19x) | (20n) | (21q) |
| 749 | (Ik), (Im) | (6t) | (10x) | (11j) | (12x) | (13t) | (14w) | (15z), (15aa) | (19x) | (20m) | (21o) |
| 750 | (Ik), (Im) | (6t) | (10x) | (11j) | (12x) | (13t) | (14w) | (15z), (15aa) | (19x) | (20n) | (21q) |
| 751 | (Ik), (Im) | (6t) | (10x) | (11j) | (12x) | (13t) | (14w) | (15z), (15aa) | (19x) | (20n) | (21o) |
| 752 | (Ik), (Im) | (6t) | (10x) | (11j) | (12x) | (13t) | (14w) | (15z), (15aa) | (19x) | (20n) | (21q) |
| 753 | (Ik), (Im) | (6t) | (10x) | (11j) | (12x) | (13t) | (14w) | (15cc) | (19x) | (20m) | (21o) |
| 754 | (Ik), (Im) | (6t) | (10x) | (11j) | (12x) | (13t) | (14w) | (15cc) | (19x) | (20n) | (21q) |
| 755 | (Ik), (Im) | (6t) | (10x) | (11j) | (12x) | (13t) | (14w) | (15cc) | (19x) | (20n) | (21o) |
| 756 | (Ik), (Im) | (6t) | (10x) | (11j) | (12x) | (13t) | (14w) | (15cc) | (19x) | (20n) | (21q) |
| 757 | (Ik), (Im) | (6t) | (10x) | (11j) | (12x) | (13t) | (14gg) | (15z), (15aa) | (19x) | (20m) | (21o) |
| 758 | (Ik), (Im) | (6t) | (10x) | (11j) | (12x) | (13t) | (14gg) | (15z), (15aa) | (19x) | (20n) | (21q) |
| 759 | (Ik), (Im) | (6t) | (10x) | (11j) | (12x) | (13t) | (14gg) | (15z), (15aa) | (19x) | (20n) | (21o) |
| 760 | (Ik), (Im) | (6t) | (10x) | (11j) | (12x) | (13t) | (14gg) | (15z), (15aa) | (19x) | (20n) | (21q) |
| 761 | (Ik), (Im) | (6t) | (10x) | (11j) | (12x) | (13t) | (14gg) | (15cc) | (19x) | (20m) | (21o) |
| 762 | (Ik), (Im) | (6t) | (10x) | (11j) | (12x) | (13t) | (14gg) | (15cc) | (19x) | (20n) | (21q) |
| 763 | (Ik), (Im) | (6t) | (10x) | (11j) | (12x) | (13t) | (14gg) | (15cc) | (19x) | (20n) | (21o) |
| 764 | (Ik), (Im) | (6t) | (10x) | (11j) | (12x) | (13t) | (14gg) | (15cc) | (19x) | (20n) | (21q) |
| 765 | (Ik), (Im) | (6t) | (10x) | (11j) | (12x) | (13s) | (14w) | (15z), (15aa) | (19x) | (20m) | (21o) |
| 766 | (Ik), (Im) | (6t) | (10x) | (11j) | (12x) | (13s) | (14w) | (15z), (15aa) | (19x) | (20n) | (21q) |
| 767 | (Ik), (Im) | (6t) | (10x) | (11j) | (12x) | (13s) | (14w) | (15z), (15aa) | (19x) | (20n) | (21o) |
| 768 | (Ik), (Im) | (6t) | (10x) | (11j) | (12x) | (13s) | (14w) | (15z), (15aa) | (19x) | (20n) | (21q) |
| 769 | (Ik), (Im) | (6t) | (10x) | (11j) | (12x) | (13s) | (14w) | (15cc) | (19x) | (20m) | (21o) |
| 770 | (Ik), (Im) | (6t) | (10x) | (11j) | (12x) | (13s) | (14w) | (15cc) | (19x) | (20n) | (21q) |
| 771 | (Ik), (Im) | (6t) | (10x) | (11j) | (12x) | (13s) | (14w) | (15cc) | (19x) | (20n) | (21o) |
| 772 | (Ik), (Im) | (6t) | (10x) | (11j) | (12x) | (13s) | (14w) | (15cc) | (19x) | (20n) | (21q) |
| 773 | (Ik), (Im) | (6t) | (10x) | (11j) | (12x) | (13s) | (14gg) | (15z), (15aa) | (19x) | (20m) | (21o) |
| 774 | (Ik), (Im) | (6t) | (10x) | (11j) | (12x) | (13s) | (14gg) | (15z), (15aa) | (19x) | (20n) | (21q) |
| 775 | (Ik), (Im) | (6t) | (10x) | (11j) | (12x) | (13s) | (14gg) | (15z), (15aa) | (19x) | (20n) | (21o) |
| 776 | (Ik), (Im) | (6t) | (10x) | (11j) | (12x) | (13s) | (14gg) | (15z), (15aa) | (19x) | (20n) | (21q) |
| 777 | (Ik), (Im) | (6t) | (10x) | (11j) | (12x) | (13s) | (14gg) | (15cc) | (19x) | (20m) | (21o) |
| 778 | (Ik), (Im) | (6t) | (10x) | (11j) | (12x) | (13s) | (14gg) | (15cc) | (19x) | (20n) | (21q) |
| 779 | (Ik), (Im) | (6t) | (10x) | (11j) | (12x) | (13s) | (14gg) | (15cc) | (19x) | (20n) | (21o) |
| 780 | (Ik), (Im) | (6t) | (10x) | (11j) | (12x) | (13s) | (14gg) | (15cc) | (19x) | (20n) | (21q) |
| 781 | (Io) | (6t) | (10w) | (11k) | (12u) | (13t) | (14w) | (15z), (15aa) | (19x) | (20m) | (21o) |
| 782 | (Io) | (6t) | (10w) | (11k) | (12u) | (13t) | (14w) | (15z), (15aa) | (19x) | (20n) | (21q) |
| 783 | (Io) | (6t) | (10w) | (11k) | (12u) | (13t) | (14w) | (15z), (15aa) | (19x) | (20n) | (21o) |
| 784 | (Io) | (6t) | (10w) | (11k) | (12u) | (13t) | (14w) | (15z), (15aa) | (19x) | (20n) | (21q) |
| 785 | (Io) | (6t) | (10w) | (11k) | (12u) | (13t) | (14w) | (15cc) | (19x) | (20m) | (21o) |
| 786 | (Io) | (6t) | (10w) | (11k) | (12u) | (13t) | (14w) | (15cc) | (19x) | (20n) | (21q) |
| 787 | (Io) | (6t) | (10w) | (11k) | (12u) | (13t) | (14w) | (15cc) | (19x) | (20n) | (21o) |
| 788 | (Io) | (6t) | (10w) | (11k) | (12u) | (13t) | (14w) | (15cc) | (19x) | (20n) | (21q) |
| 789 | (Io) | (6t) | (10w) | (11k) | (12u) | (13t) | (14gg) | (15z), (15aa) | (19x) | (20m) | (21o) |
| 790 | (Io) | (6t) | (10w) | (11k) | (12u) | (13t) | (14gg) | (15z), (15aa) | (19x) | (20n) | (21q) |
| 791 | (Io) | (6t) | (10w) | (11k) | (12u) | (13t) | (14gg) | (15z), (15aa) | (19x) | (20n) | (21o) |
| 792 | (Io) | (6t) | (10w) | (11k) | (12u) | (13t) | (14gg) | (15z), (15aa) | (19x) | (20n) | (21q) |
| 793 | (Io) | (6t) | (10w) | (11k) | (12u) | (13t) | (14gg) | (15cc) | (19x) | (20m) | (21o) |
| 794 | (Io) | (6t) | (10w) | (11k) | (12u) | (13t) | (14gg) | (15cc) | (19x) | (20n) | (21q) |
| 795 | (Io) | (6t) | (10w) | (11k) | (12u) | (13t) | (14gg) | (15cc) | (19x) | (20n) | (21o) |
| 796 | (Io) | (6t) | (10w) | (11k) | (12u) | (13t) | (14gg) | (15cc) | (19x) | (20n) | (21q) |
| 797 | (Io) | (6t) | (10w) | (11k) | (12u) | (13s) | (14w) | (15z), (15aa) | (19x) | (20m) | (21o) |
| 798 | (Io) | (6t) | (10w) | (11k) | (12u) | (13s) | (14w) | (15z), (15aa) | (19x) | (20n) | (21q) |
| 799 | (Io) | (6t) | (10w) | (11k) | (12u) | (13s) | (14w) | (15z), (15aa) | (19x) | (20n) | (21o) |
| 800 | (Io) | (6t) | (10w) | (11k) | (12u) | (13s) | (14w) | (15z), (15aa) | (19x) | (20n) | (21q) |
| 801 | (Io) | (6t) | (10w) | (11k) | (12u) | (13s) | (14w) | (15cc) | (19x) | (20m) | (21o) |
| 802 | (Io) | (6t) | (10w) | (11k) | (12u) | (13s) | (14w) | (15cc) | (19x) | (20n) | (21q) |
| 803 | (Io) | (6t) | (10w) | (11k) | (12u) | (13s) | (14w) | (15cc) | (19x) | (20n) | (21o) |
| 804 | (Io) | (6t) | (10w) | (11k) | (12u) | (13s) | (14w) | (15cc) | (19x) | (20n) | (21q) |

-continued

|   | I | L¹† | R¹ | L² | Q | L³ | R³ | L⁴†† | R⁴ | L⁵ | R⁵ |
|---|---|-----|----|----|---|----|----|------|----|----|----|
| 805 | (Io) | (6t) | (10w) | (11k) | (12u) | (13s) | (14gg) | (15z), (15aa) | (19x) | (20m) | (21o) |
| 806 | (Io) | (6t) | (10w) | (11k) | (12u) | (13s) | (14gg) | (15z), (15aa) | (19x) | (20m) | (21q) |
| 807 | (Io) | (6t) | (10w) | (11k) | (12u) | (13s) | (14gg) | (15z), (15aa) | (19x) | (20n) | (21o) |
| 808 | (Io) | (6t) | (10w) | (11k) | (12u) | (13s) | (14gg) | (15z), (15aa) | (19x) | (20n) | (21q) |
| 809 | (Io) | (6t) | (10w) | (11k) | (12u) | (13s) | (14gg) | (15cc) | (19x) | (20m) | (21o) |
| 810 | (Io) | (6t) | (10w) | (11k) | (12u) | (13s) | (14gg) | (15cc) | (19x) | (20m) | (21q) |
| 811 | (Io) | (6t) | (10w) | (11k) | (12u) | (13s) | (14gg) | (15cc) | (19x) | (20n) | (21o) |
| 812 | (Io) | (6t) | (10w) | (11k) | (12u) | (13s) | (14gg) | (15cc) | (19x) | (20n) | (21q) |
| 813 | (Io) | (6t) | (10w) | (11k) | (12x) | (13t) | (14w) | (15z), (15aa) | (19x) | (20m) | (21o) |
| 814 | (Io) | (6t) | (10w) | (11k) | (12x) | (13t) | (14w) | (15z), (15aa) | (19x) | (20m) | (21q) |
| 815 | (Io) | (6t) | (10w) | (11k) | (12x) | (13t) | (14w) | (15z), (15aa) | (19x) | (20n) | (21o) |
| 816 | (Io) | (6t) | (10w) | (11k) | (12x) | (13t) | (14w) | (15z), (15aa) | (19x) | (20n) | (21q) |
| 817 | (Io) | (6t) | (10w) | (11k) | (12x) | (13t) | (14w) | (15cc) | (19x) | (20m) | (21o) |
| 818 | (Io) | (6t) | (10w) | (11k) | (12x) | (13t) | (14w) | (15cc) | (19x) | (20m) | (21q) |
| 819 | (Io) | (6t) | (10w) | (11k) | (12x) | (13t) | (14w) | (15cc) | (19x) | (20n) | (21o) |
| 820 | (Io) | (6t) | (10w) | (11k) | (12x) | (13t) | (14w) | (15cc) | (19x) | (20n) | (21q) |
| 821 | (Io) | (6t) | (10w) | (11k) | (12x) | (13t) | (14gg) | (15z), (15aa) | (19x) | (20m) | (21o) |
| 822 | (Io) | (6t) | (10w) | (11k) | (12x) | (13t) | (14gg) | (15z), (15aa) | (19x) | (20m) | (21q) |
| 823 | (Io) | (6t) | (10w) | (11k) | (12x) | (13t) | (14gg) | (15z), (15aa) | (19x) | (20n) | (21o) |
| 824 | (Io) | (6t) | (10w) | (11k) | (12x) | (13t) | (14gg) | (15z), (15aa) | (19x) | (20n) | (21q) |
| 825 | (Io) | (6t) | (10w) | (11k) | (12x) | (13t) | (14gg) | (15cc) | (19x) | (20m) | (21o) |
| 826 | (Io) | (6t) | (10w) | (11k) | (12x) | (13t) | (14gg) | (15cc) | (19x) | (20m) | (21q) |
| 827 | (Io) | (6t) | (10w) | (11k) | (12x) | (13t) | (14gg) | (15cc) | (19x) | (20n) | (21o) |
| 828 | (Io) | (6t) | (10w) | (11k) | (12x) | (13t) | (14gg) | (15cc) | (19x) | (20n) | (21q) |
| 829 | (Io) | (6t) | (10w) | (11k) | (12x) | (13s) | (14w) | (15z), (15aa) | (19x) | (20m) | (21o) |
| 830 | (Io) | (6t) | (10w) | (11k) | (12x) | (13s) | (14w) | (15z), (15aa) | (19x) | (20m) | (21q) |
| 831 | (Io) | (6t) | (10w) | (11k) | (12x) | (13s) | (14w) | (15z), (15aa) | (19x) | (20n) | (21o) |
| 832 | (Io) | (6t) | (10w) | (11k) | (12x) | (13s) | (14w) | (15z), (15aa) | (19x) | (20n) | (21q) |
| 833 | (Io) | (6t) | (10w) | (11k) | (12x) | (13s) | (14w) | (15cc) | (19x) | (20m) | (21o) |
| 834 | (Io) | (6t) | (10w) | (11k) | (12x) | (13s) | (14w) | (15cc) | (19x) | (20m) | (21q) |
| 835 | (Io) | (6t) | (10w) | (11k) | (12x) | (13s) | (14w) | (15cc) | (19x) | (20n) | (21o) |
| 836 | (Io) | (6t) | (10w) | (11k) | (12x) | (13s) | (14w) | (15cc) | (19x) | (20n) | (21q) |
| 837 | (Io) | (6t) | (10w) | (11k) | (12x) | (13s) | (14gg) | (15z), (15aa) | (19x) | (20m) | (21o) |
| 838 | (Io) | (6t) | (10w) | (11k) | (12x) | (13s) | (14gg) | (15z), (15aa) | (19x) | (20m) | (21q) |
| 839 | (Io) | (6t) | (10w) | (11k) | (12x) | (13s) | (14gg) | (15z), (15aa) | (19x) | (20n) | (21o) |
| 840 | (Io) | (6t) | (10w) | (11k) | (12x) | (13s) | (14gg) | (15z), (15aa) | (19x) | (20n) | (21q) |
| 841 | (Io) | (6t) | (10w) | (11k) | (12x) | (13s) | (14gg) | (15cc) | (19x) | (20m) | (21o) |
| 842 | (Io) | (6t) | (10w) | (11k) | (12x) | (13s) | (14gg) | (15cc) | (19x) | (20m) | (21q) |
| 843 | (Io) | (6t) | (10w) | (11k) | (12x) | (13s) | (14gg) | (15cc) | (19x) | (20n) | (21o) |
| 844 | (Io) | (6t) | (10w) | (11k) | (12x) | (13s) | (14gg) | (15cc) | (19x) | (20n) | (21q) |
| 845 | (Io) | (6t) | (10w) | (11j) | (12u) | (13t) | (14w) | (15z), (15aa) | (19x) | (20m) | (21o) |
| 846 | (Io) | (6t) | (10w) | (11j) | (12u) | (13t) | (14w) | (15z), (15aa) | (19x) | (20m) | (21q) |
| 847 | (Io) | (6t) | (10w) | (11j) | (12u) | (13t) | (14w) | (15z), (15aa) | (19x) | (20n) | (21o) |
| 848 | (Io) | (6t) | (10w) | (11j) | (12u) | (13t) | (14w) | (15z), (15aa) | (19x) | (20n) | (21q) |
| 849 | (Io) | (6t) | (10w) | (11j) | (12u) | (13t) | (14w) | (15cc) | (19x) | (20m) | (21o) |
| 850 | (Io) | (6t) | (10w) | (11j) | (12u) | (13t) | (14w) | (15cc) | (19x) | (20m) | (21q) |
| 851 | (Io) | (6t) | (10w) | (11j) | (12u) | (13t) | (14w) | (15cc) | (19x) | (20n) | (21o) |
| 852 | (Io) | (6t) | (10w) | (11j) | (12u) | (13t) | (14w) | (15cc) | (19x) | (20n) | (21q) |
| 853 | (Io) | (6t) | (10w) | (11j) | (12u) | (13t) | (14gg) | (15z), (15aa) | (19x) | (20m) | (21o) |
| 854 | (Io) | (6t) | (10w) | (11j) | (12u) | (13t) | (14gg) | (15z), (15aa) | (19x) | (20m) | (21q) |
| 855 | (Io) | (6t) | (10w) | (11j) | (12u) | (13t) | (14gg) | (15z), (15aa) | (19x) | (20n) | (21o) |
| 856 | (Io) | (6t) | (10w) | (11j) | (12u) | (13t) | (14gg) | (15z), (15aa) | (19x) | (20n) | (21q) |
| 857 | (Io) | (6t) | (10w) | (11j) | (12u) | (13t) | (14gg) | (15cc) | (19x) | (20m) | (21o) |
| 858 | (Io) | (6t) | (10w) | (11j) | (12u) | (13t) | (14gg) | (15cc) | (19x) | (20m) | (21q) |
| 859 | (Io) | (6t) | (10w) | (11j) | (12u) | (13t) | (14gg) | (15cc) | (19x) | (20n) | (21o) |
| 860 | (Io) | (6t) | (10w) | (11j) | (12u) | (13t) | (14gg) | (15cc) | (19x) | (20n) | (21q) |
| 861 | (Io) | (6t) | (10w) | (11j) | (12u) | (13s) | (14w) | (15z), (15aa) | (19x) | (20m) | (21o) |
| 862 | (Io) | (6t) | (10w) | (11j) | (12u) | (13s) | (14w) | (15z), (15aa) | (19x) | (20m) | (21q) |
| 863 | (Io) | (6t) | (10w) | (11j) | (12u) | (13s) | (14w) | (15z), (15aa) | (19x) | (20n) | (21o) |
| 864 | (Io) | (6t) | (10w) | (11j) | (12u) | (13s) | (14w) | (15z), (15aa) | (19x) | (20n) | (21q) |
| 865 | (Io) | (6t) | (10w) | (11j) | (12u) | (13s) | (14w) | (15cc) | (19x) | (20m) | (21o) |
| 866 | (Io) | (6t) | (10w) | (11j) | (12u) | (13s) | (14w) | (15cc) | (19x) | (20m) | (21q) |
| 867 | (Io) | (6t) | (10w) | (11j) | (12u) | (13s) | (14w) | (15cc) | (19x) | (20n) | (21o) |
| 868 | (Io) | (6t) | (10w) | (11j) | (12u) | (13s) | (14w) | (15cc) | (19x) | (20n) | (21q) |
| 869 | (Io) | (6t) | (10w) | (11j) | (12u) | (13s) | (14gg) | (15z), (15aa) | (19x) | (20m) | (21o) |
| 870 | (Io) | (6t) | (10w) | (11j) | (12u) | (13s) | (14gg) | (15z), (15aa) | (19x) | (20m) | (21q) |
| 871 | (Io) | (6t) | (10w) | (11j) | (12u) | (13s) | (14gg) | (15z), (15aa) | (19x) | (20n) | (21o) |
| 872 | (Io) | (6t) | (10w) | (11j) | (12u) | (13s) | (14gg) | (15z), (15aa) | (19x) | (20n) | (21q) |
| 873 | (Io) | (6t) | (10w) | (11j) | (12u) | (13s) | (14gg) | (15cc) | (19x) | (20m) | (21o) |
| 874 | (Io) | (6t) | (10w) | (11j) | (12u) | (13s) | (14gg) | (15cc) | (19x) | (20m) | (21q) |
| 875 | (Io) | (6t) | (10w) | (11j) | (12u) | (13s) | (14gg) | (15cc) | (19x) | (20n) | (21o) |
| 876 | (Io) | (6t) | (10w) | (11j) | (12u) | (13s) | (14gg) | (15cc) | (19x) | (20n) | (21q) |
| 877 | (Io) | (6t) | (10w) | (11j) | (12x) | (13t) | (14w) | (15z), (15aa) | (19x) | (20m) | (21o) |
| 878 | (Io) | (6t) | (10w) | (11j) | (12x) | (13t) | (14w) | (15z), (15aa) | (19x) | (20m) | (21q) |
| 879 | (Io) | (6t) | (10w) | (11j) | (12x) | (13t) | (14w) | (15z), (15aa) | (19x) | (20n) | (21o) |
| 880 | (Io) | (6t) | (10w) | (11j) | (12x) | (13t) | (14w) | (15z), (15aa) | (19x) | (20n) | (21q) |
| 881 | (Io) | (6t) | (10w) | (11j) | (12x) | (13t) | (14w) | (15cc) | (19x) | (20m) | (21o) |

-continued

| | I | L¹† | R¹ | L² | Q | L³ | R³ | L⁴†† | R⁴ | L⁵ | R⁵ |
|---|---|---|---|---|---|---|---|---|---|---|---|
| 882 | (Io) | (6t) | (10w) | (11j) | (12x) | (13t) | (14w) | (15cc) | (19x) | (20m) | (21q) |
| 883 | (Io) | (6t) | (10w) | (11j) | (12x) | (13t) | (14w) | (15cc) | (19x) | (20n) | (21o) |
| 884 | (Io) | (6t) | (10w) | (11j) | (12x) | (13t) | (14w) | (15cc) | (19x) | (20n) | (21q) |
| 885 | (Io) | (6t) | (10w) | (11j) | (12x) | (13t) | (14gg) | (15z), (15aa) | (19x) | (20m) | (21o) |
| 886 | (Io) | (6t) | (10w) | (11j) | (12x) | (13t) | (14gg) | (15z), (15aa) | (19x) | (20m) | (21q) |
| 887 | (Io) | (6t) | (10w) | (11j) | (12x) | (13t) | (14gg) | (15z), (15aa) | (19x) | (20n) | (21o) |
| 888 | (Io) | (6t) | (10w) | (11j) | (12x) | (13t) | (14gg) | (15z), (15aa) | (19x) | (20n) | (21q) |
| 889 | (Io) | (6t) | (10w) | (11j) | (12x) | (13t) | (14gg) | (15cc) | (19x) | (20m) | (21o) |
| 890 | (Io) | (6t) | (10w) | (11j) | (12x) | (13t) | (14gg) | (15cc) | (19x) | (20m) | (21q) |
| 891 | (Io) | (6t) | (10w) | (11j) | (12x) | (13t) | (14gg) | (15cc) | (19x) | (20n) | (21o) |
| 892 | (Io) | (6t) | (10w) | (11j) | (12x) | (13t) | (14gg) | (15cc) | (19x) | (20n) | (21q) |
| 893 | (Io) | (6t) | (10w) | (11j) | (12x) | (13s) | (14w) | (15z), (15aa) | (19x) | (20m) | (21o) |
| 894 | (Io) | (6t) | (10w) | (11j) | (12x) | (13s) | (14w) | (15z), (15aa) | (19x) | (20m) | (21q) |
| 895 | (Io) | (6t) | (10w) | (11j) | (12x) | (13s) | (14w) | (15z), (15aa) | (19x) | (20n) | (21o) |
| 896 | (Io) | (6t) | (10w) | (11j) | (12x) | (13s) | (14w) | (15z), (15aa) | (19x) | (20n) | (21q) |
| 897 | (Io) | (6t) | (10w) | (11j) | (12x) | (13s) | (14w) | (15cc) | (19x) | (20m) | (21o) |
| 898 | (Io) | (6t) | (10w) | (11j) | (12x) | (13s) | (14w) | (15cc) | (19x) | (20m) | (21q) |
| 899 | (Io) | (6t) | (10w) | (11j) | (12x) | (13s) | (14w) | (15cc) | (19x) | (20n) | (21o) |
| 900 | (Io) | (6t) | (10w) | (11j) | (12x) | (13s) | (14w) | (15cc) | (19x) | (20n) | (21q) |
| 901 | (Io) | (6t) | (10w) | (11j) | (12x) | (13s) | (14gg) | (15z), (15aa) | (19x) | (20m) | (21o) |
| 902 | (Io) | (6t) | (10w) | (11j) | (12x) | (13s) | (14gg) | (15z), (15aa) | (19x) | (20m) | (21q) |
| 903 | (Io) | (6t) | (10w) | (11j) | (12x) | (13s) | (14gg) | (15z), (15aa) | (19x) | (20n) | (21o) |
| 904 | (Io) | (6t) | (10w) | (11j) | (12x) | (13s) | (14gg) | (15z), (15aa) | (19x) | (20n) | (21q) |
| 905 | (Io) | (6t) | (10w) | (11j) | (12x) | (13s) | (14gg) | (15cc) | (19x) | (20m) | (21o) |
| 906 | (Io) | (6t) | (10w) | (11j) | (12x) | (13s) | (14gg) | (15cc) | (19x) | (20m) | (21q) |
| 907 | (Io) | (6t) | (10w) | (11j) | (12x) | (13s) | (14gg) | (15cc) | (19x) | (20n) | (21o) |
| 908 | (Io) | (6t) | (10w) | (11j) | (12x) | (13s) | (14gg) | (15cc) | (19x) | (20n) | (21q) |
| 909 | (Io) | (6t) | (10x) | (11k) | (12u) | (13t) | (14w) | (15z), (15aa) | (19x) | (20m) | (21o) |
| 910 | (Io) | (6t) | (10x) | (11k) | (12u) | (13t) | (14w) | (15z), (15aa) | (19x) | (20m) | (21q) |
| 911 | (Io) | (6t) | (10x) | (11k) | (12u) | (13t) | (14w) | (15z), (15aa) | (19x) | (20n) | (21o) |
| 912 | (Io) | (6t) | (10x) | (11k) | (12u) | (13t) | (14w) | (15z), (15aa) | (19x) | (20n) | (21q) |
| 913 | (Io) | (6t) | (10x) | (11k) | (12u) | (13t) | (14w) | (15cc) | (19x) | (20m) | (21o) |
| 914 | (Io) | (6t) | (10x) | (11k) | (12u) | (13t) | (14w) | (15cc) | (19x) | (20m) | (21q) |
| 915 | (Io) | (6t) | (10x) | (11k) | (12u) | (13t) | (14w) | (15cc) | (19x) | (20n) | (21o) |
| 916 | (Io) | (6t) | (10x) | (11k) | (12u) | (13t) | (14w) | (15cc) | (19x) | (20n) | (21q) |
| 917 | (Io) | (6t) | (10x) | (11k) | (12u) | (13t) | (14gg) | (15z), (15aa) | (19x) | (20m) | (21o) |
| 918 | (Io) | (6t) | (10x) | (11k) | (12u) | (13t) | (14gg) | (15z), (15aa) | (19x) | (20m) | (21q) |
| 919 | (Io) | (6t) | (10x) | (11k) | (12u) | (13t) | (14gg) | (15z), (15aa) | (19x) | (20n) | (21o) |
| 920 | (Io) | (6t) | (10x) | (11k) | (12u) | (13t) | (14gg) | (15z), (15aa) | (19x) | (20n) | (21q) |
| 921 | (Io) | (6t) | (10x) | (11k) | (12u) | (13t) | (14gg) | (15cc) | (19x) | (20m) | (21o) |
| 922 | (Io) | (6t) | (10x) | (11k) | (12u) | (13t) | (14gg) | (15cc) | (19x) | (20m) | (21q) |
| 923 | (Io) | (6t) | (10x) | (11k) | (12u) | (13t) | (14gg) | (15cc) | (19x) | (20n) | (21o) |
| 924 | (Io) | (6t) | (10x) | (11k) | (12u) | (13t) | (14gg) | (15cc) | (19x) | (20n) | (21q) |
| 925 | (Io) | (6t) | (10x) | (11k) | (12u) | (13s) | (14w) | (15z), (15aa) | (19x) | (20m) | (21o) |
| 926 | (Io) | (6t) | (10x) | (11k) | (12u) | (13s) | (14w) | (15z), (15aa) | (19x) | (20m) | (21q) |
| 927 | (Io) | (6t) | (10x) | (11k) | (12u) | (13s) | (14w) | (15z), (15aa) | (19x) | (20n) | (21o) |
| 928 | (Io) | (6t) | (10x) | (11k) | (12u) | (13s) | (14w) | (15z), (15aa) | (19x) | (20n) | (21q) |
| 929 | (Io) | (6t) | (10x) | (11k) | (12u) | (13s) | (14w) | (15cc) | (19x) | (20m) | (21o) |
| 930 | (Io) | (6t) | (10x) | (11k) | (12u) | (13s) | (14w) | (15cc) | (19x) | (20m) | (21q) |
| 931 | (Io) | (6t) | (10x) | (11k) | (12u) | (13s) | (14w) | (15cc) | (19x) | (20n) | (21o) |
| 932 | (Io) | (6t) | (10x) | (11k) | (12u) | (13s) | (14w) | (15cc) | (19x) | (20n) | (21q) |
| 933 | (Io) | (6t) | (10x) | (11k) | (12u) | (13s) | (14gg) | (15z), (15aa) | (19x) | (20m) | (21o) |
| 934 | (Io) | (6t) | (10x) | (11k) | (12u) | (13s) | (14gg) | (15z), (15aa) | (19x) | (20m) | (21q) |
| 935 | (Io) | (6t) | (10x) | (11k) | (12u) | (13s) | (14gg) | (15z), (15aa) | (19x) | (20n) | (21o) |
| 936 | (Io) | (6t) | (10x) | (11k) | (12u) | (13s) | (14gg) | (15z), (15aa) | (19x) | (20n) | (21q) |
| 937 | (Io) | (6t) | (10x) | (11k) | (12u) | (13s) | (14gg) | (15cc) | (19x) | (20m) | (21o) |
| 938 | (Io) | (6t) | (10x) | (11k) | (12u) | (13s) | (14gg) | (15cc) | (19x) | (20m) | (21q) |
| 939 | (Io) | (6t) | (10x) | (11k) | (12u) | (13s) | (14gg) | (15cc) | (19x) | (20n) | (21o) |
| 940 | (Io) | (6t) | (10x) | (11k) | (12u) | (13s) | (14gg) | (15cc) | (19x) | (20n) | (21q) |
| 941 | (Io) | (6t) | (10x) | (11k) | (12x) | (13t) | (14w) | (15z), (15aa) | (19x) | (20m) | (21o) |
| 942 | (Io) | (6t) | (10x) | (11k) | (12x) | (13t) | (14w) | (15z), (15aa) | (19x) | (20m) | (21q) |
| 943 | (Io) | (6t) | (10x) | (11k) | (12x) | (13t) | (14w) | (15z), (15aa) | (19x) | (20n) | (21o) |
| 944 | (Io) | (6t) | (10x) | (11k) | (12x) | (13t) | (14w) | (15z), (15aa) | (19x) | (20n) | (21q) |
| 945 | (Io) | (6t) | (10x) | (11k) | (12x) | (13t) | (14w) | (15cc) | (19x) | (20m) | (21o) |
| 946 | (Io) | (6t) | (10x) | (11k) | (12x) | (13t) | (14w) | (15cc) | (19x) | (20m) | (21q) |
| 947 | (Io) | (6t) | (10x) | (11k) | (12x) | (13t) | (14w) | (15cc) | (19x) | (20n) | (21o) |
| 948 | (Io) | (6t) | (10x) | (11k) | (12x) | (13t) | (14w) | (15cc) | (19x) | (20n) | (21q) |
| 949 | (Io) | (6t) | (10x) | (11k) | (12x) | (13t) | (14gg) | (15z), (15aa) | (19x) | (20m) | (21o) |
| 950 | (Io) | (6t) | (10x) | (11k) | (12x) | (13t) | (14gg) | (15z), (15aa) | (19x) | (20m) | (21q) |
| 951 | (Io) | (6t) | (10x) | (11k) | (12x) | (13t) | (14gg) | (15z), (15aa) | (19x) | (20n) | (21o) |
| 952 | (Io) | (6t) | (10x) | (11k) | (12x) | (13t) | (14gg) | (15z), (15aa) | (19x) | (20n) | (21q) |
| 953 | (Io) | (6t) | (10x) | (11k) | (12x) | (13t) | (14gg) | (15cc) | (19x) | (20m) | (21o) |
| 954 | (Io) | (6t) | (10x) | (11k) | (12x) | (13t) | (14gg) | (15cc) | (19x) | (20m) | (21q) |
| 955 | (Io) | (6t) | (10x) | (11k) | (12x) | (13t) | (14gg) | (15cc) | (19x) | (20n) | (21o) |
| 956 | (Io) | (6t) | (10x) | (11k) | (12x) | (13t) | (14gg) | (15cc) | (19x) | (20n) | (21q) |
| 957 | (Io) | (6t) | (10x) | (11k) | (12x) | (13s) | (14w) | (15z), (15aa) | (19x) | (20m) | (21o) |
| 958 | (Io) | (6t) | (10x) | (11k) | (12x) | (13s) | (14w) | (15z), (15aa) | (19x) | (20m) | (21q) |

-continued

|  | I | L¹† | R¹ | L² | Q | L³ | R³ | L⁴†† | R⁴ | L⁵ | R⁵ |
|---|---|---|---|---|---|---|---|---|---|---|---|
| 959 | (Io) | (6t) | (10x) | (11k) | (12x) | (13s) | (14w) | (15z), (15aa) | (19x) | (20n) | (21o) |
| 960 | (Io) | (6t) | (10x) | (11k) | (12x) | (13s) | (14w) | (15z), (15aa) | (19x) | (20n) | (21q) |
| 961 | (Io) | (6t) | (10x) | (11k) | (12x) | (13s) | (14w) | (15cc) | (19x) | (20m) | (21o) |
| 962 | (Io) | (6t) | (10x) | (11k) | (12x) | (13s) | (14w) | (15cc) | (19x) | (20m) | (21q) |
| 963 | (Io) | (6t) | (10x) | (11k) | (12x) | (13s) | (14w) | (15cc) | (19x) | (20n) | (21o) |
| 964 | (Io) | (6t) | (10x) | (11k) | (12x) | (13s) | (14w) | (15cc) | (19x) | (20n) | (21q) |
| 965 | (Io) | (6t) | (10x) | (11k) | (12x) | (13s) | (14gg) | (15z), (15aa) | (19x) | (20m) | (21o) |
| 966 | (Io) | (6t) | (10x) | (11k) | (12x) | (13s) | (14gg) | (15z), (15aa) | (19x) | (20m) | (21q) |
| 967 | (Io) | (6t) | (10x) | (11k) | (12x) | (13s) | (14gg) | (15z), (15aa) | (19x) | (20n) | (21o) |
| 968 | (Io) | (6t) | (10x) | (11k) | (12x) | (13s) | (14gg) | (15z), (15aa) | (19x) | (20n) | (21q) |
| 969 | (Io) | (6t) | (10x) | (11k) | (12x) | (13s) | (14gg) | (15cc) | (19x) | (20m) | (21o) |
| 970 | (Io) | (6t) | (10x) | (11k) | (12x) | (13s) | (14gg) | (15cc) | (19x) | (20m) | (21q) |
| 971 | (Io) | (6t) | (10x) | (11k) | (12x) | (13s) | (14gg) | (15cc) | (19x) | (20n) | (21o) |
| 972 | (Io) | (6t) | (10x) | (11k) | (12x) | (13s) | (14gg) | (15cc) | (19x) | (20n) | (21q) |
| 973 | (Io) | (6t) | (10x) | (11j) | (12u) | (13t) | (14w) | (15z), (15aa) | (19x) | (20m) | (21o) |
| 974 | (Io) | (6t) | (10x) | (11j) | (12u) | (13t) | (14w) | (15z), (15aa) | (19x) | (20m) | (21q) |
| 975 | (Io) | (6t) | (10x) | (11j) | (12u) | (13t) | (14w) | (15z), (15aa) | (19x) | (20n) | (21o) |
| 976 | (Io) | (6t) | (10x) | (11j) | (12u) | (13t) | (14w) | (15z), (15aa) | (19x) | (20n) | (21q) |
| 977 | (Io) | (6t) | (10x) | (11j) | (12u) | (13t) | (14w) | (15cc) | (19x) | (20m) | (21o) |
| 978 | (Io) | (6t) | (10x) | (11j) | (12u) | (13t) | (14w) | (15cc) | (19x) | (20m) | (21q) |
| 979 | (Io) | (6t) | (10x) | (11j) | (12u) | (13t) | (14w) | (15cc) | (19x) | (20n) | (21o) |
| 980 | (Io) | (6t) | (10x) | (11j) | (12u) | (13t) | (14w) | (15cc) | (19x) | (20n) | (21q) |
| 981 | (Io) | (6t) | (10x) | (11j) | (12u) | (13t) | (14gg) | (15z), (15aa) | (19x) | (20m) | (21o) |
| 982 | (Io) | (6t) | (10x) | (11j) | (12u) | (13t) | (14gg) | (15z), (15aa) | (19x) | (20m) | (21q) |
| 983 | (Io) | (6t) | (10x) | (11j) | (12u) | (13t) | (14gg) | (15z), (15aa) | (19x) | (20n) | (21o) |
| 984 | (Io) | (6t) | (10x) | (11j) | (12u) | (13t) | (14gg) | (15z), (15aa) | (19x) | (20n) | (21q) |
| 985 | (Io) | (6t) | (10x) | (11j) | (12u) | (13t) | (14gg) | (15cc) | (19x) | (20m) | (21o) |
| 986 | (Io) | (6t) | (10x) | (11j) | (12u) | (13t) | (14gg) | (15cc) | (19x) | (20m) | (21q) |
| 987 | (Io) | (6t) | (10x) | (11j) | (12u) | (13t) | (14gg) | (15cc) | (19x) | (20n) | (21o) |
| 988 | (Io) | (6t) | (10x) | (11j) | (12u) | (13t) | (14gg) | (15cc) | (19x) | (20n) | (21q) |
| 989 | (Io) | (6t) | (10x) | (11j) | (12u) | (13s) | (14w) | (15z), (15aa) | (19x) | (20m) | (21o) |
| 990 | (Io) | (6t) | (10x) | (11j) | (12u) | (13s) | (14w) | (15z), (15aa) | (19x) | (20m) | (21q) |
| 991 | (Io) | (6t) | (10x) | (11j) | (12u) | (13s) | (14w) | (15z), (15aa) | (19x) | (20n) | (21o) |
| 992 | (Io) | (6t) | (10x) | (11j) | (12u) | (13s) | (14w) | (15z), (15aa) | (19x) | (20n) | (21q) |
| 993 | (Io) | (6t) | (10x) | (11j) | (12u) | (13s) | (14w) | (15cc) | (19x) | (20m) | (21o) |
| 994 | (Io) | (6t) | (10x) | (11j) | (12u) | (13s) | (14w) | (15cc) | (19x) | (20m) | (21q) |
| 995 | (Io) | (6t) | (10x) | (11j) | (12u) | (13s) | (14w) | (15cc) | (19x) | (20n) | (21o) |
| 996 | (Io) | (6t) | (10x) | (11j) | (12u) | (13s) | (14w) | (15cc) | (19x) | (20n) | (21q) |
| 997 | (Io) | (6t) | (10x) | (11j) | (12u) | (13s) | (14gg) | (15z), (15aa) | (19x) | (20m) | (21o) |
| 998 | (Io) | (6t) | (10x) | (11j) | (12u) | (13s) | (14gg) | (15z), (15aa) | (19x) | (20m) | (21q) |
| 999 | (Io) | (6t) | (10x) | (11j) | (12u) | (13s) | (14gg) | (15z), (15aa) | (19x) | (20n) | (21o) |
| 1000 | (Io) | (6t) | (10x) | (11j) | (12u) | (13s) | (14gg) | (15z), (15aa) | (19x) | (20n) | (21q) |
| 1001 | (Io) | (6t) | (10x) | (11j) | (12u) | (13s) | (14gg) | (15cc) | (19x) | (20m) | (21o) |
| 1002 | (Io) | (6t) | (10x) | (11j) | (12u) | (13s) | (14gg) | (15cc) | (19x) | (20m) | (21q) |
| 1003 | (Io) | (6t) | (10x) | (11j) | (12u) | (13s) | (14gg) | (15cc) | (19x) | (20n) | (21o) |
| 1004 | (Io) | (6t) | (10x) | (11j) | (12u) | (13s) | (14gg) | (15cc) | (19x) | (20n) | (21q) |
| 1005 | (Io) | (6t) | (10x) | (11j) | (12x) | (13t) | (14w) | (15z), (15aa) | (19x) | (20m) | (21o) |
| 1006 | (Io) | (6t) | (10x) | (11j) | (12x) | (13t) | (14w) | (15z), (15aa) | (19x) | (20m) | (21q) |
| 1007 | (Io) | (6t) | (10x) | (11j) | (12x) | (13t) | (14w) | (15z), (15aa) | (19x) | (20n) | (21o) |
| 1008 | (Io) | (6t) | (10x) | (11j) | (12x) | (13t) | (14w) | (15z), (15aa) | (19x) | (20n) | (21q) |
| 1009 | (Io) | (6t) | (10x) | (11j) | (12x) | (13t) | (14w) | (15cc) | (19x) | (20m) | (21o) |
| 1010 | (Io) | (6t) | (10x) | (11j) | (12x) | (13t) | (14w) | (15cc) | (19x) | (20m) | (21q) |
| 1011 | (Io) | (6t) | (10x) | (11j) | (12x) | (13t) | (14w) | (15cc) | (19x) | (20n) | (21o) |
| 1012 | (Io) | (6t) | (10x) | (11j) | (12x) | (13t) | (14w) | (15cc) | (19x) | (20n) | (21q) |
| 1013 | (Io) | (6t) | (10x) | (11j) | (12x) | (13t) | (14gg) | (15z), (15aa) | (19x) | (20m) | (21o) |
| 1014 | (Io) | (6t) | (10x) | (11j) | (12x) | (13t) | (14gg) | (15z), (15aa) | (19x) | (20m) | (21q) |
| 1015 | (Io) | (6t) | (10x) | (11j) | (12x) | (13t) | (14gg) | (15z), (15aa) | (19x) | (20n) | (21o) |
| 1016 | (Io) | (6t) | (10x) | (11j) | (12x) | (13t) | (14gg) | (15z), (15aa) | (19x) | (20n) | (21q) |
| 1017 | (Io) | (6t) | (10x) | (11j) | (12x) | (13t) | (14gg) | (15cc) | (19x) | (20m) | (21o) |
| 1018 | (Io) | (6t) | (10x) | (11j) | (12x) | (13t) | (14gg) | (15cc) | (19x) | (20m) | (21q) |
| 1019 | (Io) | (6t) | (10x) | (11j) | (12x) | (13t) | (14gg) | (15cc) | (19x) | (20n) | (21o) |
| 1020 | (Io) | (6t) | (10x) | (11j) | (12x) | (13t) | (14gg) | (15cc) | (19x) | (20n) | (21q) |
| 1021 | (Io) | (6t) | (10x) | (11j) | (12x) | (13s) | (14w) | (15z), (15aa) | (19x) | (20m) | (21o) |
| 1022 | (Io) | (6t) | (10x) | (11j) | (12x) | (13s) | (14w) | (15z), (15aa) | (19x) | (20m) | (21q) |
| 1023 | (Io) | (6t) | (10x) | (11j) | (12x) | (13s) | (14w) | (15z), (15aa) | (19x) | (20n) | (21o) |
| 1024 | (Io) | (6t) | (10x) | (11j) | (12x) | (13s) | (14w) | (15z), (15aa) | (19x) | (20n) | (21q) |
| 1025 | (Io) | (6t) | (10x) | (11j) | (12x) | (13s) | (14w) | (15cc) | (19x) | (20m) | (21o) |
| 1026 | (Io) | (6t) | (10x) | (11j) | (12x) | (13s) | (14w) | (15cc) | (19x) | (20m) | (21q) |
| 1027 | (Io) | (6t) | (10x) | (11j) | (12x) | (13s) | (14w) | (15cc) | (19x) | (20n) | (21o) |
| 1028 | (Io) | (6t) | (10x) | (11j) | (12x) | (13s) | (14w) | (15cc) | (19x) | (20n) | (21q) |
| 1029 | (Io) | (6t) | (10x) | (11j) | (12x) | (13s) | (14gg) | (15z), (15aa) | (19x) | (20m) | (21o) |
| 1030 | (Io) | (6t) | (10x) | (11j) | (12x) | (13s) | (14gg) | (15z), (15aa) | (19x) | (20m) | (21q) |
| 1031 | (Io) | (6t) | (10x) | (11j) | (12x) | (13s) | (14gg) | (15z), (15aa) | (19x) | (20n) | (21o) |
| 1032 | (Io) | (6t) | (10x) | (11j) | (12x) | (13s) | (14gg) | (15z), (15aa) | (19x) | (20n) | (21q) |
| 1033 | (Io) | (6t) | (10x) | (11j) | (12x) | (13s) | (14gg) | (15cc) | (19x) | (20m) | (21o) |
| 1034 | (Io) | (6t) | (10x) | (11j) | (12x) | (13s) | (14gg) | (15cc) | (19x) | (20m) | (21q) |
| 1035 | (Io) | (6t) | (10x) | (11j) | (12x) | (13s) | (14gg) | (15cc) | (19x) | (20n) | (21o) |

-continued

| | I | L¹† | R¹ | L² | Q | L³ | R³ | L⁴†† | R⁴ | L⁵ | R⁵ |
|---|---|---|---|---|---|---|---|---|---|---|---|
| 1036 | (Io) | (6t) | (10x) | (11j) | (12x) | (13s) | (14gg) | (15cc) | (19x) | (20n) | (21q) |
| 1037 | (Io) | (6t) | (10w) | (11k) | (12u) | (13t) | (14w) | (15z), (15aa) | (19x) | (20m) | (21o) |
| 1038 | (Io) | (6t) | (10w) | (11k) | (12u) | (13t) | (14w) | (15z), (15aa) | (19x) | (20m) | (21q) |
| 1039 | (Io) | (6t) | (10w) | (11k) | (12u) | (13t) | (14w) | (15z), (15aa) | (19x) | (20n) | (21o) |
| 1040 | (Io) | (6t) | (10w) | (11k) | (12u) | (13t) | (14w) | (15z), (15aa) | (19x) | (20n) | (21q) |
| 1041 | (Io) | (6t) | (10w) | (11k) | (12u) | (13t) | (14w) | (15cc) | (19x) | (20m) | (21o) |
| 1042 | (Io) | (6t) | (10w) | (11k) | (12u) | (13t) | (14w) | (15cc) | (19x) | (20m) | (21q) |
| 1043 | (Io) | (6t) | (10w) | (11k) | (12u) | (13t) | (14w) | (15cc) | (19x) | (20n) | (21o) |
| 1044 | (Io) | (6t) | (10w) | (11k) | (12u) | (13t) | (14w) | (15cc) | (19x) | (20n) | (21q) |
| 1045 | (Io) | (6t) | (10w) | (11k) | (12u) | (13t) | (14gg) | (15z), (15aa) | (19x) | (20m) | (21o) |
| 1046 | (Io) | (6t) | (10w) | (11k) | (12u) | (13t) | (14gg) | (15z), (15aa) | (19x) | (20m) | (21q) |
| 1047 | (Io) | (6t) | (10w) | (11k) | (12u) | (13t) | (14gg) | (15z), (15aa) | (19x) | (20n) | (21o) |
| 1048 | (Io) | (6t) | (10w) | (11k) | (12u) | (13t) | (14gg) | (15z), (15aa) | (19x) | (20n) | (21q) |
| 1049 | (Io) | (6t) | (10w) | (11k) | (12u) | (13t) | (14gg) | (15cc) | (19x) | (20m) | (21o) |
| 1050 | (Io) | (6t) | (10w) | (11k) | (12u) | (13t) | (14gg) | (15cc) | (19x) | (20m) | (21q) |
| 1051 | (Io) | (6t) | (10w) | (11k) | (12u) | (13t) | (14gg) | (15cc) | (19x) | (20n) | (21o) |
| 1052 | (Io) | (6t) | (10w) | (11k) | (12u) | (13t) | (14gg) | (15cc) | (19x) | (20n) | (21q) |
| 1053 | (Io) | (6t) | (10w) | (11k) | (12u) | (13s) | (14w) | (15z), (15aa) | (19x) | (20m) | (21o) |
| 1054 | (Io) | (6t) | (10w) | (11k) | (12u) | (13s) | (14w) | (15z), (15aa) | (19x) | (20m) | (21q) |
| 1055 | (Io) | (6t) | (10w) | (11k) | (12u) | (13s) | (14w) | (15z), (15aa) | (19x) | (20n) | (21o) |
| 1056 | (Io) | (6t) | (10w) | (11k) | (12u) | (13s) | (14w) | (15z), (15aa) | (19x) | (20n) | (21q) |
| 1057 | (Io) | (6t) | (10w) | (11k) | (12u) | (13s) | (14w) | (15cc) | (19x) | (20m) | (21o) |
| 1058 | (Io) | (6t) | (10w) | (11k) | (12u) | (13s) | (14w) | (15cc) | (19x) | (20m) | (21q) |
| 1059 | (Io) | (6t) | (10w) | (11k) | (12u) | (13s) | (14w) | (15cc) | (19x) | (20n) | (21o) |
| 1060 | (Io) | (6t) | (10w) | (11k) | (12u) | (13s) | (14w) | (15cc) | (19x) | (20n) | (21q) |
| 1061 | (Io) | (6t) | (10w) | (11k) | (12u) | (13s) | (14gg) | (15z), (15aa) | (19x) | (20m) | (21o) |
| 1062 | (Io) | (6t) | (10w) | (11k) | (12u) | (13s) | (14gg) | (15z), (15aa) | (19x) | (20m) | (21q) |
| 1063 | (Io) | (6t) | (10w) | (11k) | (12u) | (13s) | (14gg) | (15z), (15aa) | (19x) | (20n) | (21o) |
| 1064 | (Io) | (6t) | (10w) | (11k) | (12u) | (13s) | (14gg) | (15z), (15aa) | (19x) | (20n) | (21q) |
| 1065 | (Io) | (6t) | (10w) | (11k) | (12u) | (13s) | (14gg) | (15cc) | (19x) | (20m) | (21o) |
| 1066 | (Io) | (6t) | (10w) | (11k) | (12u) | (13s) | (14gg) | (15cc) | (19x) | (20m) | (21q) |
| 1067 | (Io) | (6t) | (10w) | (11k) | (12u) | (13s) | (14gg) | (15cc) | (19x) | (20n) | (21o) |
| 1068 | (Io) | (6t) | (10w) | (11k) | (12u) | (13s) | (14gg) | (15cc) | (19x) | (20n) | (21q) |
| 1069 | (Io) | (6t) | (10w) | (11k) | (12x) | (13t) | (14w) | (15z), (15aa) | (19x) | (20m) | (21o) |
| 1070 | (Io) | (6t) | (10w) | (11k) | (12x) | (13t) | (14w) | (15z), (15aa) | (19x) | (20m) | (21q) |
| 1071 | (Io) | (6t) | (10w) | (11k) | (12x) | (13t) | (14w) | (15z), (15aa) | (19x) | (20n) | (21o) |
| 1072 | (Io) | (6t) | (10w) | (11k) | (12x) | (13t) | (14w) | (15z), (15aa) | (19x) | (20n) | (21q) |
| 1073 | (Io) | (6t) | (10w) | (11k) | (12x) | (13t) | (14w) | (15cc) | (19x) | (20m) | (21o) |
| 1074 | (Io) | (6t) | (10w) | (11k) | (12x) | (13t) | (14w) | (15cc) | (19x) | (20m) | (21q) |
| 1075 | (Io) | (6t) | (10w) | (11k) | (12x) | (13t) | (14w) | (15cc) | (19x) | (20n) | (21o) |
| 1076 | (Io) | (6t) | (10w) | (11k) | (12x) | (13t) | (14w) | (15cc) | (19x) | (20n) | (21q) |
| 1077 | (Io) | (6t) | (10w) | (11k) | (12x) | (13t) | (14gg) | (15z), (15aa) | (19x) | (20m) | (21o) |
| 1078 | (Io) | (6t) | (10w) | (11k) | (12x) | (13t) | (14gg) | (15z), (15aa) | (19x) | (20m) | (21q) |
| 1079 | (Io) | (6t) | (10w) | (11k) | (12x) | (13t) | (14gg) | (15z), (15aa) | (19x) | (20n) | (21o) |
| 1080 | (Io) | (6t) | (10w) | (11k) | (12x) | (13t) | (14gg) | (15z), (15aa) | (19x) | (20n) | (21q) |
| 1081 | (Io) | (6t) | (10w) | (11k) | (12x) | (13t) | (14gg) | (15cc) | (19x) | (20m) | (21o) |
| 1082 | (Io) | (6t) | (10w) | (11k) | (12x) | (13t) | (14gg) | (15cc) | (19x) | (20m) | (21q) |
| 1083 | (Io) | (6t) | (10w) | (11k) | (12x) | (13t) | (14gg) | (15cc) | (19x) | (20n) | (21o) |
| 1084 | (Io) | (6t) | (10w) | (11k) | (12x) | (13t) | (14gg) | (15cc) | (19x) | (20n) | (21q) |
| 1085 | (Io) | (6t) | (10w) | (11k) | (12x) | (13s) | (14w) | (15z), (15aa) | (19x) | (20m) | (21o) |
| 1086 | (Io) | (6t) | (10w) | (11k) | (12x) | (13s) | (14w) | (15z), (15aa) | (19x) | (20m) | (21q) |
| 1087 | (Io) | (6t) | (10w) | (11k) | (12x) | (13s) | (14w) | (15z), (15aa) | (19x) | (20n) | (21o) |
| 1088 | (Io) | (6t) | (10w) | (11k) | (12x) | (13s) | (14w) | (15z), (15aa) | (19x) | (20n) | (21q) |
| 1089 | (Io) | (6t) | (10w) | (11k) | (12x) | (13s) | (14w) | (15cc) | (19x) | (20m) | (21o) |
| 1090 | (Io) | (6t) | (10w) | (11k) | (12x) | (13s) | (14w) | (15cc) | (19x) | (20m) | (21q) |
| 1091 | (Io) | (6t) | (10w) | (11k) | (12x) | (13s) | (14w) | (15cc) | (19x) | (20n) | (21o) |
| 1092 | (Io) | (6t) | (10w) | (11k) | (12x) | (13s) | (14w) | (15cc) | (19x) | (20n) | (21q) |
| 1093 | (Io) | (6t) | (10w) | (11k) | (12x) | (13s) | (14gg) | (15z), (15aa) | (19x) | (20m) | (21o) |
| 1094 | (Io) | (6t) | (10w) | (11k) | (12x) | (13s) | (14gg) | (15z), (15aa) | (19x) | (20m) | (21q) |
| 1095 | (Io) | (6t) | (10w) | (11k) | (12x) | (13s) | (14gg) | (15z), (15aa) | (19x) | (20n) | (21o) |
| 1096 | (Io) | (6t) | (10w) | (11k) | (12x) | (13s) | (14gg) | (15z), (15aa) | (19x) | (20n) | (21q) |
| 1097 | (Io) | (6t) | (10w) | (11k) | (12x) | (13s) | (14gg) | (15cc) | (19x) | (20m) | (21o) |
| 1098 | (Io) | (6t) | (10w) | (11k) | (12x) | (13s) | (14gg) | (15cc) | (19x) | (20m) | (21q) |
| 1099 | (Io) | (6t) | (10w) | (11k) | (12x) | (13s) | (14gg) | (15cc) | (19x) | (20n) | (21o) |
| 1100 | (Io) | (6t) | (10w) | (11k) | (12x) | (13s) | (14gg) | (15cc) | (19x) | (20n) | (21q) |
| 1101 | (Io) | (6t) | (10w) | (11j) | (12u) | (13t) | (14w) | (15z), (15aa) | (19x) | (20m) | (21o) |
| 1102 | (Io) | (6t) | (10w) | (11j) | (12u) | (13t) | (14w) | (15z), (15aa) | (19x) | (20m) | (21q) |
| 1103 | (Io) | (6t) | (10w) | (11j) | (12u) | (13t) | (14w) | (15z), (15aa) | (19x) | (20n) | (21o) |
| 1104 | (Io) | (6t) | (10w) | (11j) | (12u) | (13t) | (14w) | (15z), (15aa) | (19x) | (20n) | (21q) |
| 1105 | (Io) | (6t) | (10w) | (11j) | (12u) | (13t) | (14w) | (15cc) | (19x) | (20m) | (21o) |
| 1106 | (Io) | (6t) | (10w) | (11j) | (12u) | (13t) | (14w) | (15cc) | (19x) | (20m) | (21q) |
| 1107 | (Io) | (6t) | (10w) | (11j) | (12u) | (13t) | (14w) | (15cc) | (19x) | (20n) | (21o) |
| 1108 | (Io) | (6t) | (10w) | (11j) | (12u) | (13t) | (14w) | (15cc) | (19x) | (20n) | (21q) |
| 1109 | (Io) | (6t) | (10w) | (11j) | (12u) | (13t) | (14gg) | (15z), (15aa) | (19x) | (20m) | (21o) |
| 1110 | (Io) | (6t) | (10w) | (11j) | (12u) | (13t) | (14gg) | (15z), (15aa) | (19x) | (20m) | (21q) |
| 1111 | (Io) | (6t) | (10w) | (11j) | (12u) | (13t) | (14gg) | (15z), (15aa) | (19x) | (20n) | (21o) |
| 1112 | (Io) | (6t) | (10w) | (11j) | (12u) | (13t) | (14gg) | (15z), (15aa) | (19x) | (20n) | (21q) |

-continued

| | I | L¹† | R¹ | L² | Q | L³ | R³ | L⁴†† | R⁴ | L⁵ | R⁵ |
|---|---|---|---|---|---|---|---|---|---|---|---|
| 1113 | (Io) | (6t) | (10w) | (11j) | (12u) | (13t) | (14gg) | (15cc) | (19x) | (20m) | (21o) |
| 1114 | (Io) | (6t) | (10w) | (11j) | (12u) | (13t) | (14gg) | (15cc) | (19x) | (20m) | (21q) |
| 1115 | (Io) | (6t) | (10w) | (11j) | (12u) | (13t) | (14gg) | (15cc) | (19x) | (20n) | (21o) |
| 1116 | (Io) | (6t) | (10w) | (11j) | (12u) | (13t) | (14gg) | (15cc) | (19x) | (20n) | (21q) |
| 1117 | (Io) | (6t) | (10w) | (11j) | (12u) | (13s) | (14w) | (15z), (15aa) | (19x) | (20m) | (21o) |
| 1118 | (Io) | (6t) | (10w) | (11j) | (12u) | (13s) | (14w) | (15z), (15aa) | (19x) | (20m) | (21q) |
| 1119 | (Io) | (6t) | (10w) | (11j) | (12u) | (13s) | (14w) | (15z), (15aa) | (19x) | (20n) | (21o) |
| 1120 | (Io) | (6t) | (10w) | (11j) | (12u) | (13s) | (14w) | (15z), (15aa) | (19x) | (20n) | (21q) |
| 1121 | (Io) | (6t) | (10w) | (11j) | (12u) | (13s) | (14w) | (15cc) | (19x) | (20m) | (21o) |
| 1122 | (Io) | (6t) | (10w) | (11j) | (12u) | (13s) | (14w) | (15cc) | (19x) | (20m) | (21q) |
| 1123 | (Io) | (6t) | (10w) | (11j) | (12u) | (13s) | (14w) | (15cc) | (19x) | (20n) | (21o) |
| 1124 | (Io) | (6t) | (10w) | (11j) | (12u) | (13s) | (14w) | (15cc) | (19x) | (20n) | (21q) |
| 1125 | (Io) | (6t) | (10w) | (11j) | (12u) | (13s) | (14gg) | (15z), (15aa) | (19x) | (20m) | (21o) |
| 1126 | (Io) | (6t) | (10w) | (11j) | (12u) | (13s) | (14gg) | (15z), (15aa) | (19x) | (20m) | (21q) |
| 1127 | (Io) | (6t) | (10w) | (11j) | (12u) | (13s) | (14gg) | (15z), (15aa) | (19x) | (20n) | (21o) |
| 1128 | (Io) | (6t) | (10w) | (11j) | (12u) | (13s) | (14gg) | (15z), (15aa) | (19x) | (20n) | (21q) |
| 1129 | (Io) | (6t) | (10w) | (11j) | (12u) | (13s) | (14gg) | (15cc) | (19x) | (20m) | (21o) |
| 1130 | (Io) | (6t) | (10w) | (11j) | (12u) | (13s) | (14gg) | (15cc) | (19x) | (20m) | (21q) |
| 1131 | (Io) | (6t) | (10w) | (11j) | (12u) | (13s) | (14gg) | (15cc) | (19x) | (20n) | (21o) |
| 1132 | (Io) | (6t) | (10w) | (11j) | (12u) | (13s) | (14gg) | (15cc) | (19x) | (20n) | (21q) |
| 1133 | (Io) | (6t) | (10w) | (11j) | (12x) | (13t) | (14w) | (15z), (15aa) | (19x) | (20m) | (21o) |
| 1134 | (Io) | (6t) | (10w) | (11j) | (12x) | (13t) | (14w) | (15z), (15aa) | (19x) | (20m) | (21q) |
| 1135 | (Io) | (6t) | (10w) | (11j) | (12x) | (13t) | (14w) | (15z), (15aa) | (19x) | (20n) | (21o) |
| 1136 | (Io) | (6t) | (10w) | (11j) | (12x) | (13t) | (14w) | (15z), (15aa) | (19x) | (20n) | (21q) |
| 1137 | (Io) | (6t) | (10w) | (11j) | (12x) | (13t) | (14w) | (15cc) | (19x) | (20m) | (21o) |
| 1138 | (Io) | (6t) | (10w) | (11j) | (12x) | (13t) | (14w) | (15cc) | (19x) | (20m) | (21q) |
| 1139 | (Io) | (6t) | (10w) | (11j) | (12x) | (13t) | (14w) | (15cc) | (19x) | (20n) | (21o) |
| 1140 | (Io) | (6t) | (10w) | (11j) | (12x) | (13t) | (14w) | (15cc) | (19x) | (20n) | (21q) |
| 1141 | (Io) | (6t) | (10w) | (11j) | (12x) | (13t) | (14gg) | (15z), (15aa) | (19x) | (20m) | (21o) |
| 1142 | (Io) | (6t) | (10w) | (11j) | (12x) | (13t) | (14gg) | (15z), (15aa) | (19x) | (20m) | (21q) |
| 1143 | (Io) | (6t) | (10w) | (11j) | (12x) | (13t) | (14gg) | (15z), (15aa) | (19x) | (20n) | (21o) |
| 1144 | (Io) | (6t) | (10w) | (11j) | (12x) | (13t) | (14gg) | (15z), (15aa) | (19x) | (20n) | (21q) |
| 1145 | (Io) | (6t) | (10w) | (11j) | (12x) | (13t) | (14gg) | (15cc) | (19x) | (20m) | (21o) |
| 1146 | (Io) | (6t) | (10w) | (11j) | (12x) | (13t) | (14gg) | (15cc) | (19x) | (20m) | (21q) |
| 1147 | (Io) | (6t) | (10w) | (11j) | (12x) | (13t) | (14gg) | (15cc) | (19x) | (20n) | (21o) |
| 1148 | (Io) | (6t) | (10w) | (11j) | (12x) | (13t) | (14gg) | (15cc) | (19x) | (20n) | (21q) |
| 1149 | (Io) | (6t) | (10w) | (11j) | (12x) | (13s) | (14w) | (15z), (15aa) | (19x) | (20m) | (21o) |
| 1150 | (Io) | (6t) | (10w) | (11j) | (12x) | (13s) | (14w) | (15z), (15aa) | (19x) | (20m) | (21q) |
| 1151 | (Io) | (6t) | (10w) | (11j) | (12x) | (13s) | (14w) | (15z), (15aa) | (19x) | (20n) | (21o) |
| 1152 | (Io) | (6t) | (10w) | (11j) | (12x) | (13s) | (14w) | (15z), (15aa) | (19x) | (20n) | (21q) |
| 1153 | (Io) | (6t) | (10w) | (11j) | (12x) | (13s) | (14w) | (15cc) | (19x) | (20m) | (21o) |
| 1154 | (Io) | (6t) | (10w) | (11j) | (12x) | (13s) | (14w) | (15cc) | (19x) | (20m) | (21q) |
| 1155 | (Io) | (6t) | (10w) | (11j) | (12x) | (13s) | (14w) | (15cc) | (19x) | (20n) | (21o) |
| 1156 | (Io) | (6t) | (10w) | (11j) | (12x) | (13s) | (14w) | (15cc) | (19x) | (20n) | (21q) |
| 1157 | (Io) | (6t) | (10w) | (11j) | (12x) | (13s) | (14gg) | (15z), (15aa) | (19x) | (20m) | (21o) |
| 1158 | (Io) | (6t) | (10w) | (11j) | (12x) | (13s) | (14gg) | (15z), (15aa) | (19x) | (20m) | (21q) |
| 1159 | (Io) | (6t) | (10w) | (11j) | (12x) | (13s) | (14gg) | (15z), (15aa) | (19x) | (20n) | (21o) |
| 1160 | (Io) | (6t) | (10w) | (11j) | (12x) | (13s) | (14gg) | (15z), (15aa) | (19x) | (20n) | (21q) |
| 1161 | (Io) | (6t) | (10w) | (11j) | (12x) | (13s) | (14gg) | (15cc) | (19x) | (20m) | (21o) |
| 1162 | (Io) | (6t) | (10w) | (11j) | (12x) | (13s) | (14gg) | (15cc) | (19x) | (20m) | (21q) |
| 1163 | (Io) | (6t) | (10w) | (11j) | (12x) | (13s) | (14gg) | (15cc) | (19x) | (20n) | (21o) |
| 1164 | (Io) | (6t) | (10w) | (11j) | (12x) | (13s) | (14gg) | (15cc) | (19x) | (20n) | (21q) |
| 1165 | (Io) | (6t) | (10x) | (11k) | (12u) | (13t) | (14w) | (15z), (15aa) | (19x) | (20m) | (21o) |
| 1166 | (Io) | (6t) | (10x) | (11k) | (12u) | (13t) | (14w) | (15z), (15aa) | (19x) | (20m) | (21q) |
| 1167 | (Io) | (6t) | (10x) | (11k) | (12u) | (13t) | (14w) | (15z), (15aa) | (19x) | (20n) | (21o) |
| 1168 | (Io) | (6t) | (10x) | (11k) | (12u) | (13t) | (14w) | (15z), (15aa) | (19x) | (20n) | (21q) |
| 1169 | (Io) | (6t) | (10x) | (11k) | (12u) | (13t) | (14w) | (15cc) | (19x) | (20m) | (21o) |
| 1170 | (Io) | (6t) | (10x) | (11k) | (12u) | (13t) | (14w) | (15cc) | (19x) | (20m) | (21q) |
| 1171 | (Io) | (6t) | (10x) | (11k) | (12u) | (13t) | (14w) | (15cc) | (19x) | (20n) | (21o) |
| 1172 | (Io) | (6t) | (10x) | (11k) | (12u) | (13t) | (14w) | (15cc) | (19x) | (20n) | (21q) |
| 1173 | (Io) | (6t) | (10x) | (11k) | (12u) | (13t) | (14gg) | (15z), (15aa) | (19x) | (20m) | (21o) |
| 1174 | (Io) | (6t) | (10x) | (11k) | (12u) | (13t) | (14gg) | (15z), (15aa) | (19x) | (20m) | (21q) |
| 1175 | (Io) | (6t) | (10x) | (11k) | (12u) | (13t) | (14gg) | (15z), (15aa) | (19x) | (20n) | (21o) |
| 1176 | (Io) | (6t) | (10x) | (11k) | (12u) | (13t) | (14gg) | (15z), (15aa) | (19x) | (20n) | (21q) |
| 1177 | (Io) | (6t) | (10x) | (11k) | (12u) | (13t) | (14gg) | (15cc) | (19x) | (20m) | (21o) |
| 1178 | (Io) | (6t) | (10x) | (11k) | (12u) | (13t) | (14gg) | (15cc) | (19x) | (20m) | (21q) |
| 1179 | (Io) | (6t) | (10x) | (11k) | (12u) | (13t) | (14gg) | (15cc) | (19x) | (20n) | (21o) |
| 1180 | (Io) | (6t) | (10x) | (11k) | (12u) | (13t) | (14gg) | (15cc) | (19x) | (20n) | (21q) |
| 1181 | (Io) | (6t) | (10x) | (11k) | (12u) | (13s) | (14w) | (15z), (15aa) | (19x) | (20m) | (21o) |
| 1182 | (Io) | (6t) | (10x) | (11k) | (12u) | (13s) | (14w) | (15z), (15aa) | (19x) | (20m) | (21q) |
| 1183 | (Io) | (6t) | (10x) | (11k) | (12u) | (13s) | (14w) | (15z), (15aa) | (19x) | (20n) | (21o) |
| 1184 | (Io) | (6t) | (10x) | (11k) | (12u) | (13s) | (14w) | (15z), (15aa) | (19x) | (20n) | (21q) |
| 1185 | (Io) | (6t) | (10x) | (11k) | (12u) | (13s) | (14w) | (15cc) | (19x) | (20m) | (21o) |
| 1186 | (Io) | (6t) | (10x) | (11k) | (12u) | (13s) | (14w) | (15cc) | (19x) | (20m) | (21q) |
| 1187 | (Io) | (6t) | (10x) | (11k) | (12u) | (13s) | (14w) | (15cc) | (19x) | (20n) | (21o) |
| 1188 | (Io) | (6t) | (10x) | (11k) | (12u) | (13s) | (14w) | (15cc) | (19x) | (20n) | (21q) |
| 1189 | (Io) | (6t) | (10x) | (11k) | (12u) | (13s) | (14gg) | (15z), (15aa) | (19x) | (20m) | (21o) |

| | I | L¹† | R¹ | L² | Q | L³ | R³ | L⁴†† | R⁴ | L⁵ | R⁵ |
|---|---|---|---|---|---|---|---|---|---|---|---|
| 1190 | (Io) | (6t) | (10x) | (11k) | (12u) | (13s) | (14gg) | (15z), (15aa) | (19x) | (20m) | (21q) |
| 1191 | (Io) | (6t) | (10x) | (11k) | (12u) | (13s) | (14gg) | (15z), (15aa) | (19x) | (20n) | (21o) |
| 1192 | (Io) | (6t) | (10x) | (11k) | (12u) | (13s) | (14gg) | (15z), (15aa) | (19x) | (20n) | (21q) |
| 1193 | (Io) | (6t) | (10x) | (11k) | (12u) | (13s) | (14gg) | (15cc) | (19x) | (20m) | (21o) |
| 1194 | (Io) | (6t) | (10x) | (11k) | (12u) | (13s) | (14gg) | (15cc) | (19x) | (20m) | (21q) |
| 1195 | (Io) | (6t) | (10x) | (11k) | (12u) | (13s) | (14gg) | (15cc) | (19x) | (20n) | (21o) |
| 1196 | (Io) | (6t) | (10x) | (11k) | (12u) | (13s) | (14gg) | (15cc) | (19x) | (20n) | (21q) |
| 1197 | (Io) | (6t) | (10x) | (11k) | (12x) | (13t) | (14w) | (15z), (15aa) | (19x) | (20m) | (21o) |
| 1198 | (Io) | (6t) | (10x) | (11k) | (12x) | (13t) | (14w) | (15z), (15aa) | (19x) | (20m) | (21q) |
| 1199 | (Io) | (6t) | (10x) | (11k) | (12x) | (13t) | (14w) | (15z), (15aa) | (19x) | (20n) | (21o) |
| 1200 | (Io) | (6t) | (10x) | (11k) | (12x) | (13t) | (14w) | (15z), (15aa) | (19x) | (20n) | (21q) |
| 1201 | (Io) | (6t) | (10x) | (11k) | (12x) | (13t) | (14w) | (15cc) | (19x) | (20m) | (21o) |
| 1202 | (Io) | (6t) | (10x) | (11k) | (12x) | (13t) | (14w) | (15cc) | (19x) | (20m) | (21q) |
| 1203 | (Io) | (6t) | (10x) | (11k) | (12x) | (13t) | (14w) | (15cc) | (19x) | (20n) | (21o) |
| 1204 | (Io) | (6t) | (10x) | (11k) | (12x) | (13t) | (14w) | (15cc) | (19x) | (20n) | (21q) |
| 1205 | (Io) | (6t) | (10x) | (11k) | (12x) | (13t) | (14gg) | (15z), (15aa) | (19x) | (20m) | (21o) |
| 1206 | (Io) | (6t) | (10x) | (11k) | (12x) | (13t) | (14gg) | (15z), (15aa) | (19x) | (20m) | (21q) |
| 1207 | (Io) | (6t) | (10x) | (11k) | (12x) | (13t) | (14gg) | (15z), (15aa) | (19x) | (20n) | (21o) |
| 1208 | (Io) | (6t) | (10x) | (11k) | (12x) | (13t) | (14gg) | (15z), (15aa) | (19x) | (20n) | (21q) |
| 1209 | (Io) | (6t) | (10x) | (11k) | (12x) | (13t) | (14gg) | (15cc) | (19x) | (20m) | (21o) |
| 1210 | (Io) | (6t) | (10x) | (11k) | (12x) | (13t) | (14gg) | (15cc) | (19x) | (20m) | (21q) |
| 1211 | (Io) | (6t) | (10x) | (11k) | (12x) | (13t) | (14gg) | (15cc) | (19x) | (20n) | (21o) |
| 1212 | (Io) | (6t) | (10x) | (11k) | (12x) | (13t) | (14gg) | (15cc) | (19x) | (20n) | (21q) |
| 1213 | (Io) | (6t) | (10x) | (11k) | (12x) | (13s) | (14w) | (15z), (15aa) | (19x) | (20m) | (21o) |
| 1214 | (Io) | (6t) | (10x) | (11k) | (12x) | (13s) | (14w) | (15z), (15aa) | (19x) | (20m) | (21q) |
| 1215 | (Io) | (6t) | (10x) | (11k) | (12x) | (13s) | (14w) | (15z), (15aa) | (19x) | (20n) | (21o) |
| 1216 | (Io) | (6t) | (10x) | (11k) | (12x) | (13s) | (14w) | (15z), (15aa) | (19x) | (20n) | (21q) |
| 1217 | (Io) | (6t) | (10x) | (11k) | (12x) | (13s) | (14w) | (15cc) | (19x) | (20m) | (21o) |
| 1218 | (Io) | (6t) | (10x) | (11k) | (12x) | (13s) | (14w) | (15cc) | (19x) | (20m) | (21q) |
| 1219 | (Io) | (6t) | (10x) | (11k) | (12x) | (13s) | (14w) | (15cc) | (19x) | (20n) | (21o) |
| 1220 | (Io) | (6t) | (10x) | (11k) | (12x) | (13s) | (14w) | (15cc) | (19x) | (20n) | (21q) |
| 1221 | (Io) | (6t) | (10x) | (11k) | (12x) | (13s) | (14gg) | (15z), (15aa) | (19x) | (20m) | (21o) |
| 1222 | (Io) | (6t) | (10x) | (11k) | (12x) | (13s) | (14gg) | (15z), (15aa) | (19x) | (20m) | (21q) |
| 1223 | (Io) | (6t) | (10x) | (11k) | (12x) | (13s) | (14gg) | (15z), (15aa) | (19x) | (20n) | (21o) |
| 1224 | (Io) | (6t) | (10x) | (11k) | (12x) | (13s) | (14gg) | (15z), (15aa) | (19x) | (20n) | (21q) |
| 1225 | (Io) | (6t) | (10x) | (11k) | (12x) | (13s) | (14gg) | (15cc) | (19x) | (20m) | (21o) |
| 1226 | (Io) | (6t) | (10x) | (11k) | (12x) | (13s) | (14gg) | (15cc) | (19x) | (20m) | (21q) |
| 1227 | (Io) | (6t) | (10x) | (11k) | (12x) | (13s) | (14gg) | (15cc) | (19x) | (20n) | (21o) |
| 1228 | (Io) | (6t) | (10x) | (11k) | (12x) | (13s) | (14gg) | (15cc) | (19x) | (20n) | (21q) |
| 1229 | (Io) | (6t) | (10x) | (11j) | (12u) | (13t) | (14w) | (15z), (15aa) | (19x) | (20m) | (21o) |
| 1230 | (Io) | (6t) | (10x) | (11j) | (12u) | (13t) | (14w) | (15z), (15aa) | (19x) | (20m) | (21q) |
| 1231 | (Io) | (6t) | (10x) | (11j) | (12u) | (13t) | (14w) | (15z), (15aa) | (19x) | (20n) | (21o) |
| 1232 | (Io) | (6t) | (10x) | (11j) | (12u) | (13t) | (14w) | (15z), (15aa) | (19x) | (20n) | (21q) |
| 1233 | (Io) | (6t) | (10x) | (11j) | (12u) | (13t) | (14w) | (15cc) | (19x) | (20m) | (21o) |
| 1234 | (Io) | (6t) | (10x) | (11j) | (12u) | (13t) | (14w) | (15cc) | (19x) | (20m) | (21q) |
| 1235 | (Io) | (6t) | (10x) | (11j) | (12u) | (13t) | (14w) | (15cc) | (19x) | (20n) | (21o) |
| 1236 | (Io) | (6t) | (10x) | (11j) | (12u) | (13t) | (14w) | (15cc) | (19x) | (20n) | (21q) |
| 1237 | (Io) | (6t) | (10x) | (11j) | (12u) | (13t) | (14gg) | (15z), (15aa) | (19x) | (20m) | (21o) |
| 1238 | (Io) | (6t) | (10x) | (11j) | (12u) | (13t) | (14gg) | (15z), (15aa) | (19x) | (20m) | (21q) |
| 1239 | (Io) | (6t) | (10x) | (11j) | (12u) | (13t) | (14gg) | (15z), (15aa) | (19x) | (20n) | (21o) |
| 1240 | (Io) | (6t) | (10x) | (11j) | (12u) | (13t) | (14gg) | (15z), (15aa) | (19x) | (20n) | (21q) |
| 1241 | (Io) | (6t) | (10x) | (11j) | (12u) | (13t) | (14gg) | (15cc) | (19x) | (20m) | (21o) |
| 1242 | (Io) | (6t) | (10x) | (11j) | (12u) | (13t) | (14gg) | (15cc) | (19x) | (20m) | (21q) |
| 1243 | (Io) | (6t) | (10x) | (11j) | (12u) | (13t) | (14gg) | (15cc) | (19x) | (20n) | (21o) |
| 1244 | (Io) | (6t) | (10x) | (11j) | (12u) | (13t) | (14gg) | (15cc) | (19x) | (20n) | (21q) |
| 1245 | (Io) | (6t) | (10x) | (11j) | (12u) | (13s) | (14w) | (15z), (15aa) | (19x) | (20m) | (21o) |
| 1246 | (Io) | (6t) | (10x) | (11j) | (12u) | (13s) | (14w) | (15z), (15aa) | (19x) | (20m) | (21q) |
| 1247 | (Io) | (6t) | (10x) | (11j) | (12u) | (13s) | (14w) | (15z), (15aa) | (19x) | (20n) | (21o) |
| 1248 | (Io) | (6t) | (10x) | (11j) | (12u) | (13s) | (14w) | (15z), (15aa) | (19x) | (20n) | (21q) |
| 1249 | (Io) | (6t) | (10x) | (11j) | (12u) | (13s) | (14w) | (15cc) | (19x) | (20m) | (21o) |
| 1250 | (Io) | (6t) | (10x) | (11j) | (12u) | (13s) | (14w) | (15cc) | (19x) | (20m) | (21q) |
| 1251 | (Io) | (6t) | (10x) | (11j) | (12u) | (13s) | (14w) | (15cc) | (19x) | (20n) | (21o) |
| 1252 | (Io) | (6t) | (10x) | (11j) | (12u) | (13s) | (14w) | (15cc) | (19x) | (20n) | (21q) |
| 1253 | (Io) | (6t) | (10x) | (11j) | (12u) | (13s) | (14gg) | (15z), (15aa) | (19x) | (20m) | (21o) |
| 1254 | (Io) | (6t) | (10x) | (11j) | (12u) | (13s) | (14gg) | (15z), (15aa) | (19x) | (20m) | (21q) |
| 1255 | (Io) | (6t) | (10x) | (11j) | (12u) | (13s) | (14gg) | (15z), (15aa) | (19x) | (20n) | (21o) |
| 1256 | (Io) | (6t) | (10x) | (11j) | (12u) | (13s) | (14gg) | (15z), (15aa) | (19x) | (20n) | (21q) |
| 1257 | (Io) | (6t) | (10x) | (11j) | (12u) | (13s) | (14gg) | (15cc) | (19x) | (20m) | (21o) |
| 1258 | (Io) | (6t) | (10x) | (11j) | (12u) | (13s) | (14gg) | (15cc) | (19x) | (20m) | (21q) |
| 1259 | (Io) | (6t) | (10x) | (11j) | (12u) | (13s) | (14gg) | (15cc) | (19x) | (20n) | (21o) |
| 1260 | (Io) | (6t) | (10x) | (11j) | (12u) | (13s) | (14gg) | (15cc) | (19x) | (20n) | (21q) |
| 1261 | (Io) | (6t) | (10x) | (11j) | (12x) | (13t) | (14w) | (15z), (15aa) | (19x) | (20m) | (21o) |
| 1262 | (Io) | (6t) | (10x) | (11j) | (12x) | (13t) | (14w) | (15z), (15aa) | (19x) | (20m) | (21q) |
| 1263 | (Io) | (6t) | (10x) | (11j) | (12x) | (13t) | (14w) | (15z), (15aa) | (19x) | (20n) | (21o) |
| 1264 | (Io) | (6t) | (10x) | (11j) | (12x) | (13t) | (14w) | (15z), (15aa) | (19x) | (20n) | (21q) |
| 1265 | (Io) | (6t) | (10x) | (11j) | (12x) | (13t) | (14w) | (15cc) | (19x) | (20m) | (21o) |
| 1266 | (Io) | (6t) | (10x) | (11j) | (12x) | (13t) | (14w) | (15cc) | (19x) | (20m) | (21q) |

-continued

| | I | L$^{1\dagger}$ | R$^1$ | L$^2$ | Q | L$^3$ | R$^3$ | L$^{4\dagger\dagger}$ | R$^4$ | L$^5$ | R$^5$ |
|---|---|---|---|---|---|---|---|---|---|---|---|
| 1267 | (Io) | (6t) | (10x) | (11j) | (12x) | (13t) | (14w) | (15cc) | (19x) | (20n) | (21o) |
| 1268 | (Io) | (6t) | (10x) | (11j) | (12x) | (13t) | (14w) | (15cc) | (19x) | (20n) | (21q) |
| 1269 | (Io) | (6t) | (10x) | (11j) | (12x) | (13t) | (14gg) | (15z), (15aa) | (19x) | (20m) | (21o) |
| 1270 | (Io) | (6t) | (10x) | (11j) | (12x) | (13t) | (14gg) | (15z), (15aa) | (19x) | (20m) | (21q) |
| 1271 | (Io) | (6t) | (10x) | (11j) | (12x) | (13t) | (14gg) | (15z), (15aa) | (19x) | (20n) | (21o) |
| 1272 | (Io) | (6t) | (10x) | (11j) | (12x) | (13t) | (14gg) | (15z), (15aa) | (19x) | (20n) | (21q) |
| 1273 | (Io) | (6t) | (10x) | (11j) | (12x) | (13t) | (14gg) | (15cc) | (19x) | (20m) | (21o) |
| 1274 | (Io) | (6t) | (10x) | (11j) | (12x) | (13t) | (14gg) | (15cc) | (19x) | (20m) | (21q) |
| 1275 | (Io) | (6t) | (10x) | (11j) | (12x) | (13t) | (14gg) | (15cc) | (19x) | (20n) | (21o) |
| 1276 | (Io) | (6t) | (10x) | (11j) | (12x) | (13t) | (14gg) | (15cc) | (19x) | (20n) | (21q) |
| 1277 | (Io) | (6t) | (10x) | (11j) | (12x) | (13s) | (14w) | (15z), (15aa) | (19x) | (20m) | (21o) |
| 1278 | (Io) | (6t) | (10x) | (11j) | (12x) | (13s) | (14w) | (15z), (15aa) | (19x) | (20m) | (21q) |
| 1279 | (Io) | (6t) | (10x) | (11j) | (12x) | (13s) | (14w) | (15z), (15aa) | (19x) | (20n) | (21o) |
| 1280 | (Io) | (6t) | (10x) | (11j) | (12x) | (13s) | (14w) | (15z), (15aa) | (19x) | (20n) | (21q) |
| 1281 | (Io) | (6t) | (10x) | (11j) | (12x) | (13s) | (14w) | (15cc) | (19x) | (20m) | (21o) |
| 1282 | (Io) | (6t) | (10x) | (11j) | (12x) | (13s) | (14w) | (15cc) | (19x) | (20m) | (21q) |
| 1283 | (Io) | (6t) | (10x) | (11j) | (12x) | (13s) | (14w) | (15cc) | (19x) | (20n) | (21o) |
| 1284 | (Io) | (6t) | (10x) | (11j) | (12x) | (13s) | (14w) | (15cc) | (19x) | (20n) | (21q) |
| 1285 | (Io) | (6t) | (10x) | (11j) | (12x) | (13s) | (14gg) | (15z), (15aa) | (19x) | (20m) | (21o) |
| 1286 | (Io) | (6t) | (10x) | (11j) | (12x) | (13s) | (14gg) | (15z), (15aa) | (19x) | (20m) | (21q) |
| 1287 | (Io) | (6t) | (10x) | (11j) | (12x) | (13s) | (14gg) | (15z), (15aa) | (19x) | (20n) | (21o) |
| 1288 | (Io) | (6t) | (10x) | (11j) | (12x) | (13s) | (14gg) | (15z), (15aa) | (19x) | (20n) | (21q) |
| 1289 | (Io) | (6t) | (10x) | (11j) | (12x) | (13s) | (14gg) | (15cc) | (19x) | (20m) | (21o) |
| 1290 | (Io) | (6t) | (10x) | (11j) | (12x) | (13s) | (14gg) | (15cc) | (19x) | (20m) | (21q) |
| 1291 | (Io) | (6t) | (10x) | (11j) | (12x) | (13s) | (14gg) | (15cc) | (19x) | (20n) | (21o) |
| 1292 | (Io) | (6t) | (10x) | (11j) | (12x) | (13s) | (14gg) | (15cc) | (19x) | (20n) | (21q) |

In certain additional embodiments, including any of the embodiments described with reference to formulae (I)-(Io) and embodiments 1-1292 above, each optionally substituted alkylene, alkenylene, and alkynylene recited in any one of the preceding embodiments is unsubstituted. In alternative additional embodiments, including any of the embodiments described with reference to formulae (I)-(Io) and embodiments 1-1292 above, each optionally substituted alkylene, alkenylene, and alkynylene recited in any one of the preceding embodiments is unsubstituted or fluorinated.

In certain additional embodiments, including any of the embodiments described with reference to formulae (I)-(Io) and embodiments 1-1292 above and any embodiment described in the paragraph immediately above, each optionally substituted alkyl, alkenyl, and alkynyl recited in any one of preceding embodiments is unsubstituted. In alternative additional embodiments, including any of the embodiments described with reference to formulae (I)-(Io) and embodiments 1-1292 above and any embodiment described in the paragraph immediately above, each optionally substituted alkyl, alkenyl, and alkynyl recited in any one of preceding embodiments is unsubstituted.

In certain additional embodiments, including any of the embodiments described with reference to formulae (I)-(Io) and embodiments 1-1292 above and any embodiment described in the two paragraphs immediately above, each cycloalkyl recited in any one of the preceding embodiments is a 3-7 membered monocyclic cycloalkyl. For example, in certain particular embodiments, including any of the embodiments described with reference to formulae (I)-(Io) and embodiments 1-1292 above and any embodiment described in the two paragraphs immediately above, each cycloalkyl recited in any one of the preceding embodiments is a cyclopropyl, a cyclobutyl, a cyclopentyl, a cyclopentenyl, a cyclohexyl or a cyclohexenyl.

In certain additional embodiments, including any of the embodiments described with reference to formulae (I)-(Io) and embodiments 1-1292 above and any embodiment described in the three paragraphs immediately above, each heterocycloalkyl recited in any one of the preceding embodiments is a 4-7 membered monocyclic heterocycloalkyl having 1-2 heteroatoms selected from O, S and N. For example, in certain particular embodiments, including any of the embodiments described with reference to formulae (I)-(Io) and embodiments 1-1292 above and any embodiment described in the three paragraphs immediately above, each heterocycloalkyl recited in any one of the preceding embodiments is a pyrrolidinyl, a tetrahydrofuranyl, a tetrahydrothienyl, a piperidinyl, a piperazinyl, a morpholinyl, a thiomorpholinyl, a tetrahydro-2H-pyranyl, or a tetrahydro-2H-thiopyranyl.

In certain additional embodiments, including any of the embodiments described with reference to formulae (I)-(Io) and embodiments 1-1292 above and any embodiment described in the four paragraphs immediately above, each heteroaryl is a 5-6 membered monocyclic heteroaryl having 1-3 heteroatoms selected from O, S and N. For example, in certain particular embodiments, including any of the embodiments described with reference to formulae (I)-(Io) and embodiments 1-1292 above and any embodiment described in the four paragraphs immediately above, each heteroaryl is a furanyl, a thienyl, a pyrrolyl, a pyrazolyl, an imidazolyl, an oxazolyl or a thiazolyl.

In certain additional embodiments, including any of the embodiments described with reference to formulae (I)-(Io) and embodiments 1-1292 above and any embodiment described in the four paragraphs immediately above, each aryl is phenyl.

In certain additional embodiments as described above, including any of the embodiments described with reference to formulae (I)-(Io) and embodiments 1-1292 above and any embodiment described in the five paragraphs immediately above, $R^5$ is substituted with 1, 2 or 3 substituents selected from halogen (e.g., chloro- or fluoro-) and fluorinated $C_1$-$C_3$ alkyl (e.g., trifluoromethyl, difluoromethyl, fluoromethyl, pentafluoroethyl, trifluoroethyl). For example, in certain embodiment as described above, $R^5$ is phenyl substituted (e.g., 3-substituted, 4-substituted, 3,4-disubstituted, 2,4-disubstituted, or 2,5-disubstituted) with one or two substitutents selected from trifluoromethyl, fluorine and chlorine.

For example, in particular embodiments, $R^5$ can be dichlorophenyl, e.g., 3,4-dichlorophenyl, or trifluoromethylphenyl, e.g., 4-trifluoromethylphenyl.

In certain embodiments, the compound is one of the compounds of the compound table below. BJAB cell proliferation data is presented in the table; "A" indicates a measured $EC_{50}$ less than or equal to 1 μM; "B" indicates a measured $EC_{50}$ greater than 1 μM and less than or equal to 5 μM; "C" indicates a measured $EC_{50}$ greater than 5 μM and less than or equal to 10 μM; "D" indicates a measured $EC_{50}$ greater than 10 μM and less than or equal to 25 μM; "E" indicates a measured $EC_{50}$ greater than 25 μM and less than or equal to 50 μM; "F" indicates a measured $EC_{50}$ greater than 50 μM and less than or equal to 100 μM; "G" indicates that in the experiments performed there was no measured $EC_{50}$ less than or equal to 80 μM; "H" indicates that in the experiments performed there was no measured $EC_{50}$ less than or equal to 50 μM; "I" indicates that in the experiments performed there was no measured $EC_{50}$ less than or equal to 40 μM; "J" indicates that in the experiments performed there was no measured $EC_{50}$ less than or equal to 25 μM; and "K" indicates that in the experiments performed there was no measured $EC_{50}$ less than or equal to 20 μM.

| Ex. | Structure | Name | $EC_{50}$ | Characterization |
|---|---|---|---|---|
| 1 | (structure) | methyl 1-(4-(3,4-dichlorophenyl)thiazol-2-yl)-3-methyl-4-(2-nitrobenzyl)-1H-pyrazole-5-carboxylate | H | $^1$H NMR (500 MHz, DMSO) δ 8.19 (s, 1H), 8.08 (d, J = 2.0 Hz, 1H), 8.02 (dd, J = 8.1, 1.1 Hz, 1H), 7.82 (dd, J = 8.4, 2.0 Hz, 1H), 7.73 (d, J = 8.4 Hz, 1H), 7.69 (td, J = 7.6, 1.2 Hz, 1H), 7.57-7.51 (m, 1H), 7.33 (d, J = 7.5 Hz, 1H), 4.24 (s, 2H), 3.68 (s, 3H), 2.14 (s, 3H); MS (m/z): 503.12 $[M + 1]^+$. |
| 2 | (structure) | 1-(4-(3,4-dichlorophenyl)thiazol-2-yl)-3-methyl-4-(2-nitrobenzyl)-1H-pyrazole-5-carboxylic acid | H | $^1$H NMR (500 MHz, DMSO) δ 8.20 (s, 1H), 8.13 (d, J = 2.1 Hz, 1H), 7.99 (dd, J = 8.1, 1.1 Hz, 1H), 7.89 (dd, J = 8.4, 2.1 Hz, 1H), 7.72 (d, J = 8.4 Hz, 1H), 7.65 (td, J = 7.7, 1.2 Hz, 1H), 7.50 (t, J = 7.2 Hz, 1H), 7.24 (d, J = 7.6 Hz, 1H), 4.24 (s, 2H), 2.06 (s, 3H); MS (m/z): 489.1 $[M + 1]^+$ |
| 3 | (structure) | methyl 1-(4-(3,4-dichlorophenyl)-5-(ethylthio)thiazol-2-yl)-3-methyl-4-(2-nitrobenzyl)-1H-pyrazole-5-carboxylate | G | $^1$H NMR (500 MHz, DMSO) δ 8.06 (d, J = 2.1 Hz, 1H), 8.02 (dd, J = 8.1, 1.3 Hz, 1H), 7.91 (dd, J = 8.5, 2.1 Hz, 1H), 7.77 (d, J = 8.5 Hz, 1H), 7.68 (td, J = 7.6, 1.3 Hz, 1H), 7.57-7.50 (m, 1H), 7.33 (d, J = 6.9 Hz, 1H), 4.23 (s, 2H), 3.64 (s, 3H), 2.97 (q, J = 7.3 Hz, 2H), 2.15 (s, 3H), 1.21 (t, J = 7.3 Hz, 3H); MS (m/z): 563.0 $[M + 1]^+$ |
| 4 | (structure) | 1-(4-(3,4-dichlorophenyl)-5-(ethylthio)thiazol-2-yl)-3-methyl-4-(2-nitrobenzyl)-1H-pyrazole-5-carboxylic acid | F | $^1$H NMR (500 MHz, DMSO) δ 8.11 (d, J = 2.1 Hz, 1H), 7.99 (dd, J = 8.1, 1.2 Hz, 1H), 7.94 (dd, J = 8.5, 2.1 Hz, 1H), 7.76 (d, J = 8.5 Hz, 1H), 7.64 (dt, J = 7.7, 3.8 Hz, 1H), 7.50 (t, J = 7.8 Hz, 1H), 7.23 (d, J = 7.8 Hz, 1H), 4.23 (s, 2H), 2.97 (q, J = 7.3 Hz, 2H), 2.06 (s, 3H), 1.21 (t, J = 7.3 Hz, 3H); MS (m/z): 549.1 $[M + 1]^+$ |

| Ex. | Structure | Name | EC$_{50}$ | Characterization |
|---|---|---|---|---|
| 5 | 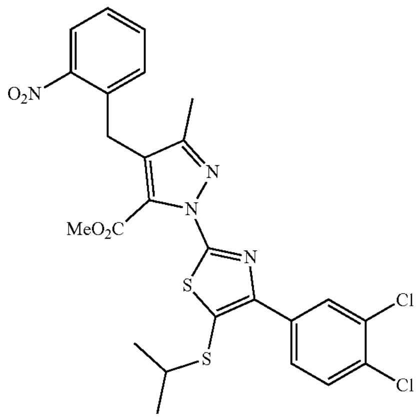 [SMILES: COC(=O)c1c(Cc2ccccc2[N+](=O)[O-])c(C)nn1-c1nc(-c2ccc(Cl)c(Cl)c2)c(SC(C)C)s1] | methyl 1-(4-(3,4-dichlorophenyl)-5-(isopropylthio)thiazol-2-yl)-3-methyl-4-(2-nitrobenzyl)-1H-pyrazole-5-carboxylate | G | $^1$H NMR (500 MHz, DMSO) δ 8.10 (d, J = 2.1 Hz, 1H), 8.02 (dd, J = 8.2, 1.2 Hz, 1H), 7.96 (dd, J = 8.5, 2.1 Hz, 1H), 7.77 (d, J = 8.5 Hz, 1H), 7.72-7.64 (m, 1H), 7.54 (t, J = 7.2 Hz, 1H), 7.33 (d, J = 7.1 Hz, 1H), 4.23 (s, 2H), 3.64 (s, 3H), 3.38-3.34 (m, 1H), 2.15 (s, 3H), 1.22 (d, J = 6.7 Hz, 6H); MS (m/z): 577.1 [M + 1]$^+$ |
| 6 | 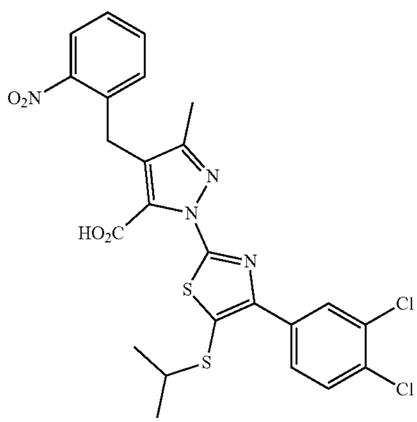 [SMILES: Cc1nn(-c2nc(-c3ccc(Cl)c(Cl)c3)c(SC(C)C)s2)c(C(=O)O)c1Cc1ccccc1[N+](=O)[O-]] | 1-(4-(3,4-dichlorophenyl)-5-(isopropylthio)thiazol-2-yl)-3-methyl-4-(2-nitrobenzyl)-1H-pyrazole-5-carboxylic acid | E | $^1$H NMR (500 MHz, DMSO) δ 8.16 (d, J = 2.1 Hz, 1H), 8.02-7.96 (m, 2H), 7.76 (dd, J = 8.5, 2.1 Hz, 1H), 7.64 (t, J = 7.6 Hz, 1H), 7.50 (t, J = 7.2 Hz, 1H), 7.23 (d, J = 7.5 Hz, 1H), 4.23 (s, 2H), 3.37-3.34 (m, 1H), 2.06 (s, 3H), 1.23 (d, J = 6.7 Hz, 6H); MS (m/z): 563.09 [M + 1]$^+$ |
| 7 | 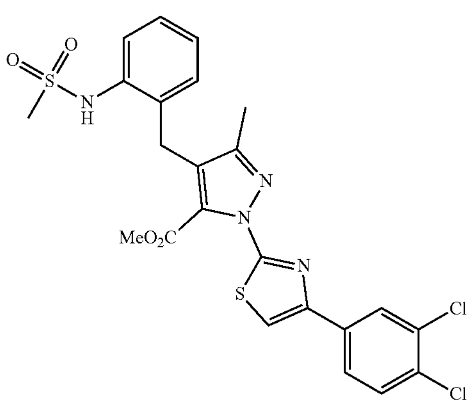 [SMILES: COC(=O)c1c(Cc2ccccc2NS(C)(=O)=O)c(C)nn1-c1nc(-c2ccc(Cl)c(Cl)c2)cs1] | methyl 1-(4-(3,4-dichlorophenyl)thiazol-2-yl)-3-methyl-4-(2-(methylsulfonamido)benzyl)-1H-pyrazole-5-carboxylate | G | $^1$H NMR (500 MHz, DMSO) δ 8.19 (s, 1H), 8.10 (d, J = 2.0 Hz, 1H), 7.85 (dd, J = 8.4, 2.1 Hz, 1H), 7.75 (d, J = 8.4 Hz, 1H), 7.33 (dd, J = 7.9, 1.2 Hz, 1H), 7.24 (t, J = 6.9 Hz, 1H), 7.14 (t, J = 7.2 Hz, 1H), 6.93 (d, J = 6.7 Hz, 1H), 4.02 (s, 2H), 3.77 (s, 3H), 2.96 (s, 3H), 2.09 (s, 3H); MS (m/z): 551.1 [M + 1]$^+$ |

| Ex. | Structure | Name | EC$_{50}$ | Characterization |
|---|---|---|---|---|
| 8 | 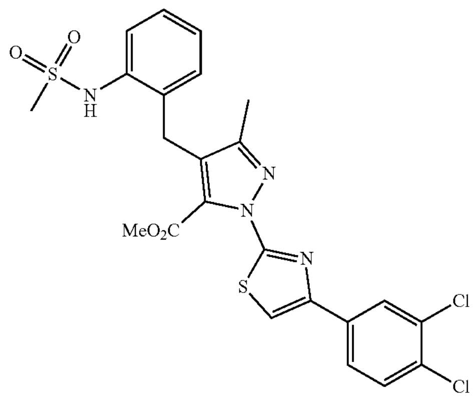 | 1-(4-(3,4-dichlorophenyl)thiazol-2-yl)-3-methyl-4-(2-(methylsulfonamido)benzyl)-1H-pyrazole-5-carboxylic acid | G | $^1$H NMR (500 MHz, DMSO) δ 14.01 (s, 1H), 9.41 (s, 1H), 8.20 (s, 1H), 8.15 (d, J = 2.0 Hz, 1H), 7.90 (dd, J = 8.4, 2.1 Hz, 1H), 7.73 (d, J = 8.4 Hz, 1H), 7.40-7.34 (m, 1H), 7.25 (td, J = 7.8, 1.4 Hz, 1H), 7.21-7.15 (m, 1H), 6.98 (s, 1H), 4.05 (s, 2H), 2.96 (s, 3H), 2.03 (s, 3H); MS (m/z): 537.1 [M + 1]$^+$ |
| 9 | 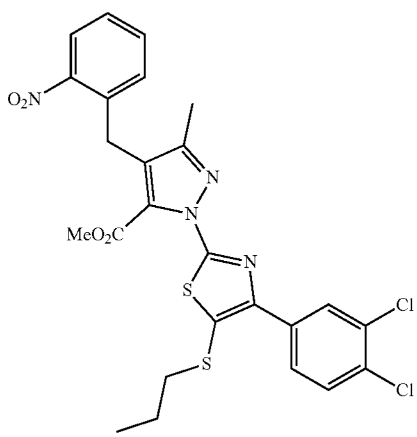 [SMILES: CCCSc1sc(-n2nc(C)c(Cc3ccccc3[N+](=O)[O-])c2C(=O)OC)nc1-c1ccc(Cl)c(Cl)c1] | methyl 1-(4-(3,4-dichlorophenyl)-5-(propylthio)thiazol-2-yl)-3-methyl-4-(2-nitrobenzyl)-1H-pyrazole-5-carboxylate | G | $^1$H NMR (500 MHz, CDCl$_3$) δ 8.14 (d, J = 2.1 Hz, 1H), 7.99 (dd, J = 8.2, 1.3 Hz, 1H), 7.92 (dd, J = 8.4, 2.1 Hz, 1H), 7.52 (td, J = 7.6, 1.3 Hz, 1H), 7.49-7.45 (m, 1H), 7.43-7.38 (m, 1H), 7.22 (d, J = 7.8 Hz, 1H), 4.28 (s, 2H), 3.75 (s, 3H), 2.81 (t, J = 10.0 Hz, 2H), 2.18 (s, 3H), 1.63 (sex, J = 10.0 Hz, 2H), 0.96 (t, J = 7.3 Hz, 3H); MS (m/z): 577.1 [M + 1]$^+$ |
| 10 | 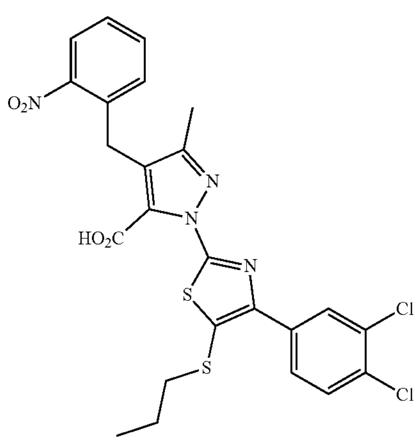 [SMILES: CCCSc1sc(-n2nc(C)c(Cc3ccccc3[N+](=O)[O-])c2C(=O)O)nc1-c1ccc(Cl)c(Cl)c1] | 1-(4-(3,4-dichlorophenyl)-5-(propylthio)thiazol-2-yl)-3-methyl-4-(2-nitrobenzyl)-1H-pyrazole-5-carboxylic acid | E | $^1$H NMR (500 MHz, DMSO) δ 8.13 (d, J = 2.1 Hz, 1H), 7.99 (dd, J = 8.1, 1.2 Hz, 1H), 7.93 (dd, J = 8.5, 2.1 Hz, 1H), 7.76 (d, J = 8.5 Hz, 1H), 7.64 (td, J = 7.6, 1.3 Hz, 1H), 7.54-7.48 (m, 1H), 7.23 (dd, J = 7.8, 0.7 Hz, 1H), 4.23 (s, 2H), 2.93 (t, J = 7.1 Hz, 2H), 2.06 (s, 3H), 1.61-1.50 (m, 2H), 0.90 (t, J = 7.3 Hz, 3H); MS (m/z): 563.1 [M + 1]$^+$ |

| Ex. | Structure | Name | EC$_{50}$ | Characterization |
|---|---|---|---|---|
| 11 | 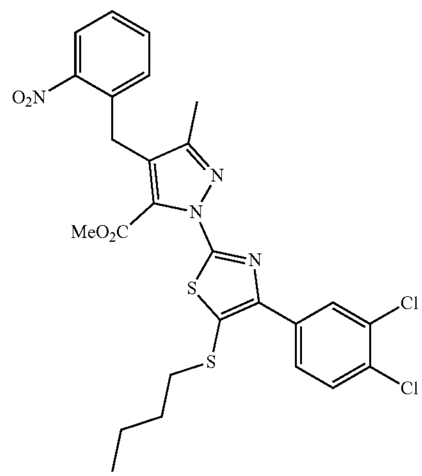 [SMILES: CCCCSc1sc(-n2nc(C)c(Cc3ccccc3[N+](=O)[O-])c2C(=O)OC)nc1-c1ccc(Cl)c(Cl)c1] | methyl 1-(5-(butylthio)-4-(3,4-dichlorophenyl)thiazol-2-yl)-3-methyl-4-(2-nitrobenzyl)-1H-pyrazole-5-carboxylate | G | $^1$H NMR (500 MHz, DMSO) δ 8.07 (d, J = 2.1 Hz, 1H), 8.02 (dd, J = 8.2, 1.3 Hz, 1H), 7.90 (dd, J = 8.5, 2.1 Hz, 1H), 7.77 (d, J = 8.5 Hz, 1H), 7.68 (td, J = 7.6, 1.4 Hz, 1H), 7.57-7.51 (m, 1H), 7.33 (dd, J = 7.8, 1.0 Hz, 1H), 4.23 (s, 2H), 3.64 (s, 3H), 2.95 (t, J = 7.2 Hz, 2H), 2.15 (s, 3H), 1.51 (dt, J = 14.7, 7.3 Hz, 2H), 1.31 (dq, J = 14.5, 7.4 Hz, 2H), 0.80 (t, J = 7.4 Hz, 3H); MS (m/z): 591.1 [M + 1]$^+$ |
| 12 | 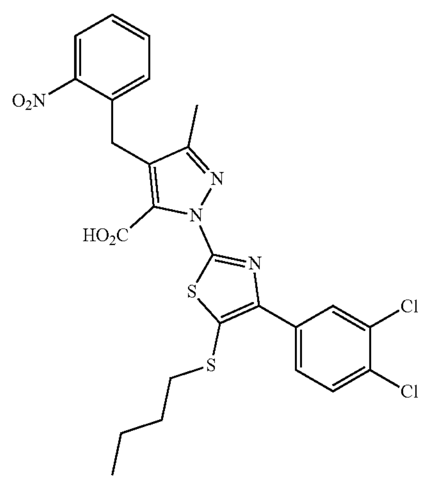 [SMILES: CCCCSc1sc(-n2nc(C)c(Cc3ccccc3[N+](=O)[O-])c2C(=O)O)nc1-c1ccc(Cl)c(Cl)c1] | 1-(5-(butylthio)-4-(3,4-dichlorophenyl)thiazol-2-yl)-3-methyl-4-(2-nitrobenzyl)-1H-pyrazole-5-carboxylic acid | G | $^1$H NMR (500 MHz, CDCl$_3$) δ 8.04 (d, J = 1.7 Hz, 1H), 7.97 (d, J = 7.9 Hz, 1H), 7.68 (dd, J = 8.6, 1.6 Hz, 1H), 7.55 (d, J = 8.3 Hz, 1H), 7.44 (t, J = 8.1 Hz, 1H), 7.36 (t, J = 7.6 Hz, 1H), 7.05 (d, J = 7.7 Hz, 1H), 4.66 (s, 2H), 2.87 (t, J = 7.3 Hz, 2H), 2.17 (s, 3H), 1.60 (dt, J = 14.9, 7.5 Hz, 2H), 1.39 (dq, J = 14.5, 7.3 Hz, 2H), 0.88 (t, J = 7.4 Hz, 3H); MS (m/z): 577.2 [M + 1]$^+$ |
| 13 | 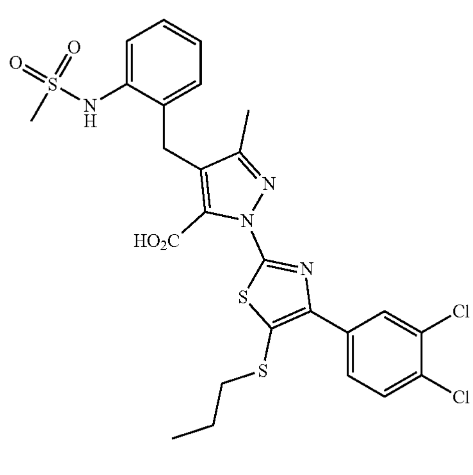 [SMILES: CCCSc1sc(-n2nc(C)c(Cc3ccccc3NS(C)(=O)=O)c2C(=O)O)nc1-c1ccc(Cl)c(Cl)c1] | 1-(4-(3,4-dichlorophenyl)-5-(propylthio)thiazol-2-yl)-3-methyl-4-(2-(methylsulfonamido)benzyl)-1H-pyrazole-5-carboxylic acid | E | $^1$H NMR (500 MHz, DMSO) δ 14.06 (s, 1H), 9.29 (s, 1H), 8.15 (d, J = 2.1 Hz, 1H), 7.95 (dd, J = 8.5, 2.1 Hz, 1H), 7.78 (d, J = 8.5 Hz, 1H), 7.36 (d, J = 7.8 Hz, 1H), 7.25 (t, J = 7.6 Hz, 1H), 7.18 (t, J = 7.5 Hz, 1H), 6.90 (d, J = 7.3 Hz, 1H), 4.05 (s, 2H), 3.01 (s, 3H), 2.94 (t, J = 7.1 Hz, 2H), 2.02 (s, 3H), 1.62-1.52 (m, 2H), 0.90 (t, J = 7.3 Hz, 3H); MS (m/z): 613.1 [M + 1]$^+$ |

| Ex. | Structure | Name | EC$_{50}$ | Characterization |
|---|---|---|---|---|
| 14 | 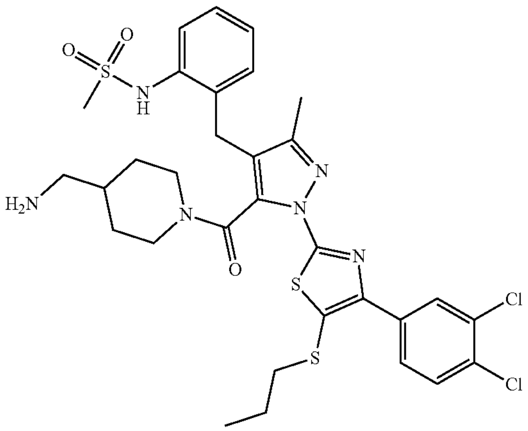 [SMILES: CCCSc1sc(-n2nc(C)c(Cc3ccccc3NS(C)(=O)=O)c2C(=O)N2CCC(CN)CC2)nc1-c1ccc(Cl)c(Cl)c1] | N-(2-((5-(4-(aminomethyl)piperidine-1-carbonyl)-1-(4-(3,4-dichlorophenyl)-5-(propylthio)thiazol-2-yl)-3-methyl-1H-pyrazol-4-yl)methyl)phenyl)methanesulfonamide | D | $^1$H NMR Mixture of 2 rotamers 1:1 (500 MHz, MeOD) δ 8.55 (s, 3H), 8.16 (d, J = 2.1 Hz, 1H), 8.11 (d, J = 2.0 Hz, 1H), 8.05 (dd, J = 8.5, 2.1 Hz, 1H), 7.95 (dd, J = 8.4, 2.1 Hz, 1H), 7.64-7.57 (m, 2H), 7.39-7.32 (m, 2H), 7.31-7.19 (m, 4H), 7.19-7.09 (m, 2H), 4.64 (d, J = 13.2 Hz, 2H), 4.53 (d, J = 13.4 Hz, 2H), 4.03 (s, 2H), 3.98 (s, 2H), 3.49-3.41 (m, 1H), 3.40-3.34 (m, 1H), 3.02 (s, 3H), 3.00 (s, 3H), 2.95-2.79 (m, 4H), 2.79-2.72 (m, 1H), 2.58 (dd, J = 36.5, 24.3 Hz, 4H), 2.25 (d, J = 4.2 Hz, 3H), 2.20 (s, 3H), 2.03 (s, 1H), 1.81 (d, J = 11.8 Hz, 1H), 1.68-1.52 (m, 4H), 1.46 (t, J = 15.3 Hz, 3H), 1.29 (s, 1H), 1.12 (d, J = 12.7 Hz, 1H), 1.00-0.91 (m, 6H), 0.84-0.59 (m, 2H); MS (m/z): 709.0 [M + 1]$^+$ |
| 15 | 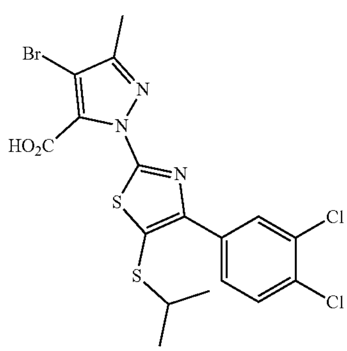 [SMILES: Cc1nn(-c2nc(-c3ccc(Cl)c(Cl)c3)c(SC(C)C)s2)c(C(=O)O)c1Br] | 4-bromo-1-(4-(3,4-dichlorophenyl)-5-(isopropylthio)thiazol-2-yl)-3-methyl-1H-pyrazole-5-carboxylic acid | D | $^1$H NMR (500 MHz, DMSO) δ 8.18 (d, J = 2.1 Hz, 1H), 7.99 (dd, J = 8.5, 2.1 Hz, 1H), 7.74 (d, J = 8.5 Hz, 1H), 2.25 (s, 3H), 1.22 (d, J = 6.7 Hz, 6H). Note: isopropyl CH is overlapping with water signal; MS (m/z): 505.7 [M + H]$^+$ |
| 16 | 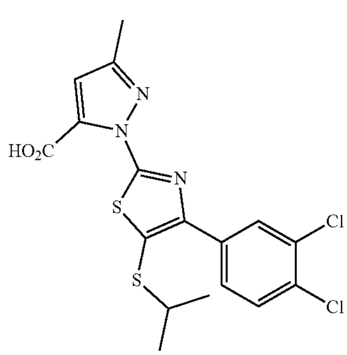 [SMILES: Cc1cc(C(=O)O)n(-c2nc(-c3ccc(Cl)c(Cl)c3)c(SC(C)C)s2)n1] | 1-(4-(3,4-dichlorophenyl)-5-(isopropylthio)thiazol-2-yl)-3-methyl-1H-pyrazole-5-carboxylic acid | F | $^1$H NMR (500 MHz, DMSO) δ 8.19 (d, J = 2.1 Hz, 1H), 8.02 (dd, J = 8.5, 2.1 Hz, 1H), 7.81 (d, J = 8.5 Hz, 1H), 6.91 (s, 1H), 3.39 (sept, J = 6.7 Hz, 1H), 2.33 (s, 3H), 1.27 (d, J = 6.7 Hz, 6H); MS (m/z): 426.0 [M − H]$^−$ |

| Ex. | Structure | Name | EC$_{50}$ | Characterization |
|---|---|---|---|---|
| 17 | 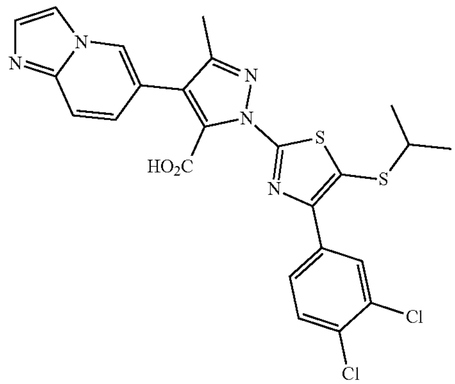 [SMILES: Cc1nn(-c2nc(-c3ccc(Cl)c(Cl)c3)c(SC(C)C)s2)c(C(=O)O)c1-c1ccc2nccn2c1] | 1-(4-(3,4-dichlorophenyl)-5-(isopropylthio)thiazol-2-yl)-4-(imidazo[1,2-a]pyridin-6-yl)-3-methyl-1H-pyrazole-5-carboxylic acid | D | $^1$H NMR (500 MHz, DMSO) δ 8.70 (s, 1H), 8.21 (d, J = 2.1 Hz, 1H), 8.06-7.99 (m, 2H), 7.76 (d, J = 8.5 Hz, 1H), 7.64 (d, J = 9.5 Hz, 2H), 7.34 (d, J = 9.0 Hz, 1H), 3.42-3.29 (m, 1H), 2.33 (s, 3H), 1.24 (d, J = 6.7 Hz, 6H); MS (m/z): 544.0 [M + 1]$^+$ |
| 18 | 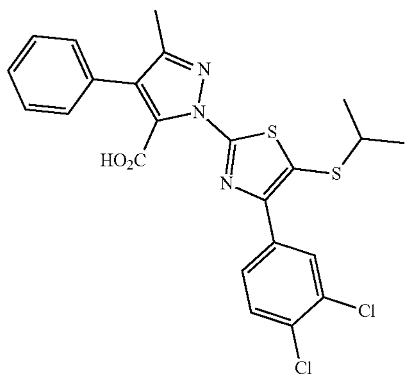 [SMILES: Cc1nn(-c2nc(-c3ccc(Cl)c(Cl)c3)c(SC(C)C)s2)c(C(=O)O)c1-c1ccccc1] | 1-(4-(3,4-dichlorophenyl)-5-(isopropylthio)thiazol-2-yl)-3-methyl-4-phenyl-1H-pyrazole-5-carboxylic acid | B | $^1$H NMR (500 MHz, DMSO) δ 8.23 (d, J = 2.0 Hz, 1H), 8.04 (dd, J = 8.5, 2.0 Hz, 1H), 7.73 (d, J = 8.5 Hz, 1H), 7.55-7.29 (m, 5H), 7.12 (br s, 1H), 3.42-3.29 (m, 1H), 2.29 (s, 3H), 1.24 (d, J = 6.7 Hz, 5H); MS (m/z): 504.5 [M + 1]$^+$ |
| 19 | 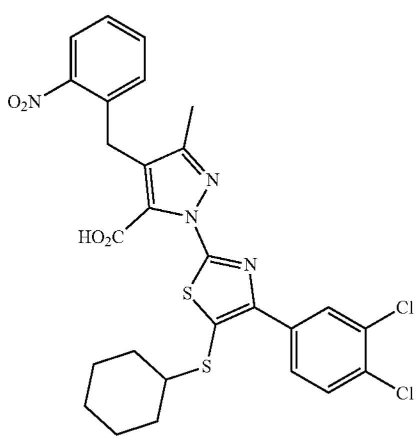 [SMILES: Cc1nn(-c2nc(-c3ccc(Cl)c(Cl)c3)c(SC3CCCCC3)s2)c(C(=O)O)c1Cc1ccccc1[N+](=O)[O-]] | 1-(5-(cyclohexylthio)-4-(3,4-dichlorophenyl)thiazol-2-yl)-3-methyl-4-(2-nitrobenzyl)-1H-pyrazole-5-carboxylic acid | D | $^1$H NMR (500 MHz, DMSO) δ 8.16 (d, J = 2.1 Hz, 1H), 8.03-7.95 (m, 2H), 7.75 (d, J = 8.5 Hz, 1H), 7.64 (dd, J = 11.4, 3.8 Hz, 1H), 7.51 (t, J = 7.7 Hz, 1H), 7.22 (d, J = 7.5 Hz, 1H), 4.24 (s, 2H), 3.17-3.09 (m, 1H), 2.07 (s, 3H), 1.95-1.81 (m, 2H), 1.65 (dd, J = 9.2, 3.8 Hz, 2H), 1.50 (dd, J = 7.6, 3.1 Hz, 1H), 1.38-1.10 (m, 5H); MS (m/z): 603.5 [M + 1]$^+$ |
| 20 | 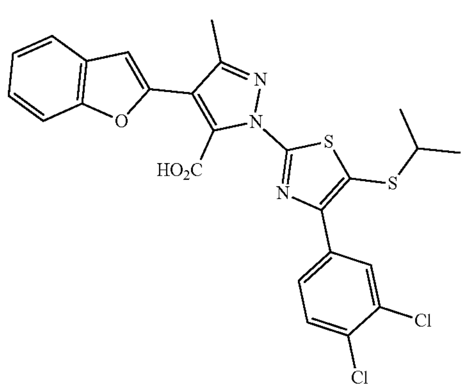 [SMILES: Cc1nn(-c2nc(-c3ccc(Cl)c(Cl)c3)c(SC(C)C)s2)c(C(=O)O)c1-c1cc2ccccc2o1] | 4-(benzofuran-2-yl)-1-(4-(3,4-dichlorophenyl)-5-(isopropylthio)thiazol-2-yl)-3-methyl-1H-pyrazole-5-carboxylic acid | C | $^1$H NMR (500 MHz, DMSO) δ 8.25 (d, J = 1.9 Hz, 1H), 8.06 (dd, J = 8.5, 2.0 Hz, 1H), 7.82-7.73 (m, 1H), 7.68 (d, J = 7.2 Hz, 1H), 7.56 (d, J = 8.3 Hz, 1H), 7.30 (dt, J = 22.9, 7.2 Hz, 2H), 7.17 (s, 1H), 3.42-3.29 (m, 1H), 2.54 (s, 3H), 1.24 (d, J = 6.7 Hz, 6H); MS (m/z): 544.0 [M + 1]$^+$ |

| Ex. | Structure | Name | EC$_{50}$ | Characterization |
|---|---|---|---|---|
| 21 | 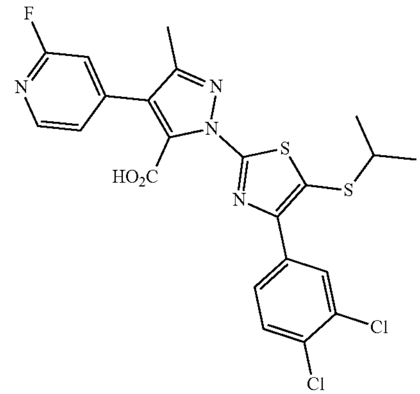 [SMILES: Cc1nn(-c2nc(-c3ccc(Cl)c(Cl)c3)c(SC(C)C)s2)c(C(=O)O)c1-c1ccnc(F)c1] | 1-(4-(3,4-dichlorophenyl)-5-(isopropylthio)thiazol-2-yl)-4-(2-fluoropyridin-4-yl)-3-methyl-1H-pyrazole-5-carboxylic acid | C | $^1$H NMR (500 MHz, DMSO) δ 8.28 (s, 1H), 8.22 (d, J = 5.5 Hz, 1H), 8.09 (dd, J = 8.4, 1.6 Hz, 1H), 7.76 (d, J = 8.5 Hz, 1H), 7.58 (d, J = 5.4 Hz, 1H), 7.41 (s, 1H), 2.37 (s, 3H), 1.24 (d, J = 6.7 Hz, 6H); MS (m/z): 523.0 [M + 1]$^+$ |
| 22 | 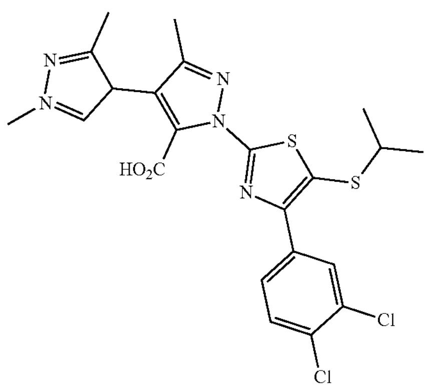 | 2-(4-(3,4-dichlorophenyl)-5-(isopropylthio)thiazol-2-yl)-2',5,5'-trimethyl-4,4'-bi(2H-pyrazole)-3-carboxylic acid | D | $^1$H NMR (500 MHz, DMSO) δ 8.19 (d, J = 2.0 Hz, 1H), 8.00 (dd, J = 8.5, 2.0 Hz, 1H), 7.73 (d, J = 8.5 Hz, 1H), 7.66 (s, 1H), 3.79 (s, 3H), 2.14 (s, 3H), 2.06 (s, 3H), 1.23 (d, J = 6.7 Hz, 6H); MS (m/z): 522.2 [M + 1]$^+$ |
| 23 | 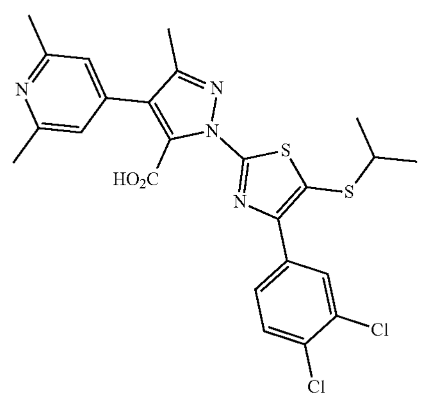 [SMILES: Cc1cc(-c2c(C)nn(-c3nc(-c4ccc(Cl)c(Cl)c4)c(SC(C)C)s3)c2C(=O)O)cc(C)n1] | 1-(4-(3,4-dichlorophenyl)-5-(isopropylthio)thiazol-2-yl)-4-(2,6-dimethylpyridin-4-yl)-3-methyl-1H-pyrazole-5-carboxylic acid | A | $^1$H NMR (500 MHz, DMSO) δ 8.20 (d, J = 2.1 Hz, 1H), 8.02 (dd, J = 8.5, 2.1 Hz, 1H), 7.76 (d, J = 8.5 Hz, 1H), 7.16 (s, 2H), 2.47 (s, 6H), 2.33 (s, 3H), 1.24 (d, J = 6.7 Hz, 6H); MS (m/z): 533.0 [M + 1]$^+$ |
| 24 | 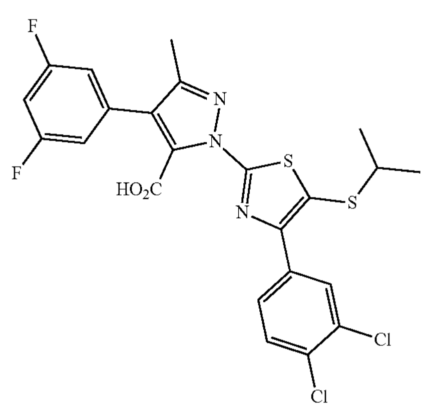 [SMILES: Cc1nn(-c2nc(-c3ccc(Cl)c(Cl)c3)c(SC(C)C)s2)c(C(=O)O)c1-c1cc(F)cc(F)c1] | 1-(4-(3,4-dichlorophenyl)-5-(isopropylthio)thiazol-2-yl)-4-(3,5-difluorophenyl)-3-methyl-1H-pyrazole-5-carboxylic acid | B | $^1$H NMR (500 MHz, DMSO) δ 8.21 (d, J = 2.0 Hz, 1H), 8.02 (dd, J = 8.5, 2.1 Hz, 1H), 7.75 (d, J = 8.5 Hz, 1H), 7.33-7.20 (m, J = 19.2, 8.0 Hz, 3H), 3.42-3.29 (m, 1H), 2.32 (s, 3H), 1.24 (d, J = 6.7 Hz, 6H); MS (m/z): 541.9 [M + 1]$^+$ |

| Ex. | Structure | Name | EC$_{50}$ | Characterization |
|---|---|---|---|---|
| 25 | 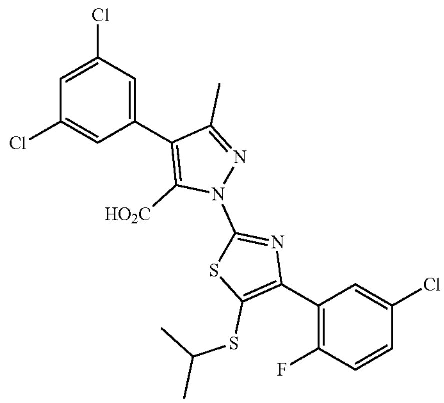 [SMILES: Cc1nn(-c2nc(-c3cc(Cl)ccc3F)c(SC(C)C)s2)c(C(=O)O)c1-c1cc(Cl)cc(Cl)c1] | 1-(4-(5-chloro-2-fluorophenyl)-5-(isopropylthio)thiazol-2-yl)-4-(3,5-dichlorophenyl)-3-methyl-1H-pyrazole-5-carboxylic acid | B | $^1$H NMR (500 MHz, DMSO) δ 7.66-7.49 (m, 5H), 7.42 (t, J = 9.1 Hz, 2H), 3.42-3.29 (m, 1H), 2.30 (s, 3H), 1.16 (d, J = 6.7 Hz, 6H); MS (m/z): 558.0 [M + 1]$^+$ |
| 26 | 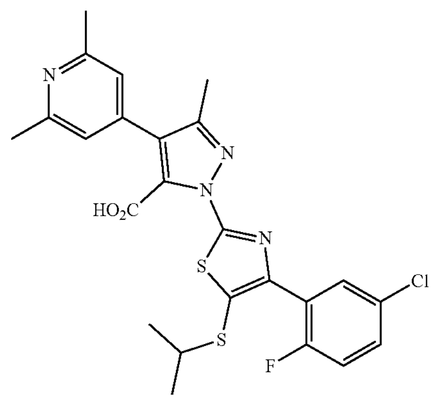 [SMILES: Cc1cc(-c2c(C)nn(-c3nc(-c4cc(Cl)ccc4F)c(SC(C)C)s3)c2C(=O)O)cc(C)n1] | 1-(4-(5-chloro-2-fluorophenyl)-5-(isopropylthio)thiazol-2-yl)-4-(2,6-dimethylpyridin-4-yl)-3-methyl-1H-pyrazole-5-carboxylic acid | C | $^1$H NMR (500 MHz, DMSO) δ 14.26 (s, 1H), 7.60 (ddd, J = 8.8, 4.3, 2.8 Hz, 1H), 7.54 (dd, J = 6.1, 2.7 Hz, 1H), 7.42 (t, J = 9.1 Hz, 1H), 7.13 (s, 2H), 3.28-3.19 (m, J = 13.3, 6.6 Hz, 2H), 2.45 (s, 6H), 2.32 (s, 3H), 1.16 (d, J = 6.7 Hz, 6H); MS (m/z): 517.1 [M + 1]$^+$ |
| 27 | 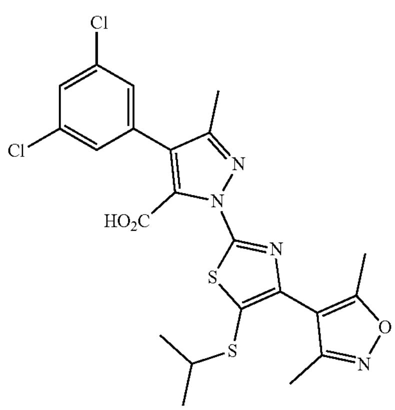 [SMILES: Cc1noc(C)c1-c1nc(-n2nc(C)c(-c3cc(Cl)cc(Cl)c3)c2C(=O)O)sc1SC(C)C] | 4-(3,5-dichlorophenyl)-1-(4-(3,5-dimethylisoxazol-4-yl)-5-(isopropylthio)thiazol-2-yl)-3-methyl-1H-pyrazole-5-carboxylic acid | J | $^1$H NMR (500 MHz, DMSO) δ 14.33 (s, 1H), 7.64 (s, 1H), 7.53 (s, 2H), 3.27-3.16 (m, J = 13.1, 6.4 Hz, 1H), 2.38 (s, 3H), 2.31 (s, 3H), 2.19 (s, 3H), 1.14 (d, J = 6.7 Hz, 6H); MS (m/z): 524.9 [M + 1]$^+$. |
| 28 | 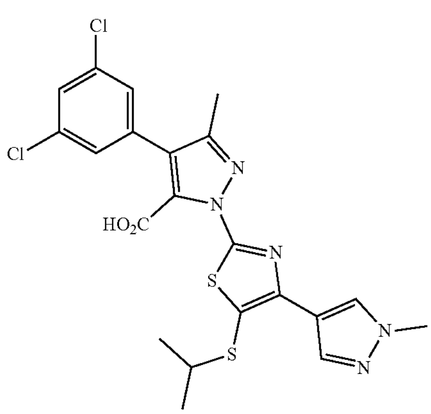 [SMILES: Cc1nn(-c2nc(-c3cnn(C)c3)c(SC(C)C)s2)c(C(=O)O)c1-c1cc(Cl)cc(Cl)c1] | 4-(3,5-dichlorophenyl)-1-(5-(isopropylthio)-4-(1-methyl-1H-pyrazol-4-yl)thiazol-2-yl)-3-methyl-1H-pyrazole-5-carboxylic acid | J | $^1$H NMR (500 MHz, DMSO) δ 14.36 (s, 1H), 8.28 (s, 1H), 7.98 (s, 1H), 7.65 (s, 1H), 7.54 (d, J = 1.4 Hz, 2H), 3.90 (s, 3H), 3.42-3.29 (m, 1H), 2.30 (s, 3H), 1.28 (d, J = 6.7 Hz, 6H); MS (m/z): 508.4 [M + 1]$^+$ |

-continued

| Ex. | Structure | Name | EC$_{50}$ | Characterization |
|---|---|---|---|---|
| 29 | 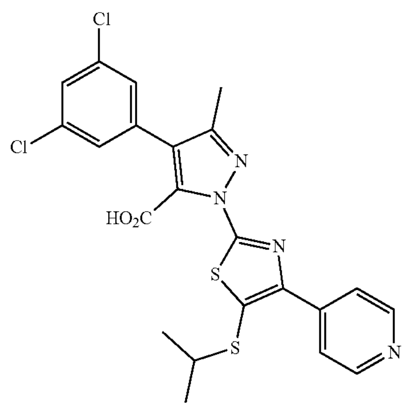 [SMILES: Cc1nn(-c2nc(-c3ccncc3)c(SC(C)C)s2)c(C(=O)O)c1-c1cc(Cl)cc(Cl)c1] | 4-(3,5-dichlorophenyl)-1-(5-(isopropylthio)-4-(pyridin-4-yl)thiazol-2-yl)-3-methyl-1H-pyrazole-5-carboxylic acid | J | $^1$H NMR (500 MHz, DMSO) δ 8.68 (d, J = 6.1 Hz, 2H), 8.03 (d, J = 6.1 Hz, 2H), 7.63 (d, J = 1.6 Hz, 2H), 7.52 (s, 1H), 3.42-3.29 (m, 1H), 2.30 (s, 3H), 1.25 (d, J = 6.7 Hz, 6H); MS (m/z): 505.0 [M + 1]$^+$ |
| 30 | 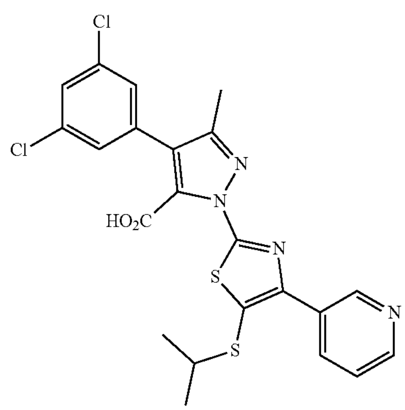 [SMILES: Cc1nn(-c2nc(-c3cccnc3)c(SC(C)C)s2)c(C(=O)O)c1-c1cc(Cl)cc(Cl)c1] | 4-(3,5-dichlorophenyl)-1-(5-(isopropylthio)-4-(pyridin-3-yl)thiazol-2-yl)-3-methyl-1H-pyrazole-5-carboxylic acid | J | $^1$H NMR (500 MHz, DMSO) δ 9.14 (d, J = 1.7 Hz, 1H), 8.61 (dd, J = 4.8, 1.6 Hz, 1H), 8.43-8.32 (m, 1H), 7.65 (s, 1H), 7.59-7.47 (m, 3H), 3.42-3.29 (m, 1H), 2.31 (s, 3H), 1.23 (d, J = 6.7 Hz, 6H); MS (m/z): 505.0 [M + 1]$^+$ |
| 31 | 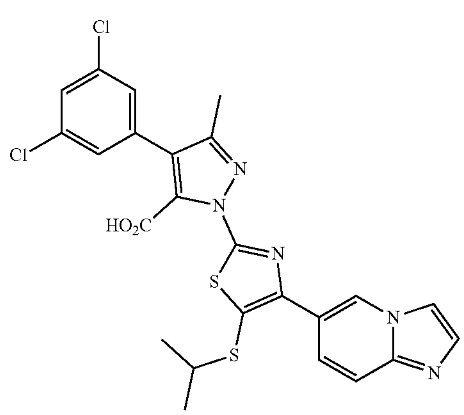 | 4-(3,5-dichlorophenyl)-1-(4-(imidazo[1,2-a]pyridin-6-yl)-5-(isopropylthio)thiazol-2-yl)-3-methyl-1H-pyrazole-5-carboxylic acid | J | $^1$H NMR (500 MHz, DMSO) δ 9.11 (s, 1H), 8.07 (s, 1H), 7.90 (d, J = 9.4 Hz, 1H), 7.68-7.52 (m, 5H), 3.42-3.29 (m, 1H), 2.31 (s, 3H), 1.23 (d, J = 6.7 Hz, 6H); MS (m/z): 505.0 [M + 1]$^+$ |

-continued

| Ex. | Structure | Name | EC$_{50}$ | Characterization |
|---|---|---|---|---|
| 32a | 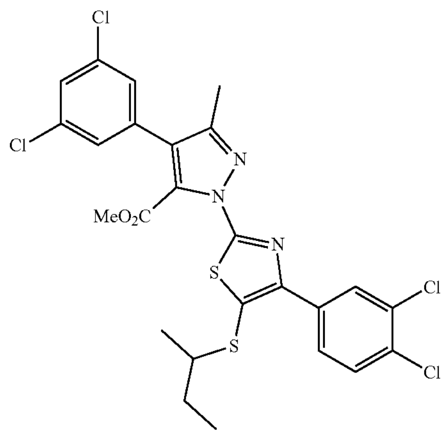 [SMILES: CCC(C)Sc1sc(-n2nc(C)c(-c3cc(Cl)cc(Cl)c3)c2C(=O)OC)nc1-c1ccc(Cl)c(Cl)c1] | methyl 1-(5-(sec-butylthio)-4-(3,4-dichlorophenyl)thiazol-2-yl)-4-(3,5-dichlorophenyl)-3-methyl-1H-pyrazole-5-carboxylate | J | $^1$H NMR (500 MHz, DMSO) δ 8.16 (d, J = 2.1 Hz, 1H), 7.98 (dd, J = 8.5, 2.1 Hz, 1H), 7.82 (d, J = 8.5 Hz, 1H), 7.72 (t, J = 1.9 Hz, 1H), 7.51 (d, J = 1.9 Hz, 1H), 3.82 (s, 3H), 3.22-3.14 (m, 1H), 2.34 (s, 3H), 1.63-1.45 (m, 2H), 1.22 (d, J = 6.8 Hz, 3H), 0.91 (t, J = 7.3 Hz, 3H); MS (m/z): 602.0 [M + 1]$^+$ |
| 32b | 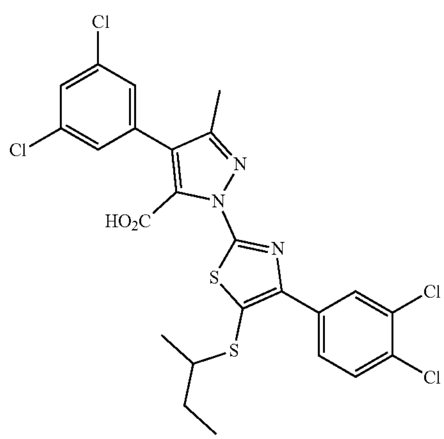 [SMILES: CCC(C)Sc1sc(-n2nc(C)c(-c3cc(Cl)cc(Cl)c3)c2C(=O)O)nc1-c1ccc(Cl)c(Cl)c1] | 1-(5-(sec-butylthio)-4-(3,4-dichlorophenyl)thiazol-2-yl)-4-(3,5-dichlorophenyl)-3-methyl-1H-pyrazole-5-carboxylic acid | B | $^1$H NMR (500 MHz, DMSO) δ 8.23 (d, J = 1.9 Hz, 1H), 8.01 (dd, J = 8.5, 1.8 Hz, 1H), 7.77 (d, J = 8.5 Hz, 1H), 7.65 (s, 1H), 7.59-7.52 (m, J = 7.3 Hz, 2H), 3.21-3.09 (m, 1H), 2.31 (s, 3H), 1.64-1.44 (m, 2H), 1.21 (d, J = 6.7 Hz, 3H), 0.90 (t, J = 7.4 Hz, 3H); MS (m/z): 588.0 [M + 1]$^+$ |
| 33a | 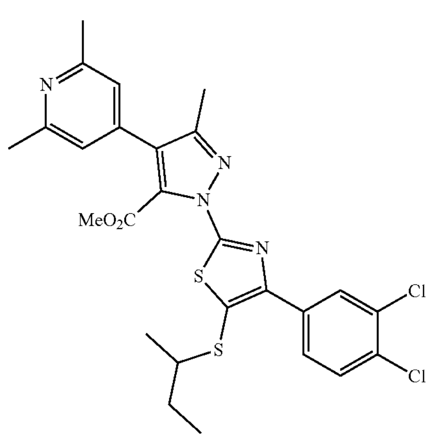 [SMILES: CCC(C)Sc1sc(-n2nc(C)c(-c3cc(C)nc(C)c3)c2C(=O)OC)nc1-c1ccc(Cl)c(Cl)c1] | methyl 1-(5-(sec-butylthio)-4-(3,4-dichlorophenyl)thiazol-2-yl)-4-(2,6-dimethylpyridin-4-yl)-3-methyl-1H-pyrazole-5-carboxylate | J | |

-continued

| Ex. | Structure | Name | EC$_{50}$ | Characterization |
|---|---|---|---|---|
| 33b | 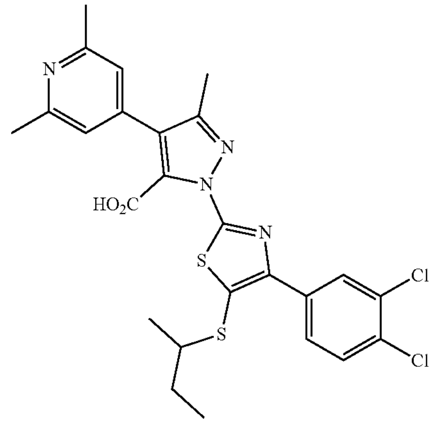 [SMILES: CCC(C)Sc1sc(-n2nc(C)c(-c3cc(C)nc(C)c3)c2C(=O)O)nc1-c1ccc(Cl)c(Cl)c1] | 1-(5-(sec-butylthio)-4-(3,4-dichlorophenyl)thiazol-2-yl)-4-(2,6-dimethylpyridin-4-yl)-3-methyl-1H-pyrazole-5-carboxylic acid | A | $^1$H NMR (500 MHz, DMSO) δ 8.22 (d, J = 2.1 Hz, 1H), 8.01 (dd, J = 8.5, 2.1 Hz, 1H), 7.76 (d, J = 8.5 Hz, 1H), 7.15 (s, 2H), 3.21-3.12 (m, J = 13.2, 6.6 Hz, 1H), 2.47 (s, 6H), 2.33 (s, 3H), 1.63-1.43 (m, 2H), 1.21 (d, J = 6.8 Hz, 3H), 0.90 (t, J = 7.4 Hz, 3H); MS (m/z): 547.1 [M + 1]$^+$ |
| 34 | 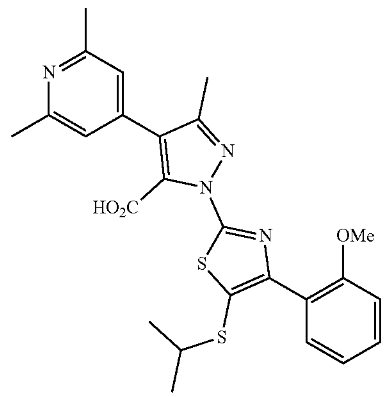 [SMILES: COc1ccccc1-c1nc(-n2nc(C)c(-c3cc(C)nc(C)c3)c2C(=O)O)sc1SC(C)C] | 4-(2,6-dimethylpyridin-4-yl)-1-(5-(isopropylthio)-4-(2-methoxyphenyl)thiazol-2-yl)-3-methyl-1H-pyrazole-5-carboxylic acid | C | $^1$H NMR (500 MHz, DMSO) δ 7.45-7.39 (m, 1H), 7.26 (dd, J = 7.5, 1.7 Hz, 1H), 7.13-7.08 (m, 2H), 7.05-6.98 (m, 1H), 3.75 (s, 3H), 3.24-3.10 (m, 1H), 2.45 (s, 6H), 2.31 (s, 3H), 1.14 (d, J = 6.7 Hz, 6H); MS (m/z): 495.1 [M + 1]$^+$ |
| 35 | 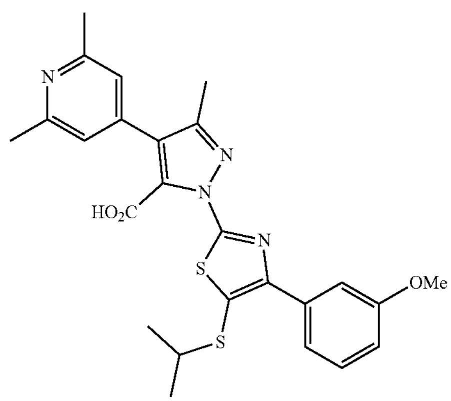 [SMILES: COc1cccc(-c2nc(-n3nc(C)c(-c4cc(C)nc(C)c4)c3C(=O)O)sc2SC(C)C)c1] | 4-(2,6-dimethylpyridin-4-yl)-1-(5-(isopropylthio)-4-(3-methoxyphenyl)thiazol-2-yl)-3-methyl-1H-pyrazole-5-carboxylic acid | B | $^1$H NMR (500 MHz, DMSO) δ 8.04-7.92 (m, 1H), 7.14 (s, 1H), 7.05-6.97 (m, 1H), 3.82 (s, 1H), 3.32-3.19 (m, 7H), 2.46 (s, 2H), 2.32 (s, 1H), 1.23 (d, J = 6.7 Hz, 2H); MS (m/z): 495.2 [M + 1]$^+$ |
| 36 | 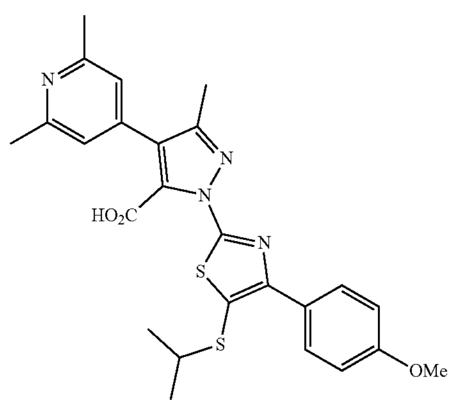 [SMILES: COc1ccc(-c2nc(-n3nc(C)c(-c4cc(C)nc(C)c4)c3C(=O)O)sc2SC(C)C)cc1] | 4-(2,6-dimethylpyridin-4-yl)-1-(5-(isopropylthio)-4-(4-methoxyphenyl)thiazol-2-yl)-3-methyl-1H-pyrazole-5-carboxylic acid | D | $^1$H NMR (500 MHz, DMSO) δ 7.66-7.58 (m, 1H), 7.39 (t, J = 8.0 Hz, 1H), 7.15 (s, 2H), 6.99 (dd, J = 7.4, 2.6 Hz, 1H), 3.81 (s, 3H), 3.38-3.31 (m, 1H), 2.46 (s, 6H), 2.33 (s, 3H), 1.24 (d, J = 6.7 Hz, 6H); MS (m/z): 495.2 [M + 1]$^+$ |

-continued

| Ex. | Structure | Name | EC$_{50}$ | Characterization |
|---|---|---|---|---|
| 37 | 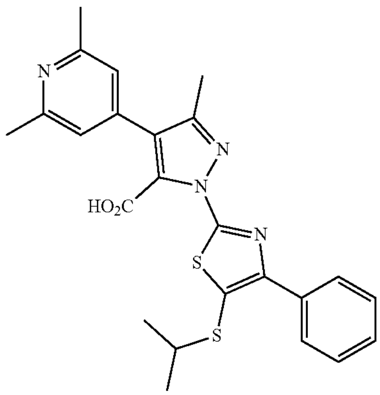 [SMILES: Cc1cc(-c2c(C)nn(-c3nc(-c4ccccc4)c(SC(C)C)s3)c2C(=O)O)cc(C)n1] | 4-(2,6-dimethylpyridin-4-yl)-1-(5-(isopropylthio)-4-phenylthiazol-2-yl)-3-methyl-1H-pyrazole-5-carboxylic acid | C | $^1$H NMR (500 MHz, DMSO) δ 8.03-7.94 (m, 2H), 7.52-7.45 (m, 2H), 7.45-7.39 (m, J = 9.5, 4.3 Hz, 1H), 7.14 (s, 2H), 3.40-3.30 (m, 1H), 2.47 (s, 6H), 2.33 (s, 3H), 1.23 (d, J = 6.7 Hz, 6H); MS (m/z): 465.2 [M + 1]$^+$ |
| 38 | 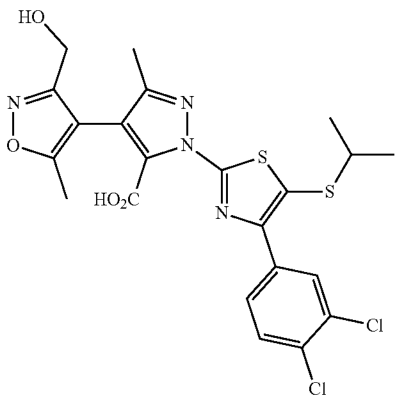 [SMILES: Cc1nn(-c2nc(-c3ccc(Cl)c(Cl)c3)c(SC(C)C)s2)c(C(=O)O)c1-c1c(CO)noc1C] | 1-(4-(3,4-dichlorophenyl)-5-(isopropylthio)thiazol-2-yl)-4-(3-(hydroxymethyl)-5-methylisoxazol-4-yl)-3-methyl-1H-pyrazole-5-carboxylic acid | H | $^1$H NMR (500 MHz, DMSO) δ 8.18 (d, J = 2.1 Hz, 1H), 8.00 (dd, J = 8.5, 2.1 Hz, 1H), 7.76 (d, J = 8.5 Hz, 1H), 4.36 (s, 2H), 3.42-3.29 (m, 1H), 2.28 (s, 3H), 2.10 (s, 3H), 1.24 (d, J = 6.7 Hz, 6H); MS (m/z): 539.3 [M + 1]$^+$ |
| 39 | 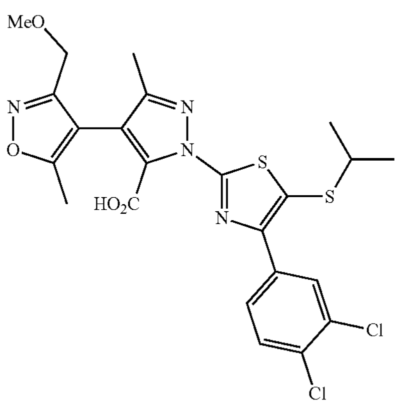 [SMILES: COCc1noc(C)c1-c1c(C)nn(-c2nc(-c3ccc(Cl)c(Cl)c3)c(SC(C)C)s2)c1C(=O)O] | 1-(4-(3,4-dichlorophenyl)-5-(isopropylthio)thiazol-2-yl)-4-(3-(methoxymethyl)-5-methylisoxazol-4-yl)-3-methyl-1H-pyrazole-5-carboxylic acid | D | $^1$H NMR (500 MHz, DMSO) δ 8.18 (d, J = 2.1 Hz, 1H), 7.99 (dd, J = 8.5, 2.1 Hz, 1H), 7.75 (d, J = 8.5 Hz, 1H), 4.42 (d, J = 12.6 Hz, 1H), 4.35 (d, J = 12.7 Hz, 1H), 3.42-3.29 (m, 1H), 3.15 (s, 3H), 2.30 (s, 3H), 2.11 (s, 3H), 1.23 (d, J = 6.7 Hz, 6H); MS (m/z): 553.3 [M + 1]$^+$ |
| 40 | 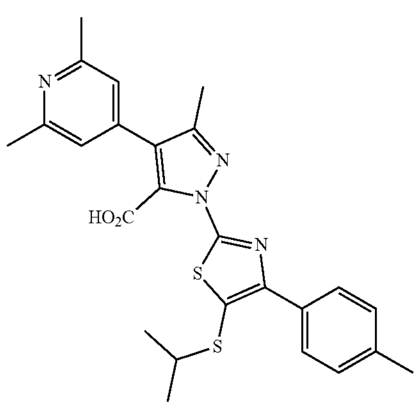 | 4-(2,6-dimethylpyridin-4-yl)-1-(5-(isopropylthio)-4-p-tolylthiazol-2-yl)-3-methyl-1H-pyrazole-5-carboxylic acid | B | $^1$H NMR (500 MHz, DMSO) δ 7.91 (d, J = 8.2 Hz, 2H), 7.28 (d, J = 8.0 Hz, 2H), 7.14 (s, 1H), 3.36-3.26 (m, 1H), 2.46 (s, 6H), 2.36 (s, 3H), 2.33 (s, 3H), 1.22 (d, J = 6.7 Hz, 6H); MS (m/z): 479.1 [M + 1]$^+$. |

-continued

| Ex. | Structure | Name | EC$_{50}$ | Characterization |
|---|---|---|---|---|
| 41 | 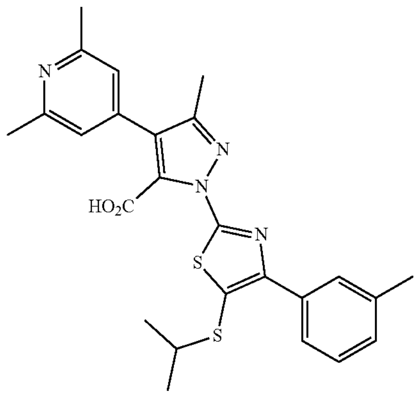 | 4-(2,6-dimethylpyridin-4-yl)-1-(5-(isopropylthio)-4-m-tolylthiazol-2-yl)-3-methyl-1H-pyrazole-5-carboxylic acid | C | $^1$H NMR (500 MHz, DMSO) δ 7.80 (d, J = 6.3 Hz, 2H), 7.40-7.32 (m, 1H), 7.23 (d, J = 7.6 Hz, 1H), 7.16 (s, 2H), 3.38-3.25 (m, 1H), 2.45 (s, 6H), 2.37 (s, 3H), 2.32 (s, 3H), 1.23 (d, J = 6.7 Hz, 6H); MS (m/z): 479.2 [M + 1]$^+$ |
| 42 | 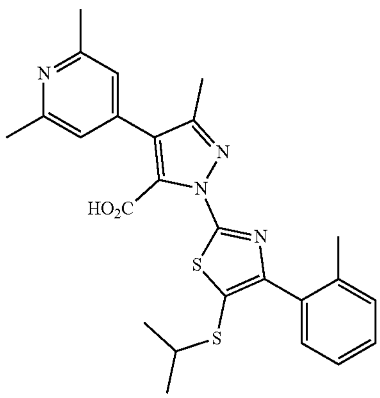 [SMILES: Cc1cc(-c2c(C)nn(-c3nc(-c4ccccc4C)c(SC(C)C)s3)c2C(=O)O)cc(C)n1] | 4-(2,6-dimethylpyridin-4-yl)-1-(5-(isopropylthio)-4-o-tolylthiazol-2-yl)-3-methyl-1H-pyrazole-5-carboxylic acid | B | $^1$H NMR (500 MHz, Acetone) δ 7.40-7.22 (m, 5H), 7.14 (s, 2H), 2.47 (s, 6H), 2.34 (s, 3H), 2.27 (s, 3H), 2.08-2.06 (m, 1H), 1.19 (d, J = 6.7 Hz, 6H); MS (m/z): 479.2 [M + 1]$^+$. |
| 43 | 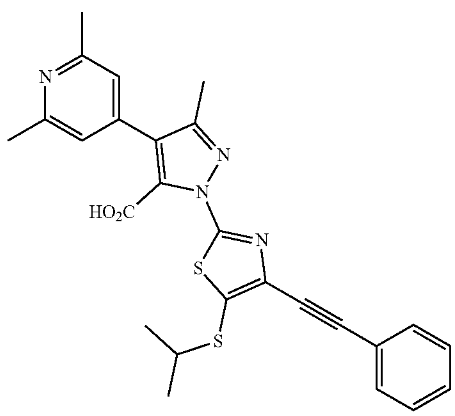 [SMILES: Cc1cc(-c2c(C)nn(-c3nc(C#Cc4ccccc4)c(SC(C)C)s3)c2C(=O)O)cc(C)n1] | 4-(2,6-dimethylpyridin-4-yl)-1-(5-(isopropylthio)-4-(phenylethynyl)thiazol-2-yl)-3-methyl-1H-pyrazole-5-carboxylic acid | C | $^1$H NMR (500 MHz, MeOD) δ 7.57-7.49 (m, 2H), 7.42-7.38 (m, 3H), 7.36 (s, 2H), 3.49-3.39 (m, 1H), 2.55 (s, 6H), 2.38 (s, 3H), 1.38 (d, J = 6.7 Hz, 6H); MS (m/z): 489.3 [M + 1]$^+$ |
| 44 | 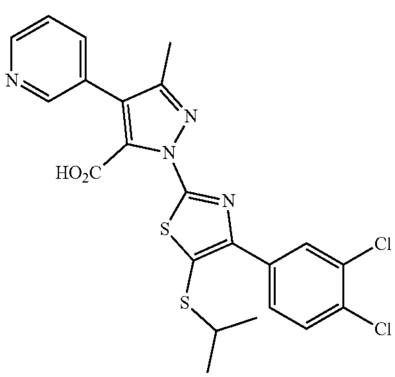 [SMILES: Cc1nn(-c2nc(-c3ccc(Cl)c(Cl)c3)c(SC(C)C)s2)c(C(=O)O)c1-c1cccnc1] | 1-(4-(3,4-dichlorophenyl)-5-(isopropylthio)thiazol-2-yl)-3-methyl-4-(pyridin-3-yl)-1H-pyrazole-5-carboxylic acid | D | $^1$H NMR (500 MHz, DMSO) δ 8.71-8.68 (m, 1H), 8.58-8.54 (m, 1H), 8.23-8.20 (m, 1H), 8.03 (d, J = 8.1 Hz, 1H), 7.92 (d, J = 7.8 Hz, 1H), 7.77 (d, J = 8.5 Hz, 1H), 7.50-7.46 (m, 1H), 2.51 (m, 1H), 2.30 (s, 3H), 1.24 (d, J = 6.7 Hz, 6H); MS (m/z): 505.0 [M + H]$^+$. |

| Ex. | Structure | Name | EC$_{50}$ | Characterization |
|---|---|---|---|---|
| 45 | 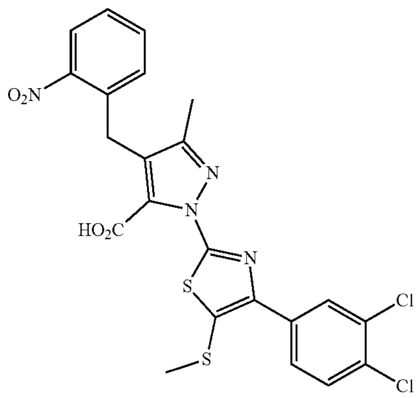 [SMILES: CSc1sc(-n2nc(C)c(Cc3ccccc3[N+](=O)[O-])c2C(=O)O)nc1-c1ccc(Cl)c(Cl)c1] | 1-(4-(3,4-dichlorophenyl)-5-(methylthio)thiazol-2-yl)-3-methyl-4-(2-nitrobenzyl)-1H-pyrazole-5-carboxylic acid | E | $^1$H NMR (500 MHz, DMSO) δ 8.06 (d, J = 2.1 Hz, 1H), 8.00 (dd, J = 8.1, 1.3 Hz, 1H), 7.88 (dd, J = 8.5, 2.1 Hz, 1H), 7.77 (d, J = 8.5 Hz, 1H), 7.65 (td, J = 7.6, 1.3 Hz, 1H), 7.54-7.49 (m, 1H), 7.22 (d, J = 6.8 Hz, 1H), 4.25 (s, 2H), 2.60 (s, 3H), 2.07 (s, 3H); MS (m/z): 533.0 [M + H]$^+$ |
| 46 | 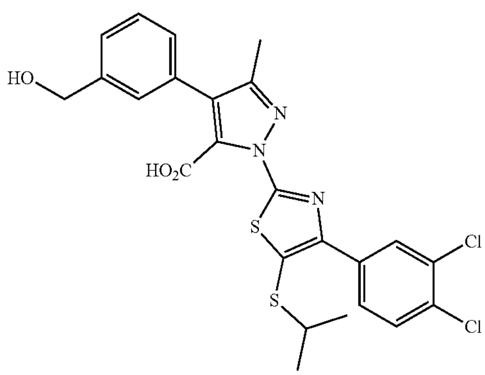 [SMILES: Cc1nn(-c2nc(-c3ccc(Cl)c(Cl)c3)c(SC(C)C)s2)c(C(=O)O)c1-c1cccc(CO)c1] | 1-(4-(3,4-dichlorophenyl)-5-(isopropylthio)thiazol-2-yl)-4-(3-(hydroxymethyl)phenyl)-3-methyl-1H-pyrazole-5-carboxylic acid | D | $^1$H NMR (500 MHz, DMSO) δ 8.21 (s, 1H), 8.03 (d, J = 9.8 Hz, 1H), 7.77 (d, J = 8.5 Hz, 1H), 7.44-7.39 (m, 2H), 7.36-7.31 (m, 2H), 5.25 (s (br), 1H), 4.54 (d, J = 5.3 Hz, 2H), 2.53-2.50 (m, 1H), 2.29 (s, 3H), 1.24 (d, J = 6.7 Hz, 6H); MS (m/z): 533.9 [M + H]$^+$ |
| 47 | 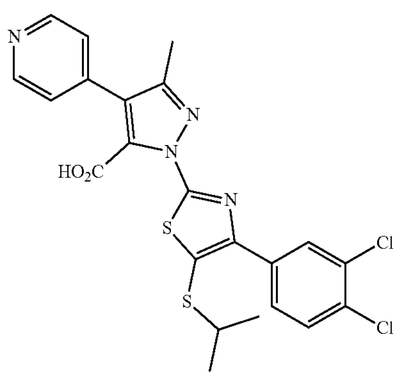 [SMILES: Cc1nn(-c2nc(-c3ccc(Cl)c(Cl)c3)c(SC(C)C)s2)c(C(=O)O)c1-c1ccncc1] | 1-(4-(3,4-dichlorophenyl)-5-(isopropylthio)thiazol-2-yl)-3-methyl-4-(pyridin-4-yl)-1H-pyrazole-5-carboxylic acid | C | $^1$H NMR (500 MHz, DMSO) δ 8.65-8.58 (m, 2H), 8.23 (s, 1H), 8.04 (d, J = 8.2 Hz, 1H), 7.77 (d, J = 8.5 Hz, 1H), 7.57-7.50 (m, 2H), 2.53-2.50 (m, 1H), 2.35 (s, 3H), 1.24 (d, J = 6.7 Hz, 6H); MS (m/z): 504.9 [M + H]$^+$ |
| 48 | 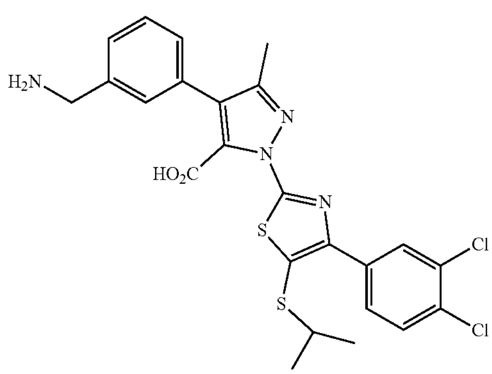 [SMILES: Cc1nn(-c2nc(-c3ccc(Cl)c(Cl)c3)c(SC(C)C)s2)c(C(=O)O)c1-c1cccc(CN)c1] | 4-(3-(aminomethyl)phenyl)-1-(4-(3,4-dichlorophenyl)-5-(isopropylthio)thiazol-2-yl)-3-methyl-1H-pyrazole-5-carboxylic acid | E | $^1$H NMR (500 MHz, DMSO) δ 8.30 (d, J = 2.1 Hz, 1H), 8.18 (s, 1H), 8.12 (dd, J = 8.5, 2.1 Hz, 1H), 7.75 (d, J = 8.5 Hz, 1H), 7.62-7.59 (m, 2H), 7.41 (t, J = 7.7, 1H), 7.34 (d, J = 7.7 Hz, 1H), 3.99 (s, 2H), 2.51 (hept, J = 6.7 Hz, 1H), 2.28 (s, 3H), 1.24 (d, J = 6.7 Hz, 6H); MS (m/z): 533.1 [M + H]$^+$ |

| Ex. | Structure | Name | EC$_{50}$ | Characterization |
|---|---|---|---|---|
| 49 | 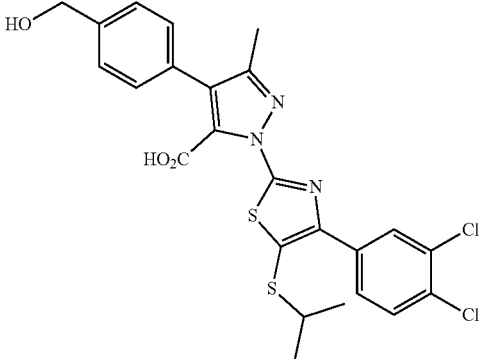 [SMILES: Cc1nn(-c2nc(-c3ccc(Cl)c(Cl)c3)c(SC(C)C)s2)c(C(=O)O)c1-c1ccc(CO)cc1] | 1-(4-(3,4-dichlorophenyl)-5-(isopropylthio)thiazol-2-yl)-4-(4-(hydroxymethyl)phenyl)-3-methyl-1H-pyrazole-5-carboxylic acid | H | $^1$H NMR (500 MHz, DMSO) δ 8.20 (d, J = 2.1 Hz, 1H), 8.01 (dd, J = 8.6, 2.1 Hz, 1H), 7.77 (d, J = 8.5 Hz, 1H), 7.42-7.40 (m, 4H), 5.23 (t, J = 5.7 Hz, 1H), 4.54 (d, J = 5.7 Hz, 2H), 2.51 (hept, J = 6.7 Hz, 1H) 2.30 (s, 3H), 1.24 (d, J = 6.7 Hz, 6H); MS (m/z): 534.2 [M + H]$^+$ |
| 50 | 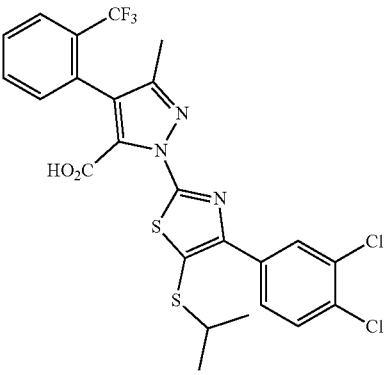 [SMILES: Cc1nn(-c2nc(-c3ccc(Cl)c(Cl)c3)c(SC(C)C)s2)c(C(=O)O)c1-c1ccccc1C(F)(F)F] | 1-(4-(3,4-dichlorophenyl)-5-(isopropylthio)thiazol-2-yl)-3-methyl-4-(2-(trifluoromethyl)phenyl)-1H-pyrazole-5-carboxylic acid | C | $^1$H NMR (500 MHz, DMSO) δ 8.16 (d, J = 2.1 Hz, 1H), 7.98 (dd, J = 8.5, 2.1 Hz, 1H), 7.86 (d, J = 7.8 Hz, 1H), 7.76 (d, J = 8.5 Hz, 1H), 7.76 (t, J = 7.7 Hz, 1H), 7.66 (t, J = 7.7 Hz, 1H), 7.45 (d, J = 7.6 Hz, 1H), 3.35 (hept, J = 6.7 Hz, 1H), 2.01 (s, 3H), 1.24 (d, J = 6.7 Hz, 3H), 1.24 (d, J = 6.7 Hz, 3H); MS (m/z): 571.9 [M + H]$^+$ |
| 51 | 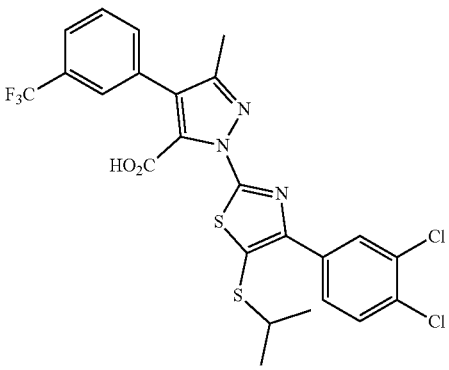 [SMILES: Cc1nn(-c2nc(-c3ccc(Cl)c(Cl)c3)c(SC(C)C)s2)c(C(=O)O)c1-c1cccc(C(F)(F)F)c1] | 1-(4-(3,4-dichlorophenyl)-5-(isopropylthio)thiazol-2-yl)-3-methyl-4-(3-(trifluoromethyl)phenyl)-1H-pyrazole-5-carboxylic acid | B | $^1$H NMR (500 MHz, DMSO) δ 8.21 (d, J = 2.0 Hz, 1H), 8.03 (dd, J = 8.4, 2.0 Hz, 1H), 7.84 (s, 1H), 7.80 (d, J = 7.5 Hz, 1H), 7.78-7.74 (m, 1H), 7.76 (d, J = 8.5 Hz, 1H), 7.71 (t, J = 7.5 Hz, 1H), 3.35 (hept, J = 6.7 Hz, 1H), 2.32 (s, 3H), 1.24 (d, J = 6.7 Hz, 6H); MS (m/z): 571.8 [M + H]$^+$ |
| 52 | 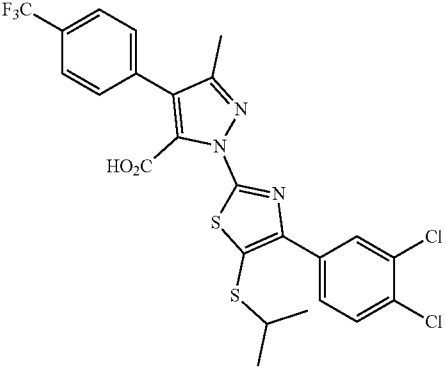 [SMILES: Cc1nn(-c2nc(-c3ccc(Cl)c(Cl)c3)c(SC(C)C)s2)c(C(=O)O)c1-c1ccc(C(F)(F)F)cc1] | 1-(4-(3,4-dichlorophenyl)-5-(isopropylthio)thiazol-2-yl)-3-methyl-4-(4-(trifluoromethyl)phenyl)-1H-pyrazole-5-carboxylic acid | D | $^1$H NMR (500 MHz, DMSO) δ 8.20 (d, J = 2.0 Hz, 1H), 8.01 (dd, J = 8.5, 2.0 Hz, 1H), 7.83 (d, J = 8.0 Hz, 2H), 7.77 (d, J = 8.5 Hz, 1H), 7.71 (d, J = 8.0 Hz, 2H), 3.35 (hept, J = 6.7 Hz, 1H), 2.32 (s, 3H), 1.24 (d, J = 6.7 Hz, 6H); MS (m/z): 571.8 [M + H]$^+$ |

| Ex. | Structure | Name | EC$_{50}$ | Characterization |
|---|---|---|---|---|
| 53 | 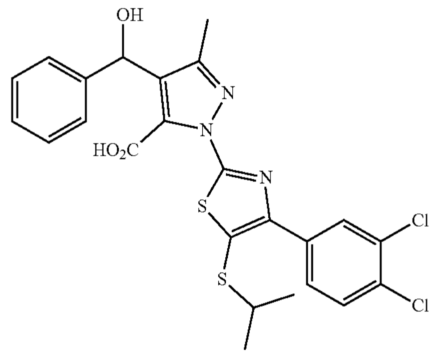 [SMILES: Cc1nn(-c2nc(-c3ccc(Cl)c(Cl)c3)c(SC(C)C)s2)c(C(=O)O)c1C(O)c1ccccc1] | 1-(4-(3,4-dichlorophenyl)-5-(isopropylthio)thiazol-2-yl)-4-(hydroxy(phenyl)methyl)-3-methyl-1H-pyrazole-5-carboxylic acid | H | $^1$H NMR (500 MHz, DMSO) δ 8.18 (d, J = 2.1 Hz, 1H), 8.01 (dd, J = 8.5, 2.1 Hz, 1H), 7.75 (d, J = 8.5 Hz, 1H), 7.41 (d, J = 7.1 Hz, 2H), 7.28 (t, J = 7.7 Hz, 2H), 7.18 (d, J = 7.5 Hz, 1H), 5.67-5.63 (m, 1H), 2.51 (hept, 1H, J = 7.1 Hz), 2.11 (s, 3H), 1.22 (d, J = 7.1 Hz, 6H); MS (m/z): 533.8 [M + H]$^+$ |
| 54 | 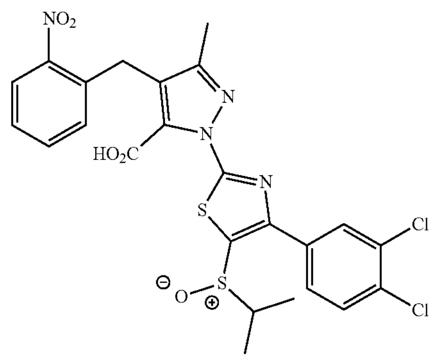 [SMILES: Cc1nn(-c2nc(-c3ccc(Cl)c(Cl)c3)c([S+]([O-])C(C)C)s2)c(C(=O)O)c1Cc1ccccc1[N+](=O)[O-]] | 1-(4-(3,4-dichlorophenyl)-5-(isopropylsulfinyl)thiazol-2-yl)-3-methyl-4-(2-nitrobenzyl)-1H-pyrazole-5-carboxylic acid | E | $^1$H NMR (500 MHz, DMSO) δ 7.98 (d, J = 8.0 Hz, 1H), 7.92 (d, J = 1.7 Hz, 1H), 7.80 (d, J = 8.4 Hz, 1H), 7.70 (dd, J = 6.7, 1.7 Hz, 1H), 7.63 (t, J = 7.1 Hz, 1H), 7.49 (t, J = 7.9 Hz, 1H), 7.26 (d, J = 8.0 Hz, 1H), 4.21 (s, 2H), 3.29 (hept, J = 6.7 Hz, 1H), 2.04 (s, 3H), 1.25 (d, J = 6.7 Hz, 3H), 1.17 (d, J = 6.7 Hz, 3H); MS (m/z): 579.0 [M + H]$^+$ |
| 55 | 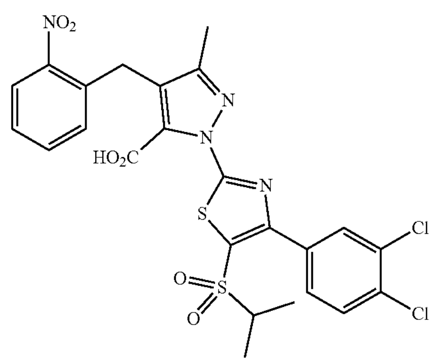 [SMILES: Cc1nn(-c2nc(-c3ccc(Cl)c(Cl)c3)c(S(=O)(=O)C(C)C)s2)c(C(=O)O)c1Cc1ccccc1[N+](=O)[O-]] | 1-(4-(3,4-dichlorophenyl)-5-(isopropylsulfonyl)thiazol-2-yl)-3-methyl-4-(2-nitrobenzyl)-1H-pyrazole-5-carboxylic acid | D | $^1$H NMR (500 MHz, DMSO) δ 8.02 (t, J = 1.2 Hz, 1H), 7.99 (d, J = 8.2 Hz, 1H), 7.79 (d, J = 1.1 Hz, 2H), 7.63 (t, J = 7.0 Hz, 1H), 7.49 (t, J = 7.5 Hz, 1H), 7.24 (d, J = 6.9 Hz, 1H), 4.21 (s, 2H), 3.38 (hept, J = 6.8 Hz, 1H), 2.05 (s, 3H), 1.17 (d, J = 6.8 Hz, 6H); MS (m/z): 595.0 [M + H]$^+$ |
| 56 | 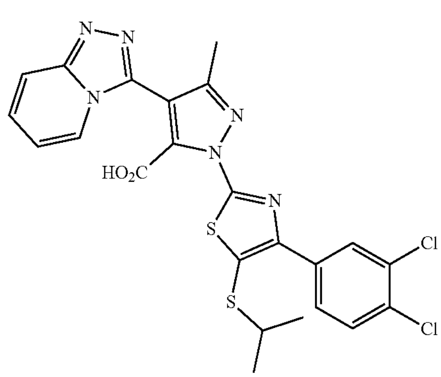 [SMILES: Cc1nn(-c2nc(-c3ccc(Cl)c(Cl)c3)c(SC(C)C)s2)c(C(=O)O)c1-c1nnc2ccccn12] | 4-([1,2,4]triazolo[4,3-a]pyridin-3-yl)-1-(4-(3,4-dichlorophenyl)-5-(isopropylthio)thiazol-2-yl)-3-methyl-1H-pyrazole-5-carboxylic acid | H | $^1$H NMR (500 MHz, DMSO) δ 8.34 (d, J = 7.0 Hz, 1H), 8.19 (d, J = 2.1 Hz, 1H), 8.02 (dd, J = 8.5, 2.1 Hz, 1H), 7.86 (d, J = 9.3 Hz, 1H), 7.78 (d, J = 8.5 Hz, 1H), 7.45 (dd, J = 9.3, 6.9 Hz, 1H), 7.01 (t, J = 6.9 Hz, 1H), 3.39 (hept, J = 6.7 Hz, 1H), 2.25 (s, 2H), 1.26 (d, J = 6.7 Hz, 6H); MS (m/z): 545.0 [M + H]$^+$ |

-continued

| Ex. | Structure | Name | EC₅₀ | Characterization |
|---|---|---|---|---|
| 57 | 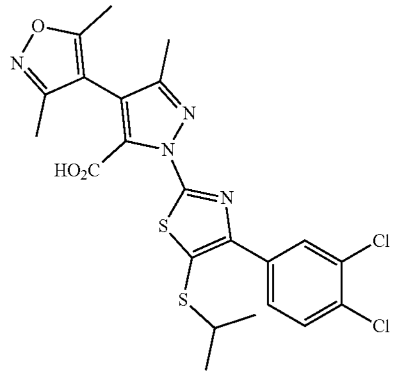 [SMILES: Cc1noc(C)c1-c1c(C)nn(-c2nc(-c3ccc(Cl)c(Cl)c3)c(SC(C)C)s2)c1C(=O)O] | 1-(4-(3,4-dichlorophenyl)-5-(isopropylthio)thiazol-2-yl)-4-(3,5-dimethylisoxazol-4-yl)-3-methyl-1H-pyrazole-5-carboxylic acid | D | $^1$H NMR (500 MHz, DMSO) δ 8.18 (d, J = 2.0 Hz, 1H), 8.00 (dd, J = 8.5, 2.0 Hz, 1H), 7.76 (d, J = 8.5 Hz, 1H), 2.51 (hept, J = 6.7 Hz, 1H), 2.28 (s, 3H), 2.12 (s, 3H), 2.09 (s, 3H), 1.23 (d, J = 6.7 Hz, 6H); MS (m/z): 523.0 [M + H]⁺ |
| 58 | 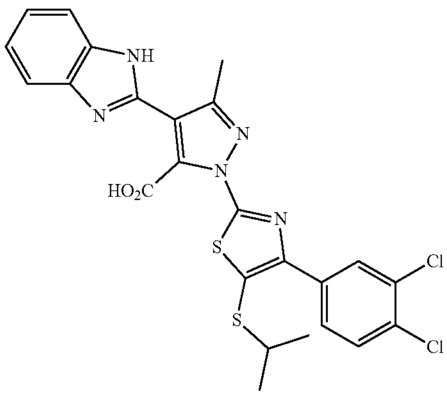 [SMILES: Cc1nn(-c2nc(-c3ccc(Cl)c(Cl)c3)c(SC(C)C)s2)c(C(=O)O)c1-c1nc2ccccc2[nH]1] | 4-(1H-benzo[d]imidazol-2-yl)-1-(4-(3,4-dichlorophenyl)-5-(isopropylthio)thiazol-2-yl)-3-methyl-1H-pyrazole-5-carboxylic acid | E | $^1$H NMR (500 MHz, DMSO) δ 8.19 (d, J = 2.1 Hz, 1H), 8.01 (dd, J = 8.5, 2.1 Hz, 1H), 7.79 (d, J = 8.5 Hz, 1H), 7.68-7.64 (m, 2H), 7.28-7.24 (m, 2H), 3.42-3.29 (m, 1H), 2.60 (s, 3H), 1.25 (d, J = 6.7 Hz, 6H).; MS (m/z): 544.1 [M + H]⁺ |
| 59 | 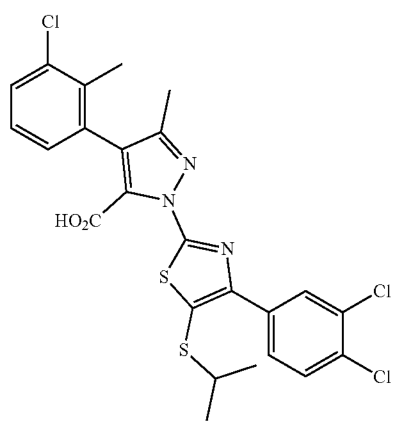 [SMILES: Cc1nn(-c2nc(-c3ccc(Cl)c(Cl)c3)c(SC(C)C)s2)c(C(=O)O)c1-c1cccc(Cl)c1C] | 4-(3-chloro-2-methylphenyl)-1-(4-(3,4-dichlorophenyl)-5-(isopropylthio)thiazol-2-yl)-3-methyl-1H-pyrazole-5-carboxylic acid | C | $^1$H NMR (500 MHz, DMSO) δ 8.18 (d, J = 1.9 Hz, 1H), 7.99 (dd, J = 8.4, 2.0 Hz, 1H), 7.76 (d, J = 8.5 Hz, 1H), 7.49 (d, J = 8.2 Hz, 1H), 7.28 (t, J = 7.8 Hz, 1H), 7.18 (d, J = 6.7 Hz, 1H), 3.42-3.29 (m, 1H), 2.17 (s, 3H), 2.06 (s, 3H), 1.24 (d, J = 6.7 Hz, 6H).; MS (m/z): 551.9 [M + H]⁺ |
| 60 | 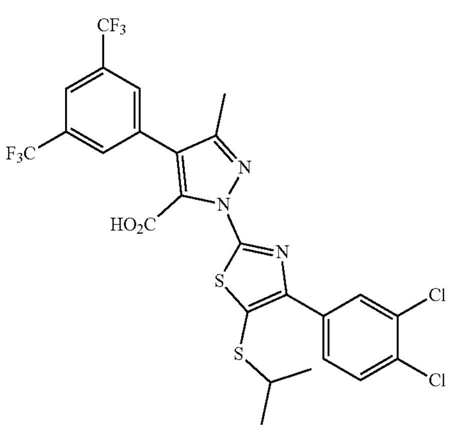 [SMILES: Cc1nn(-c2nc(-c3ccc(Cl)c(Cl)c3)c(SC(C)C)s2)c(C(=O)O)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.19-8.16 (m, 4H), 8.02 (dd, J = 8.5, 2.1 Hz, 1H), 7.77 (d, J = 8.5 Hz, 1H), 3.42-3.29 (m, 1H), 2.33 (s, 3H), 1.24 (d, J = 6.7 Hz, 6H); MS (m/z): 639.9 [M + H]⁺ |

| Ex. | Structure | Name | EC$_{50}$ | Characterization |
|---|---|---|---|---|
| 61 | 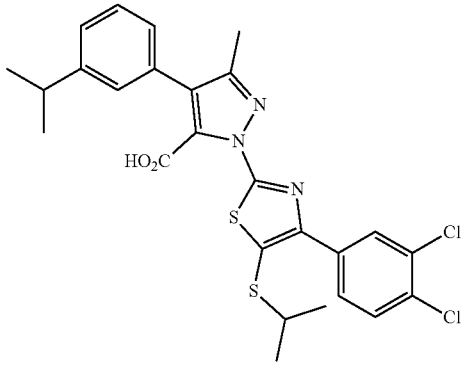 [SMILES: Cc1nn(-c2nc(-c3ccc(Cl)c(Cl)c3)c(SC(C)C)s2)c(C(=O)O)c1-c1cccc(C(C)C)c1] | 1-(4-(3,4-dichlorophenyl)-5-(isopropylthio)thiazol-2-yl)-4-(3-isopropylphenyl)-3-methyl-1H-pyrazole-5-carboxylic acid | B | $^1$H NMR (500 MHz, DMSO) δ 8.22 (d, J = 1.9 Hz, 1H), 8.03 (dd, J = 8.5, 2.0 Hz, 1H), 7.75 (d, J = 8.5 Hz, 1H), 7.39-7.34 (m, 2H), 7.30-7.24 (m, 2H), 3.42-3.29 (m, 1H), 2.92 (hept, J = 6.8 Hz, 1H), 2.31 (s, 3H), 1.24 (d, J = 6.8 Hz, 6H), 1.23 (d, J = 6.8 Hz, 3H); MS (m/z): 546.0 [M + H]$^+$ |
| 62 | 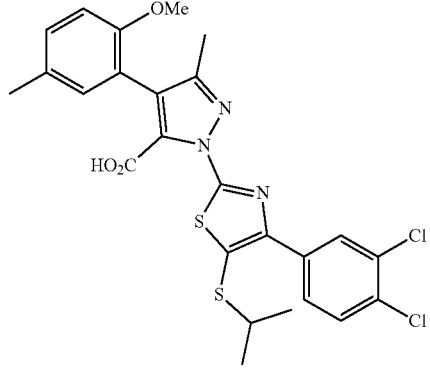 [SMILES: COc1ccc(C)cc1-c1c(C)nn(-c2nc(-c3ccc(Cl)c(Cl)c3)c(SC(C)C)s2)c1C(=O)O] | 1-(4-(3,4-dichlorophenyl)-5-(isopropylthio)thiazol-2-yl)-4-(2-methoxy-5-methylphenyl)-3-methyl-1H-pyrazole-5-carboxylic acid | C | $^1$H NMR (500 MHz, DMSO) δ 8.19 (s, 1H), 8.02 (d, J = 8.5 Hz, 1H), 7.76 (d, J = 8.5 Hz, 1H), 7.17 (d, J = 8.3 Hz 1H), 7.09 (s, 1H), 6.98 (d, J = 8.3 Hz, 1H), 3.71 (s, 3H), 3.42-3.29 (m, 1H), 2.26 (s, 3H), 2.12 (s, 3H), 1.24 (d, J = 6.7 Hz, 6H); MS (m/z): 548.1 [M + H]$^+$ |
| 63 | 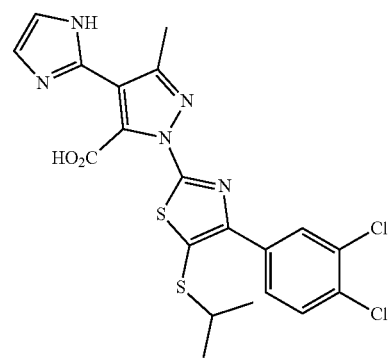 [SMILES: Cc1nn(-c2nc(-c3ccc(Cl)c(Cl)c3)c(SC(C)C)s2)c(C(=O)O)c1-c1ncc[nH]1] | 1-(4-(3,4-dichlorophenyl)-5-(isopropylthio)thiazol-2-yl)-4-(1H-imidazol-2-yl)-3-methyl-1H-pyrazole-5-carboxylic acid | D | $^1$H NMR (500 MHz, DMSO) δ 8.18 (d, J = 2.1 Hz, 1H), 8.01 (dd, J = 8.6, 2.1 Hz, 1H), 7.78 (d, J = 8.4 Hz, 1H), 7.32-7.28 (m, 2H), 3.42-3.29 (m, 1H), 2.55 (s, 3H), 1.25 (d, J = 6.7 Hz, 6H).; MS (m/z): 493.9 [M + H]$^+$ |
| 64 | 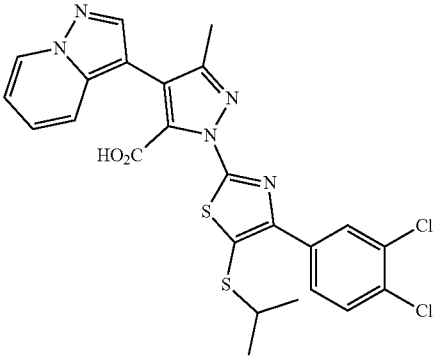 [SMILES: Cc1nn(-c2nc(-c3ccc(Cl)c(Cl)c3)c(SC(C)C)s2)c(C(=O)O)c1-c1cnn2ccccc12] | 1-(4-(3,4-dichlorophenyl)-5-(isopropylthio)thiazol-2-yl)-3-methyl-4-(pyrazolo[1,5-a]pyridin-3-yl)-1H-pyrazole-5-carboxylic acid | D | $^1$H NMR (500 MHz, DMSO) δ 8.73 (d, J = 7.0 Hz, 1H), 8.21 (s, 1H), 8.12 (s, 1H), 8.03 (d, J = 8.5 Hz, 1H), 7.76 (d, J = 8.5 Hz, 1H), 7.66-7.61 (m, 1H), 7.28 (t, J = 7.2 Hz, 1H), 6.96 (t, J = 6.8 Hz, 1H), 3.42-3.29 (m, 1H), 2.24 (s, 3H), 1.24 (d, J = 6.7 Hz, 6H).; MS (m/z): 544.0 [M + H]$^+$ |

-continued

| Ex. | Structure | Name | EC$_{50}$ | Characterization |
|---|---|---|---|---|
| 65 | 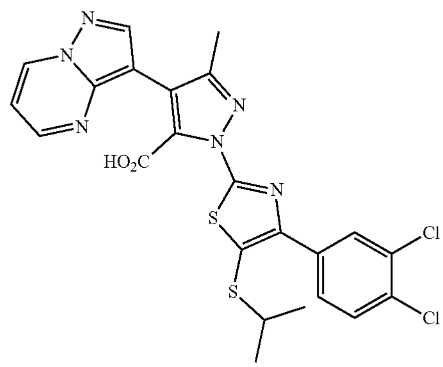 [SMILES: Cc1nn(-c2nc(-c3ccc(Cl)c(Cl)c3)c(SC(C)C)s2)c(C(=O)O)c1-c1cnn2cccnc12] | 1-(4-(3,4-dichlorophenyl)-5-(isopropylthio)thiazol-2-yl)-3-methyl-4-(pyrazolo[1,5-a]pyrimidin-3-yl)-1H-pyrazole-5-carboxylic acid | E | $^1$H NMR (500 MHz, DMSO) δ 9.18 (d, J = 7.0 Hz, 1H), 8.62 (d, J = 2.4 Hz, 1H), 8.37 (s, 1H), 8.20 (s, 1H), 8.03 (d, J = 8.0 Hz, 1H), 7.76 (d, J = 8.5 Hz, 1H), 7.12 (dd, J = 7.0, 4.0 Hz, 1H), 3.42-3.29 (m, 1H), 2.33 (s, 3H), 1.25 (d, J = 6.7 Hz, 6H).; MS (m/z): 545.0 [M + H]$^+$ |
| 66 | 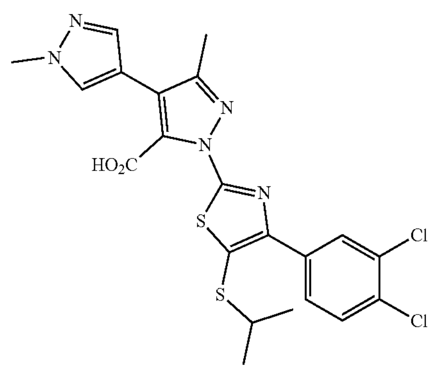 [SMILES: Cc1nn(-c2nc(-c3ccc(Cl)c(Cl)c3)c(SC(C)C)s2)c(C(=O)O)c1-c1cnn(C)c1] | 2-(4-(3,4-dichlorophenyl)-5-(isopropylthio)thiazol-2-yl)-2',5-dimethyl-4,4'-bi(2H-pyrazole)-3-carboxylic acid | C | $^1$H NMR (500 MHz, DMSO) δ 8.20 (d, J = 2.1 Hz, 1H), 8.02 (dd, J = 8.5, 2.1 Hz, 1H), 7.96 (s, 1H), 7.76 (d, J = 8.5 Hz, 1H), 7.65 (s, 1H), 3.89 (s, 3H), 3.40-3.32 (m, 1H), 2.35 (s, 3H), 1.23 (d, J = 6.7 Hz, 6H). MS (m/z): 507.9 [M + 1]$^+$ |
| 67 | 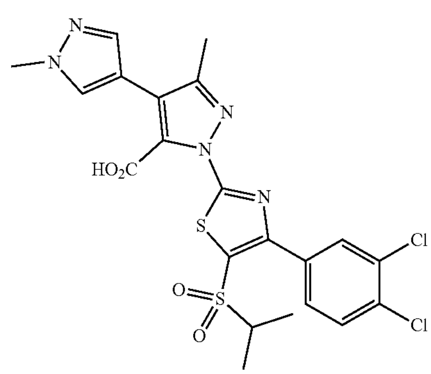 [SMILES: Cc1nn(-c2nc(-c3ccc(Cl)c(Cl)c3)c(S(=O)(=O)C(C)C)s2)c(C(=O)O)c1-c1cnn(C)c1] | 2-(4-(3,4-dichlorophenyl)-5-(isopropylsulfonyl)thiazol-2-yl)-2',5-dimethyl-4,4'-bi(2H-pyrazole)-3-carboxylic acid | E | $^1$H NMR (500 MHz, DMSO) δ 8.04 (s, 1H), 7.97 (s, 1H), 7.84-7.77 (m, 2H), 7.67 (s, 1H), 3.88 (s, 3H), 3.42-3.29 (m, 1H), 2.36 (s, 3H), 1.17 (d, J = 6.8 Hz, 6H).; MS (m/z): 539.9 [M + H]$^+$ |
| 68 | 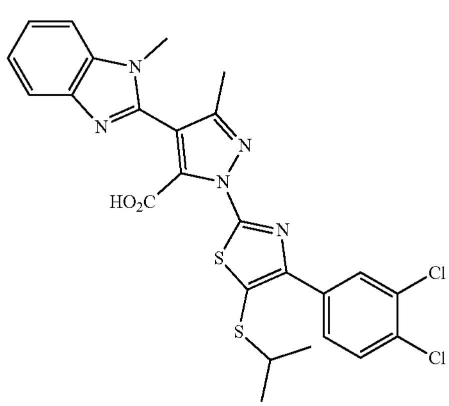 [SMILES: Cc1nn(-c2nc(-c3ccc(Cl)c(Cl)c3)c(SC(C)C)s2)c(C(=O)O)c1-c1nc2ccccc2n1C] | 1-(4-(3,4-dichlorophenyl)-5-(isopropylthio)thiazol-2-yl)-3-methyl-4-(1-methyl-1H-benzo[d]imidazol-2-yl)-1H-pyrazole-5-carboxylic acid | H | $^1$H NMR (500 MHz, DMSO) δ 8.18 (d, J = 2.0 Hz, 1H), 8.00 (dd, J = 8.5, 2.0 Hz, 1H), 7.77 (d, J = 8.5 Hz, 1H), 7.70 (d, J = 7.9 Hz, 1H), 7.63 (d, J = 8.1 Hz, 1H), 7.33 (t, J = 7.6 Hz, 1H), 7.28 (t, J = 7.5 Hz, 1H), 3.73 (s, 3H), 3.33 (1H, below water signal), 2.27 (s, 3H), 1.25 (d, J = 6.7 Hz, 6H); MS (m/z): 558.0 [M + H]$^+$ |

| Ex. | Structure | Name | EC$_{50}$ | Characterization |
|---|---|---|---|---|
| 69 | 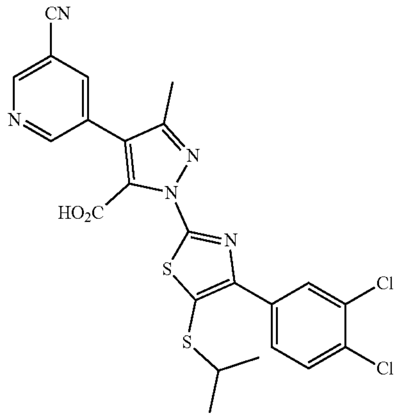 [SMILES: Cc1nn(-c2nc(-c3ccc(Cl)c(Cl)c3)c(SC(C)C)s2)c(C(=O)O)c1-c1cncc(C#N)c1] | 4-(5-cyanopyridin-3-yl)-1-(4-(3,4-dichlorophenyl)-5-(isopropylthio)thiazol-2-yl)-3-methyl-1H-pyrazole-5-carboxylic acid | D | $^1$H NMR (500 MHz, DMSO) δ 8.97 (d, J = 1.7 Hz, 1H), 8.89 (d, J = 2.1 Hz, 1H), 8.41 (t, J = 2.0 Hz, 1H), 8.12 (d, J = 2.0 Hz, 1H), 7.94 (dd, J = 8.5, 2.0 Hz, 1H), 7.70 (d, J = 8.5 Hz, 1H), 3.33 (1H, below water signal), 2.26 (s, 3H), 1.17 (d, J = 6.7 Hz, 6H); MS (m/z): 530.0 [M + H]$^+$ |
| 70 | 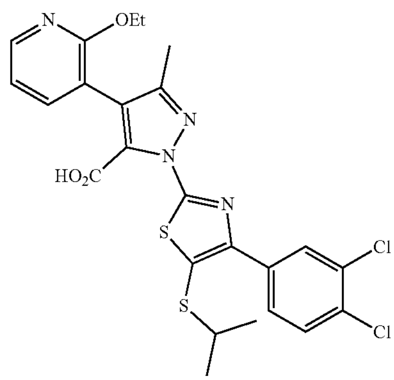 [SMILES: CCOc1ncccc1-c1c(C)nn(-c2nc(-c3ccc(Cl)c(Cl)c3)c(SC(C)C)s2)c1C(=O)O] | 1-(4-(3,4-dichlorophenyl)-5-(isopropylthio)thiazol-2-yl)-4-(2-ethoxypyridin-3-yl)-3-methyl-1H-pyrazole-5-carboxylic acid | D | $^1$H NMR (500 MHz, DMSO) δ 8.21-8.16 (m, 2H), 8.00 (dd, J = 8.5, 2.0 Hz, 1H), 7.76 (d, J = 8.5 Hz, 1H), 7.73 (dd, J = 7.3, 1.7 Hz, 1H), 7.07 (dd, J = 7.3, 5.0 Hz, 1H), 4.33 (q, J = 7.0 Hz, 2H), 3.33 (1H, below water signal), 2.19 (s, 3H), 1.28 (t, J = 7.0 Hz, 3H), 1.24 (d, J = 6.7 Hz, 6H); MS (m/z): 549.0 [M + H]$^+$ |
| 71 | 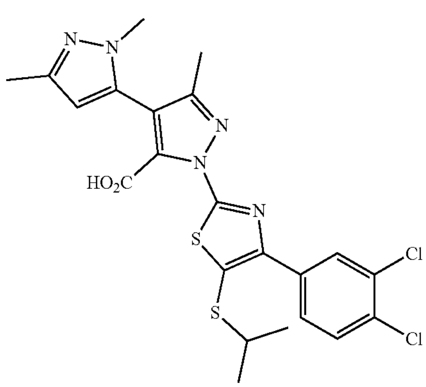 [SMILES: Cc1cc(-c2c(C)nn(-c3nc(-c4ccc(Cl)c(Cl)c4)c(SC(C)C)s3)c2C(=O)O)n(C)n1] | 2'-(4-(3,4-dichlorophenyl)-5-(isopropylthio)thiazol-2-yl)-2,5,5'-trimethyl-3,4'-bi(2H-pyrazole)-3'-carboxylic acid | D | $^1$H NMR (500 MHz, DMSO) δ 8.19 (s, 1H), 8.04-7.98 (m, 1H), 7.78 (d, J = 8.6 Hz, 1H), 6.11 (s, 1H), 3.61 (s, 3H), 3.35 (hept, J = 6.6 Hz, 1H), 2.18 (s, 3H), 2.15 (s, 3H), 1.24 (d, J = 6.6 Hz, 6H); MS (m/z): 522.0 [M + H]$^+$ |
| 72 | 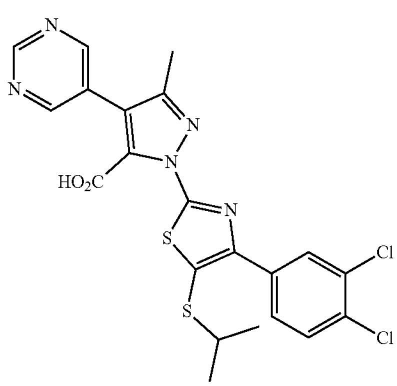 [SMILES: Cc1nn(-c2nc(-c3ccc(Cl)c(Cl)c3)c(SC(C)C)s2)c(C(=O)O)c1-c1cncnc1] | 1-(4-(3,4-dichlorophenyl)-5-(isopropylthio)thiazol-2-yl)-3-methyl-4-(pyrimidin-5-yl)-1H-pyrazole-5-carboxylic acid | D | $^1$H NMR (500 MHz, DMSO) δ 9.13 (s, 1H), 8.98 (s, 2H), 8.24 (d, J = 2.0 Hz, 1H), 8.05 (dd, J = 8.5, 2.0 Hz, 1H), 7.76 (d, J = 8.5 Hz, 1H), 3.34 (hept, J = 6.7 Hz, 1H), 2.32 (s, 3H), 1.24 (d, J = 6.7 Hz, 6H); MS (m/z): 505.9 [M + H]$^+$. |

| Ex. | Structure | Name | EC$_{50}$ | Characterization |
|---|---|---|---|---|
| 73 | 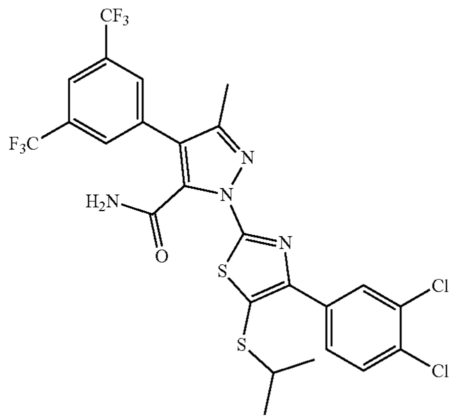 [SMILES: Cc1nn(-c2nc(-c3ccc(Cl)c(Cl)c3)c(SC(C)C)s2)c(C(N)=O)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-3-methyl-1H-pyrazole-5-carboxamide | I | $^1$H NMR (500 MHz, DMSO) δ 8.39 (s, 1H), 8.24 (d, J = 2.1 Hz, 1H), 8.19 (s, 1H), 8.17 (s (br), 2H), 8.04 (dd, J = 8.5, 2.1 Hz, 1H), 7.76 (d, J = 8.5 Hz, 1H), 3.38 (hept, J = 6.7 Hz, 1H), 2.36 (s, 3H), 1.25 (d, J = 6.7 Hz, 6H); MS (m/z): 639.2 [M + H]$^+$ |
| 74 | 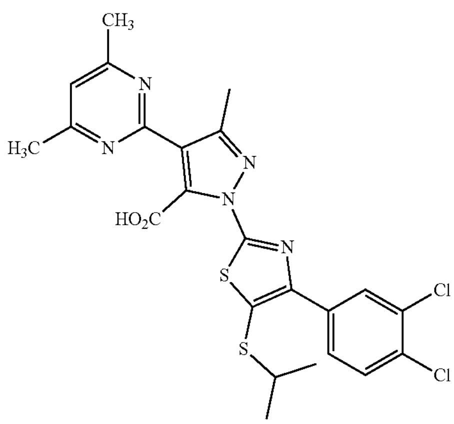 [SMILES: Cc1cc(C)nc(-c2c(C)nn(-c3nc(-c4ccc(Cl)c(Cl)c4)c(SC(C)C)s3)c2C(=O)O)n1] | 1-(4-(3,4-dichlorophenyl)-5-(isopropylthio)thiazol-2-yl)-4-(4,6-dimethylpyrimidin-2-yl)-3-methyl-1H-pyrazole-5-carboxylic acid | E | $^1$H NMR (500 MHz, DMSO) δ 8.32 (d, J = 1.9 Hz, 1H), 8.16 (dd, J = 8.5, 1.9 Hz, 1H), 7.74 (d, J = 8.5 Hz, 1H), 7.01 (s, 1H), 3.33 (1H, below water signal), 2.46 (s, 3H), 2.39 (s, 6H), 1.24 (d, J = 6.7 Hz, 6H); MS (m/z): 534.2 [M + H]$^+$ |
| 75 | 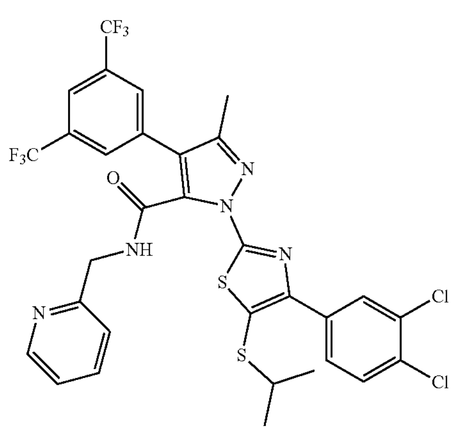 [SMILES: Cc1nn(-c2nc(-c3ccc(Cl)c(Cl)c3)c(SC(C)C)s2)c(C(=O)NCc2ccccn2)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-3-methyl-N-(pyridin-2-ylmethyl)-1H-pyrazole-5-carboxamide | I | $^1$H NMR (500 MHz, DMSO) δ 9.62 (t, J = 5.9 Hz, 1H), 8.37 (d, J = 4.2 Hz, 1H), 8.17 (s, 1H), 8.14 (d, J = 2.1 Hz, 1H), 8.13 (s, 2H), 8.04 (dd, J = 8.5, 2.1 Hz, 1H), 7.75 (d, J = 8.5 Hz, 1H), 7.35 (td, J = 7.7, 1.8 Hz, 1H), 7.15 (dd, J = 7.2, 5.1 Hz, 1H), 6.95 (d, J = 7.8 Hz, 1H), 4.52 (d, J = 5.9 Hz, 2H), 3.38 (hept, J = 6.7 Hz, 1H), 2.37 (s, 3H), 1.25 (d, J = 6.7 Hz, 6H); MS (m/z): 730.1 [M + H] |

| Ex. | Structure | Name | EC$_{50}$ | Characterization |
|---|---|---|---|---|
| 76 | 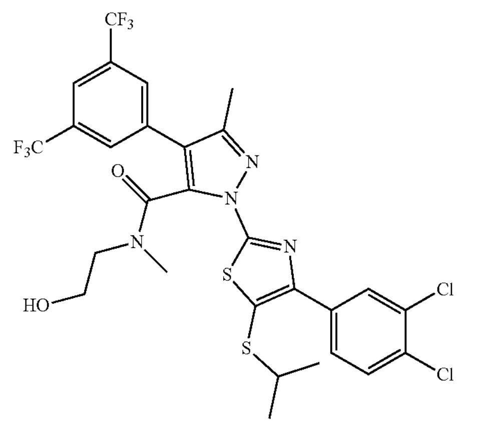 [SMILES: Cc1nn(-c2nc(-c3ccc(Cl)c(Cl)c3)c(SC(C)C)s2)c(C(=O)N(C)CCO)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-N-(2-hydroxyethyl)-N,3-dimethyl-1H-pyrazole-5-carboxamide | I | $^1$H NMR (500 MHz, DMSO) (mixture of rotamers) δ 8.18-8.13 (m, 3H), 8.07 (s, 1H), 8.09 and 7.79 (dd, J = 8.5, 4.1 Hz, 1H, rotamers), (4.67 (t, J = 5.4 Hz) and 4.56 (t, J = 4.8 Hz), 1H, rotamers), 3.88-3.82 (m, 0.5H, one rotamer), 3.52-3.33 (m, 2.5H), 3.25-3.06 (m, 3H), 3.02 and 2.83 (s, 3H, rotamers), 2.41 and 2.40 (s, 3H, rotamers), 1.26 (d, J = 6.6 Hz, 6H); MS (m/z): 697.2 [M + H]$^+$ |
| 77 | 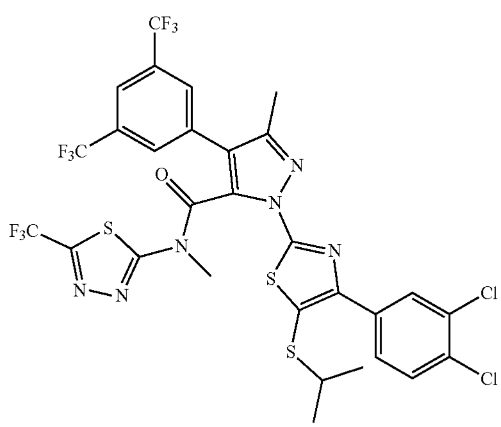 [SMILES: Cc1nn(-c2nc(-c3ccc(Cl)c(Cl)c3)c(SC(C)C)s2)c(C(=O)N(C)c2nnc(C(F)(F)F)s2)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-N,3-dimethyl-N-(5-(trifluoromethyl)-1,3,4-thiadiazol-2-yl)-1H-pyrazole-5-carboxamide | I | $^1$H NMR (500 MHz, DMSO) δ 8.20 (s, 1H), 8.11 (s, 2H), 7.78 (dd, J = 8.5, 2.1 Hz, 1H), 7.52 (d, J = 2.0 Hz, 1H), 7.51 (d, J = 8.5 Hz, 1H), 3.57 (s, 3H), 3.37 (hept, J = 6.7 Hz, 1H), 2.43 (s, 3H), 1.23 (d, J = 6.7 Hz, 6H); MS (m/z): 805.1 [M + H]$^+$ |
| 78 | 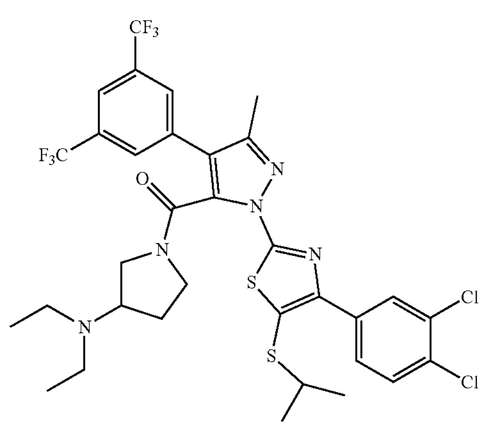 [SMILES: CCN(CC)C1CCN(C(=O)c2c(-c3cc(C(F)(F)F)cc(C(F)(F)F)c3)c(C)nn2-c2nc(-c3ccc(Cl)c(Cl)c3)c(SC(C)C)s2)C1] | (4-(3,5-bis(trifluoromethyl)phenyl)-1-(4-(3,4-dichlorophenyl)-5-(isopropylthio)thiazol-2-yl)-3-methyl-1H-pyrazol-5-yl)(3-(diethylamino)pyrrolidin-1-yl)methanone | I | $^1$H NMR (500 MHz, DMSO) 8.18 (s, 1H), 8.15-8.04 (m, 4H), 7.83-7.75 (m, 1H), 3.80-2.62 (m, 4H), 3.39 and 3.38 (hept, 1H, J = 6.7 hz, rotamers), 2.45-1.83 (m, 9H), 1.70-1.43 (m, 1H), 1.26 and 1.25 (d, 6H, J = 6.7 Hz, rotamers), 0.85-0.77 (m, 3H), 0.74-0.63 (m, 3H); MS (m/z): 764.5 [M + H]$^+$ |

| Ex. | Structure | Name | EC$_{50}$ | Characterization |
|---|---|---|---|---|
| 79 | 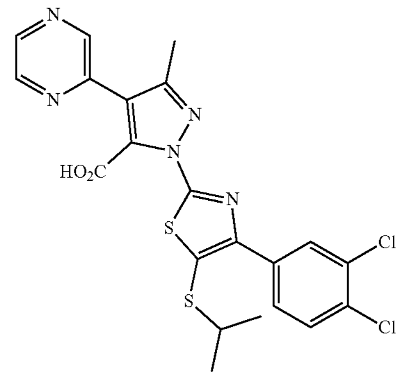 [SMILES: Cc1nn(-c2nc(-c3ccc(Cl)c(Cl)c3)c(SC(C)C)s2)c(C(=O)O)c1-c1cnccn1] | 1-(4-(3,4-dichlorophenyl)-5-(isopropylthio)thiazol-2-yl)-3-methyl-4-(pyrazin-2-yl)-1H-pyrazole-5-carboxylic acid | D | $^1$H NMR (500 MHz, DMSO) δ 8.97 (s, 1H), 8.71 (s, 1H), 8.58 (s, 1H), 8.23 (d, J = 1.9 Hz, 1H), 8.04 (dd, J = 8.4, 2.0 Hz, 1H), 7.76 (d, J = 8.5 Hz, 1H), 3.36 (hept, J = 6.7 Hz, 1H), 2.47 (s, 3H), 1.24 (d, J = 6.7 Hz, 6H); MS (m/z): 505.9 [M + H]$^+$ |
| 80 | 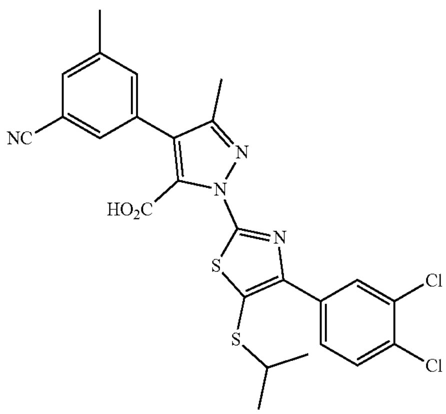 [SMILES: Cc1cc(C#N)cc(-c2c(C)nn(-c3nc(-c4ccc(Cl)c(Cl)c4)c(SC(C)C)s3)c2C(=O)O)c1] | 4-(3-cyano-5-methylphenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.19 (d, J = 2.0 Hz, 1H), 8.02 (dd, J = 8.5, 2.0 Hz, 1H), 7.76 (d, J = 8.5 Hz, 1H), 7.73 (s, 1H), 7.70 (s, 1H), 7.63 (s, 1H), 3.36 (hept, J = 6.7 Hz, 1H), 2.40 (s, 3H), 2.30 (s, 3H), 1.24 (d, J = 6.7 Hz, 6H); MS (m/z): 543.0 [M + H]$^+$ |
| 81 | 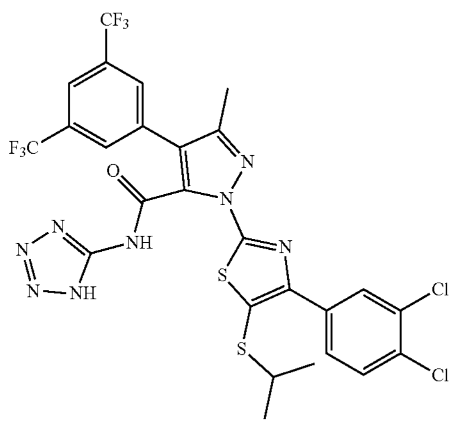 [SMILES: Cc1nn(-c2nc(-c3ccc(Cl)c(Cl)c3)c(SC(C)C)s2)c(C(=O)Nc2nnn[nH]2)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-3-methyl-N-(1H-tetrazol-5-yl)-1H-pyrazole-5-carboxamide | I | $^1$H NMR (500 MHz, DMSO) δ 8.20-8.16 (m, 3H), 7.90-7.74 (m, 2H), 7.49 (d, J = 8.4 Hz, 1H), 3.38 (hept, J = 6.7 Hz, 1H), 2.41 (s, 3H), 1.26 (d, J = 6.7 Hz, 6H); MS (m/z): 707.0 [M + H]$^+$ |
| 82 | 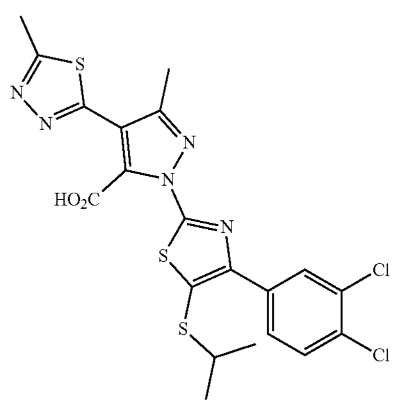 [SMILES: Cc1nnc(-c2c(C)nn(-c3nc(-c4ccc(Cl)c(Cl)c4)c(SC(C)C)s3)c2C(=O)O)s1] | 1-(4-(3,4-dichlorophenyl)-5-(isopropylthio)thiazol-2-yl)-3-methyl-4-(5-methyl-1,3,4-thiadiazol-2-yl)-1H-pyrazole-5-carboxylic acid | I | $^1$H NMR (500 MHz, DMSO) δ 8.21 (d, J = 2.1 Hz, 1H), 8.03 (dd, J = 8.5, 2.1 Hz, 1H), 7.77 (d, J = 8.5 Hz, 1H), 3.36 (hept, J = 6.7 Hz, 1H), 2.76 (s, 3H), 2.51 (s, 3H), 1.24 (d, J = 6.7 Hz, 6H); MS (m/z): 525.9 [M + H]$^+$ |

| Ex. | Structure | Name | EC$_{50}$ | Characterization |
|---|---|---|---|---|
| 83 | 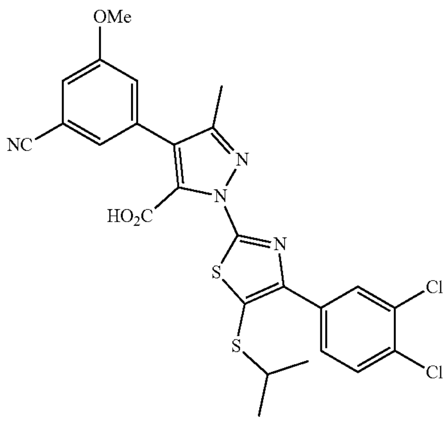 [SMILES: COc1cc(C#N)cc(-c2c(C)nn(-c3nc(-c4ccc(Cl)c(Cl)c4)c(SC(C)C)s3)c2C(=O)O)c1] | 4-(3-cyano-5-methoxyphenyl)-1-(4-(3,4-dichlorophenyl)-5-(isopropylthio)thiazol-2-yl)-3-methyl-1H-pyrazole-5-carboxylic acid | C | $^1$H NMR (500 MHz, DMSO) δ 8.21 (d, J = 1.9 Hz, 1H), 8.02 (dd, J = 8.5, 1.9 Hz, 1H), 7.76 (d, J = 8.5 Hz, 1H), 7.52 (s, 1H), 7.46 (s, 1H), 7.40 (s, 1H), 3.85 (s, 3H), 3.36 (hept, J = 6.7 Hz, 1H), 2.32 (s, 3H), 1.24 (d, J = 6.7 Hz, 6H); MS (m/z): 559.0 [M + H]$^+$ |
| 84 | 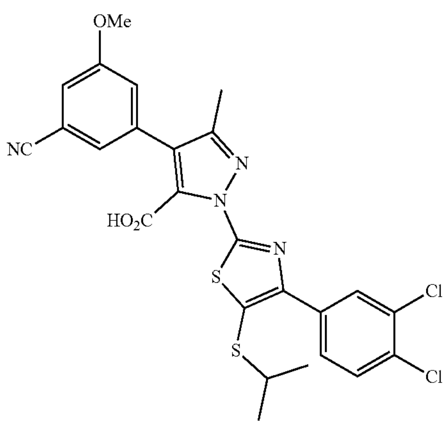 | 4-(3-cyano-5-(trifluoromethyl)phenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.35-8.30 (m, 2H), 8.28-8.22 (m, 2H), 8.08-8.04 (m, 1H), 7.77 (d, J = 8.4 Hz, 1H), 3.35 (hept, J = 6.5 Hz, 1H), 2.34 (s, 3H), 1.25 (d, J = 6.7 Hz, 6H); MS (m/z): 596.9 [M + H]$^+$ |
| 85 | 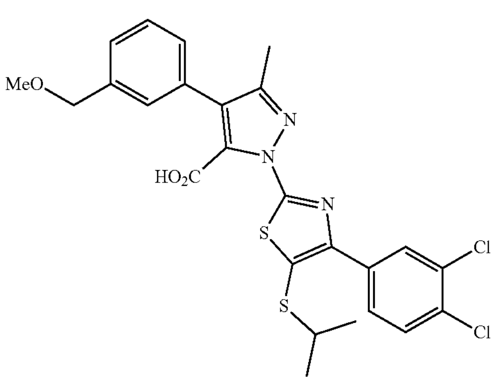 [SMILES: COCc1cccc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3-(methoxymethyl)phenyl)-3-methyl-1H-pyrazole-5-carboxylic acid | C | $^1$H NMR (500 MHz, DMSO) δ 8.25 (s, 1H), 8.06 (d, J = 8.2 Hz, 1H), 7.74 (d, J = 8.5 Hz, 1H), 7.46-7.37 (m, 3H), 7.30-7.25 (m, 1H), 7.10 (s (br), 2H), 4.44 (s, 3H), 3.33 (hept, J = 6.7 Hz, 1H), 2.28 (s, 3H), 1.24 (d, J = 6.7 Hz, 6H); MS (m/z): 548.1 [M + H]$^+$ |

| Ex. | Structure | Name | EC$_{50}$ | Characterization |
|---|---|---|---|---|
| 86 | 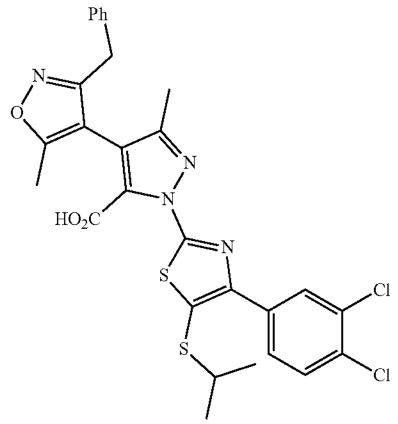 [SMILES: Cc1nn(-c2nc(-c3ccc(Cl)c(Cl)c3)c(SC(C)C)s2)c(C(=O)O)c1-c1c(Cc2ccccc2)noc1C] | 4-(3-benzyl-5-methylisoxazol-4-yl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.19 (d, J = 2.0 Hz, 1H), 8.00 (dd, J = 8.5, 2.1 Hz, 1H), 7.76 (d, J = 8.5 Hz, 1H), 7.22-7.12 (m, 3H), 7.01-6.97 (m, 2H), 3.97-3.84 (ABquartet, 2H), 3.35 (hept, J = 6.7 Hz, 1H), 2.25 (s, 3H), 1.70 (s, 3H), 1.24 (d, J = 6.7 Hz, 6H); MS (m/z): 599.1 [M + H]$^+$ |
| 87 | 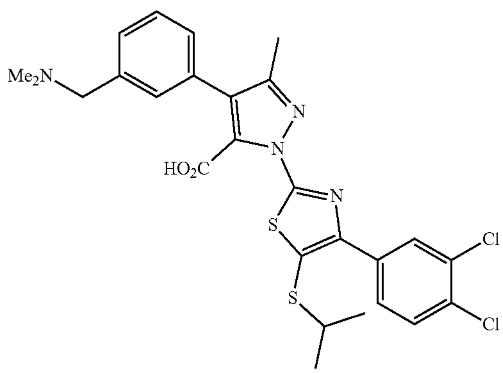 [SMILES: Cc1nn(-c2nc(-c3ccc(Cl)c(Cl)c3)c(SC(C)C)s2)c(C(=O)O)c1-c1cccc(CN(C)C)c1] | 1-(4-(3,4-dichlorophenyl)-5-(isopropylthio)thiazol-2-yl)-4-(3-((dimethylamino)methyl)phenyl)-3-methyl-1H-pyrazole-5-carboxylic acid | J | $^1$H NMR (500 MHz, DMSO) δ 8.26 (d, J = 2.1 Hz, 1H), 8.08 (dd, J = 8.4, 2.1 Hz, 1H), 7.75 (d, J = 8.5 Hz, 1H), 7.55-7.53 (m, 2H), 7.41 (t, J = 7.7 Hz, 1H), 7.31 (d, J = 7.7 Hz, 1H), 3.89 (s, 2H), 3.33 (hept, J = 6.7 Hz, 1H), 2.28 (s, 3H), 1.24 (d, J = 6.7 Hz, 6H); MS (m/z): 561.1 [M + H]$^+$ |
| 88 | 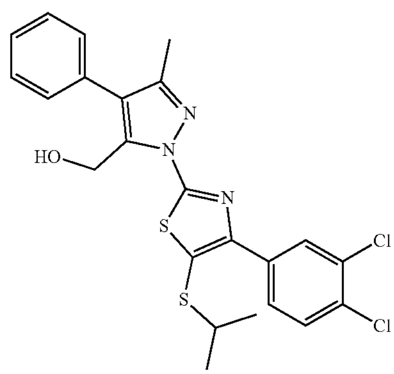 [SMILES: Cc1nn(-c2nc(-c3ccc(Cl)c(Cl)c3)c(SC(C)C)s2)c(CO)c1-c1ccccc1] | (1-(4-(3,4-dichlorophenyl)-5-(isopropylthio)thiazol-2-yl)-3-methyl-4-phenyl-1H-pyrazol-5-yl)MeOH | J | $^1$H NMR (500 MHz, DMSO) δ 8.29 (d, J = 2.1 Hz, 1H), 8.07 (dd, J = 8.5, 2.1 Hz, 1H), 7.79 (d, J = 8.5 Hz, 1H), 7.54-7.47 (m, 4H), 7.45-7.40 (m, 1H), 5.21 (t, J = 5.7 Hz, 1H), 4.86 (d, J = 5.7 Hz, 2H), 3.35 (hept, J = 6.7 Hz, 1H), 2.28 (s, 3H), 1.25 (d, J = 6.7 Hz, 6H); MS (m/z): 490.0 [M + H]$^+$ |
| 89 | 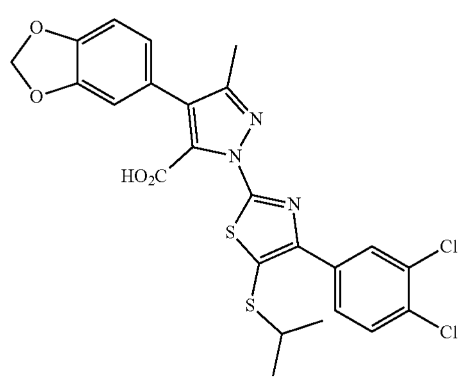 [SMILES: Cc1nn(-c2nc(-c3ccc(Cl)c(Cl)c3)c(SC(C)C)s2)c(C(=O)O)c1-c1ccc2c(c1)OCO2] | 4-(benzo[d][1,3]dioxol-5-yl)-1-(4-(3,4-dichlorophenyl)-5-(isopropylthio)thiazol-2-yl)-3-methyl-1H-pyrazole-5-carboxylic acid | C | $^1$H NMR (500 MHz, DMSO) δ 14.23 (s, 1H), 8.20 (d, J = 2.1 Hz, 1H), 8.01 (dd, J = 8.5, 2.1 Hz, 1H), 7.75 (d, J = 8.5 Hz, 1H), 7.05-6.99 (m, 2H), 6.92 (dd, J = 8.0, 1.7 Hz, 1H), 6.07 (s, 2H), 3.33 (hept, J = 6.7 Hz, 1H), 2.28 (s, 3H), 1.23 (d, J = 6.7 Hz, 6H); MS (m/z): 547.9 [M + H]$^+$ |

| Ex. | Structure | Name | EC₅₀ | Characterization |
|---|---|---|---|---|
| 90 | 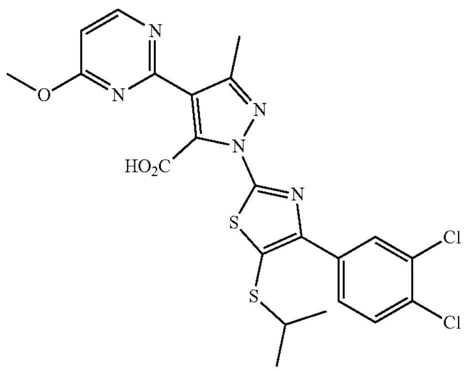 [SMILES: COc1ccnc(-c2c(C)nn(-c3nc(-c4ccc(Cl)c(Cl)c4)c(SC(C)C)s3)c2C(=O)O)n1] | 1-(4-(3,4-dichlorophenyl)-5-(isopropylthio)thiazol-2-yl)-4-(4-methoxypyrimidin-2-yl)-3-methyl-1H-pyrazole-5-carboxylic acid | J | $^1$H NMR (500 MHz, DMSO) δ 8.53 (s, 1H), 8.27 (s, 1H), 8.06 (d, J = 7.9 Hz, 1H), 7.76 (d, J = 8.4 Hz, 1H), 6.78 (s, 1H), 3.96 (s, 3H), 3.34 (hept, J = 6.7 Hz, 1H), 2.61 (s, 3H), 1.25 (d, J = 6.7 Hz, 6H); MS (m/z): 536.0 [M + H]$^+$ |
| 91 | 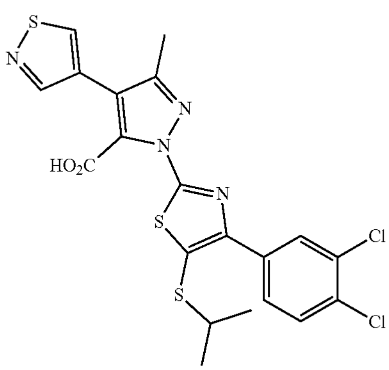 [SMILES: Cc1nn(-c2nc(-c3ccc(Cl)c(Cl)c3)c(SC(C)C)s2)c(C(=O)O)c1-c1cnsc1] | 1-(4-(3,4-dichlorophenyl)-5-(isopropylthio)thiazol-2-yl)-4-(isothiazol-4-yl)-3-methyl-1H-pyrazole-5-carboxylic acid | C | $^1$H NMR (500 MHz, DMSO) δ 9.14 (s, 1H), 8.84 (s, 1H), 8.24 (d, J = 2.1 Hz, 1H), 8.05 (dd, J = 8.5, 2.1 Hz, 1H), 7.73 (d, J = 8.5 Hz, 1H), 3.33 (hept, J = 6.7 Hz, 1H), 2.35 (s, 3H), 1.23 (d, J = 6.7 Hz, 6H); MS (m/z): 510.9 [M + H]$^+$ |
| 92 | 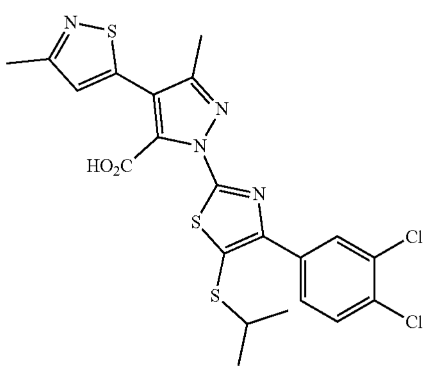 [SMILES: Cc1cc(-c2c(C)nn(-c3nc(-c4ccc(Cl)c(Cl)c4)c(SC(C)C)s3)c2C(=O)O)sn1] | 1-(4-(3,4-dichlorophenyl)-5-(isopropylthio)thiazol-2-yl)-3-methyl-4-(3-methylisothiazol-5-yl)-1H-pyrazole-5-carboxylic acid | B | $^1$H NMR (500 MHz, DMSO) δ 8.22 (d, J = 2.1 Hz, 1H), 8.04 (dd, J = 8.5, 2.1 Hz, 1H), 7.76 (d, J = 8.5 Hz, 1H), 7.40 (s, 1H), 3.35 (hept, J = 6.7 Hz, 1H), 2.45 (s, 3H), 2.41 (s, 3H), 1.24 (d, J = 6.7 Hz, 6H); MS (m/z): 524.9 [M + H]$^+$ |
| 93 | 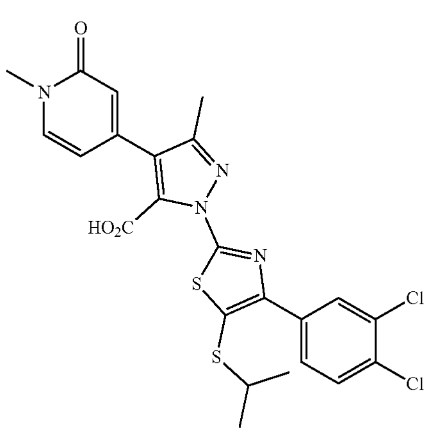 [SMILES: Cc1nn(-c2nc(-c3ccc(Cl)c(Cl)c3)c(SC(C)C)s2)c(C(=O)O)c1-c1ccn(C)c(=O)c1] | 1-(4-(3,4-dichlorophenyl)-5-(isopropylthio)thiazol-2-yl)-3-methyl-4-(1-methyl-2-oxo-1,2-dihydropyridin-4-yl)-1H-pyrazole-5-carboxylic acid | J | $^1$H NMR (500 MHz, DMSO) δ 8.25 (s, 1H), 8.06 (d, J = 6.9 Hz, 1H), 7.74 (d, J = 8.5 Hz, 1H), 7.68 (d, J = 6.7 Hz, 1H), 6.49 (s, 1H), 6.49-6.45 (m, 1H), 3.33 (hept, J = 6.7 Hz, 1H), 3.42 (s, 3H), 2.31 (s, 3H), 1.23 (d, J = 6.7 Hz, 6H); MS (m/z): 535.0 [M + H]$^+$ |

| Ex. | Structure | Name | EC$_{50}$ | Characterization |
|---|---|---|---|---|
| 94 | 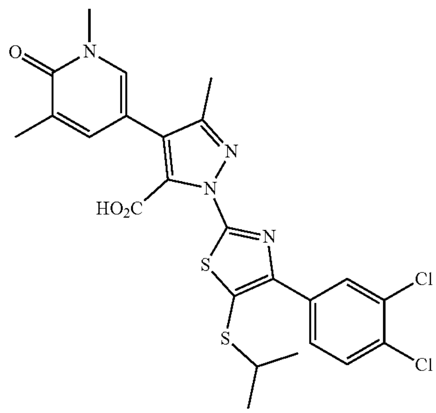 [SMILES: Cc1nn(-c2nc(-c3ccc(Cl)c(Cl)c3)c(SC(C)C)s2)c(C(=O)O)c1-c1cc(C)c(=O)n(C)c1] | 1-(4-(3,4-dichlorophenyl)-5-(isopropylthio)thiazol-2-yl)-4-(1,5-dimethyl-6-oxo-1,6-dihydropyridin-3-yl)-3-methyl-1H-pyrazole-5-carboxylic acid | J | $^1$H NMR (500 MHz, DMSO) δ 8.19 (d, J = 2.1 Hz, 1H), 8.01 (dd, J = 8.5, 2.1 Hz, 1H), 7.75 (d, J = 8.5 Hz, 1H), 7.71 (d, J = 2.2 Hz, 1H), 7.41-7.39 (m, 1H), 3.48 (s, 3H), 3.35 (hept, J = 6.7 Hz, 1H), 2.28 (s, 3H), 2.03 (s, 3H), 1.23 (d, J = 6.7 Hz, 6H); MS (m/z): 549.0 [M + H]$^+$ |
| 95 | 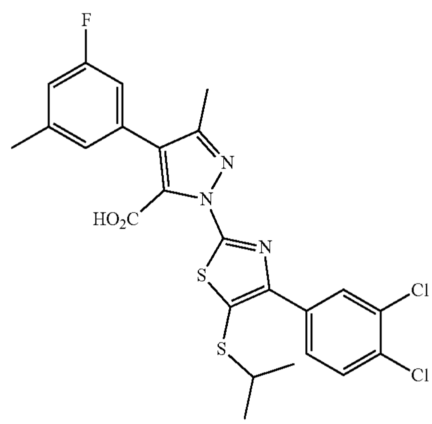 [SMILES: Cc1cc(F)cc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3-fluoro-5-methylphenyl)-3-methyl-1H-pyrazole-5-carboxylic acid | B | $^1$H NMR (500 MHz, DMSO) δ 8.21 (d, J = 2.0 Hz, 1H), 8.02 (dd, J = 8.5, 2.0 Hz, 1H), 7.75 (d, J = 8.5 Hz, 1H), 7.13 (s, 1H), 7.11 (d, J = 9.9 Hz, 1H), 7.07 (d, J = 9.7 Hz, 1H), 3.35 (hept, J = 6.7 Hz, 1H), 2.36 (s, 3H), 2.31 (s, 3H), 1.24 (d, J = 6.7 Hz, 6H); MS (m/z): 536.0 [M + H]$^+$ |
| 96 | 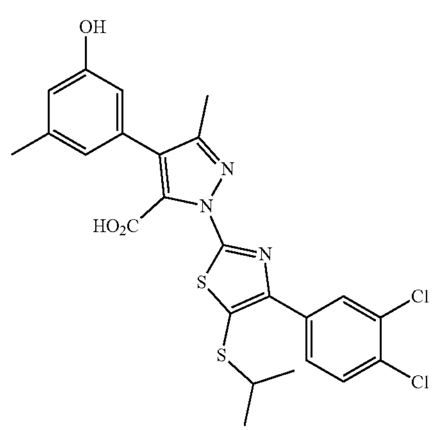 [SMILES: Cc1cc(O)cc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3-hydroxy-5-methylphenyl)-3-methyl-1H-pyrazole-5-carboxylic acid | J | $^1$H NMR (500 MHz, DMSO) δ 8.24 (s, 1H), 8.06 (d, J = 8.8 Hz, 1H), 7.75 (d, J = 8.5 Hz, 1H), 6.72 (s, 1H), 6.69 (s, 1H), 6.55 (s, 1H), 3.33 (hept, J = 6.7 Hz, 1H), 2.26 (s, 3H), 2.24 (s, 3H), 1.23 (d, J = 6.7 Hz, 6H); MS (m/z): 533.9 [M + H]$^+$ |

-continued

| Ex. | Structure | Name | EC$_{50}$ | Characterization |
|---|---|---|---|---|
| 97 | 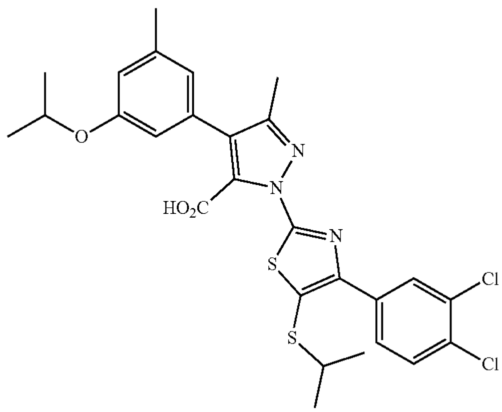 [SMILES: Cc1cc(OC(C)C)cc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3-isopropoxy-5-methylphenyl)-3-methyl-1H-pyrazole-5-carboxylic acid | B | $^1$H NMR (500 MHz, DMSO) δ 8.23 (s, 1H), 8.04 (d, J = 8.3 Hz, 1H), 7.75 (d, J = 8.3 Hz, 1H), 6.84-6.79 (m, 2H), 6.74 (s, 1H), 4.60 (hept, J = 6.0 Hz, 1H), 2.30 (s, 3H), 2.30 (s, 3H), 1.28 (d, J = 6.0 Hz, 6H), 1.24 (d, J = 6.7 Hz, 6H); MS (m/z): 576.2 [M + H]$^+$ |
| 98 | 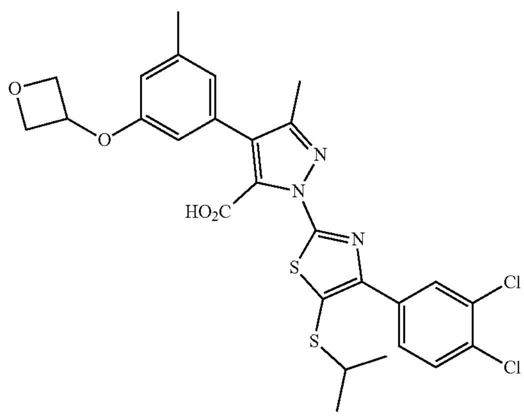 [SMILES: Cc1cc(OC2COC2)cc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic acid | B | $^1$H NMR (500 MHz, DMSO) δ 8.22 (s, 1H), 8.03 (d, J = 7.0 Hz, 1H), 7.76 (d, J = 8.6 Hz, 1H), 6.91 (s, 1H), 6.68-6.62 (m, 2H), 5.27 (q, J = 5.1 Hz, 1H), 4.94 (t, J = 6.9 Hz, 1H), 4.56 (dd, J = 7.6, 5.1 Hz, 2H), 3.36 (hept, J = 6.7 Hz, 1H), 2.32 (s, 3H), 2.30 (s, 3H), 1.25 (d, J = 6.7 Hz, 6H); MS (m/z): 590.2 [M + H]$^+$ |
| 99 | 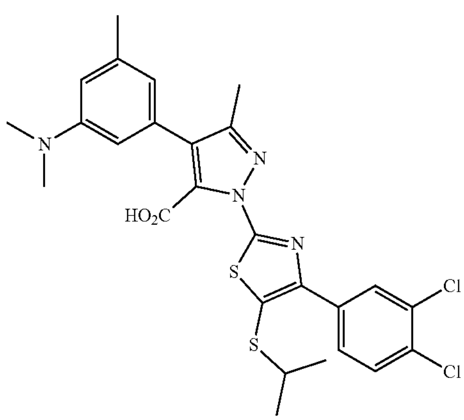 [SMILES: Cc1cc(-c2c(C)nn(-c3nc(-c4ccc(Cl)c(Cl)c4)c(SC(C)C)s3)c2C(=O)O)cc(N(C)C)c1] | 1-(4-(3,4-dichlorophenyl)-5-(isopropylthio)thiazol-2-yl)-4-(3-(dimethylamino)-5-methylphenyl)-3-methyl-1H-pyrazole-5-carboxylic acid | C | $^1$H NMR (500 MHz, DMSO) δ 8.14 (d, J = 2.0 Hz, 1H), 7.95 (dd, J = 8.5, 2.1 Hz, 1H), 7.70 (d, J = 8.5 Hz, 1H), 6.52-6.49 (m, 2H), 6.48 (s, 1H), 3.29 (hept, J = 6.7 Hz, 1H), 2.83 (s, 6H), 2.24 (s, 3H), 2.21 (s, 3H), 1.17 (d, J = 6.7 Hz, 6H); MS (m/z): 561.0 [M + H]$^+$ |

-continued

| Ex. | Structure | Name | EC$_{50}$ | Characterization |
|---|---|---|---|---|
| 100 | 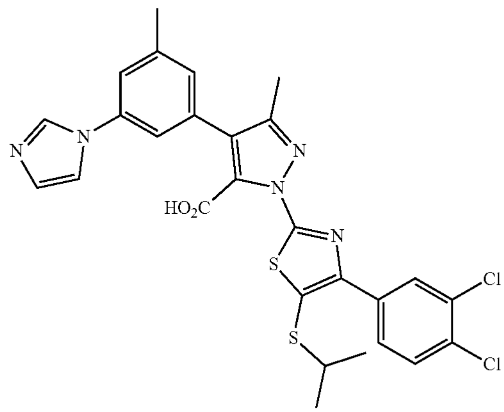 [SMILES: Cc1cc(-c2c(C)nn(-c3nc(-c4ccc(Cl)c(Cl)c4)c(SC(C)C)s3)c2C(=O)O)cc(-n2ccnc2)c1] | 4-(3-(1H-imidazol-1-yl)-5-methylphenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.19 (s, 1H), 8.14 (d, J = 2.1 Hz, 1H), 7.96 (dd, J = 8.5, 2.1 Hz, 1H), 7.70-7.67 (m, 2H), 7.48 (m, 1H), 7.46 (m, 1H), 7.20 (s, 1H), 7.06 (s, 1H), 3.29 (hept, J = 6.7 Hz, 1H), 2.35 (s, 3H), 2.27 (s, 3H), 1.18 (d, J = 6.7 Hz, 6H); MS (m/z): 584.1 [M + H]$^+$ |
| 101 | 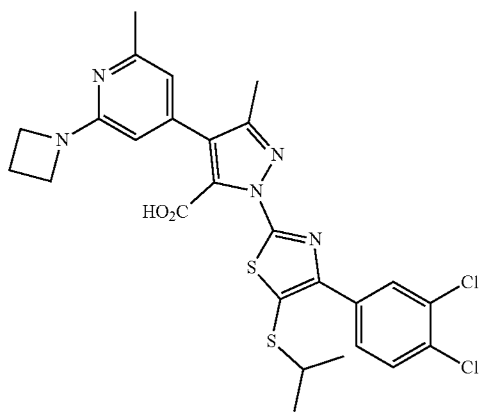 [SMILES: Cc1cc(-c2c(C)nn(-c3nc(-c4ccc(Cl)c(Cl)c4)c(SC(C)C)s3)c2C(=O)O)cc(N2CCC2)n1] | 4-(2-(azetidin-1-yl)-6-methylpyridin-4-yl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.30 (d, J = 2.1 Hz, 1H), 8.12 (dd, J = 8.5, 2.1 Hz, 1H), 7.74 (d, J = 8.5 Hz, 1H), 6.70 (s, 1H), 6.40 (s, 1H), 3.42-3.29 (m, 1H), 3.89 (t, J = 7.4 Hz, 4H), 2.33-2.27 (m, 2H), 2.29 (s 3H), 2.28 (s, 3H), 1.23 (d, J = 6.7 Hz, 6H); MS (m/z): 574.1 [M + H]$^+$ |
| 102 | 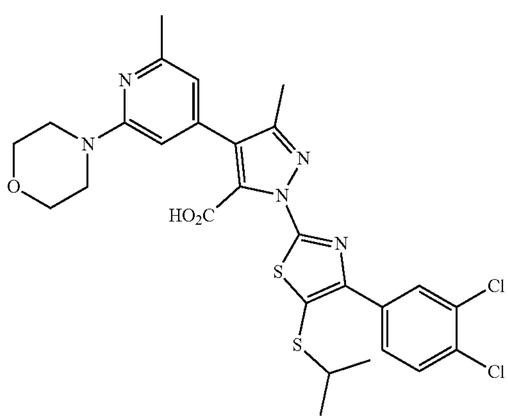 [SMILES: Cc1cc(-c2c(C)nn(-c3nc(-c4ccc(Cl)c(Cl)c4)c(SC(C)C)s3)c2C(=O)O)cc(N2CCOCC2)n1] | 1-(4-(3,4-dichlorophenyl)-5-(isopropylthio)thiazol-2-yl)-3-methyl-4-(2-methyl-6-morpholinopyridin-4-yl)-1H-pyrazole-5-carboxylic acid | C | $^1$H NMR (500 MHz, DMSO) δ 8.21 (d, J = 1.9 Hz, 1H), 8.03 (dd, J = 8.5, 2.0 Hz, 1H), 7.76 (d, J = 8.5 Hz, 1H), 6.66 (s, 1H), 6.64 (s, 1H), 3.72-3.68 (m, 4H), 3.48-3.43 (m, 4H), 3.36 (hept, J = 6.7 Hz, 1H), 2.35 (s, 3H), 2.33 (s, 3H), 1.24 (d, J = 6.7 Hz, 6H); MS (m/z): 604.0 [M + H]$^+$ |

-continued

| Ex. | Structure | Name | EC$_{50}$ | Characterization |
|---|---|---|---|---|
| 103 | 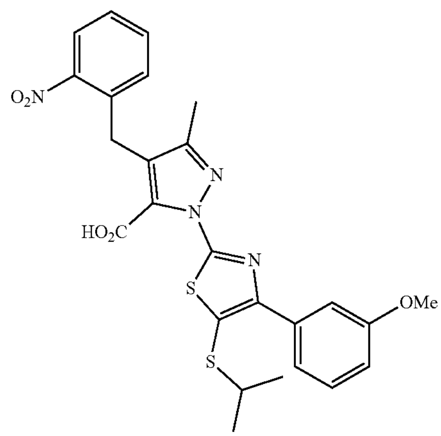 [SMILES: COc1cccc(-c2nc(-n3nc(C)c(Cc4ccccc4[N+](=O)[O-])c3C(=O)O)sc2SC(C)C)c1] | 1-(5-(isopropylthio)-4-(3-methoxyphenyl)thiazol-2-yl)-3-methyl-4-(2-nitrobenzyl)-1H-pyrazole-5-carboxylic acid | G | $^1$H NMR (500 MHz, DMSO) δ 13.96 (s, 1H), 8.00 (dd, J = 8.1, 1.2 Hz, 1H), 7.65 (td, J = 7.6, 1.3 Hz, 1H), 7.58-7.48 (m, 2H), 7.38 (t, J = 8.0 Hz, 1H), 7.22 (d, J = 6.9 Hz, 1H), 6.99 (ddd, J = 8.3, 2.6, 0.9 Hz, 1H), 4.24 (s, 2H), 3.80 (s, 3H), 3.36-3.28 (m, 1H), 2.08 (s, 3H), 1.23 (d, J = 6.7 Hz, 6H). MS (m/z): 525.1 [M + 1]$^+$ |
| 104 | 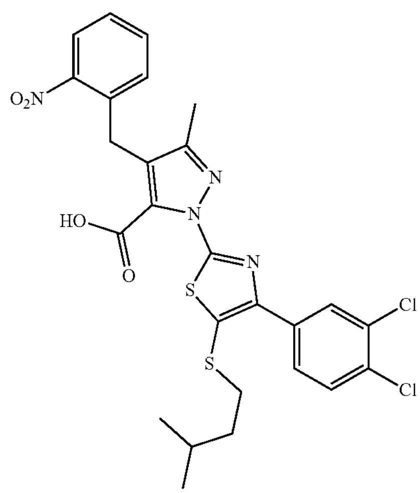 [SMILES: Cc1nn(-c2nc(-c3ccc(Cl)c(Cl)c3)c(SCCC(C)C)s2)c(C(=O)O)c1Cc1ccccc1[N+](=O)[O-]] | 1-(4-(3,4-dichlorophenyl)-5-(isopentylthio)thiazol-2-yl)-3-methyl-4-(2-nitrobenzyl)-1H-pyrazole-5-carboxylic acid | E | $^1$H NMR (500 MHz, DMSO) δ 8.13 (d, J = 2.1 Hz, 1H), 7.99 (dd, J = 8.1, 1.3 Hz, 1H), 7.92 (dd, J = 8.5, 2.1 Hz, 1H), 7.75 (d, J = 8.5 Hz, 1H), 7.64 (td, J = 7.6, 1.3 Hz, 1H), 7.53-7.47 (m, 1H), 7.23 (m, 1H), 4.22 (s, 2H), 2.97-2.91 (m, 2H), 2.05 (s, 3H), 1.64-1.56 (m, 1H), 1.45-1.39 (m, 2H), 0.81 (d, J = 6.6 Hz, 6H). MS (m/z): 591.0 [M + 1]$^+$ |
| 105 | 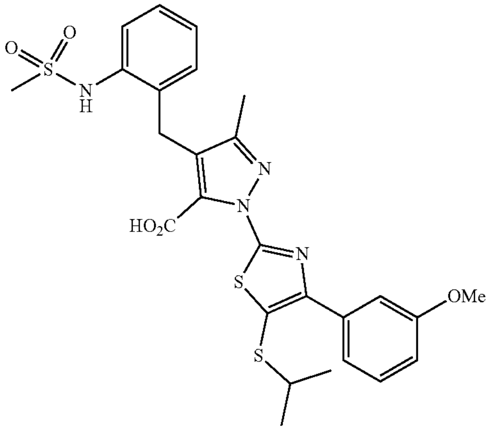 [SMILES: COc1cccc(-c2nc(-n3nc(C)c(Cc4ccccc4NS(C)(=O)=O)c3C(=O)O)sc2SC(C)C)c1] | 1-(5-(isopropylthio)-4-(3-methoxyphenyl)thiazol-2-yl)-3-methyl-4-(2-(methylsulfonamido)benzyl)-1H-pyrazole-5-carboxylic acid | G | $^1$H NMR (500 MHz, DMSO) δ 8.20 (br s, 1H), 7.61-7.55 (m, 2H), 7.45 (dd, J = 8.1, 1.1 Hz, 1H), 7.41 (d, J = 6.2 Hz, 1H), 7.37 (t, J = 8.2 Hz, 1H), 7.22-7.14 (m, 1H), 7.07 (td, J = 7.4, 1.3 Hz, 1H), 6.98-6.93 (m, 1H), 3.95 (s, 2H), 3.80 (s, 3H), 2.55 (s, 3H), 2.05 (s, 3H), 1.22 (d, J = 6.7 Hz, 6H). MS (m/z): 573.1 [M + 1]$^+$ |

-continued

| Ex. | Structure | Name | EC$_{50}$ | Characterization |
|---|---|---|---|---|
| 106 | 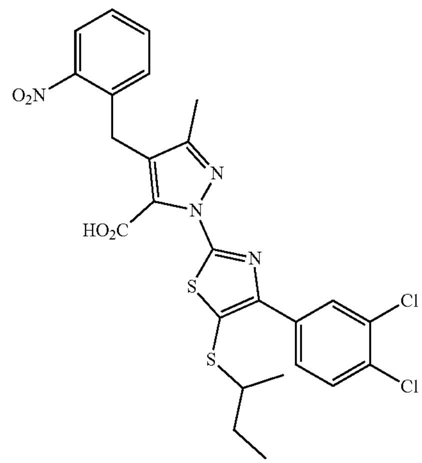 [SMILES: CCC(C)Sc1sc(-n2nc(C)c(Cc3ccccc3[N+](=O)[O-])c2C(=O)O)nc1-c1ccc(Cl)c(Cl)c1] | 1-(5-(sec-butylthio)-4-(3,4-dichlorophenyl)thiazol-2-yl)-3-methyl-4-(2-nitrobenzyl)-1H-pyrazole-5-carboxylic acid | D | $^1$H NMR (500 MHz, DMSO) δ 8.25 (d, J = 2.0 Hz, 1H), 8.03 (dd, J = 8.5, 2.1 Hz, 1H), 7.95-7.91 (m, 1H), 7.75 (d, J = 8.5 Hz, 1H), 7.59 (t, J = 7.0 Hz, 1H), 7.44 (t, J = 7.5 Hz, 1H), 7.29 (d, J = 7.7 Hz, 1H), 4.14 (s, 2H), 3.12-3.06 (m, 1H), 1.93 (s, 3H), 1.60-1.45 (m, 2H), 1.21 (d, J = 6.8 Hz, 3H), 0.90 (t, J = 7.4 Hz, 3H). MS (m/z): 577.0 [M + 1]$^+$ |
| 107 | 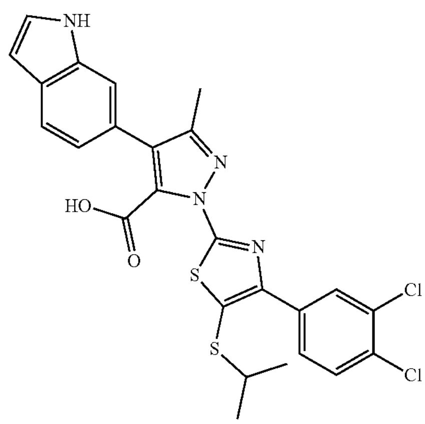 [SMILES: Cc1nn(-c2nc(-c3ccc(Cl)c(Cl)c3)c(SC(C)C)s2)c(C(=O)O)c1-c1ccc2cc[nH]c2c1] | 1-(4-(3,4-dichlorophenyl)-5-(isopropylthio)thiazol-2-yl)-4-(1H-indol-6-yl)-3-methyl-1H-pyrazole-5-carboxylic acid | E | $^1$H NMR (500 MHz, DMSO) δ 11.20 (s, 1H), 8.24 (d, J = 2.0 Hz, 1H), 8.04 (dd, J = 8.5, 2.0 Hz, 1H), 7.73 (d, J = 8.5 Hz, 1H), 7.58 (d, J = 8.2 Hz, 1H), 7.53 (s, 1H), 7.41-7.34 (m, 1H), 7.10 (dd, J = 8.2, 1.5 Hz, 1H), 6.46-6.44 (m, 1H), 3.38-3.32 (m, 1H), 2.31 (s, 3H), 1.24 (d, J = 6.7 Hz, 6H). MS (m/z): 543.0 [M + 1]$^+$ |
| 108 | 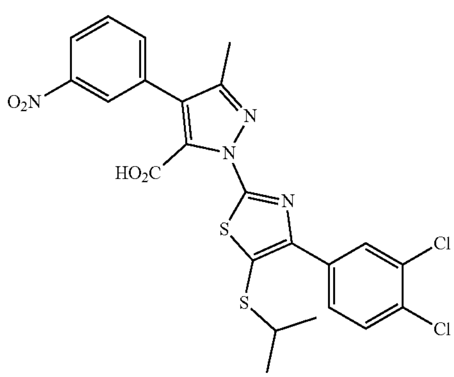 [SMILES: Cc1nn(-c2nc(-c3ccc(Cl)c(Cl)c3)c(SC(C)C)s2)c(C(=O)O)c1-c1cccc([N+](=O)[O-])c1] | 1-(4-(3,4-dichlorophenyl)-5-(isopropylthio)thiazol-2-yl)-3-methyl-4-(3-nitrophenyl)-1H-pyrazole-5-carboxylic acid | C | $^1$H NMR (500 MHz, DMSO) δ 8.36 (s, 1H), 8.24-8.20 (m, 2H), 8.04 (dd, J = 8.5, 2.0 Hz, 1H), 7.99-7.95 (m, 1H), 7.79-7.73 (m, 2H), 3.43-3.31 (m, 1H), 2.33 (s, 3H), 1.24 (d, J = 6.7 Hz, 6H). MS (m/z): 549.1 [M + 1]$^+$ |
| 109 | 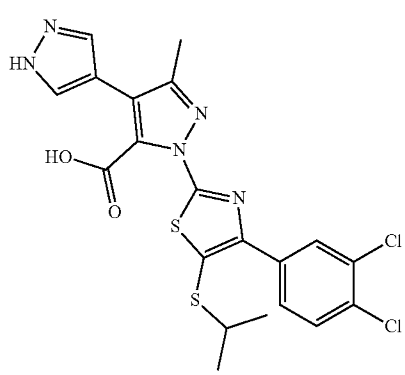 [SMILES: Cc1nn(-c2nc(-c3ccc(Cl)c(Cl)c3)c(SC(C)C)s2)c(C(=O)O)c1-c1cn[nH]c1] | 2-(4-(3,4-dichlorophenyl)-5-(isopropylthio)thiazol-2-yl)-5-methyl-4,4'-bi(2H-pyrazole)-3-carboxylic acid | E | $^1$H NMR (500 MHz, DMSO) δ 8.24 (d, J = 1.8 Hz, 1H), 8.05 (dd, J = 8.5, 1.8 Hz, 1H), 7.91-7.80 (m, 2H), 7.74 (d, J = 8.5 Hz, 1H), 2.55-2.51 (m, 1H), 2.35 (s, 3H), 1.23 (d, J = 6.7 Hz, 6H). MS (m/z): 493.9 [M + 1]$^+$ |

| Ex. | Structure | Name | EC$_{50}$ | Characterization |
|---|---|---|---|---|
| 110 | 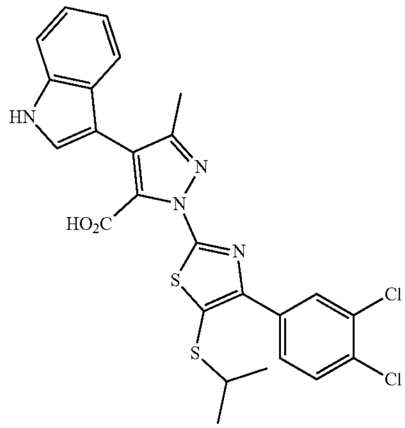 [SMILES: Cc1nn(-c2nc(-c3ccc(Cl)c(Cl)c3)c(SC(C)C)s2)c(C(=O)O)c1-c1c[nH]c2ccccc12] | 1-(4-(3,4-dichlorophenyl)-5-(isopropylthio)thiazol-2-yl)-4-(1H-indol-3-yl)-3-methyl-1H-pyrazole-5-carboxylic acid | D | $^1$H NMR (500 MHz, DMSO) δ 11.33 (s, 1H), 8.24 (s, 1H), 8.05 (m, 1H), 7.74 (d, J = 8.5 Hz, 1H), 7.48 (d, J = 8.1 Hz, 1H), 7.43 (m, 2H), 7.12 (t, J = 7.4 Hz, 1H), 7.02 (t, J = 7.4 Hz, 1H), 3.46-3.25 (m, 1H), 2.22 (s, 3H), 1.24 (d, J = 6.7 Hz, 6H). MS (m/z): 543.0 [M + 1]$^+$ |
| 111 | 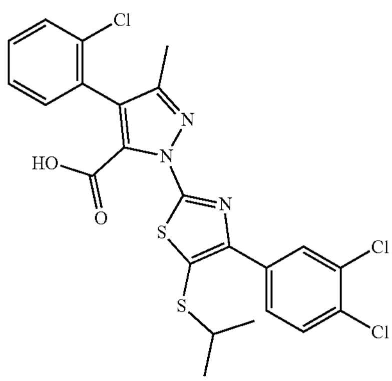 [SMILES: Cc1nn(-c2nc(-c3ccc(Cl)c(Cl)c3)c(SC(C)C)s2)c(C(=O)O)c1-c1ccccc1Cl] | 4-(2-chlorophenyl)-1-(4-(3,4-dichlorophenyl)-5-(isopropylthio)thiazol-2-yl)-3-methyl-1H-pyrazole-5-carboxylic acid | D | $^1$H NMR (500 MHz, DMSO) δ 8.18 (d, J = 2.1 Hz, 1H), 7.99 (dd, J = 8.5, 2.1 Hz, 1H), 7.76 (d, J = 8.5 Hz, 1H), 7.60 (d, J = 7.2 Hz, 1H), 7.49-7.39 (m, 3H), 3.42-3.29 (m, 1H), 2.12 (s, 3H), 1.24 (d, J = 6.7 Hz, 6H). MS (m/z): 537.9 [M + 1]$^+$ |
| 112 | 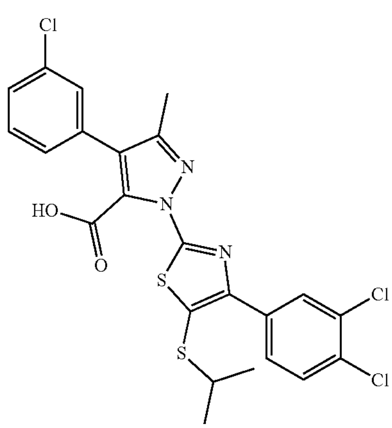 [SMILES: Cc1nn(-c2nc(-c3ccc(Cl)c(Cl)c3)c(SC(C)C)s2)c(C(=O)O)c1-c1cccc(Cl)c1] | 4-(3-chlorophenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.20 (d, J = 2.1 Hz, 1H), 8.02 (dd, J = 8.5, 2.1 Hz, 1H), 7.75 (d, J = 8.5 Hz, 1H), 7.57-7.53 (m, 1H), 7.52-7.42 (m, 3H), 3.39-3.25 (m, 1H), 2.31 (s, 3H), 1.24 (d, J = 6.7 Hz, 6H). MS (m/z): 538.0 [M + 1]$^+$ |

| Ex. | Structure | Name | EC$_{50}$ | Characterization |
|---|---|---|---|---|
| 113 | 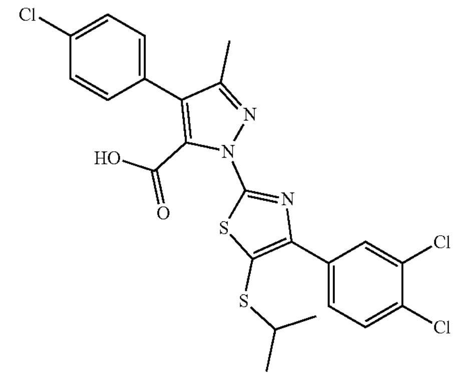 [SMILES: Cc1nn(-c2nc(-c3ccc(Cl)c(Cl)c3)c(SC(C)C)s2)c(C(=O)O)c1-c1ccc(Cl)cc1] | 4-(4-chlorophenyl)-1-(4-(3,4-dichlorophenyl)-5-(isopropylthio)thiazol-2-yl)-3-methyl-1H-pyrazole-5-carboxylic acid | D | $^1$H NMR (500 MHz, DMSO) δ 8.21 (d, J = 2.1 Hz, 1H), 8.02 (dd, J = 8.5, 2.1 Hz, 1H), 7.74 (d, J = 8.5 Hz, 1H), 7.54-7.48 (m, 4H), 3.39-3.28 (m, 1H), 2.29 (s, 3H), 1.24 (d, J = 6.7 Hz, 6H). MS (m/z): 538.0 [M + 1]$^+$ |
| 114 | 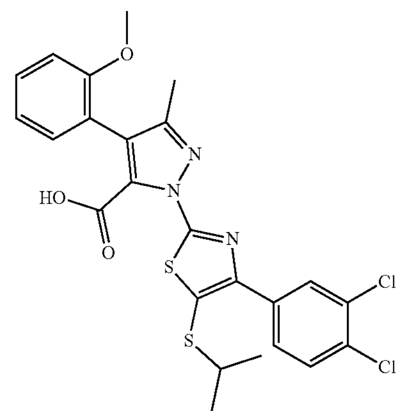 [SMILES: COc1ccccc1-c1c(C)nn(-c2nc(-c3ccc(Cl)c(Cl)c3)c(SC(C)C)s2)c1C(=O)O] | 1-(4-(3,4-dichlorophenyl)-5-(isopropylthio)thiazol-2-yl)-4-(2-methoxyphenyl)-3-methyl-1H-pyrazole-5-carboxylic acid | D | $^1$H NMR (500 MHz, DMSO) δ 8.20 (d, J = 1.9 Hz, 1H), 8.01 (dd, J = 8.5, 2.0 Hz, 1H), 7.74 (d, J = 8.5 Hz, 1H), 7.40-7.34 (m, 1H), 7.32-7.27 (m, 1H), 7.10 (d, J = 8.3 Hz, 1H), 7.00 (t, J = 7.4 Hz, 1H), 3.75 (s, 3H), 3.40-3.30 (m, 1H), 2.13 (s, 3H), 1.24 (d, J = 6.7 Hz, 6H). MS (m/z): 534.1 [M + 1]$^+$ |
| 115 | 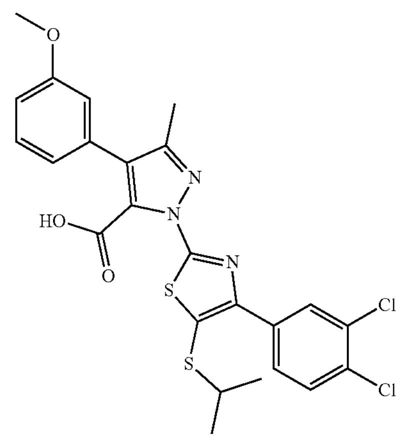 [SMILES: COc1cccc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3-methoxyphenyl)-3-methyl-1H-pyrazole-5-carboxylic acid | B | $^1$H NMR (500 MHz, DMSO) δ 8.22 (d, J = 1.9 Hz, 1H), 8.03 (dd, J = 8.5, 1.9 Hz, 1H), 7.74 (d, J = 8.5 Hz, 1H), 7.36 (t, J = 8.0 Hz, 1H), 7.09-7.03 (m, 2H), 6.94 (d, J = 8.0 Hz, 1H), 3.78 (s, 3H), 3.42-3.29 (m, 1H), 2.29 (s, 3H), 1.24 (d, J = 6.7 Hz, 6H). MS (m/z): 534.1 [M + 1]$^+$ |
| 116 | 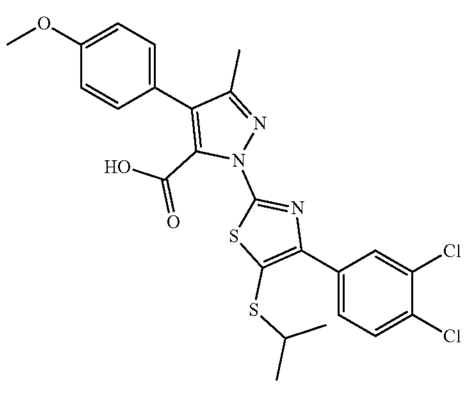 [SMILES: COc1ccc(-c2c(C)nn(-c3nc(-c4ccc(Cl)c(Cl)c4)c(SC(C)C)s3)c2C(=O)O)cc1] | 1-(4-(3,4-dichlorophenyl)-5-(isopropylthio)thiazol-2-yl)-4-(4-methoxyphenyl)-3-methyl-1H-pyrazole-5-carboxylic acid | D | $^1$H NMR (500 MHz, DMSO) δ 8.22 (d, J = 2.1 Hz, 1H), 8.02 (dd, J = 8.5, 2.1 Hz, 1H), 7.72 (d, J = 8.5 Hz, 1H), 7.43-7.38 (m, 2H), 7.03-6.98 (m, 2H), 3.79 (s, 3H), 3.48-3.24 (m, 1H), 2.27 (s, 3H), 1.23 (d, J = 6.7 Hz, 6H). MS (m/z): 534.1 [M + 1]$^+$ |

| Ex. | Structure | Name | EC$_{50}$ | Characterization |
|---|---|---|---|---|
| 117 | 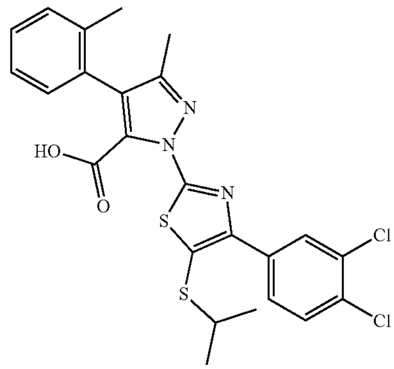 [SMILES: Cc1ccccc1-c1c(C)nn(-c2nc(-c3ccc(Cl)c(Cl)c3)c(SC(C)C)s2)c1C(=O)O] | 1-(4-(3,4-dichlorophenyl)-5-(isopropylthio)thiazol-2-yl)-3-methyl-4-o-tolyl-1H-pyrazole-5-carboxylic acid | C | $^1$H NMR (500 MHz, DMSO) δ 8.19 (d, J = 2.0 Hz, 1H), 8.00 (dd, J = 8.5, 2.0 Hz, 1H), 7.74 (d, J = 8.5 Hz, 1H), 7.34-7.28 (m, 2H), 7.27-7.20 (m, 1H), 7.18-7.15 (m, 1H), 3.40-3.28 (m, 1H), 2.14 (s, 3H), 2.04 (s, 3H), 1.24 (d, J = 6.7 Hz, 6H). MS (m/z): 518.1 [M + 1]$^+$ |
| 118 | 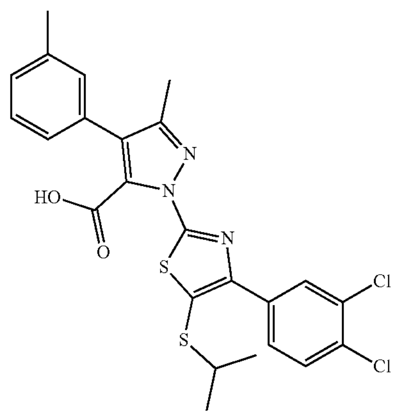 [SMILES: Cc1cccc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-3-methyl-4-m-tolyl-1H-pyrazole-5-carboxylic acid | B | $^1$H NMR (500 MHz, DMSO) δ 8.22 (d, J = 2.0 Hz, 1H), 8.03 (dd, J = 8.5, 2.0 Hz, 1H), 7.73 (d, J = 8.5 Hz, 1H), 7.35-7.23 (m, 3H), 7.18 (d, J = 7.2 Hz, 1H), 3.42-3.28 (m, 1H), 2.36 (s, 3H), 2.29 (s, 3H), 1.24 (d, J = 6.7 Hz, 6H). MS (m/z): 518.1 [M + 1]$^+$ |
| 119 | 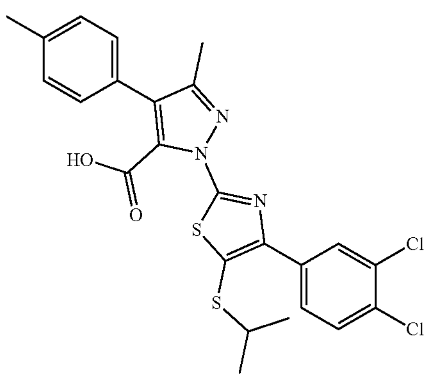 [SMILES: Cc1ccc(-c2c(C)nn(-c3nc(-c4ccc(Cl)c(Cl)c4)c(SC(C)C)s3)c2C(=O)O)cc1] | 1-(4-(3,4-dichlorophenyl)-5-(isopropylthio)thiazol-2-yl)-3-methyl-4-p-tolyl-1H-pyrazole-5-carboxylic acid | D | $^1$H NMR (500 MHz, DMSO) δ 8.22 (d, J = 2.0 Hz, 1H), 8.03 (dd, J = 8.5, 2.0 Hz, 1H), 7.73 (d, J = 8.5 Hz, 1H), 7.36 (d, J = 8.0 Hz, 2H), 7.25 (d, J = 8.0 Hz, 2H), 3.43-3.24 (m, 1H), 2.34 (s, 3H), 2.28 (s, 3H), 1.23 (d, J = 6.7 Hz, 6H). MS (m/z): 518.1 [M + 1]$^+$ |
| 120 | 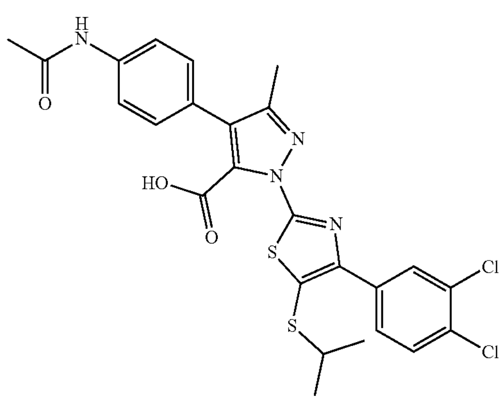 [SMILES: CC(=O)Nc1ccc(-c2c(C)nn(-c3nc(-c4ccc(Cl)c(Cl)c4)c(SC(C)C)s3)c2C(=O)O)cc1] | 4-(4-acetamidophenyl)-1-(4-(3,4-dichlorophenyl)-5-(isopropylthio)thiazol-2-yl)-3-methyl-1H-pyrazole-5-carboxylic acid | H | $^1$H NMR (500 MHz, DMSO) δ 10.05 (s, 1H), 8.21 (d, J = 2.0 Hz, 1H), 8.02 (dd, J = 8.5, 2.0 Hz, 1H), 7.74 (d, J = 8.5 Hz, 1H), 7.64 (d, J = 8.5 Hz, 2H), 7.39 (d, J = 8.5 Hz, 2H), 3.42-3.28 (m, 1H), 2.28 (s, 3H), 2.06 (s, 3H), 1.24 (d, J = 6.7 Hz, 6H). MS (m/z): 561.0 [M + 1]$^+$. |

| Ex. | Structure | Name | EC₅₀ | Characterization |
|---|---|---|---|---|
| 121 | 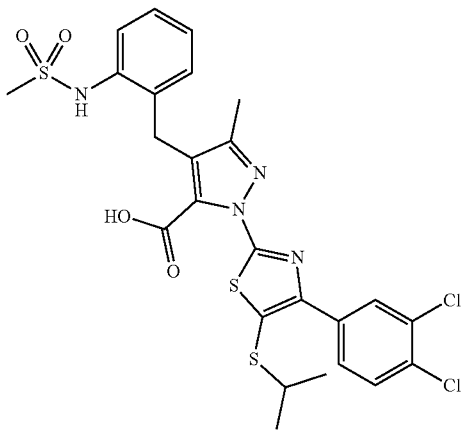 [SMILES: Cc1nn(-c2nc(-c3ccc(Cl)c(Cl)c3)c(SC(C)C)s2)c(C(=O)O)c1Cc1ccccc1NS(C)(=O)=O] | 1-(4-(3,4-dichlorophenyl)-5-(isopropylthio)thiazol-2-yl)-3-methyl-4-(2-(methylsulfonamido)benzyl)-1H-pyrazole-5-carboxylic acid | H | $^1$H NMR (500 MHz, MeOD) δ 8.38 (d, J = 2.0 Hz, 1H), 8.25-8.19 (s, 1H), 8.11 (dd, J = 8.5, 2.0 Hz, 1H), 7.59 (d, J = 8.5 Hz, 1H), 7.53 (d, J = 6.9 Hz, 1H), 7.32 (d, J = 7.7 Hz, 1H), 7.26 (t, J = 7.7 Hz, 1H), 7.17 (t, J = 6.9 Hz, 1H), 4.12 (s, 2H), 3.32-3.25 (m, 1H), 2.76 (s, 3H), 2.09 (s, 3H), 1.30 (d, J = 6.7 Hz, 6H). MS (m/z): 611.1 [M + 1]⁺ |
| 122 | 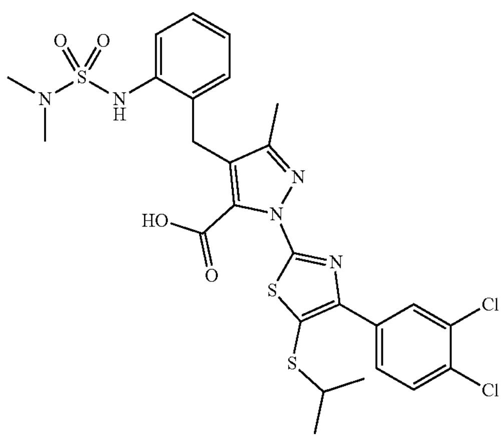 [SMILES: Cc1nn(-c2nc(-c3ccc(Cl)c(Cl)c3)c(SC(C)C)s2)c(C(=O)O)c1Cc1ccccc1NS(=O)(=O)N(C)C] | 1-(4-(3,4-dichlorophenyl)-5-(isopropylthio)thiazol-2-yl)-4-(2-(N,N-dimethylsulfamoylamino)benzyl)-3-methyl-1H-pyrazole-5-carboxylic acid | D | $^1$H NMR (500 MHz, DMSO) δ 8.17 (d, J = 2.1 Hz, 1H), 8.00 (dd, J = 8.5, 2.1 Hz, 1H), 7.77 (d, J = 8.5 Hz, 1H), 7.38 (d, J = 7.2 Hz, 1H), 7.24-7.20 (m, 1H), 7.18-7.08 (m, 1H), 6.93-6.85 (bs, 1H), 4.06 (s, 2H), 3.42-3.24 (m, 1H), 2.74 (s, 6H), 2.02 (s, 3H), 1.23 (d, J = 6.7 Hz, 6H). MS (m/z): 640.2 [M + 1]⁺. |
| 123 | 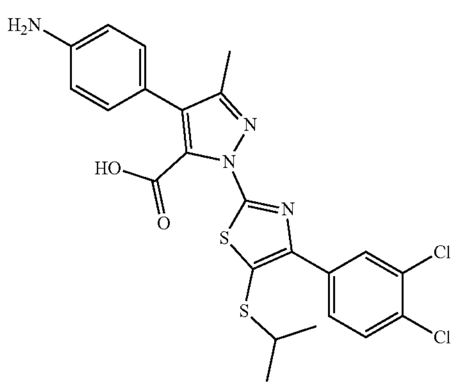 [SMILES: Cc1nn(-c2nc(-c3ccc(Cl)c(Cl)c3)c(SC(C)C)s2)c(C(=O)O)c1-c1ccc(N)cc1] | 4-(4-aminophenyl)-1-(4-(3,4-dichlorophenyl)-5-(isopropylthio)thiazol-2-yl)-3-methyl-1H-pyrazole-5-carboxylic acid | E | $^1$H NMR (500 MHz, MeOD) δ 8.44 (s, 1H), 8.19 (s, 1H), 8.17-8.13 (m, 1H), 7.58 (d, J = 8.5 Hz, 1H), 7.31 (d, J = 8.5 Hz, 2H), 6.81 (d, J = 8.5 Hz, 2H), 3.31-3.23 (m, 1H), 2.32 (s, 2H), 1.30 (d, J = 6.7 Hz, 6H). MS (m/z): 519.0 [M + 1]⁺. |

-continued

| Ex. | Structure | Name | EC$_{50}$ | Characterization |
|---|---|---|---|---|
| 124 | 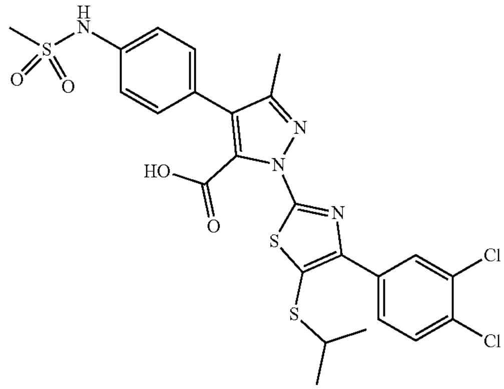 [SMILES: Cc1nn(-c2nc(-c3ccc(Cl)c(Cl)c3)c(SC(C)C)s2)c(C(=O)O)c1-c1ccc(NS(C)(=O)=O)cc1] | 1-(4-(3,4-dichlorophenyl)-5-(isopropylthio)thiazol-2-yl)-3-methyl-4-(4-(methylsulfonamido)phenyl)-1H-pyrazole-5-carboxylic acid | H | $^1$H NMR (500 MHz, DMSO) δ 9.85 (bs, 1H), 8.23 (d, J = 1.7 Hz, 1H), 8.04 (dd, J = 8.5, 1.7 Hz, 1H), 7.73 (d, J = 8.5 Hz, 1H), 7.47 (d, J = 8.4 Hz, 2H), 7.25 (d, J = 8.4 Hz, 2H), 7.09 (bs, 1H), 3.41-3.26 (m, 1H), 3.04 (s, 3H), 2.28 (s, 3H), 1.23 (d, J = 6.7 Hz, 6H). MS (m/z): 597.0 [M + 1]$^+$. |
| 125 | 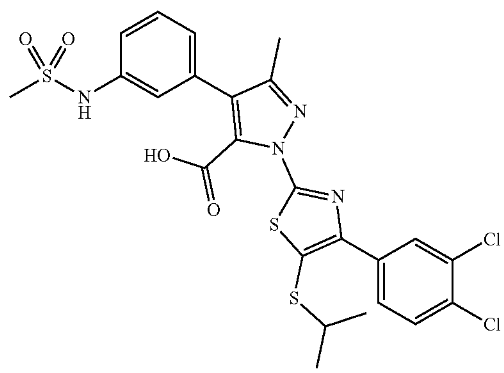 [SMILES: Cc1nn(-c2nc(-c3ccc(Cl)c(Cl)c3)c(SC(C)C)s2)c(C(=O)O)c1-c1cccc(NS(C)(=O)=O)c1] | 1-(4-(3,4-dichlorophenyl)-5-(isopropylthio)thiazol-2-yl)-3-methyl-4-(3-(methylsulfonamido)phenyl)-1H-pyrazole-5-carboxylic acid | H | $^1$H NMR (500 MHz, DMSO) δ 9.85 (s, 1H), 8.23 (s, 1H), 8.03 (dd, J = 8.5, 1.9 Hz, 1H), 7.74 (d, J = 8.5 Hz, 1H), 7.43-7.33 (m, 2H), 7.24 (d, J = 7.5 Hz, 1H), 7.15 (d, J = 7.9 Hz, 1H), 3.41-3.25 (m, 1H), 3.05 (s, 3H), 2.29 (s, 3H), 1.24 (d, J = 6.7 Hz, 6H). MS (m/z): 597.0 [M + 1]$^+$. |
| 126 | 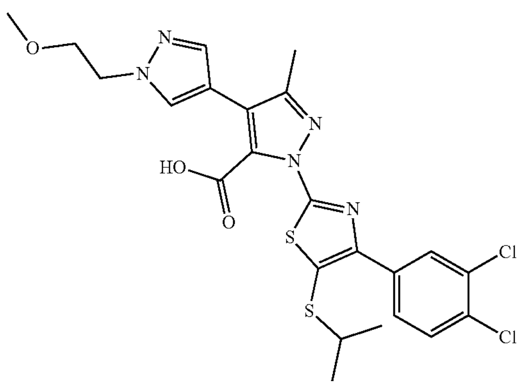 [SMILES: COCCn1cc(-c2c(C)nn(-c3nc(-c4ccc(Cl)c(Cl)c4)c(SC(C)C)s3)c2C(=O)O)cn1] | 2-(4-(3,4-dichlorophenyl)-5-(isopropylthio)thiazol-2-yl)-2'-(2-methoxyethyl)-5-methyl-4,4'-bi(2H-pyrazole)-3-carboxylic acid | D | $^1$H NMR (500 MHz, DMSO) δ 8.40 (d, J = 2.1 Hz, 1H), 8.12 (dd, J = 8.5, 2.1 Hz, 1H), 7.93 (d, J = 0.6 Hz, 1H), 7.78 (d, J = 0.6 Hz, 1H), 7.57 (d, J = 8.5 Hz, 1H), 4.33 (t, J = 5.3 Hz, 2H), 3.76 (t, J = 5.3 Hz, 2H), 3.33 (s, 3H), 3.30-3.23 (m, 1H), 2.39 (s, 3H), 1.28 (d, J = 6.7 Hz, 6H). MS (m/z): 552.0 [M + 1]$^+$. |
| 127 | 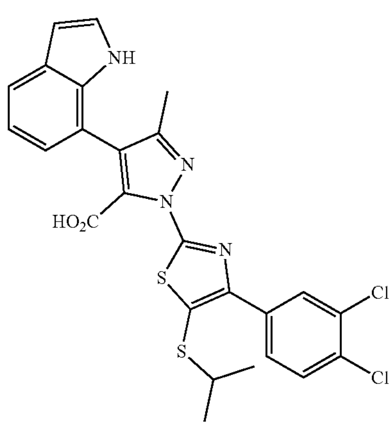 [SMILES: Cc1nn(-c2nc(-c3ccc(Cl)c(Cl)c3)c(SC(C)C)s2)c(C(=O)O)c1-c1cccc2cc[nH]c12] | 1-(4-(3,4-dichlorophenyl)-5-(isopropylthio)thiazol-2-yl)-4-(1H-indol-7-yl)-3-methyl-1H-pyrazole-5-carboxylic acid | C | $^1$H NMR (500 MHz, DMSO) δ 8.27 (s, 1H), 8.08 (d, J = 8.0 Hz, 1H), 7.76 (d, J = 8.5 Hz, 1H), 7.59-7.50 (m, 1H), 7.31 (t, J = 2.8 Hz, 1H), 7.17-6.98 (m, 3H), 6.48 (dd, J = 2.8, 1.7 Hz, 1H), 3.41-3.30 (m, 1H), 2.14 (s, 3H), 1.25 (d, J = 6.7 Hz, 6H). MS (m/z): 543.0 [M + 1]$^+$. |

-continued

| Ex. | Structure | Name | EC$_{50}$ | Characterization |
|---|---|---|---|---|
| 128 | 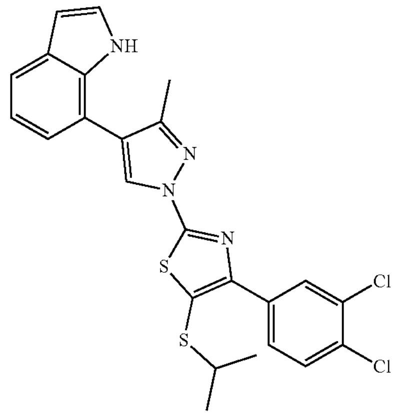 [SMILES: Cc1nn(-c2nc(-c3ccc(Cl)c(Cl)c3)c(SC(C)C)s2)cc1-c1cccc2cc[nH]c12] | 2-(4-(1H-indol-7-yl)-3-methyl-1H-pyrazol-1-yl)-4-(3,4-dichlorophenyl)-5-(isopropylthio)thiazole | D | $^1$H NMR (500 MHz, DMSO) δ 11.02 (s, 1H), 8.78 (s, 1H), 8.34 (d, J = 2.1 Hz, 1H), 8.14 (dd, J = 8.5, 2.1 Hz, 1H), 7.78 (d, J = 8.5 Hz, 1H), 7.58 (d, J = 7.5 Hz, 1H), 7.35 (t, J = 2.8 Hz, 1H), 7.19-7.02 (m, 2H), 6.53 (dd, J = 3.0, 1.8 Hz, 1H), 3.42-3.31 (m, 1H), 2.30 (s, 3H), 1.24 (d, J = 6.7 Hz, 6H). MS (m/z): 499.1 [M + 1]$^+$ |
| 129 | 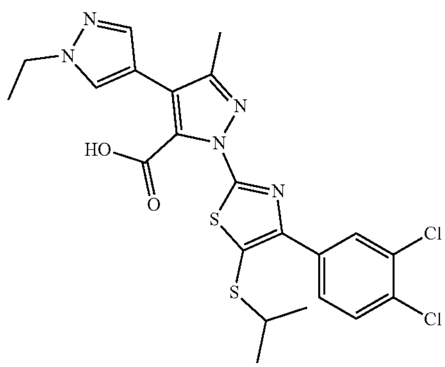 [SMILES: CCn1cc(-c2c(C)nn(-c3nc(-c4ccc(Cl)c(Cl)c4)c(SC(C)C)s3)c2C(=O)O)cn1] | 2-(4-(3,4-dichlorophenyl)-5-(isopropylthio)thiazol-2-yl)-2'-ethyl-5-methyl-4,4'-bi(2H-pyrazole)-3-carboxylic acid | C | $^1$H NMR (500 MHz, DMSO) δ 8.20 (d, J = 2.1 Hz, 1H), 8.04-7.99 (m, 2H), 7.76 (d, J = 8.5 Hz, 1H), 7.66 (d, J = 0.7 Hz, 1H), 4.18 (q, J = 7.3 Hz, 2H), 3.40-3.29 (m, 1H), 2.36 (s, 3H), 1.40 (t, J = 7.3 Hz, 3H), 1.23 (d, J = 6.7 Hz, 6H). MS (m/z): 522.0 [M + 1]$^+$ |
| 130 | 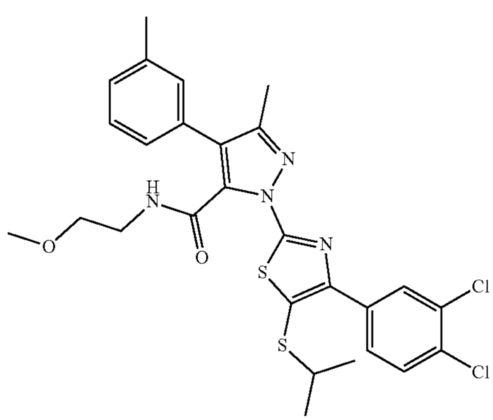 [SMILES: COCCNC(=O)c1c(-c2cccc(C)c2)c(C)nn1-c1nc(-c2ccc(Cl)c(Cl)c2)c(SC(C)C)s1] | 1-(4-(3,4-dichlorophenyl)-5-(isopropylthio)thiazol-2-yl)-N-(2-methoxyethyl)-3-methyl-4-m-tolyl-1H-pyrazole-5-carboxamide | H | $^1$H NMR (500 MHz, DMSO) δ 8.99 (t, J = 5.5 Hz, 1H), 8.17 (d, J = 2.1 Hz, 1H), 8.09 (dd, J = 8.5, 2.1 Hz, 1H), 7.79 (d, J = 8.5 Hz, 1H), 7.33 (t, J = 7.5 Hz, 1H), 7.30-7.25 (m, 2H), 7.19 (d, J = 7.5 Hz, 1H), 3.40-3.33 (m, 4H), 3.33-3.30 (m, 1H), 3.10 (s, 3H), 2.35 (s, 3H), 2.32 (s, 3H), 1.21 (d, J = 6.7 Hz, 6H). MS (m/z): 575.1 [M + 1]$^+$. |
| 131 | 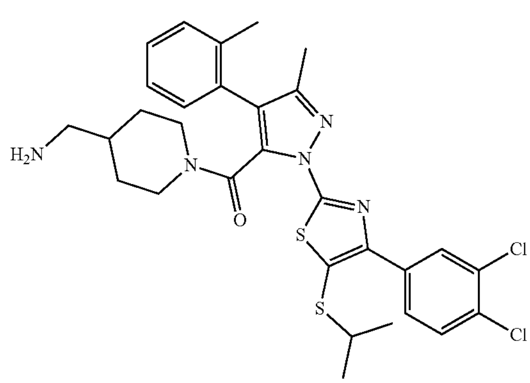 [SMILES: Cc1ccccc1-c1c(C)nn(-c2nc(-c3ccc(Cl)c(Cl)c3)c(SC(C)C)s2)c1C(=O)N1CCC(CN)CC1] | (4-(aminomethyl)piperidin-1-yl)(1-(4-(3,4-dichlorophenyl)-5-(isopropylthio)thiazol-2-yl)-3-methyl-4-o-tolyl-1H-pyrazol-5-yl)methanone | B | $^1$H NMR (500 MHz, DMSO) Complex mixture of rotamers; MS (m/z): 614.2 [M + 1]$^+$ |

| Ex. | Structure | Name | EC$_{50}$ | Characterization |
|---|---|---|---|---|
| 132 | 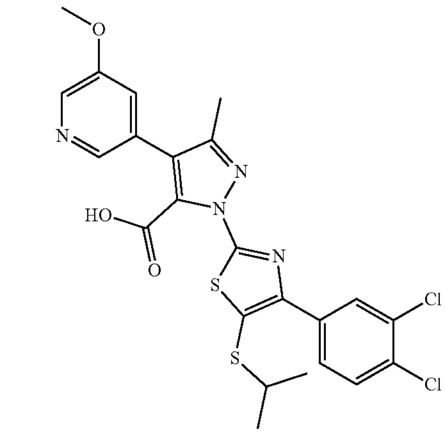 [SMILES: COc1cncc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(5-methoxypyridin-3-yl)-3-methyl-1H-pyrazole-5-carboxylic acid | D | $^1$H NMR (500 MHz, DMSO) δ 8.30 (s, 1H), 8.28 (s, 1H), 8.21 (s, 1H), 8.02 (d, J = 8.5 Hz, 1H), 7.76 (d, J = 8.5 Hz, 1H), 7.52 (s, 1H), 3.87 (s, 3H), 3.50-3.21 (m, 1H), 2.34 (s, 3H), 1.24 d, J = 6.7 Hz, 6H). MS (m/z): 535.0 [M + 1]$^+$. |
| 133 | 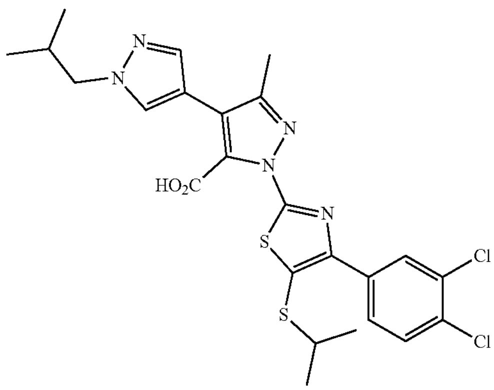 [SMILES: Cc1nn(-c2nc(-c3ccc(Cl)c(Cl)c3)c(SC(C)C)s2)c(C(=O)O)c1-c1cnn(CC(C)C)c1] | 2-(4-(3,4-dichlorophenyl)-5-(isopropylthio)thiazol-2-yl)-2'-isobutyl-5-methyl-4,4'-bi(2H-pyrazole)-3-carboxylic acid | D | $^1$H NMR (500 MHz, DMSO) δ 8.13 (d, J = 2.0 Hz, 1H), 7.95 (dd, J = 8.5, 2.0 Hz, 1H), 7.91 (s, 1H), 7.70 (d, J = 8.5 Hz, 1H), 7.61 (s, 1H), 3.90 (d, J = 7.2 Hz, 2H), 3.32-3.20 (m, 1H), 2.29 (s, 3H), 2.12-1.99 (m, 1H), 1.17 (d, J = 6.7 Hz, 6H), 0.79 (d, J = 6.7 Hz, 6H). MS (m/z): 550.0 [M + 1]$^+$ |
| 134 | 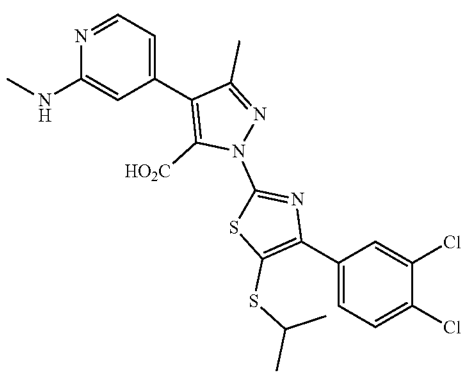 [SMILES: CNc1cc(-c2c(C)nn(-c3nc(-c4ccc(Cl)c(Cl)c4)c(SC(C)C)s3)c2C(=O)O)ccn1] | 1-(4-(3,4-dichlorophenyl)-5-(isopropylthio)thiazol-2-yl)-3-methyl-4-(2-(methylamino)pyridin-4-yl)-1H-pyrazole-5-carboxylic acid | D | $^1$H NMR (500 MHz, DMSO) δ 8.24 (s, 1H), 8.08-8.03 (m, 1H), 7.99-7.96 (m, 1H), 7.75 (d, J = 8.5 Hz, 1H), 6.67-6.51 (m, 3H), 3.37-3.26 (m, 1H), 2.77 (d, J = 4.6 Hz, 3H), 2.30 (s, 3H), 1.23 (d, J = 6.7 Hz, 6H). MS (m/z): 533.9 [M + 1]$^+$ |
| 135 | 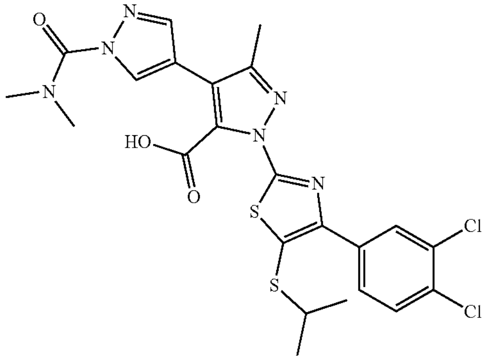 [SMILES: Cc1nn(-c2nc(-c3ccc(Cl)c(Cl)c3)c(SC(C)C)s2)c(C(=O)O)c1-c1cnn(C(=O)N(C)C)c1] | 1-(4-(3,4-dichlorophenyl)-5-(isopropylthio)thiazol-2-yl)-1'-(dimethylcarbamoyl)-3-methyl-1H,1'H-[4,4'-bipyrazole]-5-carboxylic acid | E | $^1$H NMR (500 MHz, DMSO) δ 8.39 (d, J = 0.8 Hz, 1H), 8.25 (s, 1H), 8.09-8.03 (m, 2H), 7.75 (d, J = 8.5 Hz, 1H), 3.34-3.28 (m, 1H), 3.14 (s, 6H), 2.35 (s, 3H), 1.23 (d, J = 6.7 Hz, 6H). MS (m/z): 565.1 [M + 1]$^+$ |

-continued

| Ex. | Structure | Name | EC$_{50}$ | Characterization |
|---|---|---|---|---|
| 136 | 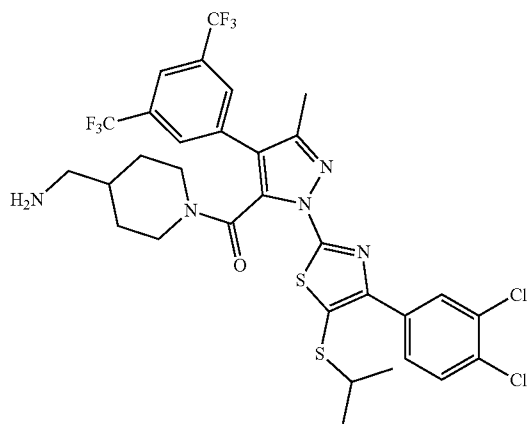 [SMILES: Cc1nn(-c2nc(-c3ccc(Cl)c(Cl)c3)c(SC(C)C)s2)c(C(=O)N2CCC(CN)CC2)c1-c1cc(C(F)(F)F)cc(C(F)(F)F)c1] | (4-(aminomethyl)piperidin-1-yl)(4-(3,5-bis(trifluoromethyl)phenyl)-1-(4-(3,4-dichlorophenyl)-5-(isopropylthio)thiazol-2-yl)-3-methyl-1H-pyrazol-5-yl)methanone | B | $^1$H NMR (500 MHz, DMSO) δ 8.20 (s, 1H), 8.14 (d, J = 2.0 Hz, 1H), 8.10-8.06 (m, 2H), 8.04 (s, 1H), 7.81 (d, 8.5 Hz, 1H), 4.57-4.48 (m, 1H), 3.59-3.48 (m, 1H), 3.41-3.31 (m, 1H), 3.03-2.90 (m, 1H), 2.77-2.59 (m, 2H), 2.41 (s, 3H), 2.26-2.17 (m, 1H), 2.15-1.96 (m, 1H), 1.89-1.79 (m, 1H), 1.66-1.50 (m, 1H), 1.48-1.30 (m, 2H), 1.27-1.5 (m, 6H), 0.76-0.60 (m, 1H), 0.28-0.15 (m 1H). MS (m/z): 738.0 [M + 1]$^+$ |
| 137 | 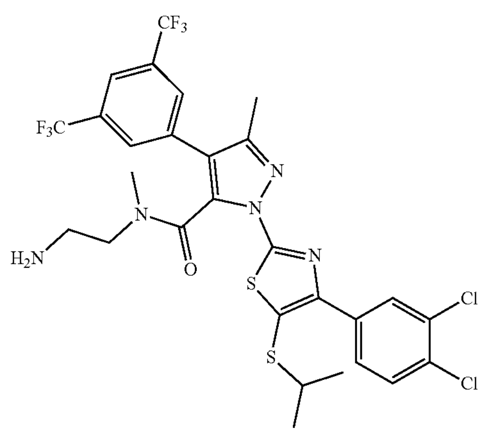 [SMILES: Cc1nn(-c2nc(-c3ccc(Cl)c(Cl)c3)c(SC(C)C)s2)c(C(=O)N(C)CCN)c1-c1cc(C(F)(F)F)cc(C(F)(F)F)c1] | N-(2-aminoethyl)-4-(3,5-bis(trifluoromethyl)phenyl)-1-(4-(3,4-dichlorophenyl)-5-(isopropylthio)thiazol-2-yl)-N,3-dimethyl-1H-pyrazole-5-carboxamide | B | $^1$H NMR (500 MHz, DMSO) δ 8.18 (s, 0.5H), 8.16 (s, 0.5H), 8.15 (d, J = 2.1 Hz, 0.5H), 8.13 (s, 1H), 8.12 (d, J = 2.1 Hz, 0.5H), 8.10 (dd, J = 2.1, 8.5 Hz, 0.5H), 8.08 (s, 1H), 8.03 (dd, J = 2.1, 8.5 Hz, 0.5H), 7.80 (d, J = 8.5 Hz, 0.5H), 7.79 (d, J = 8.5 Hz, 0.5H), 3.77-3.68 (m, 0.5H), 3.43-3.34 (m, 1.5H), 3.14-2.99 (m, 2H), 2.98 (s, 1.5H), 2.80 (s, 1.5H), 2.66-2.57 (m, 1.5H), 2.47-2.27 (m, 1.5H), 2.41 (s, 3H), 1.27-1.23 (m, 6H). MS (m/z): 696.2 [M + 1]$^+$ |
| 138 | 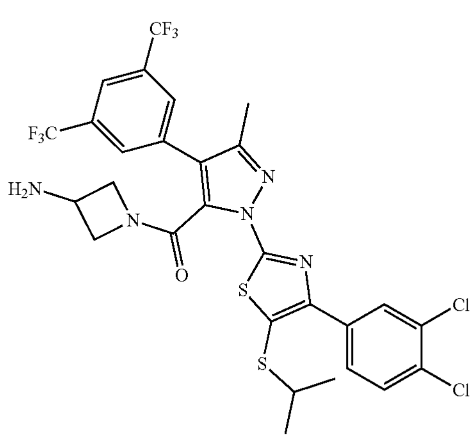 [SMILES: Cc1nn(-c2nc(-c3ccc(Cl)c(Cl)c3)c(SC(C)C)s2)c(C(=O)N2CC(N)C2)c1-c1cc(C(F)(F)F)cc(C(F)(F)F)c1] | (3-aminoazetidin-1-yl)(4-(3,5-bis(trifluoromethyl)phenyl)-1-(4-(3,4-dichlorophenyl)-5-(isopropylthio)thiazol-2-yl)-3-methyl-1H-pyrazol-5-yl)methanone | D | $^1$H NMR (500 MHz, DMSO) δ 9.65 (d, J = 7.4 Hz, 1H), 8.24 (s, 1H), 8.17 (s, 1H), 8.14 (s, 2H), 8.10 (d, J = 2.0 Hz, 1H), 8.02 (dd, J = 2.0, 8.5 Hz, 1H), 7.80 (d, J = 8.5 Hz, 1H), 4.70-4.58 (m, 1H), 3.61-3.53 (m, 2H), 3.43-3.28 (m, 3H), 2.38 (s, 3H), 1.24 (d, J = 6.7 Hz, 6H). MS (m/z): 694.2 [M + 1]$^+$ |

-continued

| Ex. | Structure | Name | EC$_{50}$ | Characterization |
|---|---|---|---|---|
| 139 | 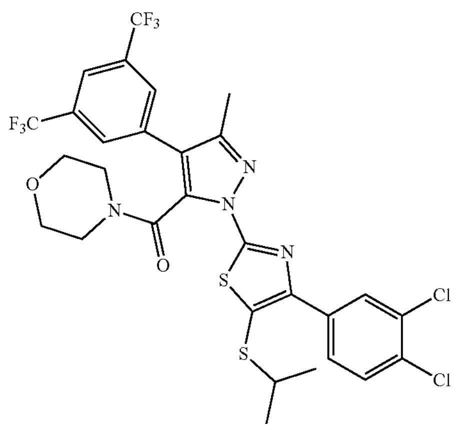 [SMILES: Cc1nn(-c2nc(-c3ccc(Cl)c(Cl)c3)c(SC(C)C)s2)c(C(=O)N2CCOCC2)c1-c1cc(C(F)(F)F)cc(C(F)(F)F)c1] | (4-(3,5-bis(trifluoromethyl)phenyl)-1-(4-(3,4-dichlorophenyl)-5-(isopropylthio)thiazol-2-yl)-3-methyl-1H-pyrazol-5-yl)(morpholino)methanone | D | $^1$H NMR (500 MHz, DMSO) δ 8.22 (s, 1H), 8.13 (d, J = 2.1 Hz, 1H), 8.08 (s, 2H), 8.04 (dd, J = 8.5, 2.1 Hz, 1H), 7.82 (d, J = 8.5 Hz, 1H), 3.84-3.77 (m, 1H), 3.73-3.66 (m, 1H), 3.48-3.44 (m, 1H), 3.42-3.36 (m, 1H), 3.35-3.19 (m, 4H), 3.04-2.96 (m, 1H), 2.40 (s, 3H), 1.27-1.23 (m, 6H). MS (m/z): 709.1 [M + 1]$^+$ |
| 140 | 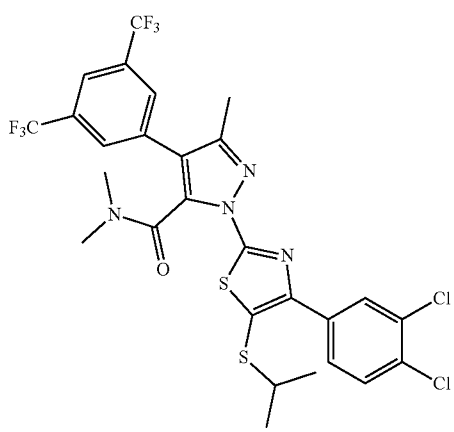 [SMILES: Cc1nn(-c2nc(-c3ccc(Cl)c(Cl)c3)c(SC(C)C)s2)c(C(=O)N(C)C)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-N,N,3-trimethyl-1H-pyrazole-5-carboxamide | I | $^1$H NMR (500 MHz, DMSO) δ 8.17 (s, 1H), 8.14 (d, J = 2.1 Hz, 1H), 8.09-8.06 (m, 3H), 7.81 (d, J = 8.5 Hz, 1H), 3.43-3.34 (m, 1H), 2.99 (s, 3H), 2.80 (s, 3H), 2.42 (s, 3H), 1.26 (d, J = 6.7 Hz, 6H). MS (m/z): 667.1 [M + 1]$^+$ |
| 141 | 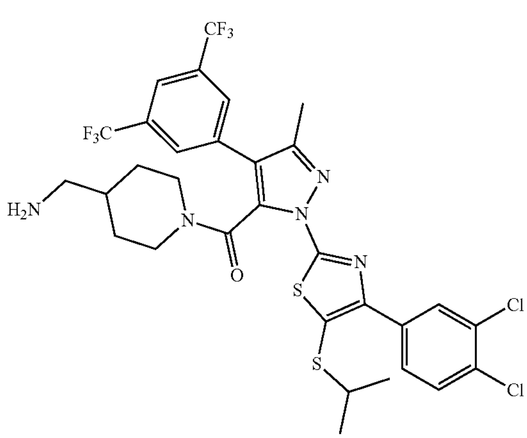 [SMILES: Cc1nn(-c2nc(-c3ccc(Cl)c(Cl)c3)c(SC(C)C)s2)c(C(=O)N2CCC(CN)CC2)c1-c1cc(C(F)(F)F)cc(C(F)(F)F)c1] | (4-(3,5-bis(trifluoromethyl)phenyl)-1-(4-(3,4-dichlorophenyl)-5-(isopropylthio)thiazol-2-yl)-3-methyl-1H-pyrazol-5-yl)(4-(hydroxymethyl)piperidin-1-yl)methanone | I | $^1$H NMR (500 MHz, DMSO) δ 8.19 (s, 1H), 8.14 (d, J = 2.0 Hz, 1H), 8.10-8.05 (m, 2H), 8.03 (s, 1H), 7.81 (d, J = 8.5 Hz, 1H), 4.58-4.51 (m, 1H), 4.49-4.43 (m, 1H), 4.11-4.06 (m, 1H), 3.56-3.50 (m, 1H), 3.42-3.34 (m, 1H), 3.07-2.93 (m, 2H), 2.76-2.64 (m, 1H), 2.41 (s, 3H), 1.82-1.74 (m, 1H), 1.63-1.44 (m, 2H), 1.27-1.24 (m, 6H), 0.78-0.65 (m, 1H), 0.31-0.17 (m, 1H). MS (m/z): 737.1 [M + 1]$^+$ |

-continued

| Ex. | Structure | Name | EC$_{50}$ | Characterization |
|---|---|---|---|---|
| 142 | 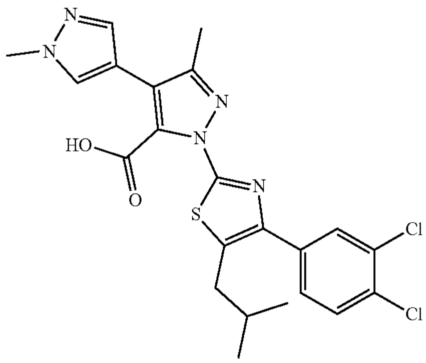 [SMILES: Cc1nn(-c2nc(-c3ccc(Cl)c(Cl)c3)c(CC(C)C)s2)c(C(=O)O)c1-c1cnn(C)c1] | 1-(4-(3,4-dichlorophenyl)-5-isobutylthiazol-2-yl)-1',3-dimethyl-1H,1'H-[4,4'-bipyrazole]-5-carboxylic acid | B | $^1$H NMR (500 MHz, DMSO) δ 7.94 (s, 1H), 7.79 (d, J = 2.0 Hz, 1H), 7.74 (d, J = 8.4 Hz, 1H), 7.64 (s, 1H), 7.60 (dd, J = 8.4, 2.0 Hz, 1H), 3.88 (s, 3H), 2.84 (d, J = 7.1 Hz, 2H), 2.34 (s, 3H), 1.93-1.82 (m, 1H), 0.93 (d, J = 6.6 Hz, 6H). MS (m/z): 490.0 [M + 1]$^+$ |
| 143 | 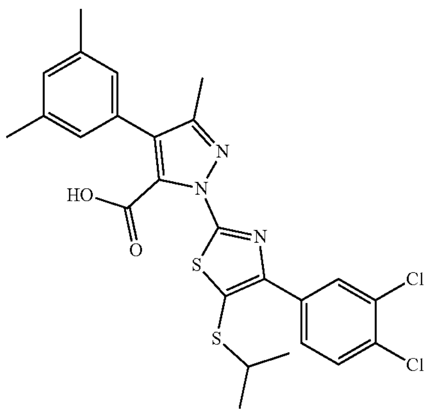 [SMILES: Cc1cc(C)cc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3,5-dimethylphenyl)-3-methyl-1H-pyrazole-5-carboxylic acid | B | $^1$H NMR (500 MHz, DMSO) δ 8.17 (s, 1H), 8.03-7.96 (m, 1H), 7.68 (d, J = 8.4 Hz, 1H), 7.02 (s, 2H), 6.90 (s, 1H), 3.30-3.25 (m, 1H), 2.23 (s, 6H), 2.20 (s, 3H), 1.17 (d, J = 6.7 Hz, 6H). MS (m/z): 532.1 [M + 1]$^+$. |
| 144 | 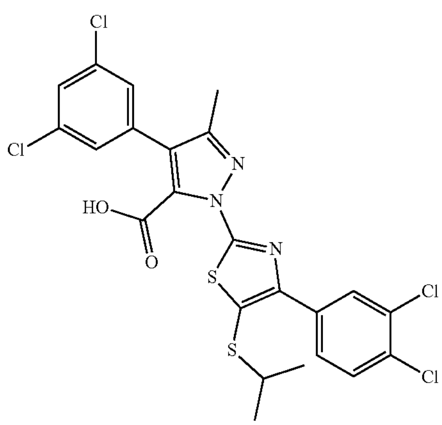 [SMILES: Cc1nn(-c2nc(-c3ccc(Cl)c(Cl)c3)c(SC(C)C)s2)c(C(=O)O)c1-c1cc(Cl)cc(Cl)c1] | 4-(3,5-dichlorophenyl)-1-(4-(3,4-dichlorophenyl)-5-(isopropylthio)thiazol-2-yl)-3-methyl-1H-pyrazole-5-carboxylic acid | A | $^1$H NMR (500 MHz, DMSO) δ 8.19 (d, J = 2.1 Hz, 1H), 8.01 (dd, J = 8.5, 2.1 Hz, 1H), 777 (d, J = 8.5 Hz, 1H), 7.68-7.65 (m, 1H), 7.54 (d, J = 1.9 Hz, 2H), 3.42-3.32 (m, 1H), 2.31 (s, 3H), 1.24 (d, J = 6.7 Hz, 6H). MS (m/z): 571.8 [M + 1]$^+$ |
| 145 | 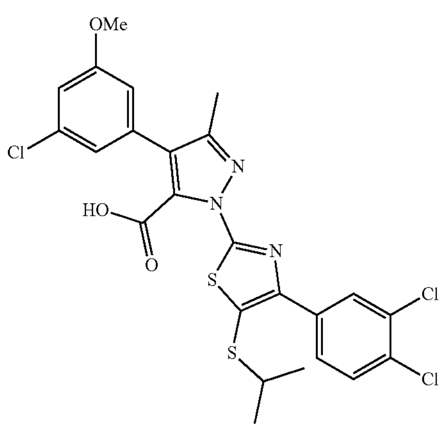 [SMILES: COc1cc(Cl)cc(-c2c(C)nn(-c3nc(-c4ccc(Cl)c(Cl)c4)c(SC(C)C)s3)c2C(=O)O)c1] | 4-(3-chloro-5-methoxyphenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.23 (d, J = 1.7 Hz, 1H), 8.04 (dd, J = 8.4, 1.7 Hz, 1H), 7.73 (d, J = 8.4 Hz, 1H), 7.13 (s, 1H), 7.05 (s, 1H), 7.02 (s, 1H), 3.80 (s, 3H), 3.38-3.32 (m, 1H), 2.30 (s, 3H), 1.23 (d, J = 6.7 Hz, 6H). MS (m/z): 568.0 [M + 1]$^+$ |

| Ex. | Structure | Name | EC$_{50}$ | Characterization |
|---|---|---|---|---|
| 146 | 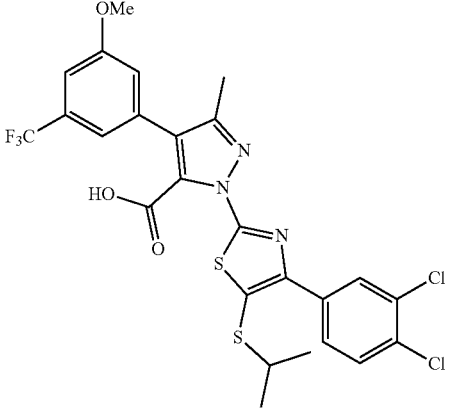 [SMILES: COc1cc(-c2c(C)nn(-c3nc(-c4ccc(Cl)c(Cl)c4)c(SC(C)C)s3)c2C(=O)O)cc(C(F)(F)F)c1] | 1-(4-(3,4-dichlorophenyl)-5-(isopropylthio)thiazol-2-yl)-4-(3-methoxy-5-(trifluoromethyl)phenyl)-3-methyl-1H-pyrazole-5-carboxylic acid | B | $^1$H NMR (500 MHz, DMSO) δ 8.20 (d, J = 2.1 Hz, 1H), 8.02 (dd, J = 8.5, 2.1 Hz, 1H), 7.76 (d, J = 8.5 Hz, 1H), 7.38 (s, 1H), 7.35 (s, 1H), 7.28 (s, 1H), 3.88 (s, 3H), 3.40-3.32 (m, 1H), 2.33 (s, 3H), 1.24 (d, J = 6.7 Hz, 6H). MS (m/z): 601.9 [M + 1]$^+$ |
| 147 | 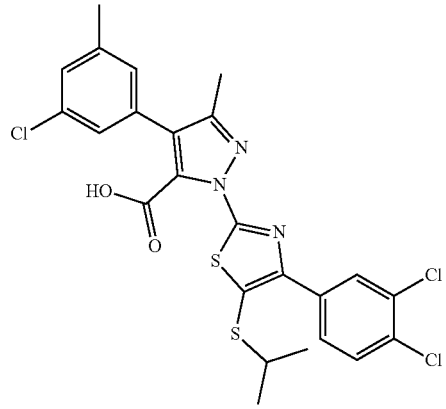 [SMILES: Cc1cc(Cl)cc(-c2c(C)nn(-c3nc(-c4ccc(Cl)c(Cl)c4)c(SC(C)C)s3)c2C(=O)O)c1] | 4-(3-chloro-5-methylphenyl)-1-(4-(3,4-dichlorophenyl)-5-(isopropylthio)thiazol-2-yl)-3-methyl-1H-pyrazole-5-carboxylic acid | A | $^1$H NMR (500 MHz, DMSO) δ 8.20 (d, J = 2.1 Hz, 1H), 8.02 (dd, J = 8.5, 2.1 Hz, 1H), 7.76 (d, J = 8.5 Hz, 1H), 7.32 (s, 1H), 7.30 (s, 1H), 7.25 (s, 1H), 3.41-3.31 (m, 1H), 2.36 (s, 3H), 2.30 (s, 3H), 1.24 (d, J = 6.7 Hz, 6H). MS (m/z): 552.0 [M + 1]$^+$. |
| 148 | 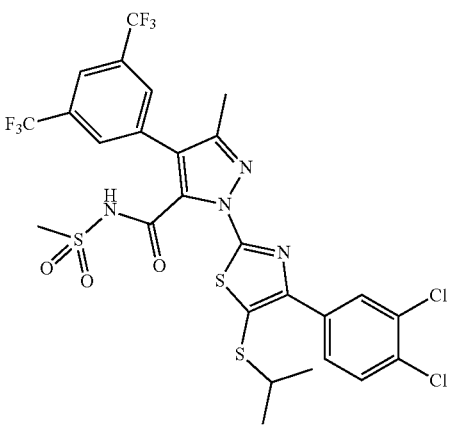 [SMILES: Cc1nn(-c2nc(-c3ccc(Cl)c(Cl)c3)c(SC(C)C)s2)c(C(=O)NS(C)(=O)=O)c1-c1cc(C(F)(F)F)cc(C(F)(F)F)c1] | 4-(3,5-bis(trifluoromethyl)phenyl)-1-(4-(3,4-dichlorophenyl)-5-(isopropylthio)thiazol-2-yl)-3-methyl-N-(methylsulfonyl)-1H-pyrazole-5-carboxamide | I | $^1$H NMR (500 MHz, DMSO) δ 8.26 (s, 1H), 8.18 (s, 2H), 8.15-8.06 (m, 2H), 7.70 (d, J = 8.5 Hz, 1H), 7.33-7.28 (m, 1H), 3.43-3.31 (m, 1H), 2.92 (bs, 3H), 2.37 (s, 3H), 1.24 (d, J = 6.7 Hz, 6H). MS (m/z): 717.1 [M + 1]$^+$. |

| Ex. | Structure | Name | EC$_{50}$ | Characterization |
|---|---|---|---|---|
| 149 | 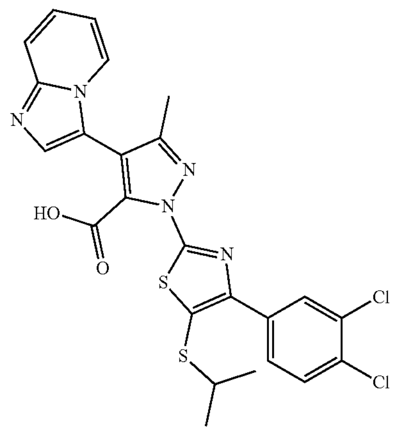 [SMILES: Cc1nn(-c2nc(-c3ccc(Cl)c(Cl)c3)c(SC(C)C)s2)c(C(=O)O)c1-c1cnc2ccccn12] | 1-(4-(3,4-dichlorophenyl)-5-(isopropylthio)thiazol-2-yl)-4-(imidazo[1,2-a]pyridin-3-yl)-3-methyl-1H-pyrazole-5-carboxylic acid | C | $^1$H NMR (500 MHz, DMSO) δ 8.25 (d, J = 6.7 Hz, 1H), 8.21 (d, J = 2.0 Hz, 1H), 8.03 (dd, J = 8.5, 2.0 Hz, 1H), 7.77 (d, J = 8.5 Hz, 1H), 7.69 (s, 1H), 7.65 (d, J = 9.1 Hz, 1H), 7.36-7.28 (m, 1H), 6.93 (t, J = 6.8 Hz, 1H), 3.43-3.33 (m, 1H), 2.16 (s, 3H), 1.25 (d, J = 6.7 Hz, 6H). MS (m/z): 544.1 [M + 1]$^+$ |
| 150 | 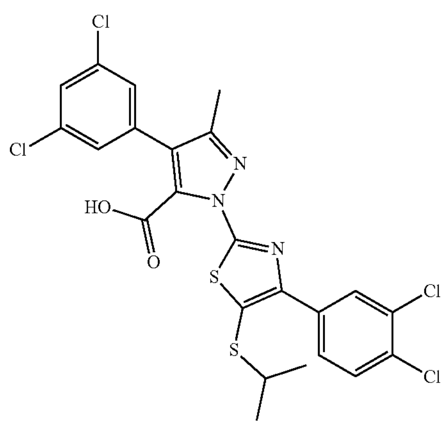 [SMILES: Cc1nn(-c2nc(-c3ccc(Cl)c(Cl)c3)c(SC(C)C)s2)c(C(=O)O)c1-c1cc(Cl)cc(Cl)c1] | 4-(3,5-dichlorophenyl)-1-(4-(3,5-dichlorophenyl)-5-(isopropylthio)thiazol-2-yl)-3-methyl-1H-pyrazole-5-carboxylic acid | B | $^1$H NMR (500 MHz, DMSO) δ 8.02-8.00 (m, 2H), 7.70-7.68 (m, 1H), 7.65-6.63 (m, 1H), 7.57-7.53 (m, 2H), 3.40-3.33 (m, 1H), 2.30 (s, 3H), 1.24 (d, J = 6.7 Hz, 6H). MS (m/z): 571.9 [M + 1]$^+$. |
| 151 | 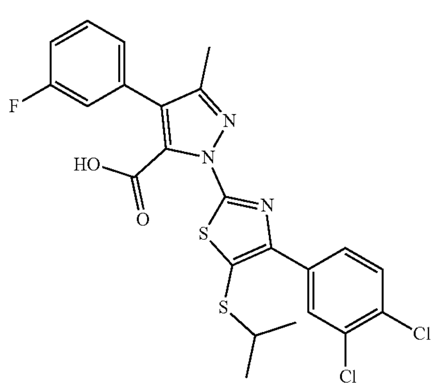 [SMILES: Cc1nn(-c2nc(-c3ccc(Cl)c(Cl)c3)c(SC(C)C)s2)c(C(=O)O)c1-c1cccc(F)c1] | 1-(4-(3,4-dichlorophenyl)-5-(isopropylthio)thiazol-2-yl)-4-(3-fluorophenyl)-3-methyl-1H-pyrazole-5-carboxylic acid | A, B | $^1$H NMR (500 MHz, DMSO) δ 8.21 (d, J = 2.1 Hz, 1H), 8.02 (dd, J = 8.5, 2.1 Hz, 1H), 7.74 (d, J = 8.5 Hz, 1H), 7.53-7.47 (m, 1H), 7.36-7.30 (m, 2H), 7.25-7.18 (m, 1H), 3.38-3.33 (m, 1H), 2.31 (s, 3H), 1.24 (d, J = 6.7 Hz, 6H). MS (m/z): 522.0 [M + 1]$^+$ |

-continued

| Ex. | Structure | Name | EC$_{50}$ | Characterization |
|---|---|---|---|---|
| 152 | 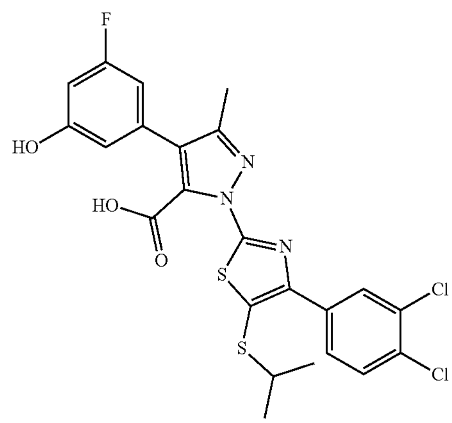 [SMILES: Cc1nn(-c2nc(-c3ccc(Cl)c(Cl)c3)c(SC(C)C)s2)c(C(=O)O)c1-c1cc(O)cc(F)c1] | 1-(4-(3,4-dichlorophenyl)-5-(isopropylthio)thiazol-2-yl)-4-(3-fluoro-5-hydroxyphenyl)-3-methyl-1H-pyrazole-5-carboxylic acid | C | $^1$H NMR (500 MHz, DMSO) δ 10.05 (s, 1H), 8.24 (d, J = 2.1 Hz, 1H), 8.04 (dd, J = 8.5, 2.1 Hz, 1H), 7.73 (d, J = 8.5 Hz, 1H), 7.09 (bs, 1H), 6.80-6.73 (m, 2H), 6.56-6.49 (m, 1H), 3.39-3.31 (m, 1H), 2.28 (s, 3H), 1.23 (d, J = 6.7 Hz, 6H). MS (m/z): 538.0 [M + 1]$^+$ |
| 153 | 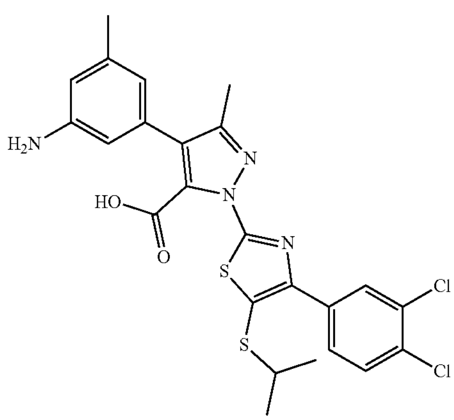 [SMILES: Cc1cc(N)cc(-c2c(C)nn(-c3nc(-c4ccc(Cl)c(Cl)c4)c(SC(C)C)s3)c2C(=O)O)c1] | 4-(3-amino-5-methylphenyl)-1-(4-(3,4-dichlorophenyl)-5-(isopropylthio)thiazol-2-yl)-3-methyl-1H-pyrazole-5-carboxylic acid | J | $^1$H NMR (500 MHz, DMSO) δ 8.21 (d, J = 1.9 Hz, 1H), 8.03 (dd, J = 8.5, 1.9 Hz, 1H), 7.75 (d, J = 8.5 Hz, 1H), 6.43 (s, 1H), 6.39 (s, 2H), 3.41-3.32 (m, 1H), 2.26 (s, 3H), 2.18 (s, 3H), 1.24 (d, J = 6.7 Hz, 6H). MS (m/z): 533.0 [M + 1]$^+$ |
| 154 | 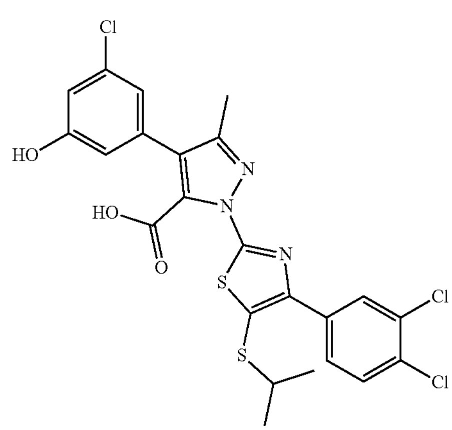 | 4-(3-chloro-5-hydroxyphenyl)-1-(4-(3,4-dichlorophenyl)-5-(isopropylthio)thiazol-2-yl)-3-methyl-1H-pyrazole-5-carboxylic acid | D | $^1$H NMR (500 MHz, DMSO) δ 10.06 (s, 1H), 8.26 (d, J = 2.1 Hz, 1H), 8.07 (dd, J = 8.5, 2.1 Hz, 1H), 7.74 (d, J = 8.5 Hz, 1H), 7.15 (bs, 1H), 7.01 (s, 1H), 6.88 (s, 1H), 6.76 (s, 1H), 3.42-3.34 (m, 1H), 2.27 (s, 3H), 1.24 (d, J = 6.7 Hz, 6H). MS (m/z): 554.0 [M + 1]$^+$ |

-continued

| Ex. | Structure | Name | EC₅₀ | Characterization |
|---|---|---|---|---|
| 155 | 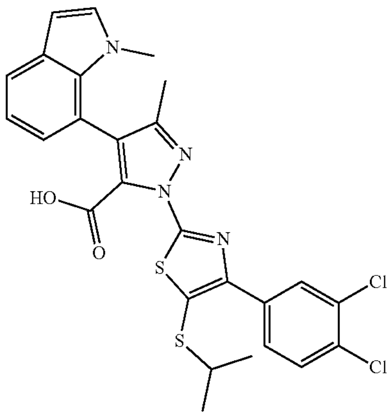 [SMILES: Cc1nn(-c2nc(-c3ccc(Cl)c(Cl)c3)c(SC(C)C)s2)c(C(=O)O)c1-c1cccc2ccn(C)c12] | 1-(4-(3,4-dichlorophenyl)-5-(isopropylthio)thiazol-2-yl)-3-methyl-4-(1-methyl-1H-indol-7-yl)-1H-pyrazole-5-carboxylic acid | C | $^1$H NMR (500 MHz, DMSO) δ 8.19 (d, J = 2.1 Hz, 1H), 7.99 (dd, J = 8.5, 2.1 Hz, 1H), 7.76 (d, J = 8.5 Hz, 1H), 7.60 (d, J = 7.2 Hz, 1H), 7.28 (d, J = 3.1 Hz, 1H), 7.10-7.03 (m, 1H), 6.91 (dd, J = 7.1, 0.9 Hz, 1H), 6.48 (d, J = 3.1 Hz, 1H), 3.47 (s, 3H), 3.42-3.34 (m, 1H), 2.04 (s, 3H), 1.25 (d, J = 6.7 Hz, 6H). MS (m/z): 557.0 [M + 1]⁺ |
| 156 | 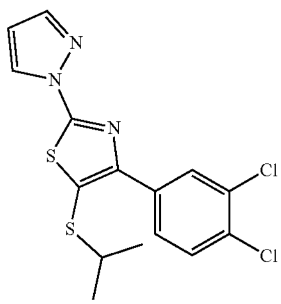 [SMILES: CC(C)Sc1sc(-n2cccn2)nc1-c1ccc(Cl)c(Cl)c1] | 4-(3,4-dichlorophenyl)-5-(isopropylthio)-2-(1H-pyrazol-1-yl)thiazole | J | |
| 157 | 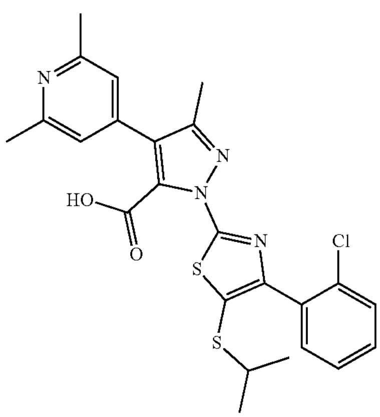 [SMILES: Cc1cc(-c2c(C)nn(-c3nc(-c4ccccc4Cl)c(SC(C)C)s3)c2C(=O)O)cc(C)n1] | 1-(4-(2-chlorophenyl)-5-(isopropylthio)thiazol-2-yl)-4-(2,6-dimethylpyridin-4-yl)-3-methyl-1H-pyrazole-5-carboxylic acid | B | $^1$H NMR (500 MHz, DMSO) δ 7.59-7.56 (m, 1H), 7.51-7.42 (m, 3H), 7.11 (s, 2H), 3.24-3.17 (m, 1H), 2.45 (s, 6H), 2.32 (s, 3H), 1.15 (d, J = 6.7 Hz, 6H). MS (m/z): 499.3 [M + 1]⁺. |
| 158 | 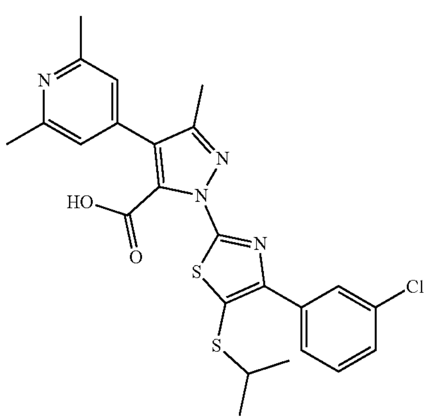 [SMILES: Cc1cc(-c2c(C)nn(-c3nc(-c4cccc(Cl)c4)c(SC(C)C)s3)c2C(=O)O)cc(C)n1] | 1-(4-(3-chlorophenyl)-5-(isopropylthio)thiazol-2-yl)-4-(2,6-dimethylpyridin-4-yl)-3-methyl-1H-pyrazole-5-carboxylic acid | C | $^1$H NMR (500 MHz, DMSO) δ 8.04-7.97 (m, 2H), 7.55-7.46 (m, 2H), 7.16 (s, 2H), 3.38-3.30 (m, 1H), 2.46 (s, 6H), 2.33 (s, 3H), 1.24 (d, J = 6.7 Hz, 6H). MS (m/z): 499.4 [M + 1]⁺ |

-continued

| Ex. | Structure | Name | EC$_{50}$ | Characterization |
|---|---|---|---|---|
| 159 | 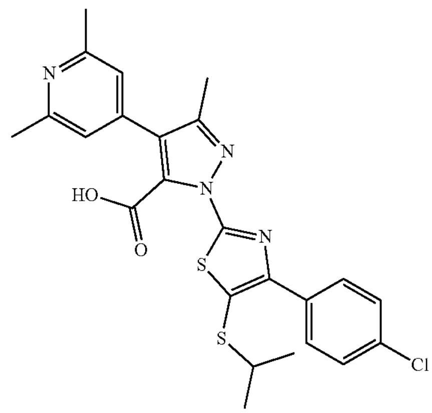 [SMILES: Cc1cc(-c2c(C)nn(-c3nc(-c4ccc(Cl)cc4)c(SC(C)C)s3)c2C(=O)O)cc(C)n1] | 1-(4-(4-chlorophenyl)-5-(isopropylthio)thiazol-2-yl)-4-(2,6-dimethylpyridin-4-yl)-3-methyl-1H-pyrazole-5-carboxylic acid | A | $^1$H NMR (500 MHz, DMSO) δ 8.06-8.01 (m, 2H), 7.55-7.51 (m, 2H), 7.15 (s, 2H), 3.38-3.29 (m, 1H), 2.45 (s, 6H), 2.32 (s, 3H), 1.23 (d, J = 6.7 Hz, 6H). MS (m/z): 499.4 [M + 1]$^+$ |
| 160 | 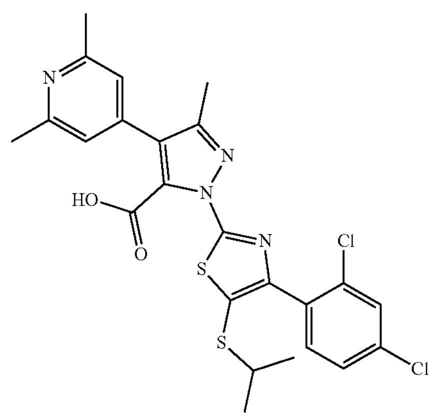 [SMILES: Cc1cc(-c2c(C)nn(-c3nc(-c4ccc(Cl)cc4Cl)c(SC(C)C)s3)c2C(=O)O)cc(C)n1] | 1-(4-(2,4-dichlorophenyl)-5-(isopropylthio)thiazol-2-yl)-4-(2,6-dimethylpyridin-4-yl)-3-methyl-1H-pyrazole-5-carboxylic acid | A | $^1$H NMR (500 MHz, DMSO) δ 7.77 (d, J = 2.1 Hz, 1H), 7.55 (dd, J = 8.3, 2.1 Hz, 1H), 7.49 (d, J = 8.3 Hz, 1H), 7.12 (s, 2H), 3.25-3.16 (m, 1H), 2.44 (s, 6H), 2.31 (s, 3H), 1.15 (d, J = 6.7 Hz, 6H). MS (m/z): 533.4 [M + 1]$^+$ |
| 161 | 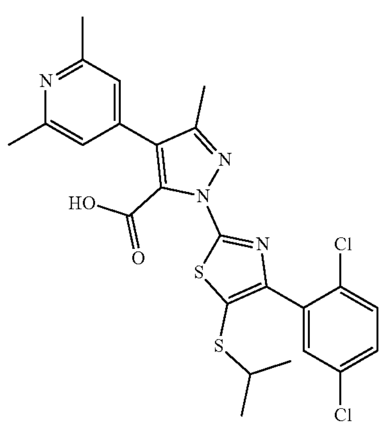 [SMILES: Cc1cc(-c2c(C)nn(-c3nc(-c4cc(Cl)ccc4Cl)c(SC(C)C)s3)c2C(=O)O)cc(C)n1] | 1-(4-(2,5-dichlorophenyl)-5-(isopropylthio)thiazol-2-yl)-4-(2,6-dimethylpyridin-4-yl)-3-methyl-1H-pyrazole-5-carboxylic acid | C | $^1$H NMR (500 MHz, DMSO) δ 7.63 (d, J = 8.5 Hz, 1H), 7.59-7.54 (m, 2H), 7.13 (s, 2H), 3.26-3.15 (m, 1H), 2.44 (s, 6H), 2.31 (s, 3H), 1.16 (d, J = 6.7 Hz, 6H). MS (m/z): 533.4 [M + 1]$^+$ |

| Ex. | Structure | Name | EC$_{50}$ | Characterization |
|---|---|---|---|---|
| 162 | 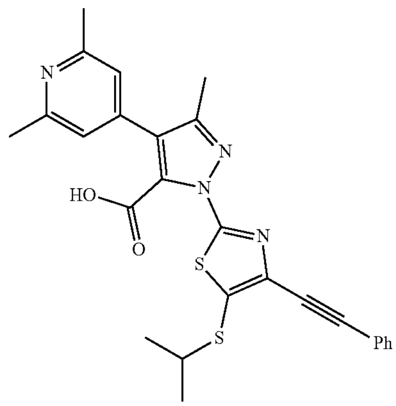 [SMILES: Cc1cc(-c2c(C)nn(-c3nc(C#Cc4ccccc4)c(SC(C)C)s3)c2C(=O)O)cc(C)n1] | 4-(2,6-dimethylpyridin-4-yl)-1-(5-(isopropylthio)-4-(phenylethynyl)thiazol-2-yl)-3-methyl-1H-pyrazole-5-carboxylic acid | C | |
| 163 | 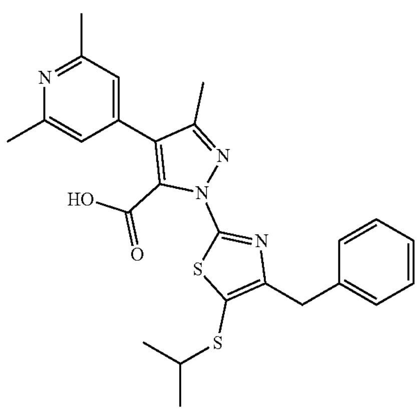 [SMILES: Cc1cc(-c2c(C)nn(-c3nc(Cc4ccccc4)c(SC(C)C)s3)c2C(=O)O)cc(C)n1] | 1-(4-benzyl-5-(isopropylthio)thiazol-2-yl)-4-(2,6-dimethylpyridin-4-yl)-3-methyl-1H-pyrazole-5-carboxylic acid | D | |
| 164 | 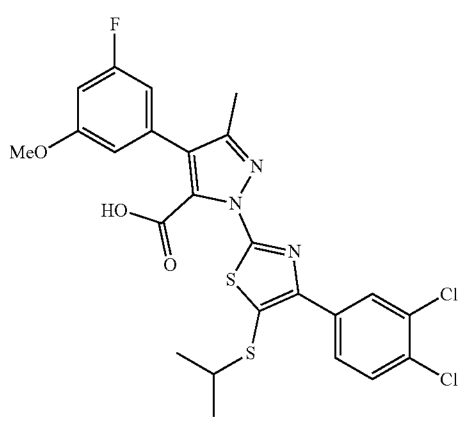 [SMILES: COc1cc(F)cc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3-fluoro-5-methoxyphenyl)-3-methyl-1H-pyrazole-5-carboxylic acid | B | $^1$H NMR (500 MHz, DMSO) δ 8.21 (d, J = 1.8 Hz, 1H), 8.03 (dd, J = 8.5. 1.8 Hz, 1H), 7.75 (d, J = 8.5 Hz, 1H), 6.94-6.89 (m, 2H), 6.86 (d, J = 11.5 Hz, 1H), 3.80 (s, 3H), 3.35 (sept, J = 6.7 Hz, 1H), 2.32 (s, 3H), 1.24 (d, J = 6.7 Hz, 6H); MS (m/z): 552.1 [M + 1]$^+$ |

-continued

| Ex. | Structure | Name | EC$_{50}$ | Characterization |
|---|---|---|---|---|
| 165 | 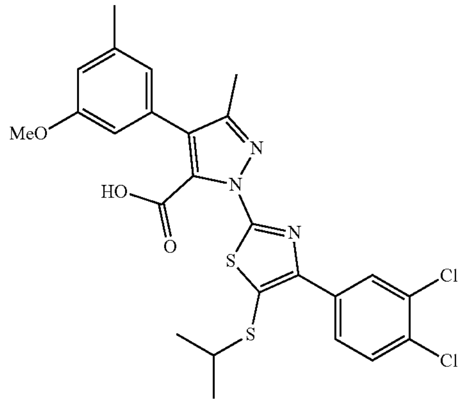 [SMILES: COc1cc(C)cc(-c2c(C)nn(-c3nc(-c4ccc(Cl)c(Cl)c4)c(SC(C)C)s3)c2C(=O)O)c1] | 1-(4-(3,4-dichlorophenyl)-5-(isopropylthio)thiazol-2-yl)-4-(3-methoxy-5-methylphenyl)-3-methyl-1H-pyrazole-5-carboxylic acid | B | $^1$H NMR (500 MHz, DMSO) δ 8.24 (s, 1H), 8.09-8.03 (m, 1H), 7.74 (d, J = 8.5 Hz, 1H), 6.91-6.85 (m, 2H), 6.74 (s, 1H), 3.75 (s, 3H), 3.33 (sept, J = 6.7 Hz, 1H), 2.31 (s, 3H), 2.29 (s, 3H), 1.24 (d, J = 6.7 Hz, 6H); MS (m/z): 548.1 [M + 1]$^+$. |
| 166 | 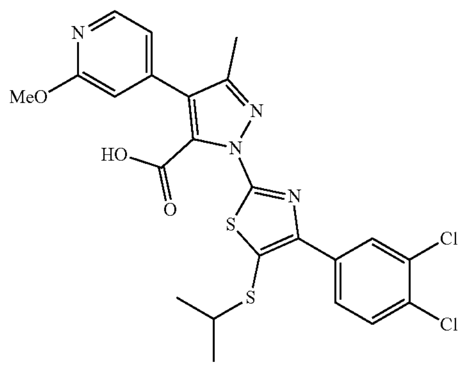 [SMILES: COc1cc(-c2c(C)nn(-c3nc(-c4ccc(Cl)c(Cl)c4)c(SC(C)C)s3)c2C(=O)O)ccn1] | 1-(4-(3,4-dichlorophenyl)-5-(isopropylthio)thiazol-2-yl)-4-(2-methoxypyridin-4-yl)-3-methyl-1H-pyrazole-5-carboxylic acid | C | $^1$H NMR (500 MHz, DMSO) δ 8.24 (d, J = 5.1 Hz, 1H), 8.20 (d, J = 2.1 Hz, 1H), 8.01 (dd, J = 8.5, 2.1 Hz, 1H), 7.77 (d, J = 8.5 Hz, 1H), 7.08 (d, J = 5.2 Hz, 1H), 6.90 (s, 1H), 3.89 (s, 3H), 3.35 (sept, J = 6.7, 1H), 2.34 (s, 3H), 1.24 (d, J = 6.7 Hz, 6H); MS (m/z): 535.0 [M + 1]$^+$. |
| 167 | 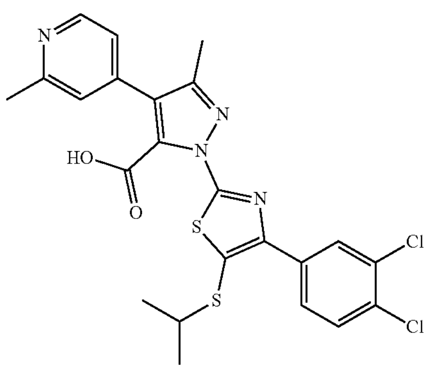 [SMILES: Cc1cc(-c2c(C)nn(-c3nc(-c4ccc(Cl)c(Cl)c4)c(SC(C)C)s3)c2C(=O)O)ccn1] | 1-(4-(3,4-dichlorophenyl)-5-(isopropylthio)thiazol-2-yl)-3-methyl-4-(2-methylpyridin-4-yl)-1H-pyrazole-5-carboxylic acid | B | $^1$H NMR (500 MHz, DMSO) δ 8.52 (d, J = 5.2 Hz, 1H), 8.20 (d, J = 2.1 Hz, 1H), 8.01 (dd, J = 6.5, 2.1 Hz, 1H), 7.77 (d, J = 8.5 Hz, 1H), 7.35 (s, 1H), 7.30-7.26 (m, 1H), 3.35 (sept, J = 6.7 Hz, 1H), 2.52 (s, 3H), 2.34 (s, 3H), 1.24 (d, J = 6.7 Hz, 6H); MS (m/z): 519.0 [M + 1]$^+$. |
| 168 | 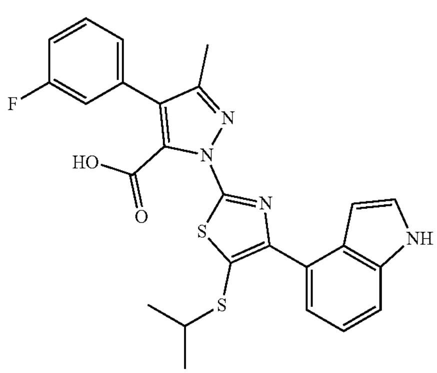 [SMILES: Cc1nn(-c2nc(-c3cccc4[nH]ccc34)c(SC(C)C)s2)c(C(=O)O)c1-c1cccc(F)c1] | 1-(4-(1H-indol-4-yl)-5-(isopropylthio)thiazol-2-yl)-4-(3-fluorophenyl)-3-methyl-1H-pyrazole-5-carboxylic acid | J | |

-continued

| Ex. | Structure | Name | EC₅₀ | Characterization |
|---|---|---|---|---|
| 169 | 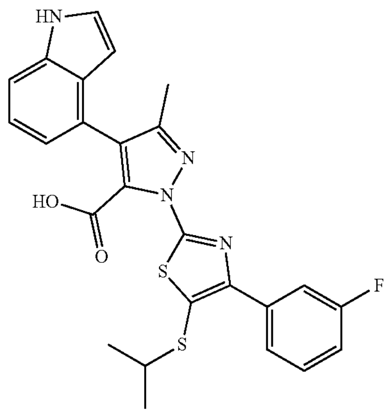 [SMILES: Cc1nn(-c2nc(-c3cccc(F)c3)c(SC(C)C)s2)c(C(=O)O)c1-c1cccc2[nH]ccc12] | 1-(4-(3-fluorophenyl)-5-(isopropylthio)thiazol-2-yl)-4-(1H-indol-4-yl)-3-methyl-1H-pyrazole-5-carboxylic acid | J | |
| 170 | 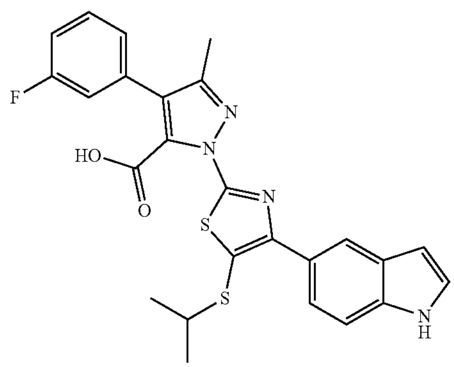 [SMILES: Cc1nn(-c2nc(-c3ccc4[nH]ccc4c3)c(SC(C)C)s2)c(C(=O)O)c1-c1cccc(F)c1] | 1-(4-(1H-indol-5-yl)-5-(isopropylthio)thiazol-2-yl)-4-(3-fluorophenyl)-3-methyl-1H-pyrazole-5-carboxylic acid | J | |
| 171 | 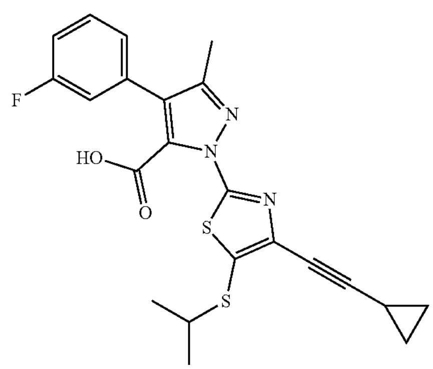 [SMILES: Cc1nn(-c2nc(C#CC3CC3)c(SC(C)C)s2)c(C(=O)O)c1-c1cccc(F)c1] | 1-(4-(cyclopropylethynyl)-5-(isopropylthio)thiazol-2-yl)-4-(3-fluorophenyl)-3-methyl-1H-pyrazole-5-carboxylic acid | J | $^1$H NMR (500 MHz, MeOD) δ 7.40 (td, J = 7.9, 6.0 Hz, 1H), 7.33-7.23 (m, 2H), 7.04 (ddd, J = 8.0, 3.1, 1.3 Hz, 1H), 3.40-3.31 (m, 1H), 2.30 (s, 3H), 1.49 (ddd, J = 10.0, 6.6, 4.2 Hz, 1H), 1.32 (d, J = 6.7 Hz, 6H), 1.00-0.87 (m, 2H), 0.82-0.73 (m, 2H); MS (m/z): 442.1 [M + 1]⁺. |
| 172 | 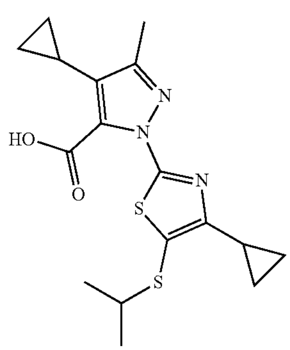 [SMILES: Cc1nn(-c2nc(C3CC3)c(SC(C)C)s2)c(C(=O)O)c1C1CC1] | 4-cyclopropyl-1-(4-cyclopropyl-5-(isopropylthio)thiazol-2-yl)-3-methyl-1H-pyrazole-5-carboxylic acid | J | $^1$H NMR (500 MHz, MeOD) δ 3.15 (hept, J = 6.7 Hz, 1H), 2.33 (tt, J = 8.2, 4.9 Hz, 1H), 2.28 (s, 3H), 1.65 (tt, J = 8.5, 5.4 Hz, 1H), 1.29 (d, J = 6.7 Hz, 6H), 0.97 (ddd, J = 7.8, 4.9, 2.5 Hz, 2H), 0.94-0.89 (m, 2H), 0.85 (ddd, J = 8.5, 6.2, 4.2 Hz, 2H), 0.71-0.66 (m, 2H); MS (m/z): 364.3 [M + 1]⁺. |

| Ex. | Structure | Name | EC$_{50}$ | Characterization |
|---|---|---|---|---|
| 173 | 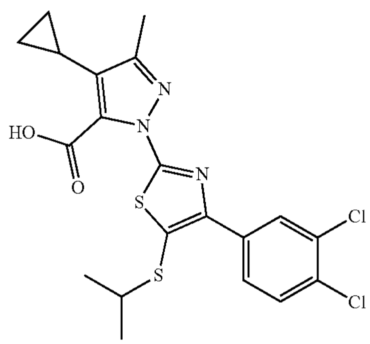 [SMILES: Cc1nn(-c2nc(-c3ccc(Cl)c(Cl)c3)c(SC(C)C)s2)c(C(=O)O)c1C1CC1] | 4-cyclopropyl-1-(4-(3,4-dichlorophenyl)-5-(isopropylthio)thiazol-2-yl)-3-methyl-1H-pyrazole-5-carboxylic acid | D | $^1$H NMR (500 MHz, DMSO) δ 8.18 (d, J = 2.1 Hz, 1H), 8.00 (dd, J = 8.5, 2.1 Hz, 1H), 7.74 (d, J = 8.5 Hz, 1H), 3.36-3.25 (m, 1H), 2.26 (s, 3H), 1.70-1.63 (m, 1H), 1.22 (d, J = 6.7 Hz, 6H), 0.88-0.79 (m, 2H), 0.69-0.61 (m, 2H). MS (m/z): 468.1 [M + 1]$^+$ |
| 174 | 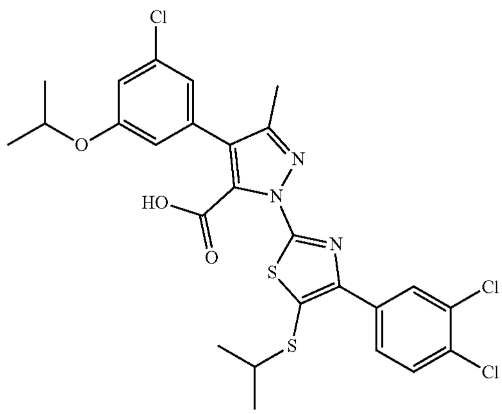 [SMILES: Cc1nn(-c2nc(-c3ccc(Cl)c(Cl)c3)c(SC(C)C)s2)c(C(=O)O)c1-c1cc(Cl)cc(OC(C)C)c1] | 4-(3-chloro-5-isopropoxyphenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.22 (s, 1H), 8.04 (d, J = 8.4 Hz, 1H), 7.74 (d, J = 8.5 Hz, 1H), 7.08 (s, 1H), 6.99 (s, 2H), 4.67 (d, J = 6.0 Hz, 1H), 3.35 (sept, J = 6.7 Hz, 1H), 2.30 (s, 3H), 1.29 (d, J = 6.0 Hz, 6H), 1.24 (d, J = 6.7 Hz, 6H); MS (m/z): 596.0 [M + 1]$^+$. |
| 175 | 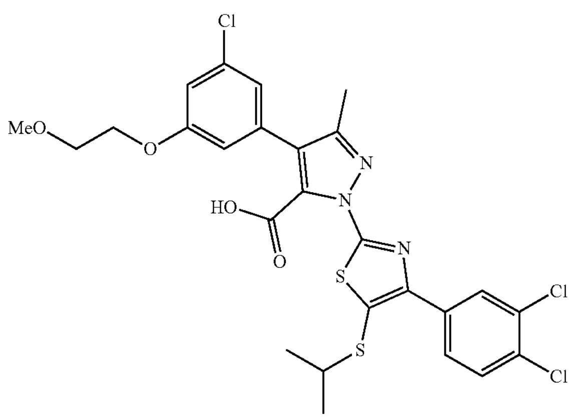 [SMILES: COCCOc1cc(Cl)cc(-c2c(C)nn(-c3nc(-c4ccc(Cl)c(Cl)c4)c(SC(C)C)s3)c2C(=O)O)c1] | 4-(3-chloro-5-(2-methoxyethoxy)phenyl)-1-(4-(3,4-dichlorophenyl)-5-(isopropylthio)thiazol-2-yl)-3-methyl-1H-pyrazole-5-carboxylic acid | B | $^1$H NMR (500 MHz, DMSO) δ 8.24 (s, 1H), 8.06 (d, J = 8.2 Hz, 1H), 7.74 (d, J = 8.5 Hz, 1H), 7.15 (s, 1H), 7.07 (s, 1H), 7.01 (s, 1H), 4.16-4.12 (m, 2H), 3.68-3.65 (m, 2H), 3.35 (sept, J = 6.7 Hz, 1H), 3.31 (s, 3H), 2.30 (s, 3H), 1.23 (d, J = 6.7 Hz, 6H); MS (m/z): 611.9 [M + 1]$^+$ |
| 176 | 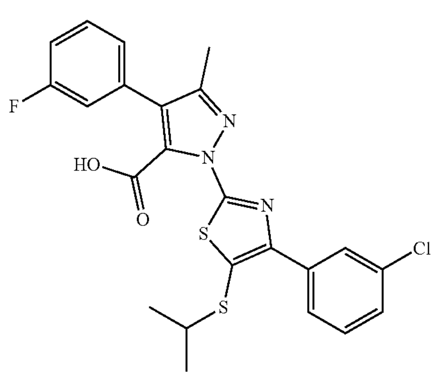 [SMILES: Cc1nn(-c2nc(-c3cccc(Cl)c3)c(SC(C)C)s2)c(C(=O)O)c1-c1cccc(F)c1] | 1-(4-(3-chlorophenyl)-5-(isopropylthio)thiazol-2-yl)-4-(3-fluorophenyl)-3-methyl-1H-pyrazole-5-carboxylic acid | C | $^1$H NMR (500 MHz, DMSO) δ 8.04-8.01 (m, 1H), 8.00-7.96 (m, 1H), 7.55-7.46 (m, 3H), 7.39-7.30 (m, 2H), 7.25-7.16 (m, 1H), 3.40-3.29 (m, 1H), 2.31 (s, 3H), 1.23 (d, J = 6.7 Hz, 6H). MS (m/z): 488.1 [M + 1] |

| Ex. | Structure | Name | EC50 | Characterization |
|---|---|---|---|---|
| 177 | 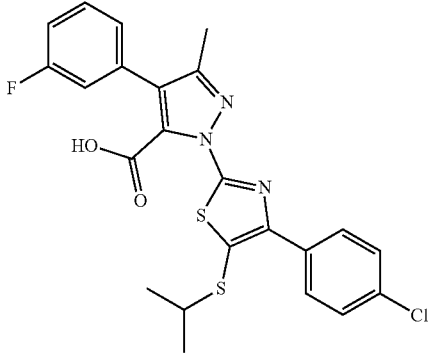 [SMILES: Cc1nn(-c2nc(-c3ccc(Cl)cc3)c(SC(C)C)s2)c(C(=O)O)c1-c1cccc(F)c1] | 1-(4-(4-chlorophenyl)-5-(isopropylthio)thiazol-2-yl)-4-(3-fluorophenyl)-3-methyl-1H-pyrazole-5-carboxylic acid | A | $^1$H NMR (500 MHz, DMSO) δ 8.06-8.02 (m, 2H), 7.56-7.47 (m, 3H), 7.37-7.30 (m, 2H), 7.24-7.17 (m, 1H), 3.36-3.27 (m, 1H), 2.31 (s, 3H), 1.23 (d, J = 6.7 Hz, 6H). MS (m/z): 488.1 [M + 1]$^+$. |
| 178 | 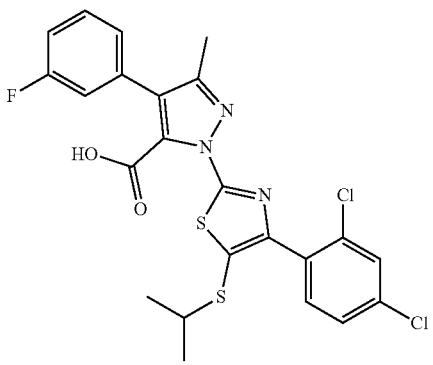 [SMILES: Cc1nn(-c2nc(-c3ccc(Cl)cc3Cl)c(SC(C)C)s2)c(C(=O)O)c1-c1cccc(F)c1] | 1-(4-(2,4-dichlorophenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 7.77 (d, J = 2.1 Hz, 1H), 7.55 (dd, J = 8.3, 2.1 Hz, 1H), 7.52-7.45 (m, 2H), 7.34-7.27 (m, 2H), 7.22-7.15 (m, 1H), 3.25-3.15 (m, 1H), 2.30 (s, 3H), 1.15 (d, J = 6.7 Hz, 6H). MS (m/z): 522.0 [M + 1]$^+$ |
| 179 | 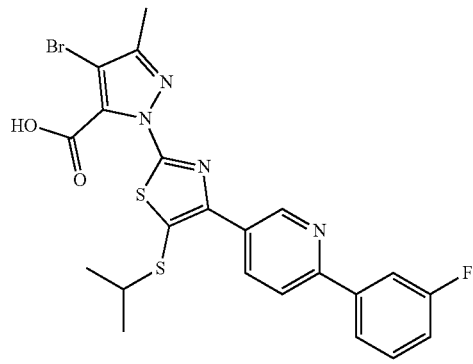 [SMILES: Cc1nn(-c2nc(-c3ccc(-c4cccc(F)c4)nc3)c(SC(C)C)s2)c(C(=O)O)c1Br] | 4-bromo-1-(4-(6-(3-fluorophenyl)pyridin-3-yl)-5-(isopropylthio)thiazol-2-yl)-3-methyl-1H-pyrazole-5-carboxylic acid | E | $^1$H NMR (500 MHz, DMSO) δ 9.29 (d, J = 1.9 Hz, 1H), 8.50 (dd, J = 8.3, 2.3 Hz, 1H), 8.20-8.11 (m, 1H), 8.03 (d, J = 7.9 Hz, 1H), 7.98 (d, J = 10.2 Hz, 1H), 7.57 (dd, J = 14.1, 8.1 Hz, 1H), 7.30 (td, J = 8.4, 2.0 Hz, 1H), 3.37-3.29 (m, 1H), 2.21 (s, 3H), 1.24 (d, J = 6.7 Hz, 6H); MS (m/z): 533.1 [M + 1]$^+$ |
| 180 | 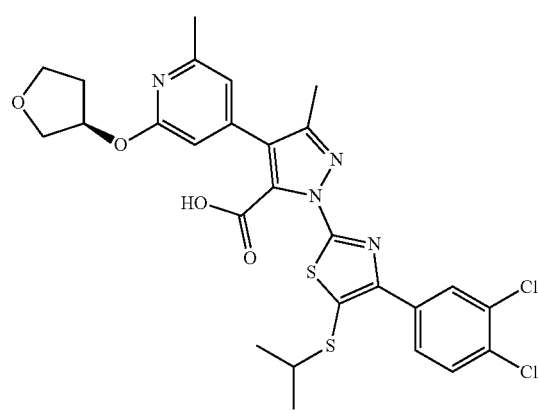 [SMILES: Cc1cc(-c2c(C)nn(-c3nc(-c4ccc(Cl)c(Cl)c4)c(SC(C)C)s3)c2C(=O)O)cc(O[C@@H]2CCOC2)n1] | (R)-1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylic acid | D | $^1$H NMR (500 MHz, DMSO) δ 8.22 (s, 1H), 8.04 (d, J = 8.3 Hz, 1H), 7.76 (d, J = 8.5 Hz, 1H), 6.97 (s, 1H), 6.72 (s, 1H), 5.53-5.48 (m, 1H), 3.93 (dd, J = 10.2, 4.8 Hz, 1H), 3.89-3.82 (m, 1H), 3.80-3.73 (m, 2H), 3.35 (hept, J = 6.7 Hz, 1H), 2.41 (s, 3H), 2.33 (s, 3H), 2.29-2.18 (m, 1H), 2.06-1.98 (m, 1H), 1.24 (d, J = 6.7 Hz, 6H); MS (m/z): 605.2 [M + 1]$^+$ |

-continued

| Ex. | Structure | Name | EC₅₀ | Characterization |
|---|---|---|---|---|
| 181 | 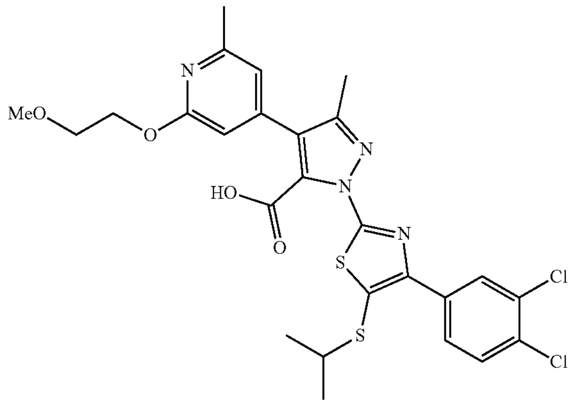 [SMILES: COCCOc1cc(-c2c(C)nn(-c3nc(-c4ccc(Cl)c(Cl)c4)c(SC(C)C)s3)c2C(=O)O)cc(C)n1] | 1-(4-(3,4-dichlorophenyl)-5-(isopropylthio)thiazol-2-yl)-4-(2-(2-methoxyethoxy)-6-methylpyridin-4-yl)-3-methyl-1H-pyrazole-5-carboxylic acid | D | $^1$H NMR (500 MHz, DMSO) δ 8.22 (s, 1H), 8.04 (d, J = 8.4 Hz, 1H), 7.76 (d, J = 8.5 Hz, 1H), 6.96 (s, 1H), 6.72 (s, 1H), 4.40-4.35 (m, 2H), 3.69-3.64 (m, 2H), 3.35 (sept, J = 6.7 Hz, 1H), 2.41 (s, 3H), 2.33 (s, 3H), 1.24 (d, J = 6.7 Hz, 6H); MS (m/z): 592.9 [M + 1]$^+$ |
| 182 | 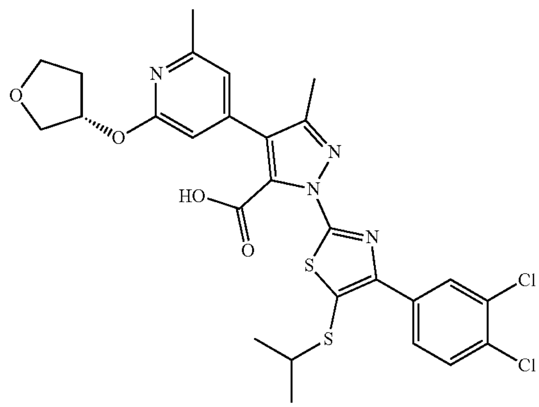 [SMILES: Cc1cc(-c2c(C)nn(-c3nc(-c4ccc(Cl)c(Cl)c4)c(SC(C)C)s3)c2C(=O)O)cc(O[C@H]2CCOC2)n1] | (S)-1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylic acid | D | $^1$H NMR (500 MHz, DMSO) δ 8.21 (s, 1H), 8.03 (d, J = 10.5 Hz, 1H), 7.77 (d, J = 8.5 Hz, 1H), 6.96 (s, 1H), 6.69 (s, 1H), 5.55-5.49 (m, 1H), 3.94 (dd, J = 10.2, 4.8 Hz, 1H), 3.90-3.82 (m, 1H), 3.81-3.74 (m, 2H), 3.36 (hept, J = 6.7 Hz, 1H), 2.42 (s, 3H), 2.34 (s, 3H), 2.30-2.20 (m, 1H), 2.06-1.98 (m, 1H), 1.24 (d, J = 6.7 Hz, 6H); MS (m/z): 605.1 [M + 1]$^+$. |
| 183 | 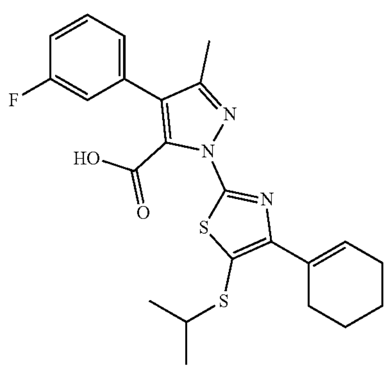 [SMILES: Cc1nn(-c2nc(C3=CCCCC3)c(SC(C)C)s2)c(C(=O)O)c1-c1cccc(F)c1] | 1-(4-(cyclohex-1-en-1-yl)-5-(isopropylthio)thiazol-2-yl)-4-(3-fluorophenyl)-3-methyl-1H-pyrazole-5-carboxylic acid | C | $^1$H NMR (500 MHz, DMSO) δ 7.52 (dd, J = 14.5, 8.1 Hz, 1H), 7.32-7.27 (m, 2H), 7.24 (t, J = 8.5 Hz, 1H), 6.41-6.37 (m, 1H), 3.28 (m, 1H), 2.46-2.41 (m, 2H), 2.29 (s, 3H), 2.21 (ddd, J = 9.8, 6.4, 3.4 Hz, 2H), 1.72-1.65 (m, 2H), 1.63-1.57 (m, 2H), 1.26 (d, J = 6.7 Hz, 6H); MS (m/z): 458.3 [M + 1]$^+$. |
| 184 | 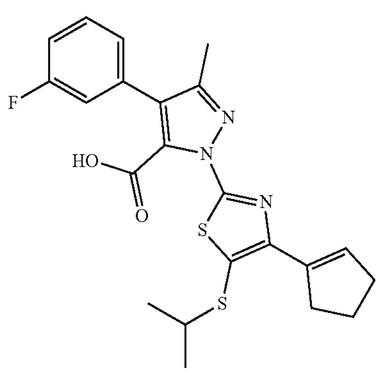 [SMILES: Cc1nn(-c2nc(C3=CCCC3)c(SC(C)C)s2)c(C(=O)O)c1-c1cccc(F)c1] | 1-(4-(cyclopent-1-en-1-yl)-5-(isopropylthio)thiazol-2-yl)-4-(3-fluorophenyl)-3-methyl-1H-pyrazole-5-carboxylic acid | D | $^1$H NMR (500 MHz, DMSO) δ 7.54-7.47 (m, 1H), 7.31 (t, J = 7.8 Hz, 2H), 7.22 (t, J = 8.2 Hz, 1H), 6.58 (t, J = 2.0 Hz, 1H), 3.30-3.25 (m, 1H), 2.83 (t, J = 6.5 Hz, 2H), 2.49-2.45 (m, 2H), 2.29 (s, 3H), 1.94 (dt, J = 14.6, 7.4 Hz, 2H), 1.27 (d, J = 6.7 Hz, 6H); MS (m/z): 444.3 [M + 1]$^+$ |

-continued

| Ex. | Structure | Name | EC$_{50}$ | Characterization |
|---|---|---|---|---|
| 185 | 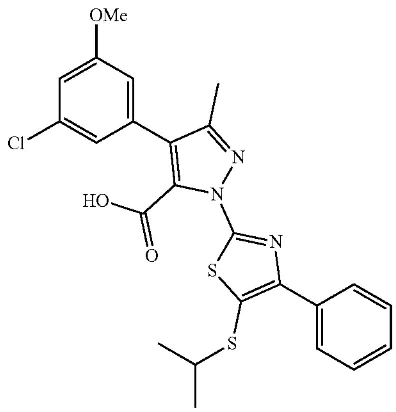 [SMILES: COc1cc(Cl)cc(-c2c(C)nn(-c3nc(-c4ccccc4)c(SC(C)C)s3)c2C(=O)O)c1] | 4-(3-chloro-5-methoxyphenyl)-1-(5-(isopropylthio)-4-phenylthiazol-2-yl)-3-methyl-1H-pyrazole-5-carboxylic acid | D | $^1$H NMR (500 MHz, DMSO) δ 8.02 (d, J = 7.5 Hz, 2H), 7.47 (t, J = 7.5 Hz, 2H), 7.40 (t, J = 7.3 Hz, 1H), 7.17-6.96 (m, 3H), 3.80 (s, 3H), 3.35-3.20 (m, 1H), 2.30 (s, 3H), 1.22 (d, J = 6.7 Hz, 6H). MS (m/z): 500.1 [M + 1]$^+$. |
| 186 | 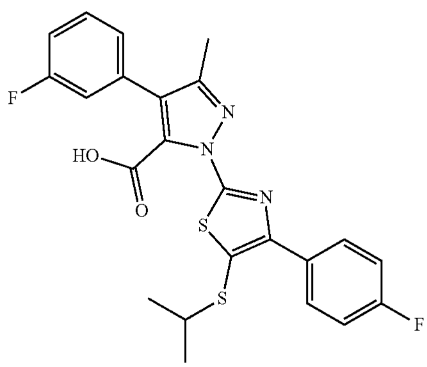 [SMILES: Cc1nn(-c2nc(-c3ccc(F)cc3)c(SC(C)C)s2)c(C(=O)O)c1-c1cccc(F)c1] | 4-(3-fluorophenyl)-1-(4-(4-fluorophenyl)-5-(isopropylthio)thiazol-2-yl)-3-methyl-1H-pyrazole-5-carboxylic acid | B | $^1$H NMR (500 MHz, DMSO) δ 8.10-8.01 (m, J = 8.7, 5.6 Hz, 2H), 7.59-7.43 (m, J = 6.6 Hz, 1H), 7.42-7.26 (m, J = 8.9 Hz, 4H), 7.25-7.14 (m, 1H), 3.32-3.24 (m, 1H), 2.30 (s, 3H), 1.22 (d, J = 6.7 Hz, 6H); MS (m/z): 472.1 [M + 1]$^+$. |
| 187 | 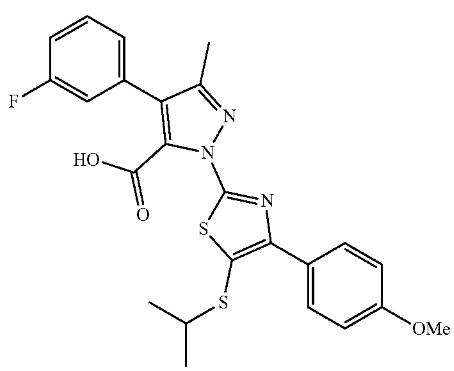 [SMILES: COc1ccc(-c2nc(-n3nc(C)c(-c4cccc(F)c4)c3C(=O)O)sc2SC(C)C)cc1] | 4-(3-fluorophenyl)-1-(5-(isopropylthio)-4-(4-methoxyphenyl)thiazol-2-yl)-3-methyl-1H-pyrazole-5-carboxylic acid | D | $^1$H NMR (500 MHz, DMSO) δ 8.00 (s, 2H), 7.54-7.11 (m, 4H), 7.02 (d, J = 8.9 Hz, 2H), 3.81 (s, 3H), 3.37-3.24 (m, 1H), 2.30 (s, 3H), 1.22 (d, J = 6.7 Hz, 6H); MS (m/z): 484.1 [M + 1]$^+$. |
| 188 | 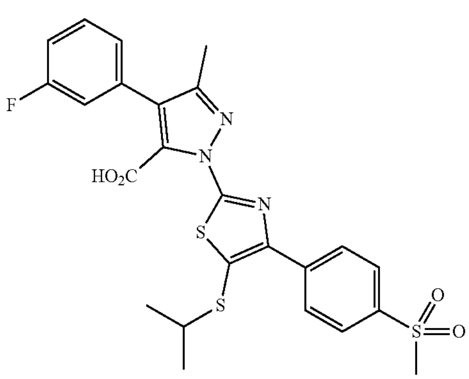 [SMILES: Cc1nn(-c2nc(-c3ccc(S(C)(=O)=O)cc3)c(SC(C)C)s2)c(C(=O)O)c1-c1cccc(F)c1] | 4-(3-fluorophenyl)-1-(5-(isopropylthio)-4-(4-(methylsulfonyl)phenyl)thiazol-2-yl)-3-methyl-1H-pyrazole-5-carboxylic acid | I | $^1$H NMR (500 MHz, DMSO) δ 8.24 (d, J = 8.4 Hz, 2H), 8.01 (d, J = 8.6 Hz, 2H), 7.55-7.43 (m, J = 6.9 Hz, 1H), 7.43-7.30 (m, J = 10.8 Hz, 2H), 7.25-7.13 (m, J = 9.8 Hz, 1H), 3.42-3.35 (m, J = 13.6, 6.9 Hz, 1H), 3.27 (s, 3H), 2.31 (s, 3H), 1.24 (d, J = 6.7 Hz, 6H); MS (m/z): 532.3 [M + 1]$^+$. |

-continued

| Ex. | Structure | Name | EC$_{50}$ | Characterization |
|---|---|---|---|---|
| 189 | 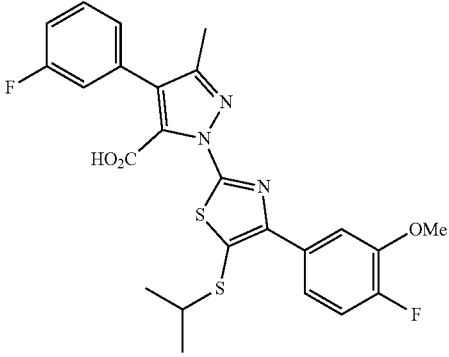 [SMILES: COc1cc(-c2nc(-n3nc(C)c(-c4cccc(F)c4)c3C(=O)O)sc2SC(C)C)ccc1F] | 1-(4-(4-fluoro-3-methoxyphenyl)-5-(isopropylthio)thiazol-2-yl)-4-(3-fluorophenyl)-3-methyl-1H-pyrazole-5-carboxylic acid | D | $^1$H NMR (500 MHz, DMSO) δ 7.95-7.86 (m, 1H), 7.73-7.65 (m, 1H), 7.51-7.44 (m, 1H), 7.40-7.27 (m, 2H), 7.22-7.13 (m, 1H), 3.90 (s, 3H), 3.37-3.24 (m, 1H), 2.31 (s, 3H), 1.24 (d, J = 6.7 Hz, 6H); MS (m/z): 502.4 [M + 1]$^+$ |
| 190 | 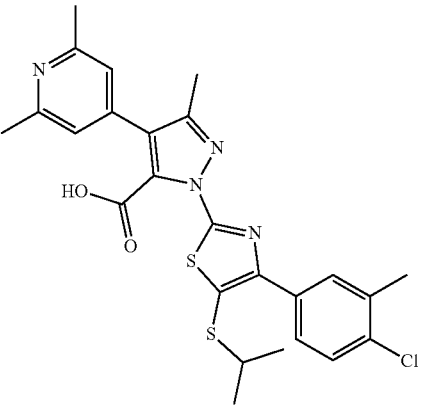 [SMILES: Cc1cc(-c2c(C)nn(-c3nc(-c4ccc(Cl)c(C)c4)c(SC(C)C)s3)c2C(=O)O)cc(C)n1] | 1-(4-(4-chloro-3-methylphenyl)-5-(isopropylthio)thiazol-2-yl)-4-(2,6-dimethylpyridin-4-yl)-3-methyl-1H-pyrazole-5-carboxylic acid | B | $^1$H NMR (500 MHz, DMSO) δ 7.94 (d, J = 1.9 Hz, 1H), 7.87 (dd, J = 8.4, 1.9 Hz, 1H), 7.50 (d, J = 8.4 Hz, 1H), 7.16 (s, 2H), 3.34-3.27 (m, 1H), 2.46 (s, 6H), 2.39 (s, 3H), 2.33 (s, 3H), 1.23 (d, J = 6.7 Hz, 6H). MS (m/z): 513.2 [M + 1]$^+$ |
| 191 | 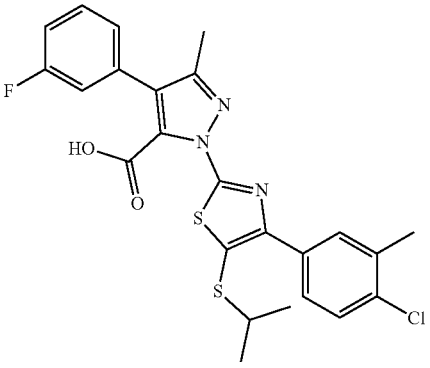 [SMILES: Cc1cc(-c2nc(-n3nc(C)c(-c4cccc(F)c4)c3C(=O)O)sc2SC(C)C)ccc1Cl] | 1-(4-(4-chloro-3-methylphenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 7.94 (m, 1H), 7.86 (dd, J = 8.4, 1.9 Hz, 1H), 7.53-7.46 (m, 2H), 7.37-7.30 (m, 2H), 7.25-7.17 (m, 1H), 3.37-3.25 (m, 1H), 2.39 (s, 3H), 2.31 (s, 3H), 1.23 (d, J = 6.7 Hz, 6H). MS (m/z): 502.2 [M + 1]$^+$ |
| 192 | 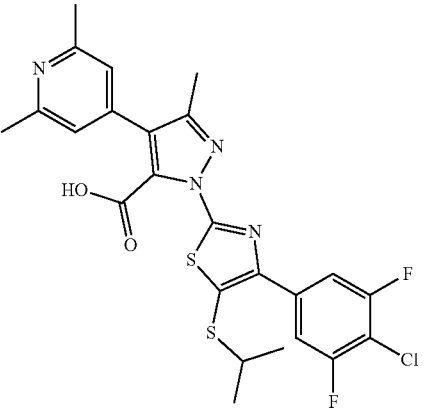 [SMILES: Cc1cc(-c2c(C)nn(-c3nc(-c4cc(F)c(Cl)c(F)c4)c(SC(C)C)s3)c2C(=O)O)cc(C)n1] | 1-(4-(4-chloro-3,5-difluorophenyl)-5-(isopropylthio)thiazol-2-yl)-4-(2,6-dimethylpyridin-4-yl)-3-methyl-1H-pyrazole-5-carboxylic acid | B | $^1$H NMR (500 MHz, DMSO) δ 7.97 (s, 1H), 7.95 (s, 1H), 7.18 (s, 2H), 3.43-3.32 (m, 1H), 2.45 (s, 6H), 2.33 (s, 3H), 1.26 (d, J = 6.7 Hz, 6H). MS (m/z): 535.2 [M + 1]$^+$ |

-continued

| Ex. | Structure | Name | EC$_{50}$ | Characterization |
|---|---|---|---|---|
| 193 | 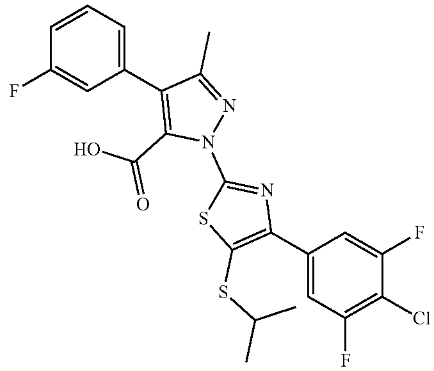 [SMILES: Cc1nn(-c2nc(-c3cc(F)c(Cl)c(F)c3)c(SC(C)C)s2)c(C(=O)O)c1-c1cccc(F)c1] | 1-(4-(4-chloro-3,5-difluorophenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 7.97 (s, 1H), 7.95 (s, 1H), 7.52-7.45 (m, 1H), 7.39-7.32 (m, 2H), 7.23-7.16 (m, 1H), 3.44-3.32 (m, 1H), 2.31 (s, 3H), 1.25 (d, J = 6.7 Hz, 6H). MS (m/z): 524.2 [M + 1]$^+$ |
| 194 | 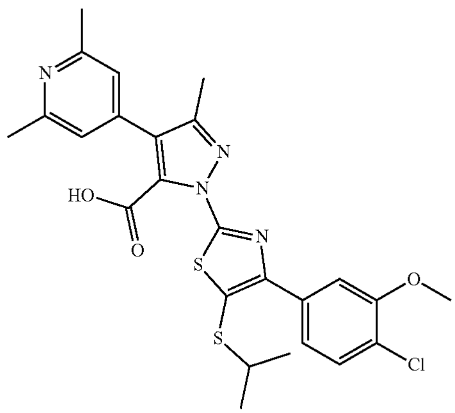 | 1-(4-(4-chloro-3-methoxyphenyl)-5-(isopropylthio)thiazol-2-yl)-4-(2,6-dimethylpyridin-4-yl)-3-methyl-1H-pyrazole-5-carboxylic acid | B | $^1$H NMR (500 MHz, DMSO) δ 7.86-7.83 (m, 1H), 7.71 (dd, J = 8.4, 1.8 Hz, 1H), 7.51 (d, J = 8.4 Hz, 1H), 7.16 (s, 2H), 3.91 (s, 3H), 3.43-3.31 (m, 1H), 2.46 (s, 6H), 2.33 (s, 3H), 1.25 (d, J = 6.7 Hz, 6H). MS (m/z): 529.3 [M + 1]$^+$ |
| 195 | 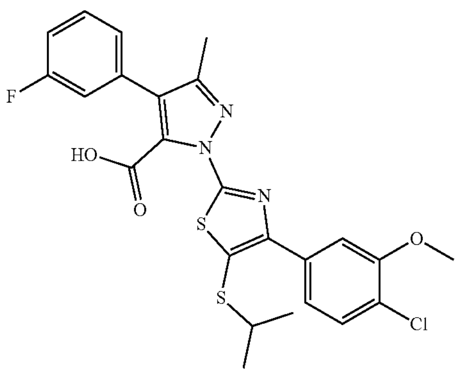 [SMILES: COc1cc(-c2nc(-n3nc(C)c(-c4cccc(F)c4)c3C(=O)O)sc2SC(C)C)ccc1Cl] | 1-(4-(4-chloro-3-methoxyphenyl)-5-(isopropylthio)thiazol-2-yl)-4-(3-fluorophenyl)-3-methyl-1H-pyrazole-5-carboxylic acid | C | $^1$H NMR (500 MHz, DMSO) δ 7.89-7.85 (m, 1H), 7.73-7.69 (m, 1H), 7.54-7.45 (m, 2H), 7.40-7.31 (m, 2H), 7.24-7.16 (m, 1H), 3.91 (s, 3H), 3.41-3.31 (m, 1H), 2.31 (s, 3H), 1.25 (d, J = 6.7 Hz, 6H). MS (m/z): 518.3 [M + 1]$^+$. |
| 196 | 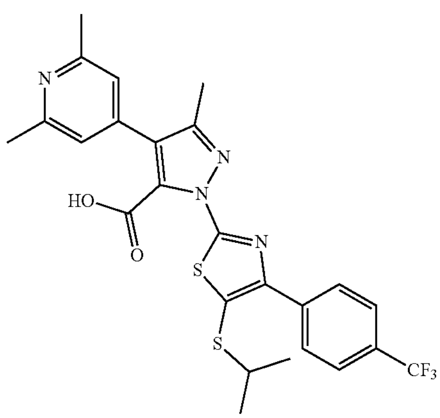 [SMILES: Cc1cc(-c2c(C)nn(-c3nc(-c4ccc(C(F)(F)F)cc4)c(SC(C)C)s3)c2C(=O)O)cc(C)n1] | 4-(2,6-dimethylpyridin-4-yl)-1-(5-(isopropylthio)-4-(4-(trifluoromethyl)phenyl)thiazol-2-yl)-3-methyl-1H-pyrazole-5-carboxylic acid | B | $^1$H NMR (500 MHz, DMSO) δ 8.21 (d, J = 8.3 Hz, 2H), 7.83 (d, J = 8.3 Hz, 2H), 7.16 (s, 2H), 3.44-3.31 (m, 1H), 2.46 (s, 6H), 2.33 (s, 3H), 1.23 (d, J = 6.7 Hz, 6H). MS (m/z): 533.4 [M + 1]$^+$ |

| Ex. | Structure | Name | EC$_{50}$ | Characterization |
|---|---|---|---|---|
| 197 | 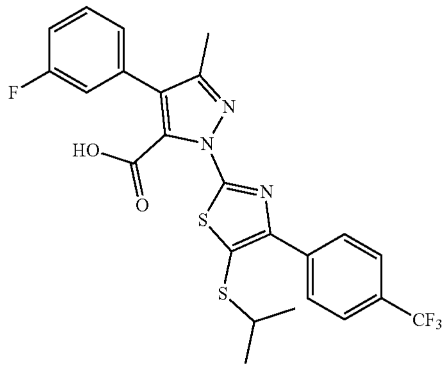 [SMILES: Cc1nn(-c2nc(-c3ccc(C(F)(F)F)cc3)c(SC(C)C)s2)c(C(=O)O)c1-c1cccc(F)c1] | 4-(3-fluorophenyl)-1-(5-(isopropylthio)-4-(4-(trifluoromethyl)phenyl)thiazol-2-yl)-3-methyl-1H-pyrazole-5-carboxylic acid | A | $^1$H NMR (500 MHz, DMSO) δ 8.21 (d, J = 8.3 Hz, 2H), 7.83 (d, J = 8.3 Hz, 2H), 7.53-7.46 (m, 1H), 7.38-7.31 (m, 2H), 7.25-7.18 (m, 1H), 3.44-3.31 (m, 1H), 2.30 (s, 3H), 1.23 (d, J = 6.7 Hz, 6H). MS (m/z): 522.3 [M + 1]$^+$ |
| 198 | 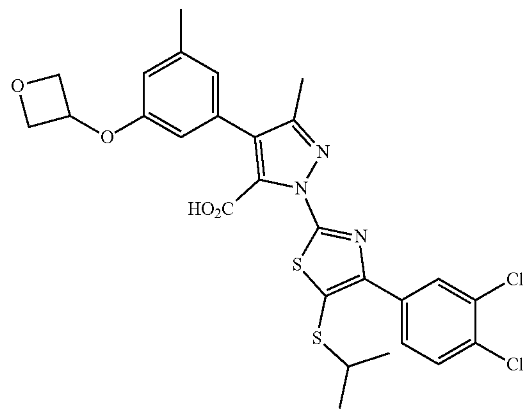 | 1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic acid | B | $^1$H NMR (500 MHz, DMSO) δ 8.22 (d, J = 1.7 Hz, 1H), 8.04 (dd, J = 8.5, 1.8 Hz, 1H), 7.74 (d, J = 8.5 Hz, 1H), 7.17 (s, 1H), 6.89 (s, 2H), 5.33 (d, J = 5.2 Hz, 1H), 4.95 (t, J = 7.0 Hz, 2H), 4.56 (dd, J = 8.0, 4.9 Hz, 2H), 3.35 (hept, J = 6.7 Hz, 1H), 2.30 (s, 3H), 1.24 (d, J = 6.7 Hz, 6H); MS (m/z): 610.0 [M + 1]$^+$ |
| 199 | 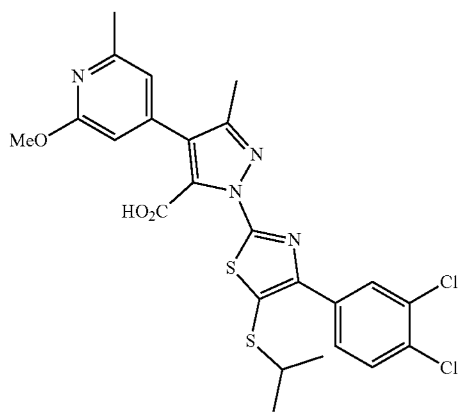 [SMILES: COc1cc(-c2c(C)nn(-c3nc(-c4ccc(Cl)c(Cl)c4)c(SC(C)C)s3)c2C(=O)O)cc(C)n1] | 1-(4-(3,4-dichlorophenyl)-5-(isopropylthio)thiazol-2-yl)-4-(2-methoxy-6-methylpyridin-4-yl)-3-methyl-1H-pyrazole-5-carboxylic acid | B | $^1$H NMR (500 MHz, DMSO) δ 8.20 (d, J = 2.0 Hz, 1H), 8.02 (dd, J = 8.5, 2.1 Hz, 1H), 7.78 (d, J = 8.5 Hz, 1H), 6.94 (s, 1H), 6.68 (s, 1H), 3.87 (s, 3H), 3.35 (hept, J = 6.7 Hz, 1H), 2.44 (s, 3H), 2.33 (s, 3H), 1.24 (d, J = 6.7 Hz, 6H); MS (m/z): 549.4 [M + 1]$^+$. |
| 200 | 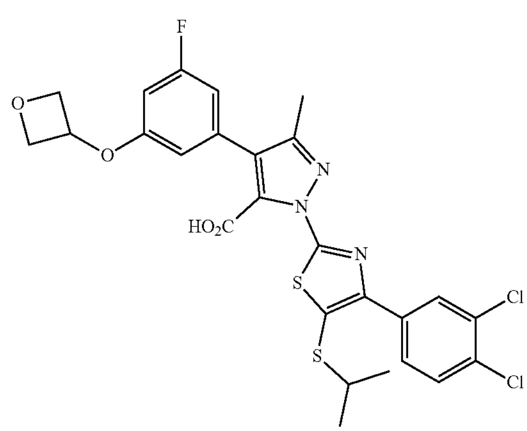 [SMILES: Cc1nn(-c2nc(-c3ccc(Cl)c(Cl)c3)c(SC(C)C)s2)c(C(=O)O)c1-c1cc(F)cc(OC2COC2)c1] | 1-(4-(3,4-dichlorophenyl)-5-(isopropylthio)thiazol-2-yl)-4-(3-fluoro-5-(oxetan-3-yloxy)phenyl)-3-methyl-1H-pyrazole-5-carboxylic acid | B | $^1$H NMR (500 MHz, DMSO) δ 8.19 (d, J = 1.9 Hz, 1H), 8.01 (dd, J = 8.5, 2.0 Hz, 1H), 7.77 (d, J = 8.5 Hz, 1H), 6.94 (d, J = 8.8 Hz, 1H), 6.76 (d, J = 10.7 Hz, 1H), 6.71 (s, 1H), 5.33 (quint., J = 5.3 Hz, 1H), 4.94 (t, J = 6.7 Hz, 2H), 4.57 (dd, J = 7.2, 5.0 Hz, 2H), 3.36 (hept, J = 6.7 Hz, 1H), 2.32 (s, 3H), 1.24 (d, J = 6.7 Hz, 6H); MS (m/z): 594.3 [M + 1]$^+$ |

| Ex. | Structure | Name | EC$_{50}$ | Characterization |
|---|---|---|---|---|
| 201a | 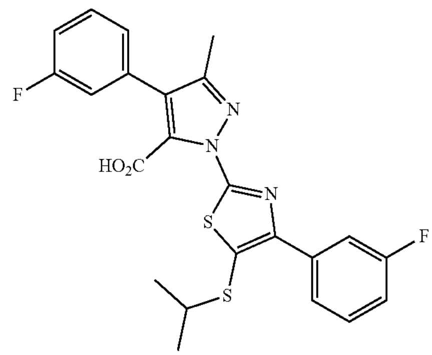 [SMILES: Cc1nn(-c2nc(-c3cccc(F)c3)c(SC(C)C)s2)c(C(=O)O)c1-c1cccc(F)c1] | 4-(3-fluorophenyl)-1-(4-(3-fluorophenyl)-5-(isopropylthio)thiazol-2-yl)-3-methyl-1H-pyrazole-5-carboxylic acid | E | $^1$H NMR (500 MHz, MeOD) δ 8.09-8.04 (m, 1H), 8.02-7.96 (m, 1H), 7.47-7.40 (m, 2H), 7.39-7.35 (m, 1H), 7.34-7.29 (m, 1H), 7.12-7.02 (m, 2H), 3.31-3.24 (m, 1H), 2.35 (s, 3H), 1.29 (d, J = 6.7 Hz, 6H); MS (m/z): 472.4 [M + 1]$^+$. |
| 201b | 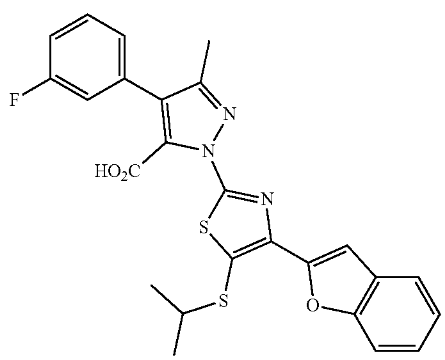 [SMILES: Cc1nn(-c2nc(-c3cc4ccccc4o3)c(SC(C)C)s2)c(C(=O)O)c1-c1cccc(F)c1] | 1-(4-(benzofuran-2-yl)-5-(isopropylthio)thiazol-2-yl)-4-(3-fluorophenyl)-3-methyl-1H-pyrazole-5-carboxylic acid | D | $^1$H NMR (500 MHz, MeOD) δ 7.66 (d, J = 7.7 Hz, 1H), 7.56-7.52 (m, 1H), 7.51 (d, J = 0.9 Hz, 1H), 7.47-7.40 (m, 1H), 7.38 (dt, J = 7.7, 1.2 Hz, 1H), 7.36-7.31 (m, 2H), 7.29-7.23 (m, 1H), 7.10-7.03 (m, 1H), 3.50-3.41 (m, 1H), 2.36 (s, 3H), 1.39 (d, J = 6.7 Hz, 6H); MS (m/z): 494.3 [M + 1]$^+$. |
| 202 | 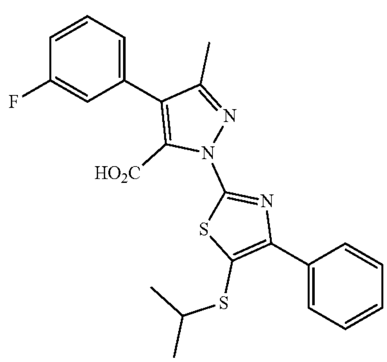 [SMILES: Cc1nn(-c2nc(-c3ccccc3)c(SC(C)C)s2)c(C(=O)O)c1-c1cccc(F)c1] | 4-(3-fluorophenyl)-1-(5-(isopropylthio)-4-phenylthiazol-2-yl)-3-methyl-1H-pyrazole-5-carboxylic acid | D | $^1$H NMR (500 MHz, DMSO) δ 8.01 (d, J = 7.2 Hz, 2H), 7.47 (t, J = 7.5 Hz, 3H), 7.43-7.29 (m, 3H), 7.18 (s, 1H), 3.33 (1H, below water signal), 2.30 (s, 3H), 1.22 (d, J = 6.7 Hz, 6H); MS (m/z): 454.4 [M + 1]$^+$ |
| 203 | 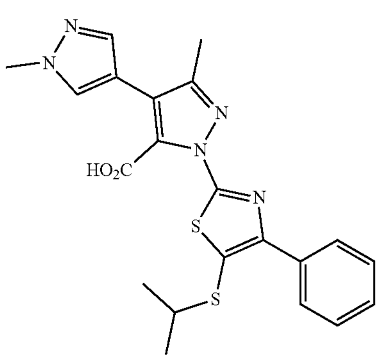 [SMILES: Cc1nn(-c2nc(-c3ccccc3)c(SC(C)C)s2)c(C(=O)O)c1-c1cnn(C)c1] | 1-(5-(isopropylthio)-4-phenylthiazol-2-yl)-1',3-dimethyl-1H,1'H-[4,4'-bipyrazole]-5-carboxylic acid | I | $^1$H NMR (500 MHz, DMSO) δ 8.02-7.97 (m, 2H), 7.95 (s, 1H), 7.64 (d, J = 0.7 Hz, 1H), 7.52-7.45 (m, 2H), 7.44-7.38 (m, 1H), 3.89 (s, 3H), 3.33 (1H, below water signal), 2.35 (s, 3H), 1.22 (d, J = 6.7 Hz, 6H); MS (m/z): 440.4 [M + 1]$^+$. |

-continued

| Ex. | Structure | Name | EC$_{50}$ | Characterization |
|---|---|---|---|---|
| 204 | 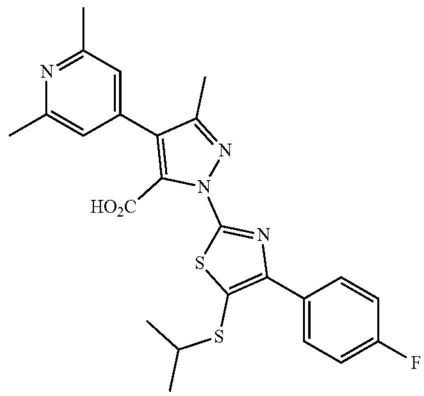 [SMILES: Cc1cc(-c2c(C)nn(-c3nc(-c4ccc(F)cc4)c(SC(C)C)s3)c2C(=O)O)cc(C)n1] | 4-(2,6-dimethylpyridin-4-yl)-1-(4-(4-fluorophenyl)-5-(isopropylthio)thiazol-2-yl)-3-methyl-1H-pyrazole-5-carboxylic acid | B | $^1$H NMR (500 MHz, DMSO) δ 8.09-8.02 (m, 2H), 7.32 (t, J = 8.9 Hz, 2H), 7.14 (s, 2H), 3.33 (1H, below water signal), 2.46 (s, 6H), 2.33 (s, 3H), 1.22 (d, J = 6.7 Hz, 6H); MS (m/z): 483.2 [M + 1]$^+$. |
| 205 | 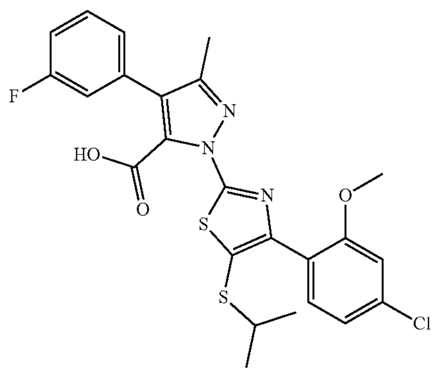 [SMILES: COc1cc(Cl)ccc1-c1nc(-n2nc(C)c(-c3cccc(F)c3)c2C(=O)O)sc1SC(C)C] | 1-(4-(4-chloro-2-methoxyphenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 7.52-7.42 (m, 1H), 7.36-7.25 (m, 3H), 7.23-7.14 (m, 2H), 7.10 (dd, J = 8.1, 2.0 Hz, 1H), 3.79 (s, 3H), 3.24-3.12 (m, 1H), 2.29 (s, 3H), 1.14 (d, J = 6.7 Hz, 6H). MS (m/z): 518.1 [M + 1]+ |
| 206 | 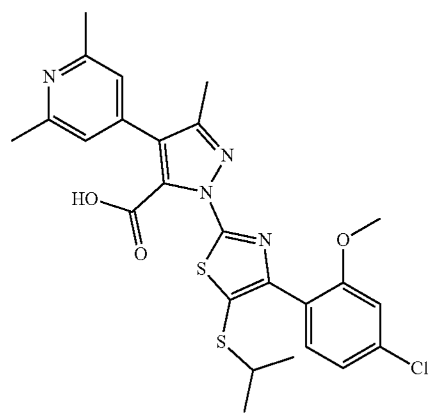 [SMILES: COc1cc(Cl)ccc1-c1nc(-n2nc(C)c(-c3cc(C)nc(C)c3)c2C(=O)O)sc1SC(C)C] | 1-(4-(4-chloro-2-methoxyphenyl)-5-(isopropylthio)thiazol-2-yl)-4-(2,6-dimethylpyridin-4-yl)-3-methyl-1H-pyrazole-5-carboxylic acid | B | $^1$H NMR (500 MHz, DMSO) δ 7.28 (d, J = 8.1 Hz, 1H), 7.21 (d, J = 2.0 Hz, 1H), 7.13-7.08 (m, 3H), 3.79 (s, 3H), 3.23-3.14 (m, 1H), 2.45 (s, 6H), 2.31 (s, 3H), 1.14 (d, J = 6.7 Hz, 6H). MS (m/z): 529.2 [M + 1]+ |
| 207 | 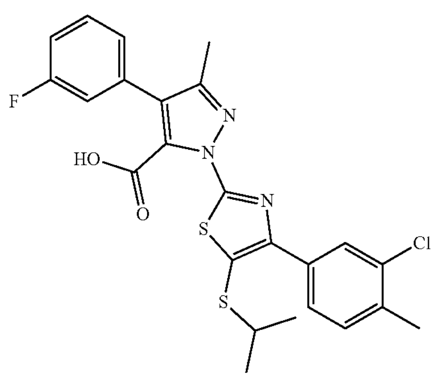 [SMILES: Cc1ccc(-c2nc(-n3nc(C)c(-c4cccc(F)c4)c3C(=O)O)sc2SC(C)C)cc1Cl] | 1-(4-(3-chloro-4-methylphenyl)-5-(isopropylthio)thiazol-2-yl)-4-(3-fluorophenyl)-3-methyl-1H-pyrazole-5-carboxylic acid | C | $^1$H NMR (500 MHz, DMSO) δ 14.36 (s, 1H), 8.04 (d, J = 1.6 Hz, 1H), 7.90 (dd, J = 8.0, 1.6 Hz, 1H), 7.54-7.47 (m, 1H), 7.45 (d, J = 8.0 Hz, 1H), 7.37-7.30 (m, 2H), 7.25-7.18 (m, 1H), 3.35-3.30 (m, 1H), 2.37 (s, 3H), 2.30 (s, 3H), 1.23 (d, J = 6.7 Hz, 6H). MS (m/z): 502.1 [M + 1]+ |

-continued

| Ex. | Structure | Name | EC$_{50}$ | Characterization |
|---|---|---|---|---|
| 208 | 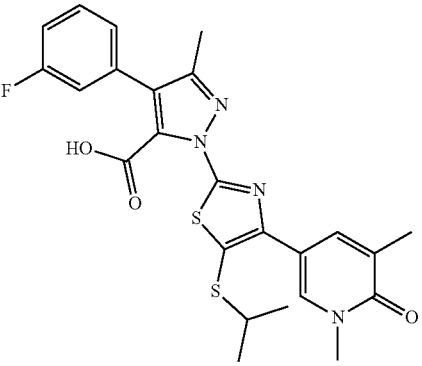 [SMILES: Cc1nn(-c2nc(-c3cc(C)c(=O)n(C)c3)c(SC(C)C)s2)c(C(=O)O)c1-c1cccc(F)c1] | 1-(4-(1,5-dimethyl-6-oxo-1,6-dihydropyridin-3-yl)-5-(isopropylthio)thiazol-2-yl)-4-(3-fluorophenyl)-3-methyl-1H-pyrazole-5-carboxylic acid | I | |
| 209 | 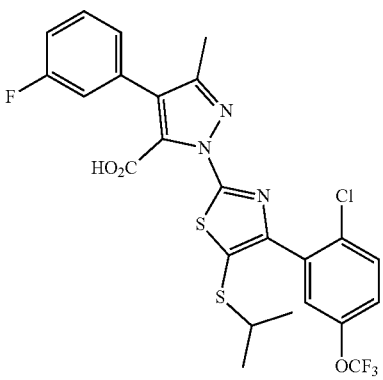 [SMILES: Cc1nn(-c2nc(-c3cc(OC(F)(F)F)ccc3Cl)c(SC(C)C)s2)c(C(=O)O)c1-c1cccc(F)c1] | 1-(4-(2-chloro-5-(trifluoromethoxy)phenyl)-5-(isopropylthio)thiazol-2-yl)-4-(3-fluorophenyl)-3-methyl-1H-pyrazole-5-carboxylic acid | D | $^1$H NMR (500 MHz, DMSO) δ 14.10 (s, 1H), 7.76-7.71 (m, 1H), 7.57-7.46 (m, 3H), 7.35-7.26 (m, 2H), 7.26-7.17 (m, 1H), 3.21 (hept, J = 6.7 Hz, 1H), 2.31 (s, 3H), 1.15 (d, J = 6.7 Hz, 6H); MS (m/z): 572.1 [M + 1]$^+$ |
| 210 | 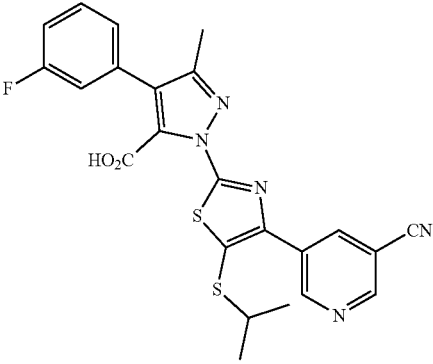 | 1-(4-(5-cyanopyridin-3-yl)-5-(isopropylthio)thiazol-2-yl)-4-(3-fluorophenyl)-3-methyl-1H-pyrazole-5-carboxylic acid | I | $^1$H NMR (500 MHz, DMSO) δ 9.11 (s, 1H), 8.97 (d, J = 2.0 Hz, 1H), 8.73 (s, 1H), 8.16 (s, 1H), 7.63 (s, 1H), 7.42 (s, 1H), 7.27 (s, 2H), 7.13 (s, 1H), 3.28 (sept, J = 6.7 Hz, 1H), 2.25 (s, 3H), 1.16 (d, J = 6.7 Hz, 6H); MS (m/z): 498.2 [M + 1]$^+$. |
| 211 | 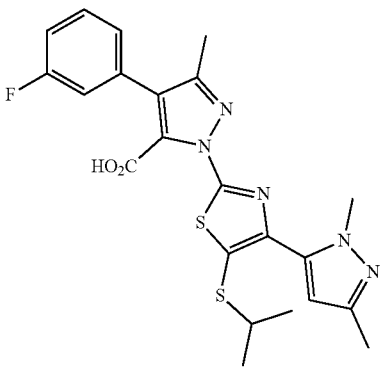 [SMILES: Cc1cc(-c2nc(-n3nc(C)c(-c4cccc(F)c4)c3C(=O)O)sc2SC(C)C)n(C)n1] | 1-(4-(1,3-dimethyl-1H-pyrazol-5-yl)-5-(isopropylthio)thiazol-2-yl)-4-(3-fluorophenyl)-3-methyl-1H-pyrazole-5-carboxylic acid | I | $^1$H NMR (500 MHz, DMSO) δ 7.56-7.50 (m, 1H), 7.33-7.24 (m, 3H), 6.53 (s, 1H), 3.82 (s, 3H), 3.35 (hept, J = 6.7 Hz, 1H), 2.32 (s, 3H), 2.19 (s, 3H), 1.24 (d, J = 6.7 Hz, 6H); MS (m/z): 472.2 [M + 1]$^+$ |

-continued

| Ex. | Structure | Name | EC₅₀ | Characterization |
|---|---|---|---|---|
| 212 | 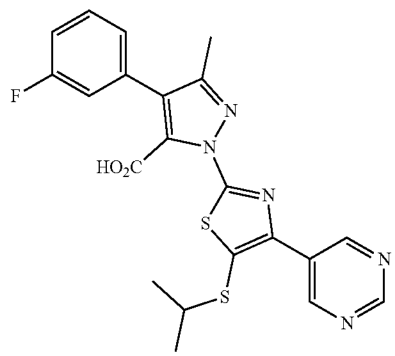 [SMILES: Cc1nn(-c2nc(-c3cncnc3)c(SC(C)C)s2)c(C(=O)O)c1-c1cccc(F)c1] | 4-(3-fluorophenyl)-1-(5-(isopropylthio)-4-(pyrimidin-5-yl)thiazol-2-yl)-3-methyl-1H-pyrazole-5-carboxylic acid | I | ¹H NMR (500 MHz, DMSO) δ 9.36 (s, 2H), 9.23 (s, 1H), 7.56-7.47 (m, 1H), 7.38-7.31 (m, 2H), 7.26-7.17 (m, 1H), 3.45-3.33 (m, 1H), 2.33 (s, 3H), 1.24 (d, J = 6.7 Hz, 6H). MS (m/z): 456.1 [M + 1]⁺. |
| 213 | 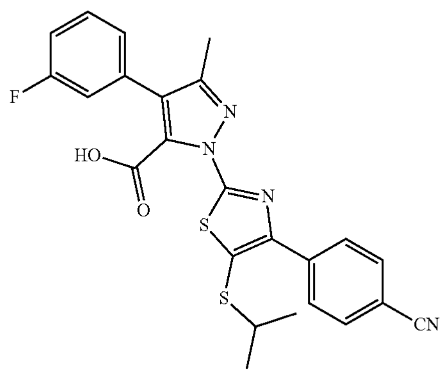 [SMILES: Cc1nn(-c2nc(-c3ccc(C#N)cc3)c(SC(C)C)s2)c(C(=O)O)c1-c1cccc(F)c1] | 1-(4-(4-cyanophenyl)-5-(isopropylthio)thiazol-2-yl)-4-(3-fluorophenyl)-3-methyl-1H-pyrazole-5-carboxylic acid | C- | ¹H NMR (500 MHz, MeOD) δ 8.38-8.34 (m, 2H), 7.81-7.76 (m, 2H), 7.48-7.42 (m, 1H), 7.34-7.30 (m, 1H), 7.29-7.24 (m, 1H), 7.13-7.07 (m, 1H), 3.37-3.26 (m, 1H), 2.34 (s, 3H), 1.28 (d, J = 6.7 Hz, 6H). MS (m/z): 479.1 [M + 1]+ |
| 214 | 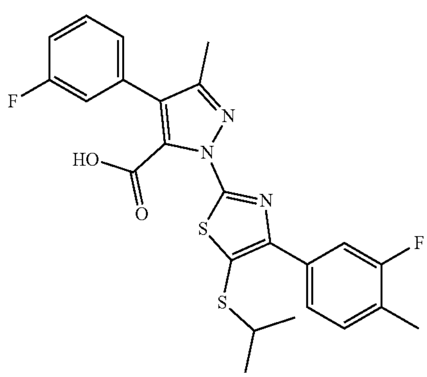 [SMILES: Cc1ccc(-c2nc(-n3nc(C)c(-c4cccc(F)c4)c3C(=O)O)sc2SC(C)C)cc1F] | 1-(4-(3-fluoro-4-methylphenyl)-5-(isopropylthio)thiazol-2-yl)-4-(3-fluorophenyl)-3-methyl-1H-pyrazole-5-carboxylic acid | B | ¹H NMR (500 MHz, DMSO) δ 7.83-7.80 (m, 1H), 7.77-7.71 (m, 1H), 7.55-7.49 (m, 1H), 7.39 (t, J = 8.1 Hz, 1H), 7.36-7.29 (m, 2H), 7.27-7.21 (m, 1H), 3.37-3.31 (m, 1H), 2.31 (s, 3H), 2.29 (s, 3H), 1.23 (d, J = 6.7 Hz, 6H). MS (m/z): 486.3 [M + 1]+ |
| 215 | 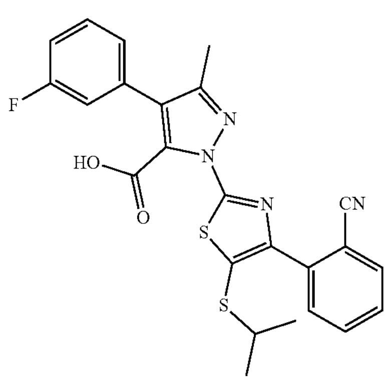 [SMILES: Cc1nn(-c2nc(-c3ccccc3C#N)c(SC(C)C)s2)c(C(=O)O)c1-c1cccc(F)c1] | 1-(4-(2-cyanophenyl)-5-(isopropylthio)thiazol-2-yl)-4-(3-fluorophenyl)-3-methyl-1H-pyrazole-5-carboxylic acid | E | ¹H NMR (500 MHz, DMSO) δ 14.07 (bs, 1H), 7.94-7.89 (m, 1H), 7.79-7.72 (m, 1H), 7.63-7.57 (m, 2H), 7.47-7.39 (m, 1H), 7.30-7.20 (m, 2H), 7.19-7.08 (m, 1H), 3.20-3.09 (m, 1H), 2.25 (s, 3H), 1.05 (d, J = 6.7 Hz, 6H). MS (m/z): 479.0 [M + 1]+ |

| Ex. | Structure | Name | EC$_{50}$ | Characterization |
|---|---|---|---|---|
| 216 | 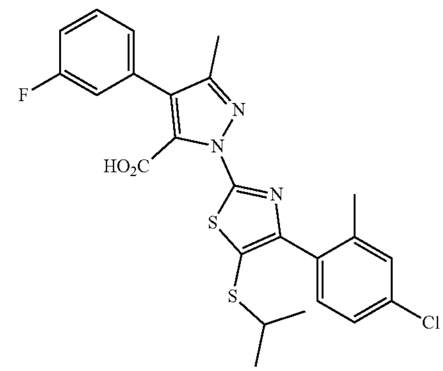 [SMILES: Cc1cc(Cl)ccc1-c1nc(-n2nc(C)c(-c3cccc(F)c3)c2C(=O)O)sc1SC(C)C] | 1-(4-(4-chloro-2-methylphenyl)-5-(isopropylthio)thiazol-2-yl)-4-(3-fluorophenyl)-3-methyl-1H-pyrazole-5-carboxylic acid | A | $^1$H NMR (500 MHz, DMSO) δ 7.49 (s, 1H), 7.43 (s, 1H), 7.37-7.32 (m, 2H), 7.32-7.17 (m, 3H), 3.18 (hept, J = 6.7 Hz, 1H), 2.30 (s, 3H), 2.23 (s, 3H), 1.14 (d, J = 6.7 Hz, 6H). MS (m/z): 502.1 [M + H]$^+$. |
| 217 | 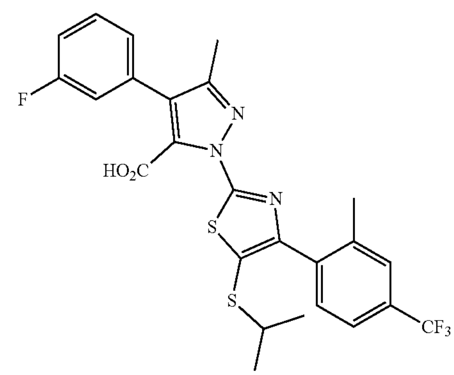 [SMILES: Cc1cc(C(F)(F)F)ccc1-c1nc(-n2nc(C)c(-c3cccc(F)c3)c2C(=O)O)sc1SC(C)C] | 4-(3-fluorophenyl)-1-(5-(isopropylthio)-4-(2-methyl-4-(trifluoromethyl)phenyl)thiazol-2-yl)-3-methyl-1H-pyrazole-5-carboxylic acid | A | $^1$H NMR (500 MHz, DMSO) δ 7.72 (s, 1H), 7.64 (d, J = 8.1 Hz, 1H), 7.55 (d, J = 8.0 Hz, 1H), 7.54-7.47 (m, 1H), 7.33-7.26 (m, 2H), 7.26-7.19 (m, 1H), 3.21 (hept, J = 6.7 Hz, 1H), 2.32 (s, 3H), 2.30 (s, 3H), 1.15 (d, J = 6.7 Hz, 6H); MS (m/z): 536.2 [M + 1]$^+$. |
| 218 | 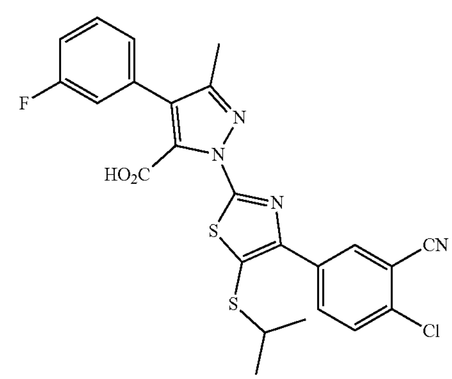 [SMILES: Cc1nn(-c2nc(-c3ccc(Cl)c(C#N)c3)c(SC(C)C)s2)c(C(=O)O)c1-c1cccc(F)c1] | 1-(4-(4-chloro-3-cyanophenyl)-5-(isopropylthio)thiazol-2-yl)-4-(3-fluorophenyl)-3-methyl-1H-pyrazole-5-carboxylic acid | C | $^1$H NMR (500 MHz, CDCl$_3$) δ 8.45 (s, 1H), 8.38 (d, J = 8.2 Hz, 1H), 7.88 (d, J = 8.6 Hz, 1H), 7.52-7.44 (m, 1H), 7.42-7.33 (m, 2H), 7.22-7.14 (m, 1H), 3.35 (hept, J = 6.7 Hz, 1H), 2.31 (s, 3H), 1.23 (d, J = 6.7 Hz, 6H); MS (m/z): 512.9 [M + 1]$^+$ |
| 219 | 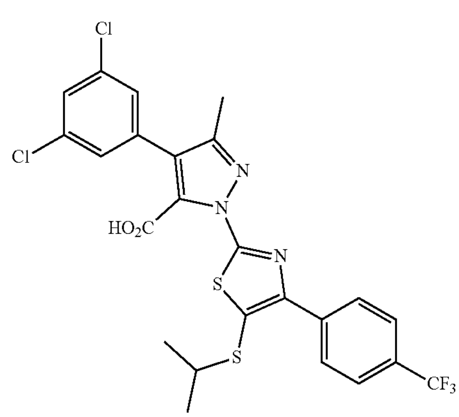 [SMILES: Cc1nn(-c2nc(-c3ccc(C(F)(F)F)cc3)c(SC(C)C)s2)c(C(=O)O)c1-c1cc(Cl)cc(Cl)c1] | 4-(3,5-dichlorophenyl)-1-(5-(isopropylthio)-4-(4-(trifluoromethyl)phenyl)thiazol-2-yl)-3-methyl-1H-pyrazole-5-carboxylic acid | A | $^1$H NMR (500 MHz, DMSO) δ 8.20 (d, J = 8.2 Hz, 2H), 7.85 (d, J = 8.2 Hz, 2H), 7.65 (s, 1H), 7.55 (d, J = 1.8 Hz, 2H), 3.41-3.28 (m, 1H), 2.32 (s, 3H), 1.23 (d, J = 6.7 Hz, 6H). MS (m/z): 571.9 [M + 1]$^+$ |

-continued

| Ex. | Structure | Name | EC$_{50}$ | Characterization |
|---|---|---|---|---|
| 220 | 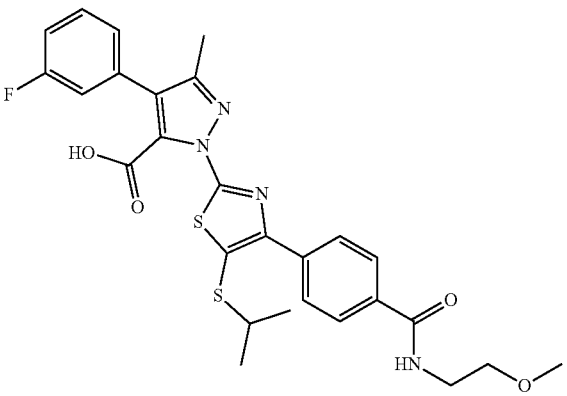 [SMILES: COCCNC(=O)c1ccc(-c2nc(-n3nc(C)c(-c4cccc(F)c4)c3C(=O)O)sc2SC(C)C)cc1] | 4-(3-fluorophenyl)-1-(5-(isopropylthio)-4-(4-((2-methoxyethyl)carbamoyl)phenyl)thiazol-2-yl)-3-methyl-1H-pyrazole-5-carboxylic acid | I | $^1$H NMR (500 MHz, DMSO) δ 8.60 (t, J = 5.3 Hz, 1H), 8.08 (d, J = 8.4 Hz, 2H), 7.95-7.89 (m, 2H), 7.54-7.47 (m, 1H), 7.40-7.30 (m, 2H), 7.25-7.16 (m, 1H), 3.50-3.41 (m, 4H), 3.36-3.30 (m, 1H), 3.28 (s, 3H), 2.32 (s, 3H), 1.22 (d, J = 6.7 Hz, 6H). MS (m/z): 555.2 [M + 1]+. |
| 221 | 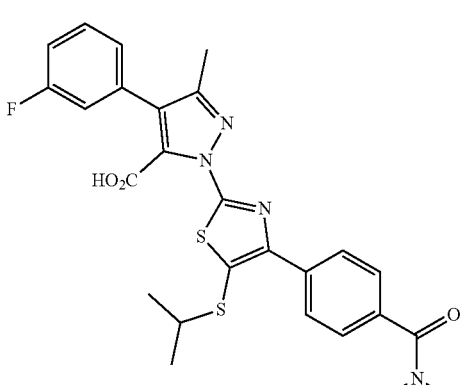 | 1-(4-(4-(dimethylcarbamoyl)phenyl)-5-(isopropylthio)thiazol-2-yl)-4-(3-fluorophenyl)-3-methyl-1H-pyrazole-5-carboxylic acid | I | $^1$H NMR (500 MHz, DMSO) δ 8.07 (d, J = 8.2 Hz, 2H), 7.53-7.44 (m, 3H), 7.39-7.30 (m, 2H), 7.24-7.14 (m, 1H), 3.41-3.26 (m, 1H), 3.00 (s, 3H), 2.94 (s, 3H), 2.31 (s, 3H), 1.24 (d, J = 6.7 Hz, 6H). MS (m/z): 525.2 [M + 1]$^+$ |
| 222 | 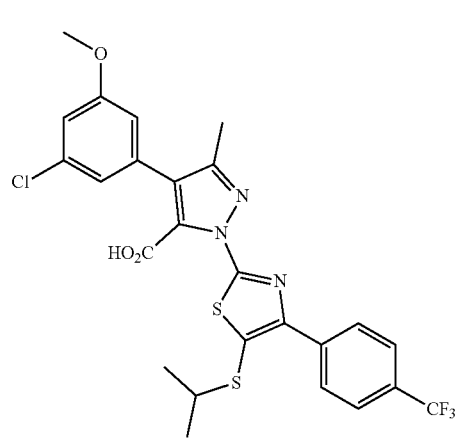 [SMILES: COc1cc(Cl)cc(-c2c(C)nn(-c3nc(-c4ccc(C(F)(F)F)cc4)c(SC(C)C)s3)c2C(=O)O)c1] | 4-(3-chloro-5-methoxyphenyl)-1-(5-(isopropylthio)-4-(4-(trifluoromethyl)phenyl)thiazol-2-yl)-3-methyl-1H-pyrazole-5-carboxylic acid | A | $^1$H NMR (500 MHz, DMSO) δ 8.21 (d, J = 8.3 Hz, 2H), 7.83 (d, J = 8.3 Hz, 2H), 7.12 (s, 1H), 7.04 (s, 2H), 3.81 (s, 3H), 3.40-3.27 (m, 1H), 2.31 (s, 3H), 1.23 (d, J = 6.7 Hz, 6H). MS (m/z): 568.1 [M + 1]+ |
| 222 | 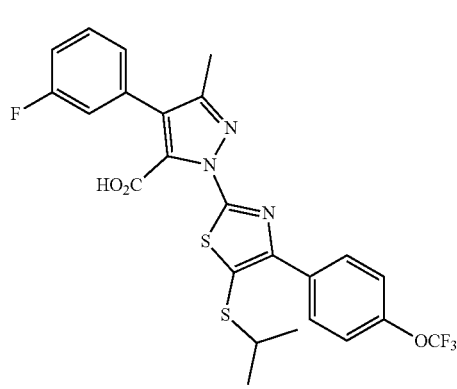 [SMILES: Cc1nn(-c2nc(-c3ccc(OC(F)(F)F)cc3)c(SC(C)C)s2)c(C(=O)O)c1-c1cccc(F)c1] | 4-(3-fluorophenyl)-1-(5-(isopropylthio)-4-(4-(trifluoromethoxy)phenyl)thiazol-2-yl)-3-methyl-1H-pyrazole-5-carboxylic acid | B | $^1$H NMR (500 MHz, DMSO) δ 8.11 (d, J = 8.8 Hz, 2H), 7.55-7.45 (m, 3H), 7.36-7.29 (m, 2H), 7.23 (t, J = 8.2 Hz, 1H), 3.34 (hept, J = 6.7 Hz, 1H), 2.31 (s, 3H), 1.23 (d, J = 6.7 Hz, 6H); MS (m/z): 538.0 [M + 1]$^+$ |

| Ex. | Structure | Name | EC$_{50}$ | Characterization |
|---|---|---|---|---|
| 224 | 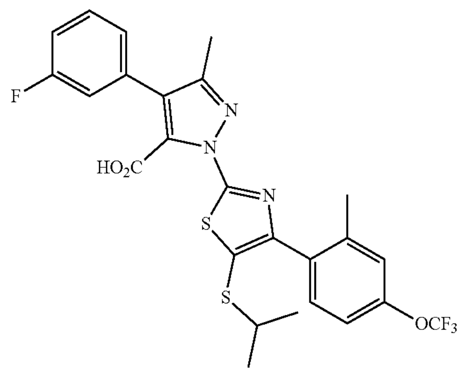 [SMILES: Cc1cc(OC(F)(F)F)ccc1-c1nc(-n2nc(C)c(-c3cccc(F)c3)c2C(=O)O)sc1SC(C)C] | 4-(3-fluorophenyl)-1-(5-(isopropylthio)-4-(2-methyl-4-(trifluoromethoxy)phenyl)thiazol-2-yl)-3-methyl-1H-pyrazole-5-carboxylic acid | A | $^1$H NMR (500 MHz, DMSO) δ 7.54-7.48 (m, 1H), 7.45 (d, J = 8.4 Hz, 1H), 7.35 (s, 1H), 7.32-7.20 (m, 4H), 3.20 (hept, J = 6.7 Hz, 1H), 2.31 (s, 3H), 2.25 (s, 3H), 1.15 (d, J = 6.7 Hz, 6H); MS (m/z): 552.1 [M + 1]$^+$ |
| 225 | 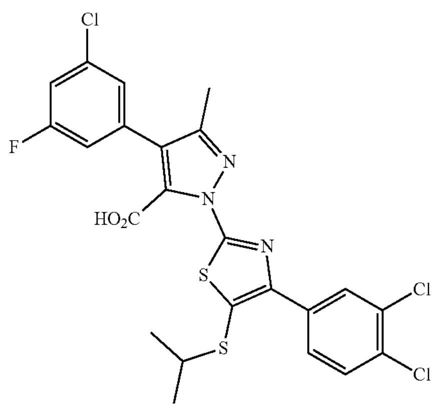 [SMILES: Cc1nn(-c2nc(-c3ccc(Cl)c(Cl)c3)c(SC(C)C)s2)c(C(=O)O)c1-c1cc(F)cc(Cl)c1] | 4-(3-chloro-5-fluorophenyl)-1-(4-(3,4-dichlorophenyl)-5-(isopropylthio)thiazol-2-yl)-3-methyl-1H-pyrazole-5-carboxylic acid | A | $^1$H NMR (500 MHz, DMSO) δ 8.20 (d, J = 2.0 Hz, 1H), 8.02 (dd, J = 8.5, 2.1 Hz, 1H), 7.75 (d, J = 8.5 Hz, 1H), 7.48 (d, J = 8.7 Hz, 1H), 7.42 (s, 1H), 7.39-7.33 (m, 1H), 2.32 (s, 3H), 1.24 (d, J = 6.7 Hz, 6H); MS (m/z): 555.8 [M + 1]$^+$ |
| 226 | 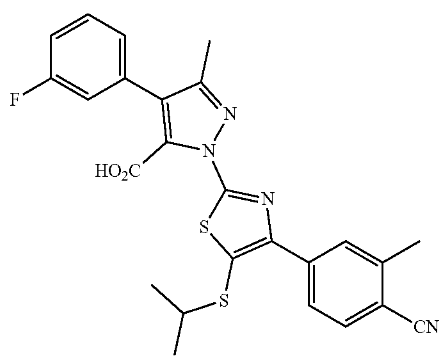 [SMILES: Cc1cc(-c2nc(-n3nc(C)c(-c4cccc(F)c4)c3C(=O)O)sc2SC(C)C)ccc1C#N] | 1-(4-(4-cyano-3-methylphenyl)-5-(isopropylthio)thiazol-2-yl)-4-(3-fluorophenyl)-3-methyl-1H-pyrazole-5-carboxylic acid | C | $^1$H NMR (500 MHz, DMSO) δ 8.04 (s, 1H), 8.01 (d, J = 8.0 Hz, 1H), 7.86 (d, J = 8.0 Hz, 1H), 7.52-7.44 (m, 1H), 7.40-7.31 (m, 2H), 7.24-7.16 (m, 1H), 3.43-3.29 (m, 1H), 2.54 (s, 3H), 2.31 (s, 3H), 1.24 (d, J = 6.7 Hz, 6H). MS (m/z): 493.1 [M + 1]$^+$ |
| 227 | 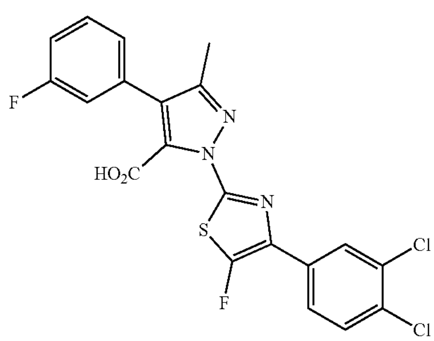 [SMILES: Cc1nn(-c2nc(-c3ccc(Cl)c(Cl)c3)c(F)s2)c(C(=O)O)c1-c1cccc(F)c1] | 1-(4-(3,4-dichlorophenyl)-5-fluorothiazol-2-yl)-4-(3-fluorophenyl)-3-methyl-1H-pyrazole-5-carboxylic acid | D | $^1$H NMR (500 MHz, DMSO) δ 7.92 (t, J = 1.1 Hz, 1H), 7.76 (d, J = 1.1 Hz, 2H), 7.48 (dd, J = 14.4, 8.0 Hz, 1H), 7.41-7.30 (m, J = 15.4, 9.1 Hz, 2H), 7.19 (t, J = 7.6 Hz, 1H), 3.33 (1H, below water signal), 2.29 (s, 3H); MS (m/z): 466.9 [M + 1]$^+$. |

-continued

| Ex. | Structure | Name | EC$_{50}$ | Characterization |
|---|---|---|---|---|
| 228 | 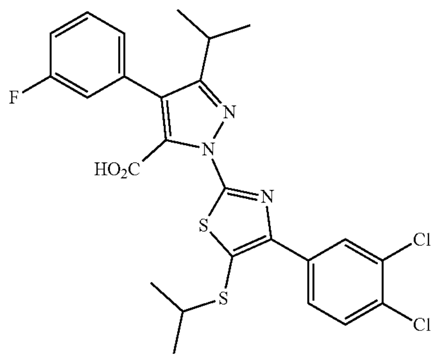 [SMILES: CC(C)Sc1sc(-n2nc(C(C)C)c(-c3cccc(F)c3)c2C(=O)O)nc1-c1ccc(Cl)c(Cl)c1] | 1-(4-(3,4-dichlorophenyl)-5-(isopropylthio)thiazol-2-yl)-4-(3-fluorophenyl)-3-isopropyl-1H-pyrazole-5-carboxylic acid | B | $^1$H NMR (500 MHz, MeOD) δ 8.45 (d, J = 2.0 Hz, 1H), 8.14 (dd, J = 8.5, 2.1 Hz, 1H), 7.55 (d, J = 8.5 Hz, 1H), 7.45-7.37 (m, 1H), 7.33-7.29 (m, 1H), 7.28-7.22 (m, 1H), 7.06 (td, J = 8.1, 2.1 Hz, 1H), 3.29-3.24 (m, 1H), 3.15-3.09 (m, 1H), 1.32-1.21 (m, 12H); MS (m/z): 552.02 [M + 1]$^+$ |
| 229 | 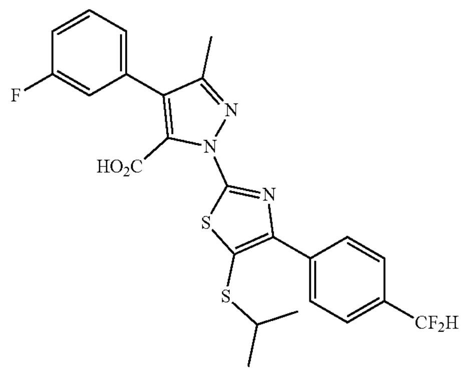 [SMILES: Cc1nn(-c2nc(-c3ccc(C(F)F)cc3)c(SC(C)C)s2)c(C(=O)O)c1-c1cccc(F)c1] | 1-(4-(4-(difluoromethyl)phenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 8.13 (d, J = 8.2 Hz, 2H), 7.67 (d, J = 8.3 Hz, 2H), 7.53-7.47 (m, 1H), 7.37-7.30 (m, 2H), 7.25-7.20 (m, 1H), 7.09 (t, J = 55.0 Hz, 1H), 3.33 (1H, below water signal), 2.31 (s, 3H), 1.23 (d, J = 6.7 Hz, 6H); MS (m/z): 504.2 [M + 1]$^+$. |
| 230 | 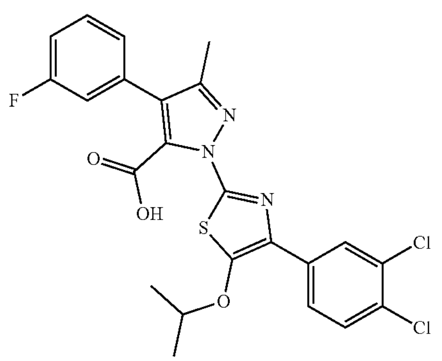 [SMILES: Cc1nn(-c2nc(-c3ccc(Cl)c(Cl)c3)c(OC(C)C)s2)c(C(=O)O)c1-c1cccc(F)c1] | 1-(4-(3,4-dichlorophenyl)-5-isopropoxythiazol-2-yl)-4-(3-fluorophenyl)-3-methyl-1H-pyrazole-5-carboxylic acid | C | $^1$H NMR (500 MHz,) δ 8.12 (s, 1H), 7.96 (d, J = 8.4 Hz, 1H), 7.73 (d, J = 8.5 Hz, 1H), 7.50 (dd, J = 14.4, 7.6 Hz, 1H), 7.42 (d, J = 10.0 Hz, 1H), 7.38 (d, J = 7.7 Hz, 1H), 7.19 (s, 1H), 4.52 (dt, J = 11.8, 6.0 Hz, 1H), 2.32 (s, 3H), 1.47 (d, J = 6.0 Hz, 6H); MS (m/z): 506.07 [M + 1]+. |
| 231 | 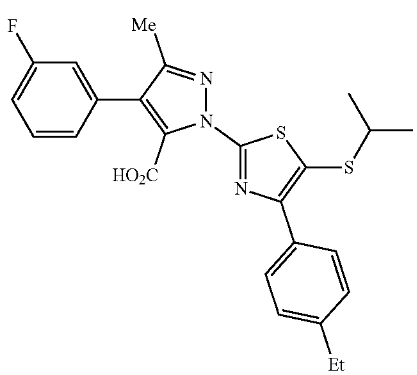 [SMILES: CCc1ccc(-c2nc(-n3nc(C)c(-c4cccc(F)c4)c3C(=O)O)sc2SC(C)C)cc1] | 1-(4-(4-ethylphenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 7.93 (d, J = 8.2 Hz, 2H), 7.50 (dd, J = 14.6, 7.7 Hz, 1H), 7.35-7.29 (m, 4H), 7.21 (t, J = 8.8 Hz, 1H), 2.65 (q, J = 7.7 Hz, 2H), 2.31 (s, 3H), 1.22 (dd, J = 8.3, 7.2 Hz, 9H); MS (m/z): 482.18 [M + 1]$^+$ |

| Ex. | Name | EC50 | Characterization |
|---|---|---|---|
| 232 | 2-(4-(2,6-dimethylpyridin-4-yl)-3,5-dimethyl-1H-pyrazol-1-yl)-5-(isopropylthio)-4-(4-(trifluoromethyl)phenyl)thiazole | E | $^{1}$H NMR (500 MHz, CDCl$_3$) δ 8.25 (d, J = 8.2 Hz, 2H), 7.69 (d, J = 8.3 Hz, 2H), 6.89 (s, 2H), 3.25 (h, J = 6.7 Hz, 1H), 2.74 (s, 3H), 2.59 (s, 6H), 2.31 (s, 3H), 1.28 (d, J = 6.7 Hz, 6H). MS (m/z): 503.17 [M + 1]$^+$ |
| 233 | 4-(3-fluorophenyl)-1-(4-(5-fluoropyridin-3-yl)-5-(isopropylthio)thiazol-2-yl)-3-methyl-1H-pyrazole-5-carboxylic acid | I | $^{1}$H NMR (500 MHz, DMSO) δ 9.16 (s, 1H), 8.63 (d, J = 2.7 Hz, 1H), 8.28-8.24 (m, 1H), 7.48-7.38 (m, 3H), 7.11 (t, J = 7.9 Hz, 1H), 2.30 (s, 3H), 1.24 (d, J = 6.7 Hz, 6H). MS (m/z): 473.07 [M + 1]$^+$ |
| 234 | 1-(4-(benzofuran-3-yl)-5-(isopropylthio)thiazol-2-yl)-4-(3-fluorophenyl)-3-methyl-1H-pyrazole-5-carboxylic acid | I | |
| 235 | 4-(3,4-difluorophenyl)-1-(5-(isopropylthio)-4-(4-(trifluoromethyl)phenyl)thiazol-2-yl)-3-methyl-1H-pyrazole-5-carboxylic acid | A | $^{1}$H NMR (500 MHz, DMSO) δ 8.25 (d, J = 8.2 Hz, 2H), 7.80 (d, J = 8.3 Hz, 2H), 7.61 (ddd, J = 12.0, 7.9, 1.9 Hz, 1H), 7.46 (dt, J = 10.7, 8.7 Hz, 1H), 7.36 (s, 1H), 2.28 (s, 3H), 1.22 (d, J = 6.7 Hz, 6H); MS (m/z): 540.22 [M + 1]$^+$ |

| Ex. | Structure | Name | EC$_{50}$ | Characterization |
|---|---|---|---|---|
| 236 | 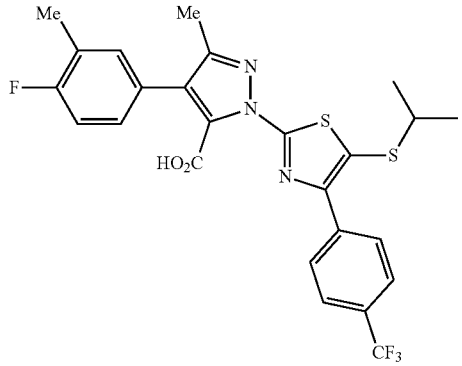 [SMILES: Cc1cc(-c2c(C)nn(-c3nc(-c4ccc(C(F)(F)F)cc4)c(SC(C)C)s3)c2C(=O)O)ccc1F] | 4-(4-fluoro-3-methylphenyl)-1-(5-(isopropylthio)-4-(4-(trifluoromethyl)phenyl)thiazol-2-yl)-3-methyl-1H-pyrazole-5-carboxylic acid | B | $^1$H NMR (500 MHz, DMSO) δ 8.24 (d, J = 8.2 Hz, 2H), 7.78 (d, J = 8.3 Hz, 2H), 7.40 (dd, J = 7.4, 1.5 Hz, 1H), 7.36-7.30 (m, 1H), 7.18-7.12 (m, 1H), 2.25 (s, 3H), 2.25 (s, 3H), 1.21 (d, J = 6.7 Hz, 6H); MS (m/z): 536.26 [M + 1]$^+$ |
| 237 | 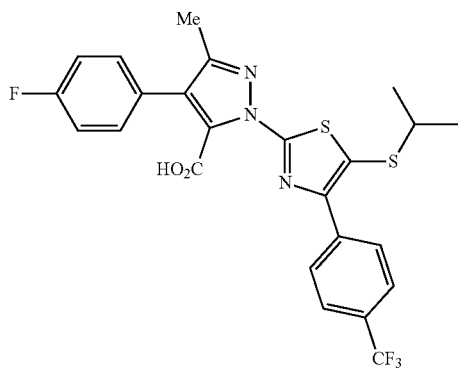 [SMILES: Cc1nn(-c2nc(-c3ccc(C(F)(F)F)cc3)c(SC(C)C)s2)c(C(=O)O)c1-c1ccc(F)cc1] | 4-(4-fluorophenyl)-1-(5-(isopropylthio)-4-(4-(trifluoromethyl)phenyl)thiazol-2-yl)-3-methyl-1H-pyrazole-5-carboxylic acid | B | $^1$H NMR (500 MHz, MeOD) δ 8.43 (d, J = 8.1 Hz, 2H), 7.72 (d, J = 8.3 Hz, 2H), 7.59-7.55 (m, 2H), 7.17-7.11 (m, 2H), 2.33 (s, 3H), 1.28 (d, J = 6.7 Hz, 6H); MS (m/z): 522.18 [M + 1]$^+$ |
| 238 | 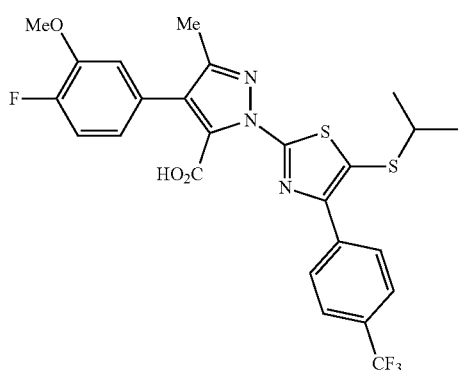 | 4-(4-fluoro-3-methoxyphenyl)-1-(5-(isopropylthio)-4-(4-(trifluoromethyl)phenyl)thiazol-2-yl)-3-methyl-1H-pyrazole-5-carboxylic acid | B | $^1$H NMR (500 MHz, MeOD) δ 8.45 (d, J = 8.2 Hz, 2H), 7.72 (d, J = 8.3 Hz, 2H), 7.36 (dd, J = 8.3, 2.0 Hz, 1H), 7.16-7.03 (m, 3H), 3.92 (s, 3H), 3.28 (dt, J = 13.3, 6.7 Hz, 1H), 2.35 (s, 3H), 1.29 (d, J = 6.7 Hz, 6H); MS (m/z): 552.14 [M + 1]$^+$ |
| 239 | 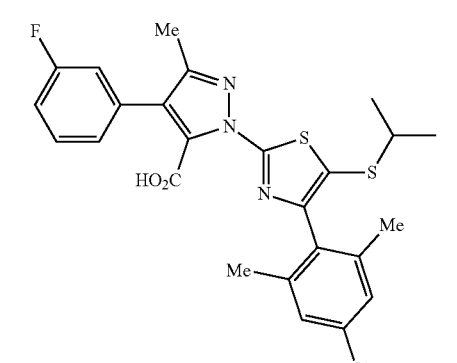 | 1-(4-(4-chloro-2,6-dimethylphenyl)-5-(isopropylthio)thiazol-2-yl)-4-(3-fluorophenyl)-3-methyl-1H-pyrazole-5-carboxylic acid | C | $^1$H NMR (500 MHz, DMSO) δ 7.50 (dd, J = 14.2, 7.7 Hz, 1H), 7.30-7.20 (m, 5H), 3.20 (dt, J = 13.2, 6.6 Hz, 1H), 2.30 (s, 3H), 2.06 (s, 6H), 1.19 (d, J = 6.7 Hz, 6H); MS (m/z): 516.24 [M + 1]$^+$. |

| Ex. | Structure | Name | EC$_{50}$ | Characterization |
|---|---|---|---|---|
| 240 | 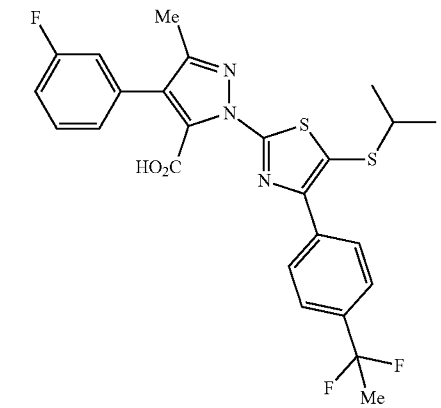 [SMILES: Cc1nn(-c2nc(-c3ccc(C(C)(F)F)cc3)c(SC(C)C)s2)c(C(=O)O)c1-c1cccc(F)c1] | 1-(4-(4-(1,1-difluoroethyl)phenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 8.09 (d, J = 8.5 Hz, 2H), 7.66 (d, J = 8.5 Hz, 2H), 7.54-7.49 (m, 1H), 7.32 (t, J = 7.7 Hz, 2H), 7.24 (t, J = 7.9 Hz, 1H), 2.32 (s, 3H), 2.01 (t, J = 18.9 Hz, 3H), 1.23 (d, J = 6.7 Hz, 6H); MS (m/z): 518.22 [M + 1]$^+$. |
| 241 | 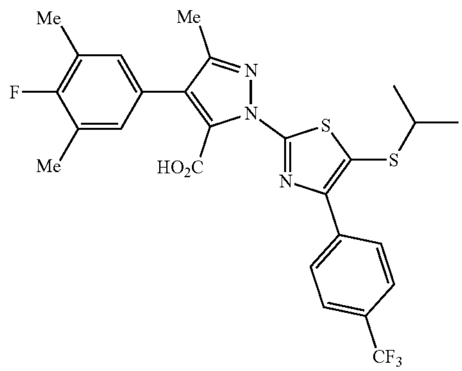 [SMILES: Cc1cc(-c2c(C)nn(-c3nc(-c4ccc(C(F)(F)F)cc4)c(SC(C)C)s3)c2C(=O)O)cc(C)c1F] | 4-(4-fluoro-3,5-dimethylphenyl)-1-(5-(isopropylthio)-4-(4-(trifluoromethyl)phenyl)thiazol-2-yl)-3-methyl-1H-pyrazole-5-carboxylic acid | A | $^1$H NMR (500 MHz, DMSO) δ 8.21 (d, J = 8.1 Hz, 2H), 7.82 (d, J = 8.3 Hz, 2H), 7.19 (d, J = 6.9 Hz, 2H), 2.28 (s, 3H), 2.25 (s, 3H), 2.25 (s, 3H), 1.24 (d, J = 6.7 Hz, 6H); MS (m/z): 550.18 [M + 1]$^+$ |
| 242 | 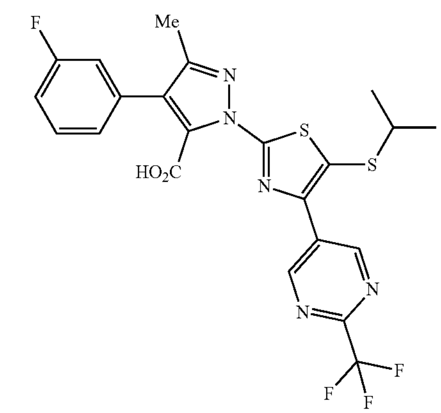 [SMILES: Cc1nn(-c2nc(-c3cnc(C(F)(F)F)nc3)c(SC(C)C)s2)c(C(=O)O)c1-c1cccc(F)c1] | 4-(3-fluorophenyl)-1-(5-(isopropylthio)-4-(2-(trifluoromethyl)pyrimidin-5-yl)thiazol-2-yl)-3-methyl-1H-pyrazole-5-carboxylic acid | C | $^1$H NMR (500 MHz, DMSO) δ 9.60 (s, 2H), 7.51 (dd, J = 15.1, 8.0 Hz, 1H), 7.36 (t, J = 8.8 Hz, 2H), 7.22 (t, J = 8.8 Hz, 1H), 2.33 (s, 3H), 1.27 (d, J = 6.7 Hz, 6H); MS (m/z): 524.25 [M + 1]$^+$ |
| 243 | 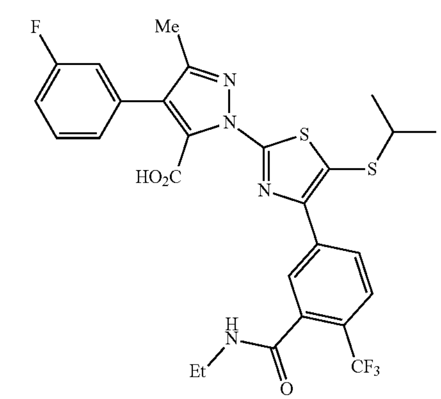 | 1-(4-(4-chloro-3-(ethylcarbamoyl)phenyl)-5-(isopropylthio)thiazol-2-yl)-4-(3-fluorophenyl)-3-methyl-1H-pyrazole-5-carboxylic acid | I | $^1$H NMR (500 MHz, DMSO) δ 8.43 (t, J = 5.6 Hz, 1H), 7.99-7.94 (m, 2H), 7.52 (d, J = 8.4 Hz, 1H), 7.43 (dd, J = 14.6, 7.8 Hz, 1H), 7.26 (t, J = 9.9 Hz, 2H), 2.24 (s, 3H), 1.18 (d, J = 6.7 Hz, 6H), 1.05 (t, J = 7.2 Hz, 3H); MS (m/z): 559.14 [M + 1]$^+$ |

| Ex. | Structure | Name | EC₅₀ | Characterization |
|---|---|---|---|---|
| 244 | 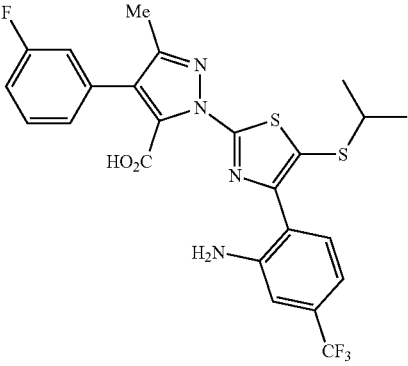 [SMILES: Cc1nn(-c2nc(-c3ccc(C(F)(F)F)cc3N)c(SC(C)C)s2)c(C(=O)O)c1-c1cccc(F)c1] | 1-(4-(2-amino-4-(trifluoromethyl)phenyl)-5-(isopropylthio)thiazol-2-yl)-4-(3-fluorophenyl)-3-methyl-1H-pyrazole-5-carboxylic acid | B | $^1$H NMR (500 MHz, DMSO) δ 7.52-7.43 (m, 2H), 7.34 (dd, J = 15.6, 9.5 Hz, 2H), 7.21-7.14 (m, 1H), 7.11 (s, 1H), 6.87 (d, J = 8.0 Hz, 1H), 2.30 (s, 3H), 1.16 (d, J = 6.7 Hz, 6H); MS (m/z): 537.23 [M + 1]⁺ |
| 245 | 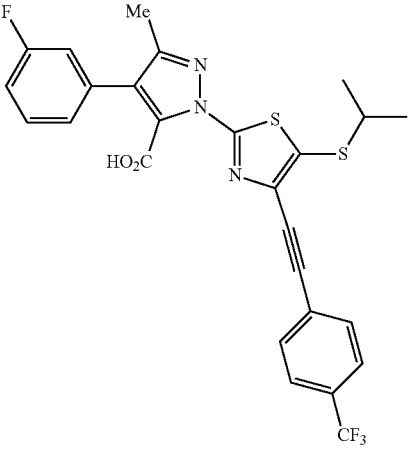 [SMILES: Cc1nn(-c2nc(C#Cc3ccc(C(F)(F)F)cc3)c(SC(C)C)s2)c(C(=O)O)c1-c1cccc(F)c1] | 4-(3-fluorophenyl)-1-(5-(isopropylthio)-4-((4-(trifluoromethyl)phenyl)ethynyl)thiazol-2-yl)-3-methyl-1H-pyrazole-5-carboxylic acid | D | $^1$H NMR (500 MHz, DMSO) δ 7.85-7.74 (m, 5H), 7.46 (dd, J = 14.4, 7.7 Hz, 1H), 7.36 (dd, J = 18.1, 9.2 Hz, 2H), 3.49 (dt, J = 13.3, 6.6 Hz, 1H), 2.29 (s, 3H), 1.34 (d, J = 6.7 Hz, 6H); MS (m/z): 546.22 [M + 1]⁺ |
| 246 | 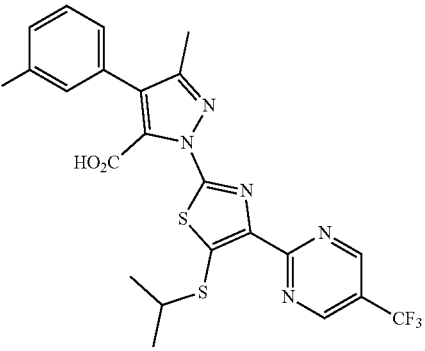 | 4-(3-fluorophenyl)-1-(5-(isopropylthio)-4-(5-(trifluoromethyl)pyrimidin-2-yl)thiazol-2-yl)-3-methyl-1H-pyrazole-5-carboxylic acid | D | $^1$H NMR (500 MHz, DMSO) δ 9.36 (s, 2H), 7.47 (dd, J = 14.5, 7.6 Hz, 1H), 7.36 (d, J = 9.3 Hz, 1H), 7.33 (d, J = 7.7 Hz, 1H), 7.21-7.15 (m, 1H), 3.57 (dt, J = 13.3, 6.7 Hz, 1H), 2.29 (s, 3H), 1.40 (d, J = 6.6 Hz, 6H); MS (m/z): 524.1 [M + 1]⁺ |
| 247 | 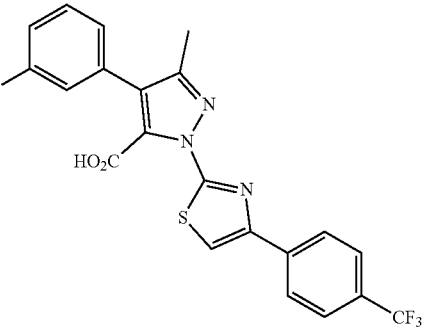 | 4-(3-fluorophenyl)-3-methyl-1-(4-(4-(trifluoromethyl)phenyl)thiazol-2-yl)-1H-pyrazole-5-carboxylic acid | D | $^1$H NMR (500 MHz, DMSO) δ 8.19 (s, 1H), 8.13 (d, J = 8.3 Hz, 2H), 7.81 (d, J = 8.3 Hz, 2H), 7.50 (dd, J = 14.6, 7.2 Hz, 1H), 7.35 (t, J = 9.9 Hz, 2H), 7.21 (t, J = 8.6 Hz, 1H), 2.32 (s, 3H). MS (m/z): 448.1 [M + 1]⁺ |

-continued

| Ex. | Structure | Name | EC$_{50}$ | Characterization |
|---|---|---|---|---|
| 248 | 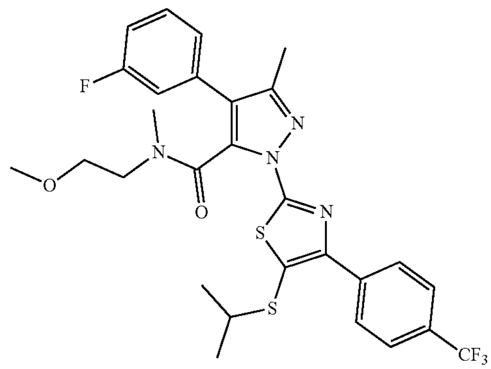 [SMILES: COCCN(C)C(=O)c1c(-c2cccc(F)c2)c(C)nn1-c1nc(-c2ccc(C(F)(F)F)cc2)c(SC(C)C)s1] | 4-(3-fluorophenyl)-1-(5-(isopropylthio)-4-(4-(trifluoromethyl)phenyl)thiazol-2-yl)-N-(2-methoxyethyl)-N,3-dimethyl-1H-pyrazole-5-carboxamide | K | $^1$H NMR (500 MHz, DMSO) δ 8.19 (d, J = 8.2 Hz, 2H), 8.14 (d, J = 8.2 Hz, 2H), 7.92-7.87 (m, 4H), 7.56-7.49 (m, 2H), 7.36-7.20 (m, 6H), 3.97-3.89 (m, 1H), 3.49-3.42 (m, 1H), 3.41-3.34 (m, , 2H), 3.24-3.17 (m, 2H), 3.07 (s, 3H), 3.02 (s, 2H), 2.91 (s, 2H), 2.82 (s, 3H), 2.54-2.52 (m, 1H), 2.39 (s, 3H), 2.38 (s, 2H), 1.24 (dd, J = 6.6, 2.8 Hz, 11H). MS (m/z): 593.2 [M + 1]$^+$ |
| 249 | 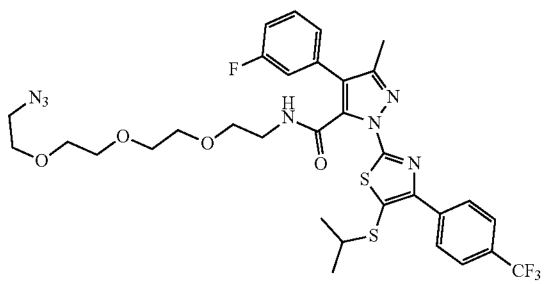 [SMILES: Cc1nn(-c2nc(-c3ccc(C(F)(F)F)cc3)c(SC(C)C)s2)c(C(=O)NCCOCCOCCOCCN=[N+]=[N-])c1-c1cccc(F)c1] | N-(2-(2-(2-(2-azidoethoxy)ethoxy)ethoxy)ethyl)-4-(3-fluorophenyl)-1-(5-(isopropylthio)-4-(4-(trifluoromethyl)phenyl)thiazol-2-yl)-3-methyl-1H-pyrazole-5-carboxamide | K | $^1$H NMR (500 MHz, MeOD) δ 8.27 (d, J = 8.2 Hz, 2H), 7.75 (d, J = 8.3 Hz, 2H), 7.47 (td, J = 8.0, 6.1 Hz, 1H), 7.32-7.28 (m, 1H), 7.26-7.20 (m, 1H), 7.16-7.10 (m, 1H), 3.60-3.56 (m, 2H), 3.56-3.50 (m, 4H), 3.50-3.41 (m, 6H), 3.31 (3H, below MeOH signal), 3.30-3.24 (m, 2H), 2.37 (s, 3H), 1.27 (d, J = 6.7 Hz, 6H). MS (m/z): 722.3 [M + 1]$^+$. |
| 250 | 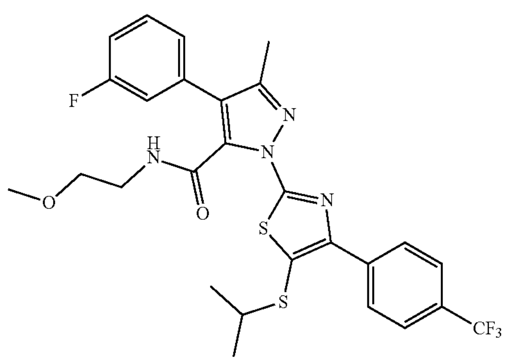 [SMILES: COCCNC(=O)c1c(-c2cccc(F)c2)c(C)nn1-c1nc(-c2ccc(C(F)(F)F)cc2)c(SC(C)C)s1] | 4-(3-fluorophenyl)-1-(5-(isopropylthio)-4-(4-(trifluoromethyl)phenyl)thiazol-2-yl)-N-(2-methoxyethyl)-3-methyl-1H-pyrazole-5-carboxamide | D | $^1$H NMR (500 MHz, DMSO) δ 9.04 (t, J = 5.6 Hz, 1H), 8.18 (d, J = 8.1 Hz, 2H), 7.88 (d, J = 8.2 Hz, 2H), 7.54-7.47 (m, 1H), 7.36-7.28 (m, 2H), 7.25-7.19 (m, 1H), 3.41-3.33 (m, 3H), 3.28 (t, J = 5.8 Hz, 2H), 3.05 (s, 3H), 2.35 (s, 3H), 1.23 (d, J = 6.7 Hz, 6H). MS (m/z): 579.1 [M + 1]$^+$ |
| 251 | 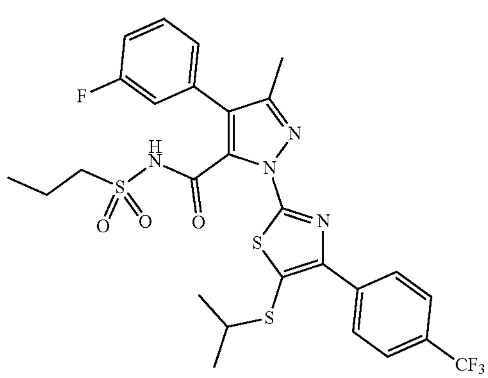 [SMILES: CCCS(=O)(=O)NC(=O)c1c(-c2cccc(F)c2)c(C)nn1-c1nc(-c2ccc(C(F)(F)F)cc2)c(SC(C)C)s1] | 4-(3-fluorophenyl)-1-(5-(isopropylthio)-4-(4-(trifluoromethyl)phenyl)thiazol-2-yl)-3-methyl-N-(propylsulfonyl)-1H-pyrazole-5-carboxamide | K | $^1$H NMR (500 MHz, MeOD) δ 8.37 (d, J = 8.1 Hz, 2H), 7.72 (d, J = 8.3 Hz, 2H), 7.46 (td, J = 8.0, 6.2 Hz, 1H), 7.35-7.31 (m, 1H), 7.30-7.25 (m, 1H), 7.11 (td, J = 8.2, 1.8 Hz, 1H), 3.30-3.20 (m, J = 13.4, 6.7 Hz, 1H), 3.13-3.05 (m, 2H), 2.34 (s, 3H), 1.55-1.44 (m, 2H), 1.26 (d, J = 6.7 Hz, 6H), 0.73 (t, J = 7.5 Hz, 3H). MS (m/z): 627.1 [M + 1]$^+$ |

| Ex. | Structure | Name | EC$_{50}$ | Characterization |
|---|---|---|---|---|
| 252 | 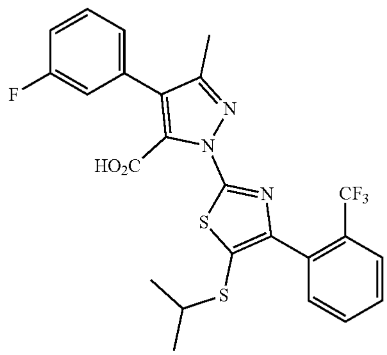 [SMILES: Cc1nn(-c2nc(-c3ccccc3C(F)(F)F)c(SC(C)C)s2)c(C(=O)O)c1-c1cccc(F)c1] | 4-(3-fluorophenyl)-1-(5-(isopropylthio)-4-(2-(trifluoromethyl)phenyl)thiazol-2-yl)-3-methyl-1H-pyrazole-5-carboxylic acid | D | $^1$H NMR (500 MHz, DMSO) δ 13.97 (s, 1H), 7.88-7.83 (m, 1H), 7.80-7.75 (m, 1H), 7.73-7.67 (m, 1H), 7.57-7.42 (m, 2H), 7.36-7.13 (m, 3H), 3.25-3.12 (m, 1H), 2.30 (s, 3H), 1.16 (d, J = 6.7 Hz, 6H). MS (m/z): 522.0 [M + 1]$^+$ |
| 253 | 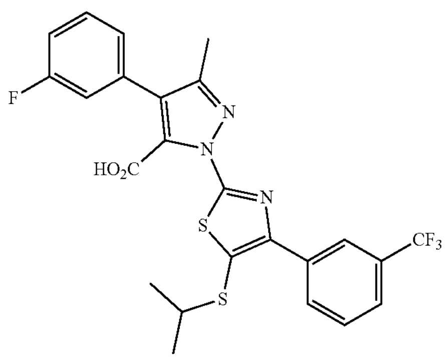 [SMILES: Cc1nn(-c2nc(-c3cccc(C(F)(F)F)c3)c(SC(C)C)s2)c(C(=O)O)c1-c1cccc(F)c1] | 4-(3-fluorophenyl)-1-(5-(isopropylthio)-4-(3-(trifluoromethyl)phenyl)thiazol-2-yl)-3-methyl-1H-pyrazole-5-carboxylic acid | C | $^1$H NMR (500 MHz, DMSO) δ 8.40 (bs, 1H), 8.31-8.25 (m, 1H), 7.81-7.77 (m, 1H), 7.76-7.71 (m, 1H), 7.54-7.46 (m, 1H), 7.39-7.30 (m, 2H), 7.26-7.16 (m, 1H), 3.39-3.28 (m, 1H), 2.32 (s, 3H), 1.24 (d, J = 6.7 Hz, 6H). MS (m/z): 521.9 [M + 1]$^+$ |
| 254 | 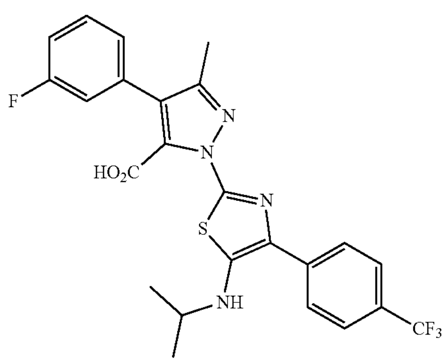 [SMILES: Cc1nn(-c2nc(-c3ccc(C(F)(F)F)cc3)c(NC(C)C)s2)c(C(=O)O)c1-c1cccc(F)c1] | 4-(3-fluorophenyl)-1-(5-(isopropylamino)-4-(4-(trifluoromethyl)phenyl)thiazol-2-yl)-3-methyl-1H-pyrazole-5-carboxylic acid | C | $^1$H NMR (500 MHz, MeOD) δ 8.10 (d, J = 8.4 Hz, 2H), 7.67 (d, J = 8.4 Hz, 2H), 7.49-7.43 (m, 1H), 7.30-7.27 (m, 1H), 7.25-7.21 (m, 1H), 7.15-7.09 (m, 1H), 3.44-3.38 (m, 1H), 2.33 (s, 3H), 1.32 (d, J = 6.3 Hz, 6H). MS (m/z): 505.2 [M + 1]$^+$ |
| 255 | 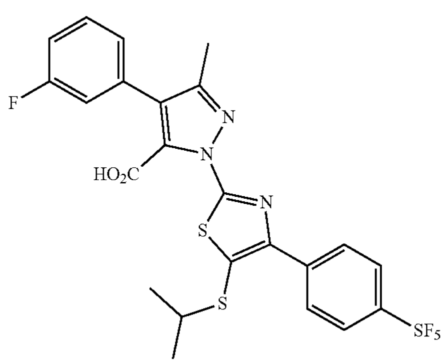 | 4-(3-fluorophenyl)-1-(5-(isopropylthio)-4-(4-(pentafluoro-λ$^6$-sulfaneyl)phenyl)thiazol-2-yl)-3-methyl-1H-pyrazole-5-carboxylic acid | A | $^1$H NMR (500 MHz, DMSO) δ 8.20 (d, J = 8.8 Hz, 2H), 8.00 (d, J = 8.8 Hz, 2H), 7.53-7.46 (m, 1H), 7.38-7.30 (m, 2H), 7.24-7.16 (m, 1H), 3.45-3.29 (m, 1H), 2.31 (s, 3H), 1.23 (d, J = 6.7 Hz, 6H). MS (m/z): 580.0 [M + 1]$^+$ |

| Ex. | Structure | Name | EC$_{50}$ | Characterization |
|---|---|---|---|---|
| 256 | 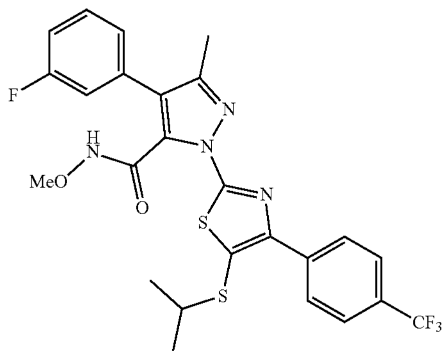 [SMILES: CONC(=O)c1c(-c2cccc(F)c2)c(C)nn1-c1nc(-c2ccc(C(F)(F)F)cc2)c(SC(C)C)s1] | 4-(3-fluorophenyl)-1-(5-(isopropylthio)-4-(4-(trifluoromethyl)phenyl)thiazol-2-yl)-N-methoxy-3-methyl-1H-pyrazole-5-carboxamide | D | $^1$H NMR (500 MHz, DMSO) δ 11.96-11.82 (bs, 1H), 8.19 (d, J = 8.3 Hz, 2H), 7.86 (d, J = 8.3 Hz, 2H), 7.64-7.45 (m, 1H), 7.37-7.19 (m, 3H), 3.57 (s, 3H), 3.41-3.32 (m, 1H), 2.36 (s, 3H), 1.23 (d, J = 6.7 Hz, 6H). MS (m/z): 551.1 [M + 1]$^+$ |
| 257 | 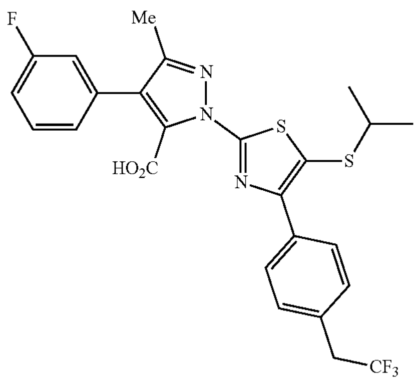 [SMILES: Cc1nn(-c2nc(-c3ccc(CC(F)(F)F)cc3)c(SC(C)C)s2)c(C(=O)O)c1-c1cccc(F)c1] | 4-(3-fluorophenyl)-1-(5-(isopropylthio)-4-(4-(2,2,2-trifluoroethyl)phenyl)thiazol-2-yl)-3-methyl-1H-pyrazole-5-carboxylic acid | B | $^1$H NMR (500 MHz, DMSO) δ 8.02 (d, J = 8.2 Hz, 2H), 7.50-7.45 (m, 3H), 7.39-7.33 (m, 2H), 7.22-7.16 (m, 1H), 3.71 (q, J = 11.6 Hz, 2H), 2.31 (s, 3H), 1.23 (d, J = 6.7 Hz, 6H). MS (m/z): 536.2 [M + 1]$^+$ |
| 258 | 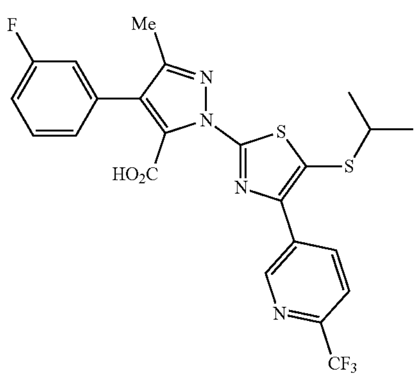 [SMILES: Cc1nn(-c2nc(-c3ccc(C(F)(F)F)nc3)c(SC(C)C)s2)c(C(=O)O)c1-c1cccc(F)c1] | 4-(3-fluorophenyl)-1-(5-(isopropylthio)-4-(6-(trifluoromethyl)pyridin-3-yl)thiazol-2-yl)-3-methyl-1H-pyrazole-5-carboxylic acid | B | $^1$H NMR (500 MHz, DMSO) δ 9.32 (d, J = 1.7 Hz, 1H), 8.67 (dd, J = 8.2, 1.8 Hz, 1H), 7.98 (d, J = 8.2 Hz, 1H), 7.49 (q, J = 10.0 Hz, 1H), 7.37-7.34 (m, 2H), 7.21-7.18 (m, 1H), 3.40-3.35 (m, 1H), 2.31 (s, 3H), 1.24 (d, J = 6.7 Hz, 6H). MS (m/z): 523.1 [M+1]$^+$ |
| 259 | 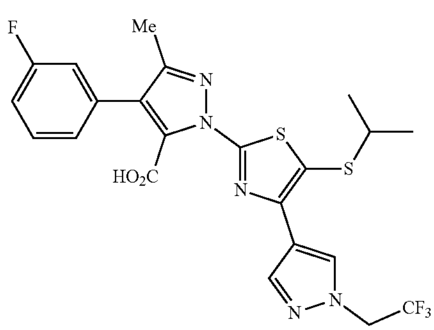 [SMILES: Cc1nn(-c2nc(-c3cnn(CC(F)(F)F)c3)c(SC(C)C)s2)c(C(=O)O)c1-c1cccc(F)c1] | 4-(3-fluorophenyl)-1-(5-(isopropylthio)-4-(1-(2,2,2-trifluoroethyl)-1H-pyrazol-4-yl)thiazol-2-yl)-3-methyl-1H-pyrazole-5-carboxylic acid | D | $^1$H NMR (500 MHz, MeOD) δ 8.51 (s, 1H), 8.39 (s, 1H), 7.43-7.31 (m, 3H), 7.05-7.02 (m, 1H), 4.98 (q, J = 8.6 Hz, 2H), 3.28-3.24 (m, 1H), 2.33 (s, 3H), 1.31 (d, J = 6.7 Hz, 6H). MS (m/z): 526.0 [M + 1]$^+$ |

In another aspect, the disclosure provides N-oxides of the compounds as recited in any of the preceding embodiments. But in certain embodiments as described above, the compounds are not provided as N-oxides.

In another aspect, the disclosure provides pharmaceutically-acceptable salts of the compounds and N-oxides as recited in any of the preceding embodiments. The person of ordinary skill in the art will appreciate that a variety of pharmaceutically-acceptable salts may be provided, as described in additional detail below. The person of ordinary skill in the art will appreciate that the phrase "optionally in the form of a pharmaceutically acceptable salt or N-oxide, or a solvate or hydrate" includes compounds in the form of a pharmaceutically acceptable salt of an N-oxide. But in certain embodiments as described above, the compounds are not provided as pharmaceutically acceptable salts.

In another aspect, the disclosure provides solvates (e.g., hydrates) of the compounds, N-oxides and salts as recited in any of the preceding embodiments. The person of ordinary skill in the art will appreciate that a variety of solvates and/or hydrates may be formed. The person of ordinary skill in the art will appreciate that the phrase "optionally in the form of a pharmaceutically acceptable salt or N-oxide, or a solvate or hydrate" includes compounds in the form of a solvates and hydrates of base compounds, pharmaceutically acceptable salts and N-oxides as described above. But in certain embodiments as described above, the compounds are not provided as solvates or hydrates.

In another aspect, the present disclosure provides pharmaceutical compositions comprising a compound, N-oxide, salt, solvate or hydrate according to any one of the preceding aspects or embodiments of the invention or any embodiment thereof, together with a pharmaceutically acceptable excipient, diluent, or carrier.

A hallmark of hyperproliferation is the need for Cap-dependent translation. Increased proliferation, for example, requires increased protein synthesis. Therefore, in another aspect, the disclosure provides the use of a compound described by any one of the preceding aspects of the disclosure or any embodiment thereof, for the preparation of a medicament for inhibiting the initiation of translation of mRNA to protein, e.g., in cases of aberrant mRNA translational regulation. Similarly, the disclosure provides the use of a compound described by any one of the preceding aspects of the disclosure or any embodiment thereof for inhibiting the initiation of translation. The disclosure also provides methods for inhibiting the initiation of translation, the methods comprising administering to a subject in need thereof an effective amount of a compound described by any of the preceding aspects of the disclosure or any embodiment thereof. The compounds described herein can be used, for example, to treat Burkitt lymphoma.

In various embodiments, but without limitation, the compounds described herein can, through inhibition of the initiation of translation, modulate (e.g., downregulate) a signaling network or pathway selected from the PI3K, Akt, mTOR, Ras, BRAF, MEK, ERK, MAPK, MNK, Myc EGFR, HER2, BCR, BCL2, MCL1, Cyclin, ER, PR and AR networks/pathways.

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-(A)$_a$, wherein a is 0 or 1. In such instances, when a is 0 the moiety is —B and when a is 1 the moiety is —B-A.

As used herein, the term "alkyl" includes a saturated hydrocarbon having a designed number of carbon atoms, such as 1 to 10 carbons (i.e., inclusive of 1 and 10), 1 to 8 carbons, 1 to 6 carbons, 1 to 3 carbons, or 1, 2, 3, 4, 5 or 6. Alkyl group may be straight or branched and depending on context, may be a monovalent radical or a divalent radical (i.e., an alkylene group). For example, the moiety "—($C_1$-$C_6$alkyl)-O—" signifies connection of an oxygen through an alkylene bridge having from 1 to 6 carbons and $C_1$-$C_3$alkyl represents methyl, ethyl, and propyl moieties. Examples of "alkyl" include, for example, methyl, ethyl, propyl, isopropyl, butyl, iso-, sec- and tert-butyl, pentyl, and hexyl.

The term "alkoxy" represents an alkyl group of indicated number of carbon atoms attached to the parent molecular moiety through an oxygen bridge. Examples of "alkoxy" include, for example, methoxy, ethoxy, propoxy, and isopropoxy.

The term "alkenyl" as used herein, unsaturated hydrocarbon containing from 2 to 10 carbons (i.e., inclusive of 2 and 10), 2 to 8 carbons, 2 to 6 carbons, or 2, 3, 4, 5 or 6, unless otherwise specified, and containing at least one carbon-carbon double bond. Alkenyl group may be straight or branched and depending on context, may be a monovalent radical or a divalent radical (i.e., an alkenylene group). For example, the moiety "—($C_2$-$C_6$ alkenyl)-O—" signifies connection of an oxygen through an alkenylene bridge having from 2 to 6 carbons. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl" as used herein, unsaturated hydrocarbon containing from 2 to 10 carbons (i.e., inclusive of 2 and 10), 2 to 8 carbons, 2 to 6 carbons, or 2, 3, 4, 5 or 6 unless otherwise specified, and containing at least one carbon-carbon triple bond. Alkynyl group may be straight or branched and depending on context, may be a monovalent radical or a divalent radical (i.e., an alkynylene group). For example, the moiety "—($C_2$-$C_6$ alkynyl)-O—" signifies connection of an oxygen through an alkynylene bridge having from 2 to 6 carbons. Representative examples of alkynyl include, but are not limited to, acetylenyl, 1-propynyl, 2-propynyl, 3-butynyl, 2-pentynyl, and 1-butynyl.

The term "aryl" represents an aromatic ring system having a single ring (e.g., phenyl) which is optionally fused to other aromatic hydrocarbon rings or non-aromatic hydrocarbon or heterocycle rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. "Aryl" also includes ring systems having a first carbocyclic, aromatic ring fused to a nonaromatic heterocycle, for example, 1H-2,3-dihydrobenzofuranyl and tetrahydroisoquinolinyl. The aryl groups herein are unsubstituted or, when specified as "optionally substituted", can unless stated otherwise be substituted in one or more substitutable positions with various groups as indicated.

The terms "halogen" or "halo" indicate fluorine, chlorine, bromine, and iodine. In certain embodiments of each and every embodiment described herein, the term "halogen" or "halo" refers to fluorine or chlorine. In certain embodiments of each and every embodiment described herein, the term "halogen" or "halo" refers to fluorine.

The term "heteroaryl" refers to an aromatic ring system containing at least one aromatic heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic rings, for example, cycloalkyl or heterocycloalkyl rings, wherein the cycloalkyl and heterocycloalkyl rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, isoindolinyl, isobenzothienyl, benzoxazolyl, pyridopyridinyl, purinyl, benzodioxolyl, triazinyl, pteridinyl, benzothiazolyl, imidazopyridinyl, imidazothiazolyl, benzisoxazinyl, benzoxazinyl, benzopyranyl, benzothiopyranyl, chromonyl, chromanonyl, pyridinyl-N-oxide, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as indicated.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as indicated.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups, as indicated.

The term "ring system" encompasses monocycles, as well as fused and/or bridged polycycles.

The term "oxo" means a doubly bonded oxygen, sometimes designated as =O or for example in describing a carbonyl "C(O)" may be used to show an oxo substituted carbon.

The term "substituted," when used to modify a specified group or radical, means that one or more hydrogen atoms of the specified group or radical are each, independently of one another, replaced with the same or different substituent groups as defined below, unless specified otherwise.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluene-sulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease. Of course, in certain embodiments, the compound has substantially the same isotopic character as naturally-occurring materials.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" or "effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder;

(3) ameliorating the disease (including a symptom thereof); for example, ameliorating a disease, condition or disorder in an individual who is experiencing or displaying the pathology or symptomatology of the disease, condition or disorder (i.e., reversing the pathology and/or symptomatology) such as decreasing the severity of disease; or (4) eliciting a referenced biological effect, e.g., inhibiting the initiation of translation. Such biological effect need not be complete, i.e., an inhibition of the initiation of translation need not be complete inhibition in order for the amount of compound administered to be therapeutically effective.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof; or (ii) eliciting the referenced biological effect (e.g., inhibiting the initiation of translation).

Pharmaceutical Formulations and Dosage Forms

The compounds of the disclosure can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to any one of structural formulae.

In the pharmaceutical compositions disclosed herein, one or more compounds of the disclosure may be present in association with one or more pharmaceutically acceptable carriers, diluents or excipients, and, if desired, other active ingredients. The pharmaceutical compositions containing compounds of the disclosure may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of the disclosure can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of the disclosure can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

The person of ordinary skill in the art will formulate a compound as described into pharmaceutical formulations herein. for example, based on the physicochemical properties of the compound, the amount of the compound needed for a pharmaceutically effective amount, and the desired route of administration.

Examples

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art in view of the particular preparative procedures described herein. One of skill in the art can adapt the reaction sequences described in examples below to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

Compounds suitable for use in the presently disclosed pharmaceutical compositions include compounds of Table 1, above. A variety of exemplary syntheses are provided below; the person of ordinary skill in the art will adapt the procedures described herein and/or other procedures familiar to the person of ordinary skill in the art, to make the compounds described herein.

The following synthetic examples and biochemical data are intended to further illustrate certain embodiments and are not intended to limit the scope of the presently disclosed compounds.

Compound 1: methyl 1-(4-(3,4-dichlorophenyl)thiazol-2-yl)-3-methyl-4-(2-nitrobenzyl)-1H-pyrazole-5-carboxylate methyl 2-(methoxyimino)-3-(2-nitrobenzyl)-4-oxopentanoate Methyl acetopyruvate (1.0 g, 6.94 mmol), methoxyhydroxylamine hydrochloride (0.58 g, 6.94 mmol) and molecular sieves (2.5 g) were placed in a flame dried round bottom flask equipped with a nitrogen inlet. Dry DMF (23 mL) was added and the round bottom flask was covered with foil and stirred overnight at room temperature. The reaction mixture was diluted with EtOAc (150 mL) and the organic phase was washed with water (3×50 mL) and brine (1×50 mL), dried with $Na_2SO_4$, filtered and concentrated under vacuum to afford the title compound (1.07 g, 6.16 mmol, 89%) as red liquid.

methyl 2-(methoxyimino)-3-(2-nitrobenzyl)-4-oxopentanoate

A mixture of ethyl 2-methoxyimino-4-oxooctanoate (3.38 g, 19.52 mmol), of o-Nitrobenzylbromide (4.22 g, 19.52 mmol), of freshly pulverized anhydrous potassium carbonate (3.24 g, 23.42 mmol), and of dry DMF (54.22 mL) was stirred vigorously for 24 h at rt. The reaction was neutralized with HCl 0.2 M and diluted in EtOAc. The phases were separated, the aqueous layer was extracted with EtOAc (2×200 mL), and then the combined organic layers were dried over $Na_2SO_4$, filtered and concentrated under vacuum. The crude product was purified by flash chromatography (dry packing) on silica gel using a solution of EtOAc in hexanes (0 to 20%). The product was then purified by reverse flash chromatography (C18, using a gradient 20 to 55% MeCN in $H_2O$) and afforded the title compound (2.62 g, 8.50 mmol, 44%) as white solid.

4-(3,4-dichlorophenyl)-2-hydrazinylthiazole

A solution of thiosemicarbazide (2.0 g, 7.46 mmol) and of 3,4-dichlorophenacyl bromide (0.68 g, 7.46 mmol) in dioxane (75 mL) was stirred at room temperature overnight. An aqueous solution of saturated $Na_2CO_3$ was added. The reaction mixture was stirred vigorously for 1 h. The reaction mixture was dissolve in $Et_2O$ and water was added. The aqueous layer was extracted with $Et_2O$ (3×). The combined organic layers were dried over $Na_2SO_4$, filtered and concentrated under vacuum. The solid was triturated in $Et_2O$, filtered and washed with $Et_2O$, resulting in the title compound (1.31 g, 5.02 mmol, 67%) as beige solid.

methyl 1-(4-(3,4-dichlorophenyl)thiazol-2-yl)-3-methyl-4-(2-nitrobenzyl)-1H-pyrazole-5-carboxylate Methyl 2-(methoxyimino)-3-(2-nitrobenzyl)-4-oxopentanoate (60.0 mg, 0.19 mmol) was dissolved in MeOH (2 mL) and 4-(3,4-dichlorophenyl)-2-hydrazinylthiazole (56.0 mg, 0.21 mmol) was added followed by HCl 12 N (32 µL, 0.39 mmol) dropwise. The reaction mixture was heated to reflux overnight. The crude product was concentrated under vacuum and was purified using a semi prep HPLC-MS (column X-Bridge 30×50, eluted with 70-90% MeCN/$NH_4CO_2H$ 10 mM, pH 3.8/Flow 45 ml/min/11 min), resulting in the title compound (9.5 mg, 0.02 mmol, 10%) as white solid after lyophilization.

$^1$H NMR (500 MHz, DMSO) δ 8.19 (s, 1H), 8.08 (d, J=2.0 Hz, 1H), 8.02 (dd, J=8.1, 1.1 Hz, 1H), 7.82 (dd, J=8.4, 2.0 Hz, 1H), 7.73 (d, J=8.4 Hz, 1H), 7.69 (td, J=7.6, 1.2 Hz, 1H), 7.57-7.51 (m, 1H), 7.33 (d, J=7.5 Hz, 1H), 4.24 (s, 2H), 3.68 (s, 3H), 2.14 (s, 3H); MS (m/z): 503.12 [M+1]$^+$.

Compound 3: methyl 1-(4-(3,4-dichlorophenyl)-5-(ethylthio)thiazol-2-yl)-3-methyl-4-(2-nitrobenzyl)-1H-pyrazole-5-carboxylate 1-(3,4-dichlorophenyl)-2-thiocyanatoethanone Potassium thiocyanate (7.2 g, 74.6 mmol) was added to a stirred solution of 2-bromo-1-(3,4-dichlorophenyl)ethanone (10 g, 37 mmol) in MeCN (93 mL) at rt. The reaction mixture was heated to reflux (90° C.) for 1 h, then cooled to room temperature and diluted with water (100 mL). The aqueous layer was extracted with EtOAc (3×100 mL) The combined organic layers were washed with brine (300 mL), dried over $MgSO_4$, filtered and concentrated in vacuo to give the title compound, which was used without further purification.

2-chloro-4-(3,4-dichlorophenyl)thiazole

A mixture of 1-(3,4-dichlorophenyl)-2-thiocyanatoethanone (49.6 g, 0.20 mol) and 4 M HCl in dioxane (302 mL, 1.21 mol) in dioxane (200 mL) was stirred for 16 h at rt. The reaction mixture was concentrated in vacuo and the residue was diluted with sat. aq. $NaHCO_3$ (400 mL) and extracted with EtOAc (3×400 mL). The combined organic layers were washed with brine (500 mL), dried over $MgSO_4$, filtered and concentrated in vacuo and afforded the title compound (45.5 g, 0.17 mol, 85%) as beige solid.

2-chloro-4-(3,4-dichlorophenyl)-5-(ethylthio)thiazole

A 2.5 M solution of n-BuLi in hexanes (2.0 mL, 5.0 mmol) was added to a THF solution (12 mL) of 2-chloro-4-(3,4-dichlorophenyl)thiazole (1.06 g, 4 mmol) at −78° C. The reaction mixture was stirred at the same temperature for 2 h. Diethyl disulfide (0.98 g, 8 mmol) was added to the reaction and after 10 min, an aqueous saturated solution of $NH_4Cl$ (25 mL) was added. The reaction mixture was extracted with EtOAc (3×25 mL). The combined organic layers were washed with brine (75 mL), and dried with $Na_2SO_4$, filtered and evaporated under reduced pressure. The crude product was purified by flash chromatography (dry packing) on silica gel using a solution of EtOAc in hexanes (5 to 10% gradient) and afforded the title compound (1.27 g, 3.92 mmol, 98%) as red liquid.

4-(3,4-dichlorophenyl)-5-(ethylthio)-2-hydrazinylthiazole

DIPEA (0.32 g, 2.5 mmol) was added to a solution of hydrazine hydrochloride (0.17 g, 2.5 mmol) and 2-chloro- 4-(3,4-dichlorophenyl)-5-(ethylthio)thiazole (0.41 g, 1.3 mmol) to NMP (2.5 mL) in a glass microwave vial. The tube was sealed and the reaction was heated to 150° C. for 2 h with microwave radiation. The reaction mixture was diluted with water (10 mL) and extracted with EtOAc (3×10 mL). The combined organic layer were washed with brine (50 mL), and dried with $Na_2SO_4$, filtered and evaporated under reduced pressure. The product was purified by reverse flash chromatography (C18, using a gradient 20 to 70% MeCN in $H_2O$) and afforded the title compound (0.31 g, 0.96 mmol, 76%) as green oil.

methyl 1-(4-(3,4-dichlorophenyl)-5-(ethylthio)thiazol-2-yl)-3-methyl-4-(2-nitrobenzyl)-1H-pyrazole-5-carboxylate Methyl 2-(methoxyimino)-3-(2-nitrobenzyl)-4-oxopentanoate (100.0 mg, 0.32 mmol) was dissolved in MeOH (3 mL). 4-(3,4-dichlorophenyl)-5-(ethylthio)-2-hydrazinylthiazole (104.0 mg, 0.32 mmol) was added and then HCl 12 N (108 µL, 1.30 mmol) was added dropwise to the reaction mixture. The reaction mixture was heated to reflux overnight. The crude product was concentrated under vacuum and was purified using a semi prep HPLC-MS (column X-Bridge 30×50, eluted with 70-90% MeCN/$NH_4CO_2H$ 10 mM, pH 3.8/Flow 45 ml/min/11 min), resulting in the title compound (100.0 mg, 0.18 mmol, 55%) as white solid after lyophilization.

$^1$H NMR (500 MHz, DMSO) δ 8.06 (d, J=2.1 Hz, 1H), 8.02 (dd, J=8.1, 1.3 Hz, 1H), 7.91 (dd, J=8.5, 2.1 Hz, 1H), 7.77 (d, J=8.5 Hz, 1H), 7.68 (td, J=7.6, 1.3 Hz, 1H), 7.57-7.50 (m, 1H), 7.33 (d, J=6.9 Hz, 1H), 4.23 (s, 2H), 3.64 (s, 3H), 2.97 (q, J=7.3 Hz, 2H), 2.15 (s, 3H), 1.21 (t, J=7.3 Hz, 3H); MS (m/z): 563.0 [M+1]$^+$.

Compound 4: 1-(4-(3,4-dichlorophenyl)-5-(ethylthio)thiazol-2-yl)-3-methyl-4-(2-nitrobenzyl)-1H-pyrazole-5-carboxylic Acid Into a 25 mL round bottom flask, methyl 1-(4-(3,4-dichlorophenyl)-5-(ethylthio)thiazol-2-yl)-3-methyl-4-(2-nitrobenzyl)-1H-pyrazole-5-carboxylate (25 mg, 0.04 mmol) was diluted with THF/MeOH (1 mL, 1:1). A solution of NaOH 1 M (89 µL, 0.09 mmol) was added and the reaction was stirred overnight at rt. The crude product was concentrated under vacuum and was purified using a semi prep HPLC-MS (column X-Bridge 30×50, eluted with 60-80% MeCN/$NH_4CO_2H$ 10 mM, pH 3.8/Flow 45 ml/min/11 min), resulting in the title compound (15.1 mg, 0.03 mmol, 62%) as white solid after lyophilization.

$^1$H NMR (500 MHz, DMSO) δ 8.11 (d, J=2.1 Hz, 1H), 7.99 (dd, J=8.1, 1.2 Hz, 1H), 7.94 (dd, J=8.5, 2.1 Hz, 1H), 7.76 (d, J=8.5 Hz, 1H), 7.64 (dt, J=7.7, 3.8 Hz, 1H), 7.50 (t, J=7.8 Hz, 1H), 7.23 (d, J=7.8 Hz, 1H), 4.23 (s, 2H), 2.97 (q, J=7.3 Hz, 2H), 2.06 (s, 3H), 1.21 (t, J=7.3 Hz, 3H); MS (m/z): 549.1 [M+1]$^+$.

Compound 5: methyl 1-(4-(3,4-dichlorophenyl)-5-(isopropylthio)thiazol-2-yl)-3-methyl-4-(2-nitrobenzyl)-1H-pyrazole-5-carboxylate 2-chloro-4-(3,4-dichlorophenyl)-5-(isopropylthio)thiazole A 2.5 M solution of n-BuLi in hexanes (37.8 mL, 94.5 mmol) was added to a THF solution (216 mL) of 2-chloro-4-(3,4-dichlorophenyl)thiazole (20.0 g, 75.6 mmol) at −78° C. The reaction mixture was stirred at the same temperature for 30 min. Diisopropyl disulfide (2.3 g, 24.2 mL, 151.2 mmol) was added to the reaction and was stirred at the same temperature for 1.5 h. Water (400 mL) was added to quench the reaction and then $Et_2O$ (300 mL). The reaction mixture was transferred into a separation funnel and the layers were separated. The aqueous layer was extracted with $Et_2O$ (2×300 mL). The combined organic layers were dried over $Na_2SO_4$ and concentrated under vacuum. The crude product was purified by flash chromatography on silica gel (dry packing) using a solution of EtOAc in hexanes (0 to 5% gradient) and afforded the title compound (19.0 g, 56.2 mmol, 74%) as orange oil.

4-(3,4-dichlorophenyl)-2-hydrazinyl-5-(isopropylthio)thiazole

DIPEA (3.2 mL, 18.2 mmol) was added to a solution of hydrazine hydrochloride (1.2 g, 18.2 mmol) and 2-chloro-4-(3,4-dichlorophenyl)-5-(methylthio)thiazole (3.1 g, 9.1 mmol) to NMP (30 mL) in two glass microwave vial. The vials were sealed and were heated to 150° C. for 2 h with microwave radiation. The reaction mixture was diluted with water (10 mL) and extracted with $Et_2O$. The combined organic layers were washed with brine (3×), and dried over $Na_2SO_4$, filtered and concentrated under vacuum. This afforded the title compound (2.9 g, 8.7 mmol, 96%) as green oil.

methyl 1-(4-(3,4-dichlorophenyl)-5-(isopropylthio)thiazol-2-yl)-3-methyl-4-(2-nitrobenzyl)-1H-pyrazole-5-carboxylate Methyl 2-(methoxyimino)-3-(2-nitrobenzyl)-4-oxopentanoate (60.0 mg, 0.19 mmol) was dissolved in MeOH (2 mL), 4-(3,4-dichlorophenyl)-2-hydrazinyl-5-(isopropylthio)thiazole (65.0 mg, 0.19 mmol) was added and then HCl 12 N (65 µL, 0.78 mmol) was added dropwise to the reaction mixture. The reaction mixture was heated to reflux overnight. The crude product was concentrated under vacuum and was purified using a semi prep HPLC-MS (column X-Bridge 30×50, eluted with 70-90% MeCN/$NH_4CO_2H$ 10 mM, pH 3.8/Flow 45 ml/min/11 min), resulting in the title compound (96.7 mg, 0.17 mmol, 86%) as white solid after lyophilization.

$^1$H NMR (500 MHz, DMSO) δ 8.10 (d, J=2.1 Hz, 1H), 8.02 (dd, J=8.2, 1.2 Hz, 1H), 7.96 (dd, J=8.5, 2.1 Hz, 1H), 7.77 (d, J=8.5 Hz, 1H), 7.72-7.64 (m, 1H), 7.54 (t, J=7.2 Hz, 1H), 7.33 (d, J=7.1 Hz, 1H), 4.23 (s, 2H), 3.64 (s, 3H), 3.38-3.34 (m, 1H), 2.15 (s, 3H), 1.22 (d, J=6.7 Hz, 6H); MS (m/z): 577.1 [M+1]$^+$.

Compound 12: 1-(5-(butylthio)-4-(3,4-dichlorophenyl)thiazol-2-yl)-3-methyl-4-(2-nitrobenzyl)-1H-pyrazole-5-carboxylic Acid 5-(butylthio)-2-chloro-4-(3,4-dichlorophenyl)thiazole A 2.5 M solution of n-BuLi in hexanes (1.0 mL, 2.5 mmol) was added to a THF solution (6 mL) of 2-chloro-4-(3,4-dichlorophenyl)thiazole (0.53 g, 2.0 mmol) at −78° C. The reaction mixture was stirred at the same temperature for 2 h. Dibutyl disulfide (0.71 g, 4.0 mmol) was added to the reaction and after 10 min, an aqueous saturated solution of $NH_4Cl$ (15 mL) was added. The reaction mixture was extracted with EtOAc (3×15 mL). The combined organic layers were washed with brine (50 mL), dried with Na$_2$SO$_4$, filtered and evaporated under reduced pressure. The crude product was purified by flash chromatography (dry packing) on silica gel eluting using a solution of EtOAc in hexanes (5 to 10% gradient) and afforded the title compound (0.68 g, 1.93 mmol, 97%) as red liquid.

5-(butylthio)-4-(3,4-dichlorophenyl)-2-hydrazinylthiazole

DIPEA (0.29 mL, 1.65 mmol) was added to a solution of hydrazine hydrochloride (0.11 g, 1.7 mmol) and 2-chloro-4-(3,4-dichlorophenyl)-5-(propylthio)thiazole (0.12 g, 0.30 mmol) to NMP (2 mL) in a glass microwave vial. The vials were sealed and were heated to 150° C. for 1 h with microwave radiation. The reaction mixture was diluted with water (5 mL) and extracted with EtOAc. The combined organic layers were washed with brine (3×), and dried over Na$_2$SO$_4$, filtered and concentrated under vacuum. The crude product was purified by flash chromatography on silica gel using a solution of DCM in hexanes (0 to 5% gradient) and afforded the title compound (61.0 mg, 0.18 mmol, 53%) as purple solid.

methyl 1-(5-(butylthio)-4-(3,4-dichlorophenyl)thiazol-2-yl)-3-methyl-4-(2-nitrobenzyl)-1H-pyrazole-5-carboxylate Methyl 2-(methoxyimino)-3-(2-nitrobenzyl)-4-oxopentanoate (38.0 mg, 0.12 mmol) was dissolved in MeOH (2 mL). 5-(butylthio)-4-(3,4-dichlorophenyl)-2-hydrazinylthiazole (134.0 mg, 0.40 mmol) was added and then HCl 12 N (41 µL, 0.49 mmol) was added dropwise to the reaction mixture. The reaction mixture was heated to reflux overnight. The crude product was concentrated under vacuum and was purified using a semi prep HPLC-MS (column X-Bridge 30×50, eluted with 80-100% MeCN/NH$_4$CO$_2$H 10 mM, pH 3.8/Flow 45 ml/min/11 min), resulting in the title compound (49.0 mg, 0.08 mmol, 67%) as white solid after lyophilization.

1-(5-(butylthio)-4-(3,4-dichlorophenyl)thiazol-2-yl)-3-methyl-4-(2-nitrobenzyl)-1H-pyrazole-5-carboxylic Acid Methyl 1-(5-(butylthio)-4-(3,4-dichlorophenyl)thiazol-2-yl)-3-methyl-4-(2-nitrobenzyl)-1H-pyrazole-5-carboxylate (25.0 mg, 0.04 mmol) was diluted with THF/MeOH (1 mL, 1:1). A solution of NaOH 1 M (85 µL, 0.08 mmol) was added and the reaction was stirred overnight at rt. The crude product was concentrated under vacuum and was purified using a semi prep HPLC-MS (column X-Bridge 30×50, eluted with 70-90% MeCN/NH$_4$CO$_2$H 10 mM, pH 3.8/Flow 45 ml/min/11 min), resulting in the title compound (6.02 mg, 0.01 mmol, 25%) as yellow solid after lyophilization.

$^1$H NMR (500 MHz, CDCl$_3$) δ 8.04 (d, J=1.7 Hz, 1H), 7.97 (d, J=7.9 Hz, 1H), 7.68 (dd, J=8.6, 1.6 Hz, 1H), 7.55 (d, J=8.3 Hz, 1H), 7.44 (t, J=8.1 Hz, 1H), 7.36 (t, J=7.6 Hz, 1H), 7.05 (d, J=7.7 Hz, 1H), 4.66 (s, 2H), 2.87 (t, J=7.3 Hz, 2H), 2.17 (s, 3H), 1.60 (dt, J=14.9, 7.5 Hz, 2H), 1.39 (dq, J=14.5, 7.3 Hz, 2H), 0.88 (t, J=7.4 Hz, 3H); MS (m/z): 577.2 [M+1]$^+$.

Compound 13: 1-(4-(3,4-dichlorophenyl)-5-(propylthio)thiazol-2-yl)-3-methyl-4-(2-(methylsulfonamido)benzyl)-1H-pyrazole-5-carboxylic Acid methyl 4-(2-aminobenzyl)-1-(4-(3,4-dichlorophenyl)-5-(propylthio)thiazol-2-yl)-3-methyl-1H-pyrazole-5-carboxylate Methyl 1-(4-(3,4-dichlorophenyl)-5-(propylthio)thiazol-2-yl)-3-methyl-4-(2-nitrobenzyl)-1H-pyrazole-5-carboxylate (79.0 mg, 0.14 mmol) was dissolved in THF/MeOH (4 mL 1:1), platinum 1% and vanadium 2%, on activated carbon (50-70% wetted powder) Evonik Noblyst® P8078 (187.0 mg, 0.96 mmol) was then added. The flask was put under vacuum until MeOH starts bubbling, and then a hydrogen balloon was inserted. The reaction mixture was stirred overnight. The reaction mixture was filtered through Celite® and washed with MeOH and THF multiple times. The title compound (75.0 mg, 0.14 mmol, 100%) was concentrated under vacuum and used in the next step without further purification.

methyl 1-(4-(3,4-dichlorophenyl)-5-(propylthio)thiazol-2-yl)-3-methyl-4-(2-(methylsulfonamido)benzyl)-1H-pyrazole-5-carboxylate Methyl 4-(2-aminobenzyl)-1-(4-(3,4-dichlorophenyl)-5-(propylthio)thiazol-2-yl)-3-methyl-1H-pyrazole-5-carboxylate (75.0 mg, 0.14 mmol) was dissolved in dry DCM (1 mL) and pyridine (1.10 mL, 13.7 mmol) was added. MsCl (106 µL, 1.37 mmol) was added and the reaction mixture was stirred overnight under a nitrogen atmosphere. The crude product was concentrated under vacuum, resulting in the title compound (86 mg, 0.14 mmol, 100%).

1-(4-(3,4-dichlorophenyl)-5-(propylthio)thiazol-2-yl)-3-methyl-4-(2-(methylsulfonamido)benzyl)-1H-pyrazole-5-carboxylic Acid Methyl 1-(4-(3,4-dichlorophenyl)-5-(propylthio)thiazol-2-yl)-3-methyl-4-(2-(methylsulfonamido)benzyl)-1H-pyrazole-5-carboxylate (86.0 mg, 0.14 mmol) was diluted with THF/MeOH (1 mL, 1:1). A solution of NaOH 1 M (3.30 mL, 3.30 mmol) was added and the reaction was stirred 5 h at rt. The reaction mixture was acidified with HCl 3M and the crude product was concentrated under vacuum and was purified by reverse flash chromatography (C18, using a gradient 0 to 100% MeCN in H$_2$O) and afforded the title compound (39.7 mg, 0.07 mmol, 47%) as white solid after lyophilization.

$^1$H NMR (500 MHz, DMSO) δ 14.06 (s, 1H), 9.29 (s, 1H), 8.15 (d, J=2.1 Hz, 1H), 7.95 (dd, J=8.5, 2.1 Hz, 1H), 7.78 (d, J=8.5 Hz, 1H), 7.36 (d, J=7.8 Hz, 1H), 7.25 (t, J=7.6 Hz, 1H), 7.18 (t, J=7.5 Hz, 1H), 6.90 (d, J=7.3 Hz, 1H), 4.05 (s, 2H), 3.01 (s, 3H), 2.94 (t, J=7.1 Hz, 2H), 2.02 (s, 3H), 1.62-1.52 (m, 2H), 0.90 (t, J=7.3 Hz, 3H); MS (m/z): 613.1 [M+1]$^+$.

Compound 14: N-(2-((5-(4-(aminomethyl)piperidine-1-carbonyl)-1-(4-(3,4-dichlorophenyl)-5-(propylthio)thiazol-2-yl)-3-methyl-1H-pyrazol-4-yl)methyl)phenyl)methanesulfonamide tert-butyl (1-(1-(4-(3,4-dichlorophenyl)-5-(propylthio)thiazol-2-yl)-3-methyl-4-(2-(methylsulfonamido)benzyl)-1H-pyrazole-5-carbonyl)piperidin-4-yl)methylcarbamate 1-(4-(3,4-dichlorophenyl)-5-(propylthio)thiazol-2-yl)-3-methyl-4-(2-(methylsulfonamido)benzyl)-1H-pyrazole-5- carboxylic acid (27.0 mg, 0.04 mmol) was diluted with DMF (1 mL). DIPEA (16 µL, 0.09 mmol) and HATU (22.0 mg, 0.06 mmol) were added and the reaction mixture was stirred at rt overnight. The reaction mixture was transferred into a separation funnel with EtOAc and water. The layers were separated and the organic layer was washed with water (1×) and brine (3×), dried over $Na_2SO_4$ and concentrated under vacuum. The crude product was purified by flash chromatography on silica gel using a solution of EtOAc in hexanes (20 to 60% gradient) and afforded the title compound (18.8 mg, 0.02 mmol, 53%) as colorless oil.

N-(2-((5-(4-(aminomethyl)piperidine-1-carbonyl)-1-(4-(3,4-dichlorophenyl)-5-(propylthio)thiazol-2-yl)-3-methyl-1H-pyrazol-4-yl)methyl)phenyl)methanesulfonamide tert-butyl (1-(1-(4-(3,4-dichlorophenyl)-5-(propylthio)thiazol-2-yl)-3-methyl-4-(2-(methylsulfonamido)benzyl)-1H-pyrazole-5-carbonyl)piperidin-4-yl)methylcarbamate (19 mg, 0.05 mmol) was diluted in dioxane (1 mL) and then HCl in dioxane (0.34 mL, 1.4 mmol) was added. The reaction mixture was stirred at room temperature overnight under a nitrogen atmosphere. The product was purified using a semi prep HPLC-MS (column X-Bridge 30×50, eluted with 50-70% MeCN/$NH_4CO_2H$ 10 mM, pH 3.8/Flow 45 ml/min/11 min), resulting in the title compound (4.2 mg, 0.02 mmol, 30%) as white solid after lyophilization.

$^1$H NMR Mixture of 2 rotamers 1:1 (500 MHz, MeOD) δ 8.55 (s, 3H), 8.16 (d, J=2.1 Hz, 1H), 8.11 (d, J=2.0 Hz, 1H), 8.05 (dd, J=8.5, 2.1 Hz, 1H), 7.95 (dd, J=8.4, 2.1 Hz, 1H), 7.64-7.57 (m, 2H), 7.39-7.32 (m, 2H), 7.31-7.19 (m, 4H), 7.19-7.09 (m, 2H), 4.64 (d, J=13.2 Hz, 2H), 4.53 (d, J=13.4 Hz, 2H), 4.03 (s, 2H), 3.98 (s, 2H), 3.49-3.41 (m, 1H), 3.40-3.34 (m, 1H), 3.02 (s, 3H), 3.00 (s, 3H), 2.95-2.79 (m, 4H), 2.79-2.72 (m, 1H), 2.58 (dd, J=36.5, 24.3 Hz, 4H), 2.25 (d, J=4.2 Hz, 3H), 2.20 (s, 3H), 2.03 (s, 1H), 1.81 (d, J=11.8 Hz, 1H), 1.68-1.52 (m, 4H), 1.46 (t, J=15.3 Hz, 3H), 1.29 (s, 1H), 1.12 (d, J=12.7 Hz, 1H), 1.00-0.91 (m, 6H), 0.84-0.59 (m, 2H); MS (m/z): 709.0 [M+1]$^+$.

Compound 15: 4-bromo-1-(4-(3,4-dichlorophenyl)-5-(isopropylthio)thiazol-2-yl)-3-methyl-1H-pyrazole-5-carboxylic Acid methyl 1-(4-(3,4-dichlorophenyl)-5-(isopropylthio)thiazol-2-yl)-3-methyl-1H-pyrazole-5-carboxylate 4-(3,4-dichlorophenyl)-2-hydrazinyl-5-(isopropylthio)thiazole (11.0 g, 32.9 mmol), prepared as in Example 5, was dissolved in methanol (395 mL). Methyl 2-(methoxyimino)-4-oxopentanoate (6.84 g, 39.5 mmol) was added followed by $HCl_{conc}$ (11.0 mL, 134 mmol). The reaction mixture was refluxed for 18 hours. Water (300 mL) was added and half the MeOH was evaporated under reduced pressure. The mixture was extracted with DCM (3×250 mL), the combined organic layers were washed with an aqueous saturated solution of $NaHCO_3$ (300 mL) and brine (300 mL), dried with sodium sulfate, filtered and evaporated under reduced pressure. The crude product was purified by flash chromatography (dry packing) using a solution of DCM in Hexanes (10 to 20%). The title compound was obtained as viscous brown oil (8.85 g, 20.0 mmol, 61%).

methyl 4-bromo-1-(4-(3,4-dichlorophenyl)-5-(isopropylthio)thiazol-2-yl)-3-methyl-1H-pyrazole-5-carboxylate A solution of bromine (6.15 mL, 120 mmol) in acetonitrile (51 mL) was added dropwise to a solution of methyl 1-(4-(3,4-dichlorophenyl)-5-(isopropylthio)thiazol-2-yl)-3-methyl-1H-pyrazole-5-carboxylate (8.85 g, 20.0 mmol) in acetonitrile (51 mL) and DCM (51 mL). The reaction was stirred for 5 hours at room temperature. A saturated aqueous solution of $Na_2SO_3$ (300 mL) was added at 0° C. and the mixture was extracted with DCM (3×300 mL). The combined organic layers were dried with sodium sulfate, filtered and evaporated under reduced pressure. The crude product was purified by flash chromatography (dry packing) on silica gel using a solution of DCM in hexanes (10 to 20%) and afforded the title compound (7.26 g, 13.9 mmol, 70%) as a white solid.

4-bromo-1-(4-(3,4-dichlorophenyl)-5-(isopropylthio)thiazol-2-yl)-3-methyl-1H-pyrazole-5-carboxylic Acid Methyl 4-bromo-1-(4-(3,4-dichlorophenyl)-5-(isopropylthio)thiazol-2-yl)-3-methyl-1H-pyrazole-5-carboxylate (50 mg, 0.10 mmol) was diluted in a 1:1 solution of THF and MeOH (1 mL). 1M NaOH (0.19 mL, 0.19 mmol) was added and the reaction was stirred for 18 hours at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column with a solution of MeCN in water (containing 10 mM of $NH_4CO_2H$) (50 to 70%). The product was lyophilized and afforded the title compound (28 mg, 0.055 mmol, 58%) as a pale yellow powder.

$^1$H NMR (500 MHz, DMSO) δ 8.18 (d, J=2.1 Hz, 1H), 7.99 (dd, J=8.5, 2.1 Hz, 1H), 7.74 (d, J=8.5 Hz, 1H), 2.25 (s, 3H), 1.22 (d, J=6.7 Hz, 6H). Note: isopropyl CH is overlapping with water signal; MS (m/z): 505.7 [M+H]$^+$.

Compound 16: 1-(4-(3,4-dichlorophenyl)-5-(isopropylthio)thiazol-2-yl)-3-methyl-1H-pyrazole-5-carboxylic Acid Methyl 1-(4-(3,4-dichlorophenyl)-5-(isopropylthio)thiazol-2-yl)-3-methyl-1H-pyrazole-5-carboxylate (22 mg, 0.049 mmol) was diluted in a 1:1 solution of THF and MeOH (0.49 mL). 1M NaOH (0.098 mL, 0.098 mmol) was added and the reaction was stirred for 18 hours at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of $NH_4CO_2H$) (20 to 100%). The product was lyophilized and afforded the title compound (3.9 mg, 0.0091 mmol, 19%) as a white powder.

$^1$H NMR (500 MHz, DMSO) δ 8.19 (d, J=2.1 Hz, 1H), 8.02 (dd, J=8.5, 2.1 Hz, 1H), 7.81 (d, J=8.5 Hz, 1H), 6.91 (s, 1H), 3.39 (sept, J=6.7 Hz, 1H), 2.33 (s, 3H), 1.27 (d, J=6.7 Hz, 6H); MS (m/z): 426.0 [M−H]$^−$.

Compound 17: 1-(4-(3,4-dichlorophenyl)-5-(isopropylthio)thiazol-2-yl)-4-(imidazo[1,2-a]pyridin-6-yl)-3-methyl-1H-pyrazole-5-carboxylic Acid In a 5 mL glass microwave vial equipped with a magnetic stirring bar and nitrogen flow at room temperature was placed the 1-(4-bromo-1-(4-(3,4-dichlorophenyl)-5-(isopropylthio)thiazol-2-yl)-3-methyl-1H-pyrazol-5-yl)ethanone (50.0 mg, 0.10 mmol), imidazo[1,2-a]pyridin-6-ylboronic acid (18.6 mg, 0.12 mmol) and Na$_2$CO$_3$ (50.8 mg, 0.48 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (11.0 mg, 0.01 mmol). The vial was capped and placed in an oil bath at 85° C. for 16 h. NaOH 1 M (0.19 mL, 0.19 mmol) was added and the reaction mixture was stirred 6 h at 50° C. The reaction mixture was acidified with HCl 3M and the product crashed out. The solid was triturated in EtOAc/water and was then filtered. The product was purified using a semi prep HPLC-MS (column X-Bridge 30×50, eluted with 40-60% MeCN/NH$_4$CO$_2$H 10 mM, pH 3.8/Flow 45 ml/min/11 min), resulting in the title compound (11.0 mg, 0.02 mmol, 21%) as white solid after lyophilization.

$^1$H NMR (500 MHz, DMSO) δ 8.70 (s, 1H), 8.21 (d, J=2.1 Hz, 1H), 8.06-7.99 (m, 2H), 7.76 (d, J=8.5 Hz, 1H), 7.64 (d, J=9.5 Hz, 2H), 7.34 (d, J=9.0 Hz, 1H), 3.42-3.29 (m, 1H), 2.33 (s, 3H), 1.24 (d, J=6.7 Hz, 6H); MS (m/z): 544.0 [M+1]$^+$.

Compound 18: 1-(4-(3,4-dichlorophenyl)-5-(isopropylthio)thiazol-2-yl)-3-methyl-4-phenyl-1H-pyrazole-5-carboxylic Acid methyl 1-(4-(3,4-dichlorophenyl)-5-(isopropylthio) thiazol-2-yl)-3-methyl-4-phenyl-1H-pyrazole-5-carboxylate In a 5 mL glass microwave vial equipped with a magnetic stirring bar and nitrogen flow at room temperature was placed 1-(4-bromo-1-(4-(3,4-dichlorophenyl)-5-(isopropylthio)thiazol-2-yl)-3-methyl-1H-pyrazol-5-yl)ethanone prepared as in (25.0 mg, 0.05 mmol), phenylboronic acid (7.0 mg, 0.06 mmol) and Na$_2$CO$_3$ (25.4 mg, 0.24 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (5.5 mg, 0.01 mmol). The vial was capped and placed in an oil bath at 85° C. for 16 h. The crude product was purified by flash chromatography on silica gel using a solution of EtOAc in hexanes (0 to 20% gradient) and afforded the title compound (20.0 mg, 0.04 mmol, 80%) as white solid.

1-(4-(3,4-dichlorophenyl)-5-(isopropylthio)thiazol-2-yl)-3-methyl-4-phenyl-1H-pyrazole-5-carboxylic Acid Into a 25 mL round bottom flask, methyl 1-(4-(3,4-dichlorophenyl)-5-(isopropylthio)thiazol-2-yl)-3-methyl-4-phenyl-1H-pyrazole-5-carboxylate (20.0 mg, 0.04 mmol) was diluted with THF/MeOH (1 mL, 1:1). A solution of NaOH 1 M (193 μL, 0.19 mmol) was added and the reaction was stirred 16 h at rt. The reaction mixture was acidified with HCl 3M and the crude product was concentrated under vacuum. The product was purified using a semi prep HPLC-MS (column X-Bridge 30×50, eluted with 60-80% MeCN/NH$_4$CO$_2$H 10 mM, pH 3.8/Flow 45 ml/min/11 min), resulting in the title compound (5.0 mg, 0.01 mmol, 26%) as yellow solid after lyophilization.

$^1$H NMR (500 MHz, DMSO) δ 8.23 (d, J=2.0 Hz, 1H), 8.04 (dd, J=8.5, 2.0 Hz, 1H), 7.73 (d, J=8.5 Hz, 1H), 7.55-7.29 (m, 5H), 7.12 (br s, 1H), 3.42-3.29 (m, 1H), 2.29 (s, 3H), 1.24 (d, J=6.7 Hz, 5H); MS (m/z): 504.5 [M+1]$^+$.

Compound 19: 1-(5-(cyclohexylthio)-4-(3,4-dichlorophenyl)thiazol-2-yl)-3-methyl-4-(2-nitrobenzyl)-1H-pyrazole-5-carboxylic Acid 2-chloro-5-(cyclohexylthio)-4-(3,4-dichlorophenyl) thiazole A 2.5 M solution of n-BuLi in hexanes (2.3 mL, 5.67 mmol) was added to a THF solution (13 mL) of 2-chloro-4-(3,4-dichlorophenyl)thiazole prepared as in (1.0 g, 3.78 mmol) at −78° C. The reaction mixture was stirred at the same temperature for 30 min. Dicyclohexyl disulfide (1.89 mL, 7.56 mmol) was added and the reaction was stirred 3 h at the same temperature. Water was added to quench the reaction and the aqueous layer was extracted with EtOAc (3×). The combined organic layers were washed with brine, dried with Na$_2$SO$_4$, filtered and evaporated under reduced pressure. The crude product was purified by flash chromatography (wet loading) on silica gel eluting using a solution of EtOAc in hexanes (5 to 10% gradient) and afforded the title compound (0.85 g, 2.23 mmol, 59%) as bright orange oil.

5-(cyclohexylthio)-4-(3,4-dichlorophenyl)-2-hydrazinylthiazole

DIPEA (184 μL, 1.06 mmol) was added to a solution of hydrazine hydrochloride (72.0 mg, 1.06 mmol) and 2-chloro-5-(cyclohexylthio)-4-(3,4-dichlorophenyl)thiazole (200 mg, 0.53 mmol) to NMP (2 mL) in a glass microwave vial. The vials were sealed and were heated to 150° C. for 2 h with microwave radiation. The product was purified by reverse flash chromatography (C18, using a gradient 20 to 100% MeCN in H$_2$O) and afforded the title compound (153 mg, 0.41 mmol, 77%) as light orange oil.

methyl 1-(5-(cyclohexylthio)-4-(3,4-dichlorophenyl) thiazol-2-yl)-3-methyl-4-(2-nitrobenzyl)-1H-pyrazole-5-carboxylate Methyl 2-(methoxyimino)-3-(2-nitrobenzyl)-4-oxopentanoate (100.0 mg, 0.32 mmol) was dissolved in MeOH (4 mL). 5-(cyclohexylthio)-4-(3,4-dichlorophenyl)-2-hydrazinylthiazole (146.0 mg, 0.39 mmol) was added and then HCl 12 N (108 μL, 1.30 mmol) was added dropwise to the reaction mixture. The reaction mixture was heated to reflux overnight. The crude product was concentrated under vacuum and was purified by flash chromatography on silica gel using a solution of EtOAc in hexanes (5 to 20% gradient) and afforded the title compound (133 mg, 0.22 mmol, 66%) as brown solid.

1-(5-(cyclohexylthio)-4-(3,4-dichlorophenyl)thiazol-2-yl)-3-methyl-4-(2-nitrobenzyl)-1H-pyrazole-5-carboxylic Acid Methyl 1-(5-(cyclohexylthio)-4-(3,4-dichlorophenyl)thiazol-2-yl)-3-methyl-4-(2-nitrobenzyl)-1H-pyrazole-5-carboxylate (133 mg, 0.022 mmol) was diluted with THF/MeOH (2 mL, 1:1). A solution of NaOH 1 M (431 μL, 0.43 mmol) was added and the reaction was stirred 16 h at rt. The reaction mixture was acidified with HCl 3M and the crude product was concentrated under vacuum and was then extracted with EtOAc (3×), the combined organic layers were dried over Na$_2$SO$_4$, filtered and concentrated under vacuum, resulting in the title compound (116 mg, 0.19 mmol, 89%) as off-white solid after lyophilization.

¹H NMR (500 MHz, DMSO) δ 8.16 (d, J=2.1 Hz, 1H), 8.03-7.95 (m, 2H), 7.75 (d, J=8.5 Hz, 1H), 7.64 (dd, J=11.4, 3.8 Hz, 1H), 7.51 (t, J=7.7 Hz, 1H), 7.22 (d, J=7.5 Hz, 1H), 4.24 (s, 2H), 3.17-3.09 (m, 1H), 2.07 (s, 3H), 1.95-1.81 (m, 2H), 1.65 (dd, J=9.2, 3.8 Hz, 2H), 1.50 (dd, J=7.6, 3.1 Hz, 1H), 1.38-1.10 (m, 5H); MS (m/z): 603.5 [M+1]⁺.

Compound 20: 4-(benzofuran-2-yl)-1-(4-(3,4-dichlorophenyl)-5-(isopropylthio)thiazol-2-yl)-3-methyl-1H-pyrazole-5-carboxylic Acid 4-(benzofuran-2-yl)-1-(4-(3,4-dichlorophenyl)-5-(isopropylthio)thiazol-2-yl)-3-methyl-1H-pyrazole-5-carboxylic Acid In a 5 mL glass microwave vial equipped with a magnetic stirring bar and nitrogen flow at room temperature was placed 1-(4-bromo-1-(4-(3,4-dichlorophenyl)-5-(isopropylthio)thiazol-2-yl)-3-methyl-1H-pyrazol-5-yl)ethanone (52 mg, 0.10 mmol), benzofuran-2-ylboronic acid (19.4 mg, 0.12 mmol) and $Na_2CO_3$ (53.0 mg, 0.50 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh₃)₄ (11.6 mg, 0.01 mmol). The vial was capped and placed in an oil bath at 85° C. for 16 h. LiOH (21.0 mg, 0.50 mmol) was added to the reaction mixture and stirred under microwave radiation at 120° C. for 10 min. The product was purified using a semi prep HPLC-MS (column X-Bridge 30×50, eluted with 60-80% MeCN/NH₄CO₂H 10 mM, pH 3.8/Flow 45 ml/min/11 min), resulting in the title compound (3.0 mg, 0.006 mmol, 6%) as yellow solid after lyophilization.

¹H NMR (500 MHz, DMSO) δ 8.25 (d, J=1.9 Hz, 1H), 8.06 (dd, J=8.5, 2.0 Hz, 1H), 7.82-7.73 (m, 1H), 7.68 (d, J=7.2 Hz, 1H), 7.56 (d, J=8.3 Hz, 1H), 7.30 (dt, J=22.9, 7.2 Hz, 2H), 7.17 (s, 1H), 3.42-3.29 (m, 1H), 2.54 (s, 3H), 1.24 (d, J=6.7 Hz, 6H); MS (m/z): 544.0 [M+1]⁺.

Compound 22: 2-(4-(3,4-dichlorophenyl)-5-(isopropylthio)thiazol-2-yl)-2',5,5'-trimethyl-4,4'-bi(2H-pyrazole)-3-carboxylic Acid methyl 2-(4-(3,4-dichlorophenyl)-5-(isopropylthio)thiazol-2-yl)-2',5,5'-trimethyl-4,4'-bi(2H-pyrazole)-3-carboxylate In a 5 mL glass microwave vial equipped with a magnetic stirring bar and nitrogen flow at room temperature was placed 1-(4-bromo-1-(4-(3,4-dichlorophenyl)-5-(isopropylthio)thiazol-2-yl)-3-methyl-1H-pyrazol-5-yl)ethanone (50.0 mg, 0.096 mmol), 1,3-dimethyl-4-(4,4,5,5-tetramethyl-1,3,2-dioxaborolan-2-yl)-1H-pyrazole (19.8 mg, 0.09 mmol) and $Na_2CO_3$ (39.1 mg, 0.37 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh₃)₄ (8.5 mg, 0.01 mmol). The vial was capped and placed in an oil bath at 85° C. for 16 h. EtOAc and water were added, the aqueous layer was extracted with EtOAc (3×) and the combined organic layers were dried over $Na_2SO_4$, filtered and concentrated under vacuum. The crude product was purified by flash chromatography on silica gel using a solution of EtOAc in hexanes (20 to 100% gradient) and afforded the title compound (20.0 g, 0.037 mmol, 39%) as colorless oil.

2-(4-(3,4-dichlorophenyl)-5-(isopropylthio)thiazol-2-yl)-2',5,5'-trimethyl-4,4'-bi(2H-pyrazole)-3-carboxylic Acid Into a 5 mL glass microwave vial, was placed methyl 2-(4-(3,4-dichlorophenyl)-5-(isopropylthio)thiazol-2-yl)-2',5,5'-trimethyl-4,4'-bi(2H-pyrazole)-3-carboxylate (20.0 mg, 0.037 mmol) and LiOH (6.0 mg, 0.14 mmol). THF (1.5 mL), MeOH (0.5 mL) and water (3 mL) were added. The vial was heated to 110° C. under microwave radiation for 10 minutes. THF and MeOH were removed under vacuum and the crude product was purified by reverse flash chromatography (C18, using a gradient 20 to 70% MeCN in $H_2O$ with 0.1% FA buffer) to afford the title compound (11.0 mg, 0.02 mmol, 75%) as white solid after lyophilization.

¹H NMR (500 MHz, DMSO) δ 8.19 (d, J=2.0 Hz, 1H), 8.00 (dd, J=8.5, 2.0 Hz, 1H), 7.73 (d, J=8.5 Hz, 1H), 7.66 (s, 1H), 3.79 (s, 3H), 2.14 (s, 3H), 2.06 (s, 3H), 1.23 (d, J=6.7 Hz, 6H); MS (m/z): 522.2 [M+1]⁺.

Compound 23: 1-(4-(3,4-dichlorophenyl)-5-(isopropylthio)thiazol-2-yl)-4-(2,6-dimethylpyridin-4-yl)-3-methyl-1H-pyrazole-5-carboxylic Acid 1-(4-(3,4-dichlorophenyl)-5-(isopropylthio)thiazol-2-yl)-5-(methoxycarbonyl)-3-methyl-1H-pyrazol-4-ylboronic Acid 2.5M in hexane n-BuLi (1.15 mL, 2.88 mmol) was added during 30 minutes (push serynge) to a solution of methyl 4-bromo-1-(4-(3,4-dichlorophenyl)-5-(isopropylthio)thiazol-2-yl)-3-methyl-1H-pyrazole-5-carboxylate (1.00 g, 1.92 mmol) and triisopropylborate (1.33 mL, 5.76 mmol) in THF (19.2 mL) at −78° C. The reaction was stirred at that temperature for 10 minutes. 1N HCl (3 mL) was added and the reaction was stirred at rt for 30 minutes. Water (30 mL) was added and the mixture was extracted with EtOAc (3×20 mL). The combined organic layers were dried with sodium sulfate, filtered and evaporated and afforded the title compound (920 mg, 1.89 mmol, 99%) as a pale yellow solid. The crude product (purity=94% by LCMS) was used without purification.

1-(4-(3,4-dichlorophenyl)-5-(isopropylthio)thiazol-2-yl)-4-(2,6-dimethylpyridin-4-yl)-3-methyl-1H-pyrazole-5-carboxylic Acid In a 5 mL glass microwave vial equipped with a magnetic stirring bar and nitrogen flow at room temperature was placed 5-acetyl-1-(4-(3,4-dichlorophenyl)-5-(isopropylthio)thiazol-2-yl)-3-methyl-1H-pyrazol-4-ylboronic acid (50.0 mg, 0.010 mmol), 4-bromo-2,6-dimethylpyridine (17.7 mg, 0.10 mmol) and $Na_2CO_3$ (42.0 mg, 0.40 mmol), nitrogen and vacuum cycles were performed (2×). Nitrogen gas was bubbled through a solution of dioxane/water (2 mL, 4:1) and then the solution was added to the microwave vial, followed by the addition of Pd(PPh₃)₄ (9.20 mg, 0.01 mmol). The vial was capped and placed in an oil bath at 85° C. for 16 h. LiOH (16.6 mg, 0.40 mmol) was added to the reaction mixture and stirred under microwave radiation at 120° C. for 10 min. The product was purified using a semi prep HPLC-MS (column X-Bridge 30×50, eluted with 35-55% MeCN/NH₄CO₂H 10 mM, pH 3.8/Flow 45 ml/min/11 min), resulting in the title compound (14.0 mg, 0.03 mmol, 26%) as white solid after lyophilization.

¹H NMR (500 MHz, DMSO) δ 8.20 (d, J=2.1 Hz, 1H), 8.02 (dd, J=8.5, 2.1 Hz, 1H), 7.76 (d, J=8.5 Hz, 1H), 7.16 (s, 2H), 2.47 (s, 6H), 2.33 (s, 3H), 1.24 (d, J=6.7 Hz, 6H); MS (m/z): 533.0 [M+1]⁺.

Compound 24: 1-(4-(3,4-dichlorophenyl)-5-(isopropylthio)thiazol-2-yl)-4-(3,5-difluorophenyl)-3-methyl-1H-pyrazole-5-carboxylic Acid In a 5 mL glass microwave vial equipped with a magnetic stirring bar and nitrogen flow at room temperature was placed 1-(4-bromo-1-(4-(3,4-dichlorophenyl)-5-(isopropylthio)thiazol-2-yl)-3-methyl-1H-pyrazol-5-yl)ethanone (50.0 mg, 0.096 mmol), 3,5-difluorophenylboronic acid (14.5 mg, 0.09 mmol) and Na$_2$CO$_3$ (40.4 mg, 0.50 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (8.8 mg, 0.01 mmol). The vial was capped and placed in an oil bath at 85° C. for 16 h. LiOH (16.0 mg, 0.38 mmol) was added to the reaction mixture and stirred under microwave radiation at 120° C. for 10 min. The product was purified using a semi prep HPLC-MS (column X-Bridge 30×50, eluted with 55-75% MeCN/NH$_4$CO$_2$H 10 mM, pH 3.8/Flow 45 ml/min/ 11 min), resulting in the title compound (15.0 mg, 0.027 mmol, 29%) as yellow solid after lyophilization.

¹H NMR (500 MHz, DMSO) δ 8.21 (d, J=2.0 Hz, 1H), 8.02 (dd, J=8.5, 2.1 Hz, 1H), 7.75 (d, J=8.5 Hz, 1H), 7.33-7.20 (m, J=19.2, 8.0 Hz, 3H), 3.42-3.29 (m, 1H), 2.32 (s, 3H), 1.24 (d, J=6.7 Hz, 6H); MS (m/z): 541.9 [M+1]⁺.

Compound 25: 1-(4-(5-chloro-2-fluorophenyl)-5-(isopropylthio)thiazol-2-yl)-4-(3,5-dichlorophenyl)-3-methyl-1H-pyrazole-5-carboxylic Acid 2-chloro-5-(isopropylthio)thiazole A 2.5 M solution of n-BuLi in hexanes (20.5 mL, 51.2 mmol) was added to a THF solution (117 mL) of 2-chlorothiazole (4.9 g, 41.0 mmol) at −78° C. The reaction mixture was stirred at the same temperature for 30 min. Diisopropyl disulfide (13.1 mL, 82.0 mmol) was added to the reaction and was stirred at the same temperature for 1.5 h. Water was added to quench the reaction and then Et$_2$O. The reaction mixture was transferred into a separation funnel and the aqueous layer was extracted with Et$_2$O (3×). The combined organic layers were dried over Na$_2$SO$_4$ and concentrated under vacuum. The crude product was purified by flash chromatography on silica gel (dry packing) using a solution of EtOAc in hexanes (0 to 5% gradient) and afforded the title compound (2.31 g, 11.9 mmol, 29%) as yellow liquid.

4-bromo-2-chloro-5-(isopropylthio)thiazole

A 2 M solution of bromine (72.7 µL, 1.42 mmol) in DCM was added dropwise to a solution of 2-chloro-5-(isopropylthio)thiazole (250 mg, 1.29 mmol) in DCM. The reaction was stirred for 3 hours at room temperature. A solution of Na$_2$SO$_3$ was added and the aqueous layer was extracted with DCM (3×). The combined organic layers were washed with brine, dried over Na$_2$SO$_4$, filtered and concentrated under vacuum. The crude product was purified by flash chromatography on silica gel using a solution of DCM in hexanes (50 to 100% gradient) and afforded the title compound (271 mg, 0.99 mmol, 77%) as colorless liquid.

4-bromo-2-hydrazinyl-5-(isopropylthio)thiazole

DIPEA (64 µL, 0.37 mmol) was added to a solution of hydrazine hydrochloride (13.0 mg, 0.18 mmol) and 4-bromo-2-chloro-5-(isopropylthio)thiazole (50.0 mg, 0.18 mmol) to NMP (2 mL) in a glass microwave vial. The vial was sealed and was heated to 150° C. for 1 h with microwave radiation. The crude product was purified by reverse flash chromatography (C18, using a gradient 0 to 40 to 70% MeCN in H$_2$O with 10 mM NH$_4$CO$_2$H buffer) and afforded the title compound (29.0 mg, 0.11 mmol, 59%) as yellow solid after extraction with Et$_2$O and concentration under vacuum.

methyl 1-(4-bromo-5-(isopropylthio)thiazol-2-yl)-3-methyl-1H-pyrazole-5-carboxylate Methyl 2-(methoxyimino)-3-(2-nitrobenzyl)-4-oxopentanoate (4.00 g, 23.1 mmol) was dissolved in MeOH (115 mL). 4-bromo-2-hydrazinyl-5-(isopropylthio)thiazole (6.19 g, 23.1 mmol) was added and then HCl 12 N (7.70 mL, 92.4 mmol) was added dropwise to the reaction mixture. The reaction mixture was heated to reflux overnight. The crude product was concentrated under vacuum and was purified by flash chromatography on silica gel (dry packing) using a solution of EtOAc in hexanes (5 to 20% gradient) and was purified a second time by flash chromatography on silica gel (dry packing) using a solution of DCM in hexanes (10 to 50% gradient) and afforded the title compound (1.89 g, 5.02 mmol, 22%) as orange oil.

methyl 1-(4-(5-chloro-2-fluorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 1-(4-bromo-5-(isopropylthio)thiazol-2-yl)-3-methyl-1H-pyrazole-5-carboxylate (150.0 mg, 0.399 mmol), 5-chloro-2-fluorophenylboronic acid (64.2 mg, 0.37 mmol) and K$_2$CO$_3$ (212 mg, 0.50 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (15.3 mg, 0.03 mmol). The vial was capped and placed in an oil bath at 90° C. for 16 h. The solvent was evaporated under vacuum and the crude product was purified by flash chromatography on silica gel (dry packing) using a solution of EtOAc in hexanes/DCM 9:1 (0 to 5% gradient) and afforded the title compound (135 mg, 0.317 mmol, 80%) as yellow oil.

methyl 4-bromo-1-(4-(5-chloro-2-fluorophenyl)-5-(isopropylthio)thiazol-2-yl)-3-methyl-1H-pyrazole-5-carboxylate A 2 M solution of bromine (790 µL, 1.58 mmol) in MeCN was added dropwise to a solution of methyl 1-(4-(5-chloro-2-fluorophenyl)-5-(isopropylthio)thiazol-2-yl)-3-methyl-1H-pyrazole-5-carboxylate (135 mg, 0.32 mmol) in a solution of DCM/MeCN (2 mL, 1:1). The reaction was stirred for 5 hours at room temperature. A saturated aqueous solution of Na$_2$SO$_3$ was added and the aqueous layer was extracted with EtOAc (3×). The combined organic layers were washed with brine, dried over Na$_2$SO$_4$, filtered and concentrated under vacuum. The crude product was purified by flash chromatography on silica gel (dry packing) using a solution of EtOAc in hexanes (0 to 5% gradient) and afforded the title compound (27.4 mg, 0.05 mmol, 17%) as colorless oil.

1-(4-(5-chloro-2-fluorophenyl)-5-(isopropylthio) thiazol-2-yl)-4-(3,5-dichlorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-(5-chloro-2-fluorophenyl)-5-(isopropylthio)thiazol-2-yl)-3-methyl-1H-pyrazole-5-carboxylate (27.4 mg, 0.054 mmol), the 3,5-dichlorophenylboronic acid (8.0 mg, 0.04 mmol) and $Na_2CO_3$ (22.1 mg, 0.21 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (4.8 mg, 0.004 mmol). The vial was capped and placed in an oil bath at 85° C. for 16 h. LiOH (8.8 mg, 0.21 mmol) was added to the reaction mixture and stirred under microwave radiation at 120° C. for 10 min. The product was purified using a semi prep HPLC-MS (column X-Bridge 30×50, eluted with 60-80% $MeCN/NH_4CO_2H$ 10 mM, pH 3.8/Flow 45 ml/min/11 min), resulting in the title compound (4.58 mg, 0.008 mmol, 15%) as yellow solid after lyophilization.
$^1$H NMR (500 MHz, DMSO) δ 7.66-7.49 (m, 5H), 7.42 (t, J=9.1 Hz, 2H), 3.42-3.29 (m, 1H), 2.30 (s, 3H), 1.16 (d, J=6.7 Hz, 6H); MS (m/z): 558.0 $[M+1]^+$.

Compound 26: 1-(4-(5-chloro-2-fluorophenyl)-5-(isopropylthio)thiazol-2-yl)-4-(2,6-dimethylpyridin-4-yl)-3-methyl-1H-pyrazole-5-carboxylic Acid 2,6-dimethylpyridin-4-ylboronic Acid A 2.5 M solution of n-BuLi in hexanes (0.26 mL, 0.65 mmol) was added to a THF solution (5 mL) of 4-bromo-2,6-dimethylpyridine (100 mg, 0.54 mmol) and triisopropylborate (149 μL, 0.65 mmol) at −78° C. The reaction mixture was warmed up to rt and stirred for 1 h. 1 N HCl was added and the reaction was stirred at rt for 30 minutes. 1 N NaOH was added to basify and the mixture was extracted with EtOAc (3×). The combined organics were dried with $Na_2SO_4$, filtered and concentrated under vacuum, resulting in the title compound (30.0 mg, 0.20 mmol, 37%) as white solid.

1-(4-(5-chloro-2-fluorophenyl)-5-(isopropylthio) thiazol-2-yl)-4-(2,6-dimethylpyridin-4-yl)-3-methyl-1H-pyrazole-5-carboxylic Acid In a 5 mL glass microwave vial equipped with a magnetic stirring bar and nitrogen flow at room temperature was placed methyl 4-bromo-1-(4-(5-chloro-2-fluorophenyl)-5-(isopropylthio)thiazol-2-yl)-3-methyl-1H-pyrazole-5-carboxylate (65.6 mg, 0.130 mmol), 2,6-dimethylpyridin-4-ylboronic acid (15.1 mg, 0.10 mmol) and $Na_2CO_3$ (53.0 mg, 0.50 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (11.6 mg, 0.01 mmol). The vial was capped and placed in an oil bath at 85° C. for 16 h. LiOH (21.0 mg, 0.50 mmol) was added to the reaction mixture and stirred under microwave radiation at 120° C. for 10 min. The product was purified using a semi prep HPLC-MS (column X-Bridge 30×50, eluted with 30-50% $MeCN/NH_4CO_2H$ 10 mM, pH 3.8/Flow 45 ml/min/11 min), resulting in the title compound (4.70 mg, 0.009 mmol, 7%) as white solid after lyophilization.
$^1$H NMR (500 MHz, DMSO) δ 14.26 (s, 1H), 7.60 (ddd, J=8.8, 4.3, 2.8 Hz, 1H), 7.54 (dd, J=6.1, 2.7 Hz, 1H), 7.42 (t, J=9.1 Hz, 1H), 7.13 (s, 2H), 3.28-3.19 (m, J=13.3, 6.6 Hz, 2H), 2.45 (s, 6H), 2.32 (s, 3H), 1.16 (d, J=6.7 Hz, 6H); MS (m/z): 517.1 $[M+1]^+$.

Compound 27: 4-(3,5-dichlorophenyl)-1-(4-(3,5-dimethylisoxazol-4-yl)-5-(isopropylthio)thiazol-2-yl)-3-methyl-1H-pyrazole-5-carboxylic Acid methyl 4-bromo-1-(4-bromo-5-(isopropylthio)thiazol-2-yl)-3-methyl-1H-pyrazole-5-carboxylate A 2 M solution of bromine (3.32 mL, 6.64 mmol) in MeCN was added dropwise to a solution of methyl 1-(4-bromo-5-(isopropylthio)thiazol-2-yl)-3-methyl-1H-pyrazole-5-carboxylate (500 mg, 1.33 mmol) in a solution of DCM/MeCN (7 mL, 1:1). The reaction was stirred for 5 hours at room temperature. A solution of $Na_2SO_3$ was added and the aqueous layer was extracted with $Et_2O$ (3×). The combined organic layers were washed with brine, dried over $Na_2SO_4$, filtered and concentrated under vacuum. The crude product was purified by flash chromatography on silica gel using a solution of DCM in hexanes (20%) and afforded the title compound (421 mg, 0.93 mmol, 70%) as orange solid.

methyl 4-bromo-1-(4-(3,5-dimethylisoxazol-4-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (70.0 mg, 0.154 mmol), 3,5-dimethylisoxazol-4-ylboronic acid (16.7 mg, 0.12 mmol) and $K_2CO_3$ (81.8 mg, 0.59 mmol), nitrogen and vacuum cycles were performed (2×). Nitrogen gas was bubbled through a solution of THF (2 mL) and then the solution was added to the microwave vial, followed by the addition of the catalyst $Pd(dtbpf)Cl_2$ (5.9 mg, 0.01 mmol). The vial was capped and placed in an oil bath at 90° C. for 16 h. The solvent was evaporated under vacuum and the crude product was purified by flash chromatography on silica gel (wet loading) using a solution of EtOAc in hexanes (5 to 20% gradient) and afforded the title compound (29.2 mg, 0.062 mmol, 52%) as brown oil.

4-(3,5-dichlorophenyl)-1-(4-(3,5-dimethylisoxazol-4-yl)-5-(isopropylthio)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(4-(3,5-dimethylisoxazol-4-yl)-5-(isopropylthio)thiazol-2-yl)-3-methyl-1H-pyrazole-5-carboxylate (29.0 mg, 0.062 mmol), 3,5-dichlorophenylboronic acid (8.60 mg, 0.06 mmol) and $Na_2CO_3$ (25.1 mg, 0.24 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (5.5 mg, 0.005 mmol). The vial was capped and placed in an oil bath at 85° C. for 16 h. LiOH (9.9 mg, 0.24 mmol) was added to the reaction mixture and stirred under microwave radiation at 120° C. for 10 min. The product was purified using a semi prep HPLC-MS (column X-Bridge 30×50, eluted with 50-70% MeCN/NH$_4$CO$_2$H 10 mM, pH 3.8/Flow 45 ml/min/11 min), resulting in the title compound (8.33 mg, 0.016 mmol, 26%) as white solid after lyophilization.

$^1$H NMR (500 MHz, DMSO) δ 14.33 (s, 1H), 7.64 (s, 1H), 7.53 (s, 2H), 3.27-3.16 (m, J=13.1, 6.4 Hz, 1H), 2.38 (s, 3H), 2.31 (s, 3H), 2.19 (s, 3H), 1.14 (d, J=6.7 Hz, 6H); MS (m/z): 524.9 [M+1]$^+$.

Compound 28: 4-(3,5-dichlorophenyl)-1-(5-(isopropylthio)-4-(1-methyl-1H-pyrazol-4-yl)thiazol-2-yl)-3-methyl-1H-pyrazole-5-carboxylic Acid methyl 4-bromo-1-(5-(isopropylthio)-4-(1-methyl-1H-pyrazol-4-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (70.0 mg, 0.154 mmol), 1-methyl-4-(4,4,5,5-tetramethyl-1,3,2-dioxaborolan-2-yl)-1H-pyrazole (24.6 mg, 0.12 mmol) and K$_2$CO$_3$ (81.8 mg, 0.59 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (5.9 mg, 0.01 mmol). The vial was capped and placed in an oil bath at 90° C. for 16 h. The solvent was evaporated under vacuum and the crude product was purified by flash chromatography on silica gel using a solution of EtOAc in hexanes (5 to 50% gradient) and afforded the title compound (51.0 mg, 0.112 mmol, 94%) as brown oil.

4-(3,5-dichlorophenyl)-1-(5-(isopropylthio)-4-(1-methyl-1H-pyrazol-4-yl)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(5-(isopropylthio)-4-(1-methyl-1H-pyrazol-4-yl)thiazol-2-yl)-3-methyl-1H-pyrazole-5-carboxylate (48.0 mg, 0.105 mmol), 3,5-dichlorophenylboronic acid (18.5 mg, 0.10 mmol) and Na$_2$CO$_3$ (42.9 mg, 0.40 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (9.4 mg, 0.01 mmol). The vial was capped and placed in an oil bath at 85° C. for 16 h. LiOH (17.0 mg, 0.40 mmol) was added to the reaction mixture and stirred under microwave radiation at 120° C. for 10 min. The product was purified using a semi prep HPLC-MS (column X-Bridge 30×50, eluted with 45-55% MeCN/NH$_4$CO$_2$H 10 mM, pH 3.8/Flow 45 ml/min/11 min), resulting in the title compound (6.73 mg, 0.013 mmol, 13%) as white solid after lyophilization.

$^1$H NMR (500 MHz, DMSO) δ 14.36 (s, 1H), 8.28 (s, 1H), 7.98 (s, 1H), 7.65 (s, 1H), 7.54 (d, J=1.4 Hz, 2H), 3.90 (s, 3H), 3.42-3.29 (m, 1H), 2.30 (s, 3H), 1.28 (d, J=6.7 Hz, 6H); MS (m/z): 508.4 [M+1]$^+$.

Compound 32: 1-(5-(sec-butylthio)-4-(3,4-dichlorophenyl)thiazol-2-yl)-4-(3,5-dichlorophenyl)-3-methyl-1H-pyrazole-5-carboxylic Acid 5-(sec-butylthio)-2-chloro-4-(3,4-dichlorophenyl)thiazole A 2.5 M solution of n-BuLi in hexanes (6.80 mL, 17.0 mmol) was added to a THF solution (38 mL) of 2-chloro-4-(3,4-dichlorophenyl)thiazole (3.00 g, 11.3 mmol) at −78° C. The reaction mixture was stirred at the same temperature for 30 min. Disecbutyl disulfide (4.21 mL, 22.7 mmol) was added and the reaction was stirred at the same temperature for 1.5 h. Water was added to quench the reaction and then Et$_2$O. The reaction mixture was transferred into a separation funnel and the aqueous layer was extracted with Et$_2$O (3×). The combined organic layers were dried over Na$_2$SO$_4$ and concentrated under vacuum. The crude product was purified by flash chromatography on silica gel (dry packing) using a solution of EtOAc in hexanes (0 to 5% gradient) and afforded the title compound (3.32 g, 9.41 mmol, 83%) as light orange oil.

5-(sec-butylthio)-4-(3,4-dichlorophenyl)-2-hydrazinylthiazole

DIPEA (3.29 mL, 18.8 mmol) was added to a solution of hydrazine hydrochloride (1.29 g, 18.8 mmol) and 5-(sec-butylthio)-2-chloro-4-(3,4-dichlorophenyl)thiazole (3.32 g, 9.41 mmol) to NMP (30 mL) in two glass microwave vials. The vials were sealed and were heated to 150° C. for 2 h with microwave radiation. The reaction mixture was diluted with water (10 mL) and extracted with Et$_2$O. The combined organic layers were washed with brine (3×), and dried over Na$_2$SO$_4$, filtered and concentrated under vacuum. This afforded the title compound (3.29 g, 9.45 mmol, 100%) as brown oil.

methyl 1-(5-(sec-butylthio)-4-(3,4-dichlorophenyl)thiazol-2-yl)-3-methyl-1H-pyrazole-5-carboxylate Methyl 2-(methoxyimino)-4-oxopentanoate (1.64 g, 9.45 mmol) was dissolved in MeOH (95 mL). 5-(sec-butylthio)-4-(3,4-dichlorophenyl)-2-hydrazinylthiazole (3.29 g, 9.45 mmol) was added and then HCl 12 N (3.15 mL, 37.8 mmol) was added dropwise to the reaction mixture. The reaction mixture was heated to reflux overnight. The crude product was concentrated under vacuum and was purified by flash chromatography (dry packing) using a solution of DCM in Hexanes (10 to 20% gradient). This afforded the title compound (1.42 g, 3.11 mmol, 33%) as green oil.

methyl 4-bromo-1-(5-(sec-butylthio)-4-(3,4-dichlorophenyl)thiazol-2-yl)-3-methyl-1H-pyrazole-5-carboxylate A 2 M solution of bromine (7.78 mL, 15.56 mmol) in acetonitrile was added dropwise to a solution of methyl 1-(5-(sec-butylthio)-4-(3,4-dichlorophenyl)thiazol-2-yl)-3-methyl-1H-pyrazole-5-carboxylate (1.42 g, 3.11 mmol) in MeCN/DCM (16 mL, 1:1). The reaction was stirred for 5 hours at room temperature. A saturated aqueous solution of Na$_2$S$_2$O$_3$ was added and the mixture was extracted with EtOAc (3×). The combined organic layers were dried with sodium sulfate, filtered and concentrated under reduced pressure. The crude product was purified by flash chromatography (dry packing) on silica gel using a solution of DCM in hexanes (10 to 50% gradient) and afforded the title compound (1.54 g, 2.88 mmol, 93%) as green solid.

methyl 1-(5-(sec-butylthio)-4-(3,4-dichlorophenyl) thiazol-2-yl)-4-(3,5-dichlorophenyl)-3-methyl-1H-pyrazole-5-carboxylate In a 5 mL glass microwave vial equipped with a magnetic stirring bar and nitrogen flow at room temperature was placed methyl 4-bromo-1-(5-(sec-butylthio)-4-(3,4-dichlorophenyl)thiazol-2-yl)-3-methyl-1H-pyrazole-5-carboxylate (150.0 mg, 0.280 mmol), 3,5-dichlorophenylboronic acid (49.4 mg, 0.26 mmol) and $Na_2CO_3$ (114 mg, 1.08 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (24.9 mg, 0.02 mmol). The vial was capped and placed in an oil bath at 85° C. for 16 h. The crude product was concentrated under vacuum and was purified by flash chromatography (wet loading with DCM) on silica gel using a solution of EtOAc in hexanes (2%) and afforded the title compound (121 mg, 0.207 mmol, 74%) as off white solid after lyophilization.
$^1$H NMR (500 MHz, DMSO) δ 8.16 (d, J=2.1 Hz, 1H), 7.98 (dd, J=8.5, 2.1 Hz, 1H), 7.82 (d, J=8.5 Hz, 1H), 7.72 (t, J=1.9 Hz, 1H), 7.51 (d, J=1.9 Hz, 1H), 3.82 (s, 3H), 3.22-3.14 (m, 1H), 2.34 (s, 3H), 1.63-1.45 (m, 2H), 1.22 (d, J=6.8 Hz, 3H), 0.91 (t, J=7.3 Hz, 3H); MS (m/z): 602.0 $[M+1]^+$.

1-(5-(sec-butylthio)-4-(3,4-dichlorophenyl)thiazol-2-yl)-4-(3,5-dichlorophenyl)-3-methyl-1H-pyrazole-5-carboxylic Acid Into a 5 mL glass microwave vial, was placed methyl 1-(5-(sec-butylthio)-4-(3,4-dichlorophenyl)thiazol-2-yl)-4-(3,5-dichlorophenyl)-3-methyl-1H-pyrazole-5-carboxylate (25.0 mg, 0.04 mmol) and LiOH (9.00 mg, 0.21 mmol). THF (1.5 mL), MeOH (0.5 mL) and water (3 mL) were added. The vial was heated to 120° C. under microwave radiation for 10 minutes. THF and MeOH were removed under vacuum and the crude product was purified using a semi prep HPLC-MS (column X-Bridge 30×50, eluted with 60-80% MeCN/$NH_4CO_2H$ 10 mM, pH 3.8/Flow 45 ml/min/ 11 min), resulting in the title compound (10.0 mg, 0.017 mmol, 41%) as white solid after lyophilization.
$^1$H NMR (500 MHz, DMSO) δ 8.23 (d, J=1.9 Hz, 1H), 8.01 (dd, J=8.5, 1.8 Hz, 1H), 7.77 (d, J=8.5 Hz, 1H), 7.65 (s, 1H), 7.59-7.52 (m, J=7.3 Hz, 2H), 3.21-3.09 (m, 1H), 2.31 (s, 3H), 1.64-1.44 (m, 2H), 1.21 (d, J=6.7 Hz, 3H), 0.90 (t, J=7.4 Hz, 3H); MS (m/z): 588.0 $[M+1]^+$.

Compound 33: 1-(5-(sec-butylthio)-4-(3,4-dichlorophenyl)thiazol-2-yl)-4-(2,6-dimethylpyridin-4-yl)-3-methyl-1H-pyrazole-5-carboxylic acid and methyl 1-(5-(sec-butylthio)-4-(3,4-dichlorophenyl)thiazol-2-yl)-4-(2,6-dimethylpyridin-4-yl)-3-methyl-1H-pyrazole-5-carboxylate 2,6-dimethyl-4-(4,4,5,5-tetramethyl-1,3,2-dioxaborolan-2-yl)pyridine A degassed solution of dioxane (2 mL) was added to a mixture of 4-bromo-2,6-dimethylpyridine (1.00 g, 5.38 mmol), 4,4,4',4',5,5,5',5'-octamethyl-2,2'-bi(1,3,2-dioxaborolane) (1.64 g, 6.45 mmol), $PdCl_2$(dppf) (393 mg, 0.537 mmol) and KOAc (1.58 g, 16.12 mmol). The reaction was heated at 85° C. for 18 hours. The reaction mixture was dissolved in EtOAc and filtered on a pad of Celite®. The filtrate was concentrated under vacuum, resulting in the crude title compound (1.88 g, 8.07 mmol, quantitative yield) as brown solid.

methyl 1-(5-(sec-butylthio)-4-(3,4-dichlorophenyl) thiazol-2-yl)-4-(2,6-dimethylpyridin-4-yl)-3-methyl-1H-pyrazole-5-carboxylate In a 5 mL glass microwave vial equipped with a magnetic stirring bar and nitrogen flow at room temperature was placed methyl 4-bromo-1-(5-(sec-butylthio)-4-(3,4-dichlorophenyl)thiazol-2-yl)-3-methyl-1H-pyrazole-5-carboxylate (100.0 mg, 0.187 mmol), 2,6-dimethyl-4-(4,4,5,5-tetramethyl-1,3,2-dioxaborolan-2-yl)pyridine (73.8 mg, 0.32 mmol) and $Na_2CO_3$ (76.2 mg, 0.72 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (16.6 mg, 0.01 mmol). The vial was capped and placed in an oil bath at 85° C. for 16 h. The crude product was concentrated under vacuum and was purified by flash chromatography (wet loading with DCM) on silica gel eluting using a solution of EtOAc in hexanes (5% to 35% gradient) and afforded the title compound (72.0 mg, 0.128 mmol, 69%) as beige solid after lyophilization.

1-(5-(sec-butylthio)-4-(3,4-dichlorophenyl)thiazol-2-yl)-4-(2,6-dimethylpyridin-4-yl)-3-methyl-1H-pyrazole-5-carboxylic Acid Into a 5 mL glass microwave vial, was placed methyl 1-(5-(sec-butylthio)-4-(3,4-dichlorophenyl)thiazol-2-yl)-4-(2,6-dimethylpyridin-4-yl)-3-methyl-1H-pyrazole-5-carboxylate (25.0 mg, 0.04 mmol) and LiOH (9.00 mg, 0.22 mmol). THF (1.5 mL), MeOH (0.5 mL) and water (3 mL) were added. The vial was heated to 120° C. under microwave radiation for 10 minutes. THF and MeOH were removed under vacuum and the crude product was purified by reverse flash chromatography (C18, using a gradient 5 to 60% to 80% MeCN in $H_2O$ with 10 mM $NH_4CO_2H$ buffer) and afforded the title compound (8.6 mg, 0.016 mmol, 35%) as off white solid after lyophilization.
$^1$H NMR (500 MHz, DMSO) δ 8.22 (d, J=2.1 Hz, 1H), 8.01 (dd, J=8.5, 2.1 Hz, 1H), 7.76 (d, J=8.5 Hz, 1H), 7.15 (s, 2H), 3.21-3.12 (m, J=13.2, 6.6 Hz, 1H), 2.47 (s, 6H), 2.33 (s, 3H), 1.63-1.43 (m, 2H), 1.21 (d, J=6.8 Hz, 3H), 0.90 (t, J=7.4 Hz, 3H); MS (m/z): 547.1 $[M+1]^+$.

Compound 35: 4-(2,6-dimethylpyridin-4-yl)-1-(5-(isopropylthio)-4-(3-methoxyphenyl)thiazol-2-yl)-3-methyl-1H-pyrazole-5-carboxylic Acid methyl 4-bromo-1-(5-(isopropylthio)-4-(3-methoxyphenyl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), 3-methoxyphenylboronic acid (25.7 mg, 0.17 mmol) and $K_2CO_3$ (117 mg, 0.85 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (11.0 mg, 0.02 mmol). The vial was capped and placed in an oil bath at 90° C. for 16 h. The solvent was evaporated under vacuum and the crude product was purified by flash chromatography on silica gel using a solution of DCM in hexanes (25 to 100% gradient) and afforded the title compound (65.8 mg, 0.136 mmol, 81%) as brown oil.

methyl 4-(2,6-dimethylpyridin-4-yl)-1-(5-(isopropylthio)-4-(3-methoxyphenyl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(5-(isopropylthio)-4-(3-methoxyphenyl)thiazol-2-yl)-3-methyl-1H-pyrazole-5-carboxylate (65.8 mg, 0.136 mmol), 2,6-dimethyl-4-(4,4,5,5-tetramethyl-1,3,2-dioxaborolan-2-yl)pyridine (54.0 mg, 0.23 mmol) and Na$_2$CO$_3$ (55.8 mg, 0.53 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (12.2 mg, 0.01 mmol). The vial was capped and placed in an oil bath at 85° C. for 16 h. The reaction mixture was concentrated under vacuum and the crude product was purified by flash chromatography on silica gel using a solution of EtOAc in hexanes (10 to 40% gradient) and afforded the title compound (41.0 mg, 0.081 mmol, 59%) as yellow oil.

4-(2,6-dimethylpyridin-4-yl)-1-(5-(isopropylthio)-4-(3-methoxyphenyl)thiazol-2-yl)-3-methyl-1H-pyrazole-5-carboxylic Acid Into a 5 mL glass microwave vial, was placed methyl 4-(2,6-dimethylpyridin-4-yl)-1-(5-(isopropylthio)-4-(3-methoxyphenyl)thiazol-2-yl)-3-methyl-1H-pyrazole-5-carboxylate (41.0 mg, 0.081 mmol) and LiOH (16.9 mg, 0.403 mmol). THF (1.5 mL), MeOH (0.5 mL) and water (3 mL) were added. The vial was heated to 120° C. under microwave radiation for 10 minutes. THF and MeOH were removed under vacuum and the crude product was purified by reverse flash chromatography (C18, using a gradient 5 to 40% to 60% MeCN in H$_2$O with 10 mM NH$_4$CO$_2$H buffer) and afforded the title compound (26.7 mg, 0.054 mmol, 67%) as yellow solid after lyophilization.
$^1$H NMR (500 MHz, DMSO) δ 8.04-7.92 (m, 1H), 7.14 (s, 1H), 7.05-6.97 (m, 1H), 3.82 (s, 1H), 3.32-3.19 (m, 7H), 2.46 (s, 2H), 2.32 (s, 1H), 1.23 (d, J=6.7 Hz, 2H); MS (m/z): 495.2 [M+1]$^+$.

Compound 37: 4-(2,6-dimethylpyridin-4-yl)-1-(5-(isopropylthio)-4-phenylthiazol-2-yl)-3-methyl-1H-pyrazole-5-carboxylic Acid methyl 4-bromo-1-(5-(isopropylthio)-4-phenylthiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (100 mg, 0.220 mmol), the phenylboronic acid (20.6 mg, 0.17 mmol) and K$_2$CO$_3$ (117 mg, 0.85 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (11.0 mg, 0.02 mmol). The vial was capped and placed in an oil bath at 90° C. for 16 h. The solvent was evaporated under vacuum and the crude product was purified by flash chromatography on silica gel (wet loading) using a solution of DCM in hexanes (25 to 100% gradient) and afforded the title compound (77.0 mg, 0.170 mmol, 100%) as brown oil.

methyl 4-(2,6-dimethylpyridin-4-yl)-1-(5-(isopropylthio)-4-phenylthiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(5-(isopropylthio)-4-phenylthiazol-2-yl)-3-methyl-1H-pyrazole-5-carboxylate (77.0 mg, 0.170 mmol), the 2,6-dimethyl-4-(4,4,5,5-tetramethyl-1,3,2-dioxaborolan-2-yl)pyridine (67.2 mg, 0.29 mmol) and Na$_2$CO$_3$ (69.5 mg, 0.66 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (15.1 mg, 0.01 mmol). The vial was capped and placed in an oil bath at 85° C. for 16 h. The reaction mixture was concentrated under vacuum and the crude product was purified by flash chromatography on silica gel (wet loading) using a solution of EtOAc in hexanes (10 to 40% gradient) and afforded the title compound (63.0 mg, 0.132 mmol, 77%) as yellow oil.

4-(2,6-dimethylpyridin-4-yl)-1-(5-(isopropylthio)-4-phenylthiazol-2-yl)-3-methyl-1H-pyrazole-5-carboxylic Acid Into a 5 mL glass microwave vial was placed the methyl 4-(2,6-dimethylpyridin-4-yl)-1-(5-(isopropylthio)-4-phenylthiazol-2-yl)-3-methyl-1H-pyrazole-5-carboxylate (66.0 mg, 0.138 mmol) and LiOH (28.9 mg, 0.689 mmol). THF (1.5 mL), MeOH (0.5 mL) and water (3 mL) were added. The vial was heated to 120° C. under microwave radiation for 10 minutes. THF and MeOH were removed under vacuum and the crude product was purified by reverse flash chromatography (C18, using a gradient 5 to 30% to 60% MeCN in H$_2$O with 10 mM NH$_4$CO$_2$H buffer) and afforded the title compound (25.6 mg, 0.055 mmol, 40%) as yellow solid after lyophilization.
$^1$H NMR (500 MHz, DMSO) δ 8.03-7.94 (m, 2H), 7.52-7.45 (m, 2H), 7.45-7.39 (m, J=9.5, 4.3 Hz, 1H), 7.14 (s, 2H), 3.40-3.30 (m, 1H), 2.47 (s, 6H), 2.33 (s, 3H), 1.23 (d, J=6.7 Hz, 6H); MS (m/z): 465.2 [M+1]$^+$.

Compound 41: 4-(2,6-dimethylpyridin-4-yl)-1-(5-(isopropylthio)-4-m-tolylthiazol-2-yl)-3-methyl-1H-pyrazole-5-carboxylic Acid methyl 4-bromo-1-(5-(isopropylthio)-4-m-tolylthiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (97.9 mg, 0.215 mmol), the m-tolylboronic acid (22.5 mg, 0.17 mmol) and K$_2$CO$_3$ (114 mg, 0.83 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl₂ (10.8 mg, 0.02 mmol). The vial was capped and placed in an oil bath at 90° C. for 16 h. The solvent was evaporated under vacuum and the crude product was purified by flash chromatography on silica gel (wet loading) using a solution of DCM in hexanes (10 to 50% gradient) and afforded the title compound (79.6 mg, 0.171 mmol, 100%) as brown oil.

methyl 4-(2,6-dimethylpyridin-4-yl)-1-(5-(isopropylthio)-4-m-tolylthiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(5-(isopropylthio)-4-m-tolylthiazol-2-yl)-3-methyl-1H-pyrazole-5-carboxylate (79.6 mg, 0.171 mmol), the 2,6-dimethyl-4-(4,4,5,5-tetramethyl-1,3,2-dioxaborolan-2-yl)pyridine (67.4 mg, 0.29 mmol) and Na₂CO₃ (69.6 mg, 0.66 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh₃)₄ (15.2 mg, 0.01 mmol). The vial was capped and placed in an oil bath at 85° C. for 16 h. The reaction mixture was concentrated under vacuum and the crude product was purified by flash chromatography on silica gel (wet loading) using a solution of EtOAc in hexanes (10 to 40% gradient) and afforded the title compound (52.8 mg, 0.107 mmol, 63%) as yellow oil.

4-(2,6-dimethylpyridin-4-yl)-1-(5-(isopropylthio)-4-m-tolylthiazol-2-yl)-3-methyl-1H-pyrazole-5-carboxylic Acid Into a 5 mL glass microwave vial was placed the methyl 4-(2,6-dimethylpyridin-4-yl)-1-(5-(isopropylthio)-4-m-tolylthiazol-2-yl)-3-methyl-1H-pyrazole-5-carboxylate (52.8 mg, 0.107 mmol) and LiOH (22.5 mg, 0.536 mmol). THF (1.5 mL), MeOH (0.5 mL) and water (3 mL) were added. The vial was heated to 120° C. under microwave radiation for 10 minutes. THF and MeOH were removed under vacuum and the crude product was purified using a semi prep HPLC-MS (X-Bridge 30×50, eluted with 30-50% MeCN/NH₄CO₂H 10 mM, pH 3.8/Flow 45 ml/min/11 min), resulting in the title compound (14.7 mg, 0.031 mmol, 19%) as yellow solid after lyophilization.

¹H NMR (500 MHz, DMSO) δ 7.80 (d, J=6.3 Hz, 2H), 7.40-7.32 (m, 1H), 7.23 (d, J=7.6 Hz, 1H), 7.16 (s, 2H), 3.38-3.25 (m, 1H), 2.45 (s, 6H), 2.37 (s, 3H), 2.32 (s, 3H), 1.23 (d, J=6.7 Hz, 6H); MS (m/z): 479.2 [M+1]⁺.

Compound 43: 4-(2,6-dimethylpyridin-4-yl)-1-(5-(isopropylthio)-4-(phenylethynyl)thiazol-2-yl)-3-methyl-1H-pyrazole-5-carboxylic Acid methyl 4-bromo-1-(5-(isopropylthio)-4-(phenylethynyl)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (95.0 mg, 0.209 mmol), the phenylacetylene (18.1 mg, 0.18 mmol), the copper iodide (3.10 mg, 0.02 mmol) the catalyst Pd(PPh₃)₂Cl₂ (11.3 mg, 0.02 mmol) and triethylamine (2 mL). Nitrogen gas was bubbled through the reaction mixture for 10 min. The vial was capped and placed in an oil bath at 80° C. for 16 h. The solvent was evaporated under vacuum and the crude product was purified by flash chromatography on silica gel (wet loading) using a solution of DCM in hexanes (10 to 50% gradient) and afforded the title compound (75.0 mg, 0.157 mmol, 98%) as brown oil.

4-(2,6-dimethylpyridin-4-yl)-1-(5-(isopropylthio)-4-(phenylethynyl)thiazol-2-yl)-3-methyl-1H-pyrazole-5-carboxylic Acid In a 5 mL glass microwave vial equipped with a magnetic stirring bar and nitrogen flow at room temperature was placed the methyl 4-bromo-1-(5-(isopropylthio)-4-(phenylethynyl)thiazol-2-yl)-3-methyl-1H-pyrazole-5-carboxylate (75.0 mg, 0.157 mmol), the 2,6-dimethyl-4-(4,4,5,5-tetramethyl-1,3,2-dioxaborolan-2-yl)pyridine (80.7 mg, 0.346 mmol) and Na₂CO₃ (83.4 mg, 0.787 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh₃)₄ (18.2 mg, 0.016 mmol). The vial was capped and placed in an oil bath at 85° C. for 16 h. LiOH (33.0 mg, 0.787 mmol) was added to the reaction mixture and stirred under microwave radiation at 120° C. for 10 min. The product was purified using a semi prep HPLC-MS (column X-Bridge 30×50, eluted with 30-50% MeCN/NH₄CO₂H 10 mM, pH 3.8/Flow 45 ml/min/11 min), resulting in the title compound (1.17 mg, 0.002 mmol, 2%) as white solid after lyophilization.

¹H NMR (500 MHz, MeOD) δ 7.57-7.49 (m, 2H), 7.42-7.38 (m, 3H), 7.36 (s, 2H), 3.49-3.39 (m, 1H), 2.55 (s, 6H), 2.38 (s, 3H), 1.38 (d, J=6.7 Hz, 6H); MS (m/z): 489.3 [M+1]⁺.

Compound 47: 1-(4-(3,4-dichlorophenyl)-5-(isopropylthio)thiazol-2-yl)-3-methyl-4-(pyridin-4-yl)-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 3-(Hydroxymethyl)phenylboronic acid (14 mg, 0.12 mmol), Pd(PPh₃)₄ (11 mg, 0.10 mmol), Na₂CO₃ (51 mg, 0.48 mmol) in degassed 1,4-dioxane and H₂O (4:1, 1.9 mL) was heated at 85° C. for 18 hours. Water (5 mL) was added and the mixture was extracted with EtOAc (3×5 mL). The combined organic layers were dried with sodium sulfate, filtered and evaporated. The crude product (ester) was used directly for the next step. It was diluted in a 1:1 solution of THF and MeOH (1 mL). 1 M NaOH (0.20 mL, 0.20 mmol) was added and the reaction was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 0.1% of formic acid) (50 to 70%). The product was lyophilized and afforded the title compound (1.9 mg, 0.0038 mmol, 3.7%) as a pale yellow powder.

¹H NMR (500 MHz, DMSO) δ 8.65-8.58 (m, 2H), 8.23 (s, 1H), 8.04 (d, J=8.2 Hz, 1H), 7.77 (d, J=8.5 Hz, 1H), 7.57-7.50 (m, 2H), 2.53-2.50 (m, 1H), 2.35 (s, 3H), 1.24 (d, J=6.7 Hz, 6H); MS (m/z): 504.9 [M+H]⁺.

Compound 51: 1-(4-(3,4-dichlorophenyl)-5-(isopropylthio)thiazol-2-yl)-3-methyl-4-(3-(trifluoromethyl)phenyl)-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 3-(trifluoromethyl)phenylboronic acid (20 mg, 0.11 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. LiOH (12 mg, 0.48 mmol) was added and the reaction was heated at 90° C. for 15 minutes under microwave radiation. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (60 to 80%). The product was lyophilized and afforded the title compound (7.4 mg, 0.013 mmol, 14%) as a white solid.

$^1$H NMR (500 MHz, DMSO) δ 8.21 (d, J=2.0 Hz, 1H), 8.03 (dd, J=8.4, 2.0 Hz, 1H), 7.84 (s, 1H), 7.80 (d, J=7.5 Hz, 1H), 7.78-7.74 (m, 1H), 7.76 (d, J=8.5 Hz, 1H), 7.71 (t, J=7.5 Hz, 1H), 3.35 (hept, J=6.7 Hz, 1H), 2.32 (s, 3H), 1.24 (d, J=6.7 Hz, 6H); MS (m/z): 571.8 [M+H]$^+$.

Compound 52: 1-(4-(3,4-dichlorophenyl)-5-(isopropylthio)thiazol-2-yl)-3-methyl-4-(4-(trifluoromethyl)phenyl)-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 4-(trifluoromethyl)phenylboronic acid (20 mg, 0.11 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. LiOH (12 mg, 0.48 mmol) was added and the reaction was heated at 90° C. for 15 minutes under microwave radiation. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (60 to 80%). The product was lyophilized and afforded the title compound (4.1 mg, 0.0072 mmol, 8%) as a white solid.

$^1$H NMR (500 MHz, DMSO) δ 8.20 (d, J=2.0 Hz, 1H), 8.01 (dd, J=8.5, 2.0 Hz, 1H), 7.83 (d, J=8.0 Hz, 2H), 7.77 (d, J=8.5 Hz, 1H), 7.71 (d, J=8.0 Hz, 2H), 3.35 (hept, J=6.7 Hz, 1H), 2.32 (s, 3H), 1.24 (d, J=6.7 Hz, 6H); MS (m/z): 571.8 [M+H]$^+$.

Compound 53: 1-(4-(3,4-dichlorophenyl)-5-(isopropylthio)thiazol-2-yl)-4-(hydroxy(phenyl)methyl)-3-methyl-1H-pyrazole-5-carboxylic Acid methyl 1-(4-(3,4-dichlorophenyl)-5-(isopropylthio)thiazol-2-yl)-4-formyl-3-methyl-1H-pyrazole-5-carboxylate n-BuLi (0.92 mL, 5.8 mmol, 2.5 M in hexane) was added during 45 minutes using a push serynge to a solution of methyl 4-bromo-1-(4-(3,4-dichlorophenyl)-5-(isopropylthio)thiazol-2-yl)-3-methyl-1H-pyrazole-5-carboxylate (1.00 g, 1.92 mmol), and methyl formate (0.59 mL, 9.6 mmol) in THF (19.2 mL) at −78° C. The reaction mixture was stirred at that temperature for 1 hour. A saturated aqueous solution of ammonium chloride (50 mL) was added and the mixture was extracted with EtOAc (2×50 mL). The combined organic layers were dried with sodium sulfate, filtered and evaporated. The crude product was purified by flash chromatography on silica gel using a solution of ethyl acetate in hexanes (2 to 5%) and afforded the title compound (594 mg, 1.26 mmol, 66%) as a white solid.

methyl 1-(4-(3,4-dichlorophenyl)-5-(isopropylthio)thiazol-2-yl)-4-(hydroxy(phenyl)methyl)-3-methyl-1H-pyrazole-5-carboxylate Phenylmagnesium bromide (0.12 mL, 0.037 mmol, 0.3 M in THF) was added slowly to a solution of methyl 1-(4-(3,4-dichlorophenyl)-5-(isopropylthio)thiazol-2-yl)-4-formyl-3-methyl-1H-pyrazole-5-carboxylate (15 mg, 0.032 mmol) in THF (0.32 mL) at r.t. The reaction mixture was stirred for two hours. Another portion of phenylmagnesium bromide (0.21 mL, 0.064 mmol, 0.3 M in THF) was added and the reaction mixture was stirred for 18 hours. An aqueous saturated ammonium chloride solution (5 mL) was added and the mixture was extracted with EtOAc (2×5 mL). The combined organic layers were dried with sodium sulfate, filtered and evaporated. The product was purified by flash chromatography on silica gel using a solution of ethyl acetate in hexanes (5 to 15%) and afforded the title compound (9.0 mg, 0.016 mmol, 52%) as an oil.

1-(4-(3,4-dichlorophenyl)-5-(isopropylthio)thiazol-2-yl)-4-(hydroxy(phenyl)methyl)-3-methyl-1H-pyrazole-5-carboxylic Acid Methyl 1-(4-(3,4-dichlorophenyl)-5-(isopropylthio)thiazol-2-yl)-4-(hydroxy(phenyl)methyl)-3-methyl-1H-pyrazole-5-carboxylate (9.0 mg, 0.016 mmol) was diluted in a 1:1 solution of THF and MeOH (0.16 mL). 1 M NaOH (0.033 mL, 0.033 mmol) was added and the reaction mixture was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (55 to 75%). The product was lyophilized and afforded the title compound (1.7 mg, 0.0032 mmol, 19%) as a white solid.

$^1$H NMR (500 MHz, DMSO) δ 8.18 (d, J=2.1 Hz, 1H), 8.01 (dd, J=8.5, 2.1 Hz, 1H), 7.75 (d, J=8.5 Hz, 1H), 7.41 (d, J=7.1 Hz, 2H), 7.28 (t, J=7.7 Hz, 2H), 7.18 (d, J=7.5 Hz, 1H), 5.67-5.63 (m, 1H), 2.51 (hept, 1H, J=7.1 Hz), 2.11 (s, 3H), 1.22 (d, J=7.1 Hz, 6H); MS (m/z): 533.8 [M+H]$^+$.

Compound 56: 4-([1,2,4]triazolo[4,3-a]pyridin-3-yl)-1-(4-(3,4-dichlorophenyl)-5-(isopropylthio)thiazol-2-yl)-3-methyl-1H-pyrazole-5-carboxylic Acid methyl 4-([1,2,4]triazolo[4,3-a]pyridin-3-yl)-1-(4-(3,4-dichlorophenyl)-5-(isopropylthio)thiazol-2-yl)-3-methyl-1H-pyrazole-5-carboxylate A solution of methyl 1-(4-(3,4-dichlorophenyl)-5-(isopropylthio)thiazol-2-yl)-4-formyl-3-methyl-1H-pyrazole-5-carboxylate (42 mg, 0.089 mmol), in MeOH (0.3 mL containing enough DCM to solubilize the aldehyde) is added to 2-hydrazinopyridine (10 mg, 0.089 mmol). The reaction mixture is heated at 70° C. for 2 hours (a precipitate forms). The reaction is cooled down at r.t. and iodobenzene diacetate (35 mg, 0.107 mmol) is added. The reaction mixture is stirred at 70° C. for 2 hours and MeOH was evaporated. The crude was purified by flash chromatography on silica gel using a solution of ethyl acetate in hexane (5 to 100%) and afforded the title compound (8.0 mg, 0.017 mmol, 19%) as a colorless oil.

4-([1,2,4]triazolo[4,3-a]pyridin-3-yl)-1-(4-(3,4-dichlorophenyl)-5-(isopropylthio)thiazol-2-yl)-3-methyl-1H-pyrazole-5-carboxylic Acid Methyl 4-([1,2,4]triazolo[4,3-a]pyridin-3-yl)-1-(4-(3,4-dichlorophenyl)-5-(isopropylthio)thiazol-2-yl)-3-methyl-1H-pyrazole-5-carboxylate (8.5 mg, 0.015 mmol) was diluted in a 1:1 solution of THF and MeOH (0.15 mL). 1 M NaOH (0.030 mL, 0.030 mmol) was added and the reaction mixture was stirred for 18 hours at room temperature. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (55 to 75%). The product was lyophilized and afforded the title compound (1.1 mg, 0.0020 mmol, 13%) as a white solid.

$^1$H NMR (500 MHz, DMSO) δ 8.34 (d, J=7.0 Hz, 1H), 8.19 (d, J=2.1 Hz, 1H), 8.02 (dd, J=8.5, 2.1 Hz, 1H), 7.86 (d, J=9.3 Hz, 1H), 7.78 (d, J=8.5 Hz, 1H), 7.45 (dd, J=9.3, 6.9 Hz, 1H), 7.01 (t, J=6.9 Hz, 1H), 3.39 (hept, J=6.7 Hz, 1H), 2.25 (s, 2H), 1.26 (d, J=6.7 Hz, 6H); MS (m/z): 545.0 [M+H]$^+$.

Compound 58: 4-(1H-benzo[d]imidazol-2-yl)-1-(4-(3,4-dichlorophenyl)-5-(isopropylthio)thiazol-2-yl)-3-methyl-1H-pyrazole-5-carboxylic Acid methyl 4-(1H-benzo[d]imidazol-2-yl)-1-(4-(3,4-dichlorophenyl)-5-(isopropylthio)thiazol-2-yl)-3-methyl-1H-pyrazole-5-carboxylate Methyl 1-(4-(3,4-dichlorophenyl)-5-(isopropylthio)thiazol-2-yl)-4-formyl-3-methyl-1H-pyrazole-5-carboxylate (45 mg, 0.10 mmol) was dissolved in MeOH (1.2 mL, containing enough DCM to dissolved the aldehyde). O-Phenyldiamine (11 mg, 0.10 mmol) and benzoquinone (13 mg, 0.12 mmol) were added and the reaction mixture was heated at 65° C. for 18 hours. The solvent was evaporated. The crude product was purified by flash chromatography on silica gel (dry packing) using ethyl acetate in hexanes and afforded the title compound (18 mg, 0.032 mmol, 32%) as a white solid.

4-(1H-benzo[d]imidazol-2-yl)-1-(4-(3,4-dichlorophenyl)-5-(isopropylthio)thiazol-2-yl)-3-methyl-1H-pyrazole-5-carboxylic Acid Methyl 4-(1H-benzo[d]imidazol-2-yl)-1-(4-(3,4-dichlorophenyl)-5-(isopropylthio)thiazol-2-yl)-3-methyl-1H-pyrazole-5-carboxylate (18 mg, 0.032 mmol) was diluted in a 1:1 solution of THF and MeOH (0.32 mL). 1 M NaOH (0.064 mL, 0.064 mmol) was added and the reaction was stirred for 5 hours at room temperature. 1 N HCl (0.030 mL) was added, followed by water (5 mL) and the mixture was extracted with EtOAc (3×5 mL). The combined organic layers were dried with sodium sulfate, filtered and evaporated under reduced pressure. The crude product was purified by reverse phase chromatography on C-18 column using a solution of MeCN in water (containing 10 mM of NH$_4$CO$_2$H) (50 to 70%). The product was lyophilized and afforded the title compound (5.4 mg, 0.0010 mmol, 31%) as a white solid.

$^1$H NMR (500 MHz, DMSO) δ 8.19 (d, J=2.1 Hz, 1H), 8.01 (dd, J=8.5, 2.1 Hz, 1H), 7.79 (d, J=8.5 Hz, 1H), 7.68-7.64 (m, 2H), 7.28-7.24 (m, 2H), 3.42-3.29 (m, 1H), 2.60 (s, 3H), 1.25 (d, J=6.7 Hz, 6H); MS (m/z): 544.1 [M+H]$^+$.

Compound 59: 4-(3-chloro-2-methylphenyl)-1-(4-(3,4-dichlorophenyl)-5-(isopropylthio)thiazol-2-yl)-3-methyl-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 3-chloro-2-methylphenylboronic acid (20 mg, 0.11 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. LiOH (12 mg, 0.48 mmol) was added and the reaction was heated at 90° C. for 15 minutes under microwave radiation. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (65 to 85%). The product was lyophilized and afforded the title compound (12 mg, 0.021 mmol, 22%) as a pale yellow solid.

$^1$H NMR (500 MHz, DMSO) δ 8.18 (d, J=1.9 Hz, 1H), 7.99 (dd, J=8.4, 2.0 Hz, 1H), 7.76 (d, J=8.5 Hz, 1H), 7.49 (d, J=8.2 Hz, 1H), 7.28 (t, J=7.8 Hz, 1H), 7.18 (d, J=6.7 Hz, 1H), 3.42-3.29 (m, 1H), 2.17 (s, 3H), 2.06 (s, 3H), 1.24 (d, J=6.7 Hz, 6H); MS (m/z): 551.9 [M+H]$^+$.

Compound 60: 4-(3,5-bis(trifluoromethyl)phenyl)-1-(4-(3,4-dichlorophenyl)-5-(isopropylthio)thiazol-2-yl)-3-methyl-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 3,5-bis(trifluoromethyl)phenylboronic acid (30 mg, 0.11 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. LiOH (12 mg, 0.48 mmol) was added and the reaction mixture was heated at 90° C. for 15 minutes under microwave radiation. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (65 to 85%). The product was lyophilized and afforded the title compound (20 mg, 0.031 mmol, 32%) as a pale yellow solid.

$^1$H NMR (500 MHz, DMSO) δ 8.19-8.16 (m, 4H), 8.02 (dd, J=8.5, 2.1 Hz, 1H), 7.77 (d, J=8.5 Hz, 1H), 3.42-3.29 (m, 1H), 2.33 (s, 3H), 1.24 (d, J=6.7 Hz, 6H); MS (m/z): 639.9 [M+H]$^+$.

Compound 61: 1-(4-(3,4-dichlorophenyl)-5-(isopropylthio)thiazol-2-yl)-4-(3-isopropylphenyl)-3-methyl-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 3-isopropylphenylboronic acid (19 mg, 0.11 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. LiOH (12 mg, 0.48 mmol) was added and the reaction mixture was heated at 90° C. for 15 minutes under microwave radiation. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (65 to 85%). The product was lyophilized and afforded the title compound (7.1 mg, 0.013 mmol, 14%) as a pale yellow solid.

$^1$H NMR (500 MHz, DMSO) δ 8.22 (d, J=1.9 Hz, 1H), 8.03 (dd, J=8.5, 2.0 Hz, 1H), 7.75 (d, J=8.5 Hz, 1H), 7.39-7.34 (m, 2H), 7.30-7.24 (m, 2H), 3.42-3.29 (m, 1H), 2.92 (hept, J=6.8 Hz, 1H), 2.31 (s, 3H), 1.24 (d, J=6.8 Hz, 6H), 1.23 (d, J=6.8 Hz, 3H); MS (m/z): 546.0 [M+H]$^+$.

Compound 69: 4-(5-cyanopyridin-3-yl)-1-(4-(3,4-dichlorophenyl)-5-(isopropylthio)thiazol-2-yl)-3-methyl-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 5-cyanopyridin-3-ylboronic acid pinacol ester (27 mg, 0.12 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (35 to 55%). The product was lyophilised and afforded the title compound (8.6 mg, 0.016 mmol, 17%) as a white solid.

$^1$H NMR (500 MHz, DMSO) δ 8.97 (d, J=1.7 Hz, 1H), 8.89 (d, J=2.1 Hz, 1H), 8.41 (t, J=2.0 Hz, 1H), 8.12 (d, J=2.0 Hz, 1H), 7.94 (dd, J=8.5, 2.0 Hz, 1H), 7.70 (d, J=8.5 Hz, 1H), 3.33 (1H, below water signal), 2.26 (s, 3H), 1.17 (d, J=6.7 Hz, 6H); MS (m/z): 530.0 [M+H]$^+$.

Compound 70: 1-(4-(3,4-dichlorophenyl)-5-(isopropylthio)thiazol-2-yl)-4-(2-ethoxypyridin-3-yl)-3-methyl-1H-pyrazole-5-carboxylic Acid methyl 1-(4-(3,4-dichlorophenyl)-5-(isopropylthio)thiazol-2-yl)-4-(2-ethoxypyridin-3-yl)-3-methyl-1H-pyrazole-5-carboxylate A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 2-ethoxypyridin-3-ylboronic acid (19 mg, 0.12 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. Water (5 mL) was added and the mixture was extracted with EtOAc (3×5 mL). The combined organic layers were dried with sodium sulfate, filtered and evaporated. The crude product was purified by flash chromatography on silica gel using a solution of EtOAc in hexanes (5 to 10%) and afforded the title compound (26 mg, 0.048 mmol, 50%) as a colorless oil.

1-(4-(3,4-dichlorophenyl)-5-(isopropylthio)thiazol-2-yl)-4-(2-ethoxypyridin-3-yl)-3-methyl-1H-pyrazole-5-carboxylic Acid methyl 1-(4-(3,4-dichlorophenyl)-5-(isopropylthio)thiazol-2-yl)-4-(2-ethoxypyridin-3-yl)-3-methyl-1H-pyrazole-5-carboxylate (26 mg, 0.046 mmol) was diluted in a 1:1 solution of THF and MeOH (0.46 mL). 1 M NaOH (0.092 mL, 0.092 mmol) was added and the reaction mixture was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse phase chromatography on C-18 column using a solution of MeCN in water (containing 10 mM of NH$_4$CO$_2$H) (50 to 100%). The product was lyophilized and afforded the title compound (9.7 mg, 0.018 mmol, 38%) as a white solid.

$^1$H NMR (500 MHz, DMSO) δ 8.21-8.16 (m, 2H), 8.00 (dd, J=8.5, 2.0 Hz, 1H), 7.76 (d, J=8.5 Hz, 1H), 7.73 (dd, J=7.3, 1.7 Hz, 1H), 7.07 (dd, J=7.3, 5.0 Hz, 1H), 4.33 (q, J=7.0 Hz, 2H), 3.33 (1H, below water signal), 2.19 (s, 3H), 1.28 (t, J=7.0 Hz, 3H), 1.24 (d, J=6.7 Hz, 6H); MS (m/z): 549.0 [M+H]$^+$.

Compound 71: 2'-(4-(3,4-dichlorophenyl)-5-(isopropylthio)thiazol-2-yl)-2,5,5'-trimethyl-3,4'-bi(2H-pyrazole)-3'-carboxylic Acid methyl 2'-(4-(3,4-dichlorophenyl)-5-(isopropylthio)thiazol-2-yl)-2,5,5'-trimethyl-3,4'-bi(2H-pyrazole)-3'-carboxylate A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), 1,3-dimethyl-1H-pyrazol-5-ylboronic acid pinacol ester (26 mg, 0.12 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. Water (5 mL) was added and the mixture was extracted with EtOAc (3×5 mL). The combined organic layers were dried with sodium sulfate, filtered and evaporated. The crude product was purified by flash chromatography on silica gel using a solution of EtOAc in hexanes (5 to 10%) and afforded the title compound (16 mg, 0.030 mmol, 31%) as a pale yellow oil.

2'-(4-(3,4-dichlorophenyl)-5-(isopropylthio)thiazol-2-yl)-2,5,5'-trimethyl-3,4'-bi(2H-pyrazole)-3'-carboxylic Acid methyl 2'-(4-(3,4-dichlorophenyl)-5-(isopropylthio)thiazol-2-yl)-2,5,5'-trimethyl-3,4'-bi(2H-pyrazole)-3'-carboxylate (16 mg, 0.030 mmol) was diluted in a 1:1 solution of THF and MeOH (0.30 mL). 1 M NaOH (0.060 mL, 0.060 mmol) was added and the reaction mixture was stirred for 18 hours at room temperature. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by reverse phase chromatography on C-18 column using a solution of MeCN in water (containing 10 mM of $NH_4CO_2H$) (50 to 100%). The product was lyophilized and afforded the title compound (4.5 mg, 0.0086 mmol, 29%) as a white solid.

$^1$H NMR (500 MHz, DMSO) δ 8.19 (s, 1H), 8.04-7.98 (m, 1H), 7.78 (d, J=8.6 Hz, 1H), 6.11 (s, 1H), 3.61 (s, 3H), 3.35 (hept, J=6.6 Hz, 1H), 2.18 (s, 3H), 2.15 (s, 3H), 1.24 (d, J=6.6 Hz, 6H); MS (m/z): 522.0 [M+H]$^+$.

Compound 72: 1-(4-(3,4-dichlorophenyl)-5-(isopropylthio)thiazol-2-yl)-3-methyl-4-(pyrimidin-5-yl)-1H-pyrazole-5-carboxylic Acid 1-(4-(3,4-dichlorophenyl)-5-(isopropylthio)thiazol-2-yl)-3-methyl-4-(pyrimidin-5-yl)-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), pyrimidin-5-ylboronic acid (14 mg, 0.12 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. 1 N HCl (1 mL) was added followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of $NH_4CO_2H$) (35 to 55%). The product was lyophylised and afforded the title compound (8.9 mg, 0.018 mmol, 18%) as a white solid.

$^1$H NMR (500 MHz, DMSO) δ 9.13 (s, 1H), 8.98 (s, 2H), 8.24 (d, J=2.0 Hz, 1H), 8.05 (dd, J=8.5, 2.0 Hz, 1H), 7.76 (d, J=8.5 Hz, 1H), 3.34 (hept, J=6.7 Hz, 1H), 2.32 (s, 3H), 1.24 (d, J=6.7 Hz, 6H); MS (m/z): 505.9 [M+H]$^+$.

Compound 73: 4-(3,5-bis(trifluoromethyl)phenyl)-1-(4-(3,4-dichlorophenyl)-5-(isopropylthio)thiazol-2-yl)-3-methyl-1H-pyrazole-5-carboxamide To 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (16 mg, 0.024 mmol) was added a 7 N solution of ammonia in MeOH (0.5 mL, 3.5 mmol) in a sealed vial. The vial was capped and the reaction mixture was heated at 65° C. for 18 hours. The solvent was evaporated and the crude product was purified by semi-prep HPLC-MS (column X-Bridge 30×50) using a solution of MeCN in water (containing 10 mM of $NH_4CO_2H$) (65 to 85%). The product was lyophilized and afforded the title compound (4.6 mg, 0.0072 mmol, 29%) as a white solid.

$^1$H NMR (500 MHz, DMSO) δ 8.39 (s, 1H), 8.24 (d, J=2.1 Hz, 1H), 8.19 (s, 1H), 8.17 (s (br), 2H), 8.04 (dd, J=8.5, 2.1 Hz, 1H), 7.76 (d, J=8.5 Hz, 1H), 3.38 (hept, J=6.7 Hz, 1H), 2.36 (s, 3H), 1.25 (d, J=6.7 Hz, 6H); MS (m/z): 639.2 [M+H]$^+$.

Compound 75: 4-(3,5-bis(trifluoromethyl)phenyl)-1-(4-(3,4-dichlorophenyl)-5-(isopropylthio)thiazol-2-yl)-3-methyl-N-(pyridin-2-ylmethyl)-1H-pyrazole-5-carboxamide HATU (12 mg, 0.030 mmol) was added to a solution of 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (15 mg, 0.023 mmol), pyridin-2-ylmethanamine (3.0 mg, 0.028 mmol) and DI EPA (8.2 µL, 0.047 mmol) in DMF (0.33 mL). The reaction was stirred at rt for three days. The reaction was dissolved up to 0.5 mL with DMSO and it was purified by semi-prep HPLC-MS (column X-Bridge 30×50) using a solution of MeCN in water (containing 10 mM of $NH_4CO_2H$) (70 to 90%). The product was lyophilized and afforded the title compound (4.2 mg, 0.0057 mmol, 25%) as a white solid.

$^1$H NMR (500 MHz, DMSO) δ 9.62 (t, J=5.9 Hz, 1H), 8.37 (d, J=4.2 Hz, 1H), 8.17 (s, 1H), 8.14 (d, J=2.1 Hz, 1H), 8.13 (s, 2H), 8.04 (dd, J=8.5, 2.1 Hz, 1H), 7.75 (d, J=8.5 Hz, 1H), 7.35 (td, J=7.7, 1.8 Hz, 1H), 7.15 (dd, J=7.2, 5.1 Hz, 1H), 6.95 (d, J=7.8 Hz, 1H), 4.52 (d, J=5.9 Hz, 2H), 3.38 (hept, J=6.7 Hz, 1H), 2.37 (s, 3H), 1.25 (d, J=6.7 Hz, 6H); MS (m/z): 730.1 [M+H]$^+$.

Compound 76: 4-(3,5-bis(trifluoromethyl)phenyl)-1-(4-(3,4-dichlorophenyl)-5-(isopropylthio)thiazol-2-yl)-N-(2-hydroxyethyl)-N,3-dimethyl-1H-pyrazole-5-carboxamide HATU (12 mg, 0.030 mmol) was added to a solution of 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (15 mg, 0.023 mmol), 2-(methylamino)ethanol (2.1 mg, 0.028 mmol) and DI EPA (8.2 µL, 0.047 mmol) in DMF (0.33 mL). The reaction was stirred at rt for three days. The reaction was dissolved up to 0.5 mL with DMSO and it was purified by semi-prep HPLC-MS (column X-Bridge 30×50) using a solution of MeCN in water (containing 10 mM of $NH_4CO_2H$) (70 to 90%). The product was lyophilized and afforded the title compound (5.1 mg, 0.0073 mmol, 31%) as a white solid.

$^1$H NMR (500 MHz, DMSO) (mixture of rotamers) δ 8.18-8.13 (m, 3H), 8.07 (s, 1H), 8.09 and 7.79 (dd, J=8.5, 4.1 Hz, 1H, rotamers), (4.67 (t, J=5.4 Hz) and 4.56 (t, J=4.8 Hz), 1H, rotamers), 3.88-3.82 (m, 0.5H, one rotamer), 3.52-3.33 (m, 2.5H), 3.25-3.06 (m, 3H), 3.02 and 2.83 (s, 3H, rotamers), 2.41 and 2.40 (s, 3H, rotamers), 1.26 (d, J=6.6 Hz, 6H); MS (m/z): 697.2 [M+H]$^+$.

Compound 77: 4-(3,5-bis(trifluoromethyl)phenyl)-1-(4-(3,4-dichlorophenyl)-5-(isopropylthio)thiazol-2-yl)-N,3-dimethyl-N-(5-(trifluoromethyl)-1,3,4-thiadiazol-2-yl)-1H-pyrazole-5-carboxamide HATU (12 mg, 0.030 mmol) was added to a solution of 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (15 mg, 0.023 mmol), N-methyl-5-(trifluoromethyl)-1,3,4-thiadiazol-2-amine (5.1 mg, 0.028 mmol) and DIEPA (8.2 µL, 0.047 mmol) in DMF (0.33 mL). The reaction was stirred at rt for three days. The reaction was dissolved up to 0.5 mL with DMSO and it was purified by semi-prep HPLC-MS (column X-Bridge 30×50) using a solution of MeCN in water (containing 10 mM of $NH_4CO_2H$) (75 to 95%). The product was lyophilized and afforded the title compound (5.9 mg, 0.0073 mmol, 31%) as a white solid.

$^1$H NMR (500 MHz, DMSO) δ 8.20 (s, 1H), 8.11 (s, 2H), 7.78 (dd, J=8.5, 2.1 Hz, 1H), 7.52 (d, J=2.0 Hz, 1H), 7.51 (d, J=8.5 Hz, 1H), 3.57 (s, 3H), 3.37 (hept, J=6.7 Hz, 1H), 2.43 (s, 3H), 1.23 (d, J=6.7 Hz, 6H); MS (m/z): 805.1 [M+H]$^+$.

Compound 78: (4-(3,5-bis(trifluoromethyl)phenyl)-1-(4-(3,4-dichlorophenyl)-5-(isopropylthio)thiazol-2-yl)-3-methyl-1H-pyrazol-5-yl)(3-(diethylamino)pyrrolidin-1-yl)methanone HATU (12 mg, 0.030 mmol) was added to a solution of 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (15 mg, 0.023 mmol), N,N-diethylpyrrolidine-3-amine (4.0 mg, 0.028 mmol) and DIEPA (8.2 µL, 0.047 mmol) in DMF (0.33 mL). The reaction was stirred at rt for three days. The reaction was dissolved up to 0.5 mL with DMSO and it was purified by semi-prep HPLC-MS (column X-Bridge 30×50) using a solution of MeCN in water (containing 10 mM of $NH_4CO_2H$) (70 to 90%). The product was lyophilized and afforded the title compound (4.2 mg, 0.0055 mmol, 24%) as a white solid.

$^1$H NMR (500 MHz, DMSO) 8.18 (s, 1H), 8.15-8.04 (m, 4H), 7.83-7.75 (m, 1H), 3.80-2.62 (m, 4H), 3.39 and 3.38 (hept, 1H, J=6.7 hz, rotamers), 2.45-1.83 (m, 9H), 1.70-1.43 (m, 1H), 1.26 and 1.25 (d, 6H, J=6.7 Hz, rotamers), 0.85-0.77 (m, 3H), 0.74-0.63 (m, 3H); MS (m/z): 764.5 $[M+H]^+$.

Compound 79: 1-(4-(3,4-dichlorophenyl)-5-(isopropylthio)thiazol-2-yl)-3-methyl-4-(pyrazin-2-yl)-1H-pyrazole-5-carboxylic Acid A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 2-bromopyrazine (20 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. LiOH (12.4 mg, 0.52 mmol) was added and the reaction was heated at 90° C. under microwave radiation for 15 minutes. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of $NH_4CO_2H$) (30 to 70%). The product was lyophylised and afforded the title compound (10 mg, 0.020 mmol, 20%) as a pale yellow solid.

$^1$H NMR (500 MHz, DMSO) δ 8.97 (s, 1H), 8.71 (s, 1H), 8.58 (s, 1H), 8.23 (d, J=1.9 Hz, 1H), 8.04 (dd, J=8.4, 2.0 Hz, 1H), 7.76 (d, J=8.5 Hz, 1H), 3.36 (hept, J=6.7 Hz, 1H), 2.47 (s, 3H), 1.24 (d, J=6.7 Hz, 6H); MS (m/z): 505.9 $[M+H]^+$.

Compound 80: 4-(3-cyano-5-methylphenyl)-1-(4-(3,4-dichlorophenyl)-5-(isopropylthio)thiazol-2-yl)-3-methyl-1H-pyrazole-5-carboxylic Acid methyl 4-(3-cyano-5-methylphenyl)-1-(4-(3,4-dichlorophenyl)-5-(isopropylthio)thiazol-2-yl)-3-methyl-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 3-bromo-5-methylbenzonitrile (24 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. Water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2 to 5%) and afforded the title compound (22 mg, 0.039 mmol, 38%).

4-(3-cyano-5-methylphenyl)-1-(4-(3,4-dichlorophenyl)-5-(isopropylthio)thiazol-2-yl)-3-methyl-1H-pyrazole-5-carboxylic Acid methyl 4-(3-cyano-5-methylphenyl)-1-(4-(3,4-dichlorophenyl)-5-(isopropylthio)thiazol-2-yl)-3-methyl-1H-pyrazole-5-carboxylate (22 mg, 0.039 mmol) was diluted in a 1:1 solution of THF and MeOH (0.39 mL). 1 M NaOH (0.077 mL, 0.077 mmol) was added and the reaction was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of $NH_4CO_2H$) (50 to 100%). The product was lyophilized and afforded the title compound (7.8 mg, 0.014 mmol, 37%) as a white solid.

$^1$H NMR (500 MHz, DMSO) δ 8.19 (d, J=2.0 Hz, 1H), 8.02 (dd, J=8.5, 2.0 Hz, 1H), 7.76 (d, J=8.5 Hz, 1H), 7.73 (s, 1H), 7.70 (s, 1H), 7.63 (s, 1H), 3.36 (hept, J=6.7 Hz, 1H), 2.40 (s, 3H), 2.30 (s, 3H), 1.24 (d, J=6.7 Hz, 6H); MS (m/z): 543.0 $[M+H]^+$.

Compound 81: 4-(3,5-bis(trifluoromethyl)phenyl)-1-(4-(3,4-dichlorophenyl)-5-(isopropylthio)thiazol-2-yl)-3-methyl-N-(1H-tetrazol-5-yl)-1H-pyrazole-5-carboxamide HATU (12 mg, 0.030 mmol) was added to a solution of 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (15 mg, 0.023 mmol), 1H-tetrazol-5-amine monohydrate (2.9 mg, 0.028 mmol) and DIEPA (8.2 µL, 0.047 mmol) in DMF (0.33 mL). The reaction was stirred at rt for three days. More HATU (12 mg, 0.030 mmol) was added and the reaction was stirred at rt for 18 hours. The reaction was dissolved up to 0.5 mL with DMSO and it was purified by semi-prep HPLC-MS (column X-Bridge 30×50) using a solution of MeCN in water (containing 10 mM of $NH_4CO_2H$) (70 to 90%). The product was lyophilized and afforded the title compound (1.0 mg, 0.0014 mmol, 6%) as a white solid.

$^1$H NMR (500 MHz, DMSO) δ 8.20-8.16 (m, 3H), 7.90-7.74 (m, 2H), 7.49 (d, J=8.4 Hz, 1H), 3.38 (hept, J=6.7 Hz, 1H), 2.41 (s, 3H), 1.26 (d, J=6.7 Hz, 6H); MS (m/z): 707.0 $[M+H]^+$.

Compound 84: 4-(3-cyano-5-(trifluoromethyl)phenyl)-1-(4-(3,4-dichlorophenyl)-5-(isopropylthio)thiazol-2-yl)-3-methyl-1H-pyrazole-5-carboxylic Acid methyl 4-(3-cyano-5-(trifluoromethyl)phenyl)-1-(4-(3,4-dichlorophenyl)-5-(isopropylthio)thiazol-2-yl)-3-methyl-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 3-bromo-5-(trifluoromethyl)benzonitrile (31 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. Water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2 to 10%) and afforded the title compound (23 mg, 0.037 mmol, 36%).

4-(3-cyano-5-(trifluoromethyl)phenyl)-1-(4-(3,4-dichlorophenyl)-5-(isopropylthio)thiazol-2-yl)-3-methyl-1H-pyrazole-5-carboxylic Acid methyl 4-(3-cyano-5-(trifluoromethyl)phenyl)-1-(4-(3,4-dichlorophenyl)-5-(isopropylthio)thiazol-2-yl)-3-methyl-1H-pyrazole-5-carboxylate (23 mg, 0.037 mmol) was diluted in a 1:1 solution of THF and MeOH (0.37 mL). 1 M NaOH (0.075 mL, 0.075 mmol) was added and the reaction was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of $NH_4CO_2H$) (50 to 70%). The product was lyophilized and afforded the title compound (1.5 mg, 0.0025 mmol, 7%) as a pale yellow solid.

$^1$H NMR (500 MHz, DMSO) δ 8.35-8.30 (m, 2H), 8.28-8.22 (m, 2H), 8.08-8.04 (m, 1H), 7.77 (d, J=8.4 Hz, 1H), 3.35 (hept, J=6.5 Hz, 1H), 2.34 (s, 3H), 1.25 (d, J=6.7 Hz, 6H); MS (m/z): 596.9 [M+H]$^+$.

Compound 86: 4-(3-benzyl-5-methylisoxazol-4-yl)-1-(4-(3,4-dichlorophenyl)-5-(isopropylthio)thiazol-2-yl)-3-methyl-1H-pyrazole-5-carboxylic Acid

3-benzyl-5-methylisoxazole

In a flask were added 3-(bromomethyl)-5-methylisoxazole (1 g, 5.68 mmol), phenylboronic acid (0.831 g, 6.82 mmol), sodium carbonate (3.01 g, 28.4 mmol), dioxane (11 ml), water (2.8 ml), then tetrakis(triphenylphosphine)palladium (0) (0.657 g, 0.568 mmol). The mixture was degassed with nitrogen bubbling for 15 minutes then was heated to 85° C. for 16 h. The reaction mixture was cooled to rt, ethyl acetate and water were added. The mixture was transferred in a sep. funnel and the phases were separated. The organic phase was washed with brine, $SiO_2$ was added to the organic phase and solvents were evaporated. The crude product on $SiO_2$ was purified on ISCO using a $SiO_2$ column employing a 0-100% ethyl acetate in hexanes gradient to obtain the title compound (0.57 g, 3.29 mmol, 57.9%) as colorless oil.

3-benzyl-4-iodo-5-methylisoxazole

In a flask containing 3-benzyl-5-methylisoxazole (0.28 g, 1.617 mmol) were added TFA (1.6 ml) and N-iodosuccinimide (0.364 g, 1.617 mmol). The mixture was stirred at 25° C. for 1 h. The mixture was diluted with EtOAc and transferred in a sep. funnel, washed with water 2× then aq. sat. $NaHCO_3$, then aq. sat. $Na_2S_2O_3$, then brine. The organic phase was dried over sodium sulfate, filtered, concentrated to dryness and afforded the title compound (0.48 g, 1.605 mmol, 99%) as a pale yellow solid.

4-(3-benzyl-5-methylisoxazol-4-yl)-1-(4-(3,4-dichlorophenyl)-5-(isopropylthio)thiazol-2-yl)-3-methyl-1H-pyrazole-5-carboxylic Acid A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 3-benzyl-4-iodo-5-methylisoxazole (30 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. LiOH (12.4 mg, 0.52 mmol) was added and the reaction was heated at 90° C. under microwave radiation for 15 minutes. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of NH$_4$CO$_2$H) (55 to 75%). The product was lyophilised and afforded the title compound (8.9 mg, 0.015 mmol, 18%) as a pale yellow solid.

$^1$H NMR (500 MHz, DMSO) δ 8.19 (d, J=2.0 Hz, 1H), 8.00 (dd, J=8.5, 2.1 Hz, 1H), 7.76 (d, J=8.5 Hz, 1H), 7.22-7.12 (m, 3H), 7.01-6.97 (m, 2H), 3.97-3.84 (ABquartet, 2H), 3.35 (hept, J=6.7 Hz, 1H), 2.25 (s, 3H), 1.70 (s, 3H), 1.24 (d, J=6.7 Hz, 6H); MS (m/z): 599.1 [M+H]$^+$.

Compound 89: 4-(benzo[d][1,3]dioxol-5-yl)-1-(4-(3,4-dichlorophenyl)-5-(isopropylthio)thiazol-2-yl)-3-methyl-1H-pyrazole-5-carboxylic Acid A solution of methyl 4-bromo-1-(4-(3,4-dichlorophenyl)-5-(isopropylthio)thiazol-2-yl)-3-methyl-1H-pyrazole-5-carboxylate (50 mg, 0.096 mmol), benzo[d][1,3]dioxol-5-ylboronic acid (19 mg, 0.12 mmol), Pd(PPh$_3$)$_4$ (11 mg, 0.10 mmol), Na$_2$CO$_3$ (51 mg, 0.48 mmol) in degassed 1,4-dioxane and H$_2$O (4:1, 1.9 mL) was heated at 85° C. for 18 hours. LiOH (12 mg, 0.48 mmol) was added and the reaction was heated at 100° C. 1 h under microwave radiation. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of NH$_4$CO$_2$H) (50 to 100%). The product was lyophilized and afforded the title compound (9.9 mg, 0.0018 mmol, 19%) as a white solid.

$^1$H NMR (500 MHz, DMSO) δ 14.23 (s, 1H), 8.20 (d, J=2.1 Hz, 1H), 8.01 (dd, J=8.5, 2.1 Hz, 1H), 7.75 (d, J=8.5 Hz, 1H), 7.05-6.99 (m, 2H), 6.92 (dd, J=8.0, 1.7 Hz, 1H), 6.07 (s, 2H), 3.33 (hept, J=6.7 Hz, 1H), 2.28 (s, 3H), 1.23 (d, J=6.7 Hz, 6H); MS (m/z): 547.9 [M+H]$^+$.

Compound 92: 1-(4-(3,4-dichlorophenyl)-5-(isopropylthio)thiazol-2-yl)-3-methyl-4-(3-methylisothiazol-5-yl)-1H-pyrazole-5-carboxylic Acid A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 5-bromo-3-methylisothiazole (22 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. LiOH (12.4 mg, 0.52 mmol) was added and the reaction was heated at 90° C. under microwave radiation for 15 minutes. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of $NH_4CO_2H$) (40 to 60%). The product was lyophylised and afforded the title compound (10 mg, 0.019 mmol, 19%) as a pale yellow solid.

$^1$H NMR (500 MHz, DMSO) δ 8.22 (d, J=2.1 Hz, 1H), 8.04 (dd, J=8.5, 2.1 Hz, 1H), 7.76 (d, J=8.5 Hz, 1H), 7.40 (s, 1H), 3.35 (hept, J=6.7 Hz, 1H), 2.45 (s, 3H), 2.41 (s, 3H), 1.24 (d, J=6.7 Hz, 6H); MS (m/z): 524.9 [M+H]$^+$.

Compound 94: 1-(4-(3,4-dichlorophenyl)-5-(isopropylthio)thiazol-2-yl)-4-(1,5-dimethyl-6-oxo-1,6-dihydropyridin-3-yl)-3-methyl-1H-pyrazole-5-carboxylic Acid A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 5-bromo-1,3-dimethylpyridin-2(1H)-one (25 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. LiOH (12.4 mg, 0.52 mmol) was added and the reaction was heated at 90° C. under microwave radiation for 45 minutes. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of $NH_4CO_2H$) (35 to 55%). The product was lyophylised and afforded the title compound (12 mg, 0.022 mmol, 22%) as a pale yellow solid.

$^1$H NMR (500 MHz, DMSO) δ 8.19 (d, J=2.1 Hz, 1H), 8.01 (dd, J=8.5, 2.1 Hz, 1H), 7.75 (d, J=8.5 Hz, 1H), 7.71 (d, J=2.2 Hz, 1H), 7.41-7.39 (m, 1H), 3.48 (s, 3H), 3.35 (hept, J=6.7 Hz, 1H), 2.28 (s, 3H), 2.03 (s, 3H), 1.23 (d, J=6.7 Hz, 6H); MS (m/z): 549.0 [M+H]$^+$.

Compound 95: 1-(4-(3,4-dichlorophenyl)-5-(isopropylthio)thiazol-2-yl)-4-(3-fluoro-5-methylphenyl)-3-methyl-1H-pyrazole-5-carboxylic Acid A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 1-bromo-3-fluoro-5-methylbenzene (23 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. LiOH (12.4 mg, 0.52 mmol) was added and the reaction was heated at 90° C. under microwave radiation for 45 minutes. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of $NH_4CO_2H$) (60 to 80%). The product was lyophylised and afforded the title compound (13 mg, 0.024 mmol, 24%) as a pale yellow solid.

$^1$H NMR (500 MHz, DMSO) δ 8.21 (d, J=2.0 Hz, 1H), 8.02 (dd, J=8.5, 2.0 Hz, 1H), 7.75 (d, J=8.5 Hz, 1H), 7.13 (s, 1H), 7.11 (d, J=9.9 Hz, 1H), 7.07 (d, J=9.7 Hz, 1H), 3.35 (hept, J=6.7 Hz, 1H), 2.36 (s, 3H), 2.31 (s, 3H), 1.24 (d, J=6.7 Hz, 6H); MS (m/z): 536.0 [M+H]$^+$.

Compound 97: 1-(4-(3,4-dichlorophenyl)-5-(isopropylthio)thiazol-2-yl)-4-(3-isopropoxy-5-methylphenyl)-3-methyl-1H-pyrazole-5-carboxylic Acid 1-bromo-3-isopropoxy-5-methylbenzene 2-iodopropane (136 mg, 0.802 mmol) was added to a mixture of 3-bromo-5-methylphenol (100 mg, 0.535 mmol) and K$_2$CO$_3$ (118 mg, 0.855 mmol) in DMF (0.53 mL). The reaction was stirred at rt for 18 hours. Water (5 mL) and ethyl acetate were added (5 mL). The phases were separated. The organic layer was washed with 1 N NaOH (2×5 mL), dried with sodium sulfate, filtered and evaporated and afforded the title compound (90 mg, 0.39 mmol, 74%) which was used directly.

methyl 1-(4-(3,4-dichlorophenyl)-5-(isopropylthio)thiazol-2-yl)-4-(3-isopropoxy-5-methylphenyl)-3-methyl-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 1-bromo-3-isopropoxy-5-methylbenzene (28 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. Water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2 to 5%) and afforded the title compound (31 mg, 0.052 mmol, 51%).

1-(4-(3,4-dichlorophenyl)-5-(isopropylthio)thiazol-2-yl)-4-(3-isopropoxy-5-methylphenyl)-3-methyl-1H-pyrazole-5-carboxylic Acid methyl 1-(4-(3,4-dichlorophenyl)-5-(isopropylthio)thiazol-2-yl)-4-(3-isopropoxy-5-methylphenyl)-3-methyl-1H-pyrazole-5-carboxylate (31 mg, 0.052 mmol) was diluted in a 1:1 solution of THF and MeOH (0.52 mL). 1 M NaOH (0.11 mL, 0.11 mmol) was added and the reaction was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of $NH_4CO_2H$) (65 to 85%). The product was lyophilized and afforded the title compound (7.3 mg, 0.013 mmol, 24%) as a white solid.

$^1$H NMR (500 MHz, DMSO) δ 8.23 (s, 1H), 8.04 (d, J=8.3 Hz, 1H), 7.75 (d, J=8.3 Hz, 1H), 6.84-6.79 (m, 2H), 6.74 (s, 1H), 4.60 (hept, J=6.0 Hz, 1H), 2.30 (s, 3H), 2.30 (s, 3H), 1.28 (d, J=6.0 Hz, 6H), 1.24 (d, J=6.7 Hz, 6H); MS (m/z): 576.2 [M+H]$^+$.

Compound 98: 1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic Acid 3-(3-bromo-5-methyl phenoxy)oxetane 3-bromooxetane (110 mg, 0.802 mmol) was added to a mixture of 3-bromo-5-methylphenol (100 mg, 0.535 mmol), KI (133 mg, 0.802 mmol) and K$_2$CO$_3$ (118 mg, 0.855 mmol) in DMF (0.53 mL). The reaction was stirred at 100° C. for 18 hours. Water (5 mL) and ethyl acetate were added (5 mL). The phases were separated. The organic layer was washed with 1 N NaOH (2×5 mL), dried with sodium sulfate, filtered and evaporated and afforded the title compound (98 mg, 0.40 mmol, 75%) which was used directly.

methyl 1-(4-(3,4-dichlorophenyl)-5-(isopropylthio) thiazol-2-yl)-3-methyl-4-(3-methyl-5-(oxetan-3-yloxy)phenyl)-1H-pyrazole-5-carboxylate A solution of 1-(4-(3,4-dichlorophenyl)-5-(isopropylthio) thiazol-2-yl)-5-(methoxycarbonyl)-3-methyl-1H-pyrazol-4-ylboronic acid (50 mg, 0.10 mmol), 3-(3-bromo-5-methylphenoxy)oxetane (30 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. Water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (10 to 20%) and afforded the title compound (18 mg, 0.029 mmol, 28%).

1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic Acid methyl 1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylate (18 mg, 0.029 mmol) was diluted in a 1:1 solution of THF and MeOH (0.29 mL). 1 M NaOH (0.058 mL, 0.058 mmol) was added and the reaction was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of NH$_4$CO$_2$H) (50 to 100%). The product was lyophilized and afforded the title compound (4.1 mg, 0.0069 mmol, 24%) as a white solid.

$^1$H NMR (500 MHz, DMSO) δ 8.22 (s, 1H), 8.03 (d, J=7.0 Hz, 1H), 7.76 (d, J=8.6 Hz, 1H), 6.91 (s, 1H), 6.68-6.62 (m, 2H), 5.27 (q, J=5.1 Hz, 1H), 4.94 (t, J=6.9 Hz, 1H), 4.56 (dd, J=7.6, 5.1 Hz, 2H), 3.36 (hept, J=6.7 Hz, 1H), 2.32 (s, 3H), 2.30 (s, 3H), 1.25 (d, J=6.7 Hz, 6H); MS (m/z): 590.2 [M+H]$^+$.

Compound 100: 4-(3-(1H-imidazol-1-yl)-5-methylphenyl)-1-(4-(3,4-dichlorophenyl)-5-(isopropylthio) thiazol-2-yl)-3-methyl-1H-pyrazole-5-carboxylic Acid 1-(3-bromo-5-methylphenyl)-1H-imidazole A solution of the 3-bromo-5-methylbenzenamine (500 mg, 2.69 mmol), ammonium acetate (207 mg, 2.69 mmol) and water (0.4 mL) in AcOH (1.35 mL) was added during 30 minutes (push serynge) to a solution of formaldehyde (37% w/w in water, 200 μL, 2.69 mmol) and glyoxal (40% w/w in water, 308 μL, 2.69 mmol) in AcOH (1.35 mL) at 70° C. The reaction was stirred at that temperature for 18 hours. The reaction was slowly pored into saturated aqueous sodium bicarbonate. Some water was added and the precipitated solid was filtered. The filtrate was extracted with DCM and the combined organic layers were dried with sodium sulfate, filtered and evaporated and afforded the title compound (378 mg, 1.59 mmol, 59%) as an orange oil.

4-(3-(1H-imidazol-1-yl)-5-methylphenyl)-1-(4-(3,4-dichlorophenyl)-5-(isopropylthio)thiazol-2-yl)-3-methyl-1H-pyrazole-5-carboxylic Acid A solution of 1-(4-(3,4-dichlorophenyl)-5-(isopropylthio) thiazol-2-yl)-5-(methoxycarbonyl)-3-methyl-1H-pyrazol-4-ylboronic acid (50 mg, 0.10 mmol), 1-(3-bromo-5-methylphenyl)-1H-imidazole (29 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. LiOH (12.4 mg, 0.52 mmol) was added and the reaction was heated at 90° C. under microwave radiation for 45 minutes. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of NH$_4$CO$_2$H) (50 to 100%). The product was lyophilised and afforded the title compound (6.6 mg, 0.011 mmol, 11%) as a pale yellow solid.

$^1$H NMR (500 MHz, DMSO) δ 8.19 (s, 1H), 8.14 (d, J=2.1 Hz, 1H), 7.96 (dd, J=8.5, 2.1 Hz, 1H), 7.70-7.67 (m, 2H), 7.48 (m, 1H), 7.46 (m, 1H), 7.20 (s, 1H), 7.06 (s, 1H), 3.29 (hept, J=6.7 Hz, 1H), 2.35 (s, 3H), 2.27 (s, 3H), 1.18 (d, J=6.7 Hz, 6H); MS (m/z): 584.1 [M+H]$^+$.

Compound 102: 1-(4-(3,4-dichlorophenyl)-5-(isopropylthio)thiazol-2-yl)-3-methyl-4-(2-methyl-6-morpholinopyridin-4-yl)-1H-pyrazole-5-carboxylic Acid 4-bromo-6-methylpyridin-2-yl trifluoromethanesulfonate Tf$_2$O (107 μL, 0.638 mmol) was added slowly to a solution of 4-bromo-6-methylpyridin-2-ol (100 mg, 0.532 mmol) and Et$_3$N (89 μL, 0.64 mmol) in DCM (2.7 mL) at 0° C. The reaction was stirred at that temperature for 10 min. An aqueous saturated solution of NaHCO$_3$ (10 mL) was added and the mixture was extracted with DCM (2×10 mL). The combined organic layers were dried with sodium sulfate, filtered and evaporated. The crude product was purified by flash chromatography using a solution of ethyl acetate in hexanes (5%) and afforded the title compound (139 mg, 0.434 mmol, 82%) as a colorless oil.

4-(4-bromo-6-methylpyridin-2-yl)morpholine

A solution of 4-bromo-6-methylpyridin-2-yl trifluoromethanesulfonate (100 mg, 0.312 mmol), and morpholine (54 mg, 0.63 mmol) in DMSO (2 mL) was heated at 80° C. for 18 hours. Water (10 mL) was added and the reaction was extracted with EtOAc (2×10 mL). The combined organic layers were washed with brine (3×10 mL), dried with sodium sulfate, filtered and evaporated. The crude product (80 mg, 0.312 mmol, quantitative yield) was used without purification.

methyl 1-(4-(3,4-dichlorophenyl)-5-(isopropylthio)thiazol-2-yl)-3-methyl-4-(2-methyl-6-morpholinopyridin-4-yl)-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (25 mg, 0.051 mmol), 4-(4-bromo-6-methylpyridin-2-yl)morpholine (16 mg, 0.062 mmol), Pd(PPh$_3$)$_4$ (6 mg, 0.005 mmol), Na$_2$CO$_3$ (27 mg, 0.26 mmol) in degassed 1,4-dioxane and H$_2$O (4:1, 1.0 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (10 to 20%) and afforded the title compound (15 mg, 0.025 mmol, 48%) as a pale orange oil.

1-(4-(3,4-dichlorophenyl)-5-(isopropylthio)thiazol-2-yl)-3-methyl-4-(2-methyl-6-morpholinopyridin-4-yl)-1H-pyrazole-5-carboxylic Acid methyl 1-(4-(3,4-dichlorophenyl)-5-(isopropylthio)thiazol-2-yl)-3-methyl-4-(2-methyl-6-morpholinopyridin-4-yl)-1H-pyrazole-5-carboxylate (15 mg, 0.025 mmol) was diluted in a 1:1 solution of THF and MeOH (0.25 mL). 1 M NaOH (0.049 mL, 0.049 mmol) was added and the reaction was stirred for 18 hours at room temperature. 1 N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of NH$_4$CO$_2$H) (30 to 70%). The product was lyophilized and afforded the title compound (4.1 mg, 0.0068 mmol, 28%) as a white solid.

$^1$H NMR (500 MHz, DMSO) δ 8.21 (d, J=1.9 Hz, 1H), 8.03 (dd, J=8.5, 2.0 Hz, 1H), 7.76 (d, J=8.5 Hz, 1H), 6.66 (s, 1H), 6.64 (s, 1H), 3.72-3.68 (m, 4H), 3.48-3.43 (m, 4H), 3.36 (hept, J=6.7 Hz, 1H), 2.35 (s, 3H), 2.33 (s, 3H), 1.24 (d, J=6.7 Hz, 6H); MS (m/z): 604.0 [M+H]$^+$.

Compound 103: 1-(5-(isopropylthio)-4-(3-methoxyphenyl)thiazol-2-yl)-3-methyl-4-(2-nitrobenzyl)-1H-pyrazole-5-carboxylic Acid

2-chloro-4-(3-methoxyphenyl)thiazole

A mixture of 1-(3-methoxyphenyl)-2-thiocyanatoethanone (4.43 g, 21.4 mmol) and 4 N HCl in dioxane (32 mL, 128 mmol) in dioxane (21 mL) was stirred at room temperature for 20 h. The mixture was concentrated in vacuo and the residue was diluted with EtOAc washed with sat. aq.NaHCO$_3$, brine and dried over MgSO$_4$, filtered and concentrated in vacuo and afforded the title compound (4.80 g, 21.3 mmol, 99%).

2-chloro-5-(isopropylthio)-4-(3-methoxyphenyl)thiazole

A 2.5 M solution of n-BuLi in hexanes (2.66 mL, 6.65 mmol) was added to a THF (14.8 mL) solution of 2-chloro-4-(3-methoxyphenyl)thiazole (1.00 g, 4.43 mmol) at −78° C. The mixture was stirred at the same temperature for 20 mins. Then diisopropyl disulfide (0.94 mL, 1.42 mmol) was added and the reaction mixture was stirred 30 mins at the same temperature. Water was added to quench the reaction mixture and then extracted with EtOAc. The organic layer was washed with brine, dried with MgSO4, filtered and concentrated under vacuum. The crude product was purified by flash chromatography (dry packing) on silica gel eluted with hexanes and afforded the title compound (685 mg, 2.29 mmol, 52%).

2-hydrazinyl-5-(isopropylthio)-4-(3-methoxyphenyl)thiazole

The hydrazine HCl salt (91.0 mg, 1.33 mmol), the 2-chloro-5-(isopropylthio)-4-(3-methoxyphenyl)thiazole (200 mg, 0.667 mmol) and DIPEA (233 µL, 1.33 mmol) were dissolved in NMP (2.2 mL) in a microwave vial. The vial was heated with microwave radiation to 150° C. for 2 h. The crude product was purified by reverse flash chromatography (C18, using a gradient 10 to 75% MeCN in H$_2$O) and afforded the title compound (119 mg, 0.403 mmol, 60%) as a grey solid.

methyl 1-(5-(isopropylthio)-4-(3-methoxyphenyl)thiazol-2-yl)-3-methyl-4-(2-nitrobenzyl)-1H-pyrazole-5-carboxylate To a solution of methyl 2-(methoxyimino)-3-(2-nitrobenzyl)-4-oxopentanoate (92 mg, 0.30 mmol) in MeOH (3.0 mL) was added 2-hydrazinyl-5-(isopropylthio)-4-(3-methoxyphenyl)thiazole (88 mg, 0.30 mmol) followed by dropwise addition of HCl 12 N (99.5 µL, 1.19 mmol). The reaction mixture was heated to reflux overnight. The crude product was concentrated under vacuum. The product was purified by flash chromatography on silica gel using a gradient 0 to 20% EtOAc in hexanes and afforded the title compound (119 mg, 0.200 mmol, 67%).

1-(5-(isopropylthio)-4-(3-methoxyphenyl)thiazol-2-yl)-3-methyl-4-(2-nitrobenzyl)-1H-pyrazole-5-carboxylic Acid To a solution of methyl 1-(5-(isopropylthio)-4-(3-methoxyphenyl)thiazol-2-yl)-3-methyl-4-(2-nitrobenzyl)-1H-pyrazole-5-carboxylate (60 mg, 0.11 mmol) in a 1/1 mixture of MeOH/THF (1 mL) was added 1 N NaOH (223 µL, 0.22 mmol). The reaction mixture was stirred at rt overnight. Quenched to pH 4 with 3 N HCl and the reaction mixture was concentrated under vacuum. The crude product was diluted with DCM and transferred into a separation funnel. The organic layer was washed with water (2×) and brine (2×), dried over Na$_2$SO$_4$ and concentrated under vacuum. The product was lyophilized, resulting in the title compound (54.7 mg, 0.104 mmol, 94%) as a white solid.

$^1$H NMR (500 MHz, DMSO) δ 13.96 (s, 1H), 8.00 (dd, J=8.1, 1.2 Hz, 1H), 7.65 (td, J=7.6, 1.3 Hz, 1H), 7.58-7.48 (m, 2H), 7.38 (t, J=8.0 Hz, 1H), 7.22 (d, J=6.9 Hz, 1H), 6.99 (ddd, J=8.3, 2.6, 0.9 Hz, 1H), 4.24 (s, 2H), 3.80 (s, 3H), 3.36-3.28 (m, 1H), 2.08 (s, 3H), 1.23 (d, J=6.7 Hz, 6H). MS (m/z): 525.1 [M+1]$^+$.

Compound 108: 1-(4-(3,4-dichlorophenyl)-5-(isopropylthio)thiazol-2-yl)-3-methyl-4-(3-nitrophenyl)-1H-pyrazole-5-carboxylic Acid

1-(4-(3,4-dichlorophenyl)-5-(isopropylthio)thiazol-2-yl)-3-methyl-4-(3-nitrophenyl)-1H-pyrazole-5-carboxylic Acid Nitrogen was passed through a solution of dioxane/H$_2$O (4/1) and this solution (2 mL) was then added to a mixture of the methyl 4-bromo-1-(4-(3,4-dichlorophenyl)-5-(isopropylthio)thiazol-2-yl)-3-methyl-1H-pyrazole-5-carboxylate (50.0 mg, 0.096 mmol), 3-nitrophenylboronic acid (19.2 mg, 0.12 mmol) and Na$_2$CO$_3$ (51.0 mg, 0.48 mmol) followed by the addition of the catalyst Pd(PPh$_3$)$_4$ (11.0 mg, 0.01 mmol). The reaction mixture was heated at 85° C. for 16 hours. 1 N NaOH (100 µL, 0.10 mmol) was added and the reaction mixture was stirred at 50° C. for 5 hours. More 1 N NaOH (100 µL, 0.10 mmol) was added and the reaction mixture was stirred at 85° C. overnight. Quenched with 1 N HCl. Diluted with EtOAc washed with water and brine. Dried MgSO4, filtered and concentrated in vacuo. The crude product was purified by reverse flash chromatography (C18, using a gradient 60 to 80% MeCN in H$_2$O) and afforded the title compound (14.9 mg, 0.03 mmol, 28%) as yellow solid.
$^1$H NMR (500 MHz, DMSO) δ 8.36 (s, 1H), 8.24-8.20 (m, 2H), 8.04 (dd, J=8.5, 2.0 Hz, 1H), 7.99-7.95 (m, 1H), 7.79-7.73 (m, 2H), 3.43-3.31 (m, 1H), 2.33 (s, 3H), 1.24 (d, J=6.7 Hz, 6H). MS (m/z): 549.1 [M+1]$^+$.

Compound 112: 4-(3-chlorophenyl)-1-(4-(3,4-dichlorophenyl)-5-(isopropylthio)thiazol-2-yl)-3-methyl-1H-pyrazole-5-carboxylic Acid 4-(3-chlorophenyl)-1-(4-(3,4-dichlorophenyl)-5-(isopropylthio)thiazol-2-yl)-3-methyl-1H-pyrazole-5-carboxylic Acid Nitrogen was passed through a solution of dioxane/H$_2$O (4/1) and this solution (2 mL) was then added to a mixture of the methyl 4-bromo-1-(4-(3,4-dichlorophenyl)-5-(isopropylthio)thiazol-2-yl)-3-methyl-1H-pyrazole-5-carboxylate (50.0 mg, 0.096 mmol), 3-chlorophenylboronic acid (18.0 mg, 0.12 mmol) and Na$_2$CO$_3$ (51.0 mg, 0.48 mmol) followed by the addition of the catalyst Pd(PPh$_3$)$_4$ (11.0 mg, 0.01 mmol). The reaction mixture was heated at 85° C. for 16 hours. LiOH (12.0 mg, 0.48 mmol) was added to the reaction mixture and stirred in the microwave at 90° C. for 10 min. Acidified with 1 N HCl and evaporated in vacuo. The crude product was purified by semi-prep HPLC-MS (column X-Bridge 30×50, eluted with 65-85% MeCN/NH$_4$CO$_2$H 10 mM, pH 3.8/Flow 45 ml/min/10 min) and afforded the title compound (20.3 mg, 0.04 mmol, 39%) as a yellow solid after lyophilization.
$^1$H NMR (500 MHz, DMSO) δ 8.20 (d, J=2.1 Hz, 1H), 8.02 (dd, J=8.5, 2.1 Hz, 1H), 7.75 (d, J=8.5 Hz, 1H), 7.57-7.53 (m, 1H), 7.52-7.42 (m, 3H), 3.39-3.25 (m, 1H), 2.31 (s, 3H), 1.24 (d, J=6.7 Hz, 6H). MS (m/z): 538.0 [M+1]$^+$.

Compound 115: 1-(4-(3,4-dichlorophenyl)-5-(isopropylthio)thiazol-2-yl)-4-(3-methoxyphenyl)-3-methyl-1H-pyrazole-5-carboxylic Acid 1-(4-(3,4-dichlorophenyl)-5-(isopropylthio)thiazol-2-yl)-4-(3-methoxyphenyl)-3-methyl-1H-pyrazole-5-carboxylic Acid Nitrogen was passed through a solution of dioxane/H$_2$O (4/1) and this solution (2 mL) was then added to a mixture of the methyl 4-bromo-1-(4-(3,4-dichlorophenyl)-5-(isopropylthio)thiazol-2-yl)-3-methyl-1H-pyrazole-5-carboxylate (50.0 mg, 0.096 mmol), 3-methoxyphenylboronic acid (18.2 mg, 0.12 mmol) and Na$_2$CO$_3$ (51.0 mg, 0.48 mmol) followed by the addition of the catalyst Pd(PPh$_3$)$_4$ (11.0 mg, 0.01 mmol). The reaction mixture was heated at 85° C. for 16 hours. LiOH (12.0 mg, 0.48 mmol) was added to the reaction mixture and stirred in the microwave at 90° C. for 25 min. Acidified with 1 N HCl and evaporated in vacuo. The crude product was purified by semi-prep HPLC-MS (column X-Bridge 30×50, eluted with 65-85% MeCN/NH$_4$CO$_2$H 10 mM, pH 3.8/Flow 45 ml/min/10 min) and afforded the title compound (10.6 mg, 0.02 mmol, 21%) as a yellow solid after lyophilization.
$^1$H NMR (500 MHz, DMSO) δ 8.22 (d, J=1.9 Hz, 1H), 8.03 (dd, J=8.5, 1.9 Hz, 1H), 7.74 (d, J=8.5 Hz, 1H), 7.36 (t, J=8.0 Hz, 1H), 7.09-7.03 (m, 2H), 6.94 (d, J=8.0 Hz, 1H), 3.78 (s, 3H), 3.42-3.29 (m, 1H), 2.29 (s, 3H), 1.24 (d, J=6.7 Hz, 6H). MS (m/z): 534.1 [M+1]$^+$.

Compound 118: 1-(4-(3,4-dichlorophenyl)-5-(isopropylthio)thiazol-2-yl)-3-methyl-4-m-tolyl-1H-pyrazole-5-carboxylic Acid 1-(4-(3,4-dichlorophenyl)-5-(isopropylthio)thiazol-2-yl)-3-methyl-4-m-tolyl-1H-pyrazole-5-carboxylic Acid Nitrogen was passed through a solution of dioxane/H$_2$O (4/1) and this solution (2 mL) was then added to a mixture of the methyl 4-bromo-1-(4-(3,4-dichlorophenyl)-5-(isopropylthio)thiazol-2-yl)-3-methyl-1H-pyrazole-5-carboxylate (50.0 mg, 0.096 mmol), m-tolylboronic acid (16.3 mg, 0.12 mmol) and Na$_2$CO$_3$ (51.0 mg, 0.48 mmol) followed by the addition of the catalyst Pd(PPh$_3$)$_4$ (11.0 mg, 0.01 mmol). The reaction mixture was heated at 85° C. for 16 hours. LiOH (12.0 mg, 0.48 mmol) was added to the reaction mixture and stirred in the microwave at 90° C. for 25 min. Acidified with 1N HCl and evaporated in vacuo. The crude product was purified by semi-prep HPLC-MS (column X-Bridge 30×50, eluted with 65-85% MeCN/NH$_4$CO$_2$H 10 mM, pH 3.8/Flow 45 ml/min/10 min) and afforded the title compound (19.0 mg, 0.04 mmol, 38%) as a yellow solid after lyophilization.
$^1$H NMR (500 MHz, DMSO) δ 8.22 (d, J=2.0 Hz, 1H), 8.03 (dd, J=8.5, 2.0 Hz, 1H), 7.73 (d, J=8.5 Hz, 1H), 7.35-7.23 (m, 3H), 7.18 (d, J=7.2 Hz, 1H), 3.42-3.28 (m, 1H), 2.36 (s, 3H), 2.29 (s, 3H), 1.24 (d, J=6.7 Hz, 6H). MS (m/z): 518.1 [M+1]$^+$.

Compound 129: 2-(4-(3,4-dichlorophenyl)-5-(isopropylthio)thiazol-2-yl)-2'-ethyl-5-methyl-4,4'-bi(2H-pyrazole)-3-carboxylic Acid 1-ethyl-4-(4,4,5,5-tetramethyl-1,3,2-dioxaborolan-2-yl)-1H-pyrazole NaH 60% dispersion in mineral oil (50.0 mg, 1.24 mmol) was suspended in DMF (2 mL) followed by the addition of a solution of 4-(4,4,5,5-tetramethyl-1,3,2-dioxaborolan-2-yl)-1H-pyrazole (200 mg, 1.03 mmol) in DMF (550 µL). The resulting mixture was stirred at r.t. for 1 hour. Iodomethane (132 µL, 1.65 mmol) was added dropwise and stirring was continued for 2 days. Water was added and the reaction mixture was extracted with EtOAc. The organic layer was washed with water and brine. Dried MgSO$_4$, filtered and concentrated in vacuo. The product was purified by flash chromatography (dry packing) on silica gel using a gradient 0 to 30% EtOAc in hexanes and afforded the title compound (62.7 mg, 0.28 mmol, 27%) as a yellow oil.

methyl 2-(4-(3,4-dichlorophenyl)-5-(isopropylthio)thiazol-2-yl)-2'-ethyl-5-methyl-4,4'-bi(2H-pyrazole)-3-carboxylate Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50.0 mg, 0.10 mmol), 1-ethyl-4-(4,4,5,5-tetramethyl-1,3,2-dioxaborolan-2-yl)-1H-pyrazole (25.6 mg, 0.12 mmol) and Na$_2$CO$_3$ (51.0 mg, 0.48 mmol) followed by the addition of the catalyst Pd(PPh$_3$)$_4$ (11.0 mg, 0.01 mmol). The reaction mixture was heated at 85° C. for 16 hours. Diluted with EtOAc washed with water and brine. Dried MgSO$_4$, filtered and concentrated in vacuo. The product was purified by flash chromatography (dry packing) on silica gel using a gradient 0 to 30% EtOAc in hexanes and afforded the title compound (24.4 mg, 0.05 mmol, 47%) as a yellow oil.

2-(4-(3,4-dichlorophenyl)-5-(isopropylthio)thiazol-2-yl)-2'-ethyl-5-methyl-4,4'-bi(2H-pyrazole)-3-carboxylic Acid methyl 2-(4-(3,4-dichlorophenyl)-5-(isopropylthio)thiazol-2-yl)-2'-ethyl-5-methyl-4,4'-bi(2H-pyrazole)-3-carboxylate (24.0 mg, 0.05 mmol) was dissolved in a mixture of H$_2$O/THF/MeOH (6/3/1) (1 mL) and treated with LiOH (5.0 mg, 0.2 mmol). The reaction mixture was stirred in the microwave at 110° C. for 15 min. Neutralized with 1N HCl and evaporated in vacuo. The crude product was purified by semi-prep HPLC-MS (column X-Bridge 30×50, eluted with 50-70% MeCN/NH$_4$CO$_2$H 10 mM, pH 3.8/Flow 45 ml/min/10 min) and afforded the title compound (13.2 mg, 0.03 mmol, 56%) as a white solid after lyophilization.
$^1$H NMR (500 MHz, DMSO) δ 8.20 (d, J=2.1 Hz, 1H), 8.04-7.99 (m, 2H), 7.76 (d, J=8.5 Hz, 1H), 7.66 (d, J=0.7 Hz, 1H), 4.18 (q, J=7.3 Hz, 2H), 3.40-3.29 (m, 1H), 2.36 (s, 3H), 1.40 (t, J=7.3 Hz, 3H), 1.23 (d, J=6.7 Hz, 6H). MS (m/z): 522.0 [M+1]$^+$.

Compound 131: (4-(aminomethyl)piperidin-1-yl)(1-(4-(3,4-dichlorophenyl)-5-(isopropylthio)thiazol-2-yl)-3-methyl-4-o-tolyl-1H-pyrazol-5-yl)methanone The 1-(4-(3,4-dichlorophenyl)-5-(isopropylthio)thiazol-2-yl)-3-methyl-4-o-tolyl-1H-pyrazole-5-carboxylic acid (10.0 mg, 0.02 mmol) and tert-butyl piperidin-4-ylmethylcarbamate (5.0 mg, 0.02 mmol) were dissolved in DMF (0.5 mL) and was added HATU (10.0 mg, 0.03 mmol) followed by DIPEA (6.6 µL, 0.04 mmol). The reaction mixture was stirred at r.t. overnight. Diluted with EtOAc washed with water and brine. Dried MgSO$_4$, filtered and concentrated in vacuo. The crude product was dissolved in dioxane (0.5 mL) and treated with 4 N HCl (200 µL) and stirred at r.t overnight. Evaporated in vacuo. The crude product was purified by semi-prep HPLC-MS (column X-Bridge 30×50, eluted with 60-80% MeCN/NH$_4$CO$_2$H 10 mM, pH 3.8/Flow 45 ml/min/10 min) and afforded the title compound (4.6 mg, 0.007 mmol, 39%) as an off-white solid after lyophilization.
$^1$H NMR (500 MHz, DMSO) Complex mixture of rotamers; MS (m/z): 614.2 [M+1]$^+$.

Compound 136: (4-(aminomethyl)piperidin-1-yl)(4-(3,5-bis(trifluoromethyl)phenyl)-1-(4-(3,4-dichlorophenyl)-5-(isopropylthio)thiazol-2-yl)-3-methyl-1H-pyrazol-5-yl)methanone The 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (20 mg, 0.031 mmol) and tert-butyl piperidin-4-ylmethylcarbamate (9.0 mg, 0.042 mmol) were dissolved in DMF (0.5 mL) and was added HATU (17 mg, 0.045 mmol) followed by DIPEA (12 µL, 0.068 mmol). The reaction mixture was stirred at r.t. for 1.5 h. Diluted with EtOAc washed with water and brine. Dried MgSO4, filtered and concentrated in vacuo. The crude product was dissolved in dioxane (0.5 mL) and treated with 4 N HCl (200 µL) and stirred at r.t overnight. More 4 N HCl (200 uL) was added and stirring was continued over the week end. Evaporated in vacuo. The crude product was purified by semi-prep HPLC-MS (column X-Bridge 30×50, eluted with 70-90% MeCN/NH$_4$CO$_2$H 10 mM, pH 3.8/Flow 45 ml/min/10 min) and afforded the title compound (4.3 mg, 0.006 mmol, 19%) as a yellow solid after lyophilization.
$^1$H NMR (500 MHz, DMSO) δ 8.20 (s, 1H), 8.14 (d, J=2.0 Hz, 1H), 8.10-8.06 (m, 2H), 8.04 (s, 1H), 7.81 (d, 8.5 Hz, 1H), 4.57-4.48 (m, 1H), 3.59-3.48 (m, 1H), 3.41-3.31 (m, 1H), 3.03-2.90 (m, 1H), 2.77-2.59 (m, 2H), 2.41 (s, 3H), 2.26-2.17 (m, 1H), 2.15-1.96 (m, 1H), 1.89-1.79 (m, 1H), 1.66-1.50 (m, 1H), 1.48-1.30 (m, 2H), 1.27-1.5 (m, 6H), 0.76-0.60 (m, 1H), 0.28-0.15 (m 1H). MS (m/z): 738.0 [M+1]+.

Compound 137: N-(2-aminoethyl)-4-(3,5-bis(trifluoromethyl)phenyl)-1-(4-(3,4-dichlorophenyl)-5-(isopropylthio)thiazol-2-yl)-N,3-dimethyl-1H-pyrazole-5-carboxamide The 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (20 mg, 0.031 mmol) and tert-butyl (2-(methylamino)ethyl)carbamate (7.0 mg, 0.042 mmol) were dissolved in DMF (0.5 mL) and was added HATU (17 mg, 0.045 mmol) followed by DIPEA (12 µL, 0.068 mmol). The reaction mixture was stirred overnight. Diluted with EtOAc washed with water and brine. Dried MgSO$_4$, filtered and concentrated in vacuo. The crude product was dissolved in dioxane (0.5 mL) and treated with 4 N HCl (200 µL) and stirred at r.t. for 4 hours. More 4N HCl (200 µL) was added and stirring was continued overnight. Evaporated in vacuo. The crude product was purified by semi-prep HPLC-MS (column X-Bridge 30×50, eluted with 80-100% MeCN/NH$_4$CO$_2$H 10 mM, pH 3.8/Flow 45 ml/min/10 min) and afforded the title compound (5.8 mg, 0.008 mmol, 27%) as a yellow solid after lyophilization.
$^1$H NMR (500 MHz, DMSO) δ 8.18 (s, 0.5H), 8.16 (s, 0.5H), 8.15 (d, J=2.1 Hz, 0.5H), 8.13 (s, 1H), 8.12 (d, J=2.1 Hz, 0.5H), 8.10 (dd, J=2.1, 8.5 Hz, 0.5H), 8.08 (s, 1H), 8.03 (dd, J=2.1, 8.5 Hz, 0.5H), 7.80 (d, J=8.5 Hz, 0.5H), 7.79 (d, J=8.5 Hz, 0.5H), 3.77-3.68 (m, 0.5H), 3.43-3.34 (m, 1.5H), 3.14-2.99 (m, 2H), 2.98 (s, 1.5H), 2.80 (s, 1.5H), 2.66-2.57 (m, 1.5H), 2.47-2.27 (m, 1.5H), 2.41 (s, 3H), 1.27-1.23 (m, 6H). MS (m/z): 696.2 [M+1]$^+$.

Compound 139: (4-(3,5-bis(trifluoromethyl)phenyl)-1-(4-(3,4-dichlorophenyl)-5-(isopropylthio)thiazol-2-yl)-3-methyl-1H-pyrazol-5-yl)(morpholino)methanone The 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (20 mg, 0.031 mmol) and morpholine (4.0 mg, 0.042 mmol) were dissolved in DMF (0.5 mL) and was added HATU (17 mg, 0.045 mmol) followed by DIPEA (12 µL, 0.068 mmol). The reaction mixture was stirred overnight. The crude product was purified by semi-prep HPLC-MS (column X-Bridge 30×50, eluted with 80-100% MeCN/NH$_4$CO$_2$H 10 mM, pH 3.8/Flow 45 ml/min/10 min) and afforded the title compound (9.4 mg, 0.013 mmol, 42%) as an off-white solid after lyophilization.

¹H NMR (500 MHz, DMSO) δ 8.22 (s, 1H), 8.13 (d, J=2.1 Hz, 1H), 8.08 (s, 2H), 8.04 (dd, J=8.5, 2.1 Hz, 1H), 7.82 (d, J=8.5 Hz, 1H), 3.84-3.77 (m, 1H), 3.73-3.66 (m, 1H), 3.48-3.44 (m, 1H), 3.42-3.36 (m, 1H), 3.35-3.19 (m, 4H), 3.04-2.96 (m, 1H), 2.40 (s, 3H), 1.27-1.23 (m, 6H). MS (m/z): 709.1 [M+1]⁺.

Compound 140: 4-(3,5-bis(trifluoromethyl)phenyl)-1-(4-(3,4-dichlorophenyl)-5-(isopropylthio)thiazol-2-yl)-N,N,3-trimethyl-1H-pyrazole-5-carboxamide The 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (20 mg, 0.031 mmol) and dimethylamine hydrochloride salt (3.0 mg, 0.042 mmol) were dissolved in DMF (0.5 mL) and was added HATU (17 mg, 0.045 mmol) followed by DIPEA (12 μL, 0.068 mmol). The reaction mixture was stirred overnight. Diluted with EtOAc washed with water and brine. Dried MgSO₄, filtered and concentrated in vacuo. The crude product was purified by semi-prep HPLC-MS (column X-Bridge 30×50, eluted with 80-100% MeCN/NH₄CO₂H 10 mM, pH 3.8/Flow 45 ml/min/10 min) and afforded the title compound (6.9 mg, 0.010 mmol, 33%) as a white solid after lyophilization.

¹H NMR (500 MHz, DMSO) δ 8.17 (s, 1H), 8.14 (d, J=2.1 Hz, 1H), 8.09-8.06 (m, 3H), 7.81 (d, J=8.5 Hz, 1H), 3.43-3.34 (m, 1H), 2.99 (s, 3H), 2.80 (s, 3H), 2.42 (s, 3H), 1.26 (d, J=6.7 Hz, 6H). MS (m/z): 667.1 [M+1]⁺.

Compound 141: (4-(3,5-bis(trifluoromethyl)phenyl)-1-(4-(3,4-dichlorophenyl)-5-(isopropylthio)thiazol-2-yl)-3-methyl-1H-pyrazol-5-yl)(4-(hydroxymethyl)piperidin-1-yl)methanone The 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (20 mg, 0.031 mmol) and piperidin-4-yl MeOH (5.0 mg, 0.042 mmol) were dissolved in DMF (0.5 mL) and was added HATU (17 mg, 0.045 mmol) followed by DIPEA (12 μL, 0.068 mmol). The reaction mixture was stirred overnight. The crude product was purified by semi-prep HPLC-MS (column X-Bridge 30×50, eluted with 80-100% MeCN/NH₄CO₂H 10 mM, pH 3.8/Flow 45 ml/min/10 min) and afforded the title compound (9.4 mg, 0.013 mmol, 41%) as a white solid after lyophilization.

¹H NMR (500 MHz, DMSO) δ 8.19 (s, 1H), 8.14 (d, J=2.0 Hz, 1H), 8.10-8.05 (m, 2H), 8.03 (s, 1H), 7.81 (d, J=8.5 Hz, 1H), 4.58-4.51 (m, 1H), 4.49-4.43 (m, 1H), 4.11-4.06 (m, 1H), 3.56-3.50 (m, 1H), 3.42-3.34 (m, 1H), 3.07-2.93 (m, 2H), 2.76-2.64 (m, 1H), 2.41 (s, 3H), 1.82-1.74 (m, 1H), 1.63-1.44 (m, 2H), 1.27-1.24 (m, 6H), 0.78-0.65 (m, 1H), 0.31-0.17 (m, 1H). MS (m/z): 737.1 [M+1]⁺.

Compound 142: 1-(4-(3,4-dichlorophenyl)-5-isobutylthiazol-2-yl)-1',3-dimethyl-1H,1'H-[4,4'-bipyrazole]-5-carboxylic Acid 1-(2-chloro-4-(3,4-dichlorophenyl)thiazol-5-yl)-2-methylpropan-1-ol To a cold −78° C. solution of 2-chloro-4-(3,4-dichlorophenyl)thiazole (2.00 g, 7.56 mmol) and isopropyl aldehyde (966 μL, 10.6 mmol) in THF (40 mL) was added dropwise 2.5M nBuLi (4.8 mL, 12 mmol). The reaction mixture was stirred 2 hours at −78° C. More isopropyl aldehyde (290 μL, 3.18 mmol) and 2.5M nBuLi (1.5 mL, 3.8 mmol) were added and stirring was continued for 1 h. The reaction mixture was quenched with sat NH4Cl and allowed to warm to r.t. Diluted with EtOAc and washed with water and brine. Dried MgSO₄, filtered and concentrated in vacuo. The product was purified by flash chromatography (dry packing) on silica gel using a gradient 0 to 10% EtOAc in hexanes and afforded the title compound (815 mg, 2.42 mmol, 32%) as a yellow oil.

2-chloro-4-(3,4-dichlorophenyl)-5-isobutylthiazole

The 1-(2-chloro-4-(3,4-dichlorophenyl)thiazol-5-yl)-2-methylpropan-1-ol (500 mg, 1.49 mmol) was dissolved in DCM (15 mL) and treated with triethylsilane (710 μL, 4.46 mmol) followed by TFA (34 μL, 0.45 mmol). The reaction mixture was stirred at r.t. for 1.5 h. More triethylsilane (1.2 mL, 7.43 mmol) followed by TFA (1.6 mL, 21 mmol) were added and stirring was continued overnight. The reaction mixture was evaporated in vacuo. The residue was treated with sat NaHCO₃ and extracted with EtOAc. The organic layer was washed with brine, dried MgSO₄, filtered and concentrated in vacuo and afforded the title compound (382 mg, 1.19 mmol, 80%) which was used without further purification.

4-(3,4-dichlorophenyl)-2-hydrazinyl-5-isobutylthiazole

The hydrazine HCl salt (163 mg, 2.38 mmol), the 2-chloro-4-(3,4-dichlorophenyl)-5-isobutylthiazole (382 mg, 1.19 mmol) and DIPEA (416 μL, 2.38 mmol) were dissolved in NMP (4.0 mL) in a microwave vial. The vial was heated with microwave radiation to 150° C. for 2 h. Add more hydrazine HCl salt (163 mg, 2.38 mmol) and DIPEA (416 μL, 2.38 mmol) and heating with microwave radiation to 150° C. was continued for another hour. The reaction mixture was diluted with Et₂O and washed with water and brine. Dried over MgSO₄, filtered and concentrated. The crude product was purified by reverse flash chromatography (C18, using a gradient 60-80% MeCN in H₂O) and afforded the title compound (33 mg, 0.10 mmol, 9%) as a yellow oil.

methyl 1-(4-(3,4-dichlorophenyl)-5-isobutylthiazol-2-yl)-3-methyl-1H-pyrazole-5-carboxylate To a solution of methyl 2-(methoxyimino)-4-oxopentanoate (17 mg, 0.10 mmol) in MeOH (1.0 mL) was added 4-(3,4-dichlorophenyl)-2-hydrazinyl-5-isobutylthiazole (32 mg, 0.10 mmol) followed by dropwise addition of HCl 12N (33 μL, 0.40 mmol). The reaction mixture was heated to reflux overnight. The crude product was concentrated under vacuum. The product was purified by flash chromatography on silica gel using a gradient 0 to 10% EtOAc in hexanes and afforded the title compound (23 mg, 0.054 mmol, 54%).

methyl 4-bromo-1-(4-(3,4-dichlorophenyl)-5-isobutylthiazol-2-yl)-3-methyl-1H-pyrazole-5-carboxylate A 2 M solution of Br₂ in DCM (55 μL, 0.11 mmol) was added to a solution of the methyl 1-(4-(3,4-dichlorophenyl)-5-isobutylthiazol-2-yl)-3-methyl-1H-pyrazole-5-carboxylate (23 mg, 0.054 mmol) in DCM (0.5 mL). The reaction mixture was stirred at r.t. for 1.5 h. Two more increments of 2 M Br₂/DCM (55 μL, 0.11 mmol, each) was added prior to stirring overnight. Three more increments of 2 M Br₂/DCM (55 μL, 0.11 mmol, each) was added over the day. The reaction mixture was quenched with aq. Na₂S₂O₃ and extracted with EtOAc. The organic layer was washed with water and brine. Dried MgSO$_4$, filtered and concentrated in vacuo. The product was purified by flash chromatography (dry packing) on silica gel using a gradient 0 to 10% EtOAc in hexanes and afforded the title compound (7.4 mg, 0.015 mmol, 29%) as a yellow oil.

1-(4-(3,4-dichlorophenyl)-5-isobutylthiazol-2-yl)-1', 3-dimethyl-1H,1'H-[4,4'-bipyrazole]-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-isobutylthiazol-2-yl)-3-methyl-1H-pyrazole-5-carboxylate (7.0 mg, 0.015 mmol), 1-methyl-4-(4,4,5,5-tetramethyl-1,3,2-dioxaborolan-2-yl)-1H-pyrazole (3.7 mg, 0.018 mmol) and Na$_2$CO$_3$ (8.0 mg, 0.075 mmol) followed by the addition of the catalyst Pd(PPh$_3$)$_4$ (2.0 mg, 0.002 mmol). The reaction mixture was heated at 85° C. for 16 hours. Add LiOH (1.8 mg, 0.075 mmol) and stirred in the microwave at 110° C. for 10 min. Evaporated in vacuo. The crude product was purified by semi-prep HPLC-MS (column X-Bridge 30×50, eluted with 50-70% MeCN/NH$_4$CO$_2$H 10 mM, pH 3.8/Flow 45 ml/min/10 min) and afforded the title compound (2.0 mg, 0.004 mmol, 28%) as a white solid after lyophilization.

$^1$H NMR (500 MHz, DMSO) δ 7.94 (s, 1H), 7.79 (d, J=2.0 Hz, 1H), 7.74 (d, J=8.4 Hz, 1H), 7.64 (s, 1H), 7.60 (dd, J=8.4, 2.0 Hz, 1H), 3.88 (s, 3H), 2.84 (d, J=7.1 Hz, 2H), 2.34 (s, 3H), 1.93-1.82 (m, 1H), 0.93 (d, J=6.6 Hz, 6H). MS (m/z): 490.0 [M+1]$^+$.

Compound 143: 1-(4-(3,4-dichlorophenyl)-5-(isopropylthio)thiazol-2-yl)-4-(3,5-dimethylphenyl)-3-methyl-1H-pyrazole-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50 mg, 0.096 mmol), (3,5-dimethylphenyl)boronic acid (17 mg, 0.12 mmol) and Na$_2$CO$_3$ (51 mg, 0.48 mmol) followed by the addition of the catalyst Pd(PPh$_3$)$_4$ (11 mg, 0.010 mmol). The reaction mixture was heated at 85° C. for 16 hours. Diluted with EtOAc washed with water and brine. Dried MgSO$_4$, filtered and concentrated in vacuo. The methyl 1-(4-(3,4-dichlorophenyl)-5-(isopropylthio)thiazol-2-yl)-4-(3,5-dimethylphenyl)-3-methyl-1H-pyrazole-5-carboxylate was purified by flash chromatography (dry packing) on silica gel using a gradient 0 to 10% EtOAc in hexanes to give the methyl 1-(4-(3,4-dichlorophenyl)-5-(isopropylthio)thiazol-2-yl)-4-(3,5-dimethylphenyl)-3-methyl-1H-pyrazole-5-carboxylate which was used directly for hydrolysis. Dissolved in a mixture of H$_2$O/THF/MeOH (6/3/1) (2.0 mL) and treated with LiOH (12 mg, 0.48 mmol). The reaction mixture was stirred in the microwave at 110° C. for 10 min. Evaporated in vacuo. The crude product was purified by semi-prep HPLC-MS (column X-Bridge 30×50, eluted with 70-90% MeCN/NH$_4$CO$_2$H 10 mM, pH 3.8/Flow 45 ml/min/10 min) and afforded the title compound (1.7 mg, 0.003 mmol, 3%) as a yellow solid after lyophilization.

$^1$H NMR (500 MHz, DMSO) δ 8.17 (s, 1H), 8.03-7.96 (m, 1H), 7.68 (d, J=8.4 Hz, 1H), 7.02 (s, 2H), 6.90 (s, 1H), 3.30-3.25 (m, 1H), 2.23 (s, 6H), 2.20 (s, 3H), 1.17 (d, J=6.7 Hz, 6H). MS (m/z): 532.1 [M+1]$^+$.

Compound 144: 4-(3,5-dichlorophenyl)-1-(4-(3,4-dichlorophenyl)-5-(isopropylthio)thiazol-2-yl)-3-methyl-1H-pyrazole-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50 mg, 0.096 mmol), (3,5-dichlorophenyl)boronic acid (23 mg, 0.12 mmol) and Na$_2$CO$_3$ (51 mg, 0.48 mmol) followed by the addition of the catalyst Pd(PPh$_3$)$_4$ (11 mg, 0.010 mmol). The reaction mixture was heated at 85° C. for 16 hours. Add LiOH (12 mg, 0.48 mmol) and the reaction mixture was stirred in the microwave at 110° C. for 10 min. More LiOH (12 mg, 0.48 mmol) was added and stirring in the microwave at 110° C. was continued for 30 min. Evaporated in vacuo. The crude product was purified by semi-prep HPLC-MS (column X-Bridge 30×50, eluted with 65-85% MeCN/NH$_4$CO$_2$H 10 mM, pH 3.8/Flow 45 ml/min/10 min) and afforded the title compound (15 mg, 0.026 mmol, 27%) as a yellow solid after lyophilization.

$^1$H NMR (500 MHz, DMSO) δ 8.19 (d, J=2.1 Hz, 1H), 8.01 (dd, J=8.5, 2.1 Hz, 1H), 777 (d, J=8.5 Hz, 1H), 7.68-7.65 (m, 1H), 7.54 (d, J=1.9 Hz, 2H), 3.42-3.32 (m, 1H), 2.31 (s, 3H), 1.24 (d, J=6.7 Hz, 6H). MS (m/z): 571.8 [M+1]+.

Compound 145: 4-(3-chloro-5-methoxyphenyl)-1-(4-(3,4-dichlorophenyl)-5-(isopropylthio)thiazol-2-yl)-3-methyl-1H-pyrazole-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50 mg, 0.096 mmol), 2-(3-chloro-5-methoxyphenyl)-4,4,5,5-tetramethyl-1,3,2-dioxaborolane (32 mg, 0.12 mmol) and Na$_2$CO$_3$ (51 mg, 0.48 mmol) followed by the addition of the catalyst Pd(PPh$_3$)$_4$ (11 mg, 0.010 mmol). The reaction mixture was heated at 85° C. for 16 hours. Add LiOH (12 mg, 0.48 mmol) and the reaction mixture was stirred in the microwave at 110° C. for 10 min. Evaporated in vacuo. The crude product was purified by semi-prep HPLC-MS (column X-Bridge 30×50, eluted with 65-85% MeCN/NH$_4$CO$_2$H 10 mM, pH 3.8/Flow 45 ml/min/10 min) and afforded the title compound (16 mg, 0.028 mmol, 29%) as a yellow solid after lyophilization.

$^1$H NMR (500 MHz, DMSO) δ 8.23 (d, J=1.7 Hz, 1H), 8.04 (dd, J=8.4, 1.7 Hz, 1H), 7.73 (d, J=8.4 Hz, 1H), 7.13 (s, 1H), 7.05 (s, 1H), 7.02 (s, 1H), 3.80 (s, 3H), 3.38-3.32 (m, 1H), 2.30 (s, 3H), 1.23 (d, J=6.7 Hz, 6H). MS (m/z): 568.0 [M+1]$^+$.

Compound 146: 1-(4-(3,4-dichlorophenyl)-5-(isopropylthio)thiazol-2-yl)-4-(3-methoxy-5-(trifluoromethyl)phenyl)-3-methyl-1H-pyrazole-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50 mg, 0.096 mmol), 2-(3-methoxy-5-(trifluoromethyl)phenyl)-4,4,5,5-tetramethyl-1,3,2-dioxaborolane (36 mg, 0.12 mmol) and Na$_2$CO$_3$ (51 mg, 0.48 mmol) followed by the addition of the catalyst Pd(PPh$_3$)$_4$ (11 mg, 0.010 mmol). The reaction mixture was heated at 85° C. for 16 hours. Add LiOH (12 mg, 0.48 mmol) and the reaction mixture was stirred in the microwave at 110° C. for 10 min. Evaporated in vacuo. The crude product was purified by semi-prep HPLC-MS (column X-Bridge 30×50, eluted with 65-85% MeCN/NH$_4$CO$_2$H 10 mM, pH 3.8/Flow 45 ml/min/10 min) and afforded the title compound (15 mg, 0.024 mmol, 25%) as a yellow solid after lyophilization.

$^1$H NMR (500 MHz, DMSO) δ 8.20 (d, J=2.1 Hz, 1H), 8.02 (dd, J=8.5, 2.1 Hz, 1H), 7.76 (d, J=8.5 Hz, 1H), 7.38 (s, 1H), 7.35 (s, 1H), 7.28 (s, 1H), 3.88 (s, 3H), 3.40-3.32 (m, 1H), 2.33 (s, 3H), 1.24 (d, J=6.7 Hz, 6H). MS (m/z): 601.9 [M+1]$^+$.

Compound 147: 4-(3-chloro-5-methylphenyl)-1-(4-(3,4-dichlorophenyl)-5-(isopropylthio)thiazol-2-yl)-3-methyl-1H-pyrazole-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50 mg, 0.096 mmol), (3-chloro-5-methylphenyl)boronic acid (20 mg, 0.12 mmol) and Na$_2$CO$_3$ (51 mg, 0.48 mmol) followed by the addition of the catalyst Pd(PPh$_3$)$_4$ (11 mg, 0.010 mmol). The reaction mixture was heated at 85° C. for 16 hours. Add LiOH (12 mg, 0.48 mmol) and the reaction mixture was stirred in the microwave at 110° C. for 10 min. Add more LiOH (12 mg, 0.48 mmol) and stirring in the microwave at 110° C. was continued for 10 min. Evaporated in vacuo. The crude product was purified by semi-prep HPLC-MS (column X-Bridge 30×50, eluted with 70-90% MeCN/NH$_4$CO$_2$H 10 mM, pH 3.8/Flow 45 ml/min/10 min) and afforded the title compound (22 mg, 0.040 mmol, 42%) as a yellow solid after lyophilization.

$^1$H NMR (500 MHz, DMSO) δ 8.20 (d, J=2.1 Hz, 1H), 8.02 (dd, J=8.5, 2.1 Hz, 1H), 7.76 (d, J=8.5 Hz, 1H), 7.32 (s, 1H), 7.30 (s, 1H), 7.25 (s, 1H), 3.41-3.31 (m, 1H), 2.36 (s, 3H), 2.30 (s, 3H), 1.24 (d, J=6.7 Hz, 6H). MS (m/z): 552.0 [M+1]$^+$.

Compound 148: 4-(3,5-bis(trifluoromethyl)phenyl)-1-(4-(3,4-dichlorophenyl)-5-(isopropylthio)thiazol-2-yl)-3-methyl-N-(methylsulfonyl)-1H-pyrazole-5-carboxamide To a suspension of 4-(3,5-bis(trifluoromethyl)phenyl)-1-(4-(3,4-dichlorophenyl)-5-(isopropylthio)thiazol-2-yl)-3-methyl-1H-pyrazole-5-carboxylic acid (43 mg, 0.068 mmol), EDCl hydrochloride salt (20 mg, 0.10 mmol) and DMAP (18 mg, 0.15 mmol) in DCM (0.5 mL) was added methanesulfonamide (9.7 mg, 0.10 mmol). The reaction mixture was stirred at r.t. for 7 hours. More methanesulfonamide (14 mg, 0.15 mmol) was added and stirring was continued overnight. More EDCl hydrochloride salt (10 mg, 0.052 mmol) and methanesulfonamide (9.7 mg, 0.10 mmol) were added and stirring was continued another day. Evaporated in vacuo. The crude product was purified by semi-prep HPLC-MS (column X-Bridge 30×50, eluted with 55-75% MeCN/AmBicarb 10 mM, pH 10.0/Flow 45 ml/min/10 min) and afforded the title compound (7.1 mg, 0.010 mmol, 15%) as a yellow solid after lyophilization.

$^1$H NMR (500 MHz, DMSO) δ 8.26 (s, 1H), 8.18 (s, 2H), 8.15-8.06 (m, 2H), 7.70 (d, J=8.5 Hz, 1H), 7.33-7.28 (m, 1H), 3.43-3.31 (m, 1H), 2.92 (bs, 3H), 2.37 (s, 3H), 1.24 (d, J=6.7 Hz, 6H). MS (m/z): 717.1 [M+1]$^+$.

Compound 150: 4-(3,5-dichlorophenyl)-1-(4-(3,5-dichlorophenyl)-5-(isopropylthio)thiazol-2-yl)-3-methyl-1H-pyrazole-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (63 mg, 0.12 mmol), (3,5-dichlorophenyl)boronic acid (28 mg, 0.15 mmol) and Na$_2$CO$_3$ (64 mg, 0.61 mmol) followed by the addition of the catalyst Pd(PPh$_3$)$_4$ (14 mg, 0.012 mmol). The reaction mixture was heated at 85° C. for 16 hours. Add LiOH (15 mg, 0.61 mmol) and the reaction mixture was stirred in the microwave at 110° C. for 10 min. Evaporated in vacuo. The crude product was purified by semi-prep HPLC-MS (column X-Bridge 30×50, eluted with 70-90% MeCN/NH$_4$CO$_2$H 10 mM, pH 3.8/Flow 45 ml/min/10 min) and afforded the title compound (15 mg, 0.026 mmol, 21%) as a yellow solid after lyophilization.

$^1$H NMR (500 MHz, DMSO) δ 8.02-8.00 (m, 2H), 7.70-7.68 (m, 1H), 7.65-6.63 (m, 1H), 7.57-7.53 (m, 2H), 3.40-3.33 (m, 1H), 2.30 (s, 3H), 1.24 (d, J=6.7 Hz, 6H). MS (m/z): 571.9 [M+1]$^+$.

Compound 151: 1-(4-(3,4-dichlorophenyl)-5-(isopropylthio)thiazol-2-yl)-4-(3-fluorophenyl)-3-methyl-1H-pyrazole-5-carboxylic Acid Nitrogen was passed through a solution of dioxane/H$_2$O (4/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50 mg, 0.096 mmol), (3-fluorophenyl)boronic acid (16 mg, 0.12 mmol) and Na$_2$CO$_3$ (51 mg, 0.48 mmol) followed by the addition of the catalyst Pd(PPh$_3$)$_4$ (11 mg, 0.010 mmol). The reaction mixture was heated at 85° C. for 16 hours. Add LiOH (12 mg, 0.48 mmol) and the reaction mixture was stirred in the microwave at 110° C. for 10 min. Evaporated in vacuo. The crude product was purified by semi-prep HPLC-MS (column X-Bridge 30×50, eluted with 60-80% MeCN/NH$_4$CO$_2$H 10 mM, pH 3.8/Flow 45 ml/min/10 min) and afforded the title compound (19 mg, 0.037 mmol, 38%) as a yellow solid after lyophilization.

$^1$H NMR (500 MHz, DMSO) δ 8.21 (d, J=2.1 Hz, 1H), 8.02 (dd, J=8.5, 2.1 Hz, 1H), 7.74 (d, J=8.5 Hz, 1H), 7.53-7.47 (m, 1H), 7.36-7.30 (m, 2H), 7.25-7.18 (m, 1H), 3.38-3.33 (m, 1H), 2.31 (s, 3H), 1.24 (d, J=6.7 Hz, 6H). MS (m/z): 522.0 [M+1]$^+$.

Compound 152: 1-(4-(3,4-dichlorophenyl)-5-(isopropylthio)thiazol-2-yl)-4-(3-fluoro-5-hydroxyphenyl)-3-methyl-1H-pyrazole-5-carboxylic Acid Nitrogen was passed through a solution of dioxane/H$_2$O (4/1) and this solution (2.0 mL) was then added to a mixture of the (1-(4-(3,4-dichlorophenyl)-5-(isopropylthio)thiazol-2-yl)-5-(methoxycarbonyl)-3-methyl-1H-pyrazol-4-yl)boronic acid (50 mg, 0.10 mmol), 3-bromo-5-fluorophenol (23 mg, 0.12 mmol) and Na$_2$CO$_3$ (55 mg, 0.52 mmol) followed by the addition of the catalyst Pd(PPh$_3$)$_4$ (12 mg, 0.010 mmol). The reaction mixture was heated at 85° C. for 16 hours. Add LiOH (12 mg, 0.51 mmol) and the reaction mixture was stirred in the microwave at 110° C. for 15 min. Evaporated in vacuo. The crude product was purified by semi-prep HPLC-MS (column X-Bridge 30×50, eluted with 55-75% MeCN/NH$_4$CO$_2$H 10 mM, pH 3.8/Flow 45 ml/min/

10 min) and afforded the title compound (12 mg, 0.022 mmol, 21%) as a yellow solid after lyophilization.

$^1$H NMR (500 MHz, DMSO) δ 10.05 (s, 1H), 8.24 (d, J=2.1 Hz, 1H), 8.04 (dd, J=8.5, 2.1 Hz, 1H), 7.73 (d, J=8.5 Hz, 1H), 7.09 (bs, 1H), 6.80-6.73 (m, 2H), 6.56-6.49 (m, 1H), 3.39-3.31 (m, 1H), 2.28 (s, 3H), 1.23 (d, J=6.7 Hz, 6H). MS (m/z): 538.0 [M+1]$^+$.

Compound 154: 4-(3-chloro-5-hydroxyphenyl)-1-(4-(3,4-dichlorophenyl)-5-(isopropylthio)thiazol-2-yl)-3-methyl-1H-pyrazole-5-carboxylic Acid Nitrogen was passed through a solution of dioxane/H$_2$O (4/1) and this solution (2.0 mL) was then added to a mixture of the (1-(4-(3,4-dichlorophenyl)-5-(isopropylthio)thiazol-2-yl)-5-(methoxycarbonyl)-3-methyl-1H-pyrazol-4-yl)boronic acid (50 mg, 0.10 mmol), 3-bromo-5-chlorophenol (25 mg, 0.12 mmol) and Na$_2$CO$_3$ (55 mg, 0.52 mmol) followed by the addition of the catalyst Pd(PPh$_3$)$_4$ (12 mg, 0.010 mmol). The reaction mixture was heated at 85° C. for 16 hours. Diluted with EtOAc washed with water and brine. Dried MgSO$_4$, filtered and concentrated in vacuo. The product was purified by flash chromatography (dry packing) on silica gel using a gradient 0 to 30% EtOAc in hexanes to give 4-(3-chloro-5-methoxyphenyl)-1-(4-(3,4-dichlorophenyl)-5-(isopropylthio)thiazol-2-yl)-3-methyl-1H-pyrazole-5-carboxylic acid vv (24 mg, 0.042 mmol, 41%) as a yellow oil. Dissolved in a mixture of H$_2$O/THF/MeOH (6/3/1) (2.0 mL) and treated with LiOH (5.0 mg, 0.21 mmol). The reaction mixture was stirred in the microwave at 110° C. for 15 min. Evaporated in vacuo. The crude product was purified by semi-prep HPLC-MS (column X-Bridge 30×50, eluted with 60-80% MeCN/NH$_4$CO$_2$H 10 mM, pH 3.8/Flow 45 ml/min/10 min) and afforded the title compound (8.9 mg, 0.016 mmol, 16%) as a yellow solid after lyophilization.

$^1$H NMR (500 MHz, DMSO) δ 10.06 (s, 1H), 8.26 (d, J=2.1 Hz, 1H), 8.07 (dd, J=8.5, 2.1 Hz, 1H), 7.74 (d, J=8.5 Hz, 1H), 7.15 (bs, 1H), 7.01 (s, 1H), 6.88 (s, 1H), 6.76 (s, 1H), 3.42-3.34 (m, 1H), 2.27 (s, 3H), 1.24 (d, J=6.7 Hz, 6H). MS (m/z): 554.0 [M+1]$^+$.

Compound 155: 1-(4-(3,4-dichlorophenyl)-5-(isopropylthio)thiazol-2-yl)-3-methyl-4-(1-methyl-1H-indol-7-yl)-1H-pyrazole-5-carboxylic Acid Nitrogen was passed through a solution of dioxane/H$_2$O (4/1) and this solution (2.0 mL) was then added to a mixture of the (1-(4-(3,4-dichlorophenyl)-5-(isopropylthio)thiazol-2-yl)-5-(methoxycarbonyl)-3-methyl-1H-pyrazol-4-yl)boronic acid (50 mg, 0.10 mmol), 7-bromo-1-methyl-1H-indole (25 mg, 0.12 mmol) and Na$_2$CO$_3$ (55 mg, 0.52 mmol) followed by the addition of the catalyst Pd(PPh$_3$)$_4$ (12 mg, 0.010 mmol). The reaction mixture was heated at 85° C. for 16 hours. Add LiOH (12 mg, 0.51 mmol) and the reaction mixture was stirred in the microwave at 110° C. for 30 min. Evaporated in vacuo. The crude product was purified by semi-prep HPLC-MS (column X-Bridge 30×50, eluted with 65-85% MeCN/NH$_4$CO$_2$H 10 mM, pH 3.8/Flow 45 ml/min/10 min) and afforded the title compound (6.7 mg, 0.012 mmol, 12%) as a yellow solid after lyophilization.

$^1$H NMR (500 MHz, DMSO) δ 8.19 (d, J=2.1 Hz, 1H), 7.99 (dd, J=8.5, 2.1 Hz, 1H), 7.76 (d, J=8.5 Hz, 1H), 7.60 (d, J=7.2 Hz, 1H), 7.28 (d, J=3.1 Hz, 1H), 7.10-7.03 (m, 1H), 6.91 (dd, J=7.1, 0.9 Hz, 1H), 6.48 (d, J=3.1 Hz, 1H), 3.47 (s, 3H), 3.42-3.34 (m, 1H), 2.04 (s, 3H), 1.25 (d, J=6.7 Hz, 6H). MS (m/z): 557.0 [M+1]$^+$.

Compound 157: 1-(4-(2-chlorophenyl)-5-(isopropylthio)thiazol-2-yl)-4-(2,6-dimethylpyridin-4-yl)-3-methyl-1H-pyrazole-5-carboxylic Acid methyl 4-bromo-1-(4-(2-chlorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (97.9 mg, 0.215 mmol), the (2-chlorophenyl)boronic acid (33.6 mg, 0.215 mmol), K$_2$CO$_3$ (149 mg, 1.08 mmol) and THF (2 mL). Nitrogen was bubbled in the solvent for 10 minutes followed by the addition of the catalyst Pd(dtbpf)Cl$_2$ (10.8 mg, 0.02 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes and afforded the title compound (40.5 mg, 0.083 mmol, 38%) as a yellow oil.

methyl 1-(4-(2-chlorophenyl)-5-(isopropylthio)thiazol-2-yl)-4-(2,6-dimethylpyridin-4-yl)-3-methyl-1H-pyrazole-5-carboxylate Nitrogen was passed through a solution of dioxane/H$_2$O (4/1) and this solution (2.0 mL) was then added to a mixture of the methyl 4-bromo-1-(4-(2-chlorophenyl)-5-(isopropylthio)thiazol-2-yl)-3-methyl-1H-pyrazole-5-carboxylate (41 mg, 0.083 mmol), 2,6-dimethyl-4-(4,4,5,5-tetramethyl-1,3,2-dioxaborolan-2-yl)pyridine (47 mg, 0.20 mmol) and Na$_2$CO$_3$ (44 mg, 0.42 mmol) followed by the addition of the catalyst Pd(PPh$_3$)$_4$ (9.6 mg, 0.008 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes and afforded the title compound (23 mg, 0.044 mmol, 53%) as a yellow oil.

1-(4-(2-chlorophenyl)-5-(isopropylthio)thiazol-2-yl)-4-(2,6-dimethylpyridin-4-yl)-3-methyl-1H-pyrazole-5-carboxylic Acid The methyl 1-(4-(2-chlorophenyl)-5-(isopropylthio)thiazol-2-yl)-4-(2,6-dimethylpyridin-4-yl)-3-methyl-1H-pyrazole-5-carboxylate (23 mg, 0.045 mmol) was dissolved in a mixture of H$_2$O/THF/MeOH (6/3/1) (2.5 mL) and treated with LiOH (5.4 mg, 0.23 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/NH$_4$CO$_2$H 10 mM, pH 3.8/Flow 45 ml/min/10 min) and afforded the title compound (7.4 mg, 0.015 mmol, 33%) as a white solid after lyophilization.

$^1$H NMR (500 MHz, DMSO) δ 7.59-7.56 (m, 1H), 7.51-7.42 (m, 3H), 7.11 (s, 2H), 3.24-3.17 (m, 1H), 2.45 (s, 6H), 2.32 (s, 3H), 1.15 (d, J=6.7 Hz, 6H). MS (m/z): 499.3 [M+1]$^+$.

Compound 158: 1-(4-(3-chlorophenyl)-5-(isopropylthio)thiazol-2-yl)-4-(2,6-dimethylpyridin-4-yl)-3-methyl-1H-pyrazole-5-carboxylic Acid methyl 4-bromo-1-(4-(3-chlorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (97.9 mg, 0.215 mmol), the (3-chlorophenyl)boronic acid (33.6 mg, 0.215 mmol), $K_2CO_3$ (149 mg, 1.08 mmol) and THF (2 mL). Nitrogen was bubbled in the solvent for 10 minutes followed by the addition of the catalyst Pd(dtbpf)Cl$_2$ (10.8 mg, 0.02 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes and afforded the title compound (91 mg, 0.19 mmol, 85%) as a yellow oil.

methyl 1-(4-(3-chlorophenyl)-5-(isopropylthio)thiazol-2-yl)-4-(2,6-dimethylpyridin-4-yl)-3-methyl-1H-pyrazole-5-carboxylate Nitrogen was passed through a solution of dioxane/H$_2$O (4/1) and this solution (2.0 mL) was then added to a mixture of the methyl 4-bromo-1-(4-(3-chlorophenyl)-5-(isopropylthio)thiazol-2-yl)-3-methyl-1H-pyrazole-5-carboxylate (91.0 mg, 0.187 mmol), 2,6-dimethyl-4-(4,4,5,5-tetramethyl-1,3,2-dioxaborolan-2-yl)pyridine (105 mg, 0.45 mmol) and Na$_2$CO$_3$ (99 mg, 0.93 mmol) followed by the addition of the catalyst Pd(PPh$_3$)$_4$ (22 mg, 0.019 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes and afforded the title compound (15 mg, 0.028 mmol, 15%) as a yellow oil.

1-(4-(3-chlorophenyl)-5-(isopropylthio)thiazol-2-yl)-4-(2,6-dimethylpyridin-4-yl)-3-methyl-1H-pyrazole-5-carboxylic Acid The methyl 1-(4-(3-chlorophenyl)-5-(isopropylthio)thiazol-2-yl)-4-(2,6-dimethylpyridin-4-yl)-3-methyl-1H-pyrazole-5-carboxylate (15 mg, 0.029 mmol) was dissolved in a mixture of H$_2$O/THF/MeOH (6/3/1) (2.5 mL) and treated with LiOH (3.5 mg, 0.15 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/NH$_4$CO$_2$H 10 mM, pH 3.8/Flow 45 ml/min/10 min) and afforded the title compound (2.2 mg, 0.004 mmol, 15%) as a yellow solid after lyophilization.

$^1$H NMR (500 MHz, DMSO) δ 8.04-7.97 (m, 2H), 7.55-7.46 (m, 2H), 7.16 (s, 2H), 3.38-3.30 (m, 1H), 2.46 (s, 6H), 2.33 (s, 3H), 1.24 (d, J=6.7 Hz, 6H). MS (m/z): 499.4 [M+1]$^+$.

Compound 159: 1-(4-(4-chlorophenyl)-5-(isopropylthio)thiazol-2-yl)-4-(2,6-dimethylpyridin-4-yl)-3-methyl-1H-pyrazole-5-carboxylic Acid methyl 4-bromo-1-(4-(4-chlorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (97.9 mg, 0.215 mmol), the (4-chlorophenyl)boronic acid (33.6 mg, 0.215 mmol), K2CO3 (149 mg, 1.08 mmol) and THF (2 mL). Nitrogen was bubbled in the solvent for 10 minutes followed by the addition of the catalyst Pd(dtbpf)Cl2 (10.8 mg, 0.02 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes and afforded the title compound (86 mg, 0.18 mmol, 80%) as a yellow oil.

methyl 1-(4-(4-chlorophenyl)-5-(isopropylthio)thiazol-2-yl)-4-(2,6-dimethylpyridin-4-yl)-3-methyl-1H-pyrazole-5-carboxylate Nitrogen was passed through a solution of dioxane/H$_2$O (4/1) and this solution (2.0 mL) was then added to a mixture of the methyl 4-bromo-1-(4-(4-chlorophenyl)-5-(isopropylthio)thiazol-2-yl)-3-methyl-1H-pyrazole-5-carboxylate (85.6 mg, 0.176 mmol), 2,6-dimethyl-4-(4,4,5,5-tetramethyl-1,3,2-dioxaborolan-2-yl)pyridine (98 mg, 0.42 mmol) and Na$_2$CO$_3$ (93 mg, 0.88 mmol) followed by the addition of the catalyst Pd(PPh$_3$)$_4$ (20 mg, 0.018 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes and afforded the title compound (54 mg, 0.11 mmol, 60%) as a yellow oil.

1-(4-(4-chlorophenyl)-5-(isopropylthio)thiazol-2-yl)-4-(2,6-dimethylpyridin-4-yl)-3-methyl-1H-pyrazole-5-carboxylic Acid The methyl methyl 1-(4-(4-chlorophenyl)-5-(isopropylthio)thiazol-2-yl)-4-(2,6-dimethylpyridin-4-yl)-3-methyl-1H-pyrazole-5-carboxylate (54 mg, 0.11 mmol) was dissolved in a mixture of H$_2$O/THF/MeOH (6/3/1) (2.5 mL) and treated with LiOH (12.6 mg, 0.525 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/NH$_4$CO$_2$H 10 mM, pH 3.8/Flow 45 ml/min/ 10 min) and afforded the title compound (11.5 mg, 0.023 mmol, 22%) as a yellow solid after lyophilization.

$^1$H NMR (500 MHz, DMSO) δ 8.06-8.01 (m, 2H), 7.55-7.51 (m, 2H), 7.15 (s, 2H), 3.38-3.29 (m, 1H), 2.45 (s, 6H), 2.32 (s, 3H), 1.23 (d, J=6.7 Hz, 6H). MS (m/z): 499.4 [M+1]$^+$.

Compound 160: 1-(4-(2,4-dichlorophenyl)-5-(isopropylthio)thiazol-2-yl)-4-(2,6-dimethylpyridin-4-yl)-3-methyl-1H-pyrazole-5-carboxylic Acid methyl 4-bromo-1-(4-(2,4-dichlorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (97.9 mg, 0.215 mmol), the (2,4-dichlorophenyl)boronic acid (41 mg, 0.22 mmol), K$_2$CO$_3$ (149 mg, 1.08 mmol) and THF (2 mL). Nitrogen was bubbled in the solvent for 10 minutes followed by the addition of the catalyst Pd(dtbpf)Cl$_2$ (10.8 mg, 0.02 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes and afforded the title compound (91 mg, 0.17 mmol, 79%) as a yellow oil.

methyl 1-(4-(2,4-dichlorophenyl)-5-(isopropylthio) thiazol-2-yl)-4-(2,6-dimethylpyridin-4-yl)-3-methyl-1H-pyrazole-5-carboxylate Nitrogen was passed through a solution of dioxane/$H_2O$ (4/1) and this solution (2.0 mL) was then added to a mixture of the methyl 4-bromo-1-(4-(2,4-dichlorophenyl)-5-(isopropylthio)thiazol-2-yl)-3-methyl-1H-pyrazole-5-carboxylate (90.7 mg, 0.174 mmol), 2,6-dimethyl-4-(4,4,5,5-tetramethyl-1,3,2-dioxaborolan-2-yl)pyridine (97 mg, 0.42 mmol) and $Na_2CO_3$ (92 mg, 0.87 mmol) followed by the addition of the catalyst $Pd(PPh_3)_4$ (20 mg, 0.017 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes and afforded the title compound (58 mg, 0.11 mmol, 61%) as a yellow oil.

1-(4-(2,4-dichlorophenyl)-5-(isopropylthio)thiazol-2-yl)-4-(2,6-dimethylpyridin-4-yl)-3-methyl-1H-pyrazole-5-carboxylic Acid The methyl 1-(4-(2,4-dichlorophenyl)-5-(isopropylthio) thiazol-2-yl)-4-(2,6-dimethylpyridin-4-yl)-3-methyl-1H-pyrazole-5-carboxylate (58 mg, 0.11 mmol) was dissolved in a mixture of $H_2O$/THF/MeOH (6/3/1) (2.5 mL) and treated with LiOH (12.7 mg, 0.530 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/$NH_4CO_2H$ 10 mM, pH 3.8/Flow 45 ml/min/ 10 min) and afforded the title compound (8.9 mg, 0.017 mmol, 16%) as a yellow solid after lyophilization.

$^1$H NMR (500 MHz, DMSO) δ 7.77 (d, J=2.1 Hz, 1H), 7.55 (dd, J=8.3, 2.1 Hz, 1H), 7.49 (d, J=8.3 Hz, 1H), 7.12 (s, 2H), 3.25-3.16 (m, 1H), 2.44 (s, 6H), 2.31 (s, 3H), 1.15 (d, J=6.7 Hz, 6H). MS (m/z): 533.4 [M+1]$^+$.

Compound 164: 1-(4-(3,4-dichlorophenyl)-5-(isopropylthio)thiazol-2-yl)-4-(3-fluoro-5-methoxyphenyl)-3-methyl-1H-pyrazole-5-carboxylic Acid

1-(4-(3,4-dichlorophenyl)-5-(isopropylthio)thiazol-2-yl)-4-(3-fluoro-5-methoxyphenyl)-3-methyl-1H-pyrazole-5-carboxylic Acid A solution of 1-(4-(3,4-dichlorophenyl)-5-(isopropylthio) thiazol-2-yl)-5-(methoxycarbonyl)-3-methyl-1H-pyrazol-4-ylboronic acid (41 mg, 0.083 mmol), 1-bromo-3-fluoro-5-methoxybenzene (20 mg, 0.10 mmol), $Pd(PPh_3)_4$ (10 mg, 0.0083 mmol), $Na_2CO_3$ (44 mg, 0.42 mmol) in degassed 1,4-dioxane and $H_2O$ (4:1, 1.7 mL) was heated at 85° C. for 18 hours. LiOH (10 mg, 0.42 mmol) was added and the reaction was heated at 95° C. under microwave radiation for 30 min. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (60 to 80%). The product was lyophilised to give the title compound (16 mg, 0.028 mmol, 34%) as a pale yellow solid.

$^1$H NMR (500 MHz, DMSO) δ 8.21 (d, J=1.8 Hz, 1H), 8.03 (dd, J=8.5, 1.8 Hz, 1H), 7.75 (d, J=8.5 Hz, 1H), 6.94-6.89 (m, 2H), 6.86 (d, J=11.5 Hz, 1H), 3.80 (s, 3H), 3.35 (sept, J=6.7 Hz, 1H), 2.32 (s, 3H), 1.24 (d, J=6.7 Hz, 6H); MS (m/z): 552.1 [M+1]$^+$.

Compound 165: 1-(4-(3,4-dichlorophenyl)-5-(isopropylthio)thiazol-2-yl)-4-(3-methoxy-5-methylphenyl)-3-methyl-1H-pyrazole-5-carboxylic Acid A solution of 1-(4-(3,4-dichlorophenyl)-5-(isopropylthio) thiazol-2-yl)-5-(methoxycarbonyl)-3-methyl-1H-pyrazol-4-ylboronic acid (41 mg, 0.083 mmol), 1-bromo-3-methoxy-5-methylbenzene (20 mg, 0.10 mmol), $Pd(PPh_3)_4$ (10 mg, 0.0083 mmol), $Na_2CO_3$ (44 mg, 0.42 mmol) in degassed 1,4-dioxane and $H_2O$ (4:1, 1.7 mL) was heated at 85° C. for 18 hours. LiOH (10 mg, 0.42 mmol) was added and the reaction was heated at 95° C. under microwave radiation for 1 h. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (60 to 80%). The product was lyophilised to give the title compound (1.8 mg, 0.0033 mmol, 7%) as a pale yellow solid.

$^1$H NMR (500 MHz, DMSO) δ 8.24 (s, 1H), 8.09-8.03 (m, 1H), 7.74 (d, J=8.5 Hz, 1H), 6.91-6.85 (m, 2H), 6.74 (s, 1H), 3.75 (s, 3H), 3.33 (sept, J=6.7 Hz, 1H), 2.31 (s, 3H), 2.29 (s, 3H), 1.24 (d, J=6.7 Hz, 6H); MS (m/z): 548.1 [M+1]$^+$.

Compound 167: 1-(4-(3,4-dichlorophenyl)-5-(isopropylthio)thiazol-2-yl)-3-methyl-4-(2-methylpyridin-4-yl)-1H-pyrazole-5-carboxylic Acid methyl 1-(4-(3,4-dichlorophenyl)-5-(isopropylthio) thiazol-2-yl)-3-methyl-4-(2-methylpyridin-4-yl)-1H-pyrazole-5-carboxylate A solution of 1-(4-(3,4-dichlorophenyl)-5-(isopropylthio) thiazol-2-yl)-5-(methoxycarbonyl)-3-methyl-1H-pyrazol-4-ylboronic acid (41 mg, 0.083 mmol), 4-bromo-2-methylpyridine (17 mg, 0.10 mmol), $Pd(PPh_3)_4$ (10 mg, 0.0083 mmol), $Na_2CO_3$ (44 mg, 0.42 mmol) in degassed 1,4-dioxane and $H_2O$ (4:1, 1.7 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (10 to 40%) to give the title compound (18 mg, 0.034 mmol, 41%) as a pale yellow solid.

1-(4-(3,4-dichlorophenyl)-5-(isopropylthio)thiazol-2-yl)-3-methyl-4-(2-methylpyridin-4-yl)-1H-pyrazole-5-carboxylic Acid Methyl 1-(4-(3,4-dichlorophenyl)-5-(isopropylthio)thiazol-2-yl)-3-methyl-4-(2-methylpyridin-4-yl)-1H-pyrazole-5-carboxylate (18 mg, 0.034 mmol) was diluted in a 1:1 solution of THF and MeOH (0.34 mL). 1M NaOH (0.067 mL, 0.067 mmol) was added and the reaction was stirred for 3 days at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of ammonium formate) (30 to 70%). The product was lyophilysed to give the title compound (11 mg, 0.022 mmol, 65%) as a pale yellow solid.

$^1$H NMR (500 MHz, DMSO) δ 8.52 (d, J=5.2 Hz, 1H), 8.20 (d, J=2.1 Hz, 1H), 8.01 (dd, J=8.5, 2.1 Hz, 1H), 7.77 (d, J=8.5 Hz, 1H), 7.35 (s, 1H), 7.30-7.26 (m, 1H), 3.35 (sept, J=6.7 Hz, 1H), 2.52 (s, 3H), 2.34 (s, 3H), 1.24 (d, J=6.7 Hz, 6H); MS (m/z): 519.0 [M+1]$^+$.

Compound 172: 4-cyclopropyl-1-(4-cyclopropyl-5-(isopropylthio)thiazol-2-yl)-3-methyl-1H-pyrazole-5-carboxylic Acid methyl 4-cyclopropyl-1-(4-cyclopropyl-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100.0 mg, 0.220 mmol), potassium cyclopropyltrifluoroborate (97.5 mg, 0.659 mmol), Cs$_2$CO$_3$ (214 mg, 0.659 mmol), Pd(OAc)$_2$ (4.93 mg, 0.022 mmol) and Butyldi-1-adamantylphosphine (15.8 mg, 0.044 mmol), nitrogen and vacuum cycles were performed (2×). A solution of Toluene/water was added (3 mL, 2:1) and nitrogen gas was bubbled through the reaction mixture for 10 min. The vial was capped and placed in an oil bath at 100° C. for 16 h. EtOAc and water were added and the aqueous layer was extracted with EtOAc (2×), dried over Na$_2$SO$_4$, filtered and concentrated under vacuum. The crude product was purified by flash chromatography on silica gel (wet loading) using a solution of DCM in hexanes (10 to 50% gradient) to give the title compound (60.6 mg, 0.161 mmol, 73%) as yellow oil.

4-cyclopropyl-1-(4-cyclopropyl-5-(isopropylthio)thiazol-2-yl)-3-methyl-1H-pyrazole-5-carboxylic Acid Into a 25 mL round bottom flask, methyl 4-cyclopropyl-1-(4-cyclopropyl-5-(isopropylthio)thiazol-2-yl)-3-methyl-1H-pyrazole-5-carboxylate (60.6 mg, 0.161 mmol) was diluted with THF/MeOH (2 mL, 1:1). A solution of NaOH 1 M (321 μL, 0.321 mmol) was added and the reaction was stirred 16 h at rt. The reaction mixture was acidified with HCl 1 M and the crude product was concentrated under vacuum. The product was purified using a semi prep HPLC-MS (column X-Bridge 30×50, eluted with 25-45% MeCN/NH$_4$CO$_3$H 10 mM, pH 3.8/Flow 45 ml/min/11 min), resulting in the title compound (15.0 mg, 0.041 mmol, 26%) as white solid after lyophilisation.

$^1$H NMR (500 MHz, MeOD) δ 3.15 (hept, J=6.7 Hz, 1H), 2.33 (tt, J=8.2, 4.9 Hz, 1H), 2.28 (s, 3H), 1.65 (tt, J=8.5, 5.4 Hz, 1H), 1.29 (d, J=6.7 Hz, 6H), 0.97 (ddd, J=7.8, 4.9, 2.5 Hz, 2H), 0.94-0.89 (m, 2H), 0.85 (ddd, J=8.5, 6.2, 4.2 Hz, 2H), 0.71-0.66 (m, 2H); MS (m/z): 364.3 [M+1]$^+$.

Compound 173: 4-cyclopropyl-1-(4-(3,4-dichlorophenyl)-5-(isopropylthio)thiazol-2-yl)-3-methyl-1H-pyrazole-5-carboxylic Acid 4-cyclopropyl-1-(4-(3,4-dichlorophenyl)-5-(isopropylthio)thiazol-2-yl)-3-methyl-1H-pyrazole-5-carboxylic Acid Nitrogene was passed through a solution of toluene/H$_2$O (2/1) and this solution (2.0 mL) was then added to a mixture of the methyl 4-bromo-1-(4-(3,4-dichlorophenyl)-5-(isopropylthio)thiazol-2-yl)-3-methyl-1H-pyrazole-5-carboxylate (50 mg, 0.096 mmol), potassium cyclopropyltrifluoroborate (43 mg, 0.29 mmol) and Cs$_2$CO$_3$ (94 mg, 0.29 mmol) followed by the addition of the ligand butyldi-1-adamantylphosphine (3 mg, 0.01 mmol) and the catalyst Pd(OAc)$_2$ (1 mg, 0.005 mmol). The reaction mixture was heated at 90° C. for 16 hours. Diluted with EtOAc washed with water and brine. Dried MgSO4, filtered and concentrated in vacuo. The residue was dissolved in a mixture of H$_2$O/THF/MeOH (6/3/1) (2.0 mL) and treated with LiOH (12 mg, 0.48 mmol). The reaction mixture was stirred in the microwave at 110° C. for 10 min. Evaporated in vacuo. The crude product was purified by semi-prep HPLC-MS (column X-Bridge 30×50, eluted with 60-80% MeCN/NH$_4$CO$_2$H 10 mM, pH 3.8/Flow 45 ml/min/10 min) and afforded the title compound (6.2 mg, 0.013 mmol, 14%) as a yellow solid after lyophilisation.

$^1$H NMR (500 MHz, DMSO) δ 8.18 (d, J=2.1 Hz, 1H), 8.00 (dd, J=8.5, 2.1 Hz, 1H), 7.74 (d, J=8.5 Hz, 1H), 3.36-3.25 (m, 1H), 2.26 (s, 3H), 1.70-1.63 (m, 1H), 1.22 (d, J=6.7 Hz, 6H), 0.88-0.79 (m, 2H), 0.69-0.61 (m, 2H). MS (m/z): 468.1 [M+1]+.

Compound 174: 4-(3-chloro-5-isopropoxyphenyl)-1-(4-(3,4-dichlorophenyl)-5-(isopropylthio)thiazol-2-yl)-3-methyl-1H-pyrazole-5-carboxylic Acid 1-bromo-3-chloro-5-isopropoxybenzene 2-iodopropane (90 μL, 1.5 mmol) was added to a mixture of 3-bromo-5-chlorophenol (200 mg, 0.964 mmol) and potassium carbonate (213 mg, 1.54 mmol) in DMF (1 mL). The reaction mixture was stirred at rt for 18 h. Water and ethyl acetate were added. The phases were separated the organic layer was washed with 1N NaOH (2×), dried with sodium sulfate, filtered and evaporated under reduced pressure to give the title compound (219 mg, 0.878 mmol, 91%).

methyl 4-(3-chloro-5-isopropoxyphenyl)-1-(4-(3,4-dichlorophenyl)-5-(isopropylthio)thiazol-2-yl)-3-methyl-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 1-bromo-3-chloro-5-isopropoxybenzene (31 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2%) to give the title compound (49 mg, 0.080 mmol, 78%) as a pale yellow oil.

4-(3-chloro-5-isopropoxyphenyl)-1-(4-(3,4-dichlorophenyl)-5-(isopropylthio)thiazol-2-yl)-3-methyl-1H-pyrazole-5-carboxylic Acid methyl 4-(3-chloro-5-isopropoxyphenyl)-1-(4-(3,4-dichlorophenyl)-5-(isopropylthio)thiazol-2-yl)-3-methyl-1H-pyrazole-5-carboxylate (49 mg, 0.080 mmol) was diluted in a 1:1 solution of THF and MeOH (0.80 mL). 1M NaOH (0.16 mL, 0.16 mmol) was added and the reaction was stirred for 3 days at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of ammonium formate) (30 to 100%). The product was lyophilysed to give the title compound (10 mg, 0.017 mmol, 21%) as a pale yellow solid.

$^1$H NMR (500 MHz, DMSO) δ 8.22 (s, 1H), 8.04 (d, J=8.4 Hz, 1H), 7.74 (d, J=8.5 Hz, 1H), 7.08 (s, 1H), 6.99 (s, 2H), 4.67 (d, J=6.0 Hz, 1H), 3.35 (sept, J—6.7 Hz, 1H), 2.30 (s, 3H), 1.29 (d, J=6.0 Hz, 6H), 1.24 (d, J=6.7 Hz, 6H); MS (m/z): 596.0 [M+1]$^+$.

Compound 175: 443-chloro-5-(2-methoxyethoxy) phenyl)-1-(4-(3,4-dichlorophenyl)-5-(isopropylthio) thiazol-2-yl)-3-methyl-1H-pyrazole-5-carboxylic Acid 1-bromo-3-chloro-5-(2-methoxyethoxy)benzene 1-bromo-2-methoxyethane (136 μL, 1.45 mmol) was added to a mixture of 3-bromo-5-chlorophenol (200 mg, 0.964 mmol), potassium iodide (240 mg, 1.45 mmol) and potassium carbonate (213 mg, 1.54 mmol) in DMF (1 mL). The reaction mixture was stirred at 100° C. for 18 h. Water and ethyl acetate were added. The phases were separated the organic layer was washed with 1N NaOH (2×), dried with sodium sulfate, filtered and evaporated under reduced pressure to give the title compound (170 mg, 0.67 mmol, 70%).

methyl 4-(3-chloro-5-(2-methoxyethoxy)phenyl)-1-(4-(3,4-dichlorophenyl)-5-(isopropylthio)thiazol-2-yl)-3-methyl-1H-pyrazole-5-carboxylate A solution of 1-(4-(3,4-dichlorophenyl)-5-(isopropylthio) thiazol-2-yl)-5-(methoxycarbonyl)-3-methyl-1H-pyrazol-4-ylboronic acid (50 mg, 0.10 mmol), 1-bromo-3-chloro-5-(2-methoxyethoxy)benzene (33 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (10 to 20%) to give the title compound (23 mg, 0.037 mmol, 36%) as a pale yellow oil.

4-(3-chloro-5-(2-methoxyethoxy)phenyl)-1-(4-(3,4-dichlorophenyl)-5-(isopropylthio)thiazol-2-yl)-3-methyl-1H-pyrazole-5-carboxylic Acid methyl 4-(3-chloro-5-(2-methoxyethoxy)phenyl)-1-(4-(3, 4-dichlorophenyl)-5-(isopropylthio)thiazol-2-yl)-3-methyl-1H-pyrazole-5-carboxylate (23 mg, 0.037 mmol) was diluted in a 1:1 solution of THF and MeOH (0.37 mL). 1M NaOH (0.073 mL, 0.073 mmol) was added and the reaction was stirred for 3 days at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of ammonium formate) (30 to 70%). The product was lyophilysed to give the title compound (10 mg, 0.016 mmol, 45%) as a pale yellow solid.

$^1$H NMR (500 MHz, DMSO) δ 8.24 (s, 1H), 8.06 (d, J=8.2 Hz, 1H), 7.74 (d, J=8.5 Hz, 1H), 7.15 (s, 1H), 7.07 (s, 1H), 7.01 (s, 1H), 4.16-4.12 (m, 2H), 3.68-3.65 (m, 2H), 3.35 (sept, J=6.7 Hz, 1H), 3.31 (s, 3H), 2.30 (s, 3H), 1.23 (d, J=6.7 Hz, 6H); MS (m/z): 611.9 [M+1]$^+$.

Compound 176: 1-(4-(3-chlorophenyl)-5-(isopropylthio)thiazol-2-yl)-4-(3-fluorophenyl)-3-methyl-1H-pyrazole-5-carboxylic Acid methyl 4-bromo-1-(4-(3-chlorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (97.9 mg, 0.215 mmol), (3-chlorophenyl)boronic acid (33.6 mg, 0.215 mmol) and K$_2$CO$_3$ (149 mg, 1.08 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (11 mg, 0.017 mmol). The vial was capped and placed in an oil bath at 90° C. for 16 h. The solvent was evaporated under vacuum and the crude product was purified by flash chromatography on silica gel using a solution of EtOAc in hexanes (0 to 10% gradient) and afforded the title compound (26 mg, 0.053 mmol, 24%) as yellow oil.

1-(4-(3-chlorophenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-(3-chlorophenyl)-5-(isopropylthio)thiazol-2-yl)-3-methyl-1H-pyrazole-5-carboxylate (26 mg, 0.053 mmol), (3-fluorophenyl)boronic acid (9.0 mg, 0.064 mmol) and Na$_2$CO$_3$ (28 mg, 0.27 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (6.2 mg, 0.0054 mmol). The vial was capped and placed in an oil bath at 85° C. for 16 h. LiOH (6.3 mg, 0.27 mmol) was added to the reaction mixture and stirred under microwave radiation at 110° C. for 30 min. The solvent was evaporated under vacuum and the product was purified using a semi prep HPLC-MS (column X-Bridge 30×50, eluted with 60-80% MeCN/NH$_4$CO$_2$H 10 mM, pH 3.8/Flow 45 ml/min/10 min), resulting in the title compound (2.8 mg, 0.0057 mmol, 11%) as yellow solid after lyophilization.

$^1$H NMR (500 MHz, DMSO) δ 8.04-8.01 (m, 1H), 8.00-7.96 (m, 1H), 7.55-7.46 (m, 3H), 7.39-7.30 (m, 2H), 7.25-7.16 (m, 1H), 3.40-3.29 (m, 1H), 2.31 (s, 3H), 1.23 (d, J=6.7 Hz, 6H). MS (m/z): 488.1 [M+1]$^+$.

Compound 177: 1-(4-(4-chlorophenyl)-5-(isopropylthio)thiazol-2-yl)-4-(3-fluorophenyl)-3-methyl-1H-pyrazole-5-carboxylic Acid methyl 4-bromo-1-(4-(4-chlorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (97.9 mg, 0.215 mmol), (4-chlorophenyl)boronic acid (33.6 mg, 0.215 mmol) and $K_2CO_3$ (149 mg, 1.08 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (11 mg, 0.017 mmol). The vial was capped and placed in an oil bath at 90° C. for 16 h. The solvent was evaporated under vacuum and the crude product was purified by flash chromatography on silica gel using a solution of EtOAc in hexanes (0 to 10% gradient) and afforded the title compound (54 mg, 0.11 mmol, 50%) as yellow oil.

1-(4-(4-chlorophenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-(4-chlorophenyl)-5-(isopropylthio)thiazol-2-yl)-3-methyl-1H-pyrazole-5-carboxylate (54 mg, 0.11 mmol), (3-fluorophenyl)boronic acid (18 mg, 0.13 mmol) and $Na_2CO_3$ (59 mg, 0.55 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (13 mg, 0.011 mmol). The vial was capped and placed in an oil bath at 85° C. for 16 h. LiOH (13 mg, 0.56 mmol) was added to the reaction mixture and stirred under microwave radiation at 110° C. for 15 min. The solvent was evaporated under vacuum and the product was purified using a semi prep HPLC-MS (column X-Bridge 30×50, eluted with 60-80% MeCN/NH$_4$CO$_2$H 10 mM, pH 3.8/Flow 45 ml/min/10 min), resulting in the title compound (8.4 mg, 0.017 mmol, 16%) as yellow solid after lyophilization.
$^1$H NMR (500 MHz, DMSO) δ 8.06-8.02 (m, 2H), 7.56-7.47 (m, 3H), 7.37-7.30 (m, 2H), 7.24-7.17 (m, 1H), 3.36-3.27 (m, 1H), 2.31 (s, 3H), 1.23 (d, J=6.7 Hz, 6H). MS (m/z): 488.1 [M+1]$^+$.

Compound 178: 1-(4-(2,4-dichlorophenyl)-5-(isopropylthio)thiazol-2-yl)-4-(3-fluorophenyl)-3-methyl-1H-pyrazole-5-carboxylic Acid methyl 4-bromo-1-(4-(2,4-dichlorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (97.9 mg, 0.215 mmol), (2,4-dichlorophenyl)boronic acid (41.0 mg, 0.215 mmol) and $K_2CO_3$ (149 mg, 1.08 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (11 mg, 0.017 mmol). The vial was capped and placed in an oil bath at 90° C. for 16 h. The solvent was evaporated under vacuum and the crude product was purified by flash chromatography on silica gel using a solution of EtOAc in hexanes (0 to 10% gradient) and afforded the title compound (54 mg, 0.10 mmol, 47%) as yellow oil.

1-(4-(2,4-dichlorophenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-(2,4-dichlorophenyl)-5-(isopropylthio)thiazol-2-yl)-3-methyl-1H-pyrazole-5-carboxylate (54 mg, 0.10 mmol), (3-fluorophenyl)boronic acid (17 mg, 0.12 mmol) and $Na_2CO_3$ (55 mg, 0.51 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (12 mg, 0.010 mmol). The vial was capped and placed in an oil bath at 85° C. for 16 h. LiOH (12 mg, 0.52 mmol) was added to the reaction mixture and stirred under microwave radiation at 110° C. for 15 min. The solvent was evaporated under vacuum and the product was purified using a semi prep HPLC-MS (column X-Bridge 30×50, eluted with 60-80% MeCN/NH$_4$CO$_2$H 10 mM, pH 3.8/Flow 45 ml/min/10 min), resulting in the title compound (8.0 mg, 0.015 mmol, 15%) as yellow solid after lyophilization.
$^1$H NMR (500 MHz, DMSO) δ 7.77 (d, J=2.1 Hz, 1H), 7.55 (dd, J=8.3, 2.1 Hz, 1H), 7.52-7.45 (m, 2H), 7.34-7.27 (m, 2H), 7.22-7.15 (m, 1H), 3.25-3.15 (m, 1H), 2.30 (s, 3H), 1.15 (d, J=6.7 Hz, 6H). MS (m/z): 522.0 [M+1]$^+$.

Compound 179: 4-bromo-1-(4-(6-(3-fluorophenyl)pyridin-3-yl)-5-(isopropylthio)thiazol-2-yl)-3-methyl-1H-pyrazole-5-carboxylic Acid methyl 4-bromo-1-(4-(6-chloropyridin-3-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), (6-chloropyridin-3-yl)boronic acid (34.6 mg, 0.220 mmol) and $K_2CO_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (14.3 mg, 0.022 mmol). The vial was capped and placed in an oil bath at 90° C. for 16 h. The solvent was evaporated under vacuum and the crude product was purified by flash chromatography on silica gel (wet loading) using a solution of EtOAc in hexanes (2 to 10% gradient) and afforded the title compound (39.0 mg, 0.080 mmol, 36%) as yellow oil.

4-bromo-1-(4-(6-(3-fluorophenyl)pyridin-3-yl)-5-(isopropylthio)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(4-(6-chloropyridin-3-yl)-5-(isopropylthio)thiazol-2-yl)-3-methyl-1H-pyrazole-5-carboxylate (39.0 mg, 0.080 mmol), 3-fluorophenylboronic acid (13.4 mg, 0.096 mmol) and $Na_2CO_3$ (42.4 mg, 0.4 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (9.24 mg, 0.008 mmol). The vial was capped and placed in an oil bath at 85° C. for 16 h. LiOH (16.8 mg, 0.400 mmol) was added to the reaction mixture and stirred under microwave radiation at 100° C. for 10 min. The product was purified using a semi prep HPLC-MS (column X-Bridge 30×50, eluted with 40-60% MeCN/NH$_4$CO$_2$H 10 mM, pH 3.8/Flow 45 ml/min/11 min), resulting in the title compound (5.65 mg, 0.011 mmol, 13%) as white solid after lyophilisation.

$^1$H NMR (500 MHz, DMSO) δ 9.29 (d, J=1.9 Hz, 1H), 8.50 (dd, J=8.3, 2.3 Hz, 1H), 8.20-8.11 (m, 1H), 8.03 (d, J=7.9 Hz, 1H), 7.98 (d, J=10.2 Hz, 1H), 7.57 (dd, J=14.1, 8.1 Hz, 1H), 7.30 (td, J=8.4, 2.0 Hz, 1H), 3.37-3.29 (m, 1H), 2.21 (s, 3H), 1.24 (d, J=6.7 Hz, 6H); MS (m/z): 533.1 [M+1]$^+$.

Compound 180: (R)-1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylic Acid 4-bromo-6-methylpyridin-2-ol 4-hydroxy-6-methylpyridin-2(1H)-one (500 mg, 4.00 mmol) was mixed with phosphoryl bromide (881 mg, 3.07 mmol) and DMF (1.8 mL) was added. The reaction mixture was heated at 110° C. After 5 min, more DMF (1.8 mL) was added and the reaction was heated at 110° C. for 1 h. The reaction was cooled down and ice cold water was carefully added, followed by solid sodium bicarbonate until pH reached 7. The precipitate was filtered, rinsed with cold water and let dry under air to give the title compound (520 mg, 2.77 mmol, 90%).

(R)-4-bromo-2-methyl-6-((tetrahydrofuran-3-yl)oxy)pyridine

Diisopropyl diazocarboxylate (242 mg, 1.20 mmol) was added to a solution of 4-bromo-6-methylpyridin-2-ol (150 mg, 0.798 mmol), (S)-tetrahydrofuran-3-ol (88 mg, 0.997 mmol) and triphenylphosphine (314 mg, 1.20 mmol) in THF (3.5 mL). The reaction mixture was stirred at r.t. for 18 h. The mixture was concentrated to dryness and purified by flash chromatography on silica gel using a solution of ethyl acetate in hexanes (40%) to give the title compound (44 mg, 0.17 mmol, 21%) as a pale yellow oil.

(R)-methyl 1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), (R)-4-bromo-2-methyl-6-((tetrahydrofuran-3-yl)oxy)pyridine (32 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (10 to 40%) to give the title compound (10 mg, 0.017 mmol, 16%) as a pale yellow oil.

(R)-1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylic Acid (R)-methyl 1-(4-(3,4-dichlorophenyl)-5-(isopropylthio)thiazol-2-yl)-3-methyl-4-(2-methyl-6-((tetrahydrofuran-3-yl)oxy)pyridin-4-yl)-1H-pyrazole-5-carboxylate (10 mg, 0.017 mmol) was diluted in a 1:1 solution of THF and MeOH (0.17 mL). 1M NaOH (0.034 mL, 0.034 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by reverse chromatography on C-18 column using a solution of MeCN in water (containing 10 mM of ammonium formate) (30 to 70%). The product was lyophilysed to give the title compound (1.8 mg, 0.0030 mmol, 18%) as a pale yellow solid.

$^1$H NMR (500 MHz, DMSO) δ 8.22 (s, 1H), 8.04 (d, J=8.3 Hz, 1H), 7.76 (d, J=8.5 Hz, 1H), 6.97 (s, 1H), 6.72 (s, 1H), 5.53-5.48 (m, 1H), 3.93 (dd, J=10.2, 4.8 Hz, 1H), 3.89-3.82 (m, 1H), 3.80-3.73 (m, 2H), 3.35 (hept, J=6.7 Hz, 1H), 2.41 (s, 3H), 2.33 (s, 3H), 2.29-2.18 (m, 1H), 2.06-1.98 (m, 1H), 1.24 (d, J=6.7 Hz, 6H); MS (m/z): 605.2 [M+1]$^+$.

Compound 181: 1-(4-(3,4-dichlorophenyl)-5-(isopropylthio)thiazol-2-yl)-4-(2-(2-methoxyethoxy)-6-methylpyridin-4-yl)-3-methyl-1H-pyrazole-5-carboxylic Acid 4-bromo-2-(2-methoxyethoxy)-6-methylpyridine Diisopropyl diazocarboxylate (161 mg, 0.798 mmol) was added to a solution of 4-bromo-6-methylpyridin-2-ol (100 mg, 0.532 mmol), 2-methoxyethanol (52 μL, 0.67 mmol) and triphenylphosphine (209 mg, 0.798 mmol) in THF (2.3 mL). The reaction mixture was stirred at r.t. for 18 h. Some methanol was added, followed by water. The mixture was extracted with ethyl acetate (3×) and the combined organic layers were dried with sodium sulfate, filtered and evaporated. The crude product was purified by flash chromatography on silica gel using a solution of ethyl acetate in hexanes to give the title compound (82 mg, 0.33 mmol, 63%).

methyl 1-(4-(3,4-dichlorophenyl)-5-(isopropylthio)thiazol-2-yl)-4-(2-(2-methoxyethoxy)-6-methylpyridin-4-yl)-3-methyl-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 4-bromo-2-(2-methoxyethoxy)-6-methylpyridine (30 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (10 to 50%) to give the title compound (28 mg, 0.046 mmol, 45%) as a pale yellow oil.

1-(4-(3,4-dichlorophenyl)-5-(isopropylthio)thiazol-2-yl)-4-(2-(2-methoxyethoxy)-6-methylpyridin-4-yl)-3-methyl-1H-pyrazole-5-carboxylic Acid methyl 1-(4-(3,4-dichlorophenyl)-5-(isopropylthio)thiazol-2-yl)-4-(2-(2-methoxyethoxy)-6-methylpyridin-4-yl)-3-methyl-1H-pyrazole-5-carboxylate (28 mg, 0.046 mmol) was diluted in a 1:1 solution of THF and MeOH (0.46 mL). 1M NaOH (0.092 mL, 0.092 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (50 to 70%). The product was lyophilysed to give the title compound (2.8 mg, 0.0047 mmol, 10%) as a pale yellow solid.
$^1$H NMR (500 MHz, DMSO) δ 8.22 (s, 1H), 8.04 (d, J=8.4 Hz, 1H), 7.76 (d, J=8.5 Hz, 1H), 6.96 (s, 1H), 6.72 (s, 1H), 4.40-4.35 (m, 2H), 3.69-3.64 (m, 2H), 3.35 (sept, J=6.7 Hz, 1H), 2.41 (s, 3H), 2.33 (s, 3H), 1.24 (d, J=6.7 Hz, 6H); MS (m/z): 592.9 [M+1]$^+$.

Compound 183: 1-(4-(cyclohex-1-en-1-yl)-5-(isopropylthio)thiazol-2-yl)-4-(3-fluorophenyl)-3-methyl-1H-pyrazole-5-carboxylic Acid methyl 4-bromo-1-(4-(cyclohex-1-en-1-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), 2-(cyclohex-1-en-1-yl)-4,4,5,5-tetramethyl-1,3,2-dioxaborolane (45.8 mg, 0.220 mmol) and K$_2$CO$_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (0 to 20% gradient) and afforded the title compound (84.4 mg, 0.185 mmol, 84%) as yellow oil.

1-(4-(cyclohex-1-en-1-yl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-(cyclohex-1-en-1-yl)-5-(isopropylthio)thiazol-2-yl)-3-methyl-1H-pyrazole-5-carboxylate (84.4 mg, 0.185 mmol), 3-fluorophenylboronic acid (31.0 mg, 0.22 mmol) and Na$_2$CO$_3$ (97.9 mg, 0.92 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (21.4 mg, 0.02 mmol). The vial was capped and placed in an oil bath at 85° C. for 16 h. The reaction mixture was diluted with EtOAc and transferred into an extraction funnel. The layers were separated and the aqueous layer was extracted with EtOAc (3×). The combined organic layers were dried over Na$_2$SO$_4$, filtered and concentrated under vacuum. Into a 5 mL glass microwave vial, was placed the crude product and LiOH (43.1 mg, 1.80 mmol). THF (1.5 mL), MeOH (0.5 mL) and water (0.5 mL) were added. The vial was heated to 120° C. under microwave radiation for 10 minutes. THF, MeOH and water were removed under vacuum and the crude product was purified using a semi prep HPLC-MS (X-Bridge 30×50, eluted with 55-75% MeCN/NH$_4$CO$_2$H 10 mM, pH 3.8/Flow 45 ml/min/11 min), resulting in the title compound (15.0 mg, 0.033 mmol, 18%) as yellow solid after lyophilisation.
$^1$H NMR (500 MHz, DMSO) δ 7.52 (dd, J=14.5, 8.1 Hz, 1H), 7.32-7.27 (m, 2H), 7.24 (t, J=8.5 Hz, 1H), 6.41-6.37 (m, 1H), 3.28 (m, 1H), 2.46-2.41 (m, 2H), 2.29 (s, 3H), 2.21 (ddd, J=9.8, 6.4, 3.4 Hz, 2H), 1.72-1.65 (m, 2H), 1.63-1.57 (m, 2H), 1.26 (d, J=6.7 Hz, 6H); MS (m/z): 458.3 [M+1]$^+$.

Compound 185: 4-(3-chloro-5-methoxyphenyl)-1-(5-(isopropylthio)-4-phenylthiazol-2-yl)-3-methyl-1H-pyrazole-5-carboxylic Acid methyl 4-bromo-1-(5-(isopropylthio)-4-phenylthiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (200 mg, 0.439 mmol), phenylboronic acid (53.6 mg, 0.439 mmol) and K$_2$CO$_3$ (304 mg, 2.20 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (28.6 mg, 0.044 mmol). The vial was capped and placed in an oil bath at 90° C. for 16 h. The solvent was evaporated under vacuum and the crude product was purified by flash chromatography on silica gel (wet loading) using a solution of DCM in hexanes (10 to 100% gradient) and afforded the title compound (163 mg, 0.360 mmol, 82%) as brown oil.

4-(3-chloro-5-methoxyphenyl)-1-(5-(isopropylthio)-4-phenylthiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(5-(isopropylthio)-4-phenylthiazol-2-yl)-3-methyl-1H-pyrazole-5-carboxylate (54.0 mg, 0.119 mmol), 2-(3-chloro-5-methoxyphenyl)-4,4,5,5-tetramethyl-1,3,2-dioxaborolane (38.5 mg, 0.096 mmol) and Na$_2$CO$_3$ (63.3 mg, 0.597 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (13.8 mg, 0.012 mmol). The vial was capped and placed in an oil bath at 85° C. for 16 h. LiOH (25.0 mg, 0.597 mmol) was added to the reaction mixture and stirred under microwave radiation at 120° C. for 10 min. The product was purified using a semi prep HPLC-MS (column X-Bridge 30×50, eluted with 55-75% MeCN/NH$_4$CO$_2$H 10 mM, pH 3.8/Flow 45 ml/min/11 min), resulting in the title compound (17.15 mg, 0.034 mmol, 29%) as white solid after lyophilisation.

$^1$H NMR (500 MHz, DMSO) δ 8.02 (d, J=7.5 Hz, 2H), 7.47 (t, J=7.5 Hz, 2H), 7.40 (t, J=7.3 Hz, 1H), 7.17-6.96 (m, 3H), 3.80 (s, 3H), 3.35-3.20 (m, 1H), 2.30 (s, 3H), 1.22 (d, J=6.7 Hz, 6H). MS (m/z): 500.1 [M+1]$^+$.

Compound 186: 4-(3-fluorophenyl)-1-(4-(4-fluorophenyl)-5-(isopropylthio)thiazol-2-yl)-3-methyl-1H-pyrazole-5-carboxylic Acid methyl 4-bromo-1-(4-(4-fluorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), 4-fluorophenylboronic acid (26.1 mg, 0.220 mmol) and K$_2$CO$_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (1% isocratic) and afforded the title compound (81.3 mg, 0.173 mmol, 79%) as yellow oil.

4-(3-fluorophenyl)-1-(4-(4-fluorophenyl)-5-(isopropylthio)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(4-(4-fluorophenyl)-5-(isopropylthio)thiazol-2-yl)-3-methyl-1H-pyrazole-5-carboxylate (40.0 mg, 0.085 mmol), 3-fluorophenylboronic acid (14.3 mg, 0.102 mmol) and Na$_2$CO$_3$ (45.1 mg, 0.425 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (9.83 mg, 0.009 mmol). The vial was capped and placed in an oil bath at 85° C. for 16 h. LiOH (17.8 mg, 0.425 mmol) was added to the reaction mixture and stirred under microwave radiation at 120° C. for 10 min. The product was purified using a semi prep HPLC-MS (column X-Bridge 30×50, eluted with 55-75% MeCN/NH$_4$CO$_2$H 10 mM, pH 3.8/Flow 45 ml/min/11 min), resulting in the title compound (7.13 mg, 0.015 mmol, 18%) as white solid after lyophilisation.

$^1$H NMR (500 MHz, DMSO) δ 8.10-8.01 (m, J=8.7, 5.6 Hz, 2H), 7.59-7.43 (m, J=6.6 Hz, 1H), 7.42-7.26 (m, J=8.9 Hz, 4H), 7.25-7.14 (m, 1H), 3.32-3.24 (m, 1H), 2.30 (s, 3H), 1.22 (d, J=6.7 Hz, 6H); MS (m/z): 472.1 [M+1]$^+$.

Compound 187: 4-(3-fluorophenyl)-1-(5-(isopropylthio)-4-(4-methoxyphenyl)thiazol-2-yl)-3-methyl-1H-pyrazole-5-carboxylic Acid methyl 4-bromo-1-(5-(isopropylthio)-4-(4-methoxyphenyl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), 4-methoxyphenylboronic acid (28.4 mg, 0.220 mmol) and K$_2$CO$_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (1 to 4% gradient) and afforded the title compound (43.6 mg, 0.090 mmol, 41%) as yellow oil.

4-(3-fluorophenyl)-1-(5-(isopropylthio)-4-(4-methoxyphenyl)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(5-(isopropylthio)-4-(4-methoxyphenyl)thiazol-2-yl)-3-methyl-1H-pyrazole-5-carboxylate (43.0 mg, 0.089 mmol), 3-fluorophenylboronic acid (15.0 mg, 0.107 mmol) and Na$_2$CO$_3$ (47.2 mg, 0.446 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (10.3 mg, 0.009 mmol). The vial was capped and placed in an oil bath at 85° C. for 16 h. LiOH (18.7 mg, 0.446 mmol) was added to the reaction mixture and stirred under microwave radiation at 120° C. for 10 min. The product was purified using a semi prep HPLC-MS (column X-Bridge 30×50, eluted with 55-75% MeCN/NH$_4$CO$_2$H 10 mM, pH 3.8/Flow 45 ml/min/11 min), resulting in the title compound (4.07 mg, 0.008 mmol, 9%) as white solid after lyophilisation.

$^1$H NMR (500 MHz, DMSO) δ 8.00 (s, 2H), 7.54-7.11 (m, 4H), 7.02 (d, J=8.9 Hz, 2H), 3.81 (s, 3H), 3.37-3.24 (m, 1H), 2.30 (s, 3H), 1.22 (d, J=6.7 Hz, 6H); MS (m/z): 484.1 [M+1]$^+$.

Compound 188: 4-(3-fluorophenyl)-1-(5-(isopropylthio)-4-(4-(methylsulfonyl)phenyl)thiazol-2-yl)-3-methyl-1H-pyrazole-5-carboxylic Acid methyl 4-bromo-1-(5-(isopropylthio)-4-(4-(methylsulfonyl)phenyl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), 4-methylsulfonylphenylboronic acid (37.4 mg, 0.187 mmol) and K2CO3 (152 mg, 1.10 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl2 (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (1 to 5% gradient) and afforded the title compound (34.9 mg, 0.066 mmol, 30%) as yellow oil.

4-(3-fluorophenyl)-1-(5-(isopropylthio)-4-(4-(methylsulfonyl)phenyl)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(5-(isopropylthio)-4-(4-(methylsulfonyl)phenyl)thiazol-2-yl)-3-methyl-1H-pyrazole-5-carboxylate (34.9 mg, 0.066 mmol), 3-fluorophenylboronic acid (11.0 mg, 0.079 mmol) and $Na_2CO_3$ (34.9 mg, 0.329 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (7.61 mg, 0.007 mmol). The vial was capped and placed in an oil bath at 85° C. for 16 h. LiOH (13.8 mg, 0.329 mmol) was added to the reaction mixture and stirred under microwave radiation at 120° C. for 10 min. The product was purified using a semi prep HPLC-MS (column X-Bridge 30×50, eluted with 30-50% MeCN/$NH_4CO_2H$ 10 mM, pH 3.8/Flow 45 ml/min/11 min), resulting in the title compound (2.28 mg, 0.004 mmol, 7%) as white solid after lyophilisation.

$^1$H NMR (500 MHz, DMSO) δ 8.24 (d, J=8.4 Hz, 2H), 8.01 (d, J=8.6 Hz, 2H), 7.55-7.43 (m, J=6.9 Hz, 1H), 7.43-7.30 (m, J=10.8 Hz, 2H), 7.25-7.13 (m, J=9.8 Hz, 1H), 3.42-3.35 (m, J=13.6, 6.9 Hz, 1H), 3.27 (s, 3H), 2.31 (s, 3H), 1.24 (d, J=6.7 Hz, 6H); MS (m/z): 532.3 [M+1]$^+$.

Compound 189: 1-(4-(4-fluoro-3-methoxyphenyl)-5-(isopropylthio)thiazol-2-yl)-4-(3-fluorophenyl)-3-methyl-1H-pyrazole-5-carboxylic Acid methyl 4-bromo-1-(4-(4-fluoro-3-methoxyphenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (100 mg, 0.220 mmol), 4-fluoro-3-methoxyphenylboronic acid (31.7 mg, 0.187 mmol) and $K_2CO_3$ (152 mg, 1.10 mmol), nitrogen and vacuum cycles were performed (2×). Nitrogen gas was bubbled through a solution of THF (2 mL) and then the solution was added to the microwave vial, followed by the addition of the catalyst $Pd(dtbpf)Cl_2$ (14.3 mg, 0.022 mmol). The vial was capped and placed in an oil bath at 90° C. for 16 h. The solvent was evaporated under vacuum and the crude product was purified by flash chromatography on silica gel (dry packing) using a solution of EtOAc in hexanes (1 to 5% gradient) and afforded the title compound (43.2 mg, 0.086 mmol, 39%) as yellow oil.

1-(4-(4-fluoro-3-methoxyphenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-(4-fluoro-3-methoxyphenyl)-5-(isopropylthio)thiazol-2-yl)-3-methyl-1H-pyrazole-5-carboxylate (43.2 mg, 0.086 mmol), 3-fluorophenylboronic acid (14.5 mg, 0.104 mmol) and $Na_2CO_3$ (45.8 mg, 0.432 mmol), nitrogen and vacuum cycles were performed (2×). Nitrogen gas was bubbled through a solution of dioxane/water (2 mL, 4:1) and then the solution was added to the microwave vial, followed by the addition of the catalyst $Pd(PPh_3)_4$ (9.98 mg, 0.009 mmol). The vial was capped and placed in an oil bath at 85° C. for 16 h. LiOH (18.1 mg, 0.432 mmol) was added to the reaction mixture and stirred under microwave radiation at 120° C. for 10 min. The product was purified using a semi prep HPLC-MS (column X-Bridge 30×50, eluted with 55-75% MeCN/$NH_4CO_2H$ 10 mM, pH 3.8/Flow 45 ml/min/11 min), resulting in the title compound (11.69 mg, 0.023 mmol, 27%) as white solid after lyophilisation.

$^1$H NMR (500 MHz, DMSO) δ 7.95-7.86 (m, 1H), 7.73-7.65 (m, 1H), 7.51-7.44 (m, 1H), 7.40-7.27 (m, 2H), 7.22-7.13 (m, 1H), 3.90 (s, 3H), 3.37-3.24 (m, 1H), 2.31 (s, 3H), 1.24 (d, J=6.7 Hz, 6H); MS (m/z): 502.4 [M+1]$^+$.

Compound 190: 1-(4-(4-chloro-3-methylphenyl)-5-(isopropylthio)thiazol-2-yl)-4-(2,6-dimethylpyridin-4-yl)-3-methyl-1H-pyrazole-5-carboxylic Acid methyl 4-bromo-1-(4-(4-chloro-3-methylphenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (100 mg, 0.220 mmol), the (4-chloro-3-methylphenyl)boronic acid (38 mg, 0.20 mmol), $K_2CO_3$ (152 mg, 1.10 mmol) and THF (2 mL). Nitrogen was bubbled in the solvent for 10 minutes followed by the addition of the catalyst $Pd(dtbpf)Cl_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes to give the title compound (90 mg, 0.18 mmol, 78%) as a yellow oil.

methyl 1-(4-(4-chloro-3-methylphenyl)-5-(isopropylthio)thiazol-2-yl)-4-(2,6-dimethylpyridin-4-yl)-3-methyl-1H-pyrazole-5-carboxylate Nitrogene was passed through a solution of dioxane/$H_2O$ (4/1) and this solution (2.0 mL) was then added to a mixture of the methyl 4-bromo-1-(4-(4-chloro-3-methylphenyl)-5-(isopropylthio)thiazol-2-yl)-3-methyl-1H-pyrazole-5-carboxylate (44 mg, 0.088 mmol), 2,6-dimethyl-4-(4,4,5,5-tetramethyl-1,3,2-dioxaborolan-2-yl)pyridine (49 mg, 0.21 mmol) and $Na_2CO_3$ (47 mg, 0.44 mmol) followed by the addition of the catalyst $Pd(PPh_3)_4$ (10 mg, 0.0087 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes to give the title compound (26 mg, 0.049 mmol, 56%) as a yellow oil.

1-(4-(4-chloro-3-methylphenyl)-5-(isopropylthio)thiazol-2-yl)-4-(2,6-dimethylpyridin-4-yl)-3-methyl-1H-pyrazole-5-carboxylic Acid The methyl 1-(4-(4-chloro-3-methylphenyl)-5-(isopropylthio)thiazol-2-yl)-4-(2,6-dimethylpyridin-4-yl)-3-methyl-1H-pyrazole-5-carboxylate (26 mg, 0.049 mmol) was dissolved in a mixture of $H_2O$/THF/MeOH (6/3/1) (2.5 mL) and treated with LiOH (5.9 mg, 0.25 mmol). The reaction mixture was stirred in the microwave at 110° C. for 15 min. Evaporated in vacuo. The crude product was purified by semi-prep HPLC-MS (column X-Bridge 30×50, eluted with 45-65% MeCN/NH$_4$CO$_2$H 10 mM, pH 3.8/Flow 45 ml/min/10 min), and afforded the title compound (4.8 mg, 0.0094 mmol, 19%) as a yellow solid after lyophilisation.

$^1$H NMR (500 MHz, DMSO) δ 7.94 (d, J=1.9 Hz, 1H), 7.87 (dd, J=8.4, 1.9 Hz, 1H), 7.50 (d, J=8.4 Hz, 1H), 7.16 (s, 2H), 3.34-3.27 (m, 1H), 2.46 (s, 6H), 2.39 (s, 3H), 2.33 (s, 3H), 1.23 (d, J=6.7 Hz, 6H). MS (m/z): 513.2 [M+1]+.

Compound 191: 1-(4-(4-chloro-3-methylphenyl)-5-(isopropylthio)thiazol-2-yl)-4-(3-fluorophenyl)-3-methyl-1H-pyrazole-5-carboxylic Acid methyl 1-(4-(4-chloro-3-methylphenyl)-5-(isopropylthio)thiazol-2-yl)-4-(3-fluorophenyl)-3-methyl-1H-pyrazole-5-carboxylate Nitrogene was passed through a solution of dioxane/H$_2$O (4/1) and this solution (2.0 mL) was then added to a mixture of the methyl 4-bromo-1-(4-(4-chloro-3-methylphenyl)-5-(isopropylthio)thiazol-2-yl)-3-methyl-1H-pyrazole-5-carboxylate (44 mg, 0.088 mmol), (3-fluorophenyl)boronic acid (15 mg, 0.11 mmol) and Na$_2$CO$_3$ (47 mg, 0.44 mmol) followed by the addition of the catalyst Pd(PPh$_3$)$_4$ (10 mg, 0.0087 mmol). The reaction mixture was heated at 85° C. for 16 hours. The solvent was evaporated under vacuum and the crude product was purified by flash chromatography (dry packing) on silica gel using a gradient 0 to 10% EtOAc in hexanes to give the title compound (22 mg, 0.042 mmol, 47%) as a yellow oil.

1-(4-(4-chloro-3-methylphenyl)-5-(isopropylthio)thiazol-2-yl)-4-(3-fluorophenyl)-3-methyl-1H-pyrazole-5-carboxylic Acid The methyl 1-(4-(4-chloro-3-methylphenyl)-5-(isopropylthio)thiazol-2-yl)-4-(3-fluorophenyl)-3-methyl-1H-pyrazole-5-carboxylate (22 mg, 0.042 mmol) was dissolved in a mixture of H$_2$O/THF/MeOH (6/3/1) (2.5 mL) and treated with LiOH (5.0 mg, 0.21 mmol). The reaction mixture was stirred in the microwave at 110° C. for 15 min. Evaporated in vacuo. The crude product was purified by semi-prep HPLC-MS (column X-Bridge 30×50, eluted with 60-80% MeCN/NH$_4$CO$_2$H 10 mM, pH 3.8/Flow 45 ml/min/10 min), and afforded the title compound (7.3 mg, 0.015 mmol, 35%) as a yellow solid after lyophilisation.

$^1$H NMR (500 MHz, DMSO) δ 7.94 (m, 1H), 7.86 (dd, J=8.4, 1.9 Hz, 1H), 7.53-7.46 (m, 2H), 7.37-7.30 (m, 2H), 7.25-7.17 (m, 1H), 3.37-3.25 (m, 1H), 2.39 (s, 3H), 2.31 (s, 3H), 1.23 (d, J=6.7 Hz, 6H). MS (m/z): 502.2 [M+1]+.

Compound 192: 1-(4-(4-chloro-3,5-difluorophenyl)-5-(isopropylthio)thiazol-2-yl)-4-(2,6-dimethylpyridin-4-yl)-3-methyl-1H-pyrazole-5-carboxylic Acid methyl 4-bromo-1-(4-(4-chloro-3,5-difluorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (100 mg, 0.220 mmol), the (4-chloro-3,5-difluorophenyl)boronic acid (38 mg, 0.20 mmol), K$_2$CO$_3$ (152 mg, 1.10 mmol) and THF (2 mL). Nitrogen was bubbled in the solvent for 10 minutes followed by the addition of the catalyst Pd(dtbpf)Cl$_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes to give the title compound (90 mg, 0.17 mmol, 78%) as a yellow oil.

methyl 1-(4-(4-chloro-3,5-difluorophenyl)-5-(isopropylthio)thiazol-2-yl)-4-(2,6-dimethylpyridin-4-yl)-3-methyl-1H-pyrazole-5-carboxylate Nitrogene was passed through a solution of dioxane/H$_2$O (4/1) and this solution (2.0 mL) was then added to a mixture of the methyl 4-bromo-1-(4-(4-chloro-3,5-difluorophenyl)-5-(isopropylthio)thiazol-2-yl)-3-methyl-1H-pyrazole-5-carboxylate (44 mg, 0.084 mmol), 2,6-dimethyl-4-(4,4,5,5-tetramethyl-1,3,2-dioxaborolan-2-yl)pyridine (47 mg, 0.20 mmol) and Na$_2$CO$_3$ (45 mg, 0.42 mmol) followed by the addition of the catalyst Pd(PPh$_3$)$_4$ (9.7 mg, 0.0084 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes to give the title compound (17 mg, 0.031 mmol, 37%) as a yellow oil.

1-(4-(4-chloro-3,5-difluorophenyl)-5-(isopropylthio)thiazol-2-yl)-4-(2,6-dimethylpyridin-4-yl)-3-methyl-1H-pyrazole-5-carboxylic Acid The methyl 1-(4-(4-chloro-3,5-difluorophenyl)-5-(isopropylthio)thiazol-2-yl)-4-(2,6-dimethylpyridin-4-yl)-3-methyl-1H-pyrazole-5-carboxylate (17 mg, 0.031 mmol) was dissolved in a mixture of H$_2$O/THF/MeOH (6/3/1) (2.5 mL) and treated with LiOH (3.7 mg, 0.16 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/NH$_4$CO$_2$H 10 mM, pH 3.8/Flow 45 ml/min/10 min), and afforded the title compound (3.2 mg, 0.0060 mmol, 19%) as a yellow solid after lyophilisation.

$^1$H NMR (500 MHz, DMSO) δ 7.97 (s, 1H), 7.95 (s, 1H), 7.18 (s, 2H), 3.43-3.32 (m, 1H), 2.45 (s, 6H), 2.33 (s, 3H), 1.26 (d, J=6.7 Hz, 6H). MS (m/z): 535.2 [M+1]+.

Compound 193: 1-(4-(4-chloro-3,5-difluorophenyl)-5-(isopropylthio)thiazol-2-yl)-4-(3-fluorophenyl)-3-methyl-1H-pyrazole-5-carboxylic Acid methyl 1-(4-(4-chloro-3,5-difluorophenyl)-5-(isopropylthio)thiazol-2-yl)-4-(3-fluorophenyl)-3-methyl-1H-pyrazole-5-carboxylate Nitrogene was passed through a solution of dioxane/H$_2$O (4/1) and this solution (2.0 mL) was then added to a mixture of the methyl 4-bromo-1-(4-(4-chloro-3,5-difluorophenyl)-5-(isopropylthio)thiazol-2-yl)-3-methyl-1H-pyrazole-5-carboxylate (44 mg, 0.084 mmol), (3-fluorophenyl)boronic acid (14 mg, 0.10 mmol) and Na$_2$CO$_3$ (45 mg, 0.42 mmol) followed by the addition of the catalyst Pd(PPh$_3$)$_4$ (9.7 mg, 0.0084 mmol). The reaction mixture was heated at 85° C. for 16 hours. The solvent was evaporated under vacuum and the crude product was purified by flash chromatography (dry packing) on silica gel using a gradient 0 to 10% EtOAc in hexanes to give the title compound (16 mg, 0.030 mmol, 36%) as a yellow oil.

1-(4-(4-chloro-3,5-difluorophenyl)-5-(isopropylthio) thiazol-2-yl)-4-(3-fluorophenyl)-3-methyl-1H-pyrazole-5-carboxylic Acid The methyl 1-(4-(4-chloro-3,5-difluorophenyl)-5-(isopropylthio)thiazol-2-yl)-4-(3-fluorophenyl)-3-methyl-1H-pyrazole-5-carboxylate (16 mg, 0.030 mmol) was dissolved in a mixture of $H_2O$/THF/MeOH (6/3/1) (2.5 mL) and treated with LiOH (3.6 mg, 0.15 mmol). The reaction mixture was stirred in the microwave at 110° C. for 15 min. Evaporated in vacuo. The crude product was purified by semi-prep HPLC-MS (column X-Bridge 30×50, eluted with 60-80% MeCN/$NH_4CO_2H$ 10 mM, pH 3.8/Flow 45 ml/min/10 min), and afforded the title compound (5.1 mg, 0.010 mmol, 32%) as a yellow solid after lyophilisation.
$^1$H NMR (500 MHz, DMSO) δ 7.97 (s, 1H), 7.95 (s, 1H), 7.52-7.45 (m, 1H), 7.39-7.32 (m, 2H), 7.23-7.16 (m, 1H), 3.44-3.32 (m, 1H), 2.31 (s, 3H), 1.25 (d, J=6.7 Hz, 6H). MS (m/z): 524.2 [M+1]+.

Compound 194: 1-(4-(4-chloro-3-methoxyphenyl)-5-(isopropylthio)thiazol-2-yl)-4-(2,6-dimethylpyridin-4-yl)-3-methyl-1H-pyrazole-5-carboxylic Acid methyl 4-bromo-1-(4-(4-chloro-3-methoxyphenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (100 mg, 0.220 mmol), the (4-chloro-3-methoxyphenyl)boronic acid (37 mg, 0.20 mmol), $K_2CO_3$ (152 mg, 1.10 mmol) and THF (2 mL). Nitrogen was bubbled in the solvent for 10 minutes followed by the addition of the catalyst Pd(dtbpf)$Cl_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes to give the title compound (83 mg, 0.16 mmol, 72%) as a yellow oil.

methyl 1-(4-(4-chloro-3-methoxyphenyl)-5-(isopropylthio)thiazol-2-yl)-4-(2,6-dimethylpyridin-4-yl)-3-methyl-1H-pyrazole-5-carboxylate Nitrogene was passed through a solution of dioxane/$H_2O$ (4/1) and this solution (2.0 mL) was then added to a mixture of the methyl 4-bromo-1-(4-(4-chloro-3-methoxyphenyl)-5-(isopropylthio)thiazol-2-yl)-3-methyl-1H-pyrazole-5-carboxylate (41 mg, 0.079 mmol), 2,6-dimethyl-4-(4,4,5,5-tetramethyl-1,3,2-dioxaborolan-2-yl)pyridine (44 mg, 0.19 mmol) and $Na_2CO_3$ (42 mg, 0.40 mmol) followed by the addition of the catalyst Pd(PPh$_3$)$_4$ (9.2 mg, 0.0080 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes to give the title compound (20 mg, 0.036 mmol, 36%) as a yellow oil.

1-(4-(4-chloro-3-methoxyphenyl)-5-(isopropylthio) thiazol-2-yl)-4-(2,6-dimethylpyridin-4-yl)-3-methyl-1H-pyrazole-5-carboxylic Acid The methyl 1-(4-(4-chloro-3-methoxyphenyl)-5-(isopropylthio)thiazol-2-yl)-4-(2,6-dimethylpyridin-4-yl)-3-methyl-1H-pyrazole-5-carboxylate (20 mg, 0.036 mmol) was dissolved in a mixture of $H_2O$/THF/MeOH (6/3/1) (2.5 mL) and treated with LiOH (4.3 mg, 0.18 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/$NH_4CO_2H$ 10 mM, pH 3.8/Flow 45 ml/min/10 min), and afforded the title compound (8.5 mg, 0.016 mmol, 44%) as a yellow solid after lyophilisation.
$^1$H NMR (500 MHz, DMSO) δ 7.86-7.83 (m, 1H), 7.71 (dd, J=8.4, 1.8 Hz, 1H), 7.51 (d, J=8.4 Hz, 1H), 7.16 (s, 2H), 3.91 (s, 3H), 3.43-3.31 (m, 1H), 2.46 (s, 6H), 2.33 (s, 3H), 1.25 (d, J=6.7 Hz, 6H). MS (m/z): 529.3 [M+1]+.

Compound 195: 1-(4-(4-chloro-3-methoxyphenyl)-5-(isopropylthio)thiazol-2-yl)-4-(3-fluorophenyl)-3-methyl-1H-pyrazole-5-carboxylic Acid methyl 1-(4-(4-chloro-3-methoxyphenyl)-5-(isopropylthio)thiazol-2-yl)-4-(3-fluorophenyl)-3-methyl-1H-pyrazole-5-carboxylate Nitrogene was passed through a solution of dioxane/$H_2O$ (4/1) and this solution (2.0 mL) was then added to a mixture of the methyl 4-bromo-1-(4-(4-chloro-3-methoxyphenyl)-5-(isopropylthio)thiazol-2-yl)-3-methyl-1H-pyrazole-5-carboxylate (41 mg, 0.079 mmol), (3-fluorophenyl)boronic acid (13 mg, 0.10 mmol) and $Na_2CO_3$ (42 mg, 0.40 mmol) followed by the addition of the catalyst Pd(PPh$_3$)$_4$ (9.2 mg, 0.0080 mmol). The reaction mixture was heated at 85° C. for 16 hours. The solvent was evaporated under vacuum and the crude product was purified by flash chromatography (dry packing) on silica gel using a gradient 0 to 10% EtOAc in hexanes to give the title compound (24 mg, 0.045 mmol, 56%) as a yellow oil.

1-(4-(4-chloro-3-methoxyphenyl)-5-(isopropylthio) thiazol-2-yl)-4-(3-fluorophenyl)-3-methyl-1H-pyrazole-5-carboxylic Acid The methyl 1-(4-(4-chloro-3-methoxyphenyl)-5-(isopropylthio)thiazol-2-yl)-4-(3-fluorophenyl)-3-methyl-1H-pyrazole-5-carboxylate (24 mg, 0.045 mmol) was dissolved in a mixture of $H_2O$/THF/MeOH (6/3/1) (2.5 mL) and treated with LiOH (5.4 mg, 0.23 mmol). The reaction mixture was stirred in the microwave at 110° C. for 15 min. Evaporated in vacuo. The crude product was purified by semi-prep HPLC-MS (column X-Bridge 30×50, eluted with 60-80% MeCN/$NH_4CO_2H$ 10 mM, pH 3.8/Flow 45 ml/min/10 min), and afforded the title compound (6.7 mg, 0.013 mmol, 29%) as a yellow solid after lyophilisation.
$^1$H NMR (500 MHz, DMSO) δ 7.89-7.85 (m, 1H), 7.73-7.69 (m, 1H), 7.54-7.45 (m, 2H), 7.40-7.31 (m, 2H), 7.24-7.16 (m, 1H), 3.91 (s, 3H), 3.41-3.31 (m, 1H), 2.31 (s, 3H), 1.25 (d, J=6.7 Hz, 6H). MS (m/z): 518.3 [M+1]+.

Compound 196: 4-(2,6-dimethylpyridin-4-yl)-1-(5-(isopropylthio)-4-(4-(trifluoromethyl)phenyl)thiazol-2-yl)-3-methyl-1H-pyrazole-5-carboxylic Acid methyl 4-bromo-1-(5-(isopropylthio)-4-(4-(trifluoromethyl)phenyl)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)

thiazol-2-yl)-3-methyl-1H-pyrazole-5-carboxylate (100 mg, 0.220 mmol), the (4-(trifluoromethyl)phenyl)boronic acid (38 mg, 0.20 mmol), K$_2$CO$_3$ (152 mg, 1.10 mmol) and THF (2 mL). Nitrogen was bubbled in the solvent for 10 minutes followed by the addition of the catalyst Pd(dtbpf)Cl$_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes to give the title compound (87 mg, 0.17 mmol, 75%) as a yellow oil.

methyl 4-(2,6-dimethylpyridin-4-yl)-1-(5-(isopropylthio)-4-(4-(trifluoromethyl)phenyl)thiazol-2-yl)-3-methyl-1H-pyrazole-5-carboxylate Nitrogene was passed through a solution of dioxane/H$_2$O (4/1) and this solution (2.0 mL) was then added to a mixture of the methyl 4-bromo-1-(5-(isopropylthio)-4-(4-(trifluoromethyl)phenyl)thiazol-2-yl)-3-methyl-1H-pyrazole-5-carboxylate (43 mg, 0.083 mmol), 2,6-dimethyl-4-(4,4,5,5-tetramethyl-1,3,2-dioxaborolan-2-yl)pyridine (46 mg, 0.20 mmol) and Na$_2$CO$_3$ (44 mg, 0.41 mmol) followed by the addition of the catalyst Pd(PPh$_3$)$_4$ (9.5 mg, 0.0082 mmol). The reaction mixture was heated at 85° C. for 16 hours. The solvent was evaporated under vacuum and the crude product was purified by flash chromatography (dry packing) on silica gel using a gradient 10 to 40% EtOAc in hexanes to give the title compound (25 mg, 0.046 mmol, 56%) as a yellow oil.

4-(2,6-dimethylpyridin-4-yl)-1-(5-(isopropylthio)-4-(4-(trifluoromethyl)phenyl)thiazol-2-yl)-3-methyl-1H-pyrazole-5-carboxylic Acid The methyl 4-(2,6-dimethylpyridin-4-yl)-1-(5-(isopropylthio)-4-(4-(trifluoromethyl)phenyl)thiazol-2-yl)-3-methyl-1H-pyrazole-5-carboxylate (25 mg, 0.046 mmol) was dissolved in a mixture of H$_2$O/THF/MeOH (6/3/1) (2.5 mL) and treated with LiOH (5.5 mg, 0.23 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/NH$_4$CO$_2$H 10 mM, pH 3.8/Flow 45 ml/min/10 min), and afforded the title compound (6.3 mg, 0.012 mmol, 26%) as a yellow solid after lyophilisation.
$^1$H NMR (500 MHz, DMSO) δ 8.21 (d, J=8.3 Hz, 2H), 7.83 (d, J=8.3 Hz, 2H), 7.16 (s, 2H), 3.44-3.31 (m, 1H), 2.46 (s, 6H), 2.33 (s, 3H), 1.23 (d, J=6.7 Hz, 6H). MS (m/z): 533.4 [M+1]+.

Compound 197: 4-(3-fluorophenyl)-1-(5-(isopropylthio)-4-(4-(trifluoromethyl)phenyl)thiazol-2-yl)-3-methyl-1H-pyrazole-5-carboxylic Acid methyl 4-(3-fluorophenyl)-1-(5-(isopropylthio)-4-(4-(trifluoromethyl)phenyl)thiazol-2-yl)-3-methyl-1H-pyrazole-5-carboxylate Nitrogene was passed through a solution of dioxane/H$_2$O (4/1) and this solution (2.0 mL) was then added to a mixture of methyl 4-bromo-1-(5-(isopropylthio)-4-(4-(trifluoromethyl)phenyl)thiazol-2-yl)-3-methyl-1H-pyrazole-5-carboxylate (43 mg, 0.083 mmol), (3-fluorophenyl)boronic acid (14 mg, 0.10 mmol) and Na$_2$CO$_3$ (44 mg, 0.41 mmol) followed by the addition of the catalyst Pd(PPh$_3$)$_4$ (9.5 mg, 0.0082 mmol). The reaction mixture was heated at 85° C. for 16 hours. The solvent was evaporated under vacuum and the crude product was purified by flash chromatography (dry packing) on silica gel using a gradient 0 to 10% EtOAc in hexanes to give the title compound (30 mg, 0.056 mmol, 68%) as a yellow oil.

4-(3-fluorophenyl)-1-(5-(isopropylthio)-4-(4-(trifluoromethyl)phenyl)thiazol-2-yl)-3-methyl-1H-pyrazole-5-carboxylic Acid The methyl 4-(3-fluorophenyl)-1-(5-(isopropylthio)-4-(4-(trifluoromethyl)phenyl)thiazol-2-yl)-3-methyl-1H-pyrazole-5-carboxylate (30 mg, 0.056 mmol) was dissolved in a mixture of H$_2$O/THF/MeOH (6/3/1) (2.5 mL) and treated with LiOH (6.7 mg, 0.28 mmol). The reaction mixture was stirred in the microwave at 110° C. for 15 min. Evaporated in vacuo. The crude product was purified by semi-prep HPLC-MS (column X-Bridge 30×50, eluted with 60-80% MeCN/NH$_4$CO$_2$H 10 mM, pH 3.8/Flow 45 ml/min/10 min), and afforded the title compound (8.9 mg, 0.017 mmol, 30%) as a yellow solid after lyophilisation.
$^1$H NMR (500 MHz, DMSO) δ 8.21 (d, J=8.3 Hz, 2H), 7.83 (d, J=8.3 Hz, 2H), 7.53-7.46 (m, 1H), 7.38-7.31 (m, 2H), 7.25-7.18 (m, 1H), 3.44-3.31 (m, 1H), 2.30 (s, 3H), 1.23 (d, J=6.7 Hz, 6H). MS (m/z): 522.3 [M+1]+.

Compound 198: 1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic Acid 3-(3-bromo-5-methyl phenoxy)oxetane Diisopropyl diazocarboxylate (292 mg, 1.45 mmol) was added to a solution of 3-bromo-5-methylphenol (200 mg, 0.964 mmol), oxetan-3-ol (89 mg, 1.2 mmol) and triphenylphosphine (379 mg, 1.45 mmol) in THF (4.2 mL). The reaction mixture was stirred at r.t. for 18 h. Ethyl acetate was added and the mixture was washed with 1N NaOH (3×). The organic layer was dried with sodium sulfate, filtered and evaporated under reduced pressure. The crude product was purified by flash chromatography on silica gel using a solution of ethyl acetate in hexanes (10%) to give the title compound (218 mg, 0.827 mmol, 86%) as a colorless oil.

methyl 1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 3-(3-bromo-5-methylphenoxy)oxetane (33 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2 to 5%) to give the title compound (50 mg, 0.080 mmol, 78%) as a pale yellow oil.

1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylic Acid methyl 1-(4-(3,4-dichlorophenyl)-5-(isopropylthio)thiazol-2-yl)-3-methyl-4-(3-methyl-5-(oxetan-3-yloxy)phenyl)-1H-pyrazole-5-carboxylate (50 mg, 0.080 mmol) was diluted in a 1:1 solution of THF and MeOH (0.8 mL). 1M NaOH (0.16 mL, 0.16 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified semi-prep HPLC-MS (column X-Bridge 30×50) using a solution of MeCN in water (containing 10 mM of ammonium formate) (55 to 75%). The product was lyophilysed to give the title compound (7.3 mg, 0.012 mmol, 15%) as a pale yellow solid.

$^1$H NMR (500 MHz, DMSO) δ 8.22 (d, J=1.7 Hz, 1H), 8.04 (dd, J=8.5, 1.8 Hz, 1H), 7.74 (d, J=8.5 Hz, 1H), 7.17 (s, 1H), 6.89 (s, 2H), 5.33 (d, J=5.2 Hz, 1H), 4.95 (t, J=7.0 Hz, 2H), 4.56 (dd, J=8.0, 4.9 Hz, 2H), 3.35 (hept, J=6.7 Hz, 1H), 2.30 (s, 3H), 1.24 (d, J=6.7 Hz, 6H); MS (m/z): 610.0 [M+1]$^+$.

Compound 199: 1-(4-(3,4-dichlorophenyl)-5-(isopropylthio)thiazol-2-yl)-4-(2-methoxy-6-methylpyridin-4-yl)-3-methyl-1H-pyrazole-5-carboxylic Acid 4-bromo-2-methoxy-6-methylpyridine Diisopropyl diazocarboxylate (323 mg, 1.60 mmol) was added to a solution of 4-bromo-6-methylpyridin-2-ol (200 mg, 1.06 mmol), methanol (54 μL, 1.3 mmol) and triphenylphosphine (419 mg, 1.60 mmol) in THF (4.6 mL). The reaction mixture was stirred at r.t. for 18 h. Ethyl acetate was added and the mixture was washed with 1N NaOH (3×). The organic layer was dried with sodium sulfate, filtered and evaporated under reduced pressure. The crude product was purified by flash chromatography on silica gel using a solution of ethyl acetate in hexanes (5 to 10%) to give the title compound (65 mg, 0.32 mmol, 30%).

methyl 1-(4-(3,4-dichlorophenyl)-5-(isopropylthio)thiazol-2-yl)-4-(2-methoxy-6-methylpyridin-4-yl)-3-methyl-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 4-bromo-2-methoxy-6-methylpyridine (25 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (5%) to give the title compound (27 mg, 0.048 mmol, 47%) as a pale yellow oil.

1-(4-(3,4-dichlorophenyl)-5-(isopropylthio)thiazol-2-yl)-4-(2-methoxy-6-methylpyridin-4-yl)-3-methyl-1H-pyrazole-5-carboxylic Acid methyl 1-(4-(3,4-dichlorophenyl)-5-(isopropylthio)thiazol-2-yl)-4-(2-methoxy-6-methylpyridin-4-yl)-3-methyl-1H-pyrazole-5-carboxylate (27 mg, 0.048 mmol) was diluted in a 1:1 solution of THF and MeOH (0.48 mL). 1M NaOH (0.096 mL, 0.096 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (50 to 70%). The product was lyophilysed to give the title compound (9.3 mg, 0.017 mmol, 35%) as a pale yellow solid.

$^1$H NMR (500 MHz, DMSO) δ 8.20 (d, J=2.0 Hz, 1H), 8.02 (dd, J=8.5, 2.1 Hz, 1H), 7.78 (d, J=8.5 Hz, 1H), 6.94 (s, 1H), 6.68 (s, 1H), 3.87 (s, 3H), 3.35 (hept, J=6.7 Hz, 1H), 2.44 (s, 3H), 2.33 (s, 3H), 1.24 (d, J=6.7 Hz, 6H); MS (m/z): 549.4 [M+1]$^+$.

Compound 200: 1-(4-(3,4-dichlorophenyl)-5-(isopropylthio)thiazol-2-yl)-4-(3-fluoro-5-(oxetan-3-yloxy)phenyl)-3-methyl-1H-pyrazole-5-carboxylic Acid 3-(3-bromo-5-fluorophenoxy)oxetane Diisopropyl diazocarboxylate (318 mg, 1.57 mmol) was added to a solution of 3-bromo-5-fluorophenol (200 mg, 1.05 mmol), oxetan-3-ol (97 mg, 1.3 mmol) and triphenylphosphine (412 mg, 1.57 mmol) in THF (4.6 mL). The reaction mixture was stirred at r.t. for 18 h. Ethyl acetate was added and the mixture was washed with 1N NaOH (3×). The organic layer was dried with sodium sulfate, filtered and evaporated under reduced pressure. The crude product was purified by flash chromatography on silica gel using a solution of ethyl acetate in hexanes (10 to 20%) to give the title compound (186 mg, 0.753 mmol, 72%) as a colorless oil.

methyl 1-(4-(3,4-dichlorophenyl)-5-(isopropylthio)thiazol-2-yl)-4-(3-fluoro-5-(oxetan-3-yloxy)phenyl)-3-methyl-1H-pyrazole-5-carboxylate A solution of 1-(4-(3,4-dichlorophenyl)-5-(isopropylthio)thiazol-2-yl)-5-(methoxycarbonyl)-3-methyl-1H-pyrazol-4-ylboronic acid (50 mg, 0.10 mmol), 3-(3-bromo-5-fluorophenoxy)oxetane (30 mg, 0.12 mmol), Pd(PPh$_3$)$_4$ (12 mg, 0.10 mmol), Na$_2$CO$_3$ (54 mg, 0.51 mmol) in degassed 1,4-dioxane and H$_2$O (4:1, 2.1 mL) was heated at 85° C. for 18 hours. water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2 to 20%) to give the title compound (26 mg, 0.043 mmol, 42%) as a pale yellow oil.

1-(4-(3,4-dichlorophenyl)-5-(isopropylthio)thiazol-2-yl)-4-(3-fluoro-5-(oxetan-3-yloxy)phenyl)-3-methyl-1H-pyrazole-5-carboxylic Acid methyl 1-(4-(3,4-dichlorophenyl)-5-(isopropylthio)thiazol-2-yl)-4-(3-fluoro-5-(oxetan-3-yloxy)phenyl)-3-methyl-1H-pyrazole-5-carboxylate (26 mg, 0.043 mmol) was diluted in a 1:1 solution of THF and MeOH (0.43 mL). 1M NaOH (0.086 mL, 0.086 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50)

using a solution of MeCN in water (containing 10 mM of ammonium formate) (50 to 70%). The product was lyophilysed to give the title compound (13 mg, 0.022 mmol, 49%) as a pale yellow solid.

$^1$H NMR (500 MHz, DMSO) δ 8.19 (d, J=1.9 Hz, 1H), 8.01 (dd, J=8.5, 2.0 Hz, 1H), 7.77 (d, J=8.5 Hz, 1H), 6.94 (d, J=8.8 Hz, 1H), 6.76 (d, J=10.7 Hz, 1H), 6.71 (s, 1H), 5.33 (quint., J=5.3 Hz, 1H), 4.94 (t, J=6.7 Hz, 2H), 4.57 (dd, J=7.2, 5.0 Hz, 2H), 3.36 (hept, J=6.7 Hz, 1H), 2.32 (s, 3H), 1.24 (d, J=6.7 Hz, 6H); MS (m/z): 594.3 [M+1]$^+$.

Compound 201: 1-(4-(benzofuran-2-yl)-5-(isopropylthio)thiazol-2-yl)-4-(3-fluorophenyl)-3-methyl-1H-pyrazole-5-carboxylic acid and 4-(3-fluorophenyl)-1-(4-(3-fluorophenyl)-5-(isopropylthio)thiazol-2-yl)-3-methyl-1H-pyrazole-5-carboxylic Acid methyl 1-(4-(benzofuran-2-yl)-5-(isopropylthio)thiazol-2-yl)-4-bromo-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (200 mg, 0.439 mmol), benzofuran-2-ylboronic acid (66.8 mg, 0.439 mmol) and K$_2$CO$_3$ (304 mg, 2.20 mmol), nitrogen and vacuum cycles were performed (2×). Nitrogen gas was bubbled through a solution of THF (2 mL) and then the solution was added to the microwave vial, followed by the addition of the catalyst Pd(dtbpf)Cl$_2$ (28.6 mg, 0.044 mmol). The vial was capped and placed in an oil bath at 90° C. for 16 h. The solvent was evaporated under vacuum and the crude product was purified by flash chromatography on silica gel (wet loading with DCM) using a solution of DCM in hexanes (10 to 50% gradient) and afforded the title compound and some starting material (43.5 mg, 0.088 mmol, 20%) as yellow oil.

methyl 1-(4-(benzofuran-2-yl)-5-(isopropylthio)thiazol-2-yl)-4-(3-fluorophenyl)-3-methyl-1H-pyrazole-5-carboxylate and methyl 4-(3-fluorophenyl)-1-(4-(3-fluorophenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the pyrazoles (43.5 mg, 0.088 mmol), 3-fluorophenylboronic acid (14.8 mg, 0.106 mmol) and Na$_2$CO$_3$ (46.8 mg, 0.441 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (10.2 mg, 0.009 mmol). The vial was capped and placed in an oil bath at 85° C. for 16 h. The crude product was purified by flash chromatography on silica gel (dry packing) using a solution of EtOAc in hexanes (2% isocratic), affording the titles compounds (14.9 mg, 0.029 mmol, 33%) as yellow oil.

1-(4-(benzofuran-2-yl)-5-(isopropylthio)thiazol-2-yl)-4-(3-fluorophenyl)-3-methyl-1H-pyrazole-5-carboxylic Acid and 4-(3-fluorophenyl)-1-(4-(3-fluorophenyl)-5-(isopropylthio)thiazol-2-yl)-3-methyl-1H-pyrazole-5-carboxylic Acid Into a 25 mL round bottom flask, the pyrazoles (14.9 mg, 0.029 mmol) was diluted with THF/MeOH (2 mL, 1:1). A solution of NaOH 1 M (58.6 μL, 0.059 mmol) was added and the reaction was stirred 16 h at rt. The reaction mixture was acidified with HCl 1 M and the crude product was concentrated under vacuum. The product was purified using a semi prep HPLC-MS (column X-Bridge 30×50, eluted with 25-45% MeCN/NH$_4$CO$_3$H 10 mM, pH 3.8/Flow 45 ml/min/11 min), resulting in the title compound A (0.74 mg, 0.001 mmol, 5%) and title compound B (2.39 mg, 0.005 mmol, 17%) as yellow solids after lyophilisation.

$^1$H NMR (500 MHz, MeOD) δ 7.66 (d, J=7.7 Hz, 1H), 7.56-7.52 (m, 1H), 7.51 (d, J=0.9 Hz, 1H), 7.47-7.40 (m, 1H), 7.38 (dt, J=7.7, 1.2 Hz, 1H), 7.36-7.31 (m, 2H), 7.29-7.23 (m, 1H), 7.10-7.03 (m, 1H), 3.50-3.41 (m, 1H), 2.36 (s, 3H), 1.39 (d, J=6.7 Hz, 6H); MS (m/z): 494.3 [M+1]$^+$.

$^1$H NMR (500 MHz, MeOD) δ 8.09-8.04 (m, 1H), 8.02-7.96 (m, 1H), 7.47-7.40 (m, 2H), 7.39-7.35 (m, 1H), 7.34-7.29 (m, 1H), 7.12-7.02 (m, 2H), 3.31-3.24 (m, 1H), 2.35 (s, 3H), 1.29 (d, J=6.7 Hz, 6H); MS (m/z): 472.4 [M+1]$^+$.

Compound 206: 1-(4-(4-chloro-2-methoxyphenyl)-5-(isopropylthio)thiazol-2-yl)-4-(2,6-dimethylpyridin-4-yl)-3-methyl-1H-pyrazole-5-carboxylic Acid methyl 1-(4-(4-chloro-2-methoxyphenyl)-5-(isopropylthio)thiazol-2-yl)-4-(2,6-dimethylpyridin-4-yl)-3-methyl-1H-pyrazole-5-carboxylate Nitrogene was passed through a solution of dioxane/H$_2$O (4/1) and this solution (2.0 mL) was then added to a mixture of the methyl 4-bromo-1-(4-(4-chloro-2-methoxyphenyl)-5-(isopropylthio)thiazol-2-yl)-3-methyl-1H-pyrazole-5-carboxylate (41 mg, 0.079 mmol), 2,6-dimethyl-4-(4,4,5,5-tetramethyl-1,3,2-dioxaborolan-2-yl)pyridine (44 mg, 0.19 mmol) and Na$_2$CO$_3$ (42 mg, 0.40 mmol) followed by the addition of the catalyst Pd(PPh$_3$)$_4$ (9.2 mg, 0.0080 mmol). The reaction mixture was heated at 85° C. for 16 hours. The solvent was evaporated under vacuum and the crude product was purified by flash chromatography (dry packing) on silica gel using a gradient 0 to 40% EtOAc in hexanes to give the title compound (18 mg, 0.034 mmol, 43%) as a yellow oil.

1-(4-(4-chloro-2-methoxyphenyl)-5-(isopropylthio)thiazol-2-yl)-4-(2,6-dimethylpyridin-4-yl)-3-methyl-1H-pyrazole-5-carboxylic Acid The methyl 1-(4-(4-chloro-2-methoxyphenyl)-5-(isopropylthio)thiazol-2-yl)-4-(2,6-dimethylpyridin-4-yl)-3-methyl-1H-pyrazole-5-carboxylate (18 mg, 0.034 mmol) was dissolved in a mixture of H$_2$O/THF/MeOH (6/3/1) (1.3 mL) and treated with LiOH (4.1 mg, 0.17 mmol). The reaction mixture was stirred in the microwave at 110° C. for 15 min. Evaporated in vacuo. The crude product was purified by semi-prep HPLC-MS (column X-Bridge 30×50, eluted with 45-65% MeCN/NH$_4$CO$_2$H 10 mM, pH 3.8/Flow 45 ml/min/10 min), and afforded the title compound (7.4 mg, 0.014 mmol, 41%) as a yellowish solid after lyophilisation.

$^1$H NMR (500 MHz, DMSO) δ 7.28 (d, J=8.1 Hz, 1H), 7.21 (d, J=2.0 Hz, 1H), 7.13-7.08 (m, 3H), 3.79 (s, 3H), 3.23-3.14 (m, 1H), 2.45 (s, 6H), 2.31 (s, 3H), 1.14 (d, J=6.7 Hz, 6H). MS (m/z): 529.2 [M+1]+.

Compound 207: 1-(4-(3-chloro-4-methylphenyl)-5-(isopropylthio)thiazol-2-yl)-4-(3-fluorophenyl)-3-methyl-1H-pyrazole-5-carboxylic Acid methyl 4-bromo-1-(4-(3-chloro-4-methylphenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (100 mg, 0.220 mmol), the (3-chloro-4-methylphenyl)boronic acid (38 mg, 0.22 mmol), $K_2CO_3$ (152 mg, 1.10 mmol) and THF (2 mL). Nitrogen was bubbled in the solvent for 10 minutes followed by the addition of the catalyst $Pd(dtbpf)Cl_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes to give the title compound (66 mg, 0.13 mmol, 60%) as a yellow oil.

methyl 1-(4-(3-chloro-4-methylphenyl)-5-(isopropylthio)thiazol-2-yl)-4-(3-fluorophenyl)-3-methyl-1H-pyrazole-5-carboxylate Nitrogene was passed through a solution of dioxane/$H_2O$ (4/1) and this solution (2.0 mL) was then added to a mixture of the methyl 4-bromo-1-(4-(3-chloro-4-methylphenyl)-5-(isopropylthio)thiazol-2-yl)-3-methyl-1H-pyrazole-5-carboxylate (66 mg, 0.13 mmol), (3-fluorophenyl)boronic acid (22 mg, 0.16 mmol) and $Na_2CO_3$ (70 mg, 0.66 mmol) followed by the addition of the catalyst $Pd(PPh_3)_4$ (15 mg, 0.013 mmol). The reaction mixture was heated at 85° C. for 16 hours. The solvent was evaporated under vacuum and the crude product was purified by flash chromatography (dry packing) on silica gel using a gradient 0 to 10% EtOAc in hexanes to give the title compound (48 mg, 0.093 mmol, 71%) as a yellow oil.

1-(4-(3-chloro-4-methylphenyl)-5-(isopropylthio)thiazol-2-yl)-4-(3-fluorophenyl)-3-methyl-1H-pyrazole-5-carboxylic Acid The methyl 1-(4-(3-chloro-4-methylphenyl)-5-(isopropylthio)thiazol-2-yl)-4-(3-fluorophenyl)-3-methyl-1H-pyrazole-5-carboxylate (48 mg, 0.093 mmol) was dissolved in a mixture of $H_2O$/THF/MeOH (6/3/1) (1.3 mL) and treated with LiOH (11 mg, 0.47 mmol). The reaction mixture was stirred in the microwave at 110° C. for 15 min. Evaporated in vacuo. The crude product was purified by semi-prep HPLC-MS (column X-Bridge 30×50, eluted with 60-80% MeCN/$NH_4CO_2H$ 10 mM, pH 3.8/Flow 45 ml/min/10 min), and afforded the title compound (14 mg, 0.028 mmol, 30%) as a yellow solid after lyophilisation.

$^1$H NMR (500 MHz, DMSO) δ 14.36 (s, 1H), 8.04 (d, J=1.6 Hz, 1H), 7.90 (dd, J=8.0, 1.6 Hz, 1H), 7.54-7.47 (m, 1H), 7.45 (d, J=8.0 Hz, 1H), 7.37-7.30 (m, 2H), 7.25-7.18 (m, 1H), 3.35-3.30 (m, 1H), 2.37 (s, 3H), 2.30 (s, 3H), 1.23 (d, J=6.7 Hz, 6H). MS (m/z): 502.1 [M+1]+.

Compound 208: 1-(4-(1,5-dimethyl-6-oxo-1,6-dihydropyridin-3-yl)-5-(isopropylthio)thiazol-2-yl)-4-(3-fluorophenyl)-3-methyl-1H-pyrazole-5-carboxylic Acid 1,3-dimethyl-5-(4,4,5,5-tetramethyl-1,3,2-dioxaborolan-2-yl)pyridin-2(1H)-one Nitrogene was passed through dioxane and this solution (2.0 mL) was then added to a mixture of the 5-bromo-1,3-dimethylpyridin-2(1H)-one (75 mg, 0.37 mmol), bis(pinacolato)diboron (113 mg, 0.445 mmol) and KOAc (109 mg, 1.11 mmol) followed by the addition of the catalyst $PdCl_2$(dppf).$CH_2Cl_2$ (30 mg, 0.037 mmol). The reaction mixture was heated at 85° C. for 16 hours then diluted with EtOAc and filtered on a pad of Celite®. The filtrate was concentrated under vacuum, resulting in the crude title compound (169 mg, 0.678 mmol, quantitative yield) as brown oil.

methyl 4-bromo-1-(4-(1,5-dimethyl-6-oxo-1,6-dihydropyridin-3-yl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (100 mg, 0.220 mmol), the 1,3-dimethyl-5-(4,4,5,5-tetramethyl-1,3,2-dioxaborolan-2-yl)pyridin-2(1H)-one (110 mg, 0.440 mmol), $K_2CO_3$ (152 mg, 1.10 mmol) and THF (2 mL). Nitrogen was bubbled in the solvent for 10 minutes followed by the addition of the catalyst $Pd(dtbpf)Cl_2$ (11 mg, 0.022 mmol). The vial was capped and placed in an oil bath at 90° C. for 16 h. The solvent was evaporated under vacuum and the crude product was purified by flash chromatography (dry packing) on silica gel using a gradient 0 to 10% EtOAc in hexanes to give the title compound (42 mg, 0.084 mmol, 38%) as a brown oil.

methyl 1-(4-(1,5-dimethyl-6-oxo-1,6-dihydropyridin-3-yl)-5-(isopropylthio)thiazol-2-yl)-4-(3-fluorophenyl)-3-methyl-1H-pyrazole-5-carboxylate Nitrogene was passed through a solution of dioxane/H2O (4/1) and this solution (2.0 mL) was then added to a mixture of the methyl 4-bromo-1-(4-(1,5-dimethyl-6-oxo-1,6-dihydropyridin-3-yl)-5-(isopropylthio)thiazol-2-yl)-3-methyl-1H-pyrazole-5-carboxylate (42 mg, 0.084 mmol), (3-fluorophenyl)boronic acid (14 mg, 0.10 mmol) and Na2CO3 (44 mg, 0.42 mmol) followed by the addition of the catalyst Pd(PPh3)4 (9.7 mg, 0.0084 mmol). The reaction mixture was heated at 85° C. for 16 hours. The solvent was evaporated under vacuum and the crude product was purified by flash chromatography (dry packing) on silica gel using a gradient 0 to 40% EtOAc in hexanes to give the title compound (14 mg, 0.027 mmol, 32%) as a yellow oil.

1-(4-(1,5-dimethyl-6-oxo-1,6-dihydropyridin-3-yl)-5-(isopropylthio)thiazol-2-yl)-4-(3-fluorophenyl)-3-methyl-1H-pyrazole-5-carboxylic Acid The methyl 1-(4-(1,5-dimethyl-6-oxo-1,6-dihydropyridin-3-yl)-5-(isopropylthio)thiazol-2-yl)-4-(3-fluorophenyl)-3-methyl-1H-pyrazole-5-carboxylate (14 mg, 0.027 mmol) was dissolved in a mixture of $H_2O$/THF/MeOH (6/3/1) (1.3 mL) and treated with LiOH (3.2 mg, 0.14 mmol). The reaction mixture was stirred in the microwave at 110° C. for 15 min. Evaporated in vacuo. The crude product was purified by semi-prep HPLC-MS (column X-Bridge 30×50, eluted with 40-60% MeCN/$NH_4CO_2H$ 10 mM, pH 3.8/Flow 45 ml/min/10 min), and afforded the title compound (4.9 mg, 0.010 mmol, 36%) as a yellowish solid after lyophilisation.

$^1$H NMR (500 MHz, DMSO) δ 8.18-8.11 (m, 1H), 8.04 (bs, 1H), 7.50-7.43 (m, 1H), 7.40-7.32 (m, 2H), 7.21-7.14 (m, 1H), 3.48 (s, 3H), 3.35-3.24 (m, 1H), 2.30 (s, 3H), 2.05 (s, 3H), 1.24 (d, J=6.7 Hz, 6H). MS (m/z): 499.2 [M+1]+.

Compound 212: 4-(3-fluorophenyl)-1-(5-(isopropylthio)-4-(pyrimidin-5-yl)thiazol-2-yl)-3-methyl-1H-pyrazole-5-carboxylic Acid methyl 4-bromo-1-(5-(isopropylthio)-4-(pyrimidin-5-yl)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (75 mg, 0.16 mmol), pyrimidin-5-ylboronic acid (20 mg, 0.16 mmol), $K_2CO_3$ (114 mg, 0.825 mmol) and THF (2 mL). Nitrogen was bubbled in the solvent for 10 minutes followed by the addition of the catalyst Pd(dtbpf)Cl$_2$(8.2 mg, 0.026 mmol). The vial was capped and placed in an oil bath at 90° C. for 16 h. The solvent was evaporated under vacuum and the crude product was purified by flash chromatography on silica gel using a solution of EtOAc in hexanes (0 to 30% gradient) and afforded the title compound (36 mg, 0.079 mmol, 48%) as brown oil.

4-(3-fluorophenyl)-1-(5-(isopropylthio)-4-(pyrimidin-5-yl)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(5-(isopropylthio)-4-(pyrimidin-5-yl)thiazol-2-yl)-3-methyl-1H-pyrazole-5-carboxylate (36 mg, 0.079 mmol), (3-fluorophenyl)boronic acid (13 mg, 0.095 mmol) and $Na_2CO_3$ (42 mg, 0.40 mmol). Nitrogen gas was bubbled through a solution of dioxane/water (2 mL, 4:1) and then the solution was added to the microwave vial, followed by the addition of the catalyst Pd(PPh$_3$)$_4$ (9.2 mg, 0.0080 mmol). The vial was capped and placed in an oil bath at 85° C. for 16 h. LiOH (9.5 mg, 0.40 mmol) was added to the reaction mixture and stirred under microwave radiation at 110° C. for 15 min. The solvent was evaporated under vacuum and the product was purified using a semi prep HPLC-MS (column X-Bridge 30×50, eluted with 50-70% MeCN/NH$_4$CO$_2$H 10 mM, pH 3.8/Flow 45 ml/min/10 min), resulting in the title compound (3.2 mg, 0.0070 mmol, 9%) as yellowish solid after lyophilization.

$^1$H NMR (500 MHz, DMSO) δ 9.36 (s, 2H), 9.23 (s, 1H), 7.56-7.47 (m, 1H), 7.38-7.31 (m, 2H), 7.26-7.17 (m, 1H), 3.45-3.33 (m, 1H), 2.33 (s, 3H), 1.24 (d, J=6.7 Hz, 6H). MS (m/z): 456.1 [M+1]$^+$.

Compound 218: 1-(4-(4-chloro-3-cyanophenyl)-5-(isopropylthio)thiazol-2-yl)-4-(3-fluorophenyl)-3-methyl-1H-pyrazole-5-carboxylic Acid methyl 4-bromo-1-(4-(4-chloro-3-cyanophenyl)-5-(isopropylthio)thiazol-2-yl)-3-methyl-1H-pyrazole-5-carboxylate Degassed THF (2 mL) was added to a mixture of methyl 4-bromo-1-(4-bromo-5-(isopropylthio)thiazol-2-yl)-3-methyl-1H-pyrazole-5-carboxylate (75.0 mg, 0.165 mmol), (4-chloro-3-cyanophenyl)boronic acid (30 mg, 0.16 mmol), [1,1'-Bis(di-tert-butylphosphino)ferrocene]dichloropalladium(II) (8.2 mg, 0.016 mmol) and potassium carbonate (114 mg, 0.824 mmol). The reaction mixture was heated at 90° C. for 18 hours. Water was added and the mixture was extracted with ethyl acetate (2×). The combined organic layers were dried with sodium sulfate, filtered and evaporated. The crude product was purified by flash chromatography on silica gel using a solution of ethyl acetate in hexanes (2 to 5%) to give the title compound (35 mg, 0.068 mmol, 42%) as a pale orange oil.

methyl 1-(4-(4-chloro-3-cyanophenyl)-5-(isopropylthio)thiazol-2-yl)-4-(3-fluorophenyl)-3-methyl-1H-pyrazole-5-carboxylate A solution of methyl 4-bromo-1-(4-(4-chloro-3-cyanophenyl)-5-(isopropylthio)thiazol-2-yl)-3-methyl-1H-pyrazole-5-carboxylate (35 mg, 0.068 mmol), (3-fluorophenyl)boronic acid (12 mg, 0.082 mmol), Pd(PPh$_3$)$_4$ (8 mg, 0.007 mmol), $Na_2CO_3$ (36 mg, 0.34 mmol) in degassed 1,4-dioxane and $H_2O$ (4:1, 1.4 mL) was heated at 85° C. for 18 hours. Water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2 to 5%) to give the title compound (9 mg, 0.017 mmol, 25%) as a colorless oil.

1-(4-(4-chloro-3-cyanophenyl)-5-(isopropylthio) thiazol-2-yl)-4-(3-fluorophenyl)-3-methyl-1H-pyrazole-5-carboxylic Acid methyl 1-(4-(4-chloro-3-cyanophenyl)-5-(isopropylthio) thiazol-2-yl)-4-(3-fluorophenyl)-3-methyl-1H-pyrazole-5-carboxylate (9 mg, 0.017 mmol) was diluted in a 1:1 solution of THF and MeOH (0.17 mL). 1M NaOH (0.034 mL, 0.034 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (50 to 70%). The product was lyophylised to give the title compound (3.2 mg, 0.006 mmol, 36%) as an off white solid.

$^1$H NMR (500 MHz, CDCl$_3$) δ 8.45 (s, 1H), 8.38 (d, J=8.2 Hz, 1H), 7.88 (d, J=8.6 Hz, 1H), 7.52-7.44 (m, 1H), 7.42-7.33 (m, 2H), 7.22-7.14 (m, 1H), 3.35 (hept, J=6.7 Hz, 1H), 2.31 (s, 3H), 1.23 (d, J=6.7 Hz, 6H); MS (m/z): 512.9 [M+1]$^+$.

Compound 219: 4-(3,5-dichlorophenyl)-1-(5-(isopropylthio)-4-(4-(trifluoromethyl)phenyl)thiazol-2-yl)-3-methyl-1H-pyrazole-5-carboxylic Acid In a 5 mL glass microwave vial equipped with a magnetic stirring bar and nitrogen flow at room temperature was methyl 4-bromo-1-(5-(isopropylthio)-4-(4-(trifluoromethyl) phenyl)thiazol-2-yl)-3-methyl-1H-pyrazole-5-carboxylate (52 mg, 0.10 mmol), (3,5-dichlorophenyl)boronic acid (23 mg, 0.12 mmol) and $Na_2CO_3$ (53 mg, 0.50 mmol) Nitrogen gas was bubbled through a solution of dioxane/water (2 mL, 4:1) and then the solution was added to the microwave vial, followed by the addition of the catalyst Pd(PPh$_3$)$_4$ (12 mg, 0.010 mmol). The vial was capped and placed in an oil bath at 85° C. for 16 h. LiOH (9.5 mg, 0.40 mmol) was added to the reaction mixture and stirred under microwave radiation at 110° C. for 15 min. The solvent was evaporated under vacuum and the product was purified using a semi prep HPLC-MS (column X-Bridge 30×50, eluted with 65-85% MeCN/NH$_4$CO$_2$H 10 mM, pH 3.8/Flow 45 ml/min/10 min), resulting in the title compound (10 mg, 0.018 mmol, 18%) as yellow solid after lyophilization.

$^1$H NMR (500 MHz, DMSO) δ 8.20 (d, J=8.2 Hz, 2H), 7.85 (d, J=8.2 Hz, 2H), 7.65 (s, 1H), 7.55 (d, J=1.8 Hz, 2H), 3.41-3.28 (m, 1H), 2.32 (s, 3H), 1.23 (d, J=6.7 Hz, 6H). MS (m/z): 571.9 [M+1]$^+$.

Compound 220: 4-(3-fluorophenyl)-1-(5-(isopropylthio)-4-(4-((2-methoxyethyl)carbamoyl)phenyl)thiazol-2-yl)-3-methyl-1H-pyrazole-5-carboxylic Acid

4-(2-(4-bromo-5-(methoxycarbonyl)-3-methyl-1H-pyrazol-1-yl)-5-(isopropylthio)thiazol-4-yl)benzoic Acid In a 5 mL glass microwave vial equipped with a magnetic stirring bar and nitrogen flow at room temperature was placed the methyl 4-bromo-1-(4-bromo-5-(isopropylthio)thiazol-2-yl)-3-methyl-1H-pyrazole-5-carboxylate (125 mg, 0.275 mmol), 4-boronobenzoic acid (46 mg, 0.27 mmol), $K_2CO_3$ (190 mg, 1.37 mmol) and THF (2 mL). Nitrogen was bubbled in the solvent for 10 minutes followed by the addition of the catalyst $Pd(dtbpf)Cl_2$ (14 mg, 0.028 mmol). The vial was capped and placed in an oil bath at 90° C. for 16 h. Acidified with aq. HCl and extracted with EtOAc. The organic layer was washed with water and brine. The crude product was purified by flash chromatography (dry packing) on silica gel using a gradient 50 to 100% EtOAc in hexanes to give the title compound (30 mg, 0.060 mmol, 22%) as a brown solid.

methyl 4-bromo-1-(5-(isopropylthio)-4-(4-((2-methoxyethyl)carbamoyl)phenyl)thiazol-2-yl)-3-methyl-1H-pyrazole-5-carboxylate 4-(2-(4-bromo-5-(methoxycarbonyl)-3-methyl-1H-pyrazol-1-yl)-5-(isopropylthio)thiazol-4-yl)benzoic acid (30 mg, 0.060 mmol) and 2-methoxyethanamine (5.4 mg, 0.072 mmol) were dissolved in DMF (1 mL) and treated with HATU (30 mg, 0.079 mmol) followed by DIPEA (16 mg, 0.12 mmol). The reaction mixture was stirred at rt for 16 h. Diluted with EtOAc washed with water and brine. Dried $MgSO_4$, filtered and concentrated in vacuo to give the title compound (43 mg, 0.077 mmol, quantitative yield) as a brown oil.

methyl 4-(3-fluorophenyl)-1-(5-(isopropylthio)-4-(4-((2-methoxyethyl)carbamoyl)phenyl)thiazol-2-yl)-3-methyl-1H-pyrazole-5-carboxylate Nitrogene was passed through a solution of dioxane/$H_2O$ (4/1) and this solution (2.0 mL) was then added to a mixture of methyl 4-bromo-1-(5-(isopropylthio)-4-(4-((2-methoxyethyl)carbamoyl)phenyl)thiazol-2-yl)-3-methyl-1H-pyrazole-5-carboxylate (33 mg, 0.060 mmol), (3-fluorophenyl)boronic acid (10 mg, 0.072 mmol) and $Na_2CO_3$ (32 mg, 0.30 mmol) followed by the addition of the catalyst $Pd(PPh_3)_4$ (6.9 mg, 0.0060 mmol). The reaction mixture was heated at 85° C. for 16 hours. The solvent was evaporated under vacuum and the crude product was purified by flash chromatography (dry packing) on silica gel using a gradient 0 to 50% EtOAc in hexanes to give the title compound (10 mg, 0.018 mmol, 30%) as a yellow oil.

4-(3-fluorophenyl)-1-(5-(isopropylthio)-4-(4-((2-methoxyethyl)carbamoyl)phenyl)thiazol-2-yl)-3-methyl-1H-pyrazole-5-carboxylic Acid The methyl 4-(3-fluorophenyl)-1-(5-(isopropylthio)-4-(4-((2-methoxyethyl)carbamoyl)phenyl)thiazol-2-yl)-3-methyl-1H-pyrazole-5-carboxylate (10 mg, 0.018 mmol) was dissolved in a mixture of $H_2O$/THF/MeOH (6/3/1) (1.3 mL) and treated with LiOH (2.2 mg, 0.090 mmol). The reaction mixture was stirred in the microwave at 110° C. for 15 min. Evaporated in vacuo. The crude product was purified by semi-prep HPLC-MS (column X-Bridge 30×50, eluted with 45-5% MeCN/$NH_4CO_2H$ 10 mM, pH 3.8/Flow 45 ml/min/10 min), and afforded the title compound (3.1 mg, 0.0056 mmol, 32%) as a yellow solid after lyophilisation.

$^1$H NMR (500 MHz, DMSO) δ 8.60 (t, J=5.3 Hz, 1H), 8.08 (d, J=8.4 Hz, 2H), 7.95-7.89 (m, 2H), 7.54-7.47 (m, 1H), 7.40-7.30 (m, 2H), 7.25-7.16 (m, 1H), 3.50-3.41 (m, 4H), 3.36-3.30 (m, 1H), 3.28 (s, 3H), 2.32 (s, 3H), 1.22 (d, J=6.7 Hz, 6H). MS (m/z): 555.2 [M+1]+.

Compound 223: 4-(3-fluorophenyl)-1-(5-(isopropylthio)-4-(4-(trifluoromethoxy)phenyl)thiazol-2-yl)-3-methyl-1H-pyrazole-5-carboxylic Acid methyl 4-bromo-1-(5-(isopropylthio)-4-(4-(trifluoromethoxy)phenyl)thiazol-2-yl)-3-methyl-1H-pyrazole-5-carboxylate Degassed THF (2 mL) was added to a mixture of methyl 4-bromo-1-(4-bromo-5-(isopropylthio)thiazol-2-yl)-3-methyl-1H-pyrazole-5-carboxylate (75.0 mg, 0.165 mmol) (4-(trifluoromethoxy)phenyl)boronic acid (34 mg, 0.16 mmol), [1,1-Bis(di-tert-butylphosphino)ferrocene]dichloropalladium(II) (8.2 mg, 0.016 mmol) and potassium carbonate (114 mg, 0.824 mmol). The reaction mixture was heated at 90° C. for 18 hours. Water was added and the mixture was extracted with ethyl acetate (2×). The combined organic layers were dried with sodium sulfate, filtered and evaporated. The crude product was purified by flash chromatography on silica gel using a solution of ethyl acetate in hexanes (2%) to give the title compound (52 mg, 0.097 mmol, 59%) as a pale orange oil.

methyl 4-(3-fluorophenyl)-1-(5-(isopropylthio)-4-(4-(trifluoromethoxy)phenyl)thiazol-2-yl)-3-methyl-1H-pyrazole-5-carboxylate A solution of methyl 4-bromo-1-(5-(isopropylthio)-4-(4-(trifluoromethoxy)phenyl)thiazol-2-yl)-3-methyl-1H-pyrazole-5-carboxylate (52 mg, 0.097 mmol), (3-fluorophenyl)boronic acid (16 mg, 0.12 mmol), $Pd(PPh_3)_4$ (11 mg, 0.010 mmol), $Na_2CO_3$ (51 mg, 0.48 mmol) in degassed 1,4-dioxane and $H_2O$ (4:1, 1.9 mL) was heated at 85° C. for 18 hours. Water (5 mL) was added and the mixture was extracted with EtOAc (3×5 mL). The combined organic layers were dried with sodium sulfate, filtered and evaporated under reduced pressure. The crude product was purified by flash chromatography on silica gel using a solution of ethyl acetate in hexanes (2%) to give the title compound (38 mg, 0.069 mmol, 71%) as a pale orange oil.

4-(3-fluorophenyl)-1-(5-(isopropylthio)-4-(4-(trifluoromethoxy)phenyl)thiazol-2-yl)-3-methyl-1H-pyrazole-5-carboxylic Acid methyl 4-(3-fluorophenyl)-1-(5-(isopropylthio)-4-(4-(trifluoromethoxy)phenyl)thiazol-2-yl)-3-methyl-1H-pyrazole-5-carboxylate (38 mg, 0.069 mmol) was diluted in a 1:1 solution of THF and MeOH (0.69 mL). 1M NaOH (0.138 mL, 0.138 mmol) was added and the reaction was stirred for 18 h at room temperature. 1N HCl (1 mL) was added, followed by water (5 mL) and the mixture was extracted with EtOAc (3×5 mL). The combined organic layers were dried with sodium sulfate, filtered and evaporated under reduced pressure. The crude product was purified by semi-prep HPLC-MS (column X-Bridge 30×50) using a solution of MeCN in water (containing 10 mM of ammonium formate) (55 to 75%). The product was lyophylised to give the title compound (8.4 mg, 0.016 mmol, 23%) as a pale yellow solid.

$^1$H NMR (500 MHz, DMSO) δ 8.11 (d, J=8.8 Hz, 2H), 7.55-7.45 (m, 3H), 7.36-7.29 (m, 2H), 7.23 (t, J=8.2 Hz, 1H), 3.34 (hept, J=6.7 Hz, 1H), 2.31 (s, 3H), 1.23 (d, J=6.7 Hz, 6H); MS (m/z): 538.0 [M+1]$^+$.

Compound 228: 1-(4-(3,4-dichlorophenyl)-5-(isopropylthio)thiazol-2-yl)-4-(3-fluorophenyl)-3-isopropyl-1H-pyrazole-5-carboxylic Acid ethyl 2-(methoxyimino)-5-methyl-4-oxohexanoate

Ethyl 5-methyl-2,4-dioxohexanoate (931 mg, 5.00 mmol), methoxyhydroxylamine hydrochloride (439 mg, 5.25 mmol) were dissolved in EtOH/water (11 mL, 1:1). The reaction mixture was stirred 2 h at rt. The reaction mixture was diluted with EtOAc and transferred into an extraction funnel. The layers were separated and the aqueous layer was extracted with EtOAc (2×). The combined organic layers were dried over Na$_2$SO$_4$, filtered and concentrated under vacuum, affording the title compound (1.07 g, 4.97 mmol, 99%) as yellow oil.

ethyl 1-(4-(3,4-dichlorophenyl)-5-(isopropylthio)thiazol-2-yl)-3-isopropyl-1H-pyrazole-5-carboxylate Ethyl 2-(methoxyimino)-5-methyl-4-oxohexanoate (1.07 g, 4.97 mmol) was dissolved in EtOH (50 mL) and 4-(3,4-dichlorophenyl)-2-hydrazinylthiazole (1.67 g, 5.00 mmol) was added followed by HCl 12 N (1.67 mL, 20.0 mmol). The reaction mixture was heated to reflux 3 h. The reaction mixture was concentrated under vacuum and was diluted with EtOAc and transferred into an extraction funnel. The layers were separated and the aqueous layer was extracted with EtOAc (3×). The combined organic layers were dried over Na$_2$SO$_4$, filtered and concentrated under vacuum. The crude product was purified by flash chromatography on silica gel (dry packing) using a solution of DCM in hexanes (0 to 20% gradient), affording the title compound (906 mg, 1.87 mmol, 37%) as yellow oil.

ethyl 4-bromo-1-(4-(3,4-dichlorophenyl)-5-(isopropylthio)thiazol-2-yl)-3-isopropyl-1H-pyrazole-5-carboxylate Bromine (0.621 mL, 12.1 mmol) was added to a solution of ethyl 1-(4-(3,4-dichlorophenyl)-5-(isopropylthio)thiazol-2-yl)-3-isopropyl-1H-pyrazole-5-carboxylate (905 mg, 2.42 mmol) in MeCN/DCM (12 mL, 1:1 mL). The reaction was stirred for 5 hours at room temperature. A saturated aqueous solution of Na$_2$SO$_3$ was added and the reaction mixture was extracted with EtOAc (3×). The combined organic layers were dried with sodium sulfate, filtered and evaporated under reduced pressure. The crude product was purified by flash chromatography (dry packing) on silica gel using a solution of DCM in hexanes (2 to 5%), affording the title compound (593 mg, 1.05 mmol, 43%) as blue oil.

ethyl 1-(4-(3,4-dichlorophenyl)-5-(isopropylthio)thiazol-2-yl)-4-(3-fluorophenyl)-3-isopropyl-1H-pyrazole-5-carboxylate In a 5 mL glass microwave vial equipped with a magnetic stirring bar and nitrogen flow at room temperature was placed ethyl 4-bromo-1-(4-(3,4-dichlorophenyl)-5-(isopropylthio)thiazol-2-yl)-3-isopropyl-1H-pyrazole-5-carboxylate (50.0 mg, 0.089 mmol), 3-fluorophenylboronic acid (14.9 mg, 0.107 mmol) and Na$_2$CO$_3$ (47.0 mg, 0.444 mmol), nitrogen and vacuum cycles were performed (2×). Nitrogen gas was bubbled through a solution of dioxane/water (2 mL, 4:1) and then the solution was added to the microwave vial, followed by the addition of the catalyst Pd(PPh$_3$)$_4$ (10.3 mg, 0.009 mmol). The vial was capped and placed in an oil bath at 85° C. for 16 h. The crude product was purified by flash chromatography on silica gel (dry packing) using a solution of EtOAc in hexanes (0 to 5% gradient), affording the title compound (51 mg, 0.088 mmol, 99%) as colorless oil.

1-(4-(3,4-dichlorophenyl)-5-(isopropylthio)thiazol-2-yl)-4-(3-fluorophenyl)-3-isopropyl-1H-pyrazole-5-carboxylic Acid Into a 5 mL glass microwave vial, was placed ethyl 1-(4-(3,4-dichlorophenyl)-5-(isopropylthio)thiazol-2-yl)-4-(3-fluorophenyl)-3-isopropyl-1H-pyrazole-5-carboxylate (51.0 mg, 0.088 mmol) and LiOH (18.5 mg, 0.441 mmol). THF (1.5 mL), MeOH (0.5 mL) and water (0.5 mL) were added. The vial was heated to 120° C. under microwave radiation for 10 minutes. THF, MeOH and water were removed under vacuum and the crude product was purified using a semi prep HPLC-MS (X-Bridge 30×50, eluted with 60-80% MeCN/Am Form 10 mM, pH 3.8/Flow 45 ml/min/11 min), resulting in the title compound (0.4 mg, 0.001 mmol, 1%) as yellow solid after lyophilisation.

$^1$H NMR (500 MHz, MeOD) δ 8.45 (d, J=2.0 Hz, 1H), 8.14 (dd, J=8.5, 2.1 Hz, 1H), 7.55 (d, J=8.5 Hz, 1H), 7.45-7.37 (m, 1H), 7.33-7.29 (m, 1H), 7.28-7.22 (m, 1H), 7.06 (td, J=8.1, 2.1 Hz, 1H), 3.29-3.24 (m, 1H), 3.15-3.09 (m, 1H), 1.32-1.21 (m, 12H); MS (m/z): 552.02 [M+1]$^+$.

Compound 231: 1-(4-(4-ethylphenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar at room temperature was placed the methyl 4-bromo-1-(4-bromo-5-(isopropylthio)thiazol-2-yl)-3-methyl-1H-pyrazole-5-carboxylate (50 mg, 0.11 mmol), the 4-ethylphenylboronic acid (16 mg, 0.11 mmol), K$_2$CO$_3$ (75 mg, 0.55 mmol), the catalyst Pd(dtbpf)Cl$_2$ (7 mg, 0.01 mmol) and THF (1 mL). Nitrogen gas was bubbled through the solution and then the vial was capped and stirred in an oil bath at 90° C. After 16 h, the 3-fluorophenylboronic acid (15 mg, 0.11 mmol), Na$_2$CO$_3$ (58 mg, 0.55 mmol), the catalyst Pd(PPh$_3$)$_4$ (13 mg, 0.011 mmol) and water (0.5 mL) were added to the vial. A flow of nitrogen was bubbled through the black mixture for 5 minutes. The vial was capped and stirred in an oil bath at 90° C. After 16 h, LiOH (26 mg, 1.1 mmol) was added to the reaction mixture and stirred under microwave radiation at 110° C. for 30 min. The crude product was purified using a semi prep HPLC-MS (X-Bridge 30×50, eluted with 65-85% MeCN/NH$_4$CO$_2$H 10 mM, pH 3.8/Flow 45 mL/min/11 min), resulting in the title compound (7 mg, 0.01 mmol, 13%) as a yellow solid after lyophilization.

$^1$H NMR (500 MHz, DMSO) δ 7.93 (d, J=8.2 Hz, 2H), 7.50 (dd, J=14.6, 7.7 Hz, 1H), 7.35-7.29 (m, 4H), 7.21 (t, J=8.8 Hz, 1H), 2.65 (q, J=7.7 Hz, 2H), 2.31 (s, 3H), 1.22 (dd, J=8.3, 7.2 Hz, 9H); MS (m/z): 482.18 [M+1]$^+$.

Compound 233: 4-(3-fluorophenyl)-1-(4-(5-fluoropyridin-3-yl)-5-(isopropylthio)thiazol-2-yl)-3-methyl-1H-pyrazole-5-carboxylic Acid In a 5 mL glass microwave vial equipped with a magnetic stirring bar at room temperature was placed the methyl 4-bromo-1-(4-bromo-5-(isopropylthio)thiazol-2-yl)-3-methyl-1H-pyrazole-5-carboxylate (50 mg, 0.11 mmol), the 5-fluoropyridin-3-ylboronic acid (15 mg, 0.109 mmol), $K_2CO_3$ (75 mg, 0.55 mmol), the catalyst Pd(dtbpf)Cl$_2$ (7 mg, 0.01 mmol) and THF (1 mL). Nitrogen gas was bubbled through the solution and then the vial was capped and stirred in an oil bath at 90° C. After 16 h, the 3-fluorophenylboronic acid (15 mg, 0.11 mmol), $Na_2CO_3$ (58 mg, 0.55 mmol), the catalyst Pd(PPh$_3$)$_4$ (13 mg, 0.011 mmol) and water (1 mL) were added to the vial. A flow of nitrogen was bubbled through the black mixture for 5 minutes. The vial was capped and stirred in an oil bath at 90° C. After 16 h, LiOH (13 mg, 0.55 mmol) was added to the reaction mixture and stirred under microwave radiation at 110° C. for 30 min. The crude product was purified using a semi prep HPLC-MS (X-Bridge 30×50, eluted with 50-70% MeCN/NH$_4$CO$_2$H 10 mM, pH 3.8/Flow 45 mL/min/11 min), resulting in the title compound (3.3 mg, 0.0070 mmol, 6%) as a yellow solid after lyophilization.
$^1$H NMR (500 MHz, DMSO) δ 9.16 (s, 1H), 8.63 (d, J=2.7 Hz, 1H), 8.28-8.24 (m, 1H), 7.48-7.38 (m, 3H), 7.11 (t, J=7.9 Hz, 1H), 2.30 (s, 3H), 1.24 (d, J=6.7 Hz, 6H). MS (m/z): 473.07 [M+1]$^+$.

Compound 234: 1-(4-(benzofuran-3-yl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar at room temperature was placed the methyl 4-bromo-1-(4-bromo-5-(isopropylthio)thiazol-2-yl)-3-methyl-1H-pyrazole-5-carboxylate (50 mg, 0.11 mmol), the benzofuran-3-ylboronic acid (18 mg, 0.109 mmol), $K_2CO_3$ (75 mg, 0.55 mmol), the catalyst Pd(dtbpf)Cl$_2$ (7 mg, 0.01 mmol) and THF (1 mL). Nitrogen gas was bubbled through the solution and then the vial was capped and stirred in an oil bath at 90° C. After 16 h, the 3-fluorophenylboronic acid (15 mg, 0.11 mmol), $Na_2CO_3$ (58 mg, 0.55 mmol), the catalyst Pd(PPh$_3$)$_4$ (13 mg, 0.011 mmol) and water (0.5 mL) were added to the vial. A flow of nitrogen was bubbled through the black mixture for 5 minutes. The vial was capped and stirred in an oil bath at 90° C. After 16 h, LiOH (13 mg, 0.55 mmol) was added to the reaction mixture and stirred under microwave radiation at 110° C. for 30 min. NaOH (44 mg, 1.1 mmol) in water (1 mL) was added to the reaction mixture and stirred under microwave radiation at 110° C. for 20 min. The crude product was purified using a semi prep HPLC-MS (X-Bridge 30×50, eluted with 60-80% MeCN/NH$_4$CO$_2$H 10 mM, pH 3.8/Flow 45 mL/min/11 min), resulting in the title compound (0.51 mg, 0.0010 mmol, 1%) as a yellow solid after lyophilization. MS (m/z): 494.19 [M+1]$^+$.

Compound 236: 4-(4-fluoro-3-methylphenyl)-1-(5-(isopropylthio)-4-(4-(trifluoromethyl)phenyl)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(5-(isopropylthio)-4-(4-(trifluoromethyl)phenyl)thiazol-2-yl)-3-methyl-1H-pyrazole-5-carboxylate (50 mg, 0.096 mmol), (4-fluoro-3-methylphenyl)boronic acid (15 mg, 0.096 mmol) and $Na_2CO_3$ (51 mg, 0.48 mmol) Nitrogen gas was bubbled through a solution of dioxane/water (2 mL, 4:1) and then the solution was added to the microwave vial, followed by the addition of the catalyst Pd(PPh$_3$)$_4$ (11 mg, 0.0096 mmol). The vial was capped and placed in an oil bath at 90° C. for 16 h. LiOH (23 mg, 0.96 mmol) was added to the reaction mixture and stirred under microwave radiation at 120° C. for 15 min. The product was purified using a semi prep HPLC-MS (column X-Bridge 30×50, eluted with 60-80% MeCN/NH$_4$CO$_2$H 10 mM, pH 3.8/Flow 45 ml/min/10 min), resulting in the title compound (18 mg, 0.034 mmol, 35%) as yellow solid after lyophilization.
$^1$H NMR (500 MHz, DMSO) δ 8.24 (d, J=8.2 Hz, 2H), 7.78 (d, J=8.3 Hz, 2H), 7.40 (dd, J=7.4, 1.5 Hz, 1H), 7.36-7.30 (m, 1H), 7.18-7.12 (m, 1H), 2.25 (s, 3H), 2.25 (s, 3H), 1.21 (d, J=6.7 Hz, 6H); MS (m/z): 536.26 [M+1]$^+$.

Compound 239: 1-(4-(4-chloro-2,6-dimethylphenyl)-5-(isopropylthio)thiazol-2-yl)-4-(3-fluorophenyl)-3-methyl-1H-pyrazole-5-carboxylic Acid

2-(4-chloro-2,6-dimethylphenyl)-4,4,5,5-tetramethyl-1,3,2-dioxaborolane

In a microwave vial equipped with a magnetic stirring bar and nitrogen flow at room temperature was placed 2-bromo-5-chloro-1,3-dimethylbenzene (250 mg, 1.14 mmol), pinacol diborane (347 mg, 1.37 mmol), KOAc (335 mg, 3.42 mmol), and the catalyst PdCl2(dppf) (83 mg, 0.11 mmol). Nitrogen gas was bubbled through a solution of dioxane (5.7 mL) and then the solution was added to the reaction mixture. The vial was capped and placed in an oil bath at 85° C. for 18 h. The reaction mixture was and filtered on a pad of Celite® and washed with dioxane. The solvent was evaporated under vacuum and the crude product was purified by flash chromatography on silica gel using a solution of EtOAc in hexanes (1 to 2% gradient) and afforded the title compound (94 mg, 0.35 mmol, 31%) as white solid.

methyl 4-bromo-1-(4-(4-chloro-2,6-dimethylphenyl)-5-(isopropylthio)thiazol-2-yl)-3-methyl-1H-pyrazole-5-carboxylate In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (75 mg, 0.16 mmol), 2-(4-chloro-2,6-dimethylphenyl)-4,4,5,5-tetramethyl-1,3,2-dioxaborolane (44 mg, 0.164 mmol) and $K_2CO_3$ (113 mg, 0.82 mmol). Nitrogen gas was bubbled through a solution of THF (1.5 mL) and then the solution was added to the microwave vial, followed by the addition of the catalyst Pd(dtbpf)Cl$_2$ (11 mg, 0.017 mmol). The vial was capped and placed in an oil bath at 90° C. for 16 h. The solvent was evaporated under vacuum and the crude product was purified by flash chromatography on silica gel eluted with hexanes and afforded the title compound (80 mg, 0.16 mmol, 95%) as brown oil.

1-(4-(4-chloro-2,6-dimethylphenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-(4-chloro-2,6-dimethylphenyl)-5-(isopropylthio)thiazol-2-yl)-3-methyl-1H-pyrazole-5-carboxylate (84 mg, 0.16 mmol), (3-fluorophenyl)boronic acid (23 mg, 0.16 mmol) and Na$_2$CO$_3$ (87 mg, 0.82 mmol). Nitrogen gas was bubbled through a solution of THF/water (1.5 mL, 4:1) and then the solution was added to the microwave vial, followed by the addition of the catalyst Pd(PPh$_3$)$_4$ (19 mg, 0.016 mmol). The vial was capped and placed in an oil bath at 90° C. for 16 h. LiOH (86 mg, 0.16 mmol) was added to the reaction mixture and stirred under microwave radiation at 110° C. for 15 min. The product was purified using a semi prep HPLC-MS (column X-Bridge 30×50, eluted with 60-80% MeCN/NH$_4$CO$_2$H 10 mM, pH 3.8/Flow 45 ml/min/10 min), resulting in the title compound (14 mg, 0.027 mmol, 17%) as white solid after lyophilization.
$^1$H NMR (500 MHz, DMSO) δ 7.50 (dd, J=14.2, 7.7 Hz, 1H), 7.30-7.20 (m, 5H), 3.20 (dt, J=13.2, 6.6 Hz, 1H), 2.30 (s, 3H), 2.06 (s, 6H), 1.19 (d, J=6.7 Hz, 6H); MS (m/z): 516.24 [M+1]$^+$.

Compound 242: 4-(3-fluorophenyl)-1-(5-(isopropylthio)-4-(2-(trifluoromethyl)pyrimidin-5-yl)thiazol-2-yl)-3-methyl-1H-pyrazole-5-carboxylic Acid 5-(4,4,5,5-tetramethyl-1,3,2-dioxaborolan-2-yl)-2-(trifluoromethyl)pyrimidine In a microwave vial equipped with a magnetic stirring bar and nitrogen flow at room temperature was placed 5-bromo-2-(trifluoromethyl)pyrimidine (250 mg, 1.10 mmol), pinacol diborane (336 mg, 1.32 mmol), KOAc (324 mg, 3.30 mmol), and the catalyst PdCl2(dppf) (81 mg, 0.11 mmol). Nitrogen gas was bubbled through a solution of dioxane (5.5 mL) and then the solution was added to the reaction mixture. The vial was capped and placed in an oil bath at 85° C. for 18 h. The reaction mixture was and filtered on a pad of Celite® and washed with dioxane. The solvent was evaporated under vacuum and the crude product was purified by flash chromatography on silica gel using a solution of EtOAc in hexanes (1 to 2% gradient) and afforded the title compound (247 mg, 0.901 mmol, 82%) as brown oil.

4-(3-fluorophenyl)-1-(5-(isopropylthio)-4-(2-(trifluoromethyl)pyrimidin-5-yl)thiazol-2-yl)-3-methyl-1H-pyrazole-5-carboxylic Acid In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (75 mg, 0.16 mmol), 5-(4,4,5,5-tetramethyl-1,3,2-dioxaborolan-2-yl)-2-(trifluoromethyl)pyrimidine (45 mg, 0.164 mmol) and K$_2$CO$_3$ (113 mg, 0.82 mmol). Nitrogen gas was bubbled through a solution of THF (1.5 mL) and then the solution was added to the microwave vial, followed by the addition of the catalyst Pd(dtbpf)Cl$_2$ (11 mg, 0.017 mmol). The vial was capped and placed in an oil bath at 90° C. After 16 h, was added (3-fluorophenyl)boronic acid (23 mg, 0.16 mmol) and Na$_2$CO$_3$ (87 mg, 0.82 mmol) Nitrogen gas was bubbled through a solution of THF/water (1.5 mL, 4:1) and then the solution was added to the microwave vial, followed by the addition of the catalyst Pd(PPh$_3$)$_4$ (19 mg, 0.016 mmol). The vial was capped and placed in an oil bath at 90° C. for 16 h. LiOH (39 mg, 1.6 mmol) was added to the reaction mixture and stirred under microwave radiation at 110° C. for 15 min. The product was purified using a semi prep HPLC-MS (column X-Bridge 30×50, eluted with 50-70% MeCN/NH$_4$CO$_2$H 10 mM, pH 3.8/Flow 45 ml/min/10 min), resulting in the title compound (9.2 mg, 0.018 mmol, 11%) as beige solid after lyophilization.
$^1$H NMR (500 MHz, DMSO) δ 9.60 (s, 2H), 7.51 (dd, J=15.1, 8.0 Hz, 1H), 7.36 (t, J=8.8 Hz, 2H), 7.22 (t, J=8.8 Hz, 1H), 2.33 (s, 3H), 1.27 (d, J=6.7 Hz, 6H); MS (m/z): 524.25 [M+1]$^+$.

Compound 243: 1-(4-(4-chloro-3-(ethylcarbamoyl)phenyl)-5-(isopropylthio)thiazol-2-yl)-4-(3-fluorophenyl)-3-methyl-1H-pyrazole-5-carboxylic Acid 1-(4-(4-chloro-3-(ethylcarbamoyl)phenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (75 mg, 0.16 mmol), (4-chloro-3-(ethylcarbamoyl)phenyl)boronic acid (37 mg, 0.16 mmol) and K$_2$CO$_3$ (113 mg, 0.82 mmol) Nitrogen gas was bubbled through a solution of THF (1.5 mL) and then the solution was added to the microwave vial, followed by the addition of the catalyst Pd(dtbpf)Cl$_2$ (11 mg, 0.017 mmol). The vial was capped and placed in an oil bath at 90° C. After 16 h, was added (3-fluorophenyl)boronic acid (23 mg, 0.16 mmol) and Na$_2$CO$_3$ (87 mg, 0.82 mmol). Nitrogen gas was bubbled through a solution of THF/water (1.5 mL, 4:1) and then the solution was added to the microwave vial, followed by the addition of the catalyst Pd(PPh$_3$)$_4$ (19 mg, 0.016 mmol). The vial was capped and placed in an oil bath at 90° C. for 16 h. LiOH (39 mg, 1.6 mmol) was added to the reaction mixture and stirred under microwave radiation at 120° C. for 15 min. The product was purified using a semi prep HPLC-MS (column X-Bridge 30×50, eluted with 50-70% MeCN/NH$_4$CO$_2$H 10 mM, pH 3.8/Flow 45 ml/min/10 min), resulting in the title compound (13 mg, 0.023 mmol, 14%) as beige solid after lyophilization.
$^1$H NMR (500 MHz, DMSO) δ 8.43 (t, J=5.6 Hz, 1H), 7.99-7.94 (m, 2H), 7.52 (d, J=8.4 Hz, 1H), 7.43 (dd, J=14.6, 7.8 Hz, 1H), 7.26 (t, J=9.9 Hz, 2H), 2.24 (s, 3H), 1.18 (d, J=6.7 Hz, 6H), 1.05 (t, J=7.2 Hz, 3H); MS (m/z): 559.14 [M+1]$^+$.

Compound 244: 1-(4-(2-amino-4-(trifluoromethyl)phenyl)-5-(isopropylthio)thiazol-2-yl)-4-(3-fluorophenyl)-3-methyl-1H-pyrazole-5-carboxylic Acid In a 5 mL glass microwave vial equipped with a magnetic stirring bar and nitrogen flow at room temperature was placed methyl 4-bromo-1-(4-bromo-5-(isopropylthio)thiazol-2-yl)-3-methyl-1H-pyrazole-5-carboxylate (75 mg, 0.16 mmol), N-(2-(4,4,5,5-tetramethyl-1,3,2-dioxaborolan-2-yl)-5-(trifluoromethyl)phenyl)acetamide (54 mg, 0.16 mmol) and K$_2$CO$_3$ (113 mg, 0.82 mmol). Nitrogen gas was bubbled through a solution of THF (1.5 mL) and then the solution was added to the microwave vial, followed by the addition of the catalyst Pd(dtbpf)Cl$_2$ (11 mg, 0.017 mmol). The vial was capped and placed in an oil bath at 90° C. After 16 h, was added (3-fluorophenyl)boronic acid (23 mg, 0.16 mmol) and Na$_2$CO$_3$ (87 mg, 0.82 mmol) Nitrogen gas was bubbled through a solution of THF/water (1.5 mL, 4:1) and then the solution was added to the microwave vial, followed by the addition of the catalyst Pd(PPh$_3$)$_4$ (19 mg, 0.016 mmol). The vial was capped and placed in an oil bath at 90° C. for 16 h. LiOH (39 mg, 1.6 mmol) was added to the reaction mixture and stirred under microwave radiation at 120° C. for 15 min. The product was purified using a semi prep HPLC-MS (column X-Bridge 30×50, eluted with 50-70% MeCN/NH$_4$CO$_2$H 10 mM, pH 3.8/Flow 45 ml/min/ 10 min), resulting in the title compound (7.4 mg, 0.014 mmol, 9%) as beige solid after lyophilization $^1$H NMR (500 MHz, DMSO) δ 7.52-7.43 (m, 2H), 7.34 (dd, J=15.6, 9.5 Hz, 2H), 7.21-7.14 (m, 1H), 7.11 (s, 1H), 6.87 (d, J=8.0 Hz, 1H), 2.30 (s, 3H), 1.16 (d, J=6.7 Hz, 6H); MS (m/z): 537.23 [M+1]$^+$.

Compound 246: 4-(3-fluorophenyl)-1-(5-(isopropylthio)-4-(5-(trifluoromethyl)pyrimidin-2-yl)thiazol-2-yl)-3-methyl-1H-pyrazole-5-carboxylic Acid methyl 4-bromo-1-(4-cyano-5-(isopropylthio)thiazol-2-yl)-3-methyl-1H-pyrazole-5-carboxylate In a 20 mL glass microwave vial equipped with a magnetic stirring bar and nitrogen flow at room temperature was placed 4-bromo-1-(4-bromo-5-(isopropylthio)thiazol-2-yl)-3-methyl-1H-pyrazole-5-carboxylate (600 mg, 1.32 mmol), zinc cyanide (93 mg, 0.79 mmol), zinc (7.8 mg, 0.12 mmol), Pd$_2$(dba)$_3$ (23 mg, 0.04 mmol) and dppf (44 mg, 0.079 mmol) in DMA (16 mL) was stirred in a microwave oven at 110° C. for 30 min. It was added to a mixture of zinc (7.8 mg, 0.12 mmol), Pd$_2$(dba)$_3$ (23 mg, 0.040 mmol) and dppf (44 mg, 0.079 mmol), which was then heated for 45 min at 110° C. The mixture was cooled to room temperature, then was extracted with Et$_2$O. The organic phase was washed with water (3×), dried with MgSO$_4$, filtered and concentrated. The residue was purified by flash chromatography on silica gel (dry pack) using a solution of EtOAc in hexanes (0 to 5% gradient) and afforded the title compound (314 mg, 0.78 mmol, 71%) as white solid.

methyl 1-(4-cyano-5-(isopropylthio)thiazol-2-yl)-4-(3-fluorophenyl)-3-methyl-1H-pyrazole-5-carboxylate In a 20 mL glass microwave vial equipped with a magnetic stirring bar and nitrogen flow at room temperature was placed methyl 4-bromo-1-(4-cyano-5-(isopropylthio)thiazol-2-yl)-3-methyl-1H-pyrazole-5-carboxylate (347 mg, 0.87 mmol), boronic acid (182 mg, 1.29 mmol), Na$_2$CO$_3$ (275 mg, 2.59 mmol) and Pd(dtbpf)Cl$_2$ (43 mg, 0.086 mmol) was stirred in dioxane/water 1:1 (17 mL) at 90° C. for 70 min in a microwave reactor. The reaction mixture was diluted with Et$_2$O, washed with water. The aqueous phase was extracted with Et$_2$O (2×), with DCM (1×) and with MeTHF (1×), the organic layer were combined, dried over MgSO$_4$, filtered and concentrated. The residue was purified by flash chromatography on silica gel (dry pack) using a solution of acetone in hexanes (0 to 3% gradient) and afforded title compound as white solid. The mixed fraction were concentrated and purified by normal flash chromatography on silica gel (dry pack) using using a solution of EtOAc in hexanes (0 to 5% gradient). The purest fractions were combined and afforded title compound (223 mg, 0.54 mmol, 62%) as white solid.

methyl 1-(4-carbamimidoyl-5-(isopropylthio)thiazol-2-yl)-4-(3-fluorophenyl)-3-methyl-1H-pyrazole-5-carboxylate In a 5 mL glass microwave vial equipped with a magnetic stirring bar and nitrogen flow at 0° C. was placed methyl 1-(4-cyano-5-(isopropylthio)thiazol-2-yl)-4-(3-fluorophenyl)-3-methyl-1H-pyrazole-5-carboxylate (40 mg, 0.096 mmol) in Et$_2$O (1.0 mL) was added a solution of LiHMDS (190 µL, 0.190 mmol). The mixture was stirred at 20° C. for 3 h. The reaction mixture was cooled at 0° C. and a solution of 10% citric acid was added, then the aqueous phase was extracted with Et$_2$O (3×). The combined organic layers were extracted two times with 10% citric acid. The aqueous phase was neutralized with Na$_2$CO$_3$ and extracted three times with Et$_2$O. The combined organic layers were dried over MgSO$_4$, filtrated and concentrated to afford the title compound as beige solid (40 mg. 0.092 mmol, 96%).

(Z)—N-(3-(dimethylamino)-2-(trifluoromethyl)allylidene)-N-methylmethanaminium chloride In a 5 mL glass microwave vial equipped with a magnetic stirring bar and nitrogen flow at 0° C. was placed DMF (1.1 mL, 13.8 mmol) and oxalyl chloride (1.17 mL, 13.59 mmol), a white solid was formed after 10 min, and 3,3,3-trifluoropropionic acid (600 µL, 6.79 mmol) was slowly added at the same temperature. After 10 minutes, the reaction was heated at 70° C. for 1 h. The mixture was concentrated under high vacuum for two days and afforded title compound (1.5 g, 6.5 mmol, 95%) as yellow solid.

methyl 4-(3-fluorophenyl)-1-(5-(isopropylthio)-4-(5-(trifluoromethyl)pyrimidin-2-yl)thiazol-2-yl)-3-methyl-1H-pyrazole-5-carboxylate In a 5 mL glass microwave vial equipped with a magnetic stirring bar and nitrogen flow at room temperature was placed methyl 1-(4-carbamimidoyl-5-(isopropylthio)thiazol-2-yl)-4-(3-fluorophenyl)-3-methyl-1H-pyrazole-5-carboxylate (42 mg, 0.10 mmol) and (Z)—N-(3-(dimethylamino)-2-(trifluoromethyl)allylidene)-N-methylmethanaminium chloride (34 mg, 0.15 mmol) followed by MeCN (1.0 mL) and Et$_3$N (40 µL, 0.29 mmol). The reaction mixture was stirred 5 min at 20° C. and 16 h at −20° C. The mixture was diluted with Et$_2$O and the organic layer was washed two times with 10% citric acid and one time with saturated NaHCO$_3$, dried with Na$_2$SO$_4$, filtrated and concentrated. The residue was purified by normal flash chromatography on silica gel (dry pack) using a solution of EtOAc in hexanes (0 to 5% gradient) afford title compound (15.8 mg, 0.029 mmol, 30%) as off-white solid.

4-(3-fluorophenyl)-1-(5-(isopropylthio)-4-(5-(trifluoromethyl)pyrimidin-2-yl)thiazol-2-yl)-3-methyl-1H-pyrazole-5-carboxylic Acid In a 5 mL glass microwave vial equipped with a magnetic stirring bar and nitrogen flow at room temperature was placed methyl 4-(3-fluorophenyl)-1-(5-(isopropylthio)-4-(5-(trifluoromethyl)pyrimidin-2-yl)thiazol-2-yl)-3-methyl-1H-pyrazole-5-carboxylate (15 mg, 0.03 mmol) in THF (0.5 mL), MeOH (0.5 mL) and water (0.5 mL) followed by LiOH (15 mg). The mixture was stirred 45 min at 60° C. The mixture was cooled and concentrated. The residue was purified by reverse phase chromatography (Isco) using a C18 column, eluting with a gradient of 0-100% MeCN/water (10 mM ammonium formate, pH 3.8) to afford title compound (9.8 mg, 0.19 mmol, 67%) as off-white solid.

$^1$H NMR (500 MHz, DMSO) δ 9.36 (s, 2H), 7.47 (dd, J=14.5, 7.6 Hz, 1H), 7.36 (d, J=9.3 Hz, 1H), 7.33 (d, J=7.7

Hz, 1H), 7.21-7.15 (m, 1H), 3.57 (dt, J=13.3, 6.7 Hz, 1H), 2.29 (s, 3H), 1.40 (d, J=6.6 Hz, 6H); MS (m/z): 524.1 [M+1]$^+$.

Biological Data

BJAB cells (DSMZ) were maintained in RPMI 1640 growth medium+10% FBS at 37° C./5% $CO_2$ and used prior to passage 34. Cells were seeded in white Corning Costar 96-well assay plates at 2500 cells/well in 50 µL of medium. Serial dilutions of test compounds were made in cell culture medium/FBS+0.2% DMSO, and transferred to assay plates in a volume of 50 µL (DMSO at 0.1% final). Plates were maintained at 37° C. for approximately 72 hours. The effect of compounds on cell proliferation was evaluated using the Cell Titer Glo reagent (Promega), according to the manufacturer's instructions. Briefly, 100 µL of reagent was added per well, and after a 10 minute incubation luminescence values were determined on a plate reader (Tecan F200PRO). The percent of luminescence signal relative to untreated controls was calculated for each compound concentration, and $EC_{50}$ values were determined from dose response data by non-linear regression analysis using Prism (GraphPad). Data are shown in the compound table above. The mTor inhibitor Torin1 (Liu, et al. (2010) J. Med. Chem. 53, 7146.) was used as a control. The data are summarized in the compound table provided above.

Further studies on various test compounds indicated that cell viability decreased in a dose-dependent manner, and that the test compounds induced cell death in a dose-dependent manner 48 hours post-treatment.

Polysome fractionation experiments performed in cells on various test compounds indicated that treatment caused a dose-dependent decrease in heavy polysomes, consistent with $EC_{50}$ values in the viability assay. There was no change observed in the phosphorylation status of eIF2A or 4E-BP, suggesting direct inhibition of translation, rather than disruption of a signaling pathway.

Similarly, the levels of cMyc and cyclin D3 proteins and the amount of mRNA was measured in cells after treatment with an example compound. Both protein levels decreased without similar changes in mRNA levels, which is consistent with an effect on translation.

It is understood that the examples and embodiments described herein are for illustrative purposes only and that various modifications or changes in light thereof will be suggested to persons skilled in the art and are to be incorporated within the spirit and purview of this application and scope of the appended claims.

We claim:

1. A compound having the structural formula

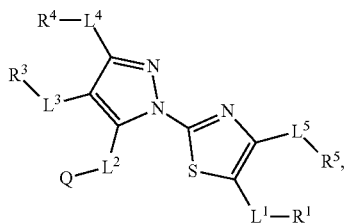

wherein
$L^2$ is selected from the group consisting of a bond, —$CH_2$—, —$CH(CH_3)$— or —$CH_2CH_2$—;
Q is selected from the group consisting of
—C(O)OH,
—C(O)O($C_1$-$C_3$ alkyl),
—C(O)NR$^{2B}$R$^{2A}$, in which R$^{2A}$ is $C_1$-$C_3$ alkyl, $C_1$-$C_3$ hydroxyalkyl, $C_1$-$C_3$ aminoalkyl or $C_1$-$C_3$ thioalkyl and R$^{2B}$ is H or $C_1$-$C_3$ alkyl,
—C(O)NR$^{2B}$R$^{2A}$, in which R$^{2A}$ and R$^{2B}$ come together with a nitrogen to which they are both directly bound to form a heterocycloalkyl optionally substituted with 1-3 substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —C(O)$C_1$-$C_3$ alkyl, and
—C(O)NR$^{2B}$R$^{2A}$, in which R$^{2A}$ is —S(O)$_{1-2}$($C_1$-$C_3$ alkyl), —S(O)$_{1-2}$($C_1$-$C_3$ fluoroalkyl), or heteroaryl optionally substituted with 1-2 groups selected from substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —C(O)$C_1$-$C_3$ alkyl and R$^{2B}$ is H or $C_1$-$C_3$ alkyl;
$L^1$ is —S—, —S(O)— or —S(O)$_2$—;
$R^1$ is selected from the group consisting of
optionally substituted $C_1$-$C_8$ alkyl, optionally-substituted $C_1$-$C_8$ alkenyl, optionally substituted $C_1$-$C_8$ alkynyl, and hydrogen;
$L^3$ is a bond, —C(O)—, —S—, —S(O)$_{1-2}$—, —O—, —NR$^6$—, —$CH_2$—, —$CH(CH_3)(OH)$—, —CH(OH)—, —$CH_2CH_2$—, —C(O)NR$^6$—, —NR$^6$C(O)—, —C(S)NR$^6$—, —NR$^6$C(S)—, —C(O)O—, —OC(O)—, —S(O)$_{1-2}$O—, —OS(O)$_{1-2}$—, —S(O)$_{1-2}$NR$^6$— or —NR$^6$S(O)$_{1-2}$—;
$R^3$ is selected from the group consisting of
phenyl and heteroaryl each (i) optionally substituted with a single substituent selected from -L$^{3C}$-(phenyl optionally substituted with 1-5 R$^{3D}$), -L$^{3C}$-(heteroaryl optionally substituted with 1-5 R$^{3D}$), -L$^{3C}$-(cycloalkyl optionally substituted with 1-5 R$^{3E}$), -L$^{3C}$-(heterocycloalkyl optionally substituted with 1-5 R$^{3E}$) and (ii) optionally substituted with 1-5 R$^{3E}$, in which
each L$^{3C}$ is a bond, methylene, ethylene, —C(O)—, —S—, —S(O)$_{1-2}$—, —O— or —NR$^{3G}$—;
each R$^{3D}$ is independently selected from optionally-substituted $C_1$-$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$, —OC(O)OR$^{3F}$, —OC(O)NR$^{3G}$R$^{3F}$, —NR$^{3G}$C(O)OR$^{3F}$, —NR$^{3G}$C(O)NR$^{3G}$R$^{3F}$, —SC(O)OR$^{3F}$, —OC(O)SR$^{3F}$, —SC(O)SR$^{3F}$, —SC(O)NR$^{3G}$R$^{3F}$, —NR$^{3G}$C(O)SR$^{3F}$, —OC(S)OR$^{3F}$, —OC(S)NR$^{3G}$R$^{3F}$, —NR$^{3G}$C(S)OR$^{3F}$, —NR$^{3G}$C(S)NR$^{3G}$R$^{3F}$, —SC(S)OR$^{3F}$, —OC(S)SR$^{3F}$, —SC(S)SR$^{3F}$, —SC(S)NR$^{3G}$R$^{3F}$, —NR$^{3G}$C(S)SR$^{3F}$, —NR$^{3G}$C(NR$^{3G}$)NR$^{3G}$R$^{3F}$ and —NR$^{3G}$S(O)$_{1-2}$NR$^{3G}$R$^{3F}$;
each R$^{3E}$ is independently selected from oxo, optionally-substituted $C_1$—$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$, —OC(O)OR$^{3F}$, —OC(O)NR$^{3G}$R$^{3F}$, —NR$^{3G}$C(O)OR$^{3F}$, —NR$^{3G}$C(O)NR$^{3G}$R$^{3F}$, —SC(O)OR$^{3F}$, —OC(O)SR$^{3F}$, —SC(O)SR$^{3F}$, —SC(O)NR$^{3G}$R$^{3F}$, —NR$^{3G}$C(O)SR$^{3F}$, —OC(S)OR$^{3F}$, —OC(S)NR$^{3G}$R$^{3F}$, —NR$^{3G}$C(S)OR$^{3F}$, —NR$^{3G}$C(S)NR$^{3G}$R$^{3F}$, —SC(S)OR$^{3F}$, —OC(S)SR$^{3F}$, —SC(S)SR$^{3F}$, —SC(S)NR$^{3G}$R$^{3F}$, —NR$^{3G}$C(S)SR$^{3F}$, —NR$^{3G}$C(NR$^{3G}$)NR$^{3G}$R$^{3F}$ and —NR$^{3G}$S(O)$_{1-2}$NR$^{3G}$R$^{3F}$;

each R$^{3F}$ is independently selected from H, C$_1$-C$_3$ alkyl, C$_1$-C$_3$ fluoroalkyl and C$_1$-C$_3$ hydroxyalkyl and each R$^{3G}$ is independently selected from H, C$_1$-C$_3$ alkyl, C$_1$-C$_3$ fluoroalkyl, C$_1$-C$_3$ hydroxyalkyl, —S(O)$_{1-2}$(C$_1$-C$_3$ alkyl), —C(O)(C$_1$-C$_3$ alkyl) and —C(O)O(C$_1$-C$_3$ alkyl);

L$^4$ is selected from the group consisting of a bond, —C(O)—, —S—, —S(O)$_{1-2}$—, —O—, —NR$^6$—, —C(O)NR$^6$—, —NR$^6$C(O)—, —C(S)NR$^6$—, —NR$^6$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^6$—and —NR$^6$S(O)$_{1-2}$—;

R$^4$ is selected from the group consisting of optionally substituted C$_1$-C$_8$ alkyl, optionally-substituted C$_1$-C$_8$ alkenyl optionally substituted C$_1$-C$_8$ alkynyl, and hydrogen;

L$^5$ is a bond, —C(O)—, —S—, —S(O)$_{1-2}$—, —O—, —NR$^6$—, —CH$_2$—, —CH(CH$_3$)(OH)—, —CH(OH)—, —CH$_2$CH$_2$—, —CH=CH—, —C≡C—, —C(O)NR$^6$—, —NR$^6$C(O)—, —C(S)NR$^6$—, —NR$^6$C(S)—, —C(O)O—, —OC(O)—, —S(O)$_{1-2}$O—, —OS(O)$_{1-2}$—, —S(O)$_{1-2}$NR$^6$—or —NR$^6$S(O)$_{1-2}$—;

R$^5$ is selected from the group consisting of phenyl and heteroaryl each optionally substituted with 1-5 R$^{5E}$, in which each R$^{5E}$ is independently selected from oxo, optionally-substituted C$_1$-C$_4$ alkyl, C$_1$-C$_4$ fluoroalkyl, halogen, —CN, —SF$_5$, —N$_3$, —C(O)R$^{5F}$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{1G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$, —NR$^{5G}$S(O)$_{1-2}$R$^{5F}$, —OC(O)OR$^{5F}$, —OC(O)NR$^{5G}$R$^{5F}$, —NR$^{5G}$C(O)OR$^{5F}$, —NR$^{5G}$C(O)NR$^{5G}$R$^{5F}$, —SC(O)OR$^{5F}$, —OC(O)SR$^{5F}$, —SC(O)SR$^{5F}$, —SC(O)NR$^{5G}$R$^{5F}$, —NR$^{5G}$C(O)SR$^{5F}$, —OC(S)OR$^{5F}$, —OC(S)NR$^{5G}$R$^{5F}$, —NR$^{5G}$C(S)OR$^{5F}$, —NR$^{5G}$C(S)NR$^{5G}$R$^{5F}$, —SC(S)OR$^{5F}$, —OC(S)SR$^{5F}$, —SC(S)SR$^{5F}$, —SC(S)NR$^{5G}$R$^{5F}$, —NR$^{5G}$C(S)SR$^{5F}$, —NR$^{5G}$C(NR$^{5G}$)NR$^{5G}$R$^{5F}$ and —NR$^{5G}$S(O)$_{1-2}$NR$^{5G}$R$^{5F}$;

each R$^{5F}$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^{5G}$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl); and in which R$^6$ is selected from the group consisting of hydrogen, C$_1$-C$_3$ alkyl, C$_1$-C$_3$ fluoroalkyl, C$_1$-C$_3$ hydroxyalkyl, C$_1$-C$_3$ aminoalkyl, C$_1$-C$_3$ thioalkyl, (C$_1$-C$_3$ alkoxy) C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

each alkyl, alkylene, alkenyl, alkenylene, alkynyl and alkynylene is straight-chain or branched;

each optionally substituted alkyl, alkene, alkyne, alkylene, alkenylene and alkynylene is unsubstituted or substituted with 1-5 substituents independently selected from oxo, halogen, —CN, —SF$_5$, —N$_3$, —C(O)R$^8$, —SR$^8$, —S(O)$_{1-2}$R$^8$, —OR$^8$, —NR$^9$R$^8$, —C(O)NR$^9$R$^8$, —NR$^9$C(O)R$^8$, —C(S)NR$^9$R$^8$, —NR$^9$C(S)R$^8$, —C(O)OR$^8$, —OC(O)R$^8$, —C(O)SR$^8$, —SC(O)R$^8$, —C(S)OR$^8$, —OC(S)R$^8$, —C(S)SR$^8$, —SC(S)R$^8$, —S(O)$_{1-2}$OR$^8$, —OS(O)$_{1-2}$R$^8$, —S(O)$_{1-2}$NR$^9$R$^8$, —NR$^9$S(O)$_{1-2}$R$^8$, —OC(O)OR$^8$, —OC(O)NR$^9$R$^8$, —NR$^9$C(O)OR$^8$, —NR$^9$C(O)NR$^9$R$^8$, —SC(O)OR$^8$, —OC(O)SR$^8$, SC(O)SR$^8$, —SC(O)NR$^9$R$^8$, —NR$^9$C(O)SR$^8$, —OC(S)OR$^8$, —OC(S)NR$^9$R$^8$, —NR$^9$C(S)OR$^8$, —NR$^9$C(S)NR$^9$R$^8$, —SC(S)OR$^8$, —OC(S)SR$^8$, —SC(S)SR$^8$, —SC(S)NR$^9$R$^8$, —NR$^9$C(S)SR$^8$, —NR$^9$C(NR$^9$)NR$^9$R$^8$ and —NR$^9$S(O)$_{1-2}$NR$^9$R$^8$, in which each R$^8$ is independently selected from H, C$_1$-C$_3$ alkyl, C$_1$-C$_3$ fluoroalkyl, C$_1$-C$_3$ hydroxyalkyl and (C$_1$-C$_3$ alkoxy)C$_1$-C$_3$ alkyl and each R$^9$ is independently selected from H, C$_1$-C$_3$ alkyl, C$_1$-C$_3$ fluoroalkyl, C$_1$-C$_3$ hydroxyalkyl, and (C$_1$-C$_3$ alkoxy)C$_1$-C$_3$ alkyl, —S(O)$_{1-2}$(C$_1$-C$_3$ alkyl), —C(O)(C$_1$-C$_3$ alkyl) and —C(O)O(C$_1$-C$_3$ alkyl);

each cycloalkyl has 3-10 ring carbons and is unsaturated or partially unsaturated, and optionally includes one or two fused aryl or heteroaryl rings, each fused ring having 3-8 ring members;

each heterocycloalkyl has 3-10 ring members and 1-3 heteroatoms independently selected from nitrogen, oxygen and sulfur and is unsaturated or partially unsaturated, and optionally includes one or two fused aryl or heteroaryl rings, each fused aryl or heteroaryl ring having 3-8 ring members;

each optionally substituted heteroaryl is a 5-6 membered monocyclic heteroaryl ring having 1-4 heteroatoms independently selected from nitrogen, oxygen and sulfur or a 8-10 membered bicyclic heteroaryl having 1-5 heteroatoms independently selected from nitrogen, oxygen or sulfur, optionally includes one or two fused cycloalkyl or heterocycloalkyl rings, each fused cycloalkyl or heterocycloalkyl ring having 4—8 ring members, the compound being optionally in the form of a pharmaceutically acceptable salt or N-oxide, or a solvate or hydrate.

2. The compound according to claim 1, wherein R$^1$ is unsubstituted C$_1$-C$_8$ alkyl, unsubstituted C$_1$-C$_8$ alkenyl or unsubstituted C$_1$-C$_8$ alkynyl.

3. The compound according to claim 2, wherein L$^1$ is —S—.

4. The compound according to claim 1, wherein L$^2$ is a bond.

5. The compound according to claim 1, wherein Q is —C(O)OH.

6. The compound according to claim 1, wherein Q is
—C(O)O($C_1$-$C_3$ alkyl);
—C(O)NR$^{2B}$R$^{2A}$, in which R$^{2A}$ is $C_1$-$C_3$ alkyl, $C_1$-$C_3$ hydroxyalkyl, $C_1$-$C_3$ aminoalkyl or $C_1$—$C_3$ thioalkyl and R$^{2B}$ is H or $C_1$-$C_3$ alkyl;
—C(O)NR$^{2B}$R$^{2A}$, in which R$^{2A}$ and R$^{2B}$ come together with a nitrogen to which they are both directly bound to form a heterocycloalkyl optionally substituted with 1-3 substituents selected from $C_1$-$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$-$C_3$ thioalkyl and —C(O)$C_1$-$C_3$ alkyl; or
—C(O)NR$^{2B}$R$^{2A}$, in which R$^{2A}$ is —S(O)$_{1-2}$($C_1$-$C_3$ alkyl), —S(O)$_{1-2}$($C_1$-$C_3$ fluoroalkyl), —or heteroaryl optionally substituted with 1-2 groups selected from substituents selected from $C_1$—$C_3$ alkyl, $C_1$-$C_3$ fluoroalkyl, hydroxyl, amino, thio, $C_1$-$C_3$ hydroxyalkyl, $C_1$-$C_3$ aminoalkyl, $C_1$—$C_3$ thioalkyl and —C(O)$C_1$-$C_3$ alkyl and R$^{2B}$ is H or $C_1$-$C_3$ alkyl.

7. The compound according to claim 1, wherein L$^3$ is a bond, —C(O)—, —S—, —S(O)$_{1-2}$—, —O—, —NR$^6$—, —CH$_2$—, —CH(CH$_3$)(OH)— or —CH(OH)—.

8. The compound according to claim 1, wherein R$^3$ is phenyl (i) substituted with a single substituent selected from -L$^{3C}$-(phenyl substituted with 0-5 R$^{3D}$), —L$^{3C}$—(heteroaryl substituted with 0-5 R$^{3D}$), -L$^{3C}$-(cycloalkyl substituted with 0-5 R$^{3E}$), —L$^{3C}$—(heterocycloalkyl substituted with 0-5 R$^{3E}$) and (ii) substituted with 0-4 R$^{3E}$.

9. The compound according to claim 1, wherein R$^3$ is phenyl substituted with 0-5 R$^{3E}$.

10. The compound according to claim 1, wherein R$^3$ is heteroaryl (i) optionally substituted with a single substituent selected from -L$^{3C}$-(phenyl substituted with 0-5 R$^{3D}$), -L$^{3C}$-(heteroaryl substituted with 0-5 R$^{3D}$), -L$^{3C}$-(cycloalkyl substituted with 0-5 R$^{3E}$), -L$^{3C}$-(heterocycloalkyl substituted with 0-5 R$^{3E}$) and (ii) substituted with 0-4 R$^{3E}$.

11. The compound according to claim 10, wherein the heteroaryl is selected from isothiazole, pyridone, thiadiazole, pyrazine, pyrazolopyrimidine, pyrazolopyridine, imidazole, benzofuran, indole, imidazopyridine, pyridine, pyrazole, isoxazole, triazolopyridine, benzimidazole, thiophene, benzothiophene, furan and pyrimidine.

12. The compound according to claim 1, wherein L$^4$ is a bond.

13. The compound according to claim 1, wherein L$^4$ is —C(O)—, —S—, —S(O)$_{1-2}$—, —O—, —NR$^6$—, —C(O)NR$^6$—, —NR$^6$C(O)—, —C(O)O—, —OC(O)—, —S(O)$_{1-2}$O—, —OS(O)$_{1-2}$—, —S(O)$_{1-2}$NR$^6$—or —NR$^6$S(O)$_{1-2}$—.

14. The compound according claim 1, wherein R$^4$ is optionally substituted $C_1$-$C_8$ alkyl, optionally-substituted $C_1$-$C_8$ alkenyl or optionally substituted $C_1$—$C_8$ alkynyl.

15. The compound according to claim 1, wherein R$^4$ is methyl, ethyl, propyl, butyl or pentyl.

16. The compound according to claim 1, wherein L$^5$ is a bond.

17. The compound according to claim 1, wherein R$^5$ is phenyl substituted with 0-5 R$^{5E}$.

18. The compound according to claim 1, wherein R$^5$ is heteroaryl substituted with 0-5 R$^{5E}$.

19. The compound according to claim 1, wherein
L$^1$ is a —S—, —S(O)— or —S(O)$_2$—;
R$^1$ is unsubstituted or fluorinated $C_1$-$C_8$ alkyl, unsubstituted or fluorinated $C_1$-$C_8$ alkenyl and unsubstituted or fluorinated $C_1$-$C_8$ alkynyl
L$^2$ is a bond or —CH$_2$—;
Q is —COOH;
L$^3$ is a bond, —C(O)—, —S—, —S(O)$_{1-2}$—, —O—, —NR$^6$—, —CH$_2$—, —CH(CH$_3$)(OH)— or —CH(OH)—;
R$^3$ is phenyl or monocyclic heteroaryl each (i) optionally substituted with a single substituent selected from -L$^{3C}$-(phenyl optionally substituted with 1-5 R$^{3D}$), -L$^{3C}$-(monocyclic heteroaryl optionally substituted with 1-5 R$^{3D}$), -L$^{3C}$-(monocyclic C3-C6 cycloalkyl optionally substituted with 1-5 R$^{3E}$), -L$^{3C}$-(monocyclic C4-C6 heterocycloalkyl optionally substituted with 1-5 R$^{3E}$) and (ii) optionally substituted with 1-5 R$^{3E}$,
in which
each L$^{3C}$ is a bond, methylene, ethylene, —C(O)—, —S—, —S(O)$_{1-2}$—, —O— or —NR$^{3G}$—;
each R$^{3D}$ is independently selected from optionally-substituted $C_1$-$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$ and —NR$^{3G}$S(O)$_{1-2}$R$^{3F}$;
each R$^{3E}$ is independently selected from oxo, optionally-substituted $C_1$—$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$;
each R$^{3F}$ is independently selected from H, $C_1$-$C_3$ alkyl and $C_1$-$C_3$ fluoroalkyl and
each R$^{3G}$ is independently selected from H and $C_1$-$C_3$ alkyl, $C_1$-$C_3$ fluoroalkyl;
L$^4$ is selected from the group consisting of a bond, —C(O)—, —S—, —S(O)$_{1-2}$—, —O— and —NR$^6$—;
R$^4$ is selected from the group consisting of unsubstituted or fluorinated $C_1$-$C_8$ alkyl, unsubstituted or fluorinated $C_1$-$C_8$ alkenyl and unsubstituted or fluorinated $C_1$-$C_8$ alkynyl;
L$^5$ is a bond, —C(O)—, —S—, —S(O)$_{1-2}$—, —O— or —NR$^6$—;
R$^5$ is phenyl or monocyclic heteroaryl each optionally substituted with 1-5 R$^{5E}$,
in which
each R$^{5E}$ is independently selected from oxo, optionally-substituted $C_1$—$C_4$ alkyl, $C_1$-$C_4$ fluoroalkyl, halogen, —CN, —SF$_5$, —N$_3$, —C(O)R$^{5F}$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{1G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$ and —NR$^{5G}$S(O)$_{1-2}$R$^{5F}$;
each R$^{5F}$ is independently selected from H, $C_1$-$C_3$ alkyl and $C_1$-$C_3$ fluoroalkyl and
each R$^{5G}$ is independently selected from H and $C_1$-$C_3$ alkyl;
wherein
each R$^6$ is selected from the group consisting of hydrogen, $C_1$-$C_3$ alkyl and —C(O)($C_1$—$C_3$ alkyl);

each optionally substituted alkyl, alkenyl and alkynyl is unsubstituted, fluorinated or substituted with one or two hydroxyl groups;

each cycloalkyl has 3-10 ring carbons and is unsaturated or partially unsaturated, and optionally includes one or two fused cycloalkyl rings, each fused ring having 3-8 ring members;

each heterocycloalkyl has 3-10 ring members and 1-3 heteroatoms independently selected from nitrogen, oxygen and sulfur and is unsaturated or partially unsaturated, and optionally includes one or two fused cycloalkyl rings, each having 3-8 ring members;

each heteroaryl is a 5-6 membered monocyclic heteroaryl ring having 1-4 heteroatoms independently selected from nitrogen, oxygen and sulfur or a 8-10 membered bicyclic heteroaryl having 1-5 heteroatoms independently selected from nitrogen, oxygen or sulfur, and optionally includes one or two fused cycloalkyl or heterocycloalkyl rings, each fused cycloalkyl or heterocycloalkyl ring having 4-8 ring members.

20. The compound according to claim 19, wherein
$R^3$ is phenyl optionally substituted with 1-5 $R^{3E}$, in which
each $L^{3C}$ is a bond, methylene, ethylene, —C(O)—, —S—, —S(O)$_{1-2}$—, —O— or —NR$^{3G}$—;
each $R^{3D}$ is independently selected from optionally-substituted $C_1$-$C_4$ alkyl, $C_1$—$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$ and —NR$^{3G}$S(O)$_{1-2}$R$^{3F}$;
each $R^{3E}$ is independently selected from oxo, optionally-substituted $C_1$-$C_4$ alkyl, $C_1$-$C_4$ fluoroalkyl, halogen, —CN, SF$_5$, —N$_3$, —C(O)R$^{3F}$, —SR$^{3F}$, —S(O)$_{1-2}$R$^{3F}$, —OR$^{3F}$, —NR$^{3G}$R$^{3F}$, —C(O)R$^{3F}$, —C(O)NR$^{3G}$R$^{3F}$, —NR$^{3G}$C(O)R$^{3F}$, —C(S)NR$^{3G}$R$^{3F}$, —NR$^{3G}$C(S)R$^{3F}$, —C(O)OR$^{3F}$, —OC(O)R$^{3F}$, —C(O)SR$^{3F}$, —SC(O)R$^{3F}$, —C(S)OR$^{3F}$, —OC(S)R$^{3F}$, —C(S)SR$^{3F}$, —SC(S)R$^{3F}$, —S(O)$_{1-2}$OR$^{3F}$, —OS(O)$_{1-2}$R$^{3F}$, —S(O)$_{1-2}$NR$^{3G}$R$^{3F}$, —NR$^{3G}$S(O)$_{1-2}$R$^{3F}$;
each $R^{3F}$ is independently selected from H, $C_1$-$C_3$ alkyl and $C_1$-$C_3$ fluoroalkyl and
each $R^{3G}$ is independently selected from H and $C_1$-$C_3$ alkyl, $C_1$-$C_3$ fluoroalkyl;
$R^5$ is phenyl optionally substituted with 1-5 $R^{5E}$, in which
each $R^{5E}$ is independently selected from oxo, optionally-substituted $C_1$-$C_4$ alkyl, $C_1$-$C_4$ fluoroalkyl, halogen, —CN, —SF$_5$, —N$_3$, —C(O)R$^{5F}$, —SR$^{5F}$, —S(O)$_{1-2}$R$^{5F}$, —OR$^{5F}$, —NR$^{5G}$R$^{5F}$, —C(O)R$^{5F}$, —C(O)NR$^{5G}$R$^{5F}$, —NR$^{5G}$C(O)R$^{5F}$, —C(S)NR$^{5G}$R$^{5F}$, —NR$^{1G}$C(S)R$^{5F}$, —C(O)OR$^{5F}$, —OC(O)R$^{5F}$, —C(O)SR$^{5F}$, —SC(O)R$^{5F}$, —C(S)OR$^{5F}$, —OC(S)R$^{5F}$, —C(S)SR$^{5F}$, —SC(S)R$^{5F}$, —S(O)$_{1-2}$OR$^{5F}$, —OS(O)$_{1-2}$R$^{5F}$, —S(O)$_{1-2}$NR$^{5G}$R$^{5F}$ and —NR$^{5G}$S(O)$_{1-2}$R$^{5F}$;
each $R^{5F}$ is independently selected from H, $C_1$-$C_3$ alkyl and $C_1$-$C_3$ fluoroalkyl and
each $R^{5G}$ is independently selected from H and $C_1$-$C_3$ alkyl.

21. The compound according to claim 20, wherein
$L^1$ is —S—;
$L^2$ is a bond;
$L^3$ is a bond;
$L^4$ is a bond; and
$L^5$ is a bond.

22. The compound according to claim 19 wherein $R^5$ is phenyl substituted with one or two substituents selected from trifluoromethyl, fluorine and chlorine.

23. The compound according to claim 1, wherein
each optionally substituted alkylene, alkenylene and alkynylene is unsubstituted;
each optionally substituted alkyl, alkenyl and alkynyl is unsubstituted;
each cycloalkyl is a 3-7 membered monocyclic cycloalkyl;
each heterocycloalkyl is a 4-7 membered monocyclic heterocycloalkyl having 1-2 heteroatoms selected from O, S and N;
each heteroaryl is a 5-6 membered monocyclic heteroaryl having 1-3 heteroatoms selected from O, S and N;
each $R^{XA}$ is hydrogen or $C_1$-$C_4$ alkyl; and
each $R^{XB}$ is hydrogen or $C_1$-$C_4$ alkyl.

24. The pharmaceutical composition comprising a compound according to claim 1 optionally in the form of a pharmaceutically acceptable salt or N-oxide, or a solvate or hydrate, and a pharmaceutically-acceptable carrier, diluent or excipient.

25. A method for inhibiting the initiation of translation of mRNA to protein, the method comprising administering to a subject in need thereof an effective amount of a compound of claim 1 optionally in the form of a pharmaceutically acceptable salt or N-oxide, or a solvate or hydrate.

26. The compound according to claim 1, wherein the compound is
1-(4-(3,4-dichlorophenyl)-5-(isopropylthio)thiazol-2-yl)—4-(2,6-dimethylpyridin-4-yl)—3-methyl-1H-pyrazole-5-carboxylic acid;
1-(5-(sec-butylthio)-4-(3,4-dichlorophenyl)thiazol-2-yl)—4-(2,6-dimethylpyridin-4-yl)—3-methyl-1H-pyrazole-5-carboxylic acid;
4-(3,5-dichlorophenyl)-1-(4-(3,4-dichlorophenyl)-5-(isopropylthio)thiazol-2-yl)—3-methyl-1H-pyrazole-5-carboxylic acid;
4-(3-chloro-5-methylphenyl)-1-(4-(3,4-dichlorophenyl)-5-(isopropylthio)thiazol-2-yl)—3-methyl-1H-pyrazole-5-carboxylic acid;
1-(4-(4-chlorophenyl)-5-(isopropylthio)thiazol-2-yl)—4-(2,6-dimethylpyridin-4-yl)—3-methyl-1H-pyrazole-5-carboxylic acid;
1-(4-(2,4-dichlorophenyl)-5-(isopropylthio)thiazol-2-yl)—4-(2,6-dimethylpyridin-4-yl)—3-methyl-1H-pyrazole-5-carboxylic acid;
1-(4-(4-chlorophenyl)-5-(isopropylthio)thiazol-2-yl)—4-(3-fluorophenyl)-3-methyl-1H-pyrazole-5-carboxylic acid;
4-(3-fluorophenyl)-1-(5-(isopropylthio)-4-(4-(trifluoromethyl)phenyl)thiazol-2-yl)—3-methyl-1H-pyrazole-5-carboxylic acid;
1-(4-(4-chloro-2-methylphenyl)-5-(isopropylthio)thiazol-2-yl)—4-(3-fluorophenyl)-3-methyl-1H-pyrazole-5-carboxylic acid;
4-(3-fluorophenyl)-1-(5-(isopropylthio)-4-(2-methyl-4-(trifluoromethyl)phenyl)thiazol-2-yl)—3-methyl-1H-pyrazole-5-carboxylic acid;
4-(3,5-dichlorophenyl)-1-(5-(isopropylthio)-4-(4-(trifluoromethyl)phenyl)thiazol-2-yl)—3-methyl-1H-pyrazole-5-carboxylic acid;
4-(3-chloro-5-methoxyphenyl)-1-(5-(isopropylthio)-4-(4-(trifluoromethyl)phenyl)thiazol-2-yl)—3-methyl-1H-pyrazole-5-carboxylic acid;

4-(3-fluorophenyl)-1-(5-(isopropylthio)-4-(2-methyl-4-(trifluoromethoxy)phenyl)thiazol-2-yl)—3-methyl-1H-pyrazole-5-carboxylic acid;

4-(4-chloro-5-fluorophenyl)-1-(4-(3,4-dichlorophenyl)-5-(isopropylthio)thiazol-2-yl)—3-methyl-1H-pyrazole-5-carboxylic acid;

4-(3,4-difluorophenyl)-1-(5-(isopropylthio)-4-(4-(trifluoromethyl)phenyl)thiazol-2-yl)—3-methyl-1H-pyrazole-5-carboxylic acid;

4-(4-fluoro-3,5-dimethylphenyl)-1-(5-(isopropylthio)-4-(4-(trifluoromethyl)phenyl)thiazol-2-yl)—3-methyl-1H-pyrazole-5-carboxylic acid;

4-(3-fluorophenyl)-1-(5-(isopropylthio)-4-(4-(pentafluoro-λ6-sulfaneyl)phenyl)thiazol-2-yl)—3-methyl-1H-pyrazole-5-carboxylic acid; or 1-(4-(3,4-dichlorophenyl)-5-(isopropylthio)thiazol-2-yl)—4-(3-fluorophenyl)-3-methyl-1H-pyrazole-5-carboxylic acid, optionally in the form of a pharmaceutically acceptable salt or N-oxide, or a solvate or hydrate.

27. The compound according to claim 1, wherein the compound is 1-(4-(3,4-dichlorophenyl)-5-(isopropylthio)thiazol-2-yl)—3-methyl-4-phenyl-1H-pyrazole-5-carboxylic acid;

1-(4-(3,4-dichlorophenyl)-5-(isopropylthio)thiazol-2-yl)—4-(3,5-difluorophenyl)-3-methyl-1H-pyrazole-5-carboxylic acid;

1-(4-(5-chloro-2-fluorophenyl)-5-(isopropylthio)thiazol-2-yl)—4-(3,5-dichlorophenyl)-3-methyl-1H-pyrazole-5-carboxylic acid;

1-(5-(sec-butylthio)-4-(3,4-dichlorophenyl)thiazol-2-yl)—4-(3,5-dichlorophenyl)-3-methyl-1H-pyrazole-5-carboxylic acid;

4-(2,6-dimethylpyridin-4-yl)—1-(5-(isopropylthio)-4-(3-methoxyphenyl)thiazol-2-yl)—3-methyl-1H-pyrazole-5-carboxylic acid;

4-(2,6-dimethylpyridin-4-yl)—1-(5-(isopropylthio)-4-p—tolylthiazol-2-yl)—3-methyl-1H-pyrazole-5-carboxylic acid;

4-(2,6-dimethylpyridin-4-yl)—1-(5-(isopropylthio)-4-o—tolylthiazol-2-yl)—3-methyl-1H-pyrazole-5-carboxylic acid;

1-(4-(3,4-dichlorophenyl)-5-(isopropylthio)thiazol-2-yl)—3-methyl-4-(3-(trifluoromethyl)phenyl)-1H-pyrazole-5-carboxylic acid;

4-(3,5-bis(trifluoromethyl)phenyl)-1-(4-(3,4-dichlorophenyl)-5-(isopropylthio)thiazol-2-yl)—3-methyl-1H-pyrazole-5-carboxylic acid;

1-(4-(3,4-dichlorophenyl)-5-(isopropylthio)thiazol-2-yl)—4-(3-isopropylphenyl)-3-methyl-1H-pyrazole-5-carboxylic acid;

4-(3-cyano-5-methylphenyl)-1-(4-(3,4-dichlorophenyl)-5-(isopropylthio)thiazol-2-yl)—3-methyl-1H-pyrazole-5-carboxylic acid;

4-(3-cyano-5-(trifluoromethyl)phenyl)-1-(4-(3,4-dichlorophenyl)-5-(isopropylthio)thiazol-2-yl)—3-methyl-1H-pyrazole-5-carboxylic acid;

4-(3-benzyl-5-methylisoxazol-4-yl)—1-(4-(3,4-dichlorophenyl)-5-(isopropylthio)thiazol-2-yl)—3-methyl-1H-pyrazole-5-carboxylic acid;

1-(4-(3,4-dichlorophenyl)-5-(isopropylthio)thiazol-2-yl)—3-methyl-4-(3-methylisothiazol-5-yl)—1H-pyrazole-5-carboxylic acid;

1-(4-(3,4-dichlorophenyl)-5-(isopropylthio)thiazol-2-yl)—4-(3-fluoro-5-methylphenyl)-3-methyl-1H-pyrazole-5-carboxylic acid;

1-(4-(3,4-dichlorophenyl)-5-(isopropylthio)thiazol-2-yl)—4-(3-isopropoxy-5-methylphenyl)-3-methyl-1H-pyrazole-5-carboxylic acid;

1-(4-(3,4-dichlorophenyl)-5-(isopropylthio)thiazol-2-yl)—3-methyl-4-(3-methyl-5-(oxetan-3-yloxy)phenyl)-1H-pyrazole-5-carboxylic acid;

4-(3-(1H-imidazol-1-yl)—5-methylphenyl)-1-(4-(3,4-dichlorophenyl)-5-(isopropylthio)thiazol-2-y1)-3-methyl-1H-pyrazole-5-carboxylic acid;

4-(2-(azetidin-1-yl)—6-methylpyridin-4-yl)—1-(4-(3,4-dichlorophenyl)-5-(isopropylthio)thiazol-2-y1)-3-methyl-1H-pyrazole-5-carboxylic acid;

4-(3-chlorophenyl)-1-(4-(3,4-dichlorophenyl)-5-(isopropylthio)thiazol-2-yl)—3-methyl-1H-pyrazole-5-carboxylic acid;

1-(4-(3,4-dichlorophenyl)-5-(isopropylthio)thiazol-2-yl)—4-(3-methoxyphenyl)-3-methyl-1H-pyrazole-5-carboxylic acid;

1-(4-(3,4-dichlorophenyl)-5-(isopropylthio)thiazol-2-yl)—3-methyl-4-m—tolyl-1H-pyrazole-5-carboxylic acid;

(4-(aminomethyl)piperidin-1-yl)(1-(4-(3,4-dichlorophenyl)-5-(isopropylthio)thiazol-2-yl)—3-methyl-4-o—tolyl-1H-pyrazol-5-yl)methanone;

(4-(aminomethyl)piperidin-1-yl)(4-(3,5-bis(trifluoromethyl)phenyl)-1-(4-(3,4-dichlorophenyl)-5-(isopropylthio)thiazol-2-yl)—3-methyl-1H-pyrazol-5- yl)methanone;

N-(2-aminoethyl)-4-(3,5-bis(trifluoromethyl)phenyl)-1-(4-(3,4-dichlorophenyl)-5-(isopropylthio)thiazol-2-yl)—N,3-dimethyl-1H-pyrazole-5-carboxamide;

1-(4-(3,4-dichlorophenyl)-5-isobutylthiazol-2-yl)—1',3-dimethyl-1H,1'H-[4,4'-bipyrazole]-5-carboxylic acid;

1-(4-(3,4-dichlorophenyl)-5-(isopropylthio)thiazol-2-yl)—4-(3,5-dimethylphenyl)-3-methyl-1H-pyrazole-5-carboxylic acid;

4-(3-chloro-5-methoxyphenyl)-1-(4-(3,4-dichlorophenyl)-5-(isopropylthio)thiazol-2-yl)—3-methyl-1H-pyrazole-5-carboxylic acid;

1-(4-(3,4-dichlorophenyl)-5-(isopropylthio)thiazol-2-yl)—4-(3-methoxy-5-(trifluoromethyl)phenyl)-3-methyl-1H-pyrazole-5-carboxylic acid;

4-(3,5-dichlorophenyl)-1-(4-(3,5-dichlorophenyl)-5-(isopropylthio)thiazol-2-yl)—3-methyl-1H-pyrazole-5-carboxylic acid;

1-(4-(2-chlorophenyl)-5-(isopropylthio)thiazol-2-yl)—4-(2,6-dimethylpyridin-4-yl)—3-methyl-1H-pyrazole-5-carboxylic acid;

1-(4-(3,4-dichlorophenyl)-5-(isopropylthio)thiazol-2-yl)—4-(3-fluoro-5-methoxyphenyl)-3-methyl-1H-pyrazole-5-carboxylic acid;

1-(4-(3,4-dichlorophenyl)-5-(isopropylthio)thiazol-2-yl)—4-(3-methoxy-5-methylphenyl)-3-methyl-1H-pyrazole-5-carboxylic acid;

1-(4-(3,4-dichlorophenyl)-5-(isopropylthio)thiazol-2-yl)—3-methyl-4-(2-methylpyridin-4-yl)—1H-pyrazole-5-carboxylic acid;

4-(3-chloro-5-isopropoxyphenyl)-1-(4-(3,4-dichlorophenyl)-5-(isopropylthio)thiazol-2-yl)—3-methyl-1H-pyrazole-5-carboxylic acid;

4-(3-chloro-5-(2-methoxyethoxy)phenyl)-1-(4-(3,4-dichlorophenyl)-5-(isopropylthio)thiazol-2-y1)-3-methyl-1H-pyrazole-5-carboxylic acid;

1-(4-(2,4-dichlorophenyl)-5-(isopropylthio)thiazol-2-yl)—4-(3-fluorophenyl)-3-methyl-1H-pyrazole-5-carboxylic acid;

4-(3-fluorophenyl)-1-(4-(4-fluorophenyl)-5-(isopropylthio)thiazol-2-yl)—3-methyl-1 H-pyrazole-5-carboxylic acid;
1-(4-(4-chloro-3-methylphenyl)-5-(isopropylthio)thiazol-2-yl)—4-(2,6-di methylpyridin-4-yl)—3-methyl-1 H-pyrazole-5-carboxylic acid;
1-(4-(4-chloro-3-methylphenyl)-5-(isopropylthio)thiazol-2-yl)—4-(3-fluorophenyl)-3-methyl-1H-pyrazole-5-carboxylic acid;
1-(4-(4-chloro-3,5-difluorophenyl)-5-(isopropylthio)thiazol-2-yl)—4-(2,6-dimethylpyridin-4-yl)—3-methyl-1 H-pyrazole-5-carboxylic acid;
1-(4-(4-chloro-3,5-difluorophenyl)-5-(isopropylthio)thiazol-2-yl)—4-(3-fluorophenyl)-3-methyl-1 H-pyrazole-5-carboxylic acid;
1-(4-(4-chloro-3-methoxyphenyl)-5-(isopropylthio)thiazol-2-yl)—4-(2,6-dimethylpyridin-4-yl)—3-methyl-1 H-pyrazole-5-carboxylic acid;
4-(2,6-di methylpyridin-4-yl)—1-(5-(isopropylthio)-4-(4-(trifluoromethyl)phenyl)thiazol-2-yl)—3-methyl-1 H-pyrazole-5-carboxylic acid;
1-(4-(3,4-dichlorophenyl)-5-(isopropylthio)thiazol-2-yl)—3-methyl-4-(3-methyl-5-(oxetan-3-yloxy)phenyl)-1H-pyrazole-5-carboxylic acid;
1-(4-(3,4-dichlorophenyl)-5-(isopropylthio)thiazol-2-yl)—4-(2-methoxy-6-methylpyridin-4-yl)—3-methyl-1 H-pyrazole-5-carboxylic acid;
1-(4-(3,4-dichlorophenyl)-5-(isopropylthio)thiazol-2-yl)—4-(3-fluoro-5-(oxetan-3-yloxy)phenyl)-3-methyl-1H-pyrazole-5-carboxylic acid;
4-(2,6-di methylpyridin-4-yl)—1-(4-(4-fluorophenyl)-5-(isopropylthio)thiazol-2-yl)—3-methyl-1 H-pyrazole-5-carboxylic acid;
1-(4-(4-chloro-2-methoxyphenyl)-5-(isopropylthio)thiazol-2-yl)—4-(3-fluorophenyl)-3-methyl-1 H-pyrazole-5-carboxylic acid;
1-(4-(4-chloro-2-methoxyphenyl)-5-(isopropylthio)thiazol-2-yl)—4-(2,6-dimethylpyridin-4-yl)—3-methyl-1 H-pyrazole-5-carboxylic acid;
1-(4-(3-fluoro-4-methylphenyl)-5-(isopropylthio)thiazol-2-yl)—4-(3-fluorophenyl)-3-methyl-1H-pyrazole-5-carboxylic acid;
4-(3-fluorophenyl)-1-(5-(isopropylthio)-4-(4-(trifluoromethoxy)phenyl)thiazol-2-yl)—3-methyl-1 H-pyrazole-5-carboxylic acid;
1-(4-(3,4-dichlorophenyl)-5-(isopropylthio)thiazol-2-yl)—4-(3-fluorophenyl)-3-isopropyl-1H-pyrazole-5-carboxylic acid;
1-(4-(4-(difluoromethyl)phenyl)-5-(isopropylthio)thiazol-2-yl)—4-(3-fluorophenyl)-3-methyl-1H-pyrazole-5-carboxylic acid;
1-(4-(4-ethyl phenyl)-5-(isopropylthio)thiazol-2-yl)—4-(3-fluorophenyl)-3-methyl-1H-pyrazole-5-carboxylic acid;
4-(4-fluoro-3-methylphenyl)-1-(5-(isopropylthio)-4-(4-(trifluoromethyl)phenyl)thiazol-2-yl)—3-methyl-1H-pyrazole-5-carboxylic acid;
4-(4-fluorophenyl)-1-(5-(isopropylthio)-4-(4-(trifluoromethyl)phenyl)thiazol-2-yl)—3-methyl-1H-pyrazole-5-carboxylic acid;
4-(4-fluoro-3-methoxyphenyl)-1-(5-(isopropylthio)-4-(4-(trifluoromethyl)phenyl)thiazol-2-yl)—3-methyl-1H-pyrazole-5-carboxylic acid;
1-(4-(4-(1,1-difluoroethyl)phenyl)-5-(isopropylthio)thiazol-2-yl)—4-(3-fluorophenyl)-3-methyl-1H-pyrazole-5-carboxylic acid;
1-(4-(2-amino-4-(trifluoromethyl)phenyl)-5-(isopropylthio)thiazol-2-yl)—4-(3-fluorophenyl)-3-methyl-1H-pyrazole-5-carboxylic acid;
4-(3-fluorophenyl)-1-(5-(isopropylthio)-4-(4-(2,2,2-trifluoroethyl)phenyl)thiazol-2-yl)—3-methyl-1H-pyrazole-5-carboxylic acid; or
4-(3-fluorophenyl)-1-(5-(isopropylthio)-4-(6-(trifluoromethyl)pyridin-3-yl)thiazol-2-yl)—3-methyl-1H-pyrazole-5-carboxylic acid,
optionally in the form of a pharmaceutically acceptable salt or N-oxide, or a solvate or hydrate.

28. The compound according to claim 1, wherein the compound is
4-(benzofuran-2-yl)—1-(4-(3,4-dichlorophenyl)-5-(isopropylthio)thiazol-2-yl)—3-methyl-1H-pyrazole-5-carboxylic acid;
1-(4-(3,4-dichlorophenyl)-5-(isopropylthio)thiazol-2-yl)—4-(2-fluoropyridin-4-yl)-3-methyl-1H-pyrazole-5-carboxylic acid;
1-(4-(5-chloro-2-fluorophenyl)-5-(isopropylthio)thiazol-2-yl)—4-(2,6-dimethylpyridin-4-yl)—3-methyl-1H-pyrazole-5-carboxylic acid;
4-(2,6-dimethylpyridin-4-yl)—1-(5-(isopropylthio)-4-(2-methoxyphenyl)thiazol-2-yl)—3-methyl-1H-pyrazole-5-carboxylic acid;
4-(2,6-dimethylpyridin-4-yl)—1-(5-(isopropylthio)-4-phenylthiazol-2-yl)—3-methyl-1H-pyrazole-5-carboxylic acid;
4-(2,6-dimethylpyridin-4-yl)—1-(5-(isopropylthio)-4-m—tolylthiazol-2-yl)—3-methyl-1H-pyrazole-5-carboxylic acid;
4-(2,6-dimethylpyridin-4-yl)—1-(5-(isopropylthio)-4-(phenylethynyl)thiazol-2-yl)—3-methyl-1H-pyrazole-5-carboxylic acid;
1-(4-(3,4-dichlorophenyl)-5-(isopropylthio)thiazol-2-yl)—3-methyl-4-(pyridin-4-yl)—1 H-pyrazole-5-carboxylic acid;
1-(4-(3,4-dichlorophenyl)-5-(isopropylthio)thiazol-2-yl)—3-methyl-4-(2-(trifluoromethyl)phenyl)-1 H-pyrazole-5-carboxylic acid;
4-(3-chloro-2-methylphenyl)-1-(4-(3,4-dichlorophenyl)-5-(isopropylthio)thiazol-2-yl)—3-methyl-1 H-pyrazole-5-carboxylic acid;
1-(4-(3,4-dichlorophenyl)-5-(isopropylthio)thiazol-2-yl)—4-(2-methoxy-5-methylphenyl)-3-methyl-1 H-pyrazole-5-carboxylic acid;
2-(4-(3,4-dichlorophenyl)-5-(isopropylthio)thiazol-2-yl)—2',5-dimethyl-4,4'-bi(2H-pyrazole)-3-carboxylic acid;
4-(3-cyano-5-methoxyphenyl)-1-(4-(3,4-dichlorophenyl)-5-(isopropylthio)thiazol-2-yl)—3-methyl-1 H-pyrazole-5-carboxylic acid;
1-(4-(3,4-dichlorophenyl)-5-(isopropylthio)thiazol-2-yl)—4-(3-(methoxymethyl)phenyl)-3-methyl-1 H-pyrazole-5-carboxylic acid;
4-(benzo[d][1,3]dioxol-5-yl)—1-(4-(3,4-dichlorophenyl)-5-(isopropylthio)thiazol-2-yl)—3-methyl-1 H-pyrazole-5-carboxylic acid;
1-(4-(3,4-dichlorophenyl)-5-(isopropylthio)thiazol-2-yl)—4-(isothiazol-4-yl)—3-methyl-1H-pyrazole-5-carboxylic acid;
1-(4-(3,4-dichlorophenyl)-5-(isopropylthio)thiazol-2-yl)—4-(3-(dimethylamino)-5-methylphenyl)-3-methyl-1H-pyrazole-5-carboxylic acid;
1-(4-(3,4-dichlorophenyl)-5-(isopropylthio)thiazol-2-yl)—3-methyl-4-(2-methyl-6-morpholinopyridin-4-yl)—1H-pyrazole-5-carboxylic acid;

1-(4-(3,4-dichlorophenyl)-5-(isopropylthio)thiazol-2-yl)—3-methyl-4-(3-nitrophenyl)-1H-pyrazole-5-carboxylic acid;

1-(4-(3,4-dichlorophenyl)-5-(isopropylthio)thiazol-2-yl)—3-methyl-4-o—tolyl-1 H-pyrazole-5-carboxylic acid;

1-(4-(3,4-dichlorophenyl)-5-(isopropylthio)thiazol-2-yl)—4-(1H-indol-7-yl)—3-methyl-1H-pyrazole-5-carboxylic acid;

2-(4-(3,4-dichlorophenyl)-5-(isopropylthio)thiazol-2-yl)—2'-ethyl-5-methyl-4,4'-bi(2H-pyrazole)-3-carboxylic acid;

1-(4-(3,4-dichlorophenyl)-5-(isopropylthio)thiazol-2-yl)—4-(imidazo[1,2-a]pyridin-3-yl)—3-methyl-1 H-pyrazole-5-carboxylic acid;

1-(4-(3,4-dichlorophenyl)-5-(isopropylthio)thiazol-2-yl)—4-(3-fluoro-5-hydroxyphenyl)-3-methyl-1 H-pyrazole-5-carboxylic acid;

1-(4-(3,4-dichlorophenyl)-5-(isopropylthio)thiazol-2-yl)—3-methyl-4-(1-methyl-1H-indol-7-yl)—1H-pyrazole-5-carboxylic acid;

1-(4-(3-chlorophenyl)-5-(isopropylthio)thiazol-2-yl)—4-(2,6-dimethylpyridin-4-yl)—3-methyl-1H-pyrazole-5-carboxylic acid;

1-(4-(2,5-dichlorophenyl)-5-(isopropylthio)thiazol-2-yl)—4-(2,6-dimethylpyridin-4-yl)—3-methyl-1H-pyrazole-5-carboxylic acid;

4-(2,6-dimethylpyridin-4-yl)—1-(5-(isopropylthio)-4-(phenylethynyl)thiazol-2-yl)—3-methyl-1H-pyrazole-5-carboxylic acid;

1-(4-(3,4-dichlorophenyl)-5-(isopropylthio)thiazol-2-yl)—4-(2-methoxypyridin-4-yl)—3-methyl-1H-pyrazole-5-carboxylic acid;

1-(4-(3-chlorophenyl)-5-(isopropylthio)thiazol-2-yl)—4-(3-fluorophenyl)-3-methyl-1H-pyrazole-5-carboxylic acid;

1-(4-(cyclohex-1-en—1-yl)—5-(isopropylthio)thiazol-2-yl)—4-(3-fluorophenyl)-3-methyl-1H-pyrazole-5-carboxylic acid;

1-(4-(4-chloro-3-methoxyphenyl)-5-(isopropylthio)thiazol-2-yl)—4-(3-fluorophenyl)-3-methyl-1H-pyrazole-5-carboxylic acid;

1-(4-(3-chloro-4-methylphenyl)-5-(isopropylthio)thiazol-2-yl)—4-(3-fluorophenyl)-3-methyl-1H-pyrazole-5-carboxylic acid;

1-(4-(4-chloro-3-cyanophenyl)-5-(isopropylthio)thiazol-2-yl)—4-(3-fluorophenyl)-3-methyl-1H-pyrazole-5-carboxylic acid;

1-(4-(4-cyano-3-methylphenyl)-5-(isopropylthio)thiazol-2-yl)—4-(3-fluorophenyl)-3-methyl-1H-pyrazole-5-carboxylic acid;

1-(4-(3,4-dichlorophenyl)-5-isopropoxythiazol-2-yl)—4-(3-fluorophenyl)-3-methyl-1H-pyrazole-5-carboxylic acid;

1-(4-(4-chloro-2,6-dimethylphenyl)-5-(isopropylthio)thiazol-2-yl)—4-(3-fluorophenyl)-3-methyl-1H-pyrazole-5-carboxylic acid;

4-(3-fluorophenyl)-1-(5-(isopropylthio)-4-(2-(trifluoromethyl)pyrimidin-5-yl)thiazol-2-yl)—3-methyl-1H-pyrazole-5-carboxylic acid;

4-(3-fluorophenyl)-1-(5-(isopropylthio)-4-(3-(trifluoromethyl)phenyl)thiazol-2-yl)—3-methyl-1H-pyrazole-5-carboxylic acid;

4-(3-fluorophenyl)-1-(5-(isopropylamino)-4-(4-(trifluoromethyl)phenyl)thiazol-2-yl)—3-methyl-1H-pyrazole-5-carboxylic acid; or 1-(4-(4-cyanophenyl)-5-(isopropylthio)thiazol-2-yl)—4-(3-fluorophenyl)-3-methyl-1H-pyrazole-5-carboxylic acid, optionally in the form of a pharmaceutically acceptable salt or N-oxide, or a solvate or hydrate.

\* \* \* \* \*